United States Patent
Zheng et al.

(10) Patent No.: US 10,988,450 B2
(45) Date of Patent: Apr. 27, 2021

(54) 3-ALKYL-4-AMIDO-BICYCLIC [4,5,0] HYDROXAMIC ACIDS AS HDAC INHIBITORS

(71) Applicant: Valo Early Discovery, Inc., Boston, MA (US)

(72) Inventors: Xiaozhang Zheng, Lexington, MA (US); Pui Yee Ng, Lexington, MA (US); Bingsong Han, Westwood, MA (US); Jennifer R. Thomason, Clinton, MA (US); Mary-Margaret Zablocki, Revere, MA (US); Cuixian Liu, Madison, CT (US); Heather Davis, Haverhill, MA (US); Aleksandra Rudnitskaya, Roslindale, MA (US); David R. Lancia, Jr., Boston, MA (US); Kenneth W. Bair, Wellesley, MA (US); David S. Millan, Watertown, MA (US); Matthew W. Martin, Arlington, MA (US)

(73) Assignee: Valo Early Discovery, Inc., Boston, MA (US)

( * ) Notice: Subject to any disclaimer, the term of this patent is extended or adjusted under 35 U.S.C. 154(b) by 0 days.

(21) Appl. No.: 16/567,007

(22) Filed: Sep. 11, 2019

(65) Prior Publication Data
US 2020/0002298 A1 Jan. 2, 2020

Related U.S. Application Data

(62) Division of application No. 16/219,648, filed on Dec. 13, 2018, now Pat. No. 10,457,652, which is a
(Continued)

(51) Int. Cl.
| | | |
|---|---|---|
| *C07D 491/08* | (2006.01) | |
| *C07D 267/14* | (2006.01) | |
| *C07D 413/06* | (2006.01) | |
| *C07D 413/12* | (2006.01) | |
| *C07D 413/04* | (2006.01) | |
| *C07D 267/12* | (2006.01) | |
| *C07D 243/14* | (2006.01) | |
| *C07D 291/08* | (2006.01) | |
| *C07D 401/06* | (2006.01) | |
| *C07D 401/10* | (2006.01) | |
| *C07D 403/06* | (2006.01) | |
| *C07D 403/10* | (2006.01) | |
| *C07D 405/06* | (2006.01) | |
| *C07D 413/14* | (2006.01) | |
| *C07D 417/04* | (2006.01) | |
| *C07D 471/04* | (2006.01) | |
| *C07D 498/04* | (2006.01) | |
| *C07D 498/08* | (2006.01) | |
| *C07D 493/08* | (2006.01) | |
| *C07D 413/08* | (2006.01) | |

(Continued)

(52) U.S. Cl.
CPC ......... *C07D 267/14* (2013.01); *C07D 243/14* (2013.01); *C07D 267/12* (2013.01); *C07D 291/08* (2013.01); *C07D 401/06* (2013.01); *C07D 401/10* (2013.01); *C07D 403/06* (2013.01); *C07D 403/10* (2013.01); *C07D 405/06* (2013.01); *C07D 413/04* (2013.01); *C07D 413/06* (2013.01); *C07D 413/08* (2013.01); *C07D 413/12* (2013.01); *C07D 413/14* (2013.01); *C07D 417/04* (2013.01); *C07D 471/04* (2013.01); *C07D 491/107* (2013.01); *C07D 493/08* (2013.01); *C07D 495/10* (2013.01); *C07D 498/04* (2013.01); *C07D 498/08* (2013.01)

(58) Field of Classification Search
CPC .................................................. C07D 491/08
See application file for complete search history.

(56) References Cited

U.S. PATENT DOCUMENTS

| | | |
|---|---|---|
| 4,332,802 A | 6/1982 | Schromm et al. |
| 4,861,784 A | 8/1989 | Rauber et al. |
| | (Continued) | |

FOREIGN PATENT DOCUMENTS

| | | |
|---|---|---|
| CN | 102558200 A | 7/2012 |
| CN | 102838625 A | 12/2012 |
| | (Continued) | |

OTHER PUBLICATIONS

Aldana-Masangkay, G.I. and Sakamoto, K.M. The Role of HDAC6 in Cancer, J. Biomed. Biotechnol., 875824: 1-10 (2011).
Amengual. J.E. et al, Dual Targeting of Protein Degradation Pathways with the Selective HDAC6 Inhibitor ACY-1215 and Bortezomib Is Synergistic in Lymphoma, Clin Cancer Res., 21(20):4663-75 (2015).
Bantscheff, M. et al., Chemoproteomics profiling of HDAC inhibitors reveal selective targeting of HDAC complexes, Nature Biotechnology, 29(3):255-265 (2011). Online Methods appended.
(Continued)

*Primary Examiner* — Brenda L Coleman
(74) *Attorney, Agent, or Firm* — Choate, Hall & Stewart LLP; Michael A. Shinall; Nicholas J. Pace

(57) ABSTRACT

The present disclosure relates to inhibitors of zinc-dependent histone deacetylases (HDACs) useful in the treatment of diseases or disorders associated with an HDAC, e.g., HDAC6, having a Formula I:

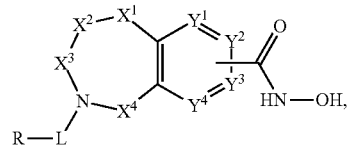

where R, L, $X^1$, $X^2$, $X^3$, $X^4$, $Y^1$, $Y^2$, $Y^3$, and $Y^4$ are described herein.

14 Claims, No Drawings

Related U.S. Application Data division of application No. 15/013,814, filed on Feb. 2, 2016, now Pat. No. 10,214,500.

(60) Provisional application No. 62/205,438, filed on Aug. 14, 2015, provisional application No. 62/110,716, filed on Feb. 2, 2015.

(51) Int. Cl.
*C07D 491/107* (2006.01)
*C07D 495/10* (2006.01)

(56) References Cited

U.S. PATENT DOCUMENTS

| | | |
|---|---|---|
| 5,153,185 A | 10/1992 | DiNinno et al. |
| 5,244,911 A | 9/1993 | Booher et al. |
| 5,294,610 A | 3/1994 | DiNinno et al. |
| 5,384,317 A | 1/1995 | DiNinno |
| 5,532,261 A | 7/1996 | DiNinno et al. |
| 5,612,356 A | 3/1997 | Yoshimura et al. |
| 5,714,518 A | 2/1998 | Reich et al. |
| 5,719,144 A | 2/1998 | Hartman et al. |
| 5,728,844 A | 3/1998 | Muller et al. |
| 5,807,854 A | 9/1998 | Bartroli et al. |
| 5,863,950 A | 1/1999 | Reich et al. |
| 6,001,823 A | 12/1999 | Hultgren et al. |
| 6,110,913 A | 8/2000 | Dorwald et al. |
| 6,153,396 A | 11/2000 | Hultgren et al. |
| 6,180,640 B1 | 1/2001 | Cuny et al. |
| 6,288,099 B1 | 9/2001 | Antane et al. |
| 6,403,632 B1 | 6/2002 | Duan et al. |
| 6,414,029 B1 | 7/2002 | Shechter et al. |
| 6,420,127 B1 | 7/2002 | Hultgren et al. |
| 6,476,019 B1 | 11/2002 | Radeke et al. |
| 6,762,177 B2 | 7/2004 | Radeke et al. |
| 6,787,554 B2 | 9/2004 | Gaudilliere |
| 6,872,542 B1 | 3/2005 | Hultgren et al. |
| 6,916,809 B2 | 7/2005 | Chen et al. |
| 6,962,791 B2 | 11/2005 | Hultgren et al. |
| 6,992,077 B2 | 1/2006 | Radeke et al. |
| 7,199,119 B2 | 4/2007 | Burkitt et al. |
| 7,214,690 B2 | 5/2007 | Higuchi et al. |
| 7,241,775 B2 | 7/2007 | Hofmeister et al. |
| 7,495,111 B2 | 2/2009 | Ramamoorthy et al. |
| 7,582,667 B2 | 9/2009 | Quagliato et al. |
| 7,622,582 B2 | 11/2009 | Kesteleyn et al. |
| 7,704,756 B2 | 4/2010 | Suich et al. |
| 7,705,017 B2 | 4/2010 | Cummings et al. |
| 7,723,349 B2 | 5/2010 | Yao et al. |
| 7,943,608 B2 | 5/2011 | Schultz et al. |
| 7,951,795 B2 | 5/2011 | Bell et al. |
| 8,058,427 B2 | 11/2011 | Hsieh et al. |
| 8,119,655 B2 | 2/2012 | Dong et al. |
| 8,148,380 B2 | 4/2012 | Guiles et al. |
| 8,178,553 B2 | 5/2012 | Lavey et al. |
| 8,198,290 B2 | 6/2012 | Hodges |
| 8,324,221 B2 | 12/2012 | Banka et al. |
| 8,349,839 B2 | 1/2013 | Sturino et al. |
| 8,367,709 B2 | 2/2013 | Pinto et al. |
| 8,426,447 B2 | 4/2013 | White et al. |
| 8,436,005 B2 | 5/2013 | Liu et al. |
| 8,471,026 B2 | 6/2013 | Blackburn et al. |
| 8,513,433 B2 | 8/2013 | Panicker et al. |
| 8,518,964 B2 | 8/2013 | Truchon et al. |
| 8,524,732 B2 | 9/2013 | Schiemann et al. |
| 8,546,410 B2 | 10/2013 | Liu et al. |
| 8,569,336 B2 | 10/2013 | Tong et al. |
| 8,575,193 B2 | 11/2013 | Maier et al. |
| 8,598,342 B2 | 12/2013 | Kahne et al. |
| 8,629,272 B2 | 1/2014 | Fuchs et al. |
| 8,642,587 B2 | 2/2014 | Lange et al. |
| 8,642,615 B2 | 2/2014 | Wentland |
| 8,658,641 B2 | 2/2014 | Barvian et al. |
| 8,673,952 B2 | 3/2014 | Blaquiere et al. |
| 8,685,969 B2 | 4/2014 | Liu et al. |
| 8,686,032 B2 | 4/2014 | Davidson et al. |
| 8,703,936 B2 | 4/2014 | Jewett et al. |
| 8,765,773 B2 | 7/2014 | England et al. |
| 8,765,810 B2 | 7/2014 | Greene et al. |
| 8,778,931 B2 | 7/2014 | Gould |
| 8,785,626 B2 | 7/2014 | Blaquiere et al. |
| 8,815,891 B2 | 8/2014 | Kim et al. |
| 8,822,462 B2 | 9/2014 | Traynelis et al. |
| 8,822,488 B2 | 9/2014 | Deaver et al. |
| 8,871,759 B2 | 10/2014 | Coburn et al. |
| 9,630,922 B2 | 4/2017 | Ng et al. |
| 9,637,453 B2 | 5/2017 | Ng et al. |
| 10,112,915 B2 | 10/2018 | Zheng et al. |
| 10,183,934 B2 | 1/2019 | Zheng et al. |
| 10,214,500 B2 | 2/2019 | Zheng et al. |
| 10,214,501 B2 | 2/2019 | Zheng et al. |
| 10,239,845 B2 | 3/2019 | Zheng et al. |
| 10,377,726 B2 | 8/2019 | Zheng et al. |
| 10,407,418 B2 | 9/2019 | Zheng et al. |
| 10,414,738 B2 | 9/2019 | Zheng et al. |
| 10,421,731 B2 | 9/2019 | Zheng et al. |
| 10,421,732 B2 | 9/2019 | Zheng et al. |
| 10,428,031 B2 | 10/2019 | Zheng et al. |
| 10,442,776 B2 | 10/2019 | Zheng et al. |
| 10,450,283 B2 | 10/2019 | Zheng et al. |
| 10,450,284 B2 | 10/2019 | Zheng et al. |
| 10,457,652 B2 | 10/2019 | Zheng et al. |
| 10,464,909 B2 | 11/2019 | Zheng et al. |
| 10,464,910 B2 | 11/2019 | Zheng et al. |
| 10,472,337 B2 | 11/2019 | Zheng et al. |
| 10,494,351 B2 | 12/2019 | Zheng et al. |
| 10,494,352 B2 | 12/2019 | Zheng et al. |
| 10,494,353 B2 | 12/2019 | Zheng et al. |
| 10,494,354 B2 | 12/2019 | Zheng et al. |
| 10,513,501 B2 | 12/2019 | Zheng et al. |
| 10,555,935 B2 | 2/2020 | Zheng et al. |
| 10,822,316 B2 | 11/2020 | Zheng et al. |
| 10,829,461 B2 | 11/2020 | Zheng et al. |
| 10,829,462 B2 | 11/2020 | Zheng et al. |
| 2002/0034774 A1 | 3/2002 | Hultgren et al. |
| 2002/0045199 A1 | 4/2002 | Hultgren et al. |
| 2003/0171355 A1 | 9/2003 | Radeke et al. |
| 2003/0198992 A1 | 10/2003 | Hultgren et al. |
| 2003/0208066 A1 | 11/2003 | Levin et al. |
| 2004/0249147 A1 | 12/2004 | Sattigeri et al. |
| 2005/0038011 A1 | 2/2005 | Radeke et al. |
| 2005/0256166 A1 | 11/2005 | Nakai et al. |
| 2006/0069083 A1 | 3/2006 | Steiner et al. |
| 2006/0194785 A1 | 8/2006 | Radeke et al. |
| 2006/0239909 A1 | 10/2006 | Anderson et al. |
| 2007/0155730 A1 | 7/2007 | Leit et al. |
| 2007/0185007 A1 | 8/2007 | Jin et al. |
| 2007/0197564 A1 | 8/2007 | Lavey et al. |
| 2007/0244154 A1 | 10/2007 | Brehm |
| 2007/0265299 A1 | 11/2007 | Lavey et al. |
| 2008/0004282 A1 | 1/2008 | Vohra et al. |
| 2008/0112889 A1 | 5/2008 | Buggy et al. |
| 2008/0113962 A1 | 5/2008 | Zimmermann et al. |
| 2008/0194638 A1 | 8/2008 | Dedhiya et al. |
| 2008/0255161 A1 | 10/2008 | Koltun et al. |
| 2008/0275029 A1 | 11/2008 | Berdini et al. |
| 2008/0280855 A1 | 11/2008 | Chiesa et al. |
| 2009/0093473 A1 | 4/2009 | Zimmermann et al. |
| 2009/0105283 A1 | 4/2009 | Koltun et al. |
| 2009/0136449 A1 | 5/2009 | Di Filippo et al. |
| 2009/0156586 A1 | 6/2009 | Lavey et al. |
| 2009/0221589 A1 | 9/2009 | Trieselmann et al. |
| 2009/0325948 A1 | 12/2009 | Hurley et al. |
| 2010/0076012 A1 | 3/2010 | Schiemann et al. |
| 2010/0120818 A1 | 5/2010 | Enderle |
| 2010/0173332 A1 | 7/2010 | Smaill et al. |
| 2010/0256082 A1 | 10/2010 | Schotzinger |
| 2010/0317678 A1 | 12/2010 | Moffat et al. |
| 2011/0039827 A1 | 2/2011 | Blackburn et al. |
| 2011/0039840 A1 | 2/2011 | Varasi et al. |
| 2011/0071136 A1 | 3/2011 | Haddach et al. |
| 2011/0076292 A1 | 3/2011 | Blaquiere et al. |
| 2011/0098267 A1 | 4/2011 | Babu et al. |
| 2011/0251184 A1 | 10/2011 | Blackburn et al. |

(56) References Cited

U.S. PATENT DOCUMENTS

| | | |
|---|---|---|
| 2011/0275762 A1 | 11/2011 | Cmiljanovic et al. |
| 2011/0288117 A1 | 11/2011 | Gould et al. |
| 2012/0015942 A1 | 1/2012 | Calderwood et al. |
| 2012/0015943 A1 | 1/2012 | Blackburn et al. |
| 2012/0083483 A1 | 4/2012 | Coburn et al. |
| 2012/0094997 A1 | 4/2012 | England et al. |
| 2012/0121502 A1 | 5/2012 | van Duzer et al. |
| 2012/0165316 A1 | 6/2012 | Gould |
| 2012/0244149 A1 | 9/2012 | Blaquiere et al. |
| 2012/0245144 A1 | 9/2012 | Heffron et al. |
| 2012/0245193 A1 | 9/2012 | Silverman et al. |
| 2012/0258949 A1 | 10/2012 | Varasi et al. |
| 2013/0029938 A1 | 1/2013 | Aquino et al. |
| 2013/0079331 A1 | 3/2013 | Blaquiere et al. |
| 2013/0281402 A1 | 10/2013 | Chen et al. |
| 2013/0289027 A1 | 10/2013 | De La Rosa et al. |
| 2013/0303567 A1 | 11/2013 | Panicker et al. |
| 2014/0018343 A1 | 1/2014 | Romero et al. |
| 2014/0018361 A1 | 1/2014 | Harriman et al. |
| 2014/0031302 A1 | 1/2014 | Winssinger et al. |
| 2014/0031340 A1 | 1/2014 | Dineen et al. |
| 2014/0038954 A1 | 2/2014 | Epstein et al. |
| 2014/0088101 A1 | 3/2014 | Ng et al. |
| 2014/0128371 A1 | 5/2014 | Barvian et al. |
| 2014/0194386 A1 | 7/2014 | Burns et al. |
| 2014/0239288 A1 | 8/2014 | Delcamp et al. |
| 2014/0241990 A1 | 8/2014 | Haydon et al. |
| 2014/0288047 A1 | 9/2014 | Blaquiere et al. |
| 2014/0296226 A1 | 10/2014 | White et al. |
| 2014/0323447 A1 | 10/2014 | Kley et al. |
| 2016/0221972 A1 | 8/2016 | Zheng et al. |
| 2016/0221973 A1 | 8/2016 | Zheng et al. |
| 2016/0221997 A1 | 8/2016 | Zheng et al. |
| 2016/0222022 A1 | 8/2016 | Zheng et al. |
| 2016/0222028 A1 | 8/2016 | Zheng et al. |
| 2016/0304456 A1 | 10/2016 | Ng et al. |
| 2016/0304462 A1 | 10/2016 | Ng et al. |
| 2019/0016692 A1 | 1/2019 | Zheng et al. |
| 2019/0016693 A1 | 1/2019 | Zheng et al. |
| 2019/0062288 A1 | 2/2019 | Zheng et al. |
| 2019/0092762 A1 | 3/2019 | Zheng et al. |
| 2019/0112279 A1 | 4/2019 | Zheng et al. |
| 2019/0112280 A1 | 4/2019 | Zheng et al. |
| 2019/0112281 A1 | 4/2019 | Zheng et al. |
| 2019/0112282 A1 | 4/2019 | Zheng et al. |
| 2019/0112283 A1 | 4/2019 | Zheng et al. |
| 2019/0112284 A1 | 4/2019 | Zheng et al. |
| 2019/0119227 A1 | 4/2019 | Zheng et al. |
| 2019/0119228 A1 | 4/2019 | Zheng et al. |
| 2019/0119229 A1 | 4/2019 | Zheng et al. |
| 2019/0119230 A1 | 4/2019 | Zheng et al. |
| 2019/0119231 A1 | 4/2019 | Zheng et al. |
| 2019/0119232 A1 | 4/2019 | Zheng et al. |
| 2019/0119233 A1 | 4/2019 | Zheng et al. |
| 2019/0119234 A1 | 4/2019 | Zheng et al. |
| 2019/0119235 A1 | 4/2019 | Zheng et al. |
| 2019/0127339 A1 | 5/2019 | Zheng et al. |
| 2019/0201384 A1 | 7/2019 | Zheng et al. |
| 2019/0345149 A1 | 11/2019 | Zheng et al. |
| 2020/0048211 A1 | 2/2020 | Zheng et al. |
| 2020/0048212 A1 | 2/2020 | Zheng et al. |
| 2020/0055830 A1 | 2/2020 | Zheng et al. |
| 2020/0121655 A1 | 4/2020 | Zheng et al. |

FOREIGN PATENT DOCUMENTS

| | | |
|---|---|---|
| EP | 2110377 A1 | 10/2009 |
| GB | 2503789 A | 1/2014 |
| JP | 2000/044562 A | 2/2000 |
| JP | 2000/357809 A | 12/2000 |
| JP | 2001/226269 A | 8/2001 |
| JP | 2004/210716 A | 7/2004 |
| JP | 4162106 B2 | 10/2008 |
| JP | 2009/191041 A | 8/2009 |
| JP | 2011-148714 A | 8/2011 |
| WO | WO-9503699 A1 | 2/1995 |
| WO | WO-9514028 A2 | 5/1995 |
| WO | WO-9748786 A1 | 12/1997 |
| WO | WO-9901607 A2 | 1/1999 |
| WO | WO-9967238 A2 | 12/1999 |
| WO | WO-2000/034285 A2 | 6/2000 |
| WO | WO-01/12630 A1 | 2/2001 |
| WO | WO-2002/036066 A2 | 5/2002 |
| WO | WO-2002/042273 A2 | 5/2002 |
| WO | WO-2003/087059 A2 | 10/2003 |
| WO | WO-2004/017950 A2 | 3/2004 |
| WO | WO-2004/056182 A1 | 7/2004 |
| WO | WO-2004/063156 A1 | 7/2004 |
| WO | WO-2004/111052 A1 | 12/2004 |
| WO | WO-2005/108367 A1 | 11/2005 |
| WO | WO-2005/123089 A2 | 12/2005 |
| WO | WO-2006/065842 A2 | 6/2006 |
| WO | WO-2006/083869 A2 | 8/2006 |
| WO | WO-2006/102557 A2 | 9/2006 |
| WO | WO-2006/138549 A1 | 12/2006 |
| WO | WO-2007/022638 A1 | 3/2007 |
| WO | WO-2007/023135 A1 | 3/2007 |
| WO | WO-2007/029035 A2 | 3/2007 |
| WO | WO-2007/061880 A1 | 5/2007 |
| WO | WO-2007/079826 A1 | 7/2007 |
| WO | WO-2007/084451 A1 | 7/2007 |
| WO | WO-2007/100536 A1 | 9/2007 |
| WO | WO-2007/109178 A2 | 9/2007 |
| WO | WO-2007/143822 A1 | 12/2007 |
| WO | WO-2008/011805 A1 | 1/2008 |
| WO | WO-2008/046155 A1 | 4/2008 |
| WO | WO-2008/048648 A2 | 4/2008 |
| WO | WO-2008/055068 A2 | 5/2008 |
| WO | WO-2008/060721 A1 | 5/2008 |
| WO | WO-2008/061160 A1 | 5/2008 |
| WO | WO-2008/071765 A1 | 6/2008 |
| WO | WO-2008/074858 A1 | 6/2008 |
| WO | WO-2008/091349 A1 | 7/2008 |
| WO | WO-2008/101186 A1 | 8/2008 |
| WO | WO-2009/100045 A1 | 8/2009 |
| WO | WO-2009/123967 A1 | 10/2009 |
| WO | WO-2009127609 A1 | 10/2009 |
| WO | WO-2009/137503 A1 | 11/2009 |
| WO | WO-2010/028192 A1 | 3/2010 |
| WO | WO-2010/042475 A1 | 4/2010 |
| WO | WO-2010/043893 A1 | 4/2010 |
| WO | WO-2010/054278 A2 | 5/2010 |
| WO | WO-2010/056230 A1 | 5/2010 |
| WO | WO-2010/092181 A1 | 8/2010 |
| WO | WO-2010/111483 A1 | 9/2010 |
| WO | WO-2010/125469 A1 | 11/2010 |
| WO | WO-2010/151317 A1 | 12/2010 |
| WO | WO-2010/151318 A1 | 12/2010 |
| WO | WO-2010/151441 A1 | 12/2010 |
| WO | WO-2011/002520 A2 | 1/2011 |
| WO | WO-2011/011186 A2 | 1/2011 |
| WO | WO-2011/036280 A1 | 3/2011 |
| WO | WO-2011/039353 A1 | 4/2011 |
| WO | WO-2011/045265 A2 | 4/2011 |
| WO | WO-2011/079036 A1 | 6/2011 |
| WO | WO-2011/084991 A2 | 7/2011 |
| WO | WO-2011/088181 A1 | 7/2011 |
| WO | WO-2011/091213 A2 | 7/2011 |
| WO | WO-2011/106627 A1 | 9/2011 |
| WO | WO-2011/106632 A1 | 9/2011 |
| WO | WO-2011/137135 A1 | 11/2011 |
| WO | WO-2011/146591 A1 | 11/2011 |
| WO | WO-2012/016081 A2 | 2/2012 |
| WO | WO-2012/027564 A1 | 3/2012 |
| WO | WO-2012/031993 A1 | 3/2012 |
| WO | WO-2012/045194 A1 | 4/2012 |
| WO | WO-2012/045804 A1 | 4/2012 |
| WO | WO-2012/054332 A1 | 4/2012 |
| WO | WO-2012/085003 A1 | 6/2012 |
| WO | WO-2012/088015 A2 | 6/2012 |
| WO | WO-2012/106343 A2 | 8/2012 |
| WO | WO-2012/110860 A1 | 8/2012 |
| WO | WO-2012/117421 A1 | 9/2012 |
| WO | WO-2012/126901 A1 | 9/2012 |

(56) References Cited

FOREIGN PATENT DOCUMENTS

| | | |
|---|---|---|
| WO | WO-2012/178208 A2 | 12/2012 |
| WO | WO-2013/006408 A1 | 1/2013 |
| WO | WO-2013/008162 A1 | 1/2013 |
| WO | WO-2013/009827 A1 | 1/2013 |
| WO | WO-2013/013113 A2 | 1/2013 |
| WO | WO-2013/033085 A1 | 3/2013 |
| WO | WO-2013/052110 A1 | 4/2013 |
| WO | WO-2013/059582 A2 | 4/2013 |
| WO | WO-2013/090210 A1 | 6/2013 |
| WO | WO-2013/134467 A1 | 9/2013 |
| WO | WO-2014/011753 A2 | 1/2014 |
| WO | WO-2014/018919 A1 | 1/2014 |
| WO | WO-2014/037342 A1 | 3/2014 |
| WO | WO-2014/048945 A1 | 4/2014 |
| WO | WO-2014/110442 A1 | 7/2014 |
| WO | WO-2014/127881 A1 | 8/2014 |
| WO | WO-2014/134127 A1 | 9/2014 |
| WO | WO-2014/178606 A1 | 11/2014 |
| WO | WO-2015/054474 A1 | 4/2015 |
| WO | WO-2015/137750 A1 | 9/2015 |
| WO | WO-2016/126721 A1 | 8/2016 |
| WO | WO-2016/126722 A1 | 8/2016 |
| WO | WO-2016/126724 A1 | 8/2016 |
| WO | WO-2016/126725 A1 | 8/2016 |
| WO | WO-2016/126726 A1 | 8/2016 |
| WO | WO-2016/168598 A1 | 10/2016 |
| WO | WO-2016/168660 A1 | 10/2016 |
| WO | WO-2017/065473 A1 | 4/2017 |
| WO | WO-2017/218950 A1 | 12/2017 |

OTHER PUBLICATIONS

Bazzaro M. et al, Ubiquitin Proteasome System Stress Underlies Synergistic Killing of Ovarian Cancer Cells by Bortezomib and a Novel HDAC6 Inhibitor, Clin. Cancer Res., 14(22):7340- 7347 (2008).

Benedetti R, Conte M, Altucci L. "Targeting Histone Deacetylases in Diseases: Where Are We?" Antioxidants & Redox Signaling, 23(1), pp. 99-126, 2015.

Bergman, J.A. et al., Selective histone deacetylase 6 inhibitors bearing substituted urea linkers inhibit melanoma cell growth, J. Med. Chem., 55:9891-9899 (2012).

Blackburn, C. et al., Potent Histone Deacetylase Inhibitors Derived from 4-(Aminomethyl)-N-hydroxybenzamide with High Selectivity for the HDAC6 Isoform, J Medicinal Chemistry, 56(18):7201-7211 (2013).

Blackburn, C. et al., Histone deacetylase inhibitors derived from 1,2,3,4-tetrahydropyrrolo[1,2-a]pyrazine and related heterocycles selective for the HDAC6 isoform, Bioorg Med Chem Lett., 24(23):5450-5454 (2014).

Bone, E.A. et al., Design and Development of HDAC6-Selective Inhibitors for Hematological Cancer Treatment and Solid Tumor Immunotherapy, Karus Therapeutics, Poster session presented at the AACR Annual Meeting, Philadelphia, PA, 1 page (2015). Abstract 3662.

Bradner, J.E. et al., Chemical phylogenetics of histone deacetylases, Nature Chemical Biology, 6:238-243 (2010). Supplemental Information appended, 26 pages.

Butler, K.V. and Kozikowski, A.P., Chemical Origins of Isoform Selectivity in Histone Deacetylase Inhibitors, Current Pharmaceutical Design, 14:505-528 (2008).

Butler, K.V. et al., Rational Design and Simple Chemistry Yield a Superior Neuroprotective HDAC6 Inhibitor, Tubastatin A, J. Am. Chem. Soc., 132:10842-10846 (2010).

Cancer, MedlinePlus, 10 pages. URL: http://www.nlm.nih.gov/medlineplus/cancer.html. [Retrieved Jul. 6, 2007].

Canet, E. and Touchon, P., Servier: Looking to the Future—Innovation-Driven Partnerships. Medicographia 120, vol. 36(3):267-429 (2014).

Cha, T.L. et al, Dual degradation of aurora A and B kinases by the histone deacetylase inhibitor LBH589 induces G2-M arrest and apoptosis of renal cancer cells, Clin. Cancer Res., 15(3): 840-850 (2009).

Choi, E. et al., Property-Based Optimization of Hydrozamate-Based γ-Lactam HDAC Inhibitors to Improve Their Metabolic Stability and Pharmacokinetic, J. Med. Chem., 55:10766-10770 (2012).

Choi, S.Y. et al, Tubastatin A suppresses renal fibrosis via regulation of epigenetic histone modification and Smad3-dependent fibrotic genes, Vascul. Pharmacol., 72:130-140 (2015).

Choi, Y., Anti-Multiple Myeloma Activity of a Novel HDAC6 Inhibitor, DC-004, in Combination with Proteosomal Inhibitors, CKD Pharmaceutical Corporation, Presentation at the DOT Meeting, 26 pages, Sep. 24, 2015.

Chuang, M.J. et al., The HDAC Inhibitor LBH589 Induces ERK-Dependent Prometaphase Arrest in Prostate Cancer via HDAC6 Inactivation and Down-Regulation, PLOS One, 8(9):e73401 (2013).

D'Ydewalle, C. et al., HDAC6 inhibitors reverse axonal loss in a mouse model of mutant HSPB1-induced Charcot-Marie-Tooth disease, Nature Medicine, 8(17):968-974 (2011). Online Methods appended, 1 page.

Dallavalle S, Pisano C, Zunino F. "Development and therapeutic impact of HDAC6-selective inhibitors",Biochemical Pharmacology, Sep. 15, 2012; 84(6):756-65.

De Ruijter, A.J. et al, Histone deacetylases (HDACs): characterization of the classical HDAC family, Biochem. J., 370: 737-749 (2003).

Dhakal, B.K. and Mulve, M.A., Uropathogenic *Escherichia coli* invades host cells via an HDAC6-modulated microtubule-dependent pathway, J. Biol. Chem., 284(1):446-454 (2008).

Di Micco, S. et al., Structural basis for the design and synthesis of selective HDAC inhibitors, Bioorganic & Medicinal Chemistry, 21:3795-3807 (2013).

Ding, G. et al, HDAC6 promotes hepatocellular carcinoma progression by inhibiting P53 transcriptional activity, FEBS Lett., 587:880-6 (2013).

Ding, N. et al, Histone deacetylase 6 activity is critical for the metastasis of Burkitt's lymphoma cells, Cancer Cell Int., 14:139 (2014).

Falkenberg, K.J. and Johnstone, R.W., Histone deacetylases and their inhibitors in cancer, neurological diseases and immune disorders, Nature Reviews, 13:673-691 (2014).

Feng, T. et al., Novel N-hydrozyfurylacrylamide-based histone deacetylase (HDAC) inhibitors with branched CAP group (Part 2), Bioorg. Med. Chem., 21(17):5339-5354 (2013).

Fiskus, W. et al, Molecular and biologic characterization and drug sensitivity of pan-histone deacetylase inhibitor-resistant acute myeloid leukemia cells, Blood, 112(7):2896-2905 (2008).

Golub et al., Molecular Classification of Cancer: Class Discovery and Class Prediction by Gene Expression Monitoring, Science (1999), vol. 286, 531-537.

Gupta, P. et al., Towards Isozyme-Selective HDAC Inhibitors for Interrogating Disease, Current Topics in Medicinal Chemistry, 12:1479-1499 (2012).

Haakenson, J. and Zhang, X., HDAC6 and Ovarian Cancer, Int. J. Mol. Sci., 14:9514-9535 (2013).

Hadley, M. et al., In Vivo Evaluation of Ames Negative HDAC6 Inhibitor in Melanoma Model. The George Washington Cancer Center. AACR Annual Meeting, Presentation Poster (2017).

Hahnen, E. et al., Histone deacetylase inhibitors: possible implications for neurodegenerative disorders, Expert Opin. Investig. Drugs, 17(2):1-16 (2008).

Hajiagha Bozorgi, A. et al., A structure-activity relationship survey of histone deacetylase (HDAC) inhibitors, Chemometrics and Intelligent Laboratory Systems, 125:132-138 (2013).

Hanessian, S. et al., Vorinostat-Like Molecules as Structural, Stereochemical, and Pharmacological Tools, ACS Med. Chem. Lett., 1:70-74 (2010).

Hideshima, T. et al, Small-molecule inhibition of proteasome and aggresome function induces synergistic antitumor activity in multiple myelomaProc. Natl. Acad. Sci. USA, 102(24):8567-8572 (2005).

Holson, E., Design of inter-class selective inhibitors and discovery of endogenous "HDAC" substrates, The Stanley Center for Psychiatric Research, The Board Institute of Harvard and MIT, Presentation at the DOT Meeting in Boston, 44 pages, Oct. 7, 2014.

(56) References Cited

OTHER PUBLICATIONS

Inks, E.S. et al., A Novel Class of Small Molecule Inhibitors of HDAC6, ACS Chem. Biol., 7:331-339 (2012).
International Search Report for PCT/US2016/016194, 4 pages (dated Mar. 23, 2016).
International Search Report for PCT/US2016/016197, 4 pages (dated Mar. 22, 2016).
International Search Report for PCT/US2016/016200, 4 pages (dated Mar. 22, 2016).
International Search Report for PCT/US2016/016201, 4 pages (dated Apr. 20, 2016).
International Search Report for PCT/US2016/016204, 4 pages (dated Mar. 22, 2016).
International Search Report for PCT/US2016/027755, 8 pages (dated Aug. 23, 2016).
International Search Report for PCT/US2016/027842, 8 pages (dated Aug. 12, 2016).
International Search Report for PCT/US2017/037970, 5 pages (dated Aug. 9, 2017).
Itoh, Y. et al., Design, Synthesis, Structure—Selectivity Relationship, and Effect on Human Cancer Cells of a Novel Series of Histone Deacetylase 6-Selective Inhibitors, J. Med. Chem., 50:5425-5438 (2007).
Jochems, J. et al., Antidepressant-Like Properties of Novel HDAC6-Selective Inhibitors with Improved Brain Bioavailability, Neuropsychopharmacology, 39:389-400 (2014).
Kalin JH, Bergman JA. "Development and therapeutic implications of selective histone deacetylase 6 inhibitors", J Med Chem. Aug. 22, 2013; 56(16):6297-313.
Kalin, J.H. et al, Second-generation histone deacetylase 6 inhibitors enhance the immunosuppressive effects of Foxp3+ T-regulatory cells, J. Med. Chem., 55:639-651 (2012).
Kaliszczak, M. et al., A novel small molecule hydroxamate preferentially inhibits HDAC6 activity and tumour growth, British Journal of Cancer, 108:342-350 (2013).
Kamemura, K. et al, Effects of downregulated HDAC6 expression on the proliferation of lung cancer cells, Biochem. Biophys. Res. Commun., 374(1):84-89 (2008).
Kanno, K. et al, Overexpression of histone deacetylase 6 contributes to accelerated migration and invasion activity of hepatocellular carcinoma cells, Oncol. Rep., 28: 867-73 (2012).
Katharaj, E. and Jayaraman, R., Histone Deacetylase Inhibitors as Therapeutics Agents for Cancer Therapy: Drug Metabolism and Pharmacokinetic Propoerties, Drug Development—A Case Study Based Insight into Modern Strategies, InTech, 21 pages (2011).
Kee, H.J. et al., HDAC Inhibition Suppresses Cardiac Hypertrophy and Fibrosis in DOCA-Salt Hypertensive Rats via Regulation of HDAC6/HDAC8 Enzyme Activity, 37(4-5):229-239 (2013).
Kim, H.J. and Bae, S.C., Histone deacetylase inhibitors: molecular mechanisms of action and clinical trials as anti-cancer drugs, Am J Transl Res, 3(2):166-179 (2011).
Kim, J. et al., A Novel Regulatory Role of HDAC6 in the Functional Inflammatory Phenotype of Glia cells. The George Washington University Cancer Center. AACR Annual Meeting, Presentation Poster (2017).
Kim, Y.H. et al., A phase 1b Study in Cutaneous T-cell lymphoma (CTCL) with the novel topically applied skin-restricted histone deacetylase inhibitor (HDAC-i) SHP-141. Journal of Clinical Oncology 32:15_suppl, 8525-8525 (2014).
Konsoula, Z. et al., Pharmacokinetics-pharmacodynamics and anti-tumor activity of mercaptoacetamide-based histone deacetylase inhibitors, Mol Cancer Ther, 8(10):2844-2851 (2009).
Kozikowski, A.P. et al., Use of the Nitrile Oxide Cycloaddition (NOC) Reaction for Molecular Probe Generation: A New Class of Enzyme Selective Histone Deacetylase Inhibitors (HDACIs) Showing Picomolar Activity of HDAC6, J. Med. Chem., 51:4370-4373 (2008).
Kozikowski, A.P., Chemistry, the Brain, and Cancer—Ups and Downs on the Road to HDAC Drugs, Department of Medicinal Chemistry and Pharmacognosy, University of Illinois at Chicago, 61 pages, 2015.
Kroesen, K. et al., HDAC inhibitors and immunotherapy; a double edged sword?, Oncotarget, 5(16):6558-6572 (2014).
Krukowski, K. et al., Abstract 1612: An HDAC6 inhibitor for treatment of chemotherapy-induced peripheral numbness and pain in a mouse model, Abstracts/Brain, Behavior, and Immunity, 49:e28 (2015).
Kwon, S.H., Selective Inhibition of HDAC6 regulates preferential cytotoxicity in cancer cells by modulating p53 and Hsp90 stability, American Association for Cancer Research Annual Meeting, Philadelphia, Abstract 5324, 16 pages (Apr. 22, 2015).
Lai, M.J. et al., Synthesis and Biological Evaluation of 1-Arylsulfonyl-5-(N-hydroxyacrylamide)indoles as Potent Histone Deacetylase Inhibitors with Antitumor Activity in Vivo, J. Med. Chem., 55:3777-3791 (2012).
Lala et al., Role of nitric oxide in tumor progression: Lessons from experimental tumors, Cancer and Metastasis Reviews (1998), 17, 91-106.
Lee, J. and Huang, S.R., Cancer Epigenetics: Mechanisms and Crosstalk of HDAC Inhibitor, Vorinostat, Chemotherapy, 2(1):1000111 (2013).
Lee, J.H. et al., Anti-Multiple Myeloma Activity of a Novel HDAC6 Inhibitor, DC-004, in Combination with Proteosomal Inhibitors. CKD Research Institute (2015).
Lee, J.H. et al., Development of a histone deacetylase 6 inhibitor and its biological effects, PNAS Early Edition, 110(39):15704-15709 (2013).
Lee, Y-S. et al, The cytoplasmic deacetylase HDAC6 is required for efficient oncogenic tumorigenesisCancer Res., 68(18):7561-7569 (2008).
Li, Y. et al, Histone deacetylase 6 plays a role as a distinct regulator of diverse cellular processes, FEBS J., 280: 775-93 (2013).
Lim, H. et al., CKD-M134, a Novel HDAC6 Inhibitor, Ameliorates Experimental Colitis Models in Mice. CKD Research Institute, Presentation Poster, 1 page (Sep. 25, 2015).
Lin, X. et al., Design and Synthesis of Orally Bioavailable Aminopyrrolidinone Histone Deacetylase 6 Inhibitors, J. Med. Chem., 58:2809-2820 (2015).
Marek, L. et al., Histone Deacetylase (HDAC) Inhibitors with a Novel Connecting Unit Linker Region Reveal a Selectivity Profile for HDAC4 and HDAC5 with Improved Activity against Chemoresistant Cancer Cells, J. Med. Chem., 56(2):427-436 (2013).
Mishima, Y. et al., Ricolinostat (ACY-1215) induced inhibition of aggresome formation accelerates carfilzomib-induced multiple myeloma cell death, British Journal of Haematology, 169(9):423-434 (2015).
Molina, A. et al., Identification of ACY-1083: A Novel, Potent, and Highly Selective HDAC6 Inhibitor, Acetylon Pharmaceuticals, Inc., Poster presentation, 1 page, 2015.
Mottamal, M. et al., Histone Deacetylase Inhibitors in Clinical Studies as Templates for New Anticancer Agents, Molecules, 20:3898-3941 (2015).
Nawrocki, S.T. et al, Aggresome disruption: a novel strategy to enhance bortezomib-induced apoptosis in pancreatic cancer cells, Cancer Res., 66(7):3773-3781 (2006).
New, M. et al., HDAC inhibitor-based therapies: Can we interpret the code?, Molecular Oncology, 6:637-656 (2012).
Olson, D.E. et al., Discovery of the First Histone Deacetylase 6/8 Dual Inhibitors, J. Med. Chem., 56:4816-4820 (2013).
Park, S.Y. et al, Histone deacetylases 1, 6 and 8 are critical for invasion in breast cancer, Oncol. Rep. 2011, 25: 1677-1681 (2011).
Quartararo, C.E. et al., High-Throughput Screening of Patient-Derived Cultures Reveals Potential for Precision Medicine in Glioblastoma, ASC Med. Chem. Lett., 6:948-952 (2015).
Quayle, S.N. et al., Selective HDAC Inhibition by Ricolinostat (ACY-1215) or ACY-241 Synergizes with IMiD® Immunomodulatory Drugs in Multiple Myeloma (MM) and Mantle Cell Lymphoma (MCL) Cells, Acetylon Pharmaceuticals, Inc., AACR Poster Presentation in Boston, MA, 1 page (2015).

(56) References Cited

OTHER PUBLICATIONS

Raje, N. et al., Ricolinostat plus Lenalidomide and Dexamethasone in Patients with Relapsed & Refractory Multiple Myeloma: Phase 1B & Early Phase 2 Results, Acetylon Pharamceuticals Inc, Poster Presentation (2015).
Rey, M. et al, HDAC6 is required for invadopodia activity and invasion by breast tumor cells, Eur. J. Cell Biol., 90: 128-135 (2011).
Rivieccio, M.A. et al, HDAC6 is a target for protection and regeneration following injury in the nervous system, Proc. Natl. Acad. Sci. USA, 106(46):19599-195604 (2009).
Rodriguez-Gonzalez, R. et al, Multiple system organ response induced by hyperoxia in a clinically relevant animal model of sepsis, Blood 2008, 1 12(1 1): Abstract 1923 (2008).
Seidel, C. et al, 4-Hydroxybenzoic acid derivatives as HDAC6-specific inhibitors modulating microtubular structure and HSP90a chaperone activity against prostate cancer, Biochem. Pharmacol., 99: 31-52 (2016).
Seki, H. et al., Synthesis/biological evaluation of hydrozamic acids and their prodrugs as inhibitors for Botulinum neurotoxin A light chain, Bioorganic & Medicinal Chemistry, 22:1208-1217 (2014).
Shen, S. et al., Bicyclic-Capped Histone Deacetylase 6 Inhibitors with Improved Activity in a Model of Axonal Charcot-Marie-Tooth Disease, ACS Chem Neurosci., 7(2):240-258 (2016).
Shon, S. et al., Abstract 1448: Therapeutic Role of a Novel Histone Deacetylase 6 Inhibitor, CKD-M808, in Rheumatoid Arthritis, ACR/ARHP Annual Meeting, 2 pages (2016). Accessed May 25, 2018. <http://acrabstracts.org/abstract/therapeutic-role-of-a-novel-histone-deacetylase-6-inhibitor-ckd-m808-in-rheumatoid-arthritis/>.
Simoes-Pires, C. et al, HDAC6 as a target for neurodegenerative diseases: what makes it different from the other HDAC6?, Mol. Neurodegener., 8: 7 (2013).
Suzuki, T. et al., Highly Potent and Selective Histone Deacetylase 6 Inhibitors Designed Based on a Small-Molecular Substrate, J. Med. Chem., 49:4809-4812 (2006).
Tang J, Yan H, Zhuang S. "Histone deacetylases as targets for treatment of multiple diseases", Clinical Science (Lond), Jun. 2013; 124(11):651-62.
Tang, G. et al., Identification of a Novel Aminotetralin Class of HDAC6 and HDAC8 Selective Inhibitors, J. Med. Chem., 57(19):8026-8034 (2014).
Tannous, P. et al, Intracellular protein aggregation is a proximal trigger of cardiomyocyte autophagy, Circulation, 117(24):3070-3078 (2008).
Tapadar, S. et al., Isoxazole moiety in the linker region of HDAC inhibitors adjacent to the Zn-chelating group: Effects on HDAC biology and antiproliferative activity, Bioorganic & Medicinal Chemistry Letters, 19:3023-3026 (2009).
Thaler, F. et al., Current trends in the development of histone deacetylase inhibitors: a review of recent patent applications, Pharm. Pat. Analyst, 1(1):75-90 (2012).

Thangapandian, S. et al., Molecular Modeling Study on Tunnel Behavior in Different Histone Deacetylase Isoforms, PLOS ONE, 7(11):e49327 (2012).
Valente, S. and Mai, A., Small-molecule inhibitors of histone deacetylase for the treatment of cancer and non-cancer diseases: a patent review (2011-2013), Expert Opin. Ther. Patents, 24(4):401-415 (2014).
Van Helleputte, L. et al., The role of histone deacetylase 6 (HDAC6) in neurodegeneration, Research and Reports in Biology, 5:1-13 (2014).
Varasi, M. et al., Discovery, Synthesis, and Pharmacological Evaluation of Spiropiperidine Hydroxamic Acid Based Derivatives as Structurally Novel Histone Deacetylase (HDAC) Inhibitors, Journal of Medicinal Chemistry, 54(8): 3051-3064 (2011).
Vishwakarma, S. et al, Tubastatin, a selective histone deacetylase 6 inhibitor shows anti-inflammatory and anti-rheumatic effects, Int. Immunopharmacol., 16:72-78 (2013).
Wagner, F.F. et al., Potent and Selective Inhibition of Histone Deacetylase 6 (HDAC6) Does Not Require a Surface-Binding Motif, J. Med. Chem., 56:1772-1776 (2013).
Wagner, F.F. et al., Small Molecule Inhibitors of Zinc-dependent Histone Deacetylases, Neurotherapeutics, 10(4):589-604 (2013).
Wang, L. et al, Immunomodulatory effects of deacetylase inhibitors: therapeutic targeting of FOXP3+ regulatory T cellsNat. Rev. Drug Disc. 2009 8(12):969-981.
Wang, Z. et al., HDAC6 promotes cell proliferation and confers resistance to temozolomide in glioblastoma. Cancer Letters 379:134-142 (2016).
West AC, Johnstone RW, "New and emerging HDAC inhibitors for cancer treatment", Journal of Clinical Investigation, Jan. 2, 2014; 124(1):30-9.
Wu, D. et al., Screening of selective histone deacetylase inhibitors by proteochemometric modeling, BMC Bioinformatics, 13:212 (2012).
Yang, M.H. et al., HDAC6 and SIRT2 regulate the acetylation state and oncogenic activity of mutant K-RAS, Mol Cancer Res, 11(9):1072-1077 (2013).
Yu, C.W. et al., Quinazolin-4-one Derivatives as Selective Histone Deacetylase-6 Inhibitors for the Treatment of Alzheimer's Disease, J. Med. Chem., 56(17):6775-6791 (2013).
Zhang, L. et al, Proteomic identification and functional characterization of MYH9, Hsc70, and DNAJA1 as novel substrates of HDAC6 deacetylase activity, Protein Cell., 6(1): 42-54 (2015).
Zhang, Y. et al., Discovery of a Tetrahydroisoquinoline-Based Hydroxamic Acid Derivative (ZYJ-34c) as Histone Deacetylase Inhibitor with Potent Oral Antitumor Activities, J. Med. Chem., 54:5532-5539 (2011).
Zhang, Y. et al., Two Catalytic Domains Are Required for Protein Deacetylation, The Journal of Biological Chemistry, 281(5):2401-2404 (2006).
Marek, M. et al. Structural basis for the inhibition of histone deacetylase 8 (HDAC8), a key epigenetic player in the blood fluke *Schistosoma mansoni*, PLoS Pathog. 9(9): 1-15, e1003645 (2013).

3-ALKYL-4-AMIDO-BICYCLIC [4,5,0] HYDROXAMIC ACIDS AS HDAC INHIBITORS

CROSS-REFERENCE TO RELATED APPLICATIONS

This application is a divisional of U.S. application Ser. No. 16/219,648, filed Dec. 13, 2018, which is a divisional of U.S. application Ser. No. 15/013,814, filed Feb. 2, 2016, which claims the benefit of priority of U.S. Provisional Application No. 62/110,716, filed Feb. 2, 2015 and U.S. Provisional Application No. 62/205,438, filed Aug. 14, 2015, all of which are incorporated herein by reference in their entirety.

FIELD OF THE DISCLOSURE

The present disclosure relates to inhibitors of zinc-dependent histone deacetylases (HDACs) useful in the treatment of diseases or disorders associated with HDACs including cell proliferation diseases (e.g., cancer), neurological and inflammatory diseases. Specifically, this disclosure is concerned with compounds and compositions inhibiting HDACs, methods of treating diseases associated with HDACs, and methods of synthesizing these compounds.

BACKGROUND OF THE DISCLOSURE

Many members of the HDAC family require zinc (Zn) to function properly. For instance, the isozyme histone deacetylase 6 (HDAC6) is a zinc-dependent histone deacetylase that possesses histone deacetylase activity. Other family members include HDACs 1-5 and 7-11. (De Ruijter et al, *Biochem. J.* 2003. 370; 737-749).

HDAC6 is known to deacetylate and associate with α-tubulin, cortactin, heat shock protein 90, β-catenin, glucose-regulated protein 78 kDa, myosin heavy chain 9, heat shock cognate protein 70, and dnaJ homolog subfamily A member 1 (reviewed in Li et al, *FEBS J.* 2013, 280: 775-93; Zhang et al, *Protein Cell.* 2015, 6(1): 42-54). Diseases in which HDAC6 inhibition could have a potential benefit include cancer (reviewed in Aldana-Masangkay et al, *J. Biomed. Biotechnol.* 2011, 875824), specifically: multiple myeloma (Hideshima et al, *Proc. Natl. Acad. Sci. USA* 2005, 102(24):8567-8572); lung cancer (Kamemura et al, *Biochem. Biophys. Res. Commun.* 2008, 374(1):84-89); ovarian cancer (Bazzaro et al, *Clin. Cancer Res.* 2008, 14(22):7340-7347); breast cancer (Lee et al, *Cancer Res.* 2008, 68(18):7561-7569; Park et al, *Oncol. Rep.* 2011, 25: 1677-81; Rey et al, *Eur. J. Cell Biol.* 2011, 90: 128-35); prostate cancer (Seidel et al, *Biochem. Pharmacol.* 2015 (15)00714-5); pancreatic cancer (Nawrocki et al, *Cancer Res.* 2006, 66(7):3773-3781); renal cancer (Cha et al, *Clin. Cancer Res.* 2009, 15(3): 840-850); hepatocellular cancer (Ding et al, *FEBS Lett.* 2013, 587:880-6; Kanno et al, *Oncol. Rep.* 2012, 28: 867-73); lymphomas (Ding et al, *Cancer Cell Int.* 2014, 14:139; Amengual et al, *Clin Cancer Res.* 2015, 21(20):4663-75); and leukemias such as acute myeloid leukemia (AML) (Fiskus et al, *Blood* 2008, 112(7):2896-2905) and acute lymphoblastic leukemia (ALL) (Rodriguez-Gonzalez et al, *Blood* 2008, 112(11): Abstract 1923)).

Inhibition of HDAC6 may also have a role in cardiovascular disease, including pressure overload, chronic ischemia, and infarction-reperfusion injury (Tannous et al, *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Alzheimer's, Parkinson's and Huntington's disease (reviewed in Simoes-Pires et al, *Mol. Neurodegener.* 2013, 8: 7) or central nervous system trauma caused by tissue injury, oxidative-stress induced neuronal or axomal degeneration (Rivieccio et al, *Proc. Natl. Acad. Sci. USA* 2009, 106(46):19599-195604); and inflammation and autoimmune diseases through enhanced T cell-mediated immune tolerance at least in part through effects on regulatory T cells, including rheumatoid arthritis, psoriasis, spondylitis arthritis, psoriatic arthritis, multiple sclerosis, lupus, colitis and graft versus host disease (reviewed in Wang et al, *Nat. Rev. Drug Disc.* 2009 8(12):969-981; Vishwakarma et al, *Int. Immunopharmacol.* 2013, 16:72-8; Kalin et al, *J. Med. Chem.* 2012, 55:639-51); and fibrotic disease, including kidney fibrosis (Choi et al, *Vascul. Pharmacol.* 2015 72:130-140).

Four HDAC inhibitors are currently approved for the treatment of some cancers. These are suberanilohydroxamic acid (Vorinostat; Zolinza®) for the treatment of cutaneous T cell lymphoma and multiple myeloma; Romidepsin (FK228; FR901228; Istodax®) for the treatment of peripheral T cell lymphoma; Panobinostat (LBH-589; Farydak®) for the treatment of multiple myeloma; and belinostat (PXD101; Beleodaq®) for the treatment of peripheral T cell lymphoma. However, these drugs are of limited effectiveness and can give rise to unwanted side effects. Thus there is a need for drugs with an improved safety-efficacy profile.

Given the complex function of HDAC6 and their potential utility in the treatment of proliferative diseases, neurological diseases, and inflammatory diseases, there is a need for HDAC inhibitors (e.g., HDAC6 inhibitors) with good therapeutic properties.

SUMMARY OF THE DISCLOSURE

One aspect of the disclosure relates to compounds of Formula I:

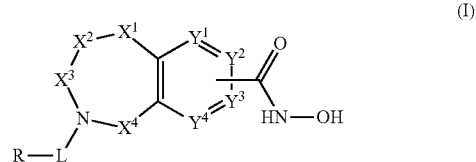

and pharmaceutically acceptable salts, prodrugs, solvates, hydrates, tautomers and isomers thereof, wherein:

$X^1$ is independently $CR^1R^2$, $NR^3$, O, or C=O;

$X^2$ and $X^4$ are each independently $CR^1R^2$, C=O, S(O) or $SO_2$;

$X^3$ is $CR^{1'}R^{2'}$;

wherein $X^4$, $X^2$, and $X^1$ are not all simultaneously $CR^1R^2$;

$Y^1$ and $Y^4$ are not bound to —C(O)NHOH and are each independently N or $CR^1$;

$Y^2$ and $Y^3$ are each independently N or $CR^1$ when not bonded to —C(O)NHOH and $Y^2$ and $Y^3$ are C when bonded to —C(O)NHOH;

L is —C(O)—, —C(O)$(CR^1R^2)_m$—, or —C(O)$(CR^1R^2)_m$O—, wherein L is bound to the ring nitrogen through the carbonyl group;

R is independently —H, —$C_1$-$C_6$ alkyl, —$C_2$-$C_6$ alkenyl, —$C_4$-$C_8$ cycloalkenyl, —$C_2$-$C_6$ alkynyl, —$C_3$-$C_8$ cycloalkyl, —$C_5$-$C_{12}$ spirocycle, heterocyclyl, spiroheterocyclyl, aryl, or heteroaryl containing 1-5 heteroatoms selected from the group consisting of N, S, P, and O, wherein each alkyl, alkenyl, cycloalkenyl, alkynyl, cycloalkyl, spirocycle, heterocyclyl, spiroheterocyclyl, aryl, or heteroaryl is optionally substituted with one or more —OH, halogen, oxo, —NO$_2$, —CN, —R$^1$, —R$^2$, —OR$^3$, —NHR$^3$, —NR$^3$R$^4$, —S(O)$_2$NR$^3$R$^4$, —S(O)$_2$R$^1$, —C(O)R$^1$, or —CO$_2$R$^1$, —NR$^3$S(O)$_2$R$^1$, —S(O)R$^1$, —S(O)NR$^3$R$^4$, —NR$^3$S(O)R$^1$, heterocycle, aryl, or heteroaryl containing 1-5 heteroatoms selected from the group consisting of N, S, P, and O, with the proviso that R is not bound to L via a nitrogen atom;

R$^1$ and R$^2$ are independently, at each occurrence, —H, —R$^3$, —R$^4$, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, or (CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more substituents selected from —OH, halogen, —NO$_2$, oxo, —CN, —R$^5$, —OR$^3$, —NHR$^3$, NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl containing 1-5 heteroatoms selected from the group consisting of N, S, P, and O;

or R$^1$ and R$^2$ can combine with the carbon atom to which they are both attached to form a spirocycle, spiroheterocycle, or a spirocycloalkenyl;

or R$^1$ and R$^2$, when on adjacent atoms, can combine to form a heterocycle, cycloalkyl, aryl, heteroaryl containing 1-5 heteroatoms selected from the group consisting of N, S, P, and O, or cycloalkenyl;

or R$^1$ and R$^2$, when on non-adjacent atoms, can combine to form a bridging cycloalkyl or heterocycloalkyl;

R$^{1'}$ and R$^{2'}$ are independently, at each occurrence, —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, or (CHR$^5$)$_n$NR$^3$R$^4$, wherein each alkyl, alkenyl, cycloalkenyl, alkynyl, cycloalkyl, or heterocyclyl is optionally substituted with one or more substituents selected from —OH, halogen, —NO$_2$, oxo, —CN, —R$^5$, —OR$^3$, —NHR$^3$, —NR$^3$R$^4$, —S(O)$_2$N(R$^3$)$_2$—, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocycle, aryl, or heteroaryl containing 1-5 heteroatoms selected from the group consisting of N, S, P, and O;

or R$^{1'}$ and R$^{2'}$ can combine with the carbon atom to which they are both attached to form a spirocycle, spiroheterocycle, or a spirocycloalkenyl;

or R$^{1'}$ and R$^{2'}$ can combine with R$^1$ or R$^2$ on adjacent atoms to form a heterocycle, cycloalkyl, aryl, heteroaryl containing 1-5 heteroatoms selected from the group consisting of N, S, P, and O, or cycloalkenyl;

or R$^{1'}$ and R$^{2'}$ can combine with R$^1$ or R$^2$ on non-adjacent atoms, to form a bridging cycloalkyl or heterocycloalkyl;

R$^3$ and R$^4$ are independently, at each occurrence, —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —S(O)$_2$N(C$_1$-C$_6$ alkyl)$_2$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, or —(CHR$^5$)$_n$N(C$_1$-C$_6$ alkyl)$_2$, wherein each alkyl, alkenyl, cycloalkenyl, alkynyl, cycloalkyl, heterocyclyl, aryl, and heteroaryl is optionally substituted with one or more substituents selected from —OH, halogen, —NO$_2$, oxo, —CN, —R$^5$, —O(C$_1$-C$_6$ alkyl), —NH(C$_1$-C$_6$ alkyl), N(C$_1$-C$_6$ alkyl)$_2$, —S(O)$_2$N(C$_1$-C$_6$ alkyl)$_2$, —S(O)$_2$NHC$_1$-C$_6$ alkyl, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, —S(O)R$^5$, —S(O)N(C$_1$-C$_6$ alkyl)$_2$, —N(C$_1$-C$_6$ alkyl)S(O)R$^5$, heterocycle, aryl, or heteroaryl containing 1-5 heteroatoms selected from the group consisting of N, S, P, and O;

R$^5$ is independently, at each occurrence, —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —OH, halogen, —NO$_2$, —CN, —NH(C$_1$-C$_6$ alkyl), —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —CO$_2$C$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, —N(C$_1$-C$_6$ alkyl)S(O)(C$_1$-C$_6$ alkyl) or —(CH$_2$)$_n$N(C$_1$-C$_6$ alkyl)$_2$;

each n is independently and at each occurrence an integer from 0 to 6; and each m is independently and at each occurrence an integer from 1 to 6; and provided that when X$^2$ and X$^4$ are both C═O, X$^1$ is not NR$^3$.

Another aspect of the disclosure relates to a method of treating a disease or disorder associated with HDAC, e.g., HDAC6 modulation in a subject in need thereof, comprising administering to the subject an effective amount of a compound of Formula I.

Another aspect of the disclosure is directed to a method of inhibiting an HDAC, e.g., HDAC6. The method involves administering to a patient in need thereof an effective amount of a compound of Formula I.

Another aspect of the disclosure relates to a compound of Formula I, or a pharmaceutically acceptable salt, prodrug, solvate, hydrate, tautomer, or isomer thereof, for use in treating or preventing a disease associated with HDAC6 modulation.

Another aspect of the disclosure relates to the use of a compound of Formula I, or a pharmaceutically acceptable salt, prodrug, solvate, hydrate, tautomer, or isomer thereof, in the manufacture of a medicament for treating or preventing a disease associated with HDAC6 modulation.

Another aspect of the disclosure is directed to pharmaceutical compositions comprising a compound of Formula I and a pharmaceutically acceptable carrier. The pharmaceutically acceptable carrier can further include an excipient, diluent, or surfactant. The pharmaceutical composition can be effective for treating a disease or disorder associated with HDAC, e.g., HDAC6 modulation in a subject in need thereof. The pharmaceutical compositions can comprise the compounds of the present disclosure for use in treating diseases described herein. The compositions can contain at least one compound of the disclosure and a pharmaceutically acceptable carrier. The disclosure also provides the use of the compounds described herein in the manufacture of a medicament for the treatment of a disease associated with HDACs.

The present disclosure also provides methods for the treatment of human diseases or disorders including, without limitation, oncological, neurological, inflammatory, autoimmune, infectious, metabolic, hematologic, or cardiovascular diseases or disorders.

The present disclosure also provides compounds that are useful in inhibiting of zinc-dependent HDAC enzymes, for instance HDAC6. These compounds can also be useful in the treatment of diseases including cancer.

The present disclosure further provides compounds that can inhibit an HDAC, e.g., HDAC6. In some embodiments, the efficacy-safety profile of the compounds of the current disclosure can be improved relative to other known HDAC (e.g. HDAC6) inhibitors. Additionally, the present technology also has the advantage of being able to be used for a number of different types of diseases, including cancer and non-cancer indications. Additional features and advantages of the present technology will be apparent to one of skill in the art upon reading the Detailed Description of the Disclosure, below.

DETAILED DESCRIPTION OF THE DISCLOSURE

HDAC6 is a zinc-dependent histone deacetylase that has two catalytic domains. HDAC6 can interact with and deacetylate non-histone proteins, including HSP90 and α-tubulin. Acetylation of HSP90 is associated with loss of function of HSP90. HDAC6 is also implicated in the degradation of misfolded proteins as part of the aggresome. Accordingly, inhibition of HDAC6 can have downstream effects that can play a role in the development of certain diseases such as cancer. The present disclosure provides inhibitors of an HDAC, e.g., HDAC6 and methods for using the same to treat disease.

In a first aspect of the disclosure, compounds of the Formula I are described:

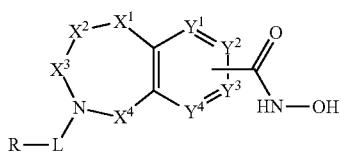

(I)

and pharmaceutically acceptable salts, prodrugs, solvates, hydrates, tautomers, and isomers thereof, wherein R, L, $X^1$, $X^2$, $X^3$, $X^4$, $Y^1$, $Y^2$, $Y^3$, and $Y^4$ are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Definitions

The articles "a" and "an" are used in this disclosure to refer to one or more than one (e.g., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (e.g. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$ alkyl, —$C_1$-$C_6$ alkyl, —O$C_2$-$C_6$ alkenyl, —O$C_2$-$C_6$ alkynyl, —$C_2$-$C_6$ alkenyl, —$C_2$-$C_6$ alkynyl, —OH, —OP(O)(OH)$_2$, —OC(O)$C_1$-$C_6$ alkyl, —C(O)$C_1$-$C_6$ alkyl, —OC(O)O$C_1$-$C_6$ alkyl, —NH$_2$, —NH($C_1$-$C_6$ alkyl), —N($C_1$-$C_6$ alkyl)$_2$, —S(O)$_2$—$C_1$-$C_6$ alkyl, —S(O)NH$C_1$-$C_6$ alkyl, and —S(O)N($C_1$-$C_6$ alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]

thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

"Alkyl" refers to a straight or branched chain saturated hydrocarbon. $C_1$-$C_6$ alkyl groups contain 1 to 6 carbon atoms. Examples of a $C_1$-$C_6$ alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Alkenyl groups can have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Alkynyl groups can have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 3-18 carbon atoms. Examples of cycloalkenyl groups include, without limitation, cyclopentenyl, cyclohexenyl, cycloheptenyl, cyclooctenyl, and norborenyl. A $C_3$-$C_8$ cycloalkenyl is a cycloalkenyl group containing between 3 and 8 carbon atoms.

The terms "heterocyclyl" or "heterocycloalkyl" or "heterocycle" refer to monocyclic or polycyclic 3 to 24-membered rings containing carbon and heteroatoms taken from oxygen, nitrogen, or sulfur and wherein there is not delocalized π electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring.

As used herein, the term "halo" or "halogen" means fluoro, chloro, bromo, or iodo.

The term "carbonyl" refers to a functional group composing a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A $C_3$-$C_{12}$ spirocycle is a spirocycle containing between 3 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. In some cases these diastereomers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (e.g., using an enzyme).

The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

In another embodiment of the disclosure are described compounds of the Formula IA:

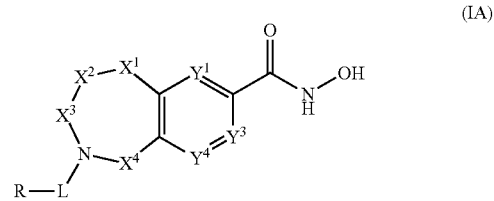

(IA)

and pharmaceutically acceptable salts, prodrugs, solvates, hydrates, tautomers or isomer thereof; where R, L, $X^1$, $X^2$, $X^3$, $X^4$, $Y^1$, $Y^3$, and $Y^4$ are defined as above in Formula I.

In one embodiment of the compounds of Formula IA, $X^4$ is $CR^1R^2$.

In another embodiment of the compounds of Formula IA, $X^1$ is $NR^3$, O, or C=O.

In another embodiment of the compounds of Formula IA, $X^1$ is O.

In another embodiment of the compounds of Formula IA, $X^1$ is O and $X^4$ is $CR^1R^2$.

In some embodiments of the disclosure, the compounds of Formula IA may be of the Formula IA-1:

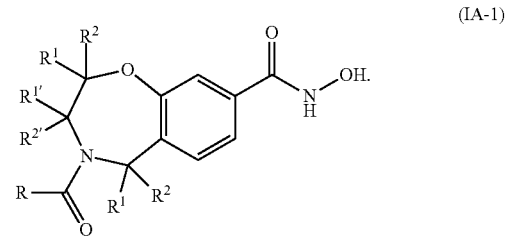

(IA-1)

For instance, in some embodiments of Formula IA-1, the compounds can be of the Formula IA-1a, Formula IA-1b, Formula IA-1c, Formula IA-1d, Formula IA-1e, or Formula IA-1f:

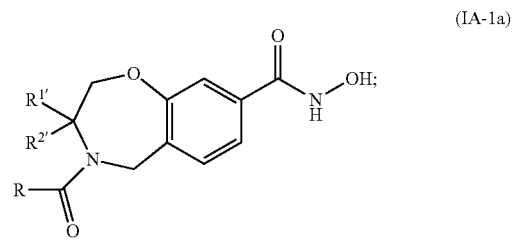

(IA-1a)

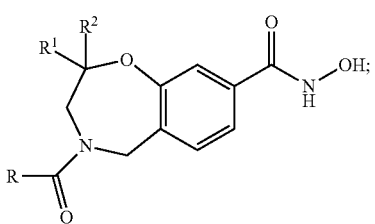
(IA-1b)

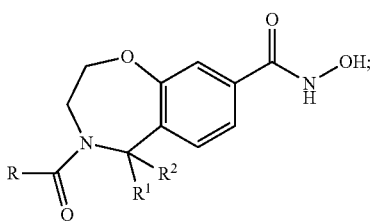
(IA-1c)

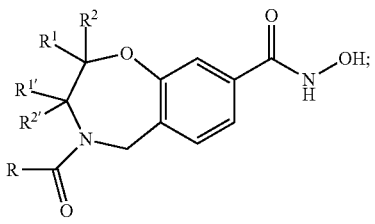
(IA-1d)

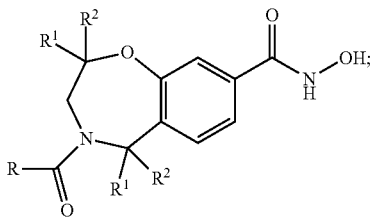
(IA-1e)

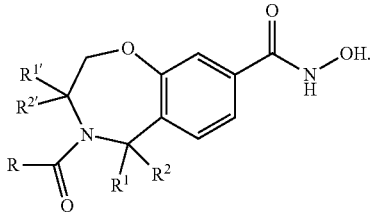
(IA-1f)

In other embodiments of the compounds of Formula IA, the compound is of the Formula IA-2:

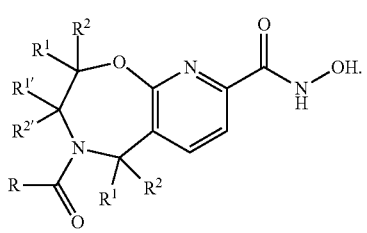
(IA-2)

In yet another embodiments of the compounds of Formula IA, the compound is of the Formula IA-3:

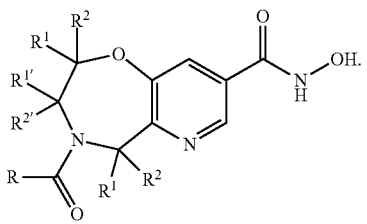
(IA-3)

In yet other embodiments of the compounds of Formula IA, the compound is of the Formula IA-4:

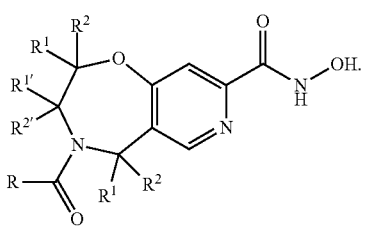
(IA-4)

In yet other another embodiments of the compounds of Formula IA, the compound is of the Formula IA-5:

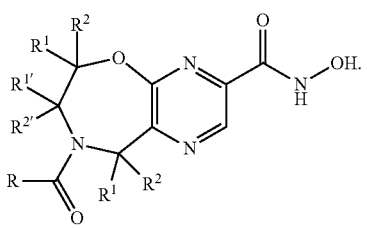
(IA-5)

In yet other another embodiments of the compounds of Formula IA, the compound is of the Formula IA-6:

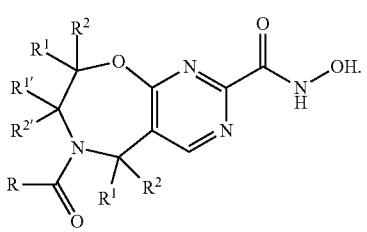
(IA-6)

In yet other another embodiments of the compounds of Formula IA, the compound is of the Formula IA-7:

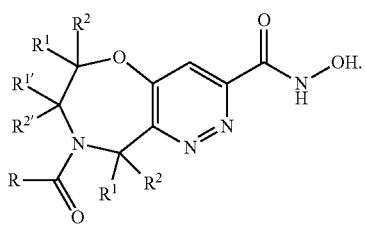

(IA-7)

In other embodiments of the compounds of Formula IA, the compound is of the Formula IA-8:

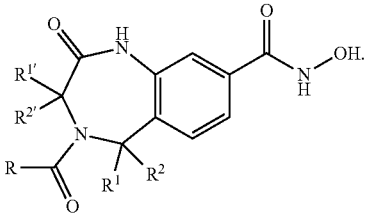

(IA-8)

In a further embodiment of the compounds of Formula IA, the compound is also of the Formula IA-9:

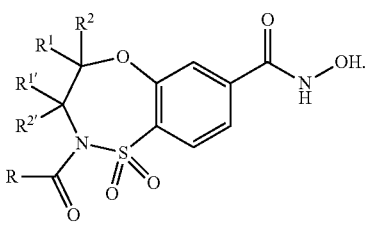

(IA-9)

In another embodiment of the compounds of Formula IA, the compound is of the Formula IA-10:

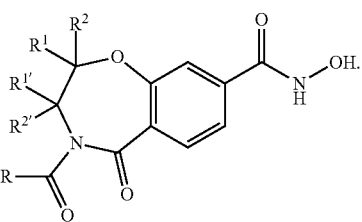

(IA-10)

In another embodiment of the compounds of Formula IA, the compound is of the Formula IA-11:

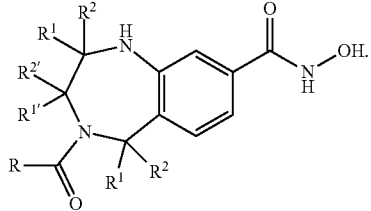

(IA-11)

In one embodiment of the disclosure are also disclosed compounds of the Formula IB:

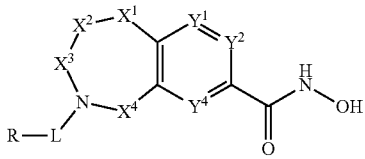

(IB)

and pharmaceutically acceptable salts, prodrugs, solvates, hydrates, enantiomers and isomers thereof where R, L, $X^1$, $X^2$, $X^3$, $X^4$, $Y^1$, $Y^2$, and $Y^4$ are defined as above in Formula I.

In one embodiment of the compounds of Formula IB, $X^4$ is $CR^1R^2$.

In another embodiment of the compounds of Formula IB, $X^1$ is $NR^3$, O, or C=O.

In another embodiment of the compounds of Formula IB, $X^1$ is O.

In another embodiment of the compounds of Formula IB, $X^1$ is O and $X^4$ is $CR^1R^2$.

In another embodiment of the compounds of Formula IB, $X^1$ is N, $X^2$ is C=O, and $X^4$ is $CR^1R^2$.

In some embodiments of the disclosure, the compounds of Formula IB, may be of the Formula IB-1:

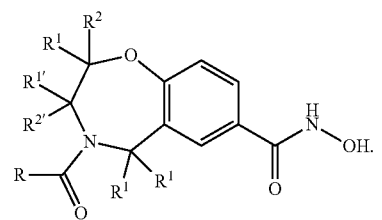

(IB-1)

In yet other embodiments of the compounds of Formula IB, the compound is of the Formula (IB-2):

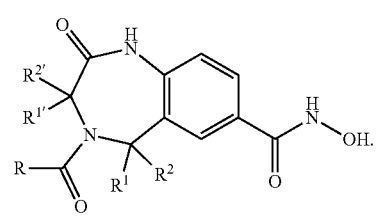

(IB-2)

For instance, in some embodiments, the compounds of the disclosure can be of the Formula IB-2a:

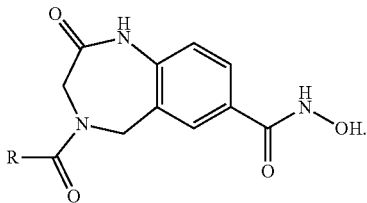

(IB-2a)

In other embodiments of the compounds of Formula IB, the compound may also be of the Formula IB-3:

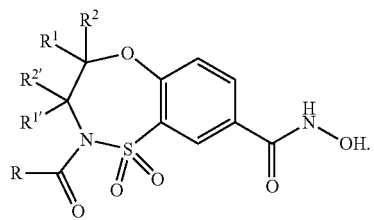

(IB-3)

In other embodiments of the compounds of Formula IB, the compound is of the Formula (IB-4):

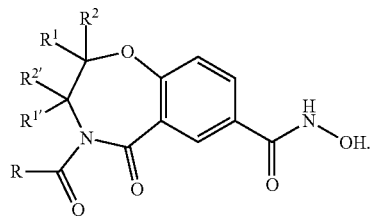

(IB-4)

In a further embodiment of the compounds of Formula IB, the compound is also of the Formula IB-5:

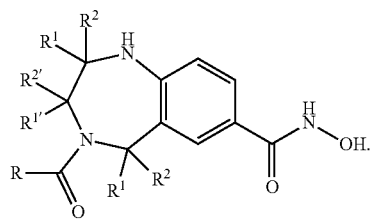

(IB-5)

In some embodiments of Formula (I), $X^1$ is O. In another embodiment, $X^1$ is O and $X^2$ is $CR^1R^2$. In yet another embodiment, $X^1$ is O, $X^2$ is $CR^1R^2$, and $X^3$ is $CR^{1'}R^{2'}$. In another embodiment, $X^1$ is O, $X^2$ is $CR^1R^2$, $X^3$ is $CR^{1'}R^{2'}$, and $X^4$ is $CR^1R^2$. In yet another embodiment, $X^1$ is O, $X^2$ is $CR^1R^2$, $X^3$ is $CR^{1'}R^{2'}$, $X^4$ is $CR^1R^2$, and $Y^1$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, and $Y^3$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, and $Y^2$ is C. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)($CR^1R^2$)$_m$—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)($CR^1R^2$)$_m$O—. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, and $Y^3$ is C. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, and $Y^2$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)($CR^1R^2$)$_m$—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)($CR^1R^2$)$_m$O—. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In some embodiments of Formula (I), $X^1$ is $NR^3$. In another embodiment, $X^1$ is $NR^3$ and $X^2$ is C=O. In yet another embodiment, $X^1$ is $NR^3$, $X^2$ is C=O, and $X^3$ is $CR^{1'}R^{2'}$. In another embodiment, $X^1$ is $NR^3$, $X^2$ is C=O, $X^3$ is $CR^{1'}R^{2'}$, and $X^4$ is $CR^1R^2$. In yet another embodiment, $X^1$ is $NR^3$, $X^2$ is C=O, $X^3$ is $CR^{1'}R^{2'}$, $X^4$ is $CR^1R^2$, and $Y^1$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is $CR^1$, and $Y^3$ is $CR^1$. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, and $Y^4$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, and $Y^2$ is C. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)—, and $R^1$ is H or —$C_1$-$C_6$ alkyl. In another embodiment $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)($CR^1R^2$)$_m$—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, and L is —C(O)($CR^1R^2$)$_m$O—. In another embodiment. $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is $CR^1$, $Y^4$ is $CR^1$, $Y^2$ is C, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is $CR^1$, and $Y^3$ is C. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, and $Y^4$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, and $Y^2$ is $CR^1$. In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)—, and $R^1$ is H or —$C_1$-$C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)($CR^1R^2$)$_m$—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, and L is —C(O)($CR^1R^2$)$_m$O—. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is $CR^1$, $Y^3$ is C, $Y^4$ is $CR^1$, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^{1'}R^{2'}$, $X^4$ is $CR^1R^2$, and $Y^1$ is N. In another embodiment, $X^1$ is O, $X^2$ is $CR^1R^2$, $X^3$ is $CR^{1'}R^{2'}$, $X^4$ is $CR^1R^2$, $Y^1$ is N, and $Y^3$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, and $Y^2$ is C. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)—. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)($CR^1R^2$)$_m$—. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is —C(O)($CR^1R^2$)$_m$O—. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is N, and $Y^3$ is C. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, and $Y^4$ is $CR^1$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, and $Y^2$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is —C(O)—. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is —C(O)—, and $R^1$ is H or —$C_1$-$C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is —C(O)—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is $-C(O)(CR^1R^2)_m-$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)(CR^1R^2)_m-$, and $R^1$ is H or $-C_1-C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $N^1$, $Y^3$ is C, $Y^4$ is $CR^1$, $Y^2$ is $CR^1$, L is $-C(O)(CR^1R^2)_m-$, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is $-C(O)(CR^1R^2)_mO-$. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)(CR^1R^2)_mO-$, and $R^1$ is H or $-C_1-C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)(CR^1R^2)_mO-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, and $Y^1$ is N. In another embodiment, $X^1$ is $NR^3$, $X^2$ is C=O, $X^3$ is $CR^{1'}R^{2'}$, $X^4$ is $CR^1R^2$, $Y^1$ is N, and $Y^3$ is $CR^1$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, and $Y^4$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, and $Y^2$ is C. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is $-C(O)-$. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is $-C(O)(CR^1R^2)_m-$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)(CR^1R^2)_m-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)(CR^1R^2)_m-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, and L is $-C(O)(CR^1R^2)_mO-$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)(CR^1R^2)_mO-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is $CR^1$, $Y^4$ is $CR^1$, $Y^2$ is C, L is $-C(O)(CR^1R^2)_mO-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is N, and $Y^3$ is C. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, and $Y^4$ is $CR^1$. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, and $Y^2$ is $CR^1$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is $-C(O)-$. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is $-C(O)(CR^1R^2)_m-$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, $L$ is $-C(O)(CR^1R^2)_m-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, $L$ is $-C(O)(CR^1R^2)_m-$, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, and L is $-C(O)(CR^1R^2)_mO-$. In yet another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)(CR^1R^2)_mO-$, and $R^1$ is H or $-C_1-C_6$ alkyl. In another embodiment, $X^1$ is $NR^3$, $X^2$ is C=O, $X^3$ is $CR^{1'}R^{2'}$, $X^4$ is $CR^1R^2$, $Y^1$ is N, $Y^3$ is C, $Y^4$ is $CR^1$, $Y^2$ is $CR^1$, L is $-C(O)(CR^1R^2)_mO-$, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, and $Y^4$ is N. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, and $Y^2$ is C. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is $-C(O)-$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)-$, and $R^1$ is H or $-C_1-C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)-$, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is $-C(O)(CR^1R^2)_m-$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)(CR^1R^2)_m-$, and $R^1$ is H or $-C_1-C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)(CR^1R^2)_m-$, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, and L is $-C(O)(CR^1R^2)_mO-$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)(CR^1R^2)_mO-$, and $R^1$ is H or $-C_1-C_6$ alkyl. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is $CR^1$, $Y^4$ is N, $Y^2$ is C, L is $-C(O)(CR^1R^2)_mO-$, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, and $Y^4$ is N. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, and $Y^2$ is $CR^1$. In yet another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, and L is $-C(O)-$. In another embodiment, $X^1$ is O, $X^2$ is $CR^1R^2$, $X^3$ is $CR^{1'}R^{2'}$, $X^4$ is $CR^1R^2$, $Y^1$ is $CR^1$, $Y^3$ is C, $Y^4$ is N, $Y^2$ is $CR^1$, L is —C(O)—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)($CR^1R^2$)$_m$—. In another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)($CR^1R^2$)$_m$O—. In another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, and $Y^4$ is N. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, and $Y^2$ is C. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —C(O)—. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —C(O)($CR^1R^2$)$_m$—. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, and L is —C(O)($CR^1R^2$)$_m$O—. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is $CR^1$, $Y^4$ is N, $Y^2$ is C, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, and $Y^4$ is N. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, and $Y^2$ is $CR^1$. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)—. In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)($CR^1R^2$)$_m$—. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In yet another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, and L is —C(O)($CR^1R^2$)$_m$O—. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is $CR^1$, $Y^3$ is C, $Y^4$ is N, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, and $Y^4$ is N. In yet another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, and $Y^2$ is C. In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)—. In yet another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)($CR^1R^2$)$_m$—. In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is $N^1$, $Y^3$ is $CR^1$, $Y^4$ is N, $Y^2$ is C, L is —C(O)($CR^1R^2$)$_m$—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)($CR^1R^2$)$_m$O—. In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, and $Y^4$ is N. In yet another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, and $Y^2$ is $CR^1$. In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)—. In yet another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)—, and $R^1$ is H or —$C_1$-$C_6$ alkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)($CR^1R^2$)$_m$—. In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is $N^1$, $Y^3$ is C, $Y^4$ is N, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)($CR^1R^2$)$_m$O—. In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$O—, and $R^1$ is H or —$C_1$-$C_6$ alkyl. In another embodiment, $X^1$ is O, $X^2$ is $CR^1R^2$, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, and $Y^4$ is N. In yet another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, and $Y^2$ is C. In yet another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)—. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)($CR^1R^2$)$_m$—. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, and L is —C(O)($CR^1R^2$)$_m$O—. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is $CR^1$, $Y^4$ is N, $Y^2$ is C, L is —C(O)($CR^1R^2$)$_m$O—, and $R^1$ and $R^2$, when on non-adjacent atoms, combine to form a bridging cycloalkyl or heterocycloalkyl In another embodiment, $X^1$ is $NR^3$, $X^2$ is C=O, $X^3$ is $CR^1R^{2'}$, $X^4$ is $CR^1R^2$, $Y^1$ is N, $Y^3$ is C, and $Y^4$ is N. In yet another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, and $Y^2$ is $CR^1$. In yet another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)—. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)($CR^1R^2$)$_m$—. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$—, and $R^1$ and $R^2$, when on non-adjacent atoms, combine to form a bridging cycloalkyl or heterocycloalkyl.

In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, and L is —C(O)($CR^1R^2$)$_m$O—. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$O—, and $R^1$ is H or —$C_1$-$C_6$ alkyl. In another embodiment, $X^1$ is $NR^3$, $X^2$ is C=O, $X^3$ is $CR^1R^{2'}$, $X^4$ is $CR^1R^2$, $Y^1$ is N, $Y^3$ is C, $Y^4$ is N, $Y^2$ is $CR^1$, L is —C(O)($CR^1R^2$)$_m$O—, and $R^1$ and $R^2$, when on non-adjacent atoms, combine to form a bridging cycloalkyl or heterocycloalkyl.

In some embodiments of Formula (I), $X^2$ is $CR^1R^2$; is —H, or —$C_1$-$C_6$ alkyl; and $R^2$ is —H, —$R^3$, aryl, or —$C_1$-$C_6$ alkyl optionally substituted with one or more substituents selected from oxo, —$OR^3$, and —$NR^3R^4$.

In some embodiments of Formula (I), $X^3$ is $CR^{1'}R^{2'}$; $R^{1'}$ is —H, or —$C_1$-$C_6$ alkyl; and $R^{2'}$ is —H, heterocyclyl, or —$C_1$-$C_6$ alkyl optionally substituted with one or more substituents selected from halogen, aryl, and —$OR^3$.

In some embodiments of Formula (I), $R^1$ and $R^2$ combine with the atom to which they are both attached to form a spirocycle. In another embodiment, $R^1$ and $R^2$ combine with the atom to which they are both attached to form a spiroheterocycle. In another embodiment, $R^1$ and $R^2$ combine with the atom to which they are both attached to form a spirocycloalkenyl.

In some embodiments of Formula (I), $R^1$ and $R^2$, when on adjacent atoms, combine to form a heterocycle. In another embodiment, $R^1$ and $R^2$, when on adjacent atoms, combine to form a cycloalkyl. In yet another embodiment, $R^1$ and $R^2$, when on adjacent atoms, combine to form a cycloalkenyl. In another embodiment, $R^1$ and $R^2$, when on adjacent atoms, combine to form an aryl. In yet another embodiment, $R^1$ and $R^2$, when on adjacent atoms, combine to form a heteroaryl containing 1 to 5 heteroatoms selected from the group consisting of N, S, P, and O.

In some embodiments of Formula (I), $R^1$ and $R^2$, when on non-adjacent atoms, combine to form a bridging cycloalkyl. In another embodiment, $R^1$ and $R^2$, when on non-adjacent atoms, combine to form a bridging cycloalkenyl. In yet another embodiment, $R^1$ and $R^2$, when on non-adjacent atoms, combine to form a heterocycloalkyl.

In some embodiments of Formula (I), $R^{1'}$ and $R^{2'}$ combine with the carbon atom to which they are both attached to form a spirocycle. In another embodiment, $R^{1'}$ and $R^{2'}$ combine with the carbon atom to which they are both attached to form a spiroheterocycle. In yet another embodiment, $R^{1'}$ and $R^{2'}$ combine with the carbon atom to which they are both attached to form a spirocycloalkenyl.

In some embodiments of Formula (I), $R^{1'}$ and $R^{2'}$ combine with $R^1$ or $R^2$ on adjacent atoms to form a heterocycle. In another embodiment, $R^{1'}$ and $R^{2'}$ combine with $R^1$ or $R^2$ on adjacent atoms to form a cycloalkyl. In yet another embodiment, $R^{1'}$ and $R^{2'}$ combine with $R^1$ or $R^2$ on adjacent atoms to form an aryl. In another embodiment, $R^{1'}$ and $R^{2'}$ combine with R¹ or R² on adjacent atoms to form a heteroaryl containing 1-5 heteroatoms selected from the group consisting of N, S, P, or O. In another embodiment, R¹' and R²' combine with R¹ or R² on adjacent atoms to form a cycloalkenyl.

In some embodiments of Formula (I), R¹' and R²' combine with R¹ or R² on non-adjacent atoms, to form a bridging cycloalkyl. In another embodiment, R¹' and R²' combine with R¹ or R² on non-adjacent atoms, to form a bridging heterocycloalkyl.

In some embodiments of Formula (I), n is 1 to 6. In another embodiment, n is 0 to 5. In yet another embodiment, n is 0 to 4. In yet another embodiment, n is 1 to 4. In another embodiment, n is 0 to 3. In yet another embodiment, n is 0 to 2. In yet another embodiment, n is 0 or 1. In another embodiment, n is 1 or 2.

In some embodiments of Formula (I), m is 1 to 6. In another embodiment, m is 1 to 5. In yet another embodiment, m is 1 to 4. In yet another embodiment, m is 1 to 3. In another embodiment, m is 1 or 2. In yet another embodiment, m is 2 or 3. In yet another embodiment, m is 2 to 4.

In some embodiments of Formula (I), $X^4$, $X^2$, and $X^1$ are not all simultaneously $CR^1R^2$.

In some embodiments of Formula (I), $X^1$ is O, $X^2$ is $CR^1R^2$, and $X^4$ is $CR^1R^2$. In another embodiment, $X^2$ is C=O, $X^4$ is C=O, and $X^1$ is $CR^1R^2$. In yet another embodiment, $X^1$ is $NR^3$, $X^2$ is C=O, and $X^4$ is $CR^1R^2$.

In an illustrative embodiment, the compound of Formula I is:

4-(2,2-dimethyltetrahydro-2H-pyran-4-carbonyl)-N-hydroxy-2,3,4,5-tetrahydrobenzo[f][1,4]oxazepine-8-carboxamide;
N-hydroxy-4-(2-methyl-2-(pyridin-2-yl)propanoyl)-2,3,4,5-tetrahydrobenzo[f][1,4]oxazepine-8-carboxamide;
4-(2,6-dimethylbenzoyl)-N-hydroxy-2,3,4,5-tetrahydrobenzo[f][1,4]oxazepine-8-carboxamide
N-hydroxy-4-(3-methoxy-2,2-dimethylpropanoyl)-2,3,4,5-tetrahydrobenzo[f][1,4]oxazepine-8-carboxamide;
4-(8-oxabicyclo[3.2.1]octane-3-carbonyl)-N-hydroxy-2,3,4,5-tetrahydrobenzo[f][1,4]oxazepine-8-carboxamide;
N-hydroxy-4-(3-(propylamino)benzo[b]thiophene-2-carbonyl)-2,3,4,5-tetrahydrobenzo[f][1,4]oxazepine-8-carboxamide;
4-(3-(dimethylamino)benzo[b]thiophene-2-carbonyl)-N-hydroxy-2,3,4,5-tetrahydrobenzo[f][1,4]oxazepine-8-carboxamide;
tert-butyl 7-(8-(hydroxycarbamoyl)-2,3,4,5-tetrahydrobenzo[f][1,4]oxazepine-4-carbonyl)-5-oxa-2-azaspiro[3.4]octane-2-carboxylate;
tert-butyl 7-(8-(hydroxycarbamoyl)-2,3,4,5-tetrahydrobenzo[f][1,4]oxazepine-4-carbonyl)-5-thia-2-azaspiro[3.4]octane-2-carboxylate 5,5-dioxide;
(S)—N-hydroxy-4-(tetrahydro-2H-pyran-3-carbonyl)-2,3,4,5-tetrahydrobenzo[f][1,4]oxazepine-8-carboxamide;
(R)—N-hydroxy-4-(tetrahydro-2H-pyran-3-carbonyl)-2,3,4,5-tetrahydrobenzo[f][1,4]oxazepine-8-carboxamide;
(R)—N-hydroxy-4-(tetrahydrofuran-3-carbonyl)-2,3,4,5-tetrahydrobenzo[f][1,4]oxazepine-8-carboxamide;
(S)—N-hydroxy-4-(tetrahydrofuran-3-carbonyl)-2,3,4,5-tetrahydrobenzo[f][1,4]oxazepine-8-carboxamide;
4-benzoyl-N-hydroxy-2,3,4,5-tetrahydrobenzo[f][1,4]oxazepine-8-carboxamide;
N-hydroxy-4-pivaloyl-2,3,4,5-tetrahydrobenzo[f][1,4]oxazepine-8-carboxamide;
4-acetyl-N-hydroxy-2,3,4,5-tetrahydrobenzo[f][1,4]oxazepine-8-carboxamide;
4-formyl-N-hydroxy-2,3,4,5-tetrahydrobenzo[f][1,4]oxazepine-8-carboxamide;
tert-butyl 3-(8-(hydroxycarbamoyl)-2,3,4,5-tetrahydrobenzo[f][1,4]oxazepine-4-carbonyl)-3H-spiro[isobenzofuran-1,4'-piperidine]-1'-carboxylate;
N-hydroxy-4-(8-azaspiro[4.5]decane-2-carbonyl)-2,3,4,5-tetrahydrobenzo[f][1,4]oxazepine-8-carboxamide;
tert-butyl 8-(8-(hydroxycarbamoyl)-2,3,4,5-tetrahydrobenzo[f][1,4]oxazepine-4-carbonyl)-2-azaspiro[4.5]decane-2-carboxylate;
N-hydroxy-4-(2-azaspiro[4.5]decane-8-carbonyl)-2,3,4,5-tetrahydrobenzo[f][1,4]oxazepine-8-carboxamide;
tert-butyl 6-(8-(hydroxycarbamoyl)-2,3,4,5-tetrahydrobenzo[f][1,4]oxazepine-4-carbonyl)-2-azaspiro[4.4]nonane-2-carboxylate;
N-hydroxy-4-(2-azaspiro[4.4]nonane-6-carbonyl)-2,3,4,5-tetrahydrobenzo[f][1,4]oxazepine-8-carboxamide;
N-hydroxy-4-(3H-spiro[isobenzofuran-1,4'-piperidine]-3-carbonyl)-2,3,4,5-tetrahydrobenzo[f][1,4]oxazepine-8-carboxamide;
tert-butyl 2-(8-(hydroxycarbamoyl)-2,3,4,5-tetrahydrobenzo[f][1,4]oxazepine-4-carbonyl)-2H-spiro[benzofuran-3,4'-piperidine]-1'-carboxylate;
N-hydroxy-4-(2H-spiro[benzofuran-3,4'-piperidine]-2-carbonyl)-2,3,4,5-tetrahydrobenzo[f][1,4]oxazepine-8-carboxamide;
tert-butyl 3-(8-(hydroxycarbamoyl)-2,3,4,5-tetrahydrobenzo[f][1,4]oxazepine-4-carbonyl)-2,3-dihydrospiro[indene-1,4'-piperidine]-1'-carboxylate;
4-(2,3-dihydrospiro[indene-1,4'-piperidine]-3-carbonyl)-N-hydroxy-2,3,4,5-tetrahydrobenzo[f][1,4]oxazepine-8-carboxamide;
tert-butyl 9-(8-(hydroxycarbamoyl)-2,3,4,5-tetrahydrobenzo[f][1,4]oxazepine-4-carbonyl)-3-azaspiro[5.5]undecane-3-carboxylate;
tert-butyl 2-(8-(hydroxycarbamoyl)-2,3,4,5-tetrahydrobenzo[f][1,4]oxazepine-4-carbonyl)-8-azaspiro[4.5]decane-8-carboxylate;
N-hydroxy-4-(3-azaspiro[5.5]undecane-9-carbonyl)-2,3,4,5-tetrahydrobenzo[f][1,4]oxazepine-8-carboxamide;
N-hydroxy-4-(5-azaspiro[2.5]octane-1-carbonyl)-2,3,4,5-tetrahydrobenzo[f][1,4]oxazepine-8-carboxamide;
N-hydroxy-4-(5-azaspiro[2.4]heptane-1-carbonyl)-2,3,4,5-tetrahydrobenzo[f][1,4]oxazepine-8-carboxamide;
N-hydroxy-4-(6-azaspiro[2.5]octane-1-carbonyl)-2,3,4,5-tetrahydrobenzo[f][1,4]oxazepine-8-carboxamide;
tert-butyl 1-(8-(hydroxycarbamoyl)-2,3,4,5-tetrahydrobenzo[f][1,4]oxazepine-4-carbonyl)-6-azaspiro[2.5]octane-6-carboxylate;
(R)—N-hydroxy-2-methyl-4-(1-methylcyclobutane-1-carbonyl)-2,3,4,5-tetrahydrobenzo[f][1,4]oxazepine-8-carboxamide;
(R)-4-formyl-N-hydroxy-2-methyl-2,3,4,5-tetrahydrobenzo[f][1,4]oxazepine-8-carboxamide;
(R)-4-acetyl-N-hydroxy-2-methyl-2,3,4,5-tetrahydrobenzo[f][1,4]oxazepine-8-carboxamide;
(S)-4-acetyl-N-hydroxy-2-methyl-2,3,4,5-tetrahydrobenzo[f][1,4]oxazepine-8-carboxamide;
(S)—N-hydroxy-2-methyl-4-(1-methylcyclobutane-1-carbonyl)-2,3,4,5-tetrahydrobenzo[f][1,4]oxazepine-8-carboxamide;
(S)-4-formyl-N-hydroxy-2-methyl-2,3,4,5-tetrahydrobenzo[f][1,4]oxazepine-8-carboxamide;
N-hydroxy-3,3-dimethyl-4-(1-methylcyclobutane-1-carbonyl)-2,3,4,5-tetrahydrobenzo[f][1,4]oxazepine-8-carboxamide;

4-acetyl-N-hydroxy-3,3-dimethyl-2,3,4,5-tetrahydrobenzo[f][1,4]oxazepine-8-carboxamide;

(R)-4-acetyl-N-hydroxy-3-isopropyl-2,3,4,5-tetrahydrobenzo[f][1,4]oxazepine-8-carboxamide;

(R)—N-hydroxy-3-isopropyl-4-(1-methylcyclobutane-1-carbonyl)-2,3,4,5-tetrahydrobenzo[f][1,4]oxazepine-8-carboxamide;

(S)-4-acetyl-N-hydroxy-3-isopropyl-2,3,4,5-tetrahydrobenzo[f][1,4]oxazepine-8-carboxamide;

(S)—N-hydroxy-3-isopropyl-4-(1-methylcyclobutane-1-carbonyl)-2,3,4,5-tetrahydrobenzo[f][1,4]oxazepine-8-carboxamide;

(R)-4-formyl-N-hydroxy-3-methyl-2,3,4,5-tetrahydrobenzo[f][1,4]oxazepine-8-carboxamide;

(R)—N-hydroxy-3-methyl-4-(1-methylcyclobutane-1-carbonyl)-2,3,4,5-tetrahydrobenzo[f][1,4]oxazepine-8-carboxamide;

(R)-4-acetyl-N-hydroxy-3-methyl-2,3,4,5-tetrahydrobenzo[f][1,4]oxazepine-8-carboxamide;

(S)—N-hydroxy-3-methyl-4-(1-methylcyclobutane-1-carbonyl)-2,3,4,5-tetrahydrobenzo[f][1,4]oxazepine-8-carboxamide;

(S)-4-(1,1-dioxidotetrahydro-2H-thiopyran-4-carbonyl)-N-hydroxy-3-methyl-2,3,4,5-tetrahydrobenzo[f][1,4]oxazepine-8-carboxamide;

(S)—N-hydroxy-4-(1-methoxycyclopentane-1-carbonyl)-3-methyl-2,3,4,5-tetrahydrobenzo[f][1,4]oxazepine-8-carboxamide;

(3S)-4-(1,1-dioxidotetrahydrothiophene-3-carbonyl)-N-hydroxy-3-methyl-2,3,4,5-tetrahydrobenzo[f][1,4]oxazepine-8-carboxamide;

(S)—N-hydroxy-4-(1-methoxycyclobutane-1-carbonyl)-3-methyl-2,3,4,5-tetrahydrobenzo[f][1,4]oxazepine-8-carboxamide;

(S)—N-hydroxy-3-methyl-4-(3-methyloxetane-3-carbonyl)-2,3,4,5-tetrahydrobenzo[f][1,4]oxazepine-8-carboxamide;

(S)—N-hydroxy-3-methyl-4-(oxetane-3-carbonyl)-2,3,4,5-tetrahydrobenzo[f][1,4]oxazepine-8-carboxamide;

(S)-4-(1,1-dioxidothietane-3-carbonyl)-N-hydroxy-3-methyl-2,3,4,5-tetrahydrobenzo[f][1,4]oxazepine-8-carboxamide;

(S)—N-hydroxy-4-(1-methoxycyclopropane-1-carbonyl)-3-methyl-2,3,4,5-tetrahydrobenzo[f][1,4]oxazepine-8-carboxamide;

(S)—N-hydroxy-3-methyl-4-(tetrahydro-2H-pyran-4-carbonyl)-2,3,4,5-tetrahydrobenzo[f][1,4]oxazepine-8-carboxamide;

(S)—N-hydroxy-4-(2-methoxy-2-methylpropanoyl)-3-methyl-2,3,4,5-tetrahydrobenzo[f][1,4]oxazepine-8-carboxamide;

(S)—N-hydroxy-3-methyl-4-(4-methyltetrahydro-2H-pyran-4-carbonyl)-2,3,4,5-tetrahydrobenzo[f][1,4]oxazepine-8-carboxamide;

(S)—N-hydroxy-4-(4-methoxytetrahydro-2H-pyran-4-carbonyl)-3-methyl-2,3,4,5-tetrahydrobenzo[f][1,4]oxazepine-8-carboxamide;

(S)—N-hydroxy-4-(1-methoxycyclohexane-1-carbonyl)-3-methyl-2,3,4,5-tetrahydrobenzo[f][1,4]oxazepine-8-carboxamide;

(3S)-4-(8-oxabicyclo[3.2.1]octane-3-carbonyl)-N-hydroxy-3-methyl-2,3,4,5-tetrahydrobenzo[f][1,4]oxazepine-8-carboxamide;

(3S)-4-(2,6-dimethyltetrahydro-2H-pyran-4-carbonyl)-N-hydroxy-3-methyl-2,3,4,5-tetrahydrobenzo[f][1,4]oxazepine-8-carboxamide;

(S)-4-formyl-N-hydroxy-3-methyl-2,3,4,5-tetrahydrobenzo[f][1,4]oxazepine-8-carboxamide;

(S)-4-acetyl-N-hydroxy-3-methyl-2,3,4,5-tetrahydrobenzo[f][1,4]oxazepine-8-carboxamide;

(S)-4-(1-acetylpiperidine-4-carbonyl)-N-hydroxy-3-methyl-2,3,4,5-tetrahydrobenzo[f][1,4]oxazepine-8-carboxamide;

(3S)-4-(1-acetylpyrrolidine-3-carbonyl)-N-hydroxy-3-methyl-2,3,4,5-tetrahydrobenzo[f][1,4]oxazepine-8-carboxamide;

(R)—N-hydroxy-5-methyl-4-(1-methylcyclobutane-1-carbonyl)-2,3,4,5-tetrahydrobenzo[f][1,4]oxazepine-7-carboxamide;

(S)—N-hydroxy-5-methyl-4-(1-methylcyclobutane-1-carbonyl)-2,3,4,5-tetrahydrobenzo[f][1,4]oxazepine-7-carboxamide;

(R)—N-hydroxy-5-methyl-4-(tetrahydro-2H-pyran-4-carbonyl)-2,3,4,5-tetrahydrobenzo[f][1,4]oxazepine-7-carboxamide;

(S)—N-hydroxy-5-methyl-4-(tetrahydro-2H-pyran-4-carbonyl)-2,3,4,5-tetrahydrobenzo[f][1,4]oxazepine-7-carboxamide;

4-(cyclohexanecarbonyl)-N-hydroxy-2,3,4,5-tetrahydropyrido[2,3-f][1,4]oxazepine-8-carboxamide;

4-(cyclohexanecarbonyl)-N-hydroxy-2,3,4,5-tetrahydropyrido[3,2-f][1,4]oxazepine-8-carboxamide;

N-hydroxy-4-(2-(4-methoxyphenyl)acetyl)-2-oxo-2,3,4,5-tetrahydro-1H-benzo[e][1,4]diazepine-7-carboxamide;

N-hydroxy-4-(4-methoxybenzoyl)-2-oxo-2,3,4,5-tetrahydro-1H-benzo[e][1,4]diazepine-7-carboxamide;

4-(cyclohexanecarbonyl)-N-hydroxy-2-oxo-2,3,4,5-tetrahydro-1H-benzo[e][1,4]diazepine-7-carboxamide;

4-(cyclohexanecarbonyl)-N-hydroxy-2,3,4,5-tetrahydrobenzo[f][1,4]oxazepine-8-carboxamide;

N-hydroxy-4-(4-methoxybenzoyl)-2,3,4,5-tetrahydrobenzo[f][1,4]oxazepine-8-carboxamide;

N-hydroxy-4-(4-methoxybenzoyl)-2,3,4,5-tetrahydrobenzo[f][1,4]oxazepine-7-carboxamide;

N-hydroxy-4-(2-(4-methoxyphenyl)acetyl)-2,3,4,5-tetrahydrobenzo[f][1,4]oxazepine-8-carboxamide;

N-hydroxy-4-(2-(4-methoxyphenyl)acetyl)-2,3,4,5-tetrahydrobenzo[f][1,4]oxazepine-7-carboxamide;

N-hydroxy-4-(4-(trifluoromethyl)benzoyl)-2,3,4,5-tetrahydrobenzo[f][1,4]oxazepine-8-carboxamide;

4-(benzo[d][1,3]dioxole-5-carbonyl)-N-hydroxy-2,3,4,5-tetrahydrobenzo[f][1,4]oxazepine-8-carboxamide;

N-hydroxy-4-(1H-indole-5-carbonyl)-2,3,4,5-tetrahydrobenzo[f][1,4]oxazepine-8-carboxamide;

N-hydroxy-4-(1-phenylcyclopropane-1-carbonyl)-2,3,4,5-tetrahydrobenzo[f][1,4]oxazepine-8-carboxamide;

N-hydroxy-4-(2-(4-methoxyphenoxy)acetyl)-2,3,4,5-tetrahydrobenzo[f][1,4]oxazepine-8-carboxamide;

N-hydroxy-4-(3-methoxybenzoyl)-2,3,4,5-tetrahydrobenzo[f][1,4]oxazepine-8-carboxamide;

4-(4-(difluoromethoxy)benzoyl)-N-hydroxy-2,3,4,5-tetrahydrobenzo[f][1,4]oxazepine-8-carboxamide;

N-hydroxy-4-(4-phenoxybenzoyl)-2,3,4,5-tetrahydrobenzo[f][1,4]oxazepine-8-carboxamide;

4-(2,3-dihydrobenzofuran-5-carbonyl)-N-hydroxy-2,3,4,5-tetrahydrobenzo[f][1,4]oxazepine-8-carboxamide;

4-(2,4-dimethoxybenzoyl)-N-hydroxy-2,3,4,5-tetrahydrobenzo[f][1,4]oxazepine-8-carboxamide;

N-hydroxy-4-(1-methyl-6-oxo-1,6-dihydropyridine-3-carbonyl)-2,3,4,5-tetrahydrobenzo[f][1,4]oxazepine-8-carboxamide;

N-hydroxy-4-(tetrahydro-2H-pyran-4-carbonyl)-2,3,4,5-tetrahydrobenzo[f][1,4]oxazepine-8-carboxamide;

4-(benzofuran-5-carbonyl)-N-hydroxy-2,3,4,5-tetrahydrobenzo[f][1,4]oxazepine-8-carboxamide;
N-hydroxy-4-(4-morpholinobenzoyl)-2,3,4,5-tetrahydrobenzo[f][1,4]oxazepine-8-carboxamide;
4-(cyclopropanecarbonyl)-N-hydroxy-2,3,4,5-tetrahydrobenzo[f][1,4]oxazepine-8-carboxamide;
4-(cyclobutanecarbonyl)-N-hydroxy-2,3,4,5-tetrahydrobenzo[f][1,4]oxazepine-8-carboxamide;
N-hydroxy-4-(1-methylcyclohexane-1-carbonyl)-2,3,4,5-tetrahydrobenzo[f][1,4]oxazepine-8-carboxamide;
N-hydroxy-4-(2-phenylbutanoyl)-2,3,4,5-tetrahydrobenzo[f][1,4]oxazepine-8-carboxamide;
4-(2-cyclohexyl-2-phenylacetyl)-N-hydroxy-2,3,4,5-tetrahydrobenzo[f][1,4]oxazepine-8-carboxamide;
4-(bicyclo[4.2.0]octa-1(6),2,4-triene-7-carbonyl)-N-hydroxy-2,3,4,5-tetrahydrobenzo[f][1,4]oxazepine-8-carboxamide;
N-hydroxy-4-(1-methylcyclobutane-1-carbonyl)-2,3,4,5-tetrahydrobenzo[f][1,4]oxazepine-8-carboxamide;
(S)—N-hydroxy-4-(2-phenylpropanoyl)-2,3,4,5-tetrahydrobenzo[f][1,4]oxazepine-8-carboxamide;
(R)—N-hydroxy-4-(2-phenylpropanoyl)-2,3,4,5-tetrahydrobenzo[f][1,4]oxazepine-8-carboxamide;
N-hydroxy-4-(3-phenylpropanoyl)-2,3,4,5-tetrahydrobenzo[f][1,4]oxazepine-8-carboxamide;
N-hydroxy-4-(2-(5-methoxy-1H-indol-3-yl)acetyl)-2,3,4,5-tetrahydrobenzo[f][1,4]oxazepine-8-carboxamide;
4-(2-(1,1-dioxidothiomorpholino)propanoyl)-N-hydroxy-2,3,4,5-tetrahydrobenzo[f][1,4]oxazepine-8-carboxamide;
N-hydroxy-4-(2-(4-(trifluoromethyl)phenyl)acetyl)-2,3,4,5-tetrahydrobenzo[f][1,4]oxazepine-8-carboxamide;
N-hydroxy-4-(2-(2-phenoxyphenyl)acetyl)-2,3,4,5-tetrahydrobenzo[f][1,4]oxazepine-8-carboxamide;
4-(2-(3-chlorophenoxy)acetyl)-N-hydroxy-2,3,4,5-tetrahydrobenzo[f][1,4]oxazepine-8-carboxamide;
N-hydroxy-4-(4,4,4-trifluorobutanoyl)-2,3,4,5-tetrahydrobenzo[f][1,4]oxazepine-8-carboxamide;
4-(cyclopentanecarbonyl)-N-hydroxy-2,3,4,5-tetrahydrobenzo[f][1,4]oxazepine-8-carboxamide;
N-hydroxy-4-isobutyryl-2,3,4,5-tetrahydrobenzo[f][1,4]oxazepine-8-carboxamide;
N-hydroxy-4-(2-(1-(methylsulfonyl)piperidin-4-yl)acetyl)-2,3,4,5-tetrahydrobenzo[f][1,4]oxazepine-8-carboxamide;
N-hydroxy-4-(2-(2-methylthiazol-4-yl)acetyl)-2,3,4,5-tetrahydrobenzo[f][1,4]oxazepine-8-carboxamide;
4-(2-(1,1-dioxidothiomorpholino)acetyl)-N-hydroxy-2,3,4,5-tetrahydrobenzo[f][1,4]oxazepine-8-carboxamide;
N-hydroxy-4-(2-morpholinoacetyl)-2,3,4,5-tetrahydrobenzo[f][1,4]oxazepine-8-carboxamide;
N-hydroxy-4-(2-methoxy-2-phenylacetyl)-2,3,4,5-tetrahydrobenzo[f][1,4]oxazepine-8-carboxamide;
4-(2-(4-fluorophenyl)propanoyl)-N-hydroxy-2,3,4,5-tetrahydrobenzo[f][1,4]oxazepine-8-carboxamide;
4-(2,3-dihydro-1H-indene-2-carbonyl)-N-hydroxy-2,3,4,5-tetrahydrobenzo[f][1,4]oxazepine-8-carboxamide;
N-hydroxy-4-(3-phenylbutanoyl)-2,3,4,5-tetrahydrobenzo[f][1,4]oxazepine-8-carboxamide;
N-hydroxy-4-(2-phenoxypropanoyl)-2,3,4,5-tetrahydrobenzo[f][1,4]oxazepine-8-carboxamide;
4-(1-acetylpiperidine-3-carbonyl)-N-hydroxy-2,3,4,5-tetrahydrobenzo[f][1,4]oxazepine-8-carboxamide;
N-hydroxy-4-(2-phenoxybutanoyl)-2,3,4,5-tetrahydrobenzo[f][1,4]oxazepine-8-carboxamide;
N-hydroxy-4-(2-phenylcyclopropane-1-carbonyl)-2,3,4,5-tetrahydrobenzo[f][1,4]oxazepine-8-carboxamide;
N-hydroxy-4-(2-(2-oxo-3-(trifluoromethyl)pyridin-1(2H)-yl)acetyl)-2,3,4,5-tetrahydrobenzo[f][1,4]oxazepine-8-carboxamide;
N-hydroxy-4-(2-isobutoxyacetyl)-2,3,4,5-tetrahydrobenzo[f][1,4]oxazepine-8-carboxamide;
4-(4,4-difluorocyclohexane-1-carbonyl)-N-hydroxy-2,3,4,5-tetrahydrobenzo[f][1,4]oxazepine-8-carboxamide;
N-hydroxy-4-(N-methyl-N-(methylsulfonyl)glycyl)-2,3,4,5-tetrahydrobenzo[f][1,4]oxazepine-8-carboxamide;
(S)-4-(2,2-dimethylcyclopropane-1-carbonyl)-N-hydroxy-2,3,4,5-tetrahydrobenzo[f][1,4]oxazepine-8-carboxamide;
4-(3,3-difluorocyclobutane-1-carbonyl)-N-hydroxy-2,3,4,5-tetrahydrobenzo[f][1,4]oxazepine-8-carboxamide;
4-(2-cyclopropylacetyl)-N-hydroxy-2,3,4,5-tetrahydrobenzo[f][1,4]oxazepine-8-carboxamide;
N-hydroxy-4-(3-hydroxypropanoyl)-2,3,4,5-tetrahydrobenzo[f][1,4]oxazepine-8-carboxamide;
N-hydroxy-4-(1-hydroxycyclopropane-1-carbonyl)-2,3,4,5-tetrahydrobenzo[f][1,4]oxazepine-8-carboxamide;
N-hydroxy-4-(2-hydroxy-2-methylpropanoyl)-2,3,4,5-tetrahydrobenzo[f][1,4]oxazepine-8-carboxamide;
4-(2-cyclopentyl-2-hydroxy-2-phenylacetyl)-N-hydroxy-2,3,4,5-tetrahydrobenzo[f][1,4]oxazepine-8-carboxamide;
N-hydroxy-4-(2-(3-methoxyphenyl)-2-methylpropanoyl)-2,3,4,5-tetrahydrobenzo[f][1,4]oxazepine-8-carboxamide;
4-(2-(4-chloro-1H-pyrazol-1-yl)-2-methylpropanoyl)-N-hydroxy-2,3,4,5-tetrahydrobenzo[f][1,4]oxazepine-8-carboxamide;
4-(2-cyclohexyl-2-methylpropanoyl)-N-hydroxy-2,3,4,5-tetrahydrobenzo[f][1,4]oxazepine-8-carboxamide;
4-(2-(3,4-dimethoxyphenyl)-2-methylpropanoyl)-N-hydroxy-2,3,4,5-tetrahydrobenzo[f][1,4]oxazepine-8-carboxamide;
4-(2-([1,1'-biphenyl]-4-yl)-2-methylpropanoyl)-N-hydroxy-2,3,4,5-tetrahydrobenzo[f][1,4]oxazepine-8-carboxamide;
N-hydroxy-4-(2-methyl-2-(3-methyl-1H-pyrazol-1-yl)propanoyl)-2,3,4,5-tetrahydrobenzo[f][1,4]oxazepine-8-carboxamide;
N-hydroxy-4-(2-methyl-2-(naphthalen-2-yl)propanoyl)-2,3,4,5-tetrahydrobenzo[f][1,4]oxazepine-8-carboxamide;
N-hydroxy-4-(2-(2-methoxyphenyl)-2-methylpropanoyl)-2,3,4,5-tetrahydrobenzo[f][1,4]oxazepine-8-carboxamide;
N-hydroxy-4-(2-methyl-2-(pyridin-3-yl)propanoyl)-2,3,4,5-tetrahydrobenzo[f][1,4]oxazepine-8-carboxamide;
4-(2-(4-fluorophenyl)-2-methylpropanoyl)-N-hydroxy-2,3,4,5-tetrahydrobenzo[f][1,4]oxazepine-8-carboxamide;
4-(2-(2,3-dihydrobenzo[b][1,4]dioxin-6-yl)-2-methylpropanoyl)-N-hydroxy-2,3,4,5-tetrahydrobenzo[f][1,4]oxazepine-8-carboxamide;
N-hydroxy-4-(2-methyl-2-(thiophen-2-yl)propanoyl)-2,3,4,5-tetrahydrobenzo[f][1,4]oxazepine-8-carboxamide;
N-hydroxy-4-(3-(4-methoxyphenyl)-2-phenylpropanoyl)-2,3,4,5-tetrahydrobenzo[f][1,4]oxazepine-8-carboxamide;
N-hydroxy-4-(2-(5-methyl-1H-tetrazol-1-yl)-2-phenylacetyl)-2,3,4,5-tetrahydrobenzo[f][1,4]oxazepine-8-carboxamide;
N-hydroxy-4-(2-phenyl-2-(1H-tetrazol-1-yl)acetyl)-2,3,4,5-tetrahydrobenzo[f][1,4]oxazepine-8-carboxamide;
N-hydroxy-4-(2-phenyl-2-((tetrahydro-2H-pyran-4-yl)oxy)acetyl)-2,3,4,5-tetrahydrobenzo[f][1,4]oxazepine-8-carboxamide;
N-hydroxy-4-(2-hydroxy-3-methyl-2-phenylbutanoyl)-2,3,4,5-tetrahydrobenzo[f][1,4]oxazepine-8-carboxamide;

N-hydroxy-4-(2-(4-hydroxypiperidin-1-yl)-2-phenylacetyl)-2,3,4,5-tetrahydrobenzo[f][1,4]oxazepine-8-carboxamide;
N-hydroxy-4-(2-phenyl-2-(2,2,2-trifluoroethoxy)acetyl)-2,3,4,5-tetrahydrobenzo[f][1,4]oxazepine-8-carboxamide;
4-(2-(tert-butoxy)-2-phenylacetyl)-N-hydroxy-2,3,4,5-tetrahydrobenzo[f][1,4]oxazepine-8-carboxamide;
N-hydroxy-4-(2-phenyl-2-(1H-pyrazol-1-yl)acetyl)-2,3,4,5-tetrahydrobenzo[f][1,4]oxazepine-8-carboxamide;
N-hydroxy-4-(2-methoxy-2-phenylpropanoyl)-2,3,4,5-tetrahydrobenzo[f][1,4]oxazepine-8-carboxamide;
N-hydroxy-4-(2-phenoxy-2-phenylacetyl)-2,3,4,5-tetrahydrobenzo[f][1,4]oxazepine-8-carboxamide;
N-hydroxy-4-(2-(2-oxopiperidin-1-yl)-2-phenylacetyl)-2,3,4,5-tetrahydrobenzo[f][1,4]oxazepine-8-carboxamide;
N-hydroxy-4-(2-methyl-2-phenylpropanoyl)-2,3,4,5-tetrahydrobenzo[f][1,4]oxazepine-8-carboxamide;
N-hydroxy-4-(2-(4-isobutoxyphenyl)-2-methylpropanoyl)-2,3,4,5-tetrahydrobenzo[f][1,4]oxazepine-8-carboxamide;
4-(1,1-dioxidotetrahydro-2H-thiopyran-4-carbonyl)-N-hydroxy-2,3,4,5-tetrahydrobenzo[f][1,4]oxazepine-8-carboxamide;
N-hydroxy-4-(4-methoxycyclohexane-1-carbonyl)-2,3,4,5-tetrahydrobenzo[f][1,4]oxazepine-8-carboxamide;
N-hydroxy-4-(1-(pyridin-2-yl)cyclopropane-1-carbonyl)-2,3,4,5-tetrahydrobenzo[f][1,4]oxazepine-8-carboxamide;
N-hydroxy-4-(4-phenyltetrahydro-2H-pyran-4-carbonyl)-2,3,4,5-tetrahydrobenzo[f][1,4]oxazepine-8-carboxamide;
N-hydroxy-4-(2-(pyridin-3-yl)propanoyl)-2,3,4,5-tetrahydrobenzo[f][1,4]oxazepine-8-carboxamide;
N-hydroxy-4-(4-methoxy-2-(pyridin-2-yl)butanoyl)-2,3,4,5-tetrahydrobenzo[f][1,4]oxazepine-8-carboxamide;
4-(3,3-difluorocyclopentane-1-carbonyl)-N-hydroxy-2,3,4,5-tetrahydrobenzo[f][1,4]oxazepine-8-carboxamide;
N-hydroxy-4-(1-methylcyclopropane-1-carbonyl)-2,3,4,5-tetrahydrobenzo[f][1,4]oxazepine-8-carboxamide;
N-hydroxy-4-(1-(methoxymethyl)cyclobutane-1-carbonyl)-2,3,4,5-tetrahydrobenzo[f][1,4]oxazepine-8-carboxamide;
4-(1-((1H-imidazol-1-yl)methyl)cyclopropane-1-carbonyl)-N-hydroxy-2,3,4,5-tetrahydrobenzo[f][1,4]oxazepine-8-carboxamide;
N-hydroxy-4-(1-(methoxymethyl)cyclopropane-1-carbonyl)-2,3,4,5-tetrahydrobenzo[f][1,4]oxazepine-8-carboxamide;
N-hydroxy-4-(2-methyl-3-phenylpropanoyl)-2,3,4,5-tetrahydrobenzo[f][1,4]oxazepine-8-carboxamide;
4-(1-acetylpyrrolidine-3-carbonyl)-N-hydroxy-2,3,4,5-tetrahydrobenzo[f][1,4]oxazepine-8-carboxamide;
N-hydroxy-4-(1-methylcyclopentane-1-carbonyl)-2,3,4,5-tetrahydrobenzo[f][1,4]oxazepine-8-carboxamide;
N-hydroxy-4-(1-(2-(trifluoromethyl)phenyl)cyclopropane-1-carbonyl)-2,3,4,5-tetrahydrobenzo[f][1,4]oxazepine-8-carboxamide;
N-hydroxy-4-(1-(3-(trifluoromethyl)phenyl)cyclopropane-1-carbonyl)-2,3,4,5-tetrahydrobenzo[f][1,4]oxazepine-8-carboxamide;
N-hydroxy-4-(tetrahydrofuran-3-carbonyl)-2,3,4,5-tetrahydrobenzo[f][1,4]oxazepine-8-carboxamide;
N-hydroxy-4-(1-(4-(trifluoromethyl)phenyl)cyclopropane-1-carbonyl)-2,3,4,5-tetrahydrobenzo[f][1,4]oxazepine-8-carboxamide;
N-hydroxy-4-(1-phenylcyclobutane-1-carbonyl)-2,3,4,5-tetrahydrobenzo[f][1,4]oxazepine-8-carboxamide;
4-(1-benzylcyclopropane-1-carbonyl)-N-hydroxy-2,3,4,5-tetrahydrobenzo[f][1,4]oxazepine-8-carboxamide;
N-hydroxy-4-(1-methoxycyclobutane-1-carbonyl)-2,3,4,5-tetrahydrobenzo[f][1,4]oxazepine-8-carboxamide;
N-hydroxy-4-(1-(phenylsulfonyl)cyclopropane-1-carbonyl)-2,3,4,5-tetrahydrobenzo[f][1,4]oxazepine-8-carboxamide;
4-(1-(4-fluorophenyl)cyclopropane-1-carbonyl)-N-hydroxy-2,3,4,5-tetrahydrobenzo[f][1,4]oxazepine-8-carboxamide;
4-(1-(4-chlorophenyl)cyclopropane-1-carbonyl)-N-hydroxy-2,3,4,5-tetrahydrobenzo[f][1,4]oxazepine-8-carboxamide;
N-hydroxy-4-(1-(4-methoxyphenyl)cyclopropane-1-carbonyl)-2,3,4,5-tetrahydrobenzo[f][1,4]oxazepine-8-carboxamide;
4-(1-(3-chlorophenyl)cyclopropane-1-carbonyl)-N-hydroxy-2,3,4,5-tetrahydrobenzo[f][1,4]oxazepine-8-carboxamide;
4-(1-(2-chlorophenyl)cyclopropane-1-carbonyl)-N-hydroxy-2,3,4,5-tetrahydrobenzo[f][1,4]oxazepine-8-carboxamide;
N-hydroxy-4-(1-(3-methoxyphenyl)cyclopropane-1-carbonyl)-2,3,4,5-tetrahydrobenzo[f][1,4]oxazepine-8-carboxamide;
N-hydroxy-4-(1-(pyridin-4-yl)cyclopropane-1-carbonyl)-2,3,4,5-tetrahydrobenzo[f][1,4]oxazepine-8-carboxamide;
N-hydroxy-4-(1-(pyrazin-2-yl)cyclopropane-1-carbonyl)-2,3,4,5-tetrahydrobenzo[f][1,4]oxazepine-8-carboxamide;
N-hydroxy-4-(1-phenoxycyclopropane-1-carbonyl)-2,3,4,5-tetrahydrobenzo[f][1,4]oxazepine-8-carboxamide;
4-(1-((1H-pyrazol-1-yl)methyl)cyclopropane-1-carbonyl)-N-hydroxy-2,3,4,5-tetrahydrobenzo[f][1,4]oxazepine-8-carboxamide;
N-hydroxy-4-(1-(thiophen-2-yl)cyclopropane-1-carbonyl)-2,3,4,5-tetrahydrobenzo[f][1,4]oxazepine-8-carboxamide;
N-hydroxy-4-(oxetane-3-carbonyl)-2,3,4,5-tetrahydrobenzo[f][1,4]oxazepine-8-carboxamide;
N-hydroxy-4-(3-methyloxetane-3-carbonyl)-2,3,4,5-tetrahydrobenzo[f][1,4]oxazepine-8-carboxamide;
N-hydroxy-8-(tetrahydro-2H-pyran-4-carbonyl)-6,7,8,9-tetrahydropyrazino[2,3-f][1,4]oxazepine-3-carboxamide;
8-(cyclohexanecarbonyl)-N-hydroxy-6,7,8,9-tetrahydropyrazino[2,3-f][1,4]oxazepine-3-carboxamide;
(R)—N-hydroxy-2-isopropyl-4-(tetrahydro-2H-pyran-4-carbonyl)-2,3,4,5-tetrahydrobenzo[f][1,4]oxazepine-8-carboxamide;
(R)—N-hydroxy-2-isopropyl-4-(1-methylcyclobutane-1-carbonyl)-2,3,4,5-tetrahydrobenzo[f][1,4]oxazepine-8-carboxamide;
(R)-4-formyl-N-hydroxy-2-isopropyl-2,3,4,5-tetrahydrobenzo[f][1,4]oxazepine-8-carboxamide;
(R)—N-hydroxy-2-(methoxymethyl)-4-(tetrahydro-2H-pyran-4-carbonyl)-2,3,4,5-tetrahydrobenzo[f][1,4]oxazepine-8-carboxamide;
(R)—N-hydroxy-2-(methoxymethyl)-4-(1-methylcyclobutane-1-carbonyl)-2,3,4,5-tetrahydrobenzo[f][1,4]oxazepine-8-carboxamide;
(R)-4-formyl-N-hydroxy-2-(methoxymethyl)-2,3,4,5-tetrahydrobenzo[f][1,4]oxazepine-8-carboxamide;
(S)—N-hydroxy-2-(methoxymethyl)-4-(tetrahydro-2H-pyran-4-carbonyl)-2,3,4,5-tetrahydrobenzo[f][1,4]oxazepine-8-carboxamide;
(S)—N-hydroxy-2-(methoxymethyl)-4-(1-methylcyclobutane-1-carbonyl)-2,3,4,5-tetrahydrobenzo[f][1,4]oxazepine-8-carboxamide;
(S)-4-formyl-N-hydroxy-2-(methoxymethyl)-2,3,4,5-tetrahydrobenzo[f][1,4]oxazepine-8-carboxamide;

(R)—N-hydroxy-2-phenyl-4-(tetrahydro-2H-pyran-4-carbonyl)-2,3,4,5-tetrahydrobenzo[f][1,4]oxazepine-8-carboxamide;
(R)—N-hydroxy-4-(1-methylcyclobutane-1-carbonyl)-2-phenyl-2,3,4,5-tetrahydrobenzo[f][1,4]oxazepine-8-carboxamide;
(R)-4-formyl-N-hydroxy-2-phenyl-2,3,4,5-tetrahydrobenzo[f][1,4]oxazepine-8-carboxamide;
(S)—N-hydroxy-2-phenyl-4-(tetrahydro-2H-pyran-4-carbonyl)-2,3,4,5-tetrahydrobenzo[f][1,4]oxazepine-8-carboxamide;
(S)—N-hydroxy-4-(1-methylcyclobutane-1-carbonyl)-2-phenyl-2,3,4,5-tetrahydrobenzo[f][1,4]oxazepine-8-carboxamide;
(S)-4-formyl-N-hydroxy-2-phenyl-2,3,4,5-tetrahydrobenzo[f][1,4]oxazepine-8-carboxamide;
(R)—N-hydroxy-4-(tetrahydro-2H-pyran-4-carbonyl)-3-(trifluoromethyl)-2,3,4,5-tetrahydrobenzo[f][1,4]oxazepine-8-carboxamide;
(R)—N-hydroxy-4-(oxetane-3-carbonyl)-3-(trifluoromethyl)-2,3,4,5-tetrahydrobenzo[f][1,4]oxazepine-8-carboxamide;
N-hydroxy-4-(tetrahydro-2H-pyran-4-carbonyl)-4,5-dihydro-2H-spiro[benzo[f][1,4]oxazepine-3,1'-cyclopropane]-8-carboxamide;
(S)-3-ethyl-N-hydroxy-4-(tetrahydro-2H-pyran-4-carbonyl)-2,3,4,5-tetrahydrobenzo[f][1,4]oxazepine-8-carboxamide;
(S)—N-hydroxy-3-isopropyl-4-(2-(tetrahydro-2H-pyran-4-yl)acetyl)-2,3,4,5-tetrahydrobenzo[f][1,4]oxazepine-8-carboxamide;
(S)—N-hydroxy-3-isopropyl-4-(tetrahydro-2H-pyran-4-carbonyl)-2,3,4,5-tetrahydrobenzo[f][1,4]oxazepine-8-carboxamide;
(S)—N-hydroxy-4-((1s,4R)-4-methoxycyclohexane-1-carbonyl)-3-methyl-2,3,4,5-tetrahydrobenzo[f][1,4]oxazepine-8-carboxamide;
(S)—N-hydroxy-4-((1r,4S)-4-methoxycyclohexane-1-carbonyl)-3-methyl-2,3,4,5-tetrahydrobenzo[f][1,4]oxazepine-8-carboxamide;
(S)-4-(1-formylpiperidine-4-carbonyl)-N-hydroxy-3-methyl-2,3,4,5-tetrahydrobenzo[f][1,4]oxazepine-8-carboxamide;
(S)—N-hydroxy-4-(3-(methoxymethyl)oxetane-3-carbonyl)-3-methyl-2,3,4,5-tetrahydrobenzo[f][1,4]oxazepine-8-carboxamide;
(S)—N-hydroxy-3-methyl-4-((R)-tetrahydro-2H-pyran-3-carbonyl)-2,3,4,5-tetrahydrobenzo[f][1,4]oxazepine-8-carboxamide;
(S)—N-hydroxy-3-methyl-4-((S)-tetrahydro-2H-pyran-3-carbonyl)-2,3,4,5-tetrahydrobenzo[f][1,4]oxazepine-8-carboxamide;
(S)—N-hydroxy-3-methyl-4-((R)-tetrahydrofuran-3-carbonyl)-2,3,4,5-tetrahydrobenzo[f][1,4]oxazepine-8-carboxamide;
(S)—N-hydroxy-3-methyl-4-((S)-tetrahydrofuran-3-carbonyl)-2,3,4,5-tetrahydrobenzo[f][1,4]oxazepine-8-carboxamide;
(S)—N-hydroxy-3-methyl-4-(2-(tetrahydro-2H-pyran-4-yl)acetyl)-2,3,4,5-tetrahydrobenzo[f][1,4]oxazepine-8-carboxamide;
(S)—N-hydroxy-4-(4-(methoxymethyl)tetrahydro-2H-pyran-4-carbonyl)-3-methyl-2,3,4,5-tetrahydrobenzo[f][1,4]oxazepine-8-carboxamide;
(S)-4-(3-ethyloxetane-3-carbonyl)-N-hydroxy-3-methyl-2,3,4,5-tetrahydrobenzo[f][1,4]oxazepine-8-carboxamide;
(S)-4-(3-(4-fluorophenoxy)propanoyl)-N-hydroxy-3-methyl-2,3,4,5-tetrahydrobenzo[f][1,4]oxazepine-8-carboxamide;
(S)—N-hydroxy-3-methyl-4-((1s,4R)-4-(trifluoromethoxy)cyclohexane-1-carbonyl)-2,3,4,5-tetrahydrobenzo[f][1,4]oxazepine-8-carboxamide;
(S)—N-hydroxy-3-methyl-4-((1r,4S)-4-(trifluoromethoxy)cyclohexane-1-carbonyl)-2,3,4,5-tetrahydrobenzo[f][1,4]oxazepine-8-carboxamide;
(S)—N-hydroxy-4-((1s,3R)-3-methoxycyclobutane-1-carbonyl)-3-methyl-2,3,4,5-tetrahydrobenzo[f][1,4]oxazepine-8-carboxamide;
(S)—N-hydroxy-4-((1r,3S)-3-methoxycyclobutane-1-carbonyl)-3-methyl-2,3,4,5-tetrahydrobenzo[f][1,4]oxazepine-8-carboxamide;
(S)-4-(3-(benzyloxy)cyclobutane-1-carbonyl)-N-hydroxy-3-methyl-2,3,4,5-tetrahydrobenzo[f][1,4]oxazepine-8-carboxamide;
(3S)—N-hydroxy-3-methyl-4-(2-(tetrahydrofuran-2-yl)acetyl)-2,3,4,5-tetrahydrobenzo[f][1,4]oxazepine-8-carboxamide;
(S)-4-(cyclohexanecarbonyl)-N-hydroxy-3-methyl-2,3,4,5-tetrahydrobenzo[f][1,4]oxazepine-8-carboxamide;
(S)—N-hydroxy-4-(3-methoxypropanol)-3-methyl-2,3,4,5-tetrahydrobenzo[f][1,4]oxazepine-8-carboxamide;
(S)-4-(4-fluorobenzoyl)-N-hydroxy-3-methyl-2,3,4,5-tetrahydrobenzo[f][1,4]oxazepine-8-carboxamide;
(S)—N-hydroxy-3-methyl-4-propionyl-2,3,4,5-tetrahydrobenzo[f][1,4]oxazepine-8-carboxamide;
(S)-4-(cyclopropanecarbonyl)-N-hydroxy-3-methyl-2,3,4,5-tetrahydrobenzo[f][1,4]oxazepine-8-carboxamide;
(S)-4-(cyclobutanecarbonyl)-N-hydroxy-3-methyl-2,3,4,5-tetrahydrobenzo[f][1,4]oxazepine-8-carboxamide;
(S)-4-(cyclopentanecarbonyl)-N-hydroxy-3-methyl-2,3,4,5-tetrahydrobenzo[f][1,4]oxazepine-8-carboxamide;
(S)—N-hydroxy-4-isobutyryl-3-methyl-2,3,4,5-tetrahydrobenzo[f][1,4]oxazepine-8-carboxamide;
(S)—N-hydroxy-4-(3-hydroxy-3-methylbutanoyl)-3-methyl-2,3,4,5-tetrahydrobenzo[f][1,4]oxazepine-8-carboxamide;
(S)—N-hydroxy-4-(3-hydroxy-2,2-dimethylpropanoyl)-3-methyl-2,3,4,5-tetrahydrobenzo[f][1,4]oxazepine-8-carboxamide;
(S)—N-hydroxy-4-(3-methoxy-3-methylbutanoyl)-3-methyl-2,3,4,5-tetrahydrobenzo[f][1,4]oxazepine-8-carboxamide;
(S)-4-(4-fluorotetrahydro-2H-pyran-4-carbonyl)-N-hydroxy-3-methyl-2,3,4,5-tetrahydrobenzo[f][1,4]oxazepine-8-carboxamide;
(3S)—N-hydroxy-3-methyl-4-(oxepane-4-carbonyl)-2,3,4,5-tetrahydrobenzo[f][1,4]oxazepine-8-carboxamide;
(S)—N-hydroxy-3-methyl-4-((S)-2-methyltetrahydro-2H-pyran-2-carbonyl)-2,3,4,5-tetrahydrobenzo[f][1,4]oxazepine-8-carboxamide;
(S)—N-hydroxy-3-methyl-4-((R)-2-methyltetrahydro-2H-pyran-2-carbonyl)-2,3,4,5-tetrahydrobenzo[f][1,4]oxazepine-8-carboxamide;
(3S)—N-hydroxy-4-(2-isopropyltetrahydrofuran-3-carbonyl)-3-methyl-2,3,4,5-tetrahydrobenzo[f][1,4]oxazepine-8-carboxamide;
(3S)-4-(5,5-dimethyltetrahydrofuran-2-carbonyl)-N-hydroxy-3-methyl-2,3,4,5-tetrahydrobenzo[f][1,4]oxazepine-8-carboxamide;
(3S)—N-hydroxy-3-methyl-4-(2-methyltetrahydrofuran-2-carbonyl)-2,3,4,5-tetrahydrobenzo[f][1,4]oxazepine-8-carboxamide;

(3S)-4-((2R)-7-oxabicyclo[2.2.1]heptane-2-carbonyl)-N-hydroxy-3-methyl-2,3,4,5-tetrahydrobenzo[f][1,4]oxazepine-8-carboxamide;
(3S)-4-((2S)-7-oxabicyclo[2.2.1]heptane-2-carbonyl)-N-hydroxy-3-methyl-2,3,4,5-tetrahydrobenzo[f][1,4]oxazepine-8-carboxamide;
(S)—N-hydroxy-4-(1-(methoxymethyl)cyclobutane-1-carbonyl)-3-methyl-2,3,4,5-tetrahydrobenzo[f][1,4]oxazepine-8-carboxamide;
(S)—N-hydroxy-3-methyl-4-(3-((tetrahydro-2H-pyran-4-yl)oxy)propanoyl)-2,3,4,5-tetrahydrobenzo[f][1,4]oxazepine-8-carboxamide;
(S)—N-hydroxy-4-(1-(methoxymethyl)cyclopropane-1-carbonyl)-3-methyl-2,3,4,5-tetrahydrobenzo[f][1,4]oxazepine-8-carboxamide;
(S)—N-hydroxy-3-methyl-4-((1r,3S)-3-phenoxycyclobutane-1-carbonyl)-2,3,4,5-tetrahydrobenzo[f][1,4]oxazepine-8-carboxamide;
(S)—N-hydroxy-3-methyl-4-((1s,3R)-3-phenoxycyclobutane-1-carbonyl)-2,3,4,5-tetrahydrobenzo[f][1,4]oxazepine-8-carboxamide;
(S)—N-hydroxy-3-methyl-4-((2R,3S)-2-methyltetrahydro-2H-pyran-3-carbonyl)-2,3,4,5-tetrahydrobenzo[f][1,4]oxazepine-8-carboxamide;
(S)—N-hydroxy-3-methyl-4-(3-(2,2,2-trifluoroethoxy)propanoyl)-2,3,4,5-tetrahydrobenzo[f][1,4]oxazepine-8-carboxamide;
(S)—N-hydroxy-4-((2S,4S)-2-isopropyltetrahydro-2H-pyran-4-carbonyl)-3-methyl-2,3,4,5-tetrahydrobenzo[f][1,4]oxazepine-8-carboxamide;
(S)-4-benzoyl-N-hydroxy-3-methyl-2,3,4,5-tetrahydrobenzo[f][1,4]oxazepine-8-carboxamide;
(S)-4-(2-(4-fluorophenyl)-2-methylpropanoyl)-N-hydroxy-3-methyl-2,3,4,5-tetrahydrobenzo[f][1,4]oxazepine-8-carboxamide;
(S)-4-(3-(4-fluorophenyl)-2,2-dimethylpropanoyl)-N-hydroxy-3-methyl-2,3,4,5-tetrahydrobenzo[f][1,4]oxazepine-8-carboxamide;
(S)-4-((S)-2,2-dimethyltetrahydro-2H-pyran-4-carbonyl)-N-hydroxy-3-methyl-2,3,4,5-tetrahydrobenzo[f][1,4]oxazepine-8-carboxamide;
(S)-4-((R)-2,2-dimethyltetrahydro-2H-pyran-4-carbonyl)-N-hydroxy-3-methyl-2,3,4,5-tetrahydrobenzo[f][1,4]oxazepine-8-carboxamide;
(R)—N-hydroxy-3-(methoxymethyl)-4-(tetrahydro-2H-pyran-4-carbonyl)-2,3,4,5-tetrahydrobenzo[f][1,4]oxazepine-8-carboxamide;
(S)—N-hydroxy-3-(methoxymethyl)-4-(tetrahydro-2H-pyran-4-carbonyl)-2,3,4,5-tetrahydrobenzo[f][1,4]oxazepine-8-carboxamide;
N-hydroxy-4-(1-methoxycyclopropane-1-carbonyl)-2,3,4,5-tetrahydrobenzo[f][1,4]oxazepine-8-carboxamide;
N-hydroxy-4-(4-methyltetrahydro-2H-pyran-4-carbonyl)-2,3,4,5-tetrahydrobenzo[f][1,4]oxazepine-8-carboxamide;
4-(3-ethyloxetane-3-carbonyl)-N-hydroxy-2,3,4,5-tetrahydrobenzo[f][1,4]oxazepine-8-carboxamide;
N-hydroxy-4-(1-methyl-1H-pyrrole-2-carbonyl)-2,3,4,5-tetrahydrobenzo[f][1,4]oxazepine-8-carboxamide;
N-hydroxy-4-(1-methyl-1H-indole-2-carbonyl)-2,3,4,5-tetrahydrobenzo[f][1,4]oxazepine-8-carboxamide;
4-(2-(3,5-bis(trifluoromethyl)phenyl)acetyl)-N-hydroxy-2,3,4,5-tetrahydrobenzo[f][1,4]oxazepine-8-carboxamide;
4-(3,5-bis(trifluoromethyl)benzoyl)-N-hydroxy-2,3,4,5-tetrahydrobenzo[f][1,4]oxazepine-8-carboxamide;
N-hydroxy-4-(1-methyl-1H-pyrazole-3-carbonyl)-2,3,4,5-tetrahydrobenzo[f][1,4]oxazepine-8-carboxamide;
N-hydroxy-4-(2-mesitylacetyl)-2,3,4,5-tetrahydrobenzo[f][1,4]oxazepine-8-carboxamide;
N8-hydroxy-N2,N2-dimethyl-4-(tetrahydro-2H-pyran-4-carbonyl)-2,3,4,5-tetrahydrobenzo[f][1,4]oxazepine-2,8-dicarboxamide;
(R)—N-hydroxy-5-isopropyl-4-(tetrahydro-2H-pyran-4-carbonyl)-2,3,4,5-tetrahydrobenzo[f][1,4]oxazepine-8-carboxamide;
(R)—N-hydroxy-5-isopropyl-4-(oxetane-3-carbonyl)-2,3,4,5-tetrahydrobenzo[f][1,4]oxazepine-8-carboxamide;
(S)—N-hydroxy-5-isopropyl-4-(tetrahydro-2H-pyran-4-carbonyl)-2,3,4,5-tetrahydrobenzo[f][1,4]oxazepine-8-carboxamide;
(S)—N-hydroxy-5-isopropyl-4-(oxetane-3-carbonyl)-2,3,4,5-tetrahydrobenzo[f][1,4]oxazepine-8-carboxamide;
(R)—N-hydroxy-5-methyl-4-(1-methylcyclobutane-1-carbonyl)-2,3,4,5-tetrahydrobenzo[f][1,4]oxazepine-8-carboxamide;
(R)—N-hydroxy-5-methyl-4-(tetrahydro-2H-pyran-4-carbonyl)-2,3,4,5-tetrahydrobenzo[f][1,4]oxazepine-8-carboxamide;
(S)—N-hydroxy-5-methyl-4-(1-methylcyclobutane-1-carbonyl)-2,3,4,5-tetrahydrobenzo[f][1,4]oxazepine-8-carboxamide;
(S)—N-hydroxy-5-methyl-4-(tetrahydro-2H-pyran-4-carbonyl)-2,3,4,5-tetrahydrobenzo[f][1,4]oxazepine-8-carboxamide;
(S)—N-hydroxy-5-methyl-4-(4-methyltetrahydro-2H-pyran-4-carbonyl)-2,3,4,5-tetrahydrobenzo[f][1,4]oxazepine-8-carboxamide;
(S)—N-hydroxy-5-methyl-4-(3-methyloxetane-3-carbonyl)-2,3,4,5-tetrahydrobenzo[f][1,4]oxazepine-8-carboxamide;
(S)—N-hydroxy-5-methyl-4-(oxetane-3-carbonyl)-2,3,4,5-tetrahydrobenzo[f][1,4]oxazepine-8-carboxamide;
(S)—N-hydroxy-4-(3-(methoxymethyl)oxetane-3-carbonyl)-5-methyl-2,3,4,5-tetrahydrobenzo[f][1,4]oxazepine-8-carboxamide;
(S)—N-hydroxy-5-methyl-4-((S)-tetrahydro-2H-pyran-3-carbonyl)-2,3,4,5-tetrahydrobenzo[f][1,4]oxazepine-8-carboxamide;
(S)—N-hydroxy-5-methyl-4-((R)-tetrahydro-2H-pyran-3-carbonyl)-2,3,4,5-tetrahydrobenzo[f][1,4]oxazepine-8-carboxamide;
(S)—N-hydroxy-5-methyl-4-((S)-tetrahydrofuran-3-carbonyl)-2,3,4,5-tetrahydrobenzo[f][1,4]oxazepine-8-carboxamide;
(S)—N-hydroxy-5-methyl-4-((R)-tetrahydrofuran-3-carbonyl)-2,3,4,5-tetrahydrobenzo[f][1,4]oxazepine-8-carboxamide;
(S)—N-hydroxy-4-((1s,4R)-4-methoxycyclohexane-1-carbonyl)-5-methyl-2,3,4,5-tetrahydrobenzo[f][1,4]oxazepine-8-carboxamide;
(S)—N-hydroxy-4-((1r,4S)-4-methoxycyclohexane-1-carbonyl)-5-methyl-2,3,4,5-tetrahydrobenzo[f][1,4]oxazepine-8-carboxamide;
(S)—N-hydroxy-5-methyl-4-((R)-3-methyltetrahydrofuran-3-carbonyl)-2,3,4,5-tetrahydrobenzo[f][1,4]oxazepine-8-carboxamide;
(S)—N-hydroxy-5-methyl-4-((S)-3-methyltetrahydrofuran-3-carbonyl)-2,3,4,5-tetrahydrobenzo[f][1,4]oxazepine-8-carboxamide;
(S)—N-hydroxy-5-methyl-4-((R)-3-methyltetrahydro-2H-pyran-3-carbonyl)-2,3,4,5-tetrahydrobenzo[f][1,4]oxazepine-8-carboxamide;

(S)—N-hydroxy-5-methyl-4-((S)-3-methyltetrahydro-2H-pyran-3-carbonyl)-2,3,4,5-tetrahydrobenzo[f][1,4]oxazepine-8-carboxamide;
(S)—N-hydroxy-4-(4-(methoxymethyl)tetrahydro-2H-pyran-4-carbonyl)-5-methyl-2,3,4,5-tetrahydrobenzo[f][1,4]oxazepine-8-carboxamide;
(2R,5R)—N-hydroxy-4-(tetrahydro-2H-pyran-4-carbonyl)-2,3,4,5-tetrahydro-2,5-methanobenzo[f][1,4]oxazepine-8-carboxamide;
(2S,5S)—N-hydroxy-4-(tetrahydro-2H-pyran-4-carbonyl)-2,3,4,5-tetrahydro-2,5-methanobenzo[f][1,4]oxazepine-8-carboxamide;
(S)—N-hydroxy-3-methyl-4-(2-methyl-2-(tetrahydro-2H-pyran-4-yl)propanoyl)-2,3,4,5-tetrahydrobenzo[f][1,4]oxazepine-8-carboxamide;
(S)—N-hydroxy-3-methyl-4-(2-methyl-2-(pyridin-3-yl)propanoyl)-2,3,4,5-tetrahydrobenzo[f][1,4]oxazepine-8-carboxamide;
(S)-4-(1H-benzo[d]imidazole-2-carbonyl)-N-hydroxy-3-methyl-2,3,4,5-tetrahydrobenzo[f][1,4]oxazepine-8-carboxamide;
(S)—N-hydroxy-3-methyl-4-((S)-tetrahydro-2H-pyran-2-carbonyl)-2,3,4,5-tetrahydrobenzo[f][1,4]oxazepine-8-carboxamide;
(S)—N-hydroxy-3-methyl-4-((R)-tetrahydro-2H-pyran-2-carbonyl)-2,3,4,5-tetrahydrobenzo[f][1,4]oxazepine-8-carboxamide;
(S)—N-hydroxy-3-methyl-4-((R)-3-methyltetrahydrofuran-3-carbonyl)-2,3,4,5-tetrahydrobenzo[f][1,4]oxazepine-8-carboxamide;
(S)—N-hydroxy-3-methyl-4-((S)-3-methyltetrahydrofuran-3-carbonyl)-2,3,4,5-tetrahydrobenzo[f][1,4]oxazepine-8-carboxamide;
N-hydroxy-4-(1-methylcyclobutane-1-carbonyl)-2-oxo-2,3,4,5-tetrahydro-1H-benzo[e][1,4]diazepine-7-carboxamide;
(S)-3-benzyl-N-hydroxy-4-(tetrahydro-2H-pyran-4-carbonyl)-2,3,4,5-tetrahydrobenzo[f][1,4]oxazepine-8-carboxamide; or
N-hydroxy-4-(tetrahydro-2H-pyran-4-carbonyl)-3-(tetrahydro-2H-pyran-4-yl)-2,3,4,5-tetrahydrobenzo[f][1,4]oxazepine-8-carboxamide.

In an illustrative embodiment, the compound of Formula I is:
(R)—N-hydroxy-4-(tetrahydro-2H-pyran-4-carbonyl)-3-((trifluoromethoxy)methyl)-2,3,4,5-tetrahydrobenzo[f][1,4]oxazepine-8-carboxamide;
(R)—N-hydroxy-4-(4-methyltetrahydro-2H-pyran-4-carbonyl)-3-((trifluoromethoxy)methyl)-2,3,4,5-tetrahydrobenzo[f][1,4]oxazepine-8-carboxamide;
(3S)—N-hydroxy-3,5-dimethyl-4-(tetrahydro-2H-pyran-4-carbonyl)-2,3,4,5-tetrahydrobenzo[f][1,4]oxazepine-8-carboxamide;
(3S)—N-hydroxy-3,5-dimethyl-4-(4-methyltetrahydro-2H-pyran-4-carbonyl)-2,3,4,5-tetrahydrobenzo[f][1,4]oxazepine-8-carboxamide;
(S)-6-fluoro-N-hydroxy-3-methyl-4-(tetrahydro-2H-pyran-4-carbonyl)-2,3,4,5-tetrahydrobenzo[f][1,4]oxazepine-8-carboxamide; or
(S)-6-fluoro-N-hydroxy-3-methyl-4-(4-methyltetrahydro-2H-pyran-4-carbonyl)-2,3,4,5-tetrahydrobenzo[f][1,4]oxazepine-8-carboxamide.

In another embodiment of the disclosure, the compounds of Formula I are enantiomers. In some embodiments the compounds are the (S)-enantiomer. In other embodiments the compounds are the (R)-enantiomer. In some embodiment, the (R)- or (S)-enantiomeric configuration may be assigned to each molecule. In other embodiments, the (R)- or (S)-enantiomeric configuration may not be assigned to the molecules despite the enantiomeric purification or separation of the molecules. In yet other embodiments, the compounds of Formula I may be (+) or (−) enantiomers.

It should be understood that all isomeric forms are included within the present disclosure, including mixtures thereof. If the compound contains a double bond, the substituent may be in the E or Z configuration or cis or trans configuration. If the compound contains a disubstituted cycloalkyl, the cycloalkyl substituent may have a cis- or trans configuration. All tautomeric forms are also intended to be included. In some embodiment, the cis or trans configuration may be assigned to each molecule. In other embodiments, the cis or trans configuration may not be assigned to the molecules despite the chemical purification or separation of the diastereomers.

Methods of Synthesizing the Disclosed Compounds

The compounds of the present disclosure may be made by a variety of methods, including standard chemistry. Suitable synthetic routes are depicted in the schemes given below.

The compounds of Formula I may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include, but are not limited, to those methods described below. Compounds of the present disclosure can be synthesized by following the steps outlined in General Schemes 1, 2, 3, 4, and 5 which comprise different sequences of assembling intermediates 2a, 2b, 2c, 2d, 2e, 2f, 2g, 2h, 2i, 2j, 2k, 2m, 2n, 2o, 2p, 2q, 2r, 2s, 2t, 2u, 2v, 2w, 2x, 2y, 2z, 2aa, 2bb, and 2cc. Starting materials are either commercially available or made by known procedures in the reported literature or as illustrated.

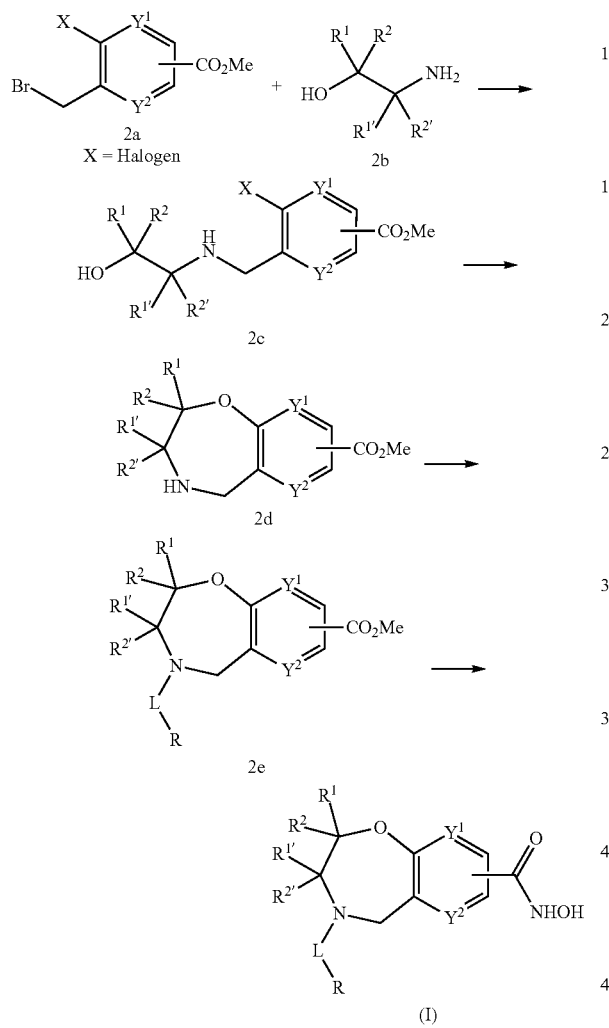

wherein L, R, $R^1$, $R^2$, $R^{1'}$, $R^{2'}$, $Y^1$ and $Y^2$ are defined as in Formula (I).

The general way of preparing target molecules of Formula (I) by using intermediates 2a, 2b, 2c, 2d, and 2e is outlined in General Scheme 1. Nucleophilic addition of alcohol 2b to Intermediate 2a using a base, e.g., potassium carbonate ($K_2CO_3$), in a solvent, e.g., acetonitrile (MeCN), provides Intermediate 2c. Cyclization of Intermediate 2c in the presence of a catalytic amount of a metal catalyst, e.g., copper iodide (CuI), palladium acetate (Pd(OAc)$_2$), etc., and a base, e.g., potassium carbonate ($K_2CO_3$), in a solvent, e.g., isopropanol (i-PrOH), optionally at elevated temperature provides Intermediate 2d. Acylation of Intermediate 2d with an acyl halide in the presence of a base, e.g., sodium hydride (NaH), and optionally at elevated temperatures provides Intermediate 2e. Alternatively, coupling of a carboxylic acid with Intermediate 2d under standard coupling conditions using a coupling reagent, e.g., 1-[bis(dimethylamino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Intermediate 2e. Intermediate 2e can also be obtained by reacting 2d with a carboxylic acid and an activating agent, e.g., 4-(4,6-dimethoxy-1,3,5-triazin-2-yl)-4-methylmorpholinium chloride (DMTMM), in a solvent, e.g., dimethylformamide (DMF). Treatment of Intermediate 2e with hydroxylamine and a base, e.g., aqueous sodium hydroxide (aq. NaOH) in a solvent, e.g., tetrahydrofuran (THF) and/or methanol (MeOH), provides compounds of Formula (I).

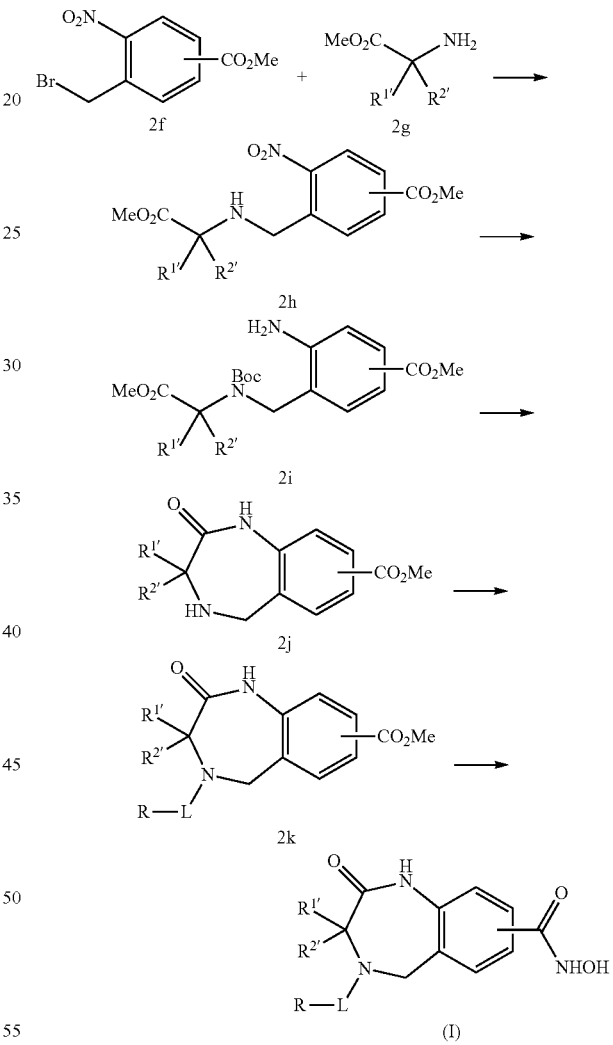

wherein L, R, $R^{1'}$, and $R^{2'}$ are defined as in Formula (I).

The general way of preparing target molecules of Formula (I) by using intermediates 2f, 2g, 2h, 2i, 2j, and 2k is outlined in General Scheme 2. Nucleophilic addition of amine 2g to Intermediate 2f using a base, e.g., N,N-diisopropylethylamine (DIEA), and in a solvent, e.g., MeCN, dichloromethane (DCM), or DMF, provides Intermediate 2h. Protection of the amine group in intermediate 2h with a typical acid labile protecting group (e.g., t-butoxycarbonyl (Boc)) using an alkyl chloride and 4-Dimethylaminopyridine (DMAP), in a solvent e.g., DCM or tetrahydrofuran (THF), followed by hydrogenation in the presence of a metal catalyst, e.g., palladium on carbon, and hydrogen ($H_2$) gas in a solvent, e.g., DCM, provides Intermediate 2i. Cyclization of Intermediate 2i in the presence of a base, e.g., potassium carbonate ($K_2CO_3$), and in a solvent, e.g., isopropanol (i-PrOH), optionally at elevated temperatures provides Intermediate 2j. Acylation of Intermediate 2j with an acyl halide in the presence of a base, e.g., sodium hydride (NaH), and optionally at elevated temperatures provides Intermediate 2k. Alternatively, coupling of a carboxylic acid with Intermediate 2j under standard coupling conditions using a coupling reagent, e.g., 1-[bis(dimethylamino)methylene]-1H-1,2,3-triazolo[4,5-b]pyridinium3-oxide hexafluorophosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Intermediate 2k. Intermediate 2k can also be obtained by reacting 2j with a carboxylic acid and an activating agent, e.g., 4-(4,6-dimethoxy-1,3,5-triazin-2-yl)-4-methylmorpholinium chloride (DMTMM), in a solvent, e.g., dimethylformamide (DMF). Treatment of Intermediate 2k with hydroxylamine and a base, e.g., aqueous sodium hydroxide (aq. NaOH) in a solvent, e.g., tetrahydrofuran (THF) and/or methanol (MeOH), provides compounds of Formula (I).

The general way of preparing target molecules of Formula (I) by using intermediates 2m, 2n, 2o, 2p, and 2q, is outlined in General Scheme 3. Sulfonylation of alcohol 2n with Intermediate 2m in the presence of a metal oxide, e.g., MgO, and in a solvent, e.g., THF and or water ($H_2O$), provides Intermediate 2o. Cyclization of Intermediate 2o in the presence of a base, e.g., sodium methoxide (NaOMe), and in a solvent, e.g., methanol (MeOH), i-PrOH, etc., provides Intermediate 2p. Acylation of Intermediate 2p with an acyl halide in the presence of a base, e.g., sodium hydride (NaH), and optionally at elevated temperatures provides Intermediate 2q. Alternatively, coupling of a carboxylic acid with Intermediate 2p under standard coupling conditions using a coupling reagent, e.g., 1-[bis(dimethylamino)methylene]-1H-1,2,3-triazolo[4,5-b]pyridinium3-oxide hexafluorophosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Intermediate 2q. Intermediate 2q can also be obtained by reacting 2p with a carboxylic acid and an activating agent, e.g., 4-(4,6-dimethoxy-1,3,5-triazin-2-yl)-4-methylmorpholinium chloride (DMTMM), in a solvent, e.g., dimethylformamide (DMF). Treatment of Intermediate 2q with hydroxylamine and a base, e.g., aqueous sodium hydroxide (aq. NaOH), in a solvent, e.g., tetrahydrofuran (THF) and/or methanol (MeOH), provides compounds of Formula (I).

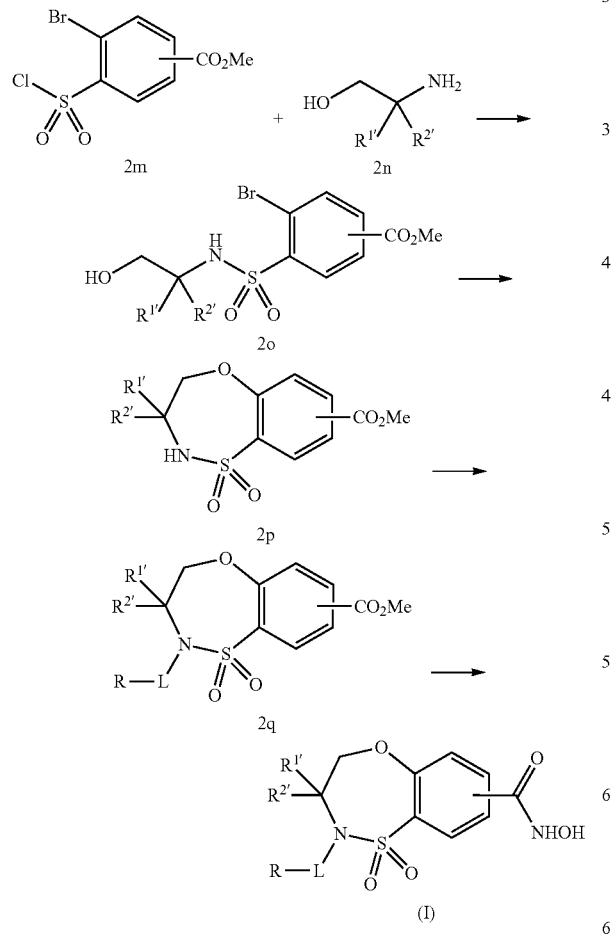

Scheme 3. General synthesis of sulfonamides described in the disclosure.

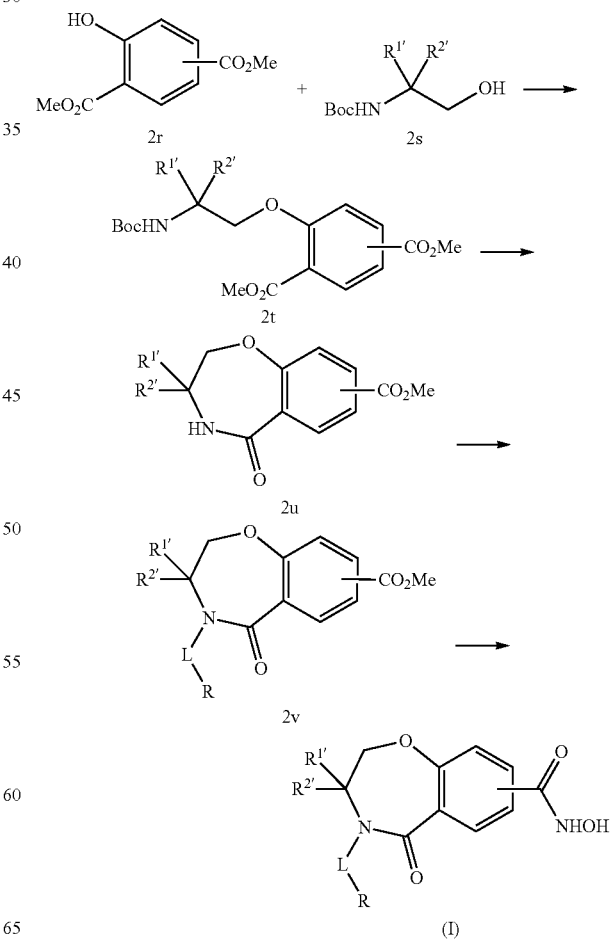

Scheme 4. General synthesis of amides described in the disclosure.

wherein L, R, $R^{1'}$, and $R^{2'}$ are defined as in Formula (I).

wherein L, R, R¹', and R²' are defined as in Formula (I).

The general way of preparing target molecules of Formula (I) by using intermediates 2r, 2s, 2t, 2u, and 2v, is outlined in General Scheme 4. Intermediate 2t can be obtained by alkylation of 2s with phenol 2r using a Mitsunobu reagent (e.g., diethyl azodicarboxylate (DEAD) or diisopropyl azodicarboxylate (DIAD)), and triphenyl phosphine in a solvent, e.g., tetrahydrofuran (THF), dichloromethane (DCM). Deprotection of intermediate 2t using a strong acid such as trifluoroacetic acid (TFA) in a solvent, e.g., dichloromethane (DCM), followed by cyclization in the presence of a base, e.g., triethylamine ($Et_3N$), and optionally in a solvent, e.g., THF, MeOH, etc., at elevated temperature provides Intermediate 2u. Acylation of Intermediate 2u with an acyl halide in the presence of a base, e.g., sodium hydride (NaH), and optionally at elevated temperatures provides Intermediate 2v. Alternatively, coupling of a carboxylic acid with Intermediate 2u under standard coupling conditions using a coupling reagent, e.g., 1-[bis(dimethylamino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Intermediate 2v. Intermediate 2v can also be obtained by reacting 2u with a carboxylic acid and an activating agent, e.g., 4-(4,6-dimethoxy-1,3,5-triazin-2-yl)-4-methylmorpholinium chloride (DMTMM), in a solvent, e.g., dimethylformamide (DMF). Treatment of Intermediate 2v with hydroxylamine and a base, e.g., aqueous sodium hydroxide (aq. NaOH) in a solvent, e.g., tetrahydrofuran (THF) and/or methanol (MeOH), provides compounds of Formula (I).

Scheme 5. General synthesis of chiral compounds described in the disclosure.

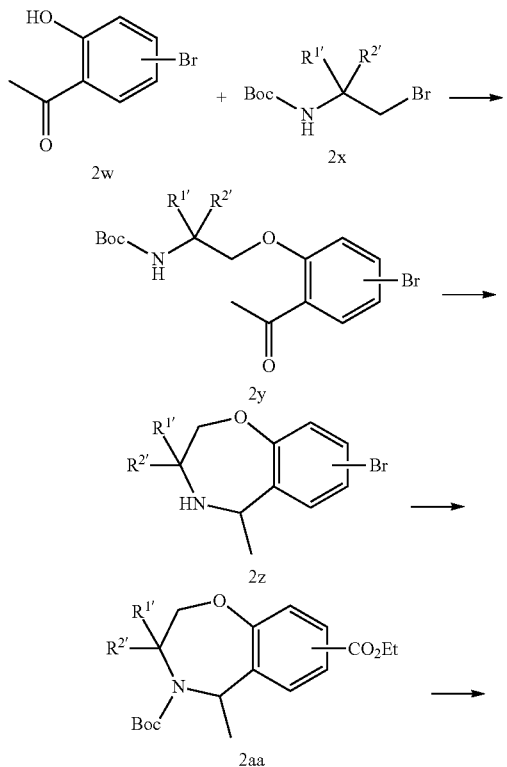

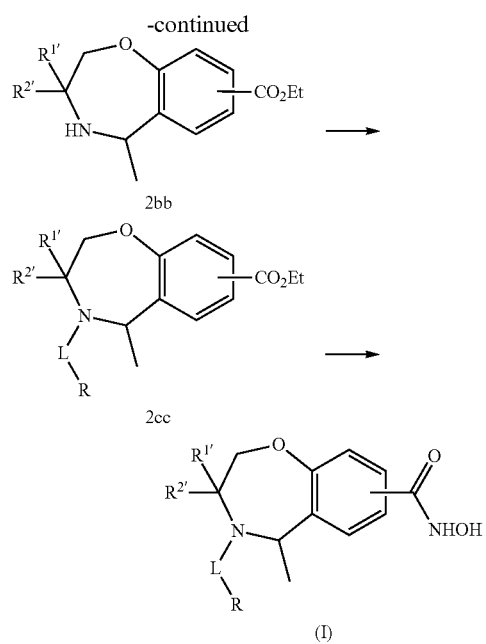

wherein L, R, R¹', and R²' are defined as in Formula (I).

The general way of preparing target molecules of Formula (I) by using intermediates 2w, 2x, 2y, 2z, 2aa, 2bb, and 2cc, is outlined in General Scheme 5. Alkylation of phenol 2w with Intermediate 2x using potassium iodide (KI) and a base, e.g., potassium carbonate ($K_2CO_3$), in a solvent, e.g., MeCN, THF, etc., provides Intermediate 2y. Deprotection of Intermediate 2y using a strong acid such as trifluoroacetic acid (TFA) in a solvent, e.g., dichloromethane (DCM) followed by cyclization via intramolecular reductive amination in the presence of sodium borohydride or sodium cyanoborohydride in a solvent, e.g., THF, MeOH, etc., provides Intermediate 2z. Protection of the amine group in intermediate 2z with a typical acid labile protecting group (e.g., t-butoxycarbonyl (Boc)) using an alkyl chloride and optionally 4-DMAP in a solvent e.g., DCM or tetrahydrofuran (THF), followed by carbonylation in the presence of a metal catalyst, e.g., [1,1'-Bis(diphenylphosphino)ferrocene]palladium(II) dichloride, and carbon monoxide (CO) gas in a solvent, e.g., DCM, provides Intermediate 2aa. Deprotection of intermediate 2aa using a strong acid such as trifluoroacetic acid (TFA) in a solvent, e.g., dichloromethane (DCM) provides Intermediate 2bb. Acylation of Intermediate 2bb with an acyl halide in the presence of a base, e.g., sodium hydride (NaH), and optionally at elevated temperatures provides Intermediate 2cc. Alternatively, coupling of a carboxylic acid with Intermediate 2bb under standard coupling conditions using a coupling reagent, e.g., 1-[bis(dimethylamino)methylene]-1H-1,2,3-triazolo[4,5-b]pyridinium3-oxide hexafluoro-phosphate (HATU), or O-benzotriazole-N,N,N',N'-tetramethyl-uronium-hexafluoro-phosphate (HBTU), and a base, e.g., triethylamine or N,N-diisopropylethylamine (DIPEA), in a solvent, e.g., dichloromethane or DMF provides Intermediate 2cc. Intermediate 2cc can also be obtained by reacting 2bb with a carboxylic acid and an activating agent, e.g., 4-(4,6-dimethoxy-1,3,5-triazin-2-yl)-4-methylmorpholinium chloride (DMTMM), in a solvent, e.g., dimethylformamide (DMF). Treatment of Intermediate 2cc with hydroxylamine and a base, e.g., aqueous sodium hydroxide (aq. NaOH), in a solvent, e.g., tetrahydrofuran (THF) and/or methanol (MeOH), provides compounds of Formula (I).

Methods of Using the Disclosed Compounds

Another aspect of the disclosure relates to a method of treating a disease associated with HDAC, e.g., HDAC6, modulation in a subject in need thereof. The method involves administering to a patient in need of treatment for diseases or disorders associated with HDAC, e.g., HDAC6, modulation an effective amount of a compound of Formula I. In an embodiment, the disease can be, but is not limited to, cancer, neurodegenerative disease, neurodevelopmental disease, inflammatory or autoimmune disease, infection, metabolic disease, hematologic disease, or cardiovascular disease.

Another aspect of the disclosure is directed to a method of inhibiting an HDAC, e.g., HDAC6. The method involves administering to a patient in need thereof an effective amount of Formula I.

The present disclosure relates to compositions capable of modulating the activity of (e.g., inhibiting) HDACs, for instance HDAC6. The present disclosure also relates to the therapeutic use of such compounds.

One therapeutic use of the compounds of the present disclosure is to treat proliferative diseases or disorders such as cancer. Cancer can be understood as abnormal or unregulated cell growth within a patient and can include but is not limited to lung cancer, ovarian cancer, breast cancer, prostate cancer, pancreatic cancer, hepatocellular cancer, renal cancer and leukemias such as acute myeloid leukemia and acute lymphoblastic leukemia. Additional cancer types include T-cell lymphoma (e.g., cutaneous T-cell lymphoma, peripheral T-cell lymphoma), and multiple myeloma.

One therapeutic use of the compounds of the present disclosure is to treat neurological diseases or disorders or neurodegeneration. Neurological disorders are understood as disorders of the nervous system (e.g., the brain and spinal cord). Neurological disorders or neurodegenerative diseases can include but are not limited to epilepsy, attention deficit disorder (ADD), Alzheimer's disease, Parkinson's Disease, Huntington's Disease, amyotrophic lateral sclerosis, spinal muscular atrophy, essential tremor, central nervous system trauma caused by tissue injury, oxidative stress-induced neuronal or axomal degeneration, and multiple sclerosis.

Another therapeutic use of the compounds of the present disclosure is to treat neurodevelopmental disorders. Neurodevelopmental disorders can include, but are not limited to, Rett syndrome.

Another therapeutic use of the compounds of the present disclosure is also to treat inflammatory diseases or disorders. Inflammation can be understood as a host's response to an initial injury or infection. Symptoms of inflammation can include but are not limited to redness, swelling, pain, heat and loss of function. Inflammation may be caused by the upregulation of pro-inflammatory cytokines such as IL-1β, and increased expression of the FOXP3 transcription factor.

Another therapeutic use of the compounds of the present disclosure is also to treat autoimmune diseases or disorders. Autoimmune disorders are understood as disorders wherein a host's own immune system responds to tissues and substances occurring naturally in the host's body. Autoimmune diseases can include but are not limited to Rheumatoid arthritis, spondylitis arthritis, psoriatic arthritis, multiple sclerosis, systemic lupus erythematosus, inflammatory bowel disease, graft versus host disease, transplant rejection, fibrotic disease, Crohn's Disease, type-1 diabetes, Eczema, and psoriasis.

Another therapeutic use of the compounds of the present disclosure is also to treat infectious diseases or disorders. Infections or infectious diseases are caused by the invasion of a foreign pathogen. The infection may be caused by, for instance, a bacteria, a fungus, or virus. For example, a bacterial infection may be caused by a *E. coli*.

Yet another therapeutic use of the compounds of the present disclosure is also to treat metabolic diseases or disorders. Metabolic diseases can be characterized as abnormalities in the way that a subject stores energy. Metabolic disorders can include but are not limited to metabolic syndrome, diabetes, obesity, high blood pressure, and heart failure.

Yet another therapeutic use of the compounds of the present disclosure is also to treat hematologic disorders. Hematologic diseases primarily affect the blood. Hematologic disorders can include but are not limited to anemia, lymphoma, and leukemia.

Yet another therapeutic use of the compounds of the present disclosure is also to treat cardiovascular diseases or disorders. Cardiovascular diseases affect the heart and blood vessels of a patient. Exemplary conditions include but are not limited to cardiovascular stress, pressure overload, chronic ischemia, infarction-reperfusion injury, hypertension, atherosclerosis, peripheral artery disease, and heart failure.

Another aspect of the present disclosure relates to a compound of Formula (I), or a pharmaceutically acceptable salt, hydrate, solvate, prodrug, stereoisomer, or tautomer thereof, for use in treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In another aspect, the present disclosure relates to the use of a compound of Formula (I), or a pharmaceutically acceptable salt, hydrate, solvate, prodrug, stereoisomer, or tautomer thereof, in the manufacture of a medicament for treating or preventing a disease associated with HDAC6 modulation. In some embodiments, the disease is cancer, neurodegenerative disease, neurodevelopmental disorder, inflammatory or autoimmune disease, infection, metabolic disease, hematologic disease, or cardiovascular disease. In some embodiments, the compound inhibits a histone deacetylase. In another embodiment, the compound inhibits a zinc-dependent histone deacetylase. In another embodiment, the compound inhibits the HDAC6 isozyme zinc-dependent histone deacetylase.

In some embodiments, the cancer is cutaneous T-cell lymphoma, peripheral T-cell lymphoma, multiple myeloma, leukemia, lung, ovarian, breast, prostate, pancreatic, hepatocellular or renal cancer. In other embodiments, the neurodegenerative disease is Alzheimer's, Huntington's, Parkinson's, Amyotrophic Lateral Sclerosis, or spinal muscular atrophy. In other embodiments, the neurodevelopmental disorder is Rett syndrome. In yet other embodiments, the inflammatory or autoimmune disease is rheumatoid arthritis, spondylitis arthritis, psoriatic arthritis, psoriasis, multiple sclerosis, systemic lupus erythematosus, inflammatory bowel diseases, graft versus host disease, transplant rejection or fibrotic disease.

The disclosed compound can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the disclosure relates to a pharmaceutical composition comprising a compound of Formula I and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present disclosure can inhibit HDACs such as HDAC6 by interacting with the zinc ($Zn^{2+}$) ion in the protein's active site via the hydroxamic acid group bound to the aromatic ring of the compound. The binding can prevent the zinc ion from interacting with its natural substrates, thus inhibiting the enzyme.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The present disclosure includes a number of unique features and advantages compared with other inhibitors of HDAC enzymes, for instance HDAC6. For instance, the present disclosure features a unique class of small molecule therapeutic agents of Formula I. The compounds were designed by using crystal structure information of HDAC ligand-protein complexes as well as advanced computational chemistry tools. These techniques led to the development of new chemical scaffolds that were iteratively refined to optimize key recognition features between the ligand and receptor known to be necessary for potency.

Definitions used in the following examples and elsewhere herein are:

Boc: t-butoxycarbonyl
BOP: (benzotriazol-1-yloxy)tris(dimethylamino)phosphonium hexafluorophosphate
$CCl_4$: carbon tetrachloride
$CDCl_3$: deuterated chloroform
$CH_2Cl_2$: methylene chloride, dichloromethane
CO (g): carbon monoxide gas
$Cs_2CO_3$: cesium carbonate
CuI: copper (I) iodide
DIEA: diisopropylethylamine
DMA: dimethylacetamide
DMC: 2-chloro-1,3-dimethylimidazolinium chloride
DMF: N,N-dimethylformamide
DMSO: dimethylsulfoxide
DMTMM: 4-(4,6-Dimethoxy-1,3,5-triazin-2-yl)-4-methylmorpholinium chloride
$Et_3N$: triethylamine
$Et_2O$: diethyl ether
EtOAc: ethyl acetate
h: hours
$H_2O$: water
HATU: 1-[bis(dimethylamino)methylene]-1H-1,2,3-triazolo[4,5-b]pyridinium 3-oxid hexafluorophosphate
HBTU: N,N,N',N'-tetramethyl-O-(1H-benzotriazol-1-yl)uronium hexafluorophosphate
HCl: hydrochloric acid
$H_4NHCO_3$: ammonium bicarbonate
Johnphos: (2-biphenyl)di-tert-butylphosphine
$K_2CO_3$: potassium carbonate
m-CPBA: 3-chloroperbenzoic acid
MeCN: acetonitrile
MeOH: methanol
$MgSO_4$: magnesium sulfate
min: minutes
$Na(CN)BH_3$: sodium cyanoborohydride
$Na_2SO_4$: sodium sulfate
$NaHCO_3$: sodium bicarbonate
$NaHSO_4$: Sodium hydrogen sulfate
NaOH: sodium hydroxide
NBS: N-bromosuccinimide
$NH_2OH$: hydroxylamine
$NH_4Cl$: ammonium chloride
$NH_4HCO_3$: ammonium bicarbonate
$Pd(dppf)Cl_2$: [1,1'-bis(diphenylphosphino)ferrocene]dichloropalladium(II)
$Pd(dppf)Cl_2.CH_2Cl_2$: [1,1'-bis(diphenylphosphino)ferrocene]dichloropalladium(II)-dichloromethane adduct
$Pd(OAc)_2$: palladium(II) acetate
pet. ether: petroleum ether
t-BuOK: potassium tert-butoxide
prep-HPLC: preparatory high pressure liquid chromatography
prep-SFC: preparatory supercritical fluid chromatography
prep-TLC: preparatory thin layer chromatography
TFA: trifluoroacetic acid
THF: tetrahydrofuran Example 1

Preparation of 4-[(2,2-Dimethyloxan-4-yl)carbonyl]-N-hydroxy-2,3,4,5-tetrahydro-1,4-benzoxazepine-8-carboxamide

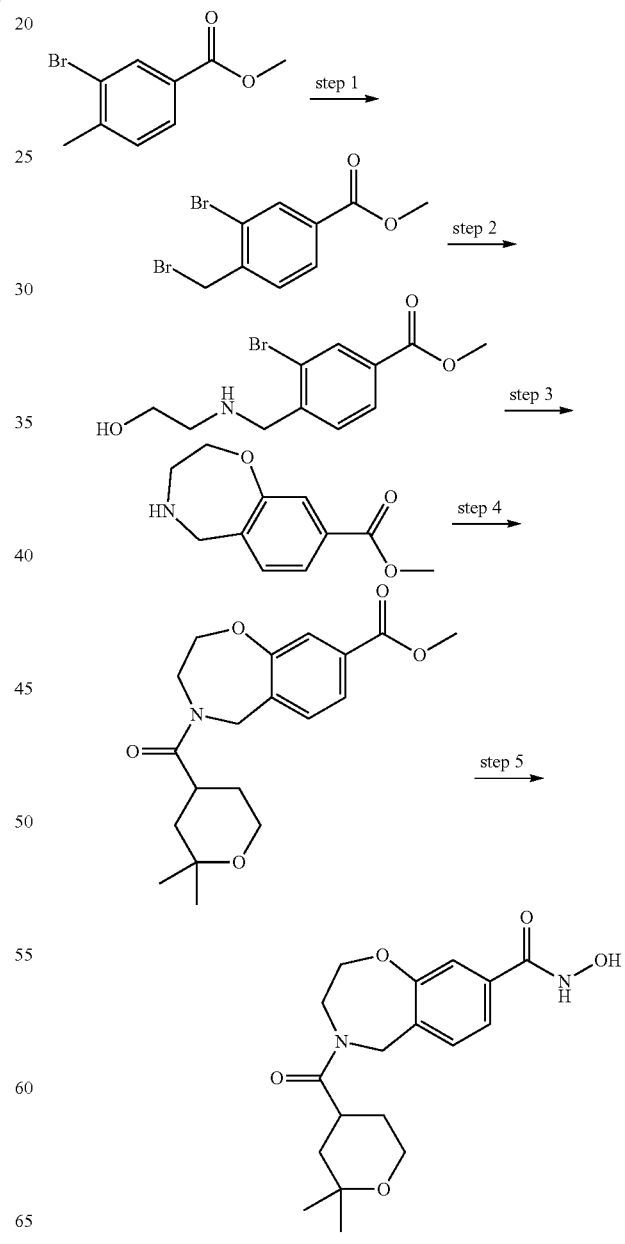

Step-1: Methyl 3-bromo-4-(bromomethyl)benzoate

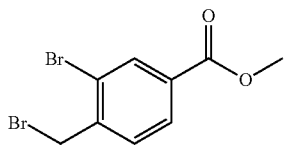

Methyl 3-bromo-4-methylbenzoate (25 g, 109.14 mmol, 1 equiv), NBS (21.5 g, 120.80 mmol, 1.11 equiv), benzoyl peroxide (146 mg, 0.57 mmol, 0.01 equiv), and CCl$_4$ (120 mL) were placed in a 250-mL round-bottom flask. The resulting solution was stirred overnight at 85° C. in an oil bath. The resulting mixture was cooled and concentrated under vacuum. The residue was purified by silica gel chromatography (EtOAc/pet. ether, 1:10) to afford the title compound as a white solid (20 g) and used without further purification.

Step-2: Methyl 3-bromo-4-((2-hydroxyethylamino)methyl)benzoate

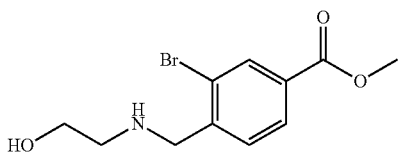 [SMILES: COC(=O)c1ccc(CNCCO)c(Br)c1]

Methyl 3-bromo-4-(bromomethyl)benzoate (20 g, 64.94 mmol, 1 equiv), potassium carbonate (26.9 g, 194.63 mmol, 3 equiv), MeCN (100 mL), and 2-aminoethan-1-ol (4.76 g, 77.93 mmol, 1.20 equiv) were placed in a 250-mL round-bottom flask. The resulting solution was stirred for 2 h at −5° C. The resulting mixture was concentrated under vacuum, washed with water (50 mL) and EtOAc (50 mL). The organic layer was concentrated under vacuum and were placed in a 250-mL round-bottom flask. (MeOH/CH$_2$Cl$_2$, 1:20) to afford the title compound as a light yellow oil (16 g, 56% yield over 2 steps). MS: (ES, m/z): 288 [M+H]$^+$.

Step-3: Methyl 2,3,4,5-tetrahydrobenzo[f][1,4]oxazepine-8-carboxylate

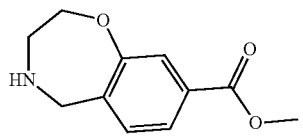

Methyl 3-bromo-4-[[(2-hydroxyethyl)amino]methyl]benzoate (7 g, 24.29 mmol, 1 equiv), potassium carbonate (6.6 g, 47.75 mmol, 1.97 equiv), CuI (912 mg, 4.79 mmol, 0.20 equiv), and isopropanol (100 mL) were placed in a 250-mL round-bottom flask. The resulting solution was stirred overnight at 110° C. in an oil bath. The solution was cooled and the solids were filtered out. The filtrate was concentrated under vacuum and purified by silica gel chromatography (EtOAc/pet. ether, 1:1) to afford the title compound as a yellow oil (3 g, 60% yield). $^1$H-NMR (300 MHz, CDCl$_3$) δ(ppm): 7.70-7.68 (t, 2H), 7.26-7.22 (t, 1H), 4.13-4.09 (t, 2H), 4.05 (s, 2H), 3.93 (s, 3H), 3.50 (s, 1H), 3.30-3.28 (t, 2H). MS: (ES, m/z): 208 [M+H]$^+$.

Step-4: Methyl 4-[(2,2-dimethyloxan-4-yl)carbonyl]-2,3,4,5-tetrahydro-1,4-benzoxazepine-8-carboxylate

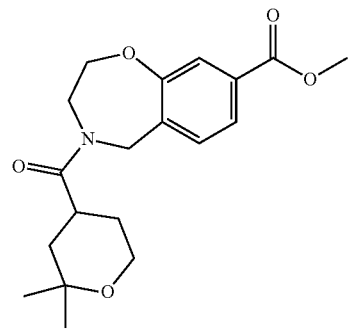 [SMILES: COC(=O)c1ccc2c(c1)OCCN(C(=O)C1CCOC(C)(C)C1)C2]

Into a 25-mL round-bottom flask, was placed 2,2-dimethyloxane-4-carboxylic acid (31 mg, 0.19596 mmol, 1 equiv), methyl 2,3,4,5-tetrahydro-1,4-benzoxazepine-8-carboxylate (40 mg, 0.19303 mmol, 1 equiv), BOP (130 mg, 0.29647 mmol, 1.50 equiv), Et$_3$N (30 mg, 0.29647 mmol, 1.50 equiv) and DMF (5 mL). The resulting mixture was stirred for 4 h at 45° C. in an oil bath. The reaction mixture was cooled to 10° C. with a water/ice bath. The reaction was quenched by the addition of sat. NH$_4$Cl/H$_2$O. The resulting solution was extracted with EtOAc (3×30 mL) and dried over anhydrous Na$_2$SO$_4$. The solids were filtered out and the filtrate was concentrated under vacuum. The residue was purified by silica gel chromatography (EtOAc/pet. ether, 1:5) to afford the title compound as yellow oil (60 mg). MS: (ES, m/z): 348 [M+H]$^+$.

Step-5: 4-[(2,2-Dimethyloxan-4-yl)carbonyl]-N-hydroxy-2,3,4,5-tetrahydro-1,4-benzoxazepine-8-carboxamide

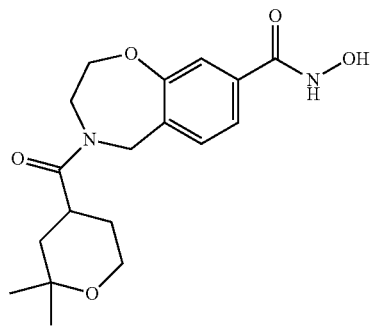 [SMILES: CC1(C)CC(C(=O)N2CCOc3cc(C(=O)NO)ccc3C2)CCO1]

Into a 10-mL round-bottom flask, was placed methyl 4-[(2,2-dimethyloxan-4-yl)carbonyl]-2,3,4,5-tetrahydro-1,4-benzoxazepine-8-carboxylate (60 mg, 0.17 mmol, 1 equiv), NH$_2$OH (50% in water, 343 mg, 30 equiv), aq. 1N NaOH (0.346 mL, 2 equiv), and MeOH/THF (1:4, 2 mL). The resulting solution was stirred for 2 h at 25° C. The pH value of the solution was adjusted to 6 with HCl (3N). The crude product was purified by Prep-HPLC (Column:

XBridge RP C18 OBD, 5 μm, 19×150 mm; Mobile Phase A: Water/10 mmol HN$_4$HCO$_3$; Mobile Phase B: MeCN; Flow rate: 25 mL/min; Gradient: 5% B to 47% B in 7 min; Detector, UV 254 nm) to afford the title compound as a white solid (32 mg, 53% yield). $^1$H-NMR (400 MHz, DMSO-d$_6$) δ(ppm): 11.18 (s, 1H), 7.37-7.49 (m, 1H), 7.30-7.32 (t, 2H), 4.68-4.89 (m, 1H), 4.59-4.61 (d, 1H), 4.20-4.24 (t, 1H), 4-4.05 (m, 1H), 3.92-3.94 (d, 1H), 3.62-3.68 (m, 1H), 3.57-3.59 (t, 2H), 3-3.13 (t, 1H), 1.26-1.44 (m, 4H), 1.18-1.19 (d, 3H), 1.04-1.12 (t, 3H). MS: (ES, m/z): 349 [M+H]$^+$.

Example 2

Preparation of 2-methyl-2-(pyridin-2-yl)propanoic acid

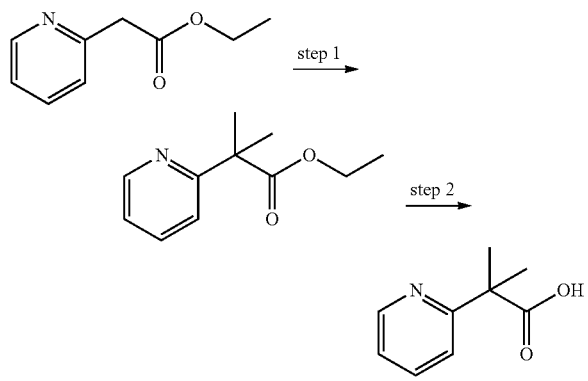

Step-1: Ethyl 2-methyl-2-(pyridin-2-yl)propanoate

Into a 40-mL vial purged and maintained with an inert atmosphere of nitrogen, was placed ethyl 2-(pyridin-2-yl)acetate (500 mg, 3.03 mmol, 1 equiv), THF (10 mL) and t-BuOK (7.5 mL, 2.50 equiv, 1M). The resulting mixture was stirred for 1 h at 20° C. This was followed by the addition of iodomethane (3.4 g, 23.95 mmol, 8 equiv) dropwise with stirring at 0° C. over 10 min. The mixture was allowed to react for an additional 3 h at 20° C. The reaction was then quenched by the addition of water (20 mL). The resulting solution was extracted with EtOAc (3×20 mL), washed with brine (2×20 mL) and dried over anhydrous Na$_2$SO$_4$. The solids were filtered out. The filtrate was concentrated under vacuum to afford the title compound as yellow oil (500 mg, 85% yield). MS: (ES, m/z): 194 [M+H]$^+$.

Step-2: Methyl-2-(pyridin-2-yl)propanoic acid

Into a 100-mL round-bottom flask, was placed methyl 2-methyl-2-(pyridin-2-yl)propanoate (4 g, 22.32 mmol, 1 equiv), MeOH (50 mL), water (15 mL) and NaOH (4.1 g, 102.50 mmol, 5 equiv). The resulting solution was stirred for 6 h at 20° C. The reaction mixture was concentrated under vacuum. The pH value of the solution was adjusted to 2 with 2N HCl. The resulting solution was extracted with EtOAc (3×50 mL), washed with brine (2×50 mL) and dried over anhydrous Na$_2$SO$_4$. The solids were filtered out. The filtrate was concentrated under vacuum to afford the title compound as a light brown solid which was used without further purification. MS: (ES, m/z): 166 [M+H]$^+$.

TABLE 1

The following compound was prepared according to the methods of Examples 1 and 2.

| Structure | Found M + H | $^1$H-NMR (300 MHz, DMSO-d$_6$) δ(ppm) |
|---|---|---|
| 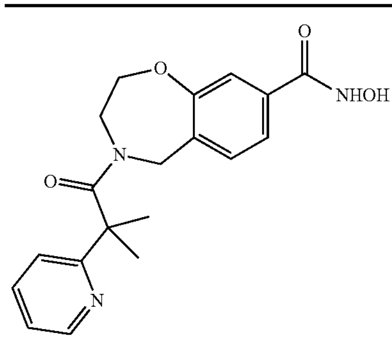 | (ES, m/z): 356 [M + H]$^+$ | 11.13-11.20 (s, 1H), 8.48 (s, 1H), 7.51 (s, 1H), 7.27 (m, 5H), 4.24 (s, 2H), 3.27-3.34 (s, 2H), 2.82 (s, 2H), 1.66 (s, 6H) |

Example 3

Preparation of 4-[(2,6-Dimethylphenyl)carbonyl]-N-hydroxy-2,3,4,5-tetrahydro-1,4-benzoxazepine-8-carboxamide

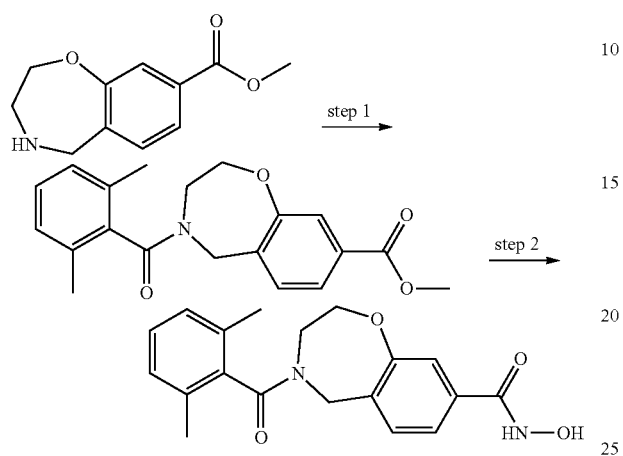

Step-1: 4-[(2,6-Dimethylphenyl)carbonyl]-2,3,4,5-tetrahydro-1,4-benzoxazepine-8-carboxylate

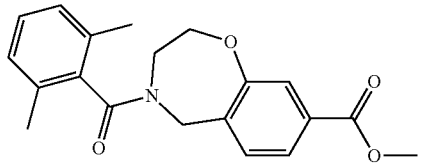 [SMILES: COC(=O)c1ccc2c(c1)OCCN(C(=O)c1c(C)cccc1C)C2]

Into a 25-mL round-bottom flask, was placed methyl 2,3,4,5-tetrahydro-1,4-benzoxazepine-8-carboxylate (72.45 mg, 0.35 mmol, 1 equiv) and $CH_2Cl_2$ (8 mL). This was followed by the addition of DIEA (124.24 mg, 0.96 mmol, 2 equiv) and DMC (97.98 mg, 1.20 equiv) at 0° C. The mixture was stirred for 5 min at room temperature. To the mixture was added 2,6-dimethylbenzoic acid (100 mg, 0.67 mmol, 1 equiv) dropwise with stirring. The resulting solution was stirred for 8 h at room temperature. The reaction was then quenched by the addition of water (2 mL). The resulting solution was extracted with $CH_2Cl_2$ (3×10 mL), dried over anhydrous $Na_2SO_4$ and concentrated under vacuum. The residue was purified by silica gel chromatography (EtOAc/pet. ether, 1:1) to afford the title compound as a light yellow oil (86 mg, 72% yield). MS: (ES, m/z): 340 $[M+H]^+$.

Step-2: 4-[(2,6-Dimethylphenyl)carbonyl]-N-hydroxy-2,3,4,5-tetrahydro-1,4-benzoxazepine-8-carboxamide

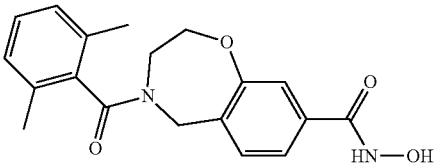 [SMILES: Cc1cccc(C)c1C(=O)N1CCOc2cc(C(=O)NO)ccc2C1]

Into a 25-mL round-bottom flask, was placed methyl 4-[(2,6-dimethylphenyl)carbonyl]-2,3,4,5-tetrahydro-1,4-benzoxazepine-8-carboxylate (86 mg, 0.25 mmol, 1 equiv), MeOH/THF (1:4, 1.5 mL), $NH_2OH$ (50% in water, 418 mg, 12.68 mmol, 50 equiv), aq. 1N NaOH (0.51 mL, 2 equiv). The resulting solution was stirred for 1 h at room temperature. The reaction mixture was cooled to 0° C. with a water/ice bath. The pH value of the solution was adjusted to 6 with HCl (6N). The crude product was purified by Prep-HPLC (Column: HSS C18 OBD, 1.8 µm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254 nm) to afford the title compound as a white solid (36 mg, 31% yield). $^1$H-NMR (400 MHz, DMSO-$d_6$) δ(ppm): 11.21 (s, 1H), 7.05-7.42 (m, 5H), 4.89 (s, 1H), 3.95-4.31 (m, 4H), 3.47-3.49 (m, 1H), 2.04 (s, 4H), 1.86 (s, 2H). MS: (ES, m/z): 341 $[M+H]^+$.

TABLE 2

The following compounds were prepared according to the method of Example 3.

| Structure | Found M + H | $^1$H-NMR (400 MHz, DMSO-$d_6$) δ(ppm) |
|---|---|---|
| 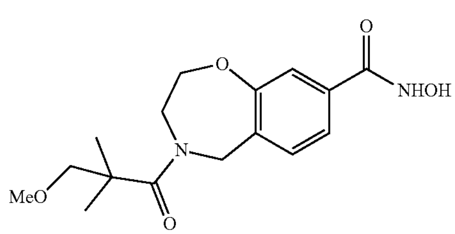 | (ES, m/z): 323 $[M + H]^+$ | 11.17 (s, 1H), 7.28-7.39 (m, 3H), 4.62 (s, 2H), 4.17-4.20 (m, 2H), 3.96-3.97 (m, 2H), 3.33 (s, 2H), 3.15 (s, 3H), 1.14 (s, 6H) |

TABLE 2-continued

The following compounds were prepared according to the method of Example 3.

| Structure | Found M + H | ¹H-NMR (400 MHz, DMSO-$d_6$) δ(ppm) |
|---|---|---|
| 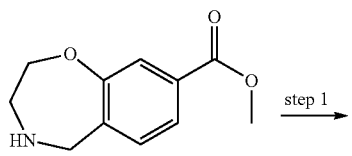 | (ES, m/z): 347 [M + H]⁺ | 11.17 (m, 1H), 9.04 (s, 1H), 7.21-7.48 (m, 3H), 4.78 (s, 1H), 4.58 (s, 1H), 4.11-4.26 (m, 4H), 3.84-3.91 (m, 2H), 2.99-3.16 (m, 1H), 180-1.82 (m, 4H), 1.61-1.68 (m, 2H), 1.34-1.36 (m, 1H), 1.12-1.15 (m, 1H) |

Example 4

Preparation of N-Hydroxy-4-[[3-(propylamino)-1-benzothiophen-2-yl]carbonyl]-2,3,4,5-tetrahydro-1,4-benzoxazepine-8-carboxamide

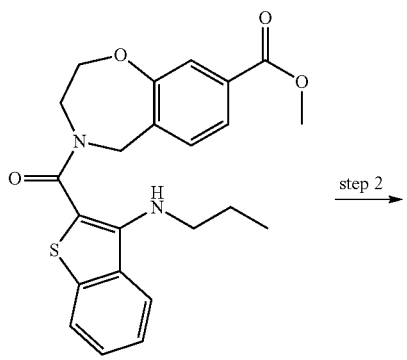

Step-1: Methyl 4-[[3-(propylamino)-1-benzothiophen-2-yl]carbonyl]-2,3,4,5-tetrahydro-1,4-benzoxazepine-8-carboxylate

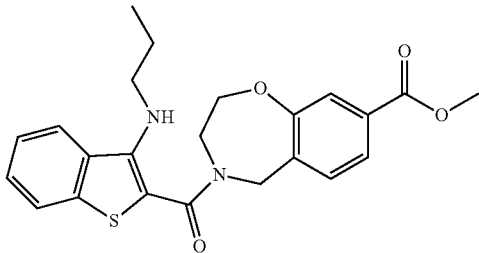 [SMILES: CCCNc1c(C(=O)N2CCOc3cc(C(=O)OC)ccc3C2)sc2ccccc12]

A mixture of methyl 2,3,4,5-tetrahydro-1,4-benzoxazepine-8-carboxylate (30 mg, 0.14 mmol, 1 equiv), lithium 3-(propylamino)benzo[b]thiophene-2-carboxylate (36 mg, 0.15 mmol, 1 equiv), HATU (66 mg, 0.17 mmol, 1.20 equiv), DIEA (57 mg, 0.44 mmol, 3 equiv) and DMF (2 mL) was stirred for 2 h at room temperature. The reaction was then quenched by the addition of water (2 mL). The resulting solution was extracted with $CH_2Cl_2$ (5×5 mL) and washed with brine. The organic layer was dried over anhydrous $Na_2SO_4$ filtered and concentrated under vacuum to afford the title compound as yellow oil (15 mg, 24% yield) which was used without further purification. MS: (ES, m/z): 425 [M+H]⁺.

Step-2: N-Hydroxy-4-[[3-(propylamino)-1-benzothiophen-2-yl]carbonyl]-2,3,4,5-tetrahydro-1,4-benzoxazepine-8-carboxamide

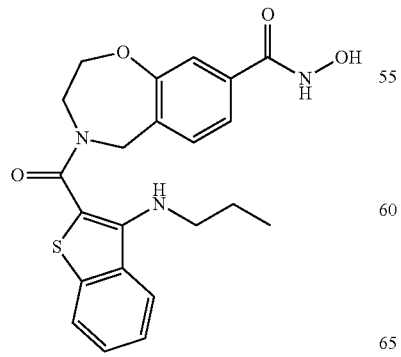

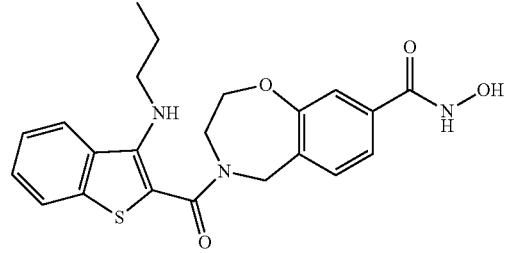 [SMILES: CCCNc1c(C(=O)N2CCOc3cc(C(=O)NO)ccc3C2)sc2ccccc12]

Into a 8-mL round-bottom flask, was placed methyl 4-[[3-(propylamino)-1-benzothiophen-2-yl]carbonyl]-2,3,4, 5-tetrahydro-1,4-benzoxazepine-8-carboxylate (13 mg, 0.03 mmol, 1 equiv), MeOH/THF (1:4, 0.5 mL), aq. 1N NaOH (0.062 mL, 2 equiv), $NH_2OH$ (50% in water, 243 mg, 120 equiv). The resulting solution was stirred for 5 h at room temperature. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254 nm) to afford the title compound as a yellow solid (8 mg, 48% yield). $^1$H-NMR (400 MHz, DMSO-$d_6$) δ(ppm): 11.20 (s, 1H), 8.05-8.07 (d, J=8.0 Hz, 1H), 7.80-7.82 (d, J=7.2 Hz, 1H), 7.34-7.47 (m, 4H), 7.12-7.15 (m, 1H), 4.80 (s, 2H), 4.19 (s, 2H), 3.93 (s, 1H), 2.85-2.88 (t, $J_1$=7.2 Hz, $J_2$=14.4 Hz, 2H), 1.35-1.44 (m, 2H), 0.64-0.67 (t, $J_1$=7.2 Hz, $J_2$=14.4 Hz, 3H). MS: (ES, m/z): 426 [M+H]$^+$.

Example 5

Preparation of lithium 3-(propylamino)benzo[b]thiophene-2-carboxylate

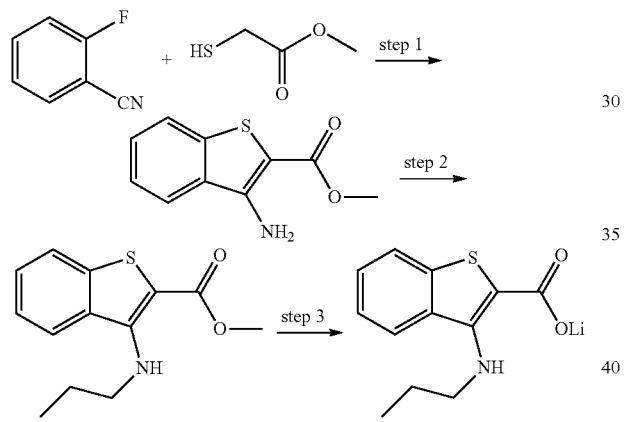

Step-1: Methyl 3-amino-1-benzothiophene-2-carboxylate

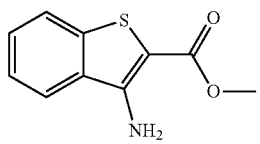

Into a 250-mL round-bottom flask, was placed a solution of 2-fluorobenzonitrile (10 g, 82.57 mmol, 1 equiv), methyl 2-sulfanylacetate (17.5 g, 164.87 mmol, 2 equiv) in DMF (30 mL). This was followed by the addition of a solution of t-BuOK (18.51 g, 164.96 mmol, 2 equiv) in DMF (50 mL) dropwise with stirring at 0° C. The resulting mixture was stirred for 1 h at room temperature and poured into water/ice. The solid was collected by filtration and dried to afford the title compound as a yellow solid (13.5 g) which was used without any purification. MS: (ES, m/z): 208 [M+H]$^+$.

Step-2: Methyl 3-(propylamino)-1-benzothiophene-2-carboxylate

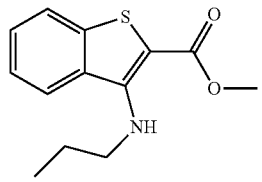 [SMILES: CCCNc1c(C(=O)OC)sc2ccccc12]

Into a 25-mL round-bottom flask, was placed methyl 3-amino-1-benzothiophene-2-carboxylate (1 g, 4.83 mmol, 1 equiv), DMF (10 mL), sodium hydride (193 mg, 8.04 mmol, 1 equiv), after stirring for 0.5 h, 1-iodopropane (740 mg, 4.35 mmol, 0.90 equiv) was added. The resulting mixture was stirred for 2 days at room temperature. The reaction was then quenched by the addition of water (10 mL). The resulting solution was extracted with $CH_2Cl_2$ (5×20 mL), washed with brine (3×20 mL) and dried over anhydrous $Na_2SO_4$. The solids were filtered out. The filtrate was concentrated under vacuum. The crude product was purified by silica gel chromatography (Gradient 0-20% EtOAc/pet. ether) to afford the title compound as a yellow solid (0.8 g, 66% yield). MS: (ES, m/z): 250 [M+H]$^+$.

Step-3: Lithium 3-(propylamino)benzo[b]thiophene-2-carboxylate

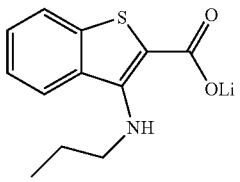

Into a 100-mL round-bottom flask, was placed methyl 3-(propylamino)-1-benzothiophene-2-carboxylate (200 mg, 0.80 mmol, 1 equiv), MeOH/$H_2O$ (10 mL, 1:1) and lithium hydroxide (193 mg, 8.06 mmol, 10 equiv). The resulting solution was stirred for 3 h at 70° C. in an oil bath. The reaction mixture was concentrated under vacuum to afford the title compound as a yellow solid (0.39 g) which was used without further purification. MS: (ES, m/z): 236 [M−Li+H]$^+$.

Example 6

Preparation of lithium 3-(dimethylamino)benzo[b]thiophene-2-carboxylate

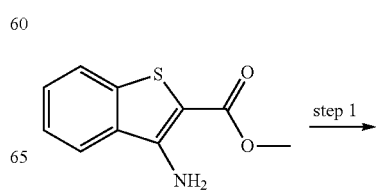

-continued

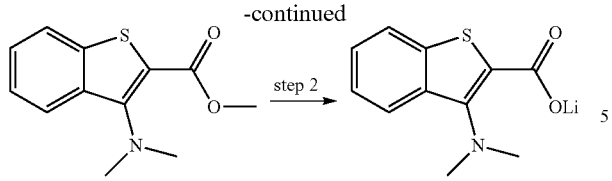

Step-1: Methyl 3-(dimethylamino)-1-benzothiophene-2-carboxylate

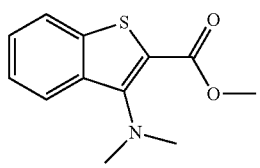 [SMILES: COC(=O)c1sc2ccccc2c1N(C)C]

Into a 20-mL sealed tube, was placed methyl 3-amino-1-benzothiophene-2-carboxylate (400 mg, 1.93 mmol, 1 equiv), DMF (5 mL), sodium hydride (77 mg, 1.93 mmol, 2 equiv, 60%) and iodomethane (0.8 mL). The resulting solution was stirred for 15 min at 150° C. in a microwave reactor. The reaction was then quenched by the addition of water (10 mL). The resulting solution was extracted with $CH_2Cl_2$ (3×5 mL) and dried over anhydrous $Na_2SO_4$. The solids were filtered out. The filtrate was concentrated under vacuum and purified by silica gel chromatography (EtOAc/pet. ether, 1:1) to afford the title compound as a yellow oil (0.13 g, 29% yield). MS: (ES, m/z): 236 [M+H]$^+$.

Step-2: Lithium 3-(dimethylamino)benzo[b]thiophene-2-carboxylate

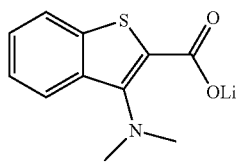

Into a 25-mL round-bottom flask, was placed methyl 3-(dimethylamino)-1-benzothiophene-2-carboxylate (130 mg, 0.55 mmol, 1 equiv), LiOH (130 mg, 5.43 mmol, 10 equiv) and MeOH/$H_2O$ (5 mL/2 mL). The mixture was stirred for 5 h at 70° C. in an oil bath. The reaction mixture was concentrated under vacuum to afford the title compound as a yellow solid (0.1 g) which was used without purification. MS: (ES, m/z): 222 [M+Li+H]$^+$.

Example 7

Preparation of sodium 2-[tert-butoxy)carbonyl]-5-oxa-2-azaspiro[3.4]octane-7-carboxylic acid

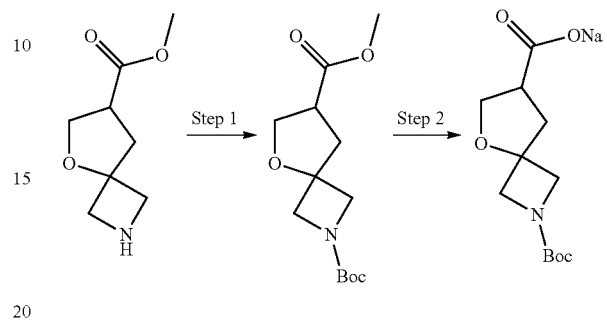

Step-1: 2-tert-Butyl 7-methyl 5-oxa-2-azaspiro[3.4]octane-2,7-dicarboxylate

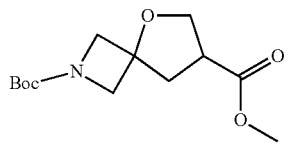 [SMILES: COC(=O)C1COC2(C1)CN(C(=O)OC(C)(C)C)C2]

Into a 25-mL round-bottom flask, was placed methyl 5-oxa-2-azaspiro[3.4]octane-7-carboxylate (248 mg, 1.45 mmol, 1 equiv), $Et_3N$ (439.44 mg, 4.34 mmol, 3 equiv), di-tert-butyl-dicarboxylate (316.2 mg, 3.17 mmol, 1 equiv) and $CH_2Cl_2$ (5 mL). The resulting solution was stirred overnight at room temperature and then concentrated under vacuum. The residue was purified by silica gel chromatography (MeOH/$CH_2Cl_2$, 1:20) to afford the title compound as a light yellow solid (205 mg, 52% yield). MS: (ES, m/z): 216 [M+H]$^+$.

Step-2: Sodium 2-[(tert-butoxy)carbonyl]-5-oxa-2-azaspiro[3.4]octane-7-carboxylic acid

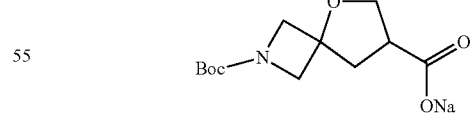

Into a 50-mL round-bottom flask, was placed 2-tert-butyl 7-methyl 5-oxa-2-azaspiro[3.4]octane-2,7-dicarboxylate (100 mg, 0.37 mmol, 1 equiv), THF/$H_2O$ (2 mL/2 mL), and NaOH (0.74 mL, 2 equiv, 1N). The resulting solution was stirred for 3 h at room temperature. The reaction mixture was concentrated under vacuum to afford the title compound as a yellow solid (110 mg) which was used without further purification. MS: (ES, m/z): 258 [M+H—Na$^+$]$^+$.

Example 8

Preparation of 2-(tert-butoxycarbonyl)-5-thia-2-azaspiro[3.4]octane-7-carboxylic acid 5,5-dioxide

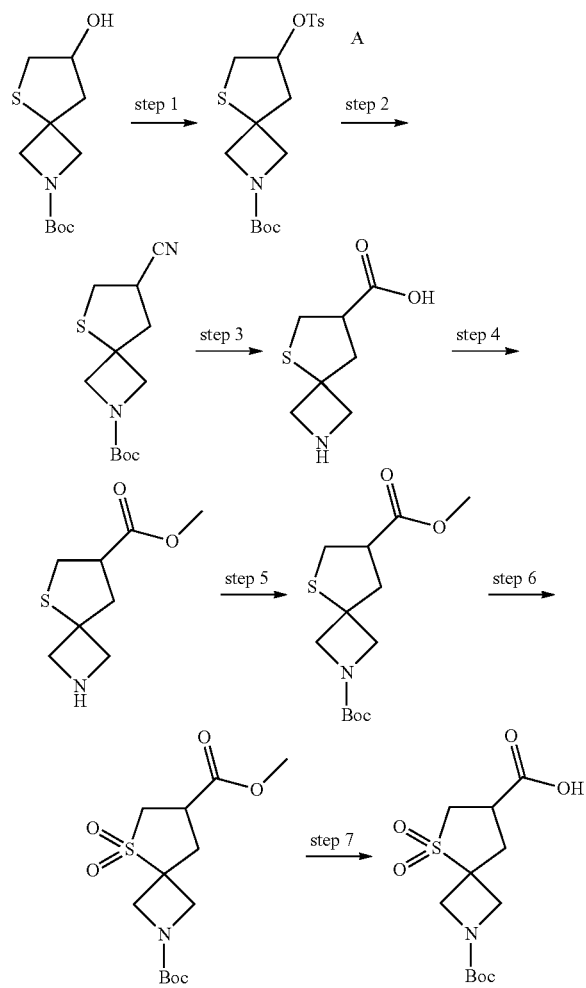

Step-1: tert-Butyl 7-[[(4-methylbenzene)sulfonyl]oxy]-5-thia-2-azaspiro[3.4]octane-2-carboxylate

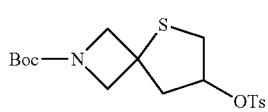 [SMILES: Cc1ccc(S(=O)(=O)OC2CSC3(C2)CN(C(=O)OC(C)(C)C)C3)cc1]

Into a 250-mL round-bottom flask purged and maintained with an inert atmosphere of nitrogen, was placed tert-butyl 7-hydroxy-5-thia-2-azaspiro[3.4]octane-2-carboxylate (8 g, 32.61 mmol, 1 equiv), m-toluenesulfonyl chloride (6.8 g, 35.67 mmol, 1.10 equiv), $CH_2Cl_2$ (100 mL) and 4-dimethylaminopyridine (7.9 g, 64.66 mmol, 2 equiv). The solution was stirred for 4 h at 20° C. The solution was diluted with $CH_2Cl_2$ (100 mL) and washed with 0.5M HCl (2×50 mL) and brine (3×50 mL). The mixture was dried over anhydrous $Na_2SO_4$. The solids were filtered out. The filtrate was concentrated under vacuum to afford the title compound as a yellow solid (8.5 g, 65% yield) which was used without further purification. MS: (ES, m/z): 400 [M+H]+.

Step-2: tert-Butyl 7-cyano-5-thia-2-azaspiro[3.4]octane-2-carboxylate

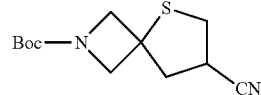 [SMILES: CC(C)(C)OC(=O)N1CC2(CC(C#N)CS2)C1]

Into a 250-mL round-bottom flask purged and maintained with an inert atmosphere of nitrogen, was placed tert-butyl 7-[[(4-methylbenzene)sulfonyl]oxy]-5-thia-2-azaspiro[3.4]octane-2-carboxylate (8.5 g, 21.28 mmol, 1 equiv), DMSO (100 mL) and potassium cyanide (2 g, 30.71 mmol, 1.50 equiv). The resulting mixture was stirred for 15 h at 90° C. in an oil bath. The reaction was then quenched by the addition of 200 mL of water/ice. The resulting solution was extracted with EtOAc (4×100 mL), washed with brine (2×100 mL) and dried over anhydrous $Na_2SO_4$. The solids were filtered out. The filtrate was concentrated under vacuum. The residue was purified by silica gel chromatography (EtOAc/pet. ether, 1:5) to afford the title compound as colorless oil (3 g, 55% yield). MS: (ES, m/z): 255 [M+H]+.

Step-3: 5-Thia-2-azaspiro[3.4]octane-7-carboxylic acid hydrochloride

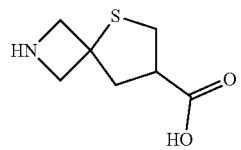 [SMILES: O=C(O)C1CSC2(CNC2)C1]

Into a 50-mL round-bottom flask, was placed tert-butyl 7-cyano-5-thia-2-azaspiro[3.4]octane-2-carboxylate (3 g, 11.79 mmol, 1 equiv) and conc. HCl (30 mL). The above solution was stirred for 12 h at 60° C. in an oil bath. The resulting mixture was concentrated under vacuum to afford the title compound as light yellow oil (2.8 g) which was used without further purification. MS: (ES, m/z): 174 [M+H]+.

Step-4: Methyl 5-thia-2-azaspiro[3.4]octane-7-carboxylate hydrochloride

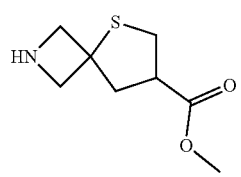

Into a 100-mL round-bottom flask purged and maintained with an inert atmosphere of nitrogen, was placed MeOH (50 mL). This was followed by the addition of thionyl chloride (2.37 g, 20.08 mmol, 1.50 equiv) dropwise with stirring at 0° C. over 10 min. After the addition was finished the solution was stirred for an additional 30 min at 20° C. To this was added a solution of 5-thia-2-azaspiro[3.4]octane-7-carboxylic acid hydrochloride (2.8 g, 13.35 mmol, 1 equiv) in MeOH (5 mL) dropwise at 0° C. over 10 min. The resulting solution was stirred for an additional 2 h at 70° C. in an oil bath. The reaction mixture was concentrated under vacuum to afford the title compound as yellow oil (2.5 g, 84% yield) which was used without further purification. MS: (ES, m/z): 188 [M+H]+.

Step-5: 2-tert-Butyl 7-methyl 5-thia-2-azaspiro[3.4]octane-2,7-dicarboxylate

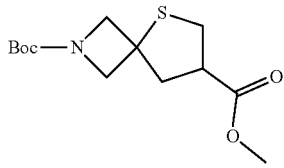

Into a 100-mL round-bottom flask, was placed methyl 5-thia-2-azaspiro[3.4]octane-7-carboxylate (2.5 g, 13.35 mmol, 1 equiv), di-tert-butyl dicarbonate (2.9 g, 13.29 mmol, 1.20 equiv), CH$_2$Cl$_2$ (50 mL), and Et$_3$N (3.4 g, 33.60 mmol, 3 equiv). The above mixture was stirred for 3 h at 20° C. and then diluted with CH$_2$Cl$_2$ (100 mL). The mixture was washed with brine (3×50 mL) and dried over anhydrous Na$_2$SO$_4$. The solids were filtered out and the filtrate was concentrated under vacuum. The residue was purified by silica gel chromatography (EtOAc/pet. ether, 8:1) to afford the title compound as a white solid (2.6 g, 68% yield). MS: (ES, m/z): 288 [M+H]+.

Step-6: 2-(tert-Butyl) 7-methyl 5-thia-2-azaspiro[3.4]octane-2,7-dicarboxylate 5,5-dioxide

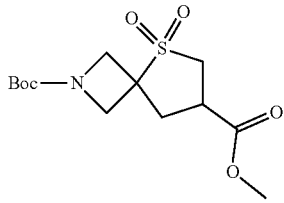 [SMILES: COC(=O)C1CC2(CN(C(=O)OC(C)(C)C)C2)S(=O)(=O)C1]

Into a 100-mL round-bottom flask purged and maintained with an inert atmosphere of nitrogen, was placed 2-tert-butyl 7-methyl 5-thia-2-azaspiro[3.4]octane-2,7-dicarboxylate (2.6 g, 9.05 mmol, 1 equiv), CH$_2$Cl$_2$ (50 mL) and m-CPBA (4.6 g, 26.66 mmol, 3 equiv). The resulting solution was stirred for 4 h at 20° C. The reaction mixture was diluted with CH$_2$Cl$_2$ (100 mL), washed with sat. aq. NaHCO$_3$ solution (50 mL), sat. aq. NaHSO$_4$ solution (50 mL) and brine (2×50 mL). The organic layer was dried over anhydrous Na$_2$SO$_4$, filtered and concentrated under vacuum. The residue was purified by silica gel chromatography (EtOAc/pet. ether, 1:2) to afford the title compound as a white solid (2.2 g, 76% yield). MS: (ES, m/z): 320 [M+H]+.

Step-7: 2-(tert-Butoxycarbonyl)-5-thia-2-azaspiro[3.4]octane-7-carboxylic acid 5,5-dioxide

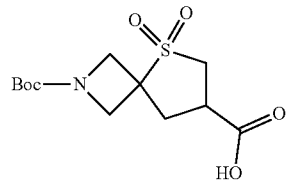 [SMILES: CC(C)(C)OC(=O)N1CC2(CC(C(=O)O)CS2(=O)=O)C1]

Into a 25-mL round-bottom flask, was placed 2-(tert-Butyl) 7-methyl 5-thia-2-azaspiro[3.4]octane-2,7-dicarboxylate 5,5-dioxide (500 mg, 1.57 mmol, 1 equiv), THF/H$_2$O (10 mL, 1:1) and NaOH (125.4 mg, 3.14 mmol, 2 equiv). The resulting solution was stirred for 4 h at room temperature. The pH value of the solution was adjusted to 6 with 1N HCl then concentrated under vacuum. The residue was washed with CH$_2$Cl$_2$ (3×10 mL), and the organic layer was concentrated under vacuum to afford the title compound as a light yellow solid (560 mg) which was used without further purification. MS: (ES, m/z): 206 [M+H-Boc]+.

TABLE 3

The following compounds were prepared according to the methods of Examples 4 through 8.

| Structure | Found M + H | $^1$H-NMR (400 MHz, DMSO-d$_6$) δ(ppm) |
|---|---|---|
| 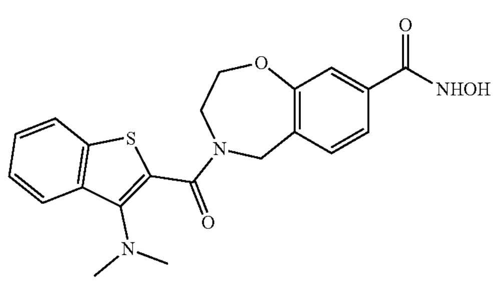 | (ES, m/z): 412 [M + H]+ | 11.18 (s, 1H), 7.90-7.91 (d, J = 2.4 Hz, 1H) 7.88-7.89 (d, J = 3.2 Hz, 1H), 7.33-7.44 (m, 5H), 4.83 (s, 2H), 3.91-4.23 (m, 4H), 2.67-2.77 (m, 6H) |

TABLE 3-continued

The following compounds were prepared according to the methods of Examples 4 through 8.

| Structure | Found M + H | ¹H-NMR (400 MHz, DMSO-d₆) δ(ppm) |
|---|---|---|
| (structure with Boc-azetidine spiro tetrahydrofuran, benzoxazepine, NHOH) | (ES, m/z): 477 [M + H]⁺ | 11.17-11.19 (m, 1H), 8.40-9.35 (br, 1H), 7.30-7.54 (m, 3H), 4.60-4.73 (m, 2H), 3.44-4.17 (m, 11H), 2.09-2.04 (m, 2H), 1.34 (s, 9H) |
| (structure with Boc-azetidine spiro sulfone, benzoxazepine, NHOH) | (ES, m/z): 496 [M + H]⁺ | 11.18-11.21 (m, 1H), 9.06 (br, 1H), 7.33-7.56 (m, 3H), 4.61-4.78 (m, 2H), 3.84-4.16 (m, 8H), 3.26-3.38 (m, 3H), 2.40-2.57 (m, 1H), 2.20-2.28 (m, 1H), 1.37 (s, 9H) |

Example 9

Preparation of (S)—N-Hydroxy-4-(tetrahydro-2H-pyran-3-carbonyl)-2,3,4,5-tetrahydrobenzo[f][1,4]oxazepine-8-carboxamide and (R)—N-Hydroxy-4-(tetrahydro-2H-pyran-3-carbonyl)-2,3,4,5-tetrahydrobenzo[f][1,4]oxazepine-8-carboxamide

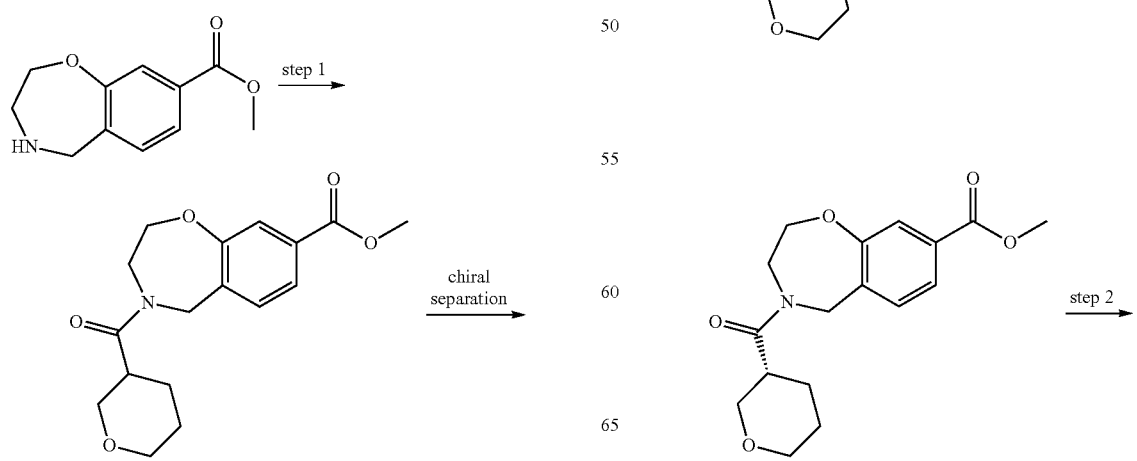

-continued

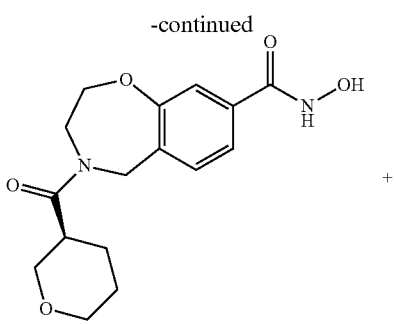

Step-1: methyl (S)-4-(tetrahydro-2H-pyran-3-carbonyl)-2,3,4,5-tetrahydrobenzo[f][1,4]oxazepine-8-carboxylate and methyl (R)-4-(tetrahydro-2H-pyran-3-carbonyl)-2,3,4,5-tetrahydrobenzo[f][1,4]oxazepine-8-carboxylate

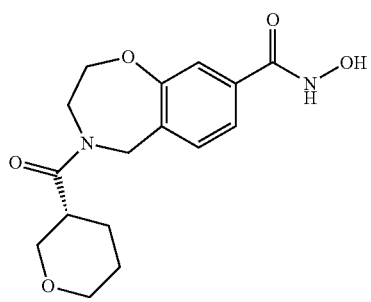

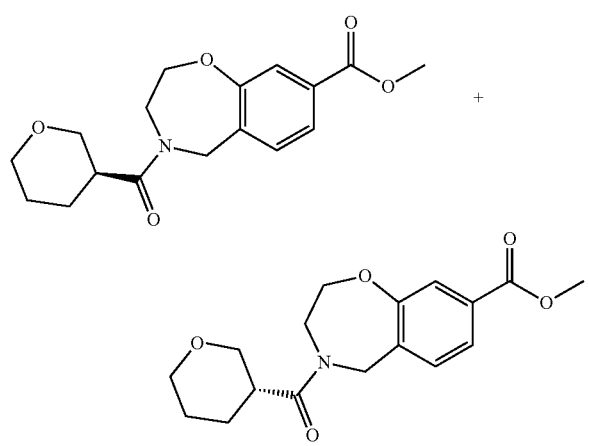

A mixture of methyl 2,3,4,5-tetrahydro-1,4-benzoxazepine-8-carboxylate (250 mg, 1.21 mmol, 1 equiv), tetrahydro-2H-pyran-3-carboxylic acid (157 mg, 1.21 mmol, 1 equiv), DIEA (469 mg, 3.63 mmol, 3 equiv), and HATU (552 mg, 1.45 mmol, 1.2 equiv) and in DMF (4 mL) was stirred overnight at room temperature. The reaction was then quenched by the addition of water (2 mL). The resulting solution was extracted with $CH_2Cl_2$ (3×10 mL) and washed with brine. The organic layer was dried over anhydrous $Na_2SO_4$, filtered, and concentrated under vacuum. The crude racemic mixture was purified by chiral Prep-HPLC (Column: Chiralpak IA 2×25 cm, 5 μm; Mobile Phase A: hexanes; Mobile Phase B: EtOH; Flow rate: 20 mL/min; Gradient: 30% B for 26 min; Detector, UV 254, 220 nm) to afford single isomers of the title compound. The first eluting isomer was isolated as a white solid (55 mg, 14% yield). MS: (ES, m/z): 320 [M+H]$^+$. The second eluting isomer was isolated as a white solid (55 mg, 14% yield). MS: (ES, m/z): 320 [M+H]$^+$.

Step-2: (S)—N-Hydroxy-4-(tetrahydro-2H-pyran-3-carbonyl)-2,3,4,5-tetrahydrobenzo[f][1,4]oxazepine-8-carboxamide and (R)—N-Hydroxy-4-(tetrahydro-2H-pyran-3-carbonyl)-2,3,4,5-tetrahydrobenzo[f][1,4]oxazepine-8-carboxamide

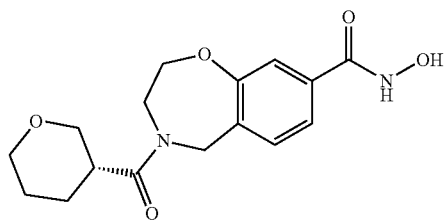

A solution of methyl 4-(tetrahydro-2H-pyran-3-carbonyl)-2,3,4,5-tetrahydrobenzo[f][1,4]oxazepine-8-carboxylate (55 mg, 0.17 mmol, 1 equiv) in MeOH/THF (1:4, 2 mL), aq. 1N NaOH (0.35 mL, 2 equiv), $NH_2OH$ (50% in water, 569 mg, 50 equiv) was stirred for 1 h at room temperature. The reaction mixture was cooled to 0° C. with an ice-water bath. The pH value of the solution was adjusted to 6 with aq. 6N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254 nm). Reaction with the first eluting isomer from Step 1 afforded the title compound as a pink solid (15.2 mg, 28% yield). $^1$H-NMR (400 MHz, DMSO-$d_6$) δ(ppm): 11.17 (s, 1H), 9.00 (br, 1H), 7.26-7.52 (m, 3H), 4.76 (s, 1H), 4.57 (s, 1H), 4.11-4.18 (m, 2H), 3.31-3.91 (m, 4H), 3.20-3.29 (m, 2H), 2.80-2.98 (m, 1H), 1.44-1.79 (m, 4H). MS: (ES, m/z): 321 [M+H]$^+$. Reaction with the second eluting isomer from Step 1 afforded the title compound as a pink solid (15.8 mg, 29% yield). $^1$H-NMR (400 MHz, DMSO-$d_6$) δ(ppm): 11.17 (s, 1H), 9.00 (br, 1H), 7.26-7.52 (m, 3H), 4.76 (s, 1H), 4.57 (s, 1H), 4.06-4.18 (m, 2H), 3.56-3.91 (m, 4H), 3.20-3.31 (m, 2H), 2.82-2.98 (m, 1H), 1.43-1.79 (m, 4H). MS: (ES, m/z): 321 [M+H]$^+$.

TABLE 4

The following compounds were prepared according to the method of Example 9.

| Structure | Found M + H | ¹H-NMR (400 MHz, DMSO-$d_6$) δ(ppm) |
|---|---|---|
| (structure) (R)/(S) isomer | (ES, m/z): 307 [M + H]$^+$ | 11.18-11.16 (m, 1H), 9.01 (br, 1H), 7.53-7.51 (m, 1H), 7.42-7.38 (m, 1H), 4.75 (s, 1H), 4.61 (s, 1H), 4.18-4.12 (m, 2H), 3.92-3.78 (m, 3H), 3.68-3.60 (m, 3H), 3.53-3.50 (m, 1H), 3.36-3.30 (m, 1H), 2.01-1.84 (m, 2H) |
| (structure) (R)/(S) isomer | (ES, m/z): 307 [M + H]$^+$ | 11.18-11.16 (m, 1H), 9.01 (br, 1H), 7.53-7.51 (m, 1H), 7.42-7.38 (m, 1H), 4.75 (s, 1H), 4.61 (s, 1H), 4.18-4.12 (m, 2H), 3.92-3.78 (m, 3H), 3.68-3.60 (m, 3H), 3.53-3.50 (m, 1H), 3.36-3.30 (m, 1H), 2.01-1.84 (m, 2H) |

The compounds of Table 4 were separated at the methyl ester intermediate by Prep-HPLC (Column: Chiralpak IA-3 0.46 × 5 cm, 3 μm; Mobile Phase A: hexanes; Mobile Phase B: EtOH; Flow rate: 20 mL/min; Gradient: 50% B for 25 min; Detector, UV 254, 220 nm)

Example 10

Preparation of N-hydroxy-4-(1-methoxycyclopropane-1-carbonyl)-2,3,4,5-tetrahydrobenzo[f][1,4]oxazepine-8-carboxamide

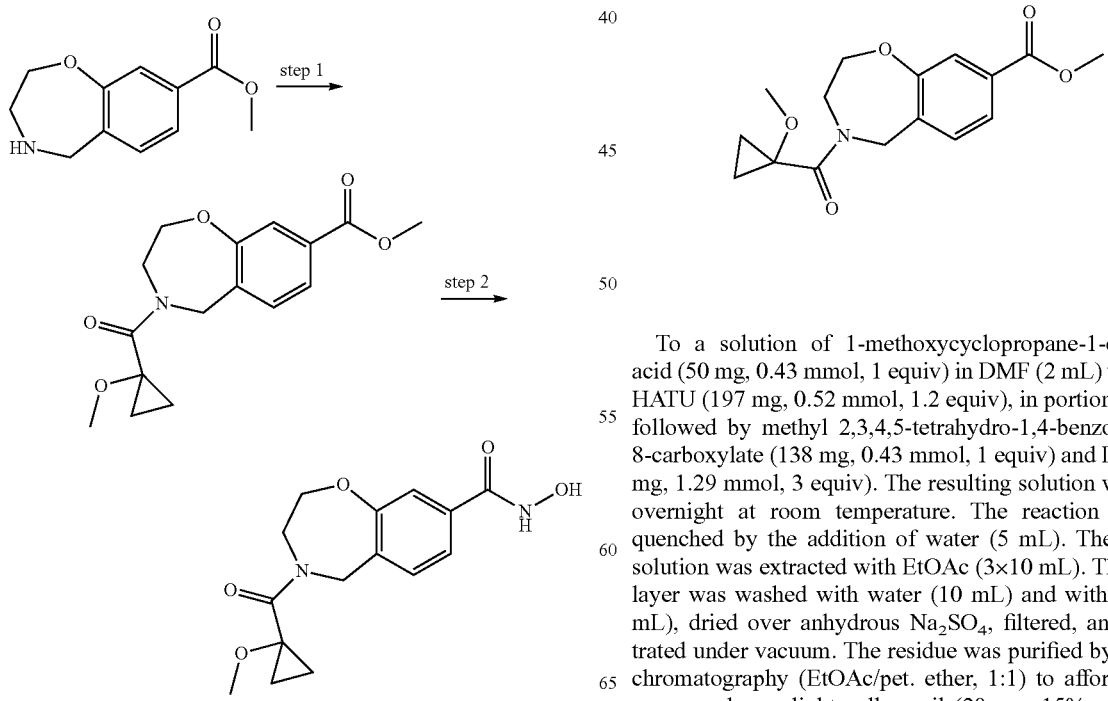

Step-1: Methyl 4-(1-methoxycyclopropane-1-carbonyl)-2,3,4,5-tetrahydrobenzo[f][1,4]oxazepine-8-carboxylate To a solution of 1-methoxycyclopropane-1-carboxylic acid (50 mg, 0.43 mmol, 1 equiv) in DMF (2 mL) was added HATU (197 mg, 0.52 mmol, 1.2 equiv), in portions at 0° C., followed by methyl 2,3,4,5-tetrahydro-1,4-benzoxazepine-8-carboxylate (138 mg, 0.43 mmol, 1 equiv) and DIEA (167 mg, 1.29 mmol, 3 equiv). The resulting solution was stirred overnight at room temperature. The reaction was then quenched by the addition of water (5 mL). The resulting solution was extracted with EtOAc (3×10 mL). The organic layer was washed with water (10 mL) and with brine (10 mL), dried over anhydrous $Na_2SO_4$, filtered, and concentrated under vacuum. The residue was purified by silica gel chromatography (EtOAc/pet. ether, 1:1) to afford the title compound as a light yellow oil (20 mg, 15% yield). MS: (ES, m/z): 306 [M+H]$^+$.

Step-2: N-Hydroxy-4-(1-methoxycyclopropane-1-carbonyl)-2,3,4,5-tetrahydrobenzo[f][1,4]oxazepine-8-carboxamide

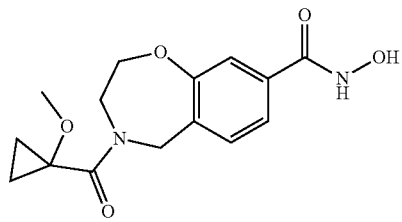 [SMILES: COC1(C(=O)N2CCOc3cc(C(=O)NO)ccc3C2)CC1]

To a solution of methyl 4-(1-methoxycyclopropane-1-carbonyl)-2,3,4,5-tetrahydrobenzo[f][1,4]oxazepine-8-carboxylate (20 mg, 0.07 mmol, 1 equiv) in MeOH/THF (1:4, 1 mL) was added simultaneously aq. 6N NaOH (0.13 mL, 2 equiv), NH$_2$OH (50% in water, 0.12 mL, 50 equiv). The resulting solution was stirred for 1 h at room temperature. The crude product was purified by Prep-HPLC (Column Sunfire C18 5 μm, 19×100 mm; Mobile Phase A: Water/ 0.05% TFA; Mobile Phase B: MeCN; Flow rate: 25 mL/min; Gradient: 6% B to 48% B in 8 min, hold 0.6 min; Detector, UV 254, 220 nm) to afforded the title compound as an orange solid (7.9 mg, 39% yield). $^1$H-NMR (400 MHz, DMSO-d$_6$) δ(ppm): 11.17 (br, 1H), 9.01 (br, 1H), 7.47-7.25 (m, 3H), 5.03-4.53 (m, 2H), 4.66-4.29 (m, 3H), 3.95-3.78 (m, 1H), 3.20-2.80 (m, 3H), 0.98-0.75 (m, 4H). MS: (ES, m/z): 307 [M+H]$^+$.

TABLE 5

The following compounds were prepared according to the method of Example 10.

| Structure | Found M + H | $^1$H-NMR (400 MHz, DMSO-d$_6$) δ(ppm) |
|---|---|---|
|  | 335 [M + H]$^+$ | (ES, m/z): 11.15 (br, 1H), 9.03 (br, 1H), 7.39-7.34 (m, 2H), 7.28 (s, 1H), 4.64 (s, 2H), 4.20-4.18 (m, 2H), 3.98-3.95 (m, 2H), 3.59-3.54 (m, 2H), 3.41-3.32 (m, 2H), 1.97-1.93 (m, 2H), 1.47-1.44 (m, 2H), 1.21 (s, 3H) |
|  | 321 [M + H]$^+$ | (ES, m/z): 11.18 (br, 1H), 9.03 (br, 1H), 7.46-7.27 (m, 3H), 4.78-4.60 (m, 3.5H), 4.45-4.35 (m, 0.5H), 4.36-4.21 (m, 3H), 4.22-4.13 (m, 1.5H), 3.92-3.83 (m, 0.5H), 3.46-3.37 (m, 1H), 2.02-1.87 (m, 2H), 0.81-0.66 (m, 3H) |
|  | 316 [M + H]$^+$ | (ES, m/z): 11.20 (s, 1H), 7.42-7.41 (m, 1H), 7.40-7.39 (m, 1H), 7.33-7.23 (br, 1H), 6.91 (s, 1H), 6.23 (s, 1H), 6.04-6.02 (m, 1H), 4.78 (s, 2H), 4.26-4.25 (m, 2H), 4.00-3.99 (m, 2H), 3.58 (s, 3H) |
|  | 366 [M + H]$^+$ | (ES, m/z): 11.28 (br, 1H), 8.79-8.46 7.72-7.69 (m, 1H), 7.61-7.59 (m, 2H), 7.49-43 (m, 2H), 7.28-7.20 (m, 1H), 7.12-7.09 (m, 1H), 6.92-6.46 (m, 1H), 5.04-5.00 (m, 2H), 4.65-4.62 (m, 2H) 4.05-3.90 (m, 2H), 3.64 (s, 3H) |

TABLE 5-continued

The following compounds were prepared according to the method of Example 10.

| Structure | Found M + H | $^1$H-NMR (400 MHz, DMSO-$d_6$) δ(ppm) |
|---|---|---|
| 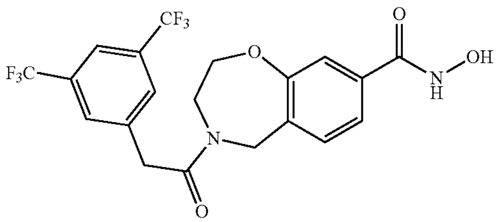 [SMILES: O=C(NO)c1ccc2c(c1)OCCN(C(=O)Cc1cc(C(F)(F)F)cc(C(F)(F)F)c1)C2] | (ES, m/z): 463 [M + H]$^+$ | 11.19 (br, 1H), 9.06-9.04 (br, 1H), 7.95-7.87 (m, 3H), 7.48-7.28 (m, 3H), 4.83 (s, 1H), 4.64 (s, 1H), 4.24-4.23 (m, 1H), 4.16-4.14 (m, 1H), 4.05 (s, 1H), 4.01-3.98 (m, 2H), 3.91-3.90 (m, 1H) |
| 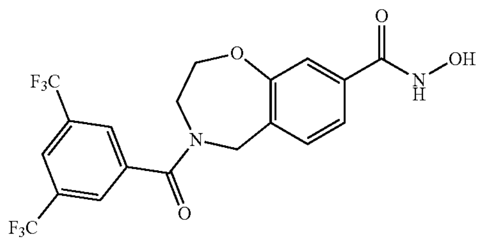 [SMILES: O=C(NO)c1ccc2c(c1)OCCN(C(=O)c1cc(C(F)(F)F)cc(C(F)(F)F)c1)C2] | (ES, m/z): 449 [M + H]$^+$ | 11.20 (br, 1H), 9.07 (br, 1H), 8.27-8.22 (m, 1H), 8.15 (s, 1H), 7.83 (s, 1H), 7.44-7.32, 6.82-6.80 (m, 3H), 4.82 (s, 1H), 4.49 (s, 1H), 4.35 (m, 1H), 4.18 (m, 1H), 4.02 (m, 1H), 3.73 (m, 1H) |
| 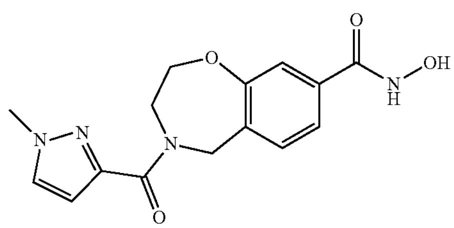 [SMILES: Cn1ccc(C(=O)N2CCOc3cc(C(=O)NO)ccc3C2)n1] | (ES, m/z): 317 [M + H]$^+$ | 11.17 (br, 1H), 9.04 (br, 1H), 7.76-7.74 (m, 1H), 7.42-7.22 (m, 3H), 6.52-6.51 (d, J = 4.0 Hz, 1H), 5.17 (s, 1H), 4.74 (m, 1H), 4.33-4.32 (m, 1H), 4.20-4.17 (m, 2H), 3.99-3.96 (m, 2H), 3.89-3.86 (m, 2H) |
| 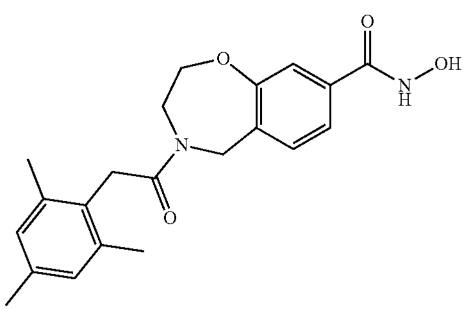 [SMILES: Cc1cc(C)c(CC(=O)N2CCOc3cc(C(=O)NO)ccc3C2)c(C)c1] | (ES, m/z): 369 [M + H]$^+$ | 11.21 (br, 1H), 9.05 (br, 1H), 7.56-7.24 (m, 3H), 6.74-6.72 (d, J = 8.0 Hz, 2H), 4.84 (s, 1H), 4.62 (s, 1H), 4.23-4.22 (m, 1H), 4.15-4.13 (m, 1H), 4.05-4.04 (m, 1H), 3.88-3.87 (m, 1H), 3.66-3.63 (m, 2H), 2.17-2.16 (m, 3H), 2.01 (m, 2H), 1.85 (m, 4H) |

Example 11

Preparation of N-hydroxy-4-pivaloyl-2,3,4,5-tetrahydrobenzo[f][1,4]oxazepine-8-carboxamide

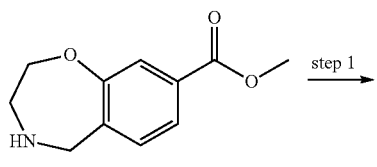

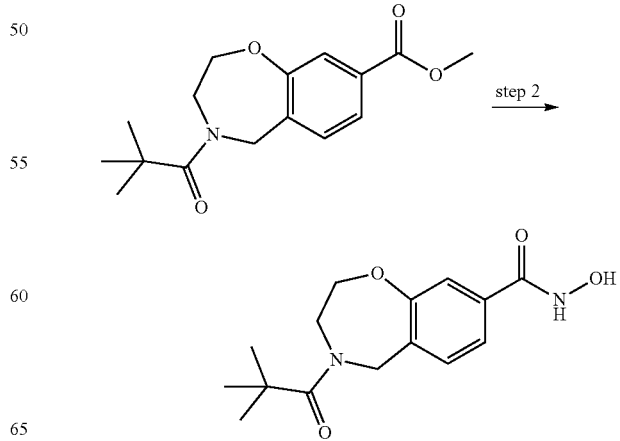

Step-1: Methyl 4-pivaloyl-2,3,4,5-tetrahydrobenzo[f][1,4]oxazepine-8-carboxylate Step-2: N-hydroxy-4-pivaloyl-2,3,4,5-tetrahydrobenzo[f][1,4]oxazepine-8-carboxamide

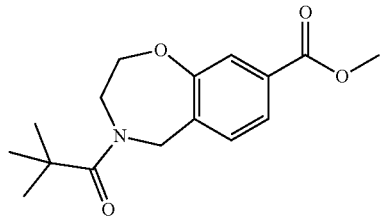 [SMILES: COC(=O)c1ccc2c(c1)OCCN(C(=O)C(C)(C)C)C2]

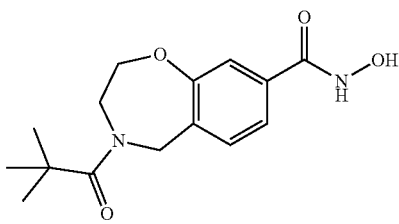 [SMILES: CC(C)(C)C(=O)N1CCOc2cc(C(=O)NO)ccc2C1]

Into a 25-mL round-bottom flask, was placed a solution of methyl 2,3,4,5-tetrahydro-1,4-benzoxazepine-8-carboxylate (80 mg, 0.39 mmol, 1 equiv) in CH$_2$Cl$_2$ (2 mL), and Et$_3$N (118 mg, 1.17 mmol, 3 equiv). This was followed by the addition of 2,2-dimethylpropanoyl chloride (46.6 mg, 0.39 mmol, 1 equiv) dropwise with stirring at 0° C. The resulting solution was stirred for 30 min at room temperature. The reaction was then quenched by the addition of water (2 mL). The mixture was extracted with CH$_2$Cl$_2$ (3×10 mL). The organic layer was dried over anhydrous Na$_2$SO$_4$, filtered, and concentrated under vacuum. The residue was purified by silica gel chromatography (EtOAc/pet. ether, 1:1) to afford the title compound as a light yellow solid (90 mg, 80% yield). MS: (ES, m/z): 292 [M+H]$^+$.

Into a 25-mL round-bottom flask, was placed a solution of methyl 4-pivaloyl-2,3,4,5-tetrahydrobenzo[f][1,4]oxazepine-8-carboxylate (90 mg, 0.31 mmol, 1 equiv) in THF/MeOH (4:1, 2 mL), aq. 1N NaOH (0.62 mL, 2 equiv) and NH$_2$OH (50% in water, 510 mg, 15.46 mmol, 50 equiv). The resulting solution was stirred for 1 h at room temperature. The pH value of the solution was adjusted to 6 with aq. 6N HCl at 0°. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector, UV 254 nm) to afford the title compound as a white solid (34.2 mg, 27% yield). $^1$H-NMR (400 MHz, DMSO-d$_6$) δ(ppm): 11.17 (s, 1H), 9.03 (s, 1H), 7.29-7.39 (m, 3H), 4.61 (s, 2H), 4.18-4.20 (t, J$_1$=4.8 HZ, J$_2$=9.2 Hz, 2H), 3.97-3.99 (d, J=5.2 Hz, 2H), 1.16 (s, 9H). MS: (ES, m/z): 293 [M+H]$^+$.

TABLE 6

The following compounds were prepared according to the method of Example 11.

| Structure | Found M + H | $^1$H-NMR (400 MHz, DMSO-d$_6$) δ(ppm) |
|---|---|---|
| | 313 [M + H]$^+$ | (ES, m/z): 11.20 (s, 1H), 7.13-7.45 (m, 8H), 4.79 (s, 1H), 4.51 (s, 1H), 4.15-4.29 (m, 3H), 3.99 (s, 1H) |
| | 251 [M + H]$^+$ | (ES, m/z): 11.16-11.18 (d, 1H), 10.10 (s, 1H), 9.03 (s, 1H), 7.29-7.44 (m, 3H), 4.57-4.64 (d, 2H), 4.15-4.17 (t, 1H), 4.07-4.09 (t, 1H), 3.43 (m, 2H), 1.98-2.03 (m, 3H) |

Example 12

Preparation of 4-formyl-N-hydroxy-2,3,4,5-tetrahydrobenzo[f][1,4]oxazepine-8-carboxamide 2,2,2-trifluoroacetate

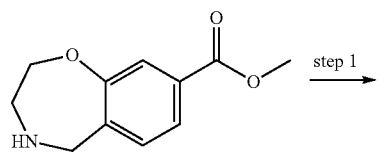

step 1 →

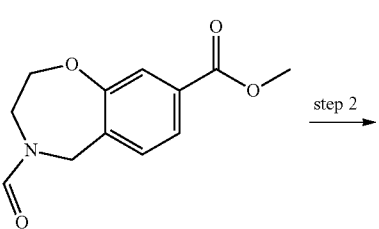

step 2 →

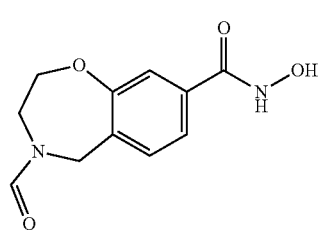

Step-1: Methyl 4-formyl-2,3,4,5-tetrahydro-1,4-benzoxazepine-8-carboxylate

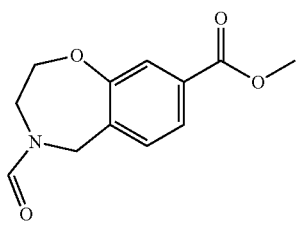 [SMILES: COC(=O)c1ccc2c(c1)OCCN(C=O)C2]

Into a 8-mL vial, was placed methyl 2,3,4,5-tetrahydro-1,4-benzoxazepine-8-carboxylate (150 mg, 0.47 mmol, 1 equiv) and ethyl formate (2 mL). The resulting solution was stirred for 16 h at 60° C. in an oil bath. The resulting mixture was concentrated under vacuum to afford the title compound as yellow oil which was used without further purification. MS: (ES, m/z): 236 [M+H]+.

Step-2: 4-Formyl-N-hydroxy-2,3,4,5-tetrahydrobenzo[f][1,4]oxazepine-8-carboxamide

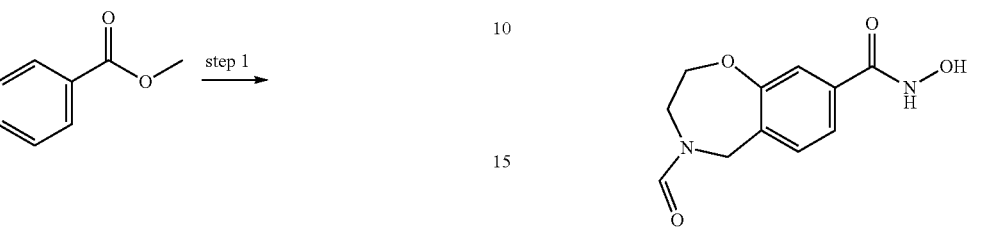

Into a 8-mL vial, was placed methyl 4-formyl-2,3,4,5-tetrahydro-1,4-benzoxazepine-8-carboxylate (100 mg, 0.43 mmol, 1 equiv) in THF/MeOH (4:1, 2 mL), aq. 1N NaOH (0.85 mL, 0.85 mmol, 2 equiv), and NH$_2$OH (50% in water, 0.85 mL, 12.72 mmol, 30 equiv). The resulting solution was stirred for 2 h at room temperature. The crude product was purified by Prep-HPLC (Column: XBridge RP C18 OBD, 5 μm, 19×150 mm; Mobile Phase A: Water/0.05% TFA; Mobile Phase B: MeCN; Flow rate: 25 mL/min; Gradient: 4% B to 58% B in 7 min; Detector, UV 254, 220 nm) to afford the title compound as a pink solid (15 mg, 10% yield). $^1$H-NMR (400 MHz, DMSO-d$_6$) δ(ppm): 11.19 (s, 1H), 10-10.11 (s, 1H), 9.03 (s, 1H), 8.20 (s, 0.4H), 8.04 (s, 0.6H), 7.33-7.43 (m, 3H), 4.61-4.64 (d, 0.9H), 4.52-4.55 (d, 1.2H), 4.10-4.14 (m, 2H), 3.76-3.78 (m, 2H). MS: (ES, m/z): 237 [M+H]+.

Example 13

Preparation of tert-Butyl 3-[8-(hydroxycarbamoyl)-2,3,4,5-tetrahydro-1,4-benzoxazepine-4-carbonyl]-3H-spiro[2-benzofuran-1,4'-piperidine]-1'-carboxylate and N-hydroxy-4-(3H-spiro[isobenzofuran-1,4'-piperidine]-3-carbonyl)-2,3,4,5-tetrahydrobenzo[f][1,4]oxazepine-8-carboxamide

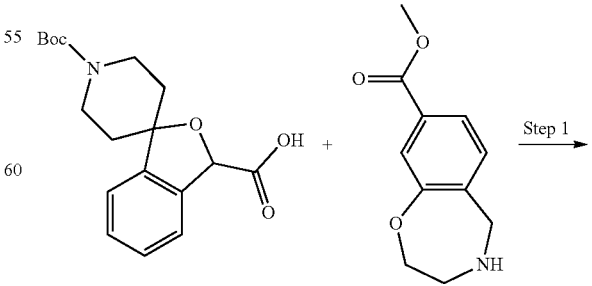

Step 1 →

-continued

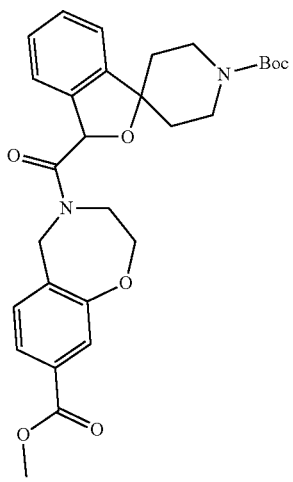

Step 2 →

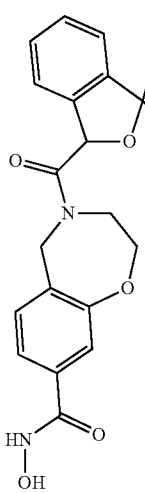

Step 3 →

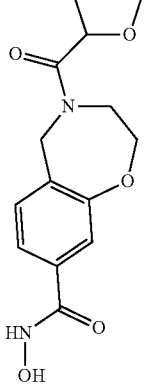

Step-1: tert-Butyl 3-(8-(methoxycarbonyl)-2,3,4,5-tetrahydrobenzo[f][1,4]oxazepine-4-carbonyl)-3H-spiro[isobenzofuran-1,4'-piperidine]-1'-carboxylate

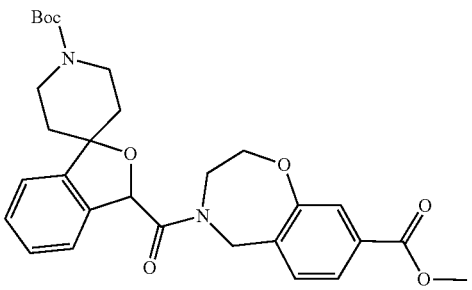 [SMILES: COC(=O)c1ccc2c(c1)OCCN(C(=O)C1OC3(CCN(C(=O)OC(C)(C)C)CC3)c3ccccc31)C2]

Into a 20 ml scintillation vial, was placed methyl 2,3,4,5-tetrahydrobenzo[f][1,4]oxazepine-8-carboxylate (21 mg, 0.1 mmol), 1'-(tert-butoxycarbonyl)-3H-spiro[isobenzofuran-1,4'-piperidine]-3-carboxylic acid (33 mg, 0.1 mmol,) and chloroform (3 mL). This was followed by the addition of DIEA (0.052 ml, 0.3 mmol) and DMC (20 mg, 0.12 mmol) at ambient temperature. The resulting solution was stirred for 3 h at room temperature. The reaction was then diluted with $CH_2Cl_2$ (10 mL) and washed with 75% aqueous brine (20 mL). The resulting solution was passed through an Isolute© phase separator, then concentrated to dryness. The residue gave a quantitative yield of the title compound as an yellow semi-solid which was used without further purification. MS: (ES, m/z): 523 $[M+H]^+$.

Step-2: tert-Butyl 3-(8-(hydroxycarbamoyl)-2,3,4,5-tetrahydrobenzo[f][1,4]oxazepine-4-carbonyl)-3H-spiro[isobenzofuran-1,4'-piperidine]-1'-carboxylate

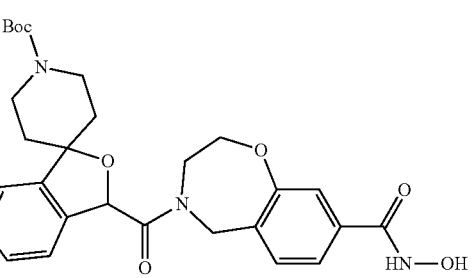

In a 20-ml scintillation vial, tert-butyl 3-(8-(methoxycarbonyl)-2,3,4,5-tetrahydrobenzo[f][1,4]oxazepine-4-carbonyl)-3H-spiro[isobenzofuran-1,4'-piperidine]-1'-carboxylate (52 mg, 0.1 mmol) was dissolved in MeOH/THF (1:1, 1 mL), $NH_2OH$ (50% in water, 0.5 ml, 7.57 mmol), and aq. 1N NaOH (0.5 mL, 0.5 mmol). The resulting solution was stirred for 2 hours at ambient temperature, then concentrated to dryness. The crude product was purified by Prep-HPLC (Column: XBridge RP C18 OBD, 5 μm, 19×150 mm; Mobile Phase A: Water/0.05% formic acid; Mobile Phase B: MeCN/0.05% formic acid; Flow rate: 23 mL/min; Gradient: 0% B to 35% B in 8 min; Detector, UV 254, 220 nm) to afford the title compound. MS: (ES, m/z): 524 $[M+H]^+$.

Step-3: N-hydroxy-4-(3H-spiro[isobenzofuran-1,4'-piperidine]-3-carbonyl)-2,3,4,5-tetrahydrobenzo[f][1,4]oxazepine-8-carboxamide

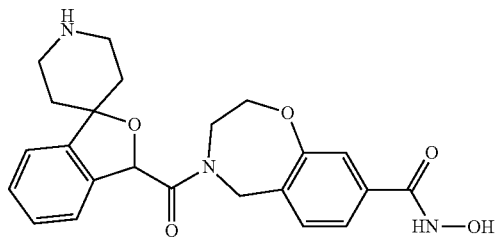 [SMILES: O=C(NO)c1ccc2c(c1)OCCN(C(=O)C1OC3(CCNCC3)c3ccccc31)C2]

In a 20-ml scintillation vial, tert-butyl 3-(8-(hydroxycarbamoyl)-2,3,4,5-tetrahydrobenzo[f][1,4]oxazepine-4-carbonyl)-3H-spiro[isobenzofuran-1,4'-piperidine]-1'-carboxylate (40 mg, 0.19 mmol) was taken up in $CH_2Cl_2$ (2 mL) then TFA (1 mL) was added. The resulting solution was stirred at ambient temperature for 1 h, then concentrated to dryness. The crude product was purified by Prep-HPLC (Column: XBridge RP C18 OBD, 5 μm, 19×150 mm; Mobile Phase A: Water/0.1% formic acid; Mobile Phase B: MeCN/0.1% formic acid; Flow rate: 23 mL/min; Gradient: 0% B to 35% B in 8 min; Detector, UV 254, 220 nm) to afford the title compound as the formic acid salt as a white solid (9 mg, 28% yield). $^1$H-NMR (400 MHz, DMSO-$d_6$) δ(ppm): 6.93-7.63 (m, 7H) 5.97-6.30 (m, 1H) 4.46-4.81 (m, 1H) 3.92-4.45 (m, 4H) 2.57-3.18 (m, 6H) 1.49-2.05 (m, 4H). MS: (ES, m/z): 424 [M+H]$^+$.

TABLE 7

The following compounds were prepared according to the method of Example 13.

| Structure | Found M + H | $^1$H-NMR (400 MHz, DMSO-$d_6$) δ(ppm) |
|---|---|---|
| | (ES, m/z): 374 [M + H]$^+$ | |
| 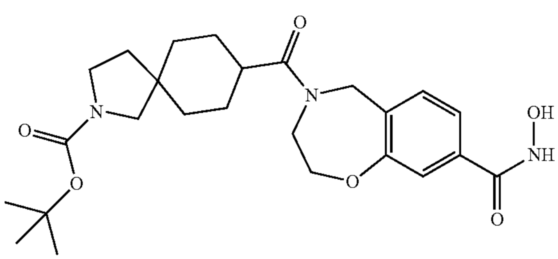 [SMILES: CC(C)(C)OC(=O)N1CCC2(CCC(C(=O)N3CCOc4cc(C(=O)NO)ccc4C3)CC2)C1] | (ES, m/z): 474 [M + H]$^+$ | 10.88-11.41 (m, 1 H) 8.88-9.27 (m, 1 H) 7.24-7.55 (m, 3 H) 4.53-4.79 (m, 2 H) 3.99-4.27 (m, 2 H) 3.87 (br d, J = 15.54 Hz, 1 H) 3.24 (br s, 3 H) 2.96 (br d, J = 8.79 Hz, 2 H) 1.66 (q, J = 6.94 Hz, 2 H) 1.34-1.49 (m, 18 H) |
| | (ES, m/z): 374 [M + H]$^+$ | |
| 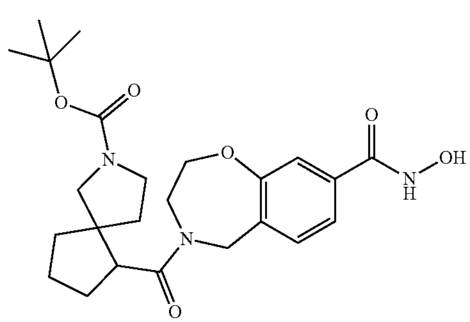 [SMILES: CC(C)(C)OC(=O)N1CCC2(CCCC2C(=O)N2CCOc3cc(C(=O)NO)ccc3C2)C1] | (ES, m/z): 460 [M + H]$^+$ | 11.16 (br s, 1 H) 9.02 (br s, 1 H) 7.19-7.58 (m, 3 H) 4.73 (br s, 1 H) 4.03 (br s, 3 H) 3.65 (s, 1 H) 2.98-3.28 (m, 6 H) 1.67 (br d, J = 9.97 Hz, 5 H) 1.47-1.60 (m, 3 H) 1.28-1.46 (m, 9 H) |

TABLE 7-continued

The following compounds were prepared according to the method of Example 13.

| Structure | Found M + H | $^1$H-NMR (400 MHz, DMSO-d$_6$) δ(ppm) |
|---|---|---|
| (structure) | (ES, m/z): 360 [M + H]$^+$ | |
| (structure) | (ES, m/z): 524 [M + H]$^+$ | |
| (structure) | (ES, m/z): 424 [M + H]$^+$ | 8.31 (s, 1 H) 7.21-7.60 (m, 4 H) 7.15 (td, J = 7.33, 3.52 Hz, 1 H) 6.89 (td, J = 7.33, 3.52 Hz, 1 H) 6.72-6.83 (m, 1 H) 5.53-5.60 (m, 1 H) 4.65-5.01 (m, 2 H) 4.19-4.58 (m, 4 H) 3.87-4.19 (m, 4 H) 2.80-3.26 (m, 4 H) 1.74-2.05 (m, 4 H) |
| (structure) | (ES, m/z): 522 [M + H]$^+$ | |
| (structure) | (ES, m/z): 422 [M + H]$^+$ | 8.40 (br s, 1 H) 6.69-7.62 (m, 7 H) 4.54-5.03 (m, 2 H) 3.98-4.31 (m, 3 H) 3.03-3.23 (m, 3 H) 2.62-3 (m, 3 H) 2.20-2.44 (m, 1 H) 1.83-2.18 (m, 2 H) 1.49-1.78 (m, 3 H) |
| (structure) | (ES, m/z): 488 [M + H]$^+$ | 11.17 (br s, 1 H) 9.05 (br s, 1 H) 7.19-7.51 (m, 3 H) 4.72 (s, 1 H) 4.58 (s, 1 H) 4.03-4.25 (m, 2 H) 3.86 (br d, J = 14.07 Hz, 2 H) 3.18-3.31 (m, 4 H) 2.71 (br d, J = 12.31 Hz, 1 H) 1.61 (br d, J = 10.55 Hz, 2 H) 1.32-1.51 (m, 14 H) 1.06-1.27 (m, 5 H) |

TABLE 7-continued

The following compounds were prepared according to the method of Example 13.

| Structure | Found M + H | ¹H-NMR (400 MHz, DMSO-d₆) δ(ppm) |
|---|---|---|
| | (ES, m/z): 474 [M + H]⁺ | 11.15 (br s, 1 H) 9.06 (br s, 1 H) 7.28-7.51 (m, 3 H) 4.73 (s, 1 H) 4.59 (s, 1 H) 4.06-4.19 (m, 2 H) 3.88 (br d, J = 14.95 Hz, 2 H) 3.12-3.29 (m, 4 H) 1.56-1.83 (m, 3 H) 1.28-1.49 (m, 17 H) |
| | (ES, m/z): 388 [M + H]⁺ | |

Example 14

Preparation of N-hydroxy-4-(5-azaspiro[2.5]octane-1-carbonyl)-2,3,4,5-tetrahydrobenzo[f][1,4]oxazepine-8-carboxamide Step-1: Methyl 4-(5-(tert-butoxycarbonyl)-5-azaspiro[2.5]octane-1-carbonyl)-2,3,4,5-tetrahydrobenzo[f][1,4]oxazepine-8-carboxylate

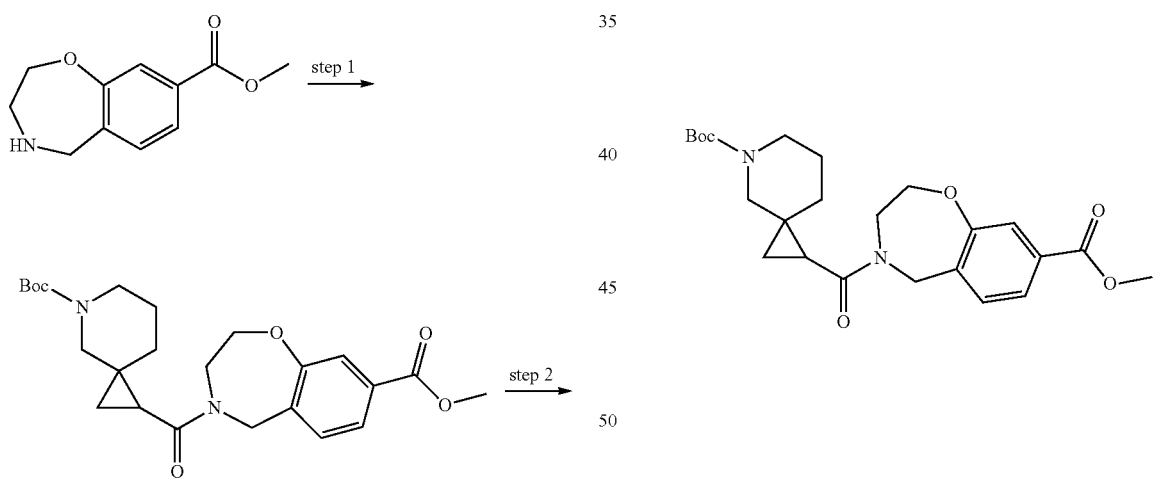

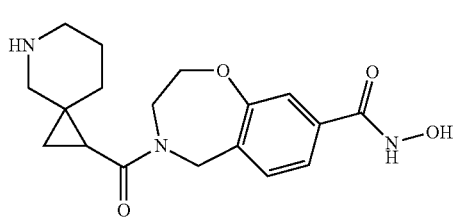

Into a 1-dram vial, was placed methyl 2,3,4,5-tetrahydrobenzo[f][1,4]oxazepine-8-carboxylate (15 mg, 0.072 mmol, 1 equiv), 5-(tert-butoxycarbonyl)-5-azaspiro[2.5]octane-1-carboxylic acid (27.7 mg, 0.109 mmol, 1.5 equiv) and dichloroethane (1 mL). This was followed by the addition of Et₃N (18.3 mg, 0.181 mmol, 2.50 equiv) and DMC (18.36 mg, 0.109 mmol, 1.5 equiv) at room temperature. The resulting solution was stirred for 2 h at room temperature. The reaction was then quenched by the addition of water (1 mL). The resulting solution was extracted with CH₂Cl₂ (2×1 mL). The organic layer was concentrated under vacuum to afford the title compound as a light yellow oil (16 mg, 50% yield) which was used without further purification. MS: (ES, m/z): 445 [M+H]⁺.

Step-2: N-Hydroxy-4-(5-azaspiro[2.5]octane-1-carbonyl)-2,3,4,5-tetrahydrobenzo[f][1,4]oxazepine-8-carboxamide

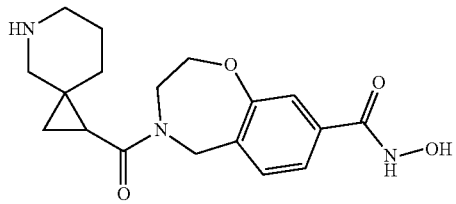 [SMILES: O=C(NO)c1ccc2c(c1)OCCN(C(=O)C1CC13CCCNC3)C2]

Methyl 4-(5-(tert-butoxycarbonyl)-5-azaspiro[2.5]octane-1-carbonyl)-2,3,4,5-tetrahydrobenzo[f][1,4]oxazepine-8-carboxylate (16 mg, 0.036 mmol, 1 equiv) was dissolved in EtOAc (0.5 mL). This was followed by the addition of HCl (4M in Dioxane, 90 μL, 0.36 mmol, 10 equiv) at room temperature. The resulting solution was stirred for 4 h at room temperature. The solution was concentrated under vacuum. The resulting off-white solid was dissolved in MeOH/THF (1:4, 0.5 mL), NH$_2$OH (50% in water, 24 mg, 0.36 mmol, 10 equiv), and aq. 1N NaOH (0.072 mL, 2 equiv). The pH of the reaction was measured to be ~11. The resulting solution was stirred overnight at room temperature. The crude product was purified by Prep-HPLC (Column: XBridge RP C18 OBD, 5 μm, 19×150 mm; Mobile Phase A: Water/0.05% formic acid; Mobile Phase B: MeCN/0.05% formic acid; Flow rate: 23 mL/min; Gradient: 5% B to 35% B in 6.6 min, hold 0.9 min; Detector, UV 254, 220 nm) to afford the title compound as an off-white solid (1.8 mg, 15% yield). MS: (ES, m/z): 346 [M+H]$^+$.

TABLE 8

The following compounds were prepared according to the method of Example 14.

| Structure | Found M + H |
|---|---|
| 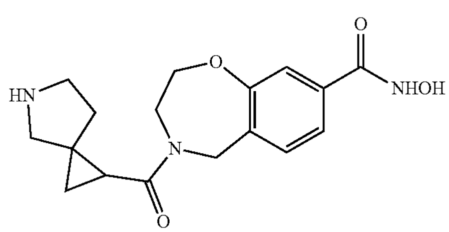 | (ES, m/z): 332 [M + H]$^+$ |
| 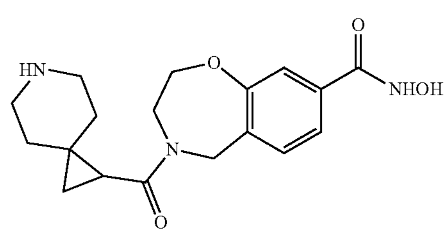 | (ES, m/z): 346 [M + H]$^+$ |

Example 15

Preparation of tert-butyl 1-(8-(hydroxycarbamoyl)-2,3,4,5-tetrahydrobenzo[f][1,4]oxazepine-4-carbonyl)-6-azaspiro[2.5]octane-6-carboxylate

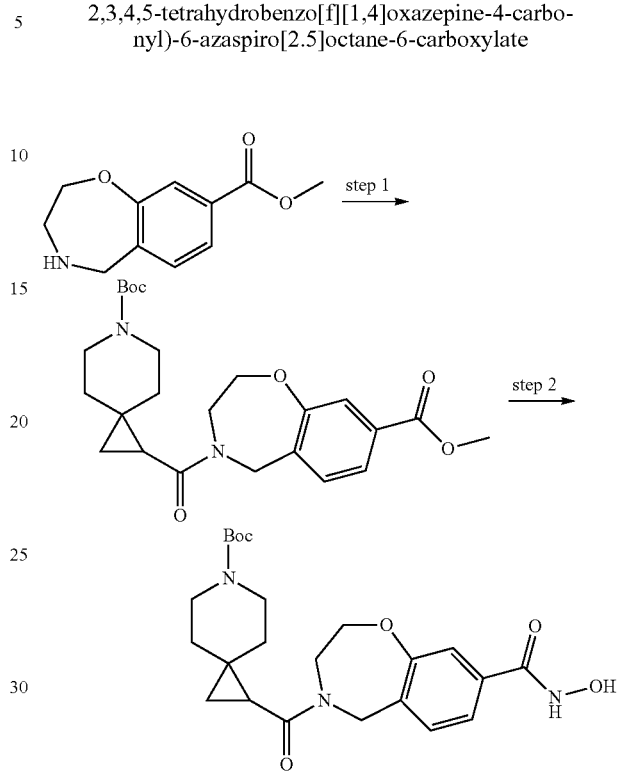

Step-1: Methyl 4-(6-(tert-butoxycarbonyl)-6-azaspiro[2.5]octane-1-carbonyl)-2,3,4,5-tetrahydrobenzo[f][1,4]oxazepine-8-carboxylate

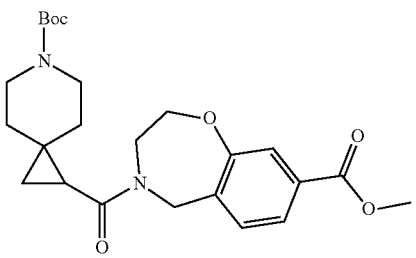 [SMILES: COC(=O)c1ccc2c(c1)OCCN(C(=O)C1CC13CCN(C(=O)OC(C)(C)C)CC3)C2]

Into a 1-dram vial, was placed methyl 2,3,4,5-tetrahydrobenzo[f][1,4]oxazepine-8-carboxylate (32 mg, 0.072 mmol, 1 equiv), 5-(tert-butoxycarbonyl)-5-azaspiro[2.5]octane-1-carboxylic acid (22.1 mg, 0.086 mmol, 1.2 equiv) and dichloroethane (1 mL). This was followed by the addition of Et$_3$N (18.2 mg, 0.18 mmol, 2.50 equiv) and DMC (14.6 mg, 0.086 mmol, 1.2 equiv) at room temperature. The resulting solution was stirred for 2 h at room temperature. The reaction was then quenched by the addition of water (1 mL). The resulting solution was extracted with CH$_2$Cl$_2$ (2×2 mL). The organic layer was concentrated under vacuum to afford the title compound as a yellow oil (24 mg, 34% yield) which was used without further purification. MS: (ES, m/z): 445 [M+H]$^+$.

Step-2: tert-Butyl 1-(8-(hydroxycarbamoyl)-2,3,4,5-tetrahydrobenzo[f][1,4]oxazepine-4-carbonyl)-6-azaspiro[2.5]octane-6-carboxylate

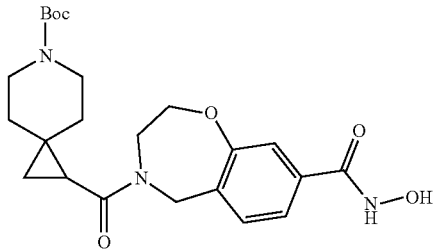 [SMILES: CC(C)(C)OC(=O)N1CCC2(CC1)CC2C(=O)N1CCOc2cc(C(=O)NO)ccc2C1]

4-(6-(tert-Butoxycarbonyl)-6-azaspiro[2.5]octane-1-carbonyl)-2,3,4,5-tetrahydrobenzo[f][1,4]oxazepine-8-carboxylate (24 mg, 0.053 mmol, 1 equiv) was dissolved in MeOH/THF (1:4, 0.5 mL), NH$_2$OH (50% in water, 35 mg, 0.53 mmol, 10 equiv), and aq. 1N NaOH (0.106 mL, 2 equiv). The resulting solution was stirred overnight at room temperature. The crude product was purified by Prep-HPLC (Column: XBridge RP C18 OBD, 5 μm, 19×150 mm; Mobile Phase A: Water/0.05% formic acid; Mobile Phase B: MeCN/0.05% formic acid; Flow rate: 23 mL/min; Gradient: 25% B to 65% B in 6.6 min, hold 0.9 min; Detector, UV 254, 220 nm) to afford the title compound as an off-white solid (2.4 mg, 10% yield). MS: (ES, m/z): 446 [M+H]$^+$.

Example 16

Preparation of (R)—N-hydroxy-2-methyl-4-(1-methylcyclobutane-1-carbonyl)-2,3,4,5-tetrahydrobenzo[f][1,4]oxazepine-8-carboxamide

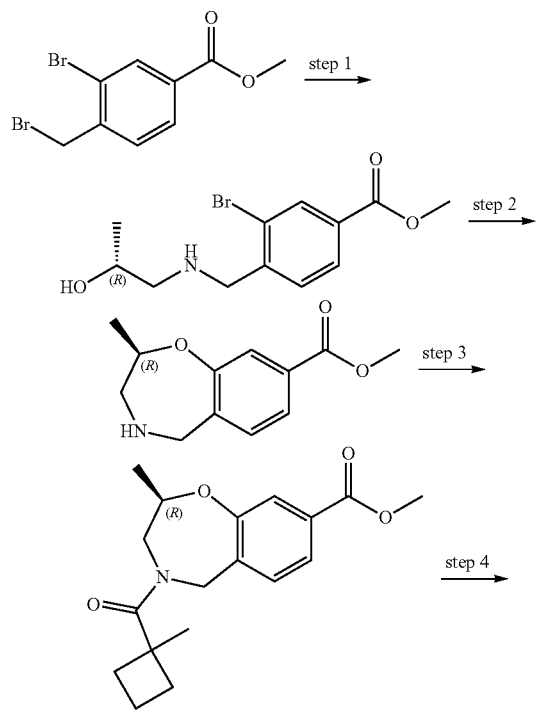

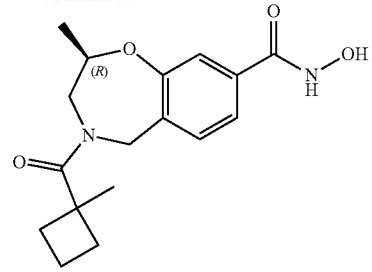

Step-1: Methyl (R)-3-bromo-4-(((2-hydroxypropyl)amino)methyl)benzoate

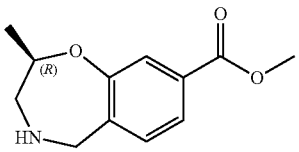

Into a 250-mL round-bottom flask, was placed a solution of methyl 3-bromo-4-(bromomethyl)benzoate (7 g, 22.73 mmol, 1 equiv) in MeCN (80 mL), potassium carbonate (4.69 g, 33.93 mmol, 1.50 equiv) and (2R)-1-aminopropan-2-ol (1.7 g, 22.63 mmol, 1 equiv). The resulting mixture was stirred for 3 h at room temperature and then concentrated under vacuum. The residue was diluted with EtOAc (80 mL) and the resulting solution was washed with water (3×30 mL). The organic phase was concentrated under vacuum to afford the title compound as an off-white solid (3 g) which was used without further purification. MS: (ES, m/z): 302 [M+H]$^+$.

Step-2: Methyl (R)-2-methyl-2,3,4,5-tetrahydrobenzo[f][1,4]oxazepine-8-carboxylate Into a 100-mL round-bottom flask purged and maintained with an inert atmosphere of nitrogen, was placed a solution of methyl (R)-3-bromo-4-(((2-hydroxypropyl)amino)methyl)benzoate (2.75 g, 9.10 mmol, 1 equiv) in isopropanol (32 mL), potassium carbonate (2.53 g, 18.31 mmol, 2 equiv) and CuI (520 mg, 2.73 mmol, 0.30 equiv). The resulting solution was stirred for 21 h at 110° C. in an oil bath. The resulting mixture was concentrated under vacuum and the residue was diluted with EtOAc (100 mL). The resulting mixture was washed with water (3×150 mL) and the organic phase was concentrated, then the residue was purified by silica gel chromatography (CH$_2$Cl$_2$/MeOH, 99:1) to afford the title compound as a brown oil (1.1 g, 55% yield). MS: (ES, m/z): 222 [M+H]$^+$.

Step-3: Methyl (R)-2-methyl-4-(1-methylcyclobutane-1-carbonyl)-2,3,4,5-tetrahydrobenzo[f][1,4]oxazepine-8-carboxylate

Step-4: (R)—N-Hydroxy-2-methyl-4-(1-methylcyclobutane-1-carbonyl)-2,3,4,5-tetrahydrobenzo[f][1,4]oxazepine-8-carboxamide

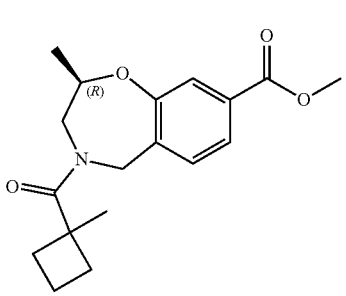

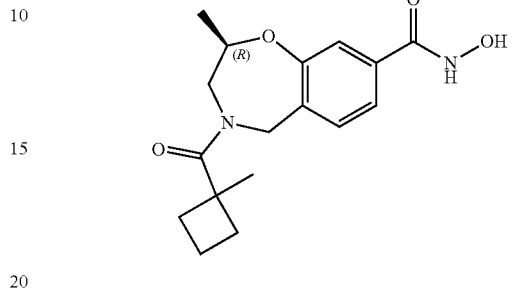

Into a 8-mL vial, was placed 1-methylcyclobutane-1-carboxylic acid (52 mg, 0.46 mmol, 1 equiv), DMF (4 mL), HATU (205 mg, 0.54 mmol, 1.20 equiv), methyl (R)-2-methyl-2,3,4,5-tetrahydrobenzo[f][1,4]oxazepine-8-carboxylate (100 mg, 0.45 mmol, 1 equiv) and DIEA (174 mg, 1.35 mmol, 3 equiv). The resulting mixture was stirred for 16 h at room temperature and then diluted with water (20 mL). The resulting solution was extracted with EtOAc (2×20 mL). The organic layers combined and concentrated. The residue was purified by silica gel chromatography (EtOAc/pet. ether, 1:3) to afford the title compound as a yellow oil (88 mg, 61% yield). MS: (ES, m/z): 318 [M+H]$^+$.

Into a 8-mL vial, were placed methyl (R)-2-methyl-4-(1-methylcyclobutane-1-carbonyl)-2,3,4,5-tetrahydrobenzo[f][1,4]oxazepine-8-carboxylate (88 mg, 0.28 mmol, 1 equiv) and THF/MeOH (4:1, 2 mL). This was followed by addition of NH$_2$OH (50% in water, 0.55 mL, 30 equiv.) and aq. 1N NaOH (0.55 mL, 2 equiv). The resulting solution was stirred for 3 h at room temperature. The crude product was purified by Prep-HPLC (Column XBridge XP C18 OBD, 5 μm, 19×150 mm; Mobile Phase A: Water/0.05% TFA; Mobile Phase B: MeCN/0.05% TFA; Flow rate: 0.7 mL/min; Gradient: 5% B to 40% B in 7 min; Detector, UV 254 nm) to afford the title compound as an off-white solid (53 mg, 60% yield). $^1$H-NMR (300 MHz, DMSO-d$_6$) δ(ppm): 11.17 (br, 1H), 7.39-7.37 (m, 1H), 7.31 (m, 2H), 4.82-4.60 (m, 1H), 4.49-4.21 (m, 2H), 4.11-4.00 (s, 1H), 3.51-3.36 (m, 2H), 2.21 (m, 2H), 1.95-1.75 (m, 3H), 1.57-1.54 (m, 1H), 1.33 (m, 6H). MS: (ES, m/z): 319 [M+H]$^+$.

TABLE 9

The following compound was prepared according to the method of Example 16, using (2S)-1-aminopropan-2-ol.

| Structure | Found M + H | $^1$H-NMR (400 MHz, DMSO-d$_6$) δ(ppm) |
|---|---|---|
| 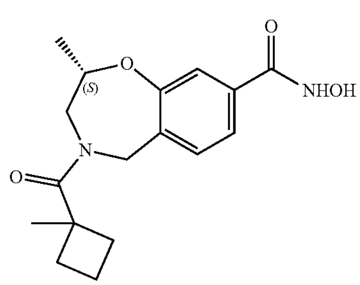 | (ES, m/z): 319 [M + H]$^+$ | 11.16 (br, 1H), 7.39-7.37 (m, 1H), 7.31-7.29 (m, 2H), 4.82-4-62 (m, 1H), 4.43-4.27 (m, 1H), 4.19-4.08 (m, 1H), 3.80-3.60 (m, 1H), 3.45-3.35 (m, 1H), 2.43-2.33 (m, 2H), 1.96-1.80 (m, 2H), 1.79-1.54 (m, 1H), 1.53-1.44 (m, 1H), 1.23 (m, 3H) |

Example 17

Preparation of (R)-4-formyl-N-hydroxy-2-methyl-2,3,4,5-tetrahydrobenzo[f][1,4]oxazepine-8-carboxamide

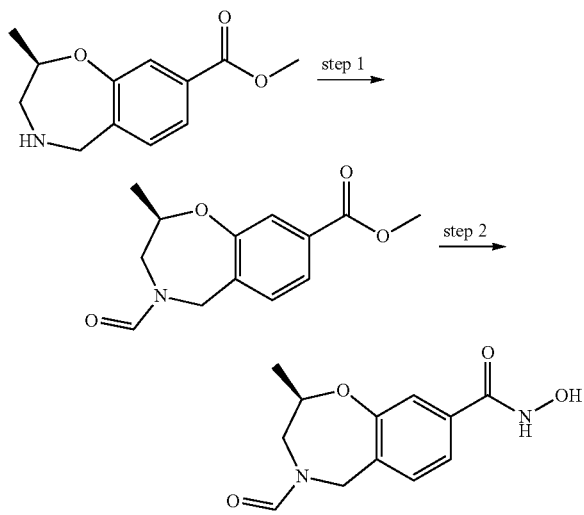

Step-1: Methyl (R)-4-formyl-2-methyl-2,3,4,5-tetrahydrobenzo[f][1,4]oxazepine-8-carboxylate Into a 8-mL vial, was placed methyl (R)-2-methyl-2,3,4,5-tetrahydro-1,4-benzoxazepine-8-carboxylate (80 mg, 0.36 mmol, 1 equiv) and ethyl formate (2 mL, 1 equiv). The resulting solution was refluxed for 16 h in an oil bath. The resulting mixture was concentrated under vacuum to afford the title compound as a yellow oil which was used without further purification. MS: (ES, m/z): 250 [M+H]$^+$.

Step-2: (R)-4-formyl-N-hydroxy-2-methyl-2,3,4,5-tetrahydrobenzo[f][1,4]oxazepine-8-carboxamide

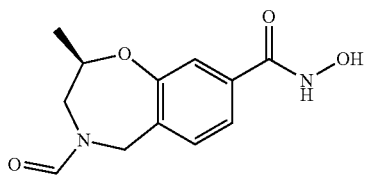 [SMILES: C[C@@H]1CN(C=O)Cc2ccc(C(=O)NO)cc2O1]

Into a 8-mL vial, was placed methyl (R)-4-formyl-2-methyl-2,3,4,5-tetrahydrobenzo[f][1,4]oxazepine-8-carboxylate (100 mg, 0.40 mmol, 1 equiv) in THF/MeOH (4:1, 2 mL). To the above solution was added aq. 1N NaOH (0.8 mL, 0.80 mmol, 2 equiv) and NH$_2$OH (50% in water, 0.8 mL, 0.80 mmol, 30 equiv). The resulting solution was stirred for 3 h at room temperature. The crude product was purified by Prep-HPLC (Column: Waters XBridge XP C18 OBD, 5 μm, 19×150 mm; Mobile Phase A: Water/0.05% TFA; Mobile Phase B: MeCN; Flow rate: 0.7 mL/min; Gradient: 5% B to 53% B in 7 min; Detector, UV 254 nm) to afford the title compound as a brown solid (7.5 mg, 7% yield). $^1$H-NMR (400 MHz, DMSO-d$_6$) δ(ppm): 11.18 (s, 1H), 9.03 (s, 1H), 8.02 (s, 1H), 7.43-7.32 (m, 3H), 4.73-4.67 (m, 1H), 4.32-4.28 (d, J=14.4 Hz, 1H), 4.06-3.81 (m, 2H), 3.49-3.40 (m, 1H), 1.28-1.26 (m, 3H). MS: (ES, m/z): 251 [M+H]$^+$.

TABLE 10

The following compound was prepared according to the method of Example 17, using methyl (S)-2-methyl-2,3,4,5-tetrahydro-1,4-benzoxazepine-8-carboxylate.

| Structure | Found M + H | $^1$H-NMR (400 MHz, DMSO-d$_6$) δ (ppm) |
|---|---|---|
| (S)-isomer structure | (ES, m/z): 251 [M + H]$^+$ | 11.17 (s, 1H), 9.01 (br, 1H), 7.43-7.32 (m, 3H), 4.73-4.71 (m, 1H), 4.32-4.28 (m, 1H), 4.11-3.80 (m, 3H), 3.68 (m, 1H), 1.26-1.29 (m, 3H) |

Example 18

Preparation of (R)-4-acetyl-N-hydroxy-2-methyl-2,3,4,5-tetrahydrobenzo[f][1,4]oxazepine-8-carboxamide

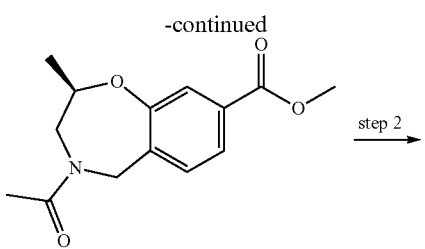

step 2

Into a 8-mL vial, was placed a solution of methyl (R)-2-methyl-2,3,4,5-tetrahydro-1,4-benzoxazepine-8-carboxylate (80 mg, 0.36 mmol, 1 equiv) in $CH_2Cl_2$ (2 mL) and triethylamine (110 mg, 1.09 mmol, 3 equiv). This was followed by the addition of a solution of acetyl chloride (31 mg, 0.39 mmol, 1.10 equiv) in $CH_2Cl_2$ (0.5 mL) dropwise with stirring at 0° C. The resulting solution was stirred for 18 h at room temperature. The reaction mixture was concentrated under vacuum to afford the title compound as a green oil which was used without further purification. MS: (ES, m/z): 264 [M+H]$^+$.

Step-2: (R)-4-Acetyl-N-hydroxy-2-methyl-2,3,4,5-tetrahydrobenzo[f][1,4]oxazepine-8-carboxamide

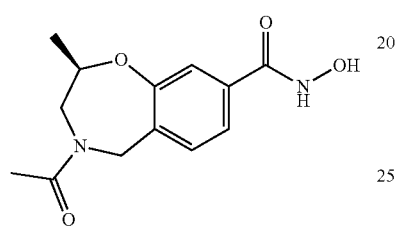

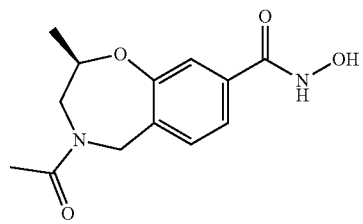

Step-1: Methyl (R)-4-acetyl-2-methyl-2,3,4,5-tetrahydrobenzo[f][1,4]oxazepine-8-carboxylate

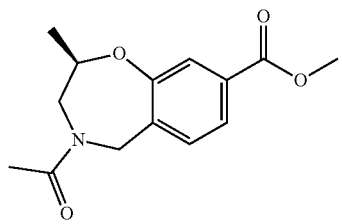 [SMILES: COC(=O)c1ccc2c(c1)O[C@H](C)CN(C(C)=O)C2]

Into a 8-mL vial, was placed a solution of methyl (R)-4-acetyl-2-methyl-2,3,4,5-tetrahydrobenzo[f][1,4]oxazepine-8-carboxylate (90 mg, 0.34 mmol, 1 equiv) in THF/MeOH (4:1, 2 mL). aq. 1N NaOH (0.68 mL, 2 equiv) and $NH_2OH$ (50% in water, 0.67 mL, 30 equiv) were added. The resulting solution was stirred for 14 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 18% B in 6 min; Detector, UV 254, 220 nm) to afford the title compound as a green oil (12.5 mg, 10% yield). $^1$H-NMR (400 MHz, DMSO-$d_6$) δ(ppm): 11.18-11.16 (br, 1H), 9.03 (s, 1H), 7.42-7.25 (m, 3H), 4.76-4.68 (m, 1H), 4.53-4.49 (d, J=8.2 Hz, 1H), 4.12-3.86 (m, 2H), 3.42-3.41 (m, 1H), 2.01-1.98 (d, J=12.8 Hz, 3H), 1.31-1.25 (m, 3H). MS: (ES, m/z): 265 [M+H]$^+$.

TABLE 11

The following compound was prepared according to the method of Example 18, using methyl (S)-2-methyl-2,3,4,5-tetrahydro-1,4-benzoxazepine-8-carboxylate.

| Structure | Found M + H | $^1$H-NMR (400 MHz, DMSO-$d_6$) δ (ppm) |
|---|---|---|
| 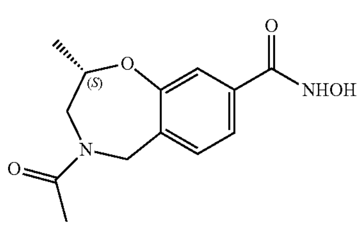 | (ES, m/z): 265 [M + H]$^+$ | 11.17-11.15 (br, 1H), 9.03 (s, 1H), 7.44-7.28 (m, 3H), 4.77-4.72 (m, 1H), 4.68-4.34 (m, 1H), 4.15-3.98 (m, 2H), 3.67-3.39 (m, 1H), 2.07-1.98 (d, J = 12.8 Hz, 3H), 1.31-1.26 (m, 3H) |

Example 19

Preparation of (R)—N-hydroxy-2-isopropyl-4-(tetrahydro-2H-pyran-4-carbonyl)-2,3,4,5-tetrahydrobenzo[f][1,4]oxazepine-8-carboxamide

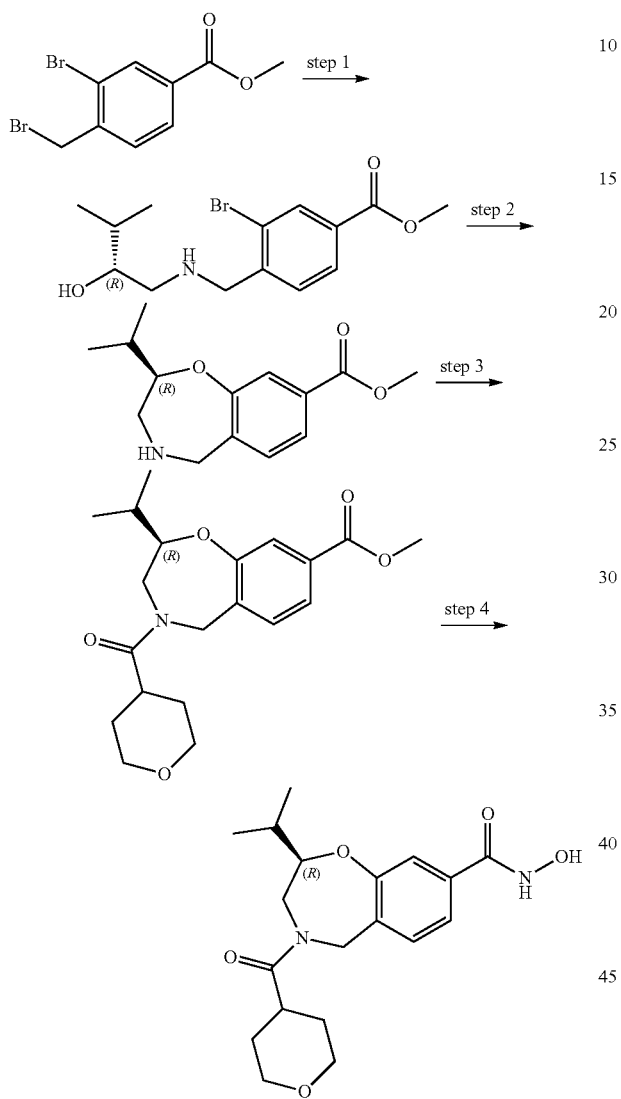

Step-1: Methyl (R)-3-bromo-4-(((2-hydroxy-3-methylbutyl)amino)methyl)benzoate

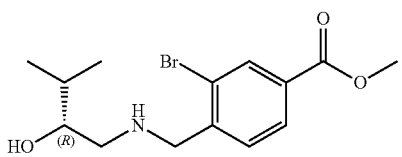

Into a 500-mL round-bottom flask, was placed (R)-1-amino-3-methylbutan-2-ol (6.41 g, 62.13 mmol, 2 equiv), MeCN (100 mL) and K₂CO₃ (6.44 g, 46.60 mmol, 1.5 equiv). This was followed by the addition of methyl 3-bromo-4-(bromomethyl)benzoate (9.52 g, 30.91 mmol, 1 equiv) in several batches. The resulting solution was stirred for 16 h at room temperature. The resulting mixture was concentrated under vacuum. The residue was dissolved in EtOAc (200 mL) and washed with H₂O (2×100 mL). The organic layer was dried over anhydrous Na₂SO₄, filtered, and concentrated. The residue was purified by silica gel chromatography (EtOAc/pet. ether, 3:2) to afford the title compound as a yellow solid (6.48 g, 63% yield). MS: (ES, m/z): 330 [M+H]⁺.

Step-2: Methyl (R)-2-isopropyl-2,3,4,5-tetrahydrobenzo[f][1,4]oxazepine-8-carboxylate

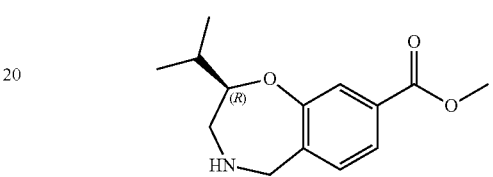

Into a 100-mL pressure tank reactor purged and maintained with an inert atmosphere of nitrogen, was placed methyl (R)-3-bromo-4-(((2-hydroxy-3-methylbutyl)amino)methyl)benzoate (4.91 g, 14.87 mmol, 1 equiv), isopropanol (50 mL), K₂CO₃ (3.09 g, 22.36 mmol, 1.5 equiv) and CuI (1.42 g, 7.46 mmol, 0.5 equiv). The resulting solution was stirred for 16 h at 110° C. in an oil bath. The resulting mixture was concentrated under vacuum. The residue was dissolved in CH₂Cl₂ (200 mL) and washed with H₂O (3×100 mL). The organic layer was dried over anhydrous MgSO₄, filtered, and concentrated. The residue was purified by C18 chromatography (MeCN/H₂O+0.05% TFA, 1:3) to afford the TFA salt of the title compound as a green solid (1.5 g, 40% yield). MS: (ES, m/z): 250 [M+H]⁺.

Step-3: Methyl (R)-2-isopropyl-4-(tetrahydro-2H-pyran-4-carbonyl)-2,3,4,5-tetrahydrobenzo[f][1,4]oxazepine-8-carboxylate

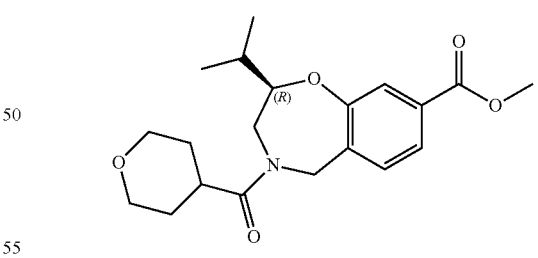

Into a 8-mL vial, were placed methyl (R)-2-isopropyl-2,3,4,5-tetrahydrobenzo[f][1,4]oxazepine-8-carboxylate.TFA (100 mg, 0.40 mmol, 1 equiv) and DMF (10 mL). This was followed by the addition of tetrahydro-2H-pyran-4-carboxylic acid (62.4 mg, 0.48 mmol, 1.2 equiv), HATU (183 mg, 0.76 mmol, 1.2 equiv) and DIEA (155 mg, 1.20 mmol, 3 equiv) at 0° C. The resulting mixture was stirred for 16 h at room temperature and then diluted with EtOAc (50 mL). The resulting mixture was washed with H₂O (5×50 mL). The organic layer was dried over anhydrous Na₂SO₄, filtered, and concentrated to afford the title compound as yellow oil (150 mg) which was used without further purification. MS: (ES, m/z): 362 [M+H]+.

Step-4: (R)—N-hydroxy-2-isopropyl-4-(tetrahydro-2H-pyran-4-carbonyl)-2,3,4,5-tetrahydrobenzo[f][1,4]oxazepine-8-carboxamide

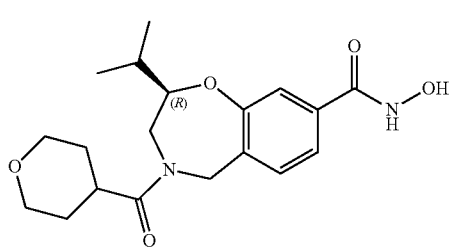

Into a 8-mL vial, was placed methyl (R)-2-isopropyl-4-(tetrahydro-2H-pyran-4-carbonyl)-2,3,4,5-tetrahydrobenzo[f][1,4]oxazepine-8-carboxylate (150 mg, 0.42 mmol, 1 equiv) and THF/MeOH (4:1, 1.5 mL). Then NH$_2$OH (50% in water, 0.84 mL, 12.73 mmol, 30 equiv) and aq. 1N NaOH (0.84 mL, 0.82 mmol, 2 equiv) were added at the same time. The resulting solution was stirred for 16 h at room temperature. The crude product was purified by Prep-HPLC (Column: Sunfire Prep C18 OBD, 5 μm, 19×150 mm; Mobile Phase A: Water/0.05% formic acid; Mobile Phase B: MeCN; Flow rate: 25 mL/min; Gradient: 10% B to 30% B in 8 min; Detector, UV 254, 220 nm) to afford the title compound as a yellow solid (21.6 mg, 13% yield). $^1$H-NMR (400 MHz, DMSO-d$_6$) δ(ppm): 11.20 (br, 1H), 7.52-7.50 (d, J=8.0 Hz, 1H), 7.44-7.42 (d, J=8.8 Hz, 1H), 7.39-7.36 (m, 1H), 7.31-7.27 (m, 1H), 4.92-4.88 (d, J=16.4 Hz, 0.5H), 4.80-4.76 (d, J=14.8 Hz, 0.4H), 4.61-4.57 (d, J=16.0 Hz, 0.5H), 4.40-4.36 (d, J=15.2 Hz, 0.4H), 4.15-4.12 (d, J=11.6 Hz, 0.5H), 3.99-3.96 (d, J=11.6 Hz, 0.5H), 3.80-3.78 (m, 2H), 3.70-3.68 (m, 1H), 3.54-3.48 (m, 1H), 3.41-3.32 (m, 2H), 2.98 (m, 0.5H), 2.88-2.86 (m, 0.4H), 1.98-1.86 (m, 1H), 1.57-1.48 (m, 2H), 1.41-1.33 (m, 1H), 1.22-1.19 (d, J=13.6 Hz, 1H), 1.08-1.02 (m, 6H). MS: (ES, m/z): 363 [M+H]+.

Example 20

Preparation of (R)-4-formyl-N-hydroxy-2-isopropyl-2,3,4,5-tetrahydrobenzo[f][1,4]oxazepine-8-carboxamide

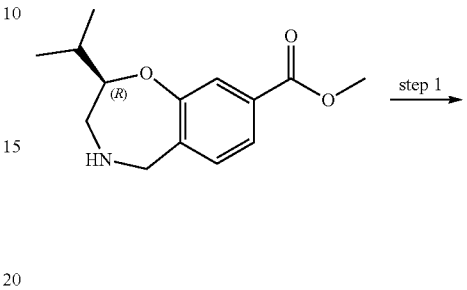

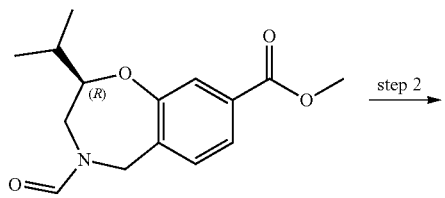

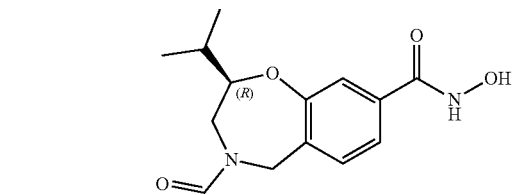

TABLE 12

The following compound was prepared according to the method of Example 19.

| Structure | Found M + H | $^1$H-NMR (400 MHz, DMSO-d$_6$) δ (ppm) |
|---|---|---|
| 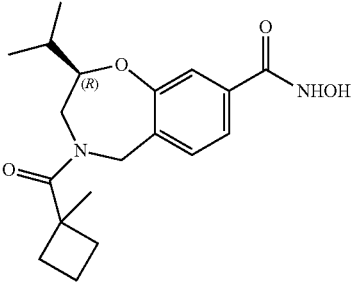 | (ES, m/z): 347 [M + H]+ | 11.19 (br, 1H), 7.39-7.28 (m, 3H), 4.78-4.64 (m, 1H), 4.44-4.36 (t, 1H), 3.90-3.64 (m, 2H), 3.53-3.47 (m, 1H), 2.39-2.32 (m, 2H), 1.94-1.89 (m, 2H), 1.88-1.75 (m, 1H), 1.59-1.56 (m, 1H), 1.34 (s, 3H), 1.08-1.03 (m, 6H) |

Step-1: Methyl (R)-4-formyl-2-isopropyl-2,3,4,5-tetrahydrobenzo[f][1,4]oxazepine-8-carboxylate

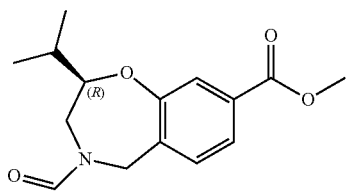

Into a 8-mL vial, was placed methyl (R)-2-isopropyl-2,3,4,5-tetrahydrobenzo[f][1,4]oxazepine-8-carboxylate.TFA (80 mg, 0.32 mmol, 1 equiv) and ethyl formate (1.5 mL). The resulting solution was stirred for 16 h at 60° C. in an oil bath. The resulting mixture was concentrated under vacuum to afford the title compound as yellow oil (90 mg) which was used without further purification. MS: (ES, m/z): 278 [M+H]$^+$.

Step-2: (R)-4-Formyl-N-hydroxy-2-isopropyl-2,3,4,5-tetrahydrobenzo[f][1,4]oxazepine-8-carboxamide

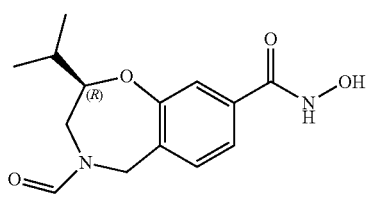

Into a 8-mL vial, was placed methyl (R)-4-formyl-2-isopropyl-2,3,4,5-tetrahydrobenzo[f][1,4]oxazepine-8-carboxylate (89 mg, 0.32 mmol, 1 equiv) in THF/MeOH (4:1, 1.5 mL). Then NH$_2$OH (50% in water, 0.64 mL, 9.70 mmol, 30 equiv) and aq. 1N NaOH (0.64 mL, 0.65 mmol, 2 equiv) were added at the same time. The resulting solution was stirred for 2 h at room temperature. The crude product was purified by Prep-HPLC (Column: Sunfire Prep C18 OBD, 5 µm, 19×150 mm; Mobile Phase A: Water/0.05% formic acid; Mobile Phase B: MeCN; Flow rate: 25 mL/min; Gradient: 5% B to 36% B in 7 min; Detector, UV 254, 220 nm) to afford the title compound as a white solid (11.3 mg, 11% yield). $^1$H-NMR (400 MHz, DMSO-d$_6$) δ(ppm): 11.20 (br, 1H), 8.20 (s, 4H), 8.06 (s, 0.6H), 7.45-7.32 (m, 3H), 4.81-4.72 (m, 1H), 4.54-4.50 (d, J=16.0 Hz, 0.4H), 4.30-4.27 (d, J=14.8 Hz, 0.6H), 4.09-4.05 (d, J=13.2 Hz, 0.4H), 3.90-3.83 (m, 0.6H), 3.61-3.49 (m, 1.5H), 3.43-3.37 (m, 0.5H), 1.95-1.88 (m, 1H), 1.09-1.03 (m, 6H). MS: (ES, m/z): 279 [M+H]$^+$.

Example 21

Preparation of (R)—N-hydroxy-2-(methoxymethyl)-4-(tetrahydro-2H-pyran-4-carbonyl)-2,3,4,5-tetrahydrobenzo[f][1,4]oxazepine-8-carboxamide

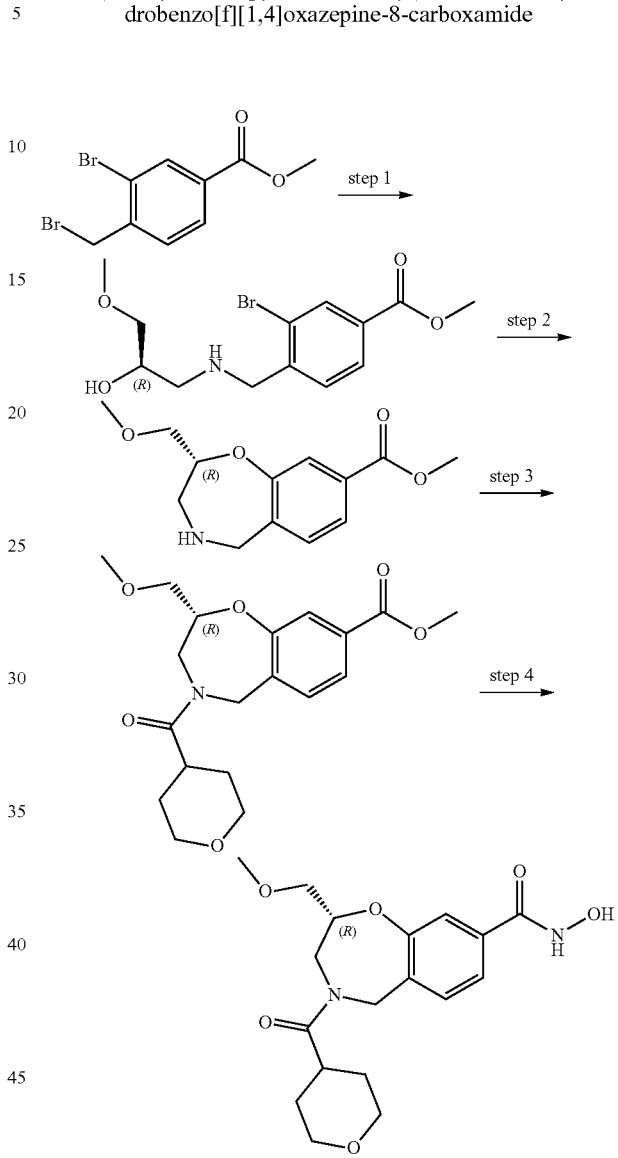

Step-1: Methyl (R)-3-bromo-4-(((2-hydroxy-3-methoxypropyl)amino)methyl)benzoate

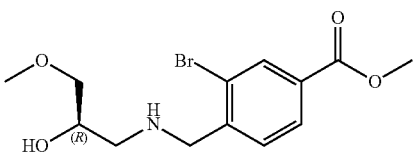

Into a 500-mL round-bottom flask, was placed a solution of (R)-1-amino-3-methoxypropan-2-ol (5.7 g, 54.22 mmol, 1.1 equiv) in MeCN (150 mL) and K$_2$CO$_3$ (10 g, 72.46 mmol, 1.5 equiv). This was followed by the addition of a solution of methyl 3-bromo-4-(bromomethyl)benzoate (15.2 g, 49.36 mmol, 1 equiv) in MeCN (100 mL) dropwise with stirring at room temperature. The resulting mixture was stirred for 16 h at room temperature. The resulting mixture was concentrated under vacuum. The residue was diluted with H₂O (100 mL) and extracted with EtOAc (3×100 mL). The organic layer was washed with H₂O (2×100 mL) and concentrated under vacuum. The residue was purified by silica gel chromatography (EtOAc/pet. ether, 1:4) to afford the title compound as a yellow solid (6.4 g, 39% yield). MS: (ES, m/z): 332 [M+H]⁺.

Step-2: Methyl (R)-2-(methoxymethyl)-2,3,4,5-tetrahydrobenzo[f][1,4]oxazepine-8-carboxylate

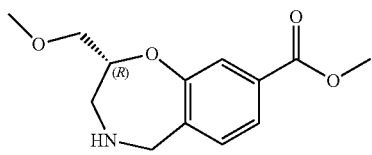

Into a 150-mL pressure tank reactor purged and maintained with an inert atmosphere of nitrogen, was placed a solution of methyl (R)-3-bromo-4-(((2-hydroxy-3-methoxypropyl)amino)methyl)benzoate (6.4 g, 19.27 mmol, 1 equiv) in isopropanol (130 mL), K₂CO₃ (4.01 g, 29.06 mmol, 1.5 equiv) and CuI (1.47 g, 7.74 mmol, 0.4 equiv). The resulting solution was stirred for 16 h at 110° C. in an oil bath. The resulting mixture was concentrated under vacuum. The residue was diluted with H₂O (100 mL) and extracted with CH₂Cl₂ (3×100 mL). The organic layer was washed with H₂O (2×100 mL) and concentrated under vacuum. The residue was purified by C18 chromatography (MeCN/H₂O+ 0.05% TFA, 88:12) to afford the TFA salt of the title compound as a yellow solid (3.5 g, 50% yield). MS: (ES, m/z): 252 [M+H]⁺.

Step-3: Methyl (R)-2-(methoxymethyl)-4-(tetrahydro-2H-pyran-4-carbonyl)-2,3,4,5-tetrahydrobenzo[f][1,4]oxazepine-8-carboxylate

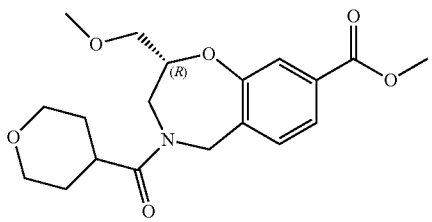

Into a 8-mL vial, was placed a solution of methyl (R)-2-(methoxymethyl)-2,3,4,5-tetrahydrobenzo[f][1,4]oxazepine-8-carboxylate.TFA (100 mg, 0.27 mmol, 1 equiv) in DMF (2 mL) and HATU (125 mg, 0.33 mmol, 1.20 equiv). This was followed by the addition of a solution of tetrahydro-2H-pyran-4-carboxylic acid (43 mg, 0.33 mmol, 1.2 equiv) in DMF (0.5 mL) dropwise with stirring at 0° C. To this was added DIEA (106 mg, 0.82 mmol, 3 equiv) at 0° C. The resulting mixture was stirred for 18 h at room temperature and then diluted with H₂O (10 mL). The resulting solution was extracted with EtOAc (3×20 mL). The organic layer was washed with H₂O (2×20 mL) and brine (20 mL), then dried over anhydrous Na₂SO₄, filtered, and concentrated under vacuum. The residue was purified by silica gel chromatography (EtOAc/pet. ether, 2:1) to afford the title compound as a colorless oil (94 mg, 94% yield). MS: (ES, m/z): 364 [M+H]⁺.

Step-4: (R)—N-Hydroxy-2-(methoxymethyl)-4-(tetrahydro-2H-pyran-4-carbonyl)-2,3,4,5-tetrahydrobenzo[f][1,4]oxazepine-8-carboxamide

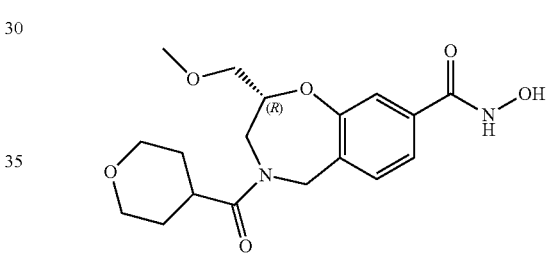

Into a 8-mL vial, was placed a solution of methyl (R)-2-(methoxymethyl)-4-(tetrahydro-2H-pyran-4-carbonyl)-2,3,4,5-tetrahydrobenzo[f][1,4]oxazepine-8-carboxylate (94 mg, 0.26 mmol, 1 equiv) in THF/MeOH (4:1, 3 mL). Then aq. 1N NaOH (0.52 mL, 2.00 equiv) and NH₂OH (50% in H₂O, 0.51 mL, 30 equiv) were added simultaneously. The resulting solution was stirred for 3 h at room temperature. The crude product was purified by Prep-HPLC (Column: XBridge RP C18 OBD, 5 μm, 19×150 mm; Mobile Phase A: Water/0.05% formic acid; Mobile Phase B: MeCN; Flow rate: 23 mL/min; Gradient: 5% B to 30% B in 7 min; Detector, UV 254 nm) to afford the title compound as a white solid (27.7 mg, 29% yield). ¹H-NMR (400 MHz, DMSO-d₆) δ(ppm): 11.15 (br, 1H), 9.08 (br, 1H), 7.53-7.29 (m, 3H), 4.91-4.43 (m, 2H), 4.18-4.01 (m, 1H), 3.98-3.93 (m, 1H), 3.80-3.49 (m, 5H), 3.40-3.32 (m, 5H), 2.98-2.85 (m, 1H), 1.57-1.41 (m, 3H), 1.30-1.27 (m, 1H). MS: (ES, m/z): 365 [M+H]⁺.

TABLE 13

The following compounds were prepared according to the method of Example 21, using (S)-1-amino-3-methoxypropan-2-ol where appropriate.

| Structure | Found M + H | $^1$H-NMR (400 MHz, DMSO-$d_6$) δ (ppm) |
|---|---|---|
| | (ES, m/z): 349 [M + H]$^+$ | 11.18 (br, 1H), 9.02 (br, 1H), 7.40-7.30 (m, 3H), 4.81-4.68 (m, 1H), 4.38-4.13 (m, 2H), 3.76-3.47 (m, 4H), 3.35-3.32 (d, J = 12.0 Hz, 3H), 2.35-2.33 (m, 2H), 1.94-1.75 (m, 3H), 1.58-1.55 (m, 1H), 1.33 (s, 3H) |
| | (ES, m/z): 365 [M + H]$^+$ | 11.18 (br, 1H), 9.03 (br, 1H), 7.53-7.29 (m, 3H), 4.91-4.43 (m, 2H), 4.19-4.09 (m, 1H), 4.01-3.96 (m, 1H), 3.93-3.51 (m, 5H), 3.41-3.32 (m, 5H), 2.99-2.87 (m, 1H), 1.54-1.45 (m, 3H), 1.30-1.27 (d, J = 12.8 Hz, 1H) |
| | (ES, m/z): 349 [M + H]$^+$ | 11.18 (br, 1H), 9.03 (br, 1H), 7.40-7.30 (m, 3H), 4.81-4.68 (m, 1H), 4.44-4.13 (m, 2H), 3.76-3.48 (m, 4H), 3.35-3.33 (d, J = 8.0 Hz, 3H), 2.35-2.33 (m, 2H), 1.94-1.75 (m, 3H), 1.58-1.55 (m, 1H), 1.33 (s, 3H) |

Example 22

Preparation of (R)-4-formyl-N-hydroxy-2-(methoxymethyl)-2,3,4,5-tetrahydrobenzo[f][1,4]oxazepine-8-carboxamide

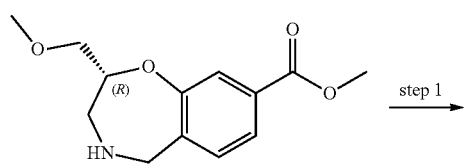

step 1

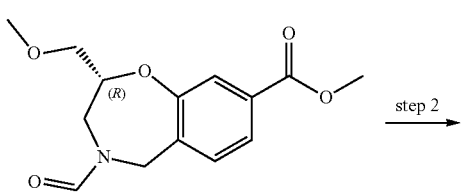

step 2

-continued

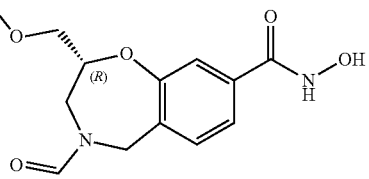

Step-1: Methyl (R)-4-formyl-2-(methoxymethyl)-2,3,4,5-tetrahydrobenzo[f][1,4]oxazepine-8-carboxylate

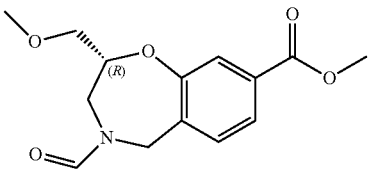

Methyl (R)-2-(methoxymethyl)-2,3,4,5-tetrahydrobenzo[f][1,4]oxazepine-8-carboxylate.TFA (100 mg, 0.27 mmol, 1 equiv) was dissolved in CH$_2$Cl$_2$ (2 mL) and Et$_3$N (28 mg, 0.27 mmol, 1 equiv) was added. The resulting mixture was concentrated under vacuum. The residue and ethyl formate (2.5 mL) were added to a 10 mL sealed tube. The resulting solution was stirred for 18 h at 60° C. in an oil bath. The mixture was concentrated under vacuum to afford the title compound as light yellow oil (70 mg), which was used without further purification. MS: (ES, m/z): 280 [M+H]$^+$.

Step-2: (R)-4-Formyl-N-hydroxy-2-(methoxymethyl)-2,3,4,5-tetrahydrobenzo[f][1,4]oxazepine-8-carboxamide

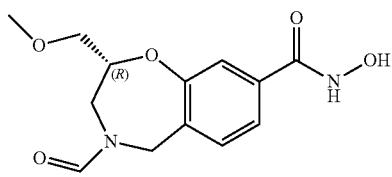

Into a 8-mL vial, was placed a solution of methyl (R)-4-formyl-2-(methoxymethyl)-2,3,4,5-tetrahydrobenzo[f][1,4]oxazepine-8-carboxylate (70 mg, 0.25 mmol, 1 equiv) in THF/MeOH (4:1, 2 mL). Then aq. 1N NaOH (0.50 mL, 2 equiv) and NH$_2$OH (50% in H$_2$O, 0.50 mL, 30 equiv) were added simultaneously. The resulting solution was stirred for 3 h at room temperature. The crude product was purified by Prep-HPLC (Column: XBridge RP C18 OBD, 5 μm, 19×150 mm; Mobile Phase A: Water/0.05% formic acid; Mobile Phase B: MeCN; Flow rate: 20 mL/min; Gradient: 5% B to 15% B in 7 min; Detector, UV 254, 220 nm) to afford the title compound as a brown solid (7.5 mg, 11% yield). $^1$H-NMR (400 MHz, DMSO-d$_6$) δ(ppm): 11.13 (br, 1H), 9.05-9.04 (br, 1H), 8.20-8.04 (d, 1H), 7.45-7.33 (m, 3H), 4.78-4.73 (m, 1H), 4.55-4.31 (m, 1H), 4.09-3.83 (m, 2H), 3.61-3.43 (m, 3H), 3.34-3.33 (d, 3H). MS: (ES, m/z): 281 [M+H]$^+$.

Example 23

Preparation of (R)—N-hydroxy-2-phenyl-4-(tetrahydro-2H-pyran-4-carbonyl)-2,3,4,5-tetrahydrobenzo[f][1,4]oxazepine-8-carboxamide

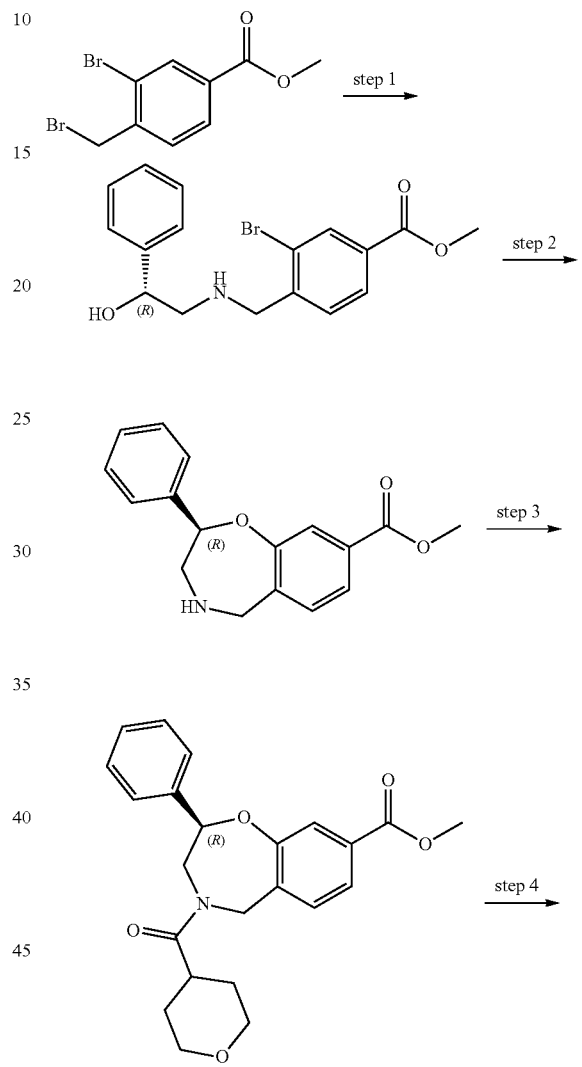

TABLE 14

The following compounds were prepared according to the method of Example 22, using methyl (S)-2-(methoxymethyl)-2,3,4,5-tetrahydrobenzo[f][1,4]oxazepine-8-carboxylate •TFA.

| Structure | Found M + H | $^1$H-NMR (400 MHz, DMSO-d$_6$) δ (ppm) |
|---|---|---|
| 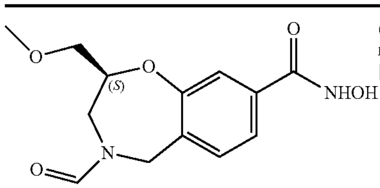 | (ES, m/z): 281 [M + H]$^+$ | 11.18 (br, 1H), 9.08 (br, 1H), 8.21-8.04 (d, 1H), 7.45-7.34 (m, 3H), 4.78-4.73 (m, 1H), 4.56-4.32 (m, 1H), 4.09-3.84 (m, 2H), 3.62-3.44 (m, 3H), 3.34-3.33 (d, J = 3.60 Hz, 3H) |

-continued

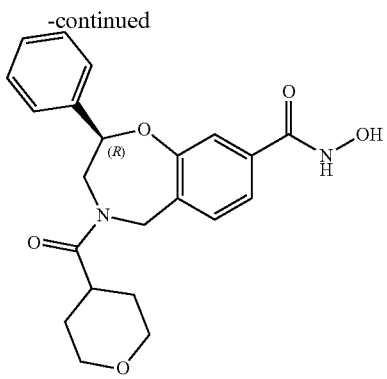

Step-1: Methyl (R)-3-bromo-4-(((2-hydroxy-2-phenylethyl)amino)methyl)benzoate

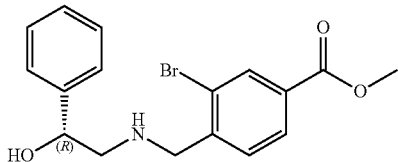

Into a 500-mL round-bottom flask, was placed a solution of (R)-2-amino-1-phenylethan-1-ol (10 g, 72.90 mmol, 1.5 equiv) in MeCN (100 mL), then K$_2$CO$_3$ (8.7 g, 62.49 mmol, 1.3 equiv) was added. This was followed by the slow addition of a solution of methyl 3-bromo-4-(bromomethyl) benzoate (15 g, 48.71 mmol, 1 equiv) in MeCN (120 mL). The resulting mixture was stirred overnight at room temperature and then concentrated under vacuum. The residue was dissolved in EtOAc (350 mL) and washed with H$_2$O (3×100 mL). The organic layer was concentrated under vacuum and purified by silica gel chromatography (EtOAc/ pet. ether, 1:3) to afford the title compound as a yellow solid (9.7 g, 57% yield). MS: (ES, m/z): 364 [M+H]$^+$.

Step-2: Methyl (R)-2-phenyl-2,3,4,5-tetrahydrobenzo[f][1,4]oxazepine-8-carboxylate

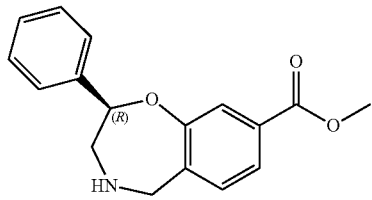

Into a 100-mL sealed tube, was placed a solution of methyl (R)-3-bromo-4-(((2-hydroxy-2-phenylethyl)amino) methyl)benzoate (4.0 g, 10.98 mmol, 1 equiv) in isopropanol (80 mL), then K$_2$CO$_3$ (3.1 g, 22.43 mmol, 2 equiv) was added. This was followed by the addition of CuI (630 mg, 3.31 mmol, 0.3 equiv). The resulting mixture was stirred overnight at 110° C. in an oil bath. The solids were filtered out and the filtrate was concentrated under vacuum. The residue was dissolved in EtOAc (300 mL) and washed with H$_2$O (3×150 mL). The organic layer was concentrated under vacuum. The residue was dissolved in DMF and purified by C18 chromatography (MeCN/H$_2$O+0.05% TFA, 5% to 20% in 15 min) to afford the TFA salt of the title compound as a white solid (1.9 g, 61% yield). MS: (ES, m/z): 284 [M+H]$^+$.

Step-3: Methyl (R)-2-phenyl-4-(tetrahydro-2H-pyran-4-carbonyl)-2,3,4,5-tetrahydrobenzo[f][1,4] oxazepine-8-carboxylate

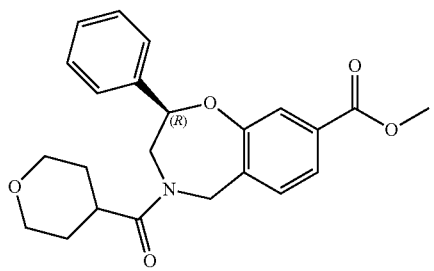

Into a 8-mL vial, was placed a solution of methyl (R)-2-phenyl-2,3,4,5-tetrahydrobenzo[f][1,4]oxazepine-8-carboxylate.TFA (100 mg, 0.77 mmol, 1 equiv) in DMF (2.0 mL), then HATU (114.8 mg, 0.30 mmol, 1.2 equiv) and tetrahydro-2H-pyran-4-carboxylic acid (39.3 mg, 0.10 mmol, 1.2 equiv) were added. To this was added DIEA (97.2 mg, 0.75 mmol, 3 equiv) at 0° C. The resulting mixture was stirred overnight at room temperature. The reaction was diluted with EtOAc (20 mL) and washed with H$_2$O (3×15 mL). The organic layer was concentrated under vacuum. The residue was purified by silica gel chromatography (EtOAc/ pet. ether, 3:2) to afford the title compound as a colorless oil (90 mg, 30% yield). MS: (ES, m/z): 396 [M+H]$^+$.

Step-4: (R)—N-Hydroxy-2-phenyl-4-(tetrahydro-2H-pyran-4-carbonyl)-2,3,4,5-tetrahydrobenzo[f][1, 4]oxazepine-8-carboxamide

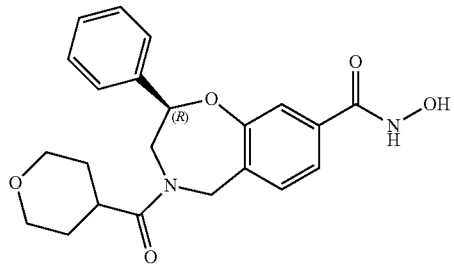

Into a 8-mL vial, was placed a solution of methyl (R)-2-phenyl-4-(tetrahydro-2H-pyran-4-carbonyl)-2,3,4,5-tetrahydrobenzo[f][1,4]oxazepine-8-carboxylate (90 mg, 0.23 mmol, 1 equiv) in THF/MeOH (4:1, 2 mL), then aq. 1N NaOH (0.48 mL, 2 equiv) and NH$_2$OH (50% in H$_2$O, 0.48 mL, 30 equiv) were added simultaneously. The resulting solution was stirred for 2 h at room temperature. The crude product was purified by Prep-HPLC (Column: XBridge RP C18 OBD, 5 μm, 19×150 mm; Mobile Phase A: Water/0.1% formic acid; Mobile Phase B: MeCN; Flow rate: 25 mL/min; Gradient: 30% B to 70% B in 7 min; Detector, UV 254, 220 nm) to afford the title compound as a white solid (60.9 mg, 67% yield). $^1$H-NMR (400 MHz, DMSO-d$_6$) δ(ppm): 11.16 (s,1H), 9.02 (s,1H), 7.61-7.35 (m, 8H), 5.15-5.03 (m, 1H), 4.95-4.90 (m, 1H), 4.74-4.48 (m, 1H), 4.29-4.08 (m, 1H), 3.94-3.66 (m, 3H), 3.45-3.32 (m, 2H), 3.27-2.87 (m, 1H), 1.54-1.49 (m, 4H). MS: (ES, m/z): 397 [M+H]$^+$.

TABLE 15

The following compounds were prepared according to the method of Example 23.

| Structure | Found M + H | ¹H-NMR (400 MHz, DMSO-$d_6$) δ (ppm) |
|---|---|---|
| 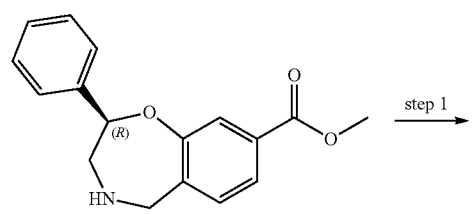 | (ES, m/z): 381 [M + H]⁺ | 11.15 (s, 1H), 9.02 (s, 1H), 7.51-7.35 (m, 8H), 5.11 (m, 1H), 4.98-4.94 (m, 1H), 4.45-3.72 (m, 2H), 2.50 (s, 2H), 1.91-1.57 (m, 4H), 1.35 (m, 3H) |

Example 24

Preparation of (R)-4-formyl-N-hydroxy-2-phenyl-2,3,4,5-tetrahydrobenzo[f][1,4]oxazepine-8-carboxamide

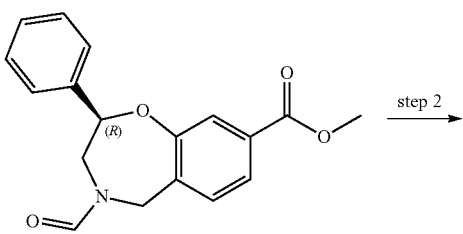

Step-1: Methyl (R)-4-formyl-2-phenyl-2,3,4,5-tetrahydrobenzo[f][1,4]oxazepine-8-carboxylate

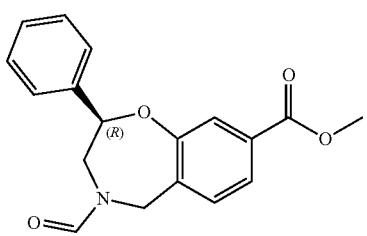

Into a 8-mL vial, was placed a solution of methyl (R)-2-phenyl-2,3,4,5-tetrahydrobenzo[f][1,4]oxazepine-8-carboxylate.TFA (110 mg, 1.48 mmol, 1 equiv) in CH$_2$Cl$_2$ (2.0 mL). This was followed by the addition of Et$_3$N (27.6 mg, 1 equiv). The resulting mixture was concentrated under vacuum. Then ethyl formate (3.0 mL) was added. The resulting solution was stirred overnight at room temperature. The resulting mixture was concentrated under vacuum. The residue was purified by silica gel chromatography (EtOAc/pet. ether, 3:1) to afford the title compound as a yellow oil (140 mg, 30% yield). MS: (ES, m/z): 312 [M+H]⁺.

Step-2: (R)-4-Formyl-N-hydroxy-2-phenyl-2,3,4,5-tetrahydrobenzo[f][1,4]oxazepine-8-carboxamide

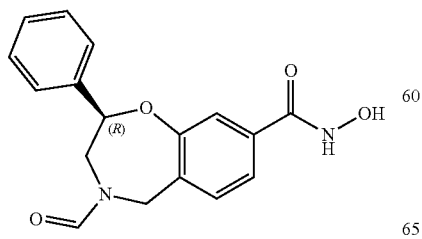

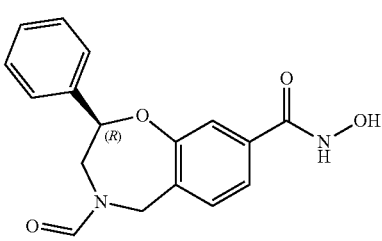

Into a 8-mL vial, was placed a solution of methyl (R)-4-formyl-2-phenyl-2,3,4,5-tetrahydrobenzo[f][1,4]oxazepine-8-carboxylate (140 mg, 0.45 mmol, 1 equiv) in THF/MeOH (4:1, 2.5 mL), then aq. 1N NaOH (0.88 mL, 2 equiv) and NH$_2$OH (50% in H$_2$O, 0.88 mL, 30 equiv) were added simultaneously. The resulting solution was stirred for 2 h at room temperature. The crude product was purified by Prep-HPLC (Column: XBridge RP C18 OBD, 5 μm, 19×150 mm; Mobile Phase A: Water/0.1% formic acid; Mobile Phase B: MeCN; Flow rate: 25 mL/min; Gradient: 30% B to 70% B in 7 min; Detector, UV 254, 220 nm) to afford the title compound as a white solid (60.9 mg, 67% yield). $^1$H-NMR (400 MHz, DMSO-d$_6$) δ(ppm): 11.14 (br, 1H), 9.03 (s, 1H), 8.27-8.15 (m, 1H), 7.57-7.38 (m, 8H), 4.99-4.86 (m, 2H), 4.66-4.37 (m, 1H), 4.33-4.02 (m, 1H), 3.81-3.57 (m, 1H). MS: (ES, m/z): 313 [M+H]$^+$.

Example 25

Preparation of (S)—N-hydroxy-2-phenyl-4-(tetrahydro-2H-pyran-4-carbonyl)-2,3,4,5-tetrahydrobenzo[f][1,4]oxazepine-8-carboxamide

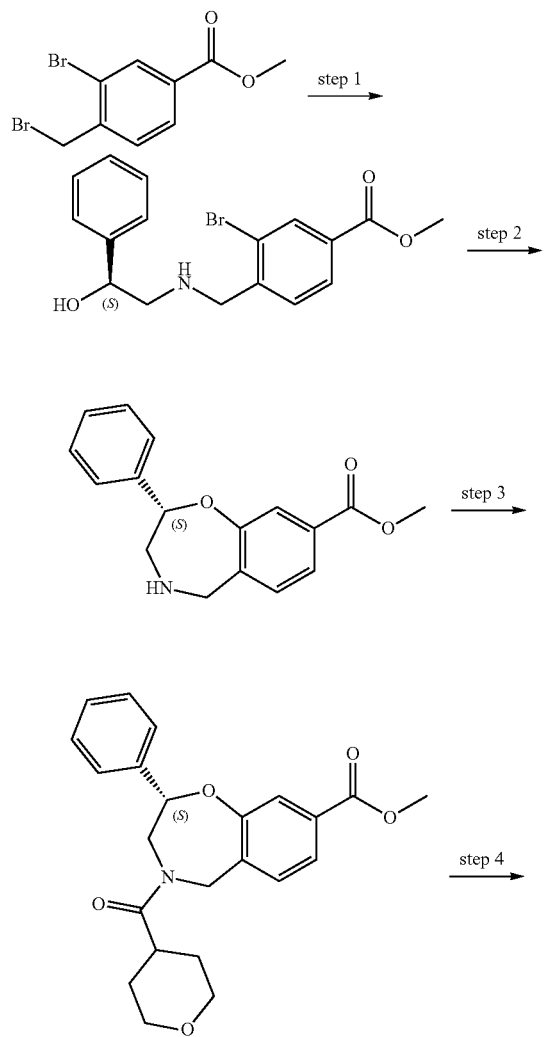

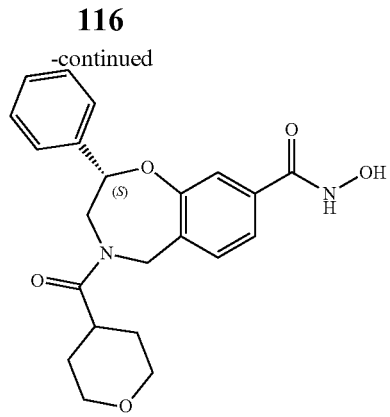

Step-1: Methyl (S)-3-bromo-4-(((2-hydroxy-2-phenylethyl)amino)methyl)benzoate

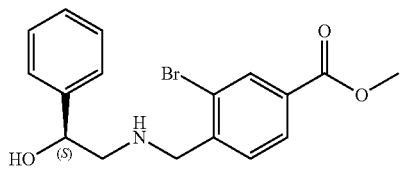

Into a 500-mL round-bottom flask, was placed a solution of (S)-2-amino-1-phenylethan-1-ol (10 g, 72.90 mmol, 1.5 equiv) in MeCN (150 mL), then K$_2$CO$_3$ (8.7 g, 62.49 mmol, 1.3 equiv) was added. This was followed by the slow addition of a solution of methyl 3-bromo-4-(bromomethyl)benzoate (15 g, 48.71 mmol, 1 equiv) in MeCN (100 mL). The resulting mixture was stirred overnight at room temperature and then concentrated under vacuum. The solution was diluted with H$_2$O (200 mL) and extracted with EtOAc (3×200 mL). The organic layer was washed with H$_2$O (2×200 mL) and concentrated under vacuum. The residue was purified by silica gel chromatography (EtOAc/pet. ether, 1:2) to afford the title compound as a white solid (7.9 g, 45% yield). MS: (ES, m/z): 364 [M+H]$^+$.

Step-2: Methyl (S)-2-phenyl-2,3,4,5-tetrahydrobenzo[f][1,4]oxazepine-8-carboxylate

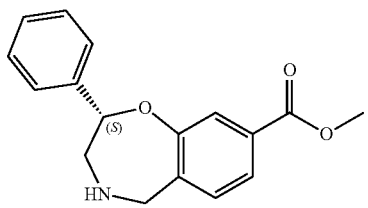

Into a 100-mL sealed tube, was placed a solution of methyl (S)-3-bromo-4-(((2-hydroxy-2-phenylethyl)amino)methyl)benzoate (7.9 g, 21.69 mmol, 1 equiv) in isopropanol (180 mL), then K$_2$CO$_3$ (4.49 g, 32.54 mmol, 1.5 equiv) was added. This was followed by the addition of CuI (1.24 g, 6.53 mmol, 0.3 equiv). The resulting mixture was stirred overnight at 110° C. in an oil bath. The reaction was concentrated under vacuum and diluted with H$_2$O (150 mL)

and extracted with CH$_2$Cl$_2$ (3×100 mL). The organic layer was concentrated under vacuum. The residue was purified by silica gel chromatography (EtOAc/pet. ether, 1:1) to afford the title compound as a brown oil (2.9 g, 47% yield). MS: (ES, m/z): 284 [M+H]$^+$.

Step-3: Methyl (S)-2-phenyl-4-(tetrahydro-2H-pyran-4-carbonyl)-2,3,4,5-tetrahydrobenzo[f][1,4]oxazepine-8-carboxylate

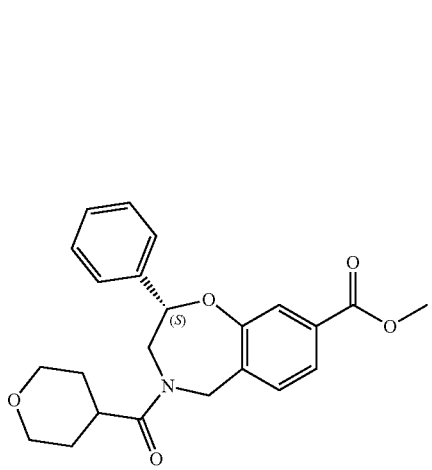

Into a 8-mL vial, a solution of methyl (S)-2-phenyl-2,3,4,5-tetrahydrobenzo[f][1,4]oxazepine-8-carboxylate (100 mg, 0.35 mmol, 1 equiv) in DMF (2.0 mL), HATU (161 mg, 0.42 mmol, 1.2 equiv) and tetrahydro-2H-pyran-4-carboxylic acid (46 mg, 0.35 mmol, 1 equiv), and DIEA (136 mg, 1.05 mmol, 3 equiv) was stirred overnight at room temperature. The reaction was diluted with H$_2$O (10 mL) and extracted with EtOAc (3×10 mL). The organic layer was washed with H$_2$O (3×10 mL) and concentrated under vacuum. The residue was purified by silica gel chromatography (EtOAc/pet. ether, 1:3) to afford the title compound as a yellow oil (100 mg, 72% yield). MS: (ES, m/z): 396 [M+H]$^+$.

Step-4: (S)—N-Hydroxy-2-phenyl-4-(tetrahydro-2H-pyran-4-carbonyl)-2,3,4,5-tetrahydrobenzo[f][1,4]oxazepine-8-carboxamide

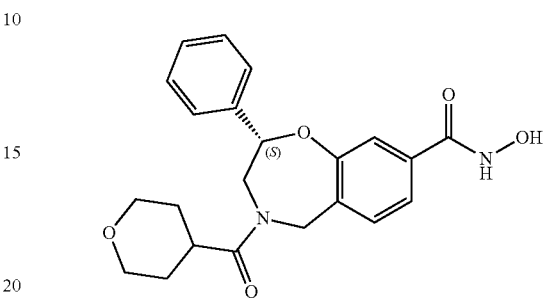

Into a 8-mL vial, was placed a solution of methyl (S)-2-phenyl-4-(tetrahydro-2H-pyran-4-carbonyl)-2,3,4,5-tetrahydrobenzo[f][1,4]oxazepine-8-carboxylate (100 mg, 0.25 mmol, 1 equiv) in THF/MeOH (4:1, 2 mL), then aq. 1N NaOH (0.42 mL, 2 equiv) and NH$_2$OH (50% in H$_2$O, 0.42 mL, 30 equiv) were added simultaneously. The resulting solution was stirred for 2 h at room temperature. The crude product was purified by Prep-HPLC (Column: XBridge RP C18 OBD, 5 μm, 19×150 mm; Mobile Phase A: Water/0.05% formic acid; Mobile Phase B: MeCN; Flow rate: 20 mL/min; Gradient: 30% B to 70% B in 10 min; Detector, UV 254 nm) to afford the title compound as a white solid (54.3 mg, 54% yield). $^1$H-NMR (400 MHz, DMSO-d$_6$) δ(ppm): 11.16 (s, 1H), 9.03 (s, 1H), 7.61-7.52 (m, 2H), 7.51-7.32 (m, 6H), 5.15-5.03 (m, 1H), 4.95-4.86 (m, 1H), 4.81-4.46 (m, 1H), 4.33-4.06 (m, 1H), 3.98-3.89 (m, 0.5H), 3.88-3.77 (m, 2H), 3.76-3.66 (m, 0.5H), 3.48-3.35 (m, 2H), 3.13-2.98 (m, 0.5H), 2.97-2.84 (m, 0.5H), 1.65-1.37 (m, 3H), 1.31-1.20 (m, 1H). MS: (ES, m/z): 397 [M+H]$^+$.

TABLE 16

The following compounds were prepared according to the method of Example 25.

| Structure | Found M + H | $^1$H-NMR (400 MHz, DMSO-d$_6$) δ (ppm) |
| --- | --- | --- |
| 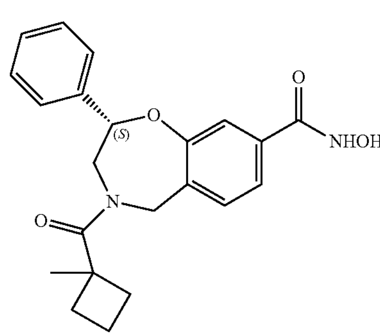 | (ES, m/z): 381 [M + H]$^+$ | 11.16 (s, 1H), 9.02 (s, 1H), 7.51-7.35 (m, 8H), 5.26-5.08 (m, 1H), 5.03-4.79 (m, 1H), 4.56-4.41 (m, 1H), 4.11-3.62 (m, 2H), 2.49-2.18 (m, 2H), 1.98-1.53 (m, 4H), 1.41-1.28 (s, 3H) |

Example 26

Preparation of (S)-4-formyl-N-hydroxy-2-phenyl-2,3,4,5-tetrahydrobenzo[f][1,4]oxazepine-8-carboxamide

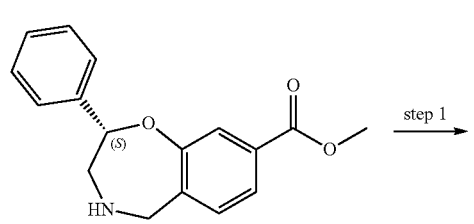

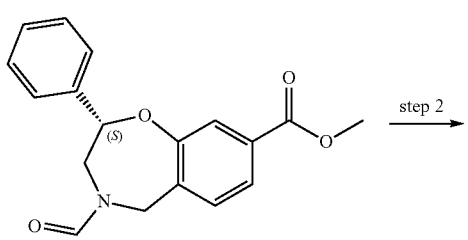

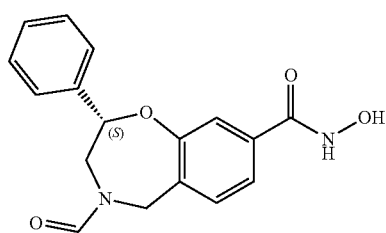

Step-1: Methyl (S)-4-formyl-2-phenyl-2,3,4,5-tetrahydrobenzo[f][1,4]oxazepine-8-carboxylate

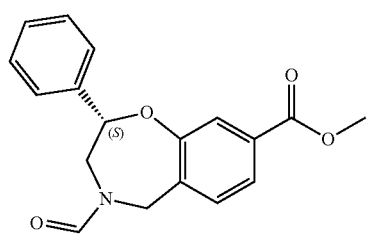

Into a 8-mL vial, was placed methyl (S)-2-phenyl-2,3,4,5-tetrahydrobenzo[f][1,4]oxazepine-8-carboxylate (100 mg, 0.35 mmol, 1 equiv) and ethyl formate (3 mL). The resulting solution was stirred overnight at 61° C. in an oil bath. The resulting mixture was concentrated under vacuum. The residue was purified by silica gel chromatography (EtOAc/pet. ether, 1:3) to afford the title compound as a yellow oil (50 mg, 46% yield). MS: (ES, m/z): 312 [M+H]$^+$.

Step-2: (S)-4-Formyl-N-hydroxy-2-phenyl-2,3,4,5-tetrahydrobenzo[f][1,4]oxazepine-8-carboxamide

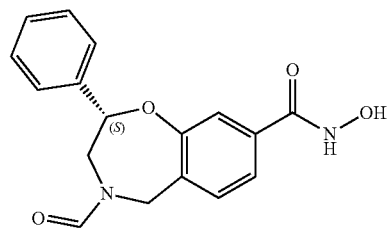

Into a 8-mL vial, was placed a solution of methyl (S)-4-formyl-2-phenyl-2,3,4,5-tetrahydrobenzo[f][1,4]oxazepine-8-carboxylate (50 mg, 0.16 mmol, 1 equiv) in THF/MeOH (4:1, 1.5 mL), then aq. 1N NaOH (0.32 mL, 2 equiv) and NH$_2$OH (50% in H$_2$O, 0.31 mL, 30 equiv) were added simultaneously. The resulting solution was stirred for 2 h at room temperature. The crude product was purified by Prep-HPLC (Column: XBridge RP C18 OBD, 5 μm, 19×150 mm; Mobile Phase A: Water/0.1% formic acid; Mobile Phase B: MeCN; Flow rate: 20 mL/min; Gradient: 30% B to 70% B in 10 min; Detector, UV 254, 220 nm) to afford the title compound as a white solid (3.8 mg, 8% yield). $^1$H-NMR (400 MHz, DMSO-d$_6$) δ(ppm): 11.38-10.89 (br, 1H), 9.23-8.89 (br, 1H), 8.27-8.13 (m, 1H), 7.57-7.49 (m, 3H), 7.48-7.38 (m, 5H), 5.01-4.86 (m, 2H), 4.66-4.33 (m, 1H), 4.23-4.03 (m, 1H), 3.81-3.58 (m, 1H). MS: (ES, m/z): 313 [M+H]$^+$.

Example 27

Preparation of N$^8$-hydroxy-N$^2$,N$^2$-dimethyl-4-(tetrahydro-2H-pyran-4-carbonyl)-2,3,4,5-tetrahydrobenzo[f][1,4]oxazepine-2,8-dicarboxamide

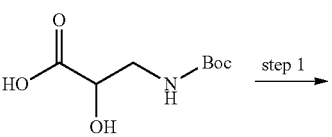

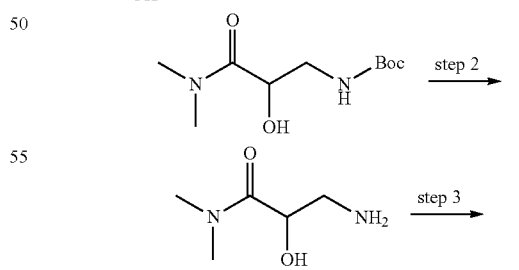

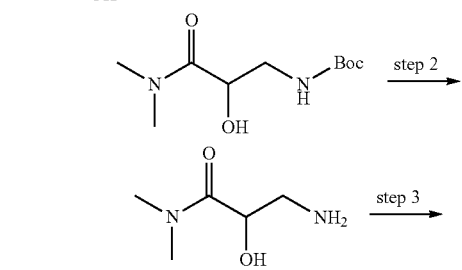

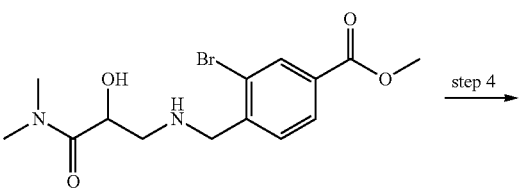

121

-continued

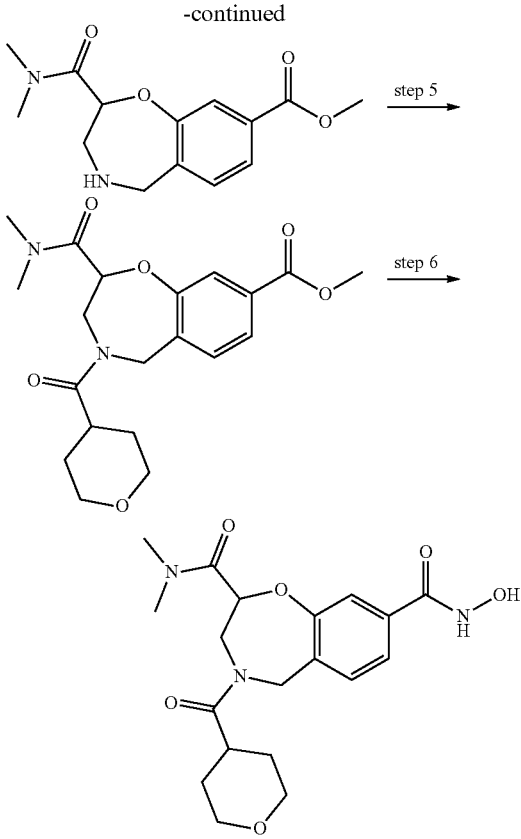

Step-1: tert-Butyl (3-(dimethylamino)-2-hydroxy-3-oxopropyl)carbamate

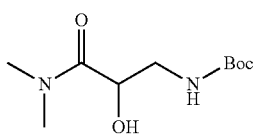 [SMILES: CN(C)C(=O)C(O)CNC(=O)OC(C)(C)C]

Into a 25-mL round-bottom flask, were placed a solution of 3-((tert-butoxycarbonyl)amino)-2-hydroxypropanoic acid (1 g, 4.87 mmol, 1 equiv) in CH$_2$Cl$_2$ (24 mL), dimethylamine hydrochloride (800 mg, 9.81 mmol, 2 equiv), and 4-dimethylaminopyridine (1.49 g, 12.21 mmol, 2.5 equiv). This was followed by the addition of a solution of N,N'-dicyclohexylcarbodiimide (1.51 g, 7.33 mmol, 1.5 equiv) in CH$_2$Cl$_2$ (5 mL) dropwise at room temperature and the resulting solution was stirred at this temperature for 3 days. The resulting mixture was concentrated under vacuum and the residue was re-dissolved with Et$_2$O (20 mL). The precipitated solid was filtered out and the filtrate was concentrated under vacuum. The residue was re-dissolved with EtOAc (20 mL) and the resulting mixture was washed with aq. NH$_4$Cl (3×10 mL). The organic layer was dried over anhydrous Na$_2$SO$_4$, filtered, and the solvent was removed in vacuo to afford the title compound as brown oil (800 mg crude), which was used without further purification.

122

Step-2: 3-Amino-2-hydroxy-N,N-dimethylpropanamide

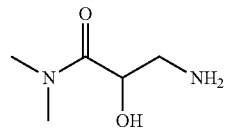

Into a 25-mL round-bottom flask, was placed a solution of tert-butyl (3-(dimethylamino)-2-hydroxy-3-oxopropyl)carbamate (800 mg, 3.44 mmol, 1 equiv) in CH$_2$Cl$_2$ (8 mL). This was followed by the addition of TFA (3 mL) dropwise with stirring at 0° C. The resulting solution was stirred at room temperature for 6 h. The solvent was removed in vacuo and the residue was re-dissolved with H$_2$O (2 mL). Aqueous 2N NaOH was added to adjust the pH value to 7 and the resulting mixture was concentrated under vacuum. The residue was dissolved with EtOAc (20 mL) and the solid was filtered out. The filtrate was concentrated under vacuum to afford the title compound as light yellow oil (500 mg crude), which was used without further purification.

Step-3: Methyl 3-bromo-4-(((3-(dimethylamino)-2-hydroxy-3-oxopropyl)amino)methyl)benzoate

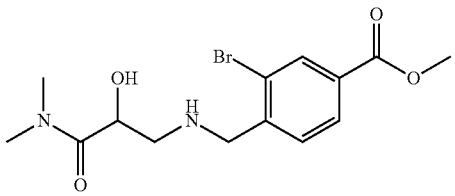

Into a 25-mL round-bottom flask, were placed a solution of 3-amino-2-hydroxy-N,N-dimethylpropanamide (500 mg, 3.78 mmol, 2 equiv) in MeCN (8 mL) and K$_2$CO$_3$ (389 mg, 2.82 mmol, 1.5 equiv). This was followed by the addition of a solution of methyl 3-bromo-4-(bromomethyl)benzoate (618 mg, 2.01 mmol, 1 equiv) in MeCN (5 mL) dropwise at room temperature and the resulting solution was stirred at this temperature for 24 h. The solvent was removed in vacuo and the residue was re-dissolved with H$_2$O (10 mL). The resulting solution was extracted with EtOAc (3×10 mL) and the organic layer was washed with H$_2$O (2×10 mL). The solvent was removed in vacuo and the residue was purified by silica gel chromatography (MeOH/CH$_2$Cl$_2$, 1:13) to afford the title compound as an off-white solid (80 mg, 11% yield). MS: (ES, m/z): 359 [M+H]$^+$.

Step-4: Methyl 2-(dimethylcarbamoyl)-2,3,4,5-tetrahydrobenzo[f][1,4]oxazepine-8-carboxylate

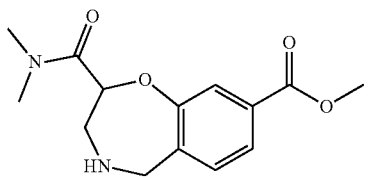

Into a 8-mL sealed tube purged and maintained with an inert atmosphere of nitrogen, were placed a mixture of methyl 3-bromo-4-(((3-(dimethylamino)-2-hydroxy-3-oxopropyl)amino)methyl)benzoate (80 mg, 0.22 mmol, 1 equiv) in isopropanol (4 mL), $K_2CO_3$ (46 mg, 0.33 mmol, 1.5 equiv) and CuI (13 mg, 0.07 mmol, 0.3 equiv). The resulting solution was stirred at 120° C. for 17 h. After cooling to room temperature, the resulting mixture was concentrated under vacuum. Water was added and the resulting solution was extracted with $CH_2Cl_2$ (3×10 mL). The organic layer was washed with $H_2O$ (2×10 mL), dried over anhydrous $Na_2SO_4$, and filtered. The solvent was removed in vacuo and the residue was purified by silica gel chromatography (MeOH/$CH_2Cl_2$, 1:13) to afford the title compound as a colorless oil (30 mg, 48% yield). MS: (ES, m/z): 279 [M+H]$^+$.

Step-5: Methyl 2-(dimethylcarbamoyl)-4-(tetrahydro-2H-pyran-4-carbonyl)-2,3,4,5-tetrahydrobenzo[f][1,4]oxazepine-8-carboxylate

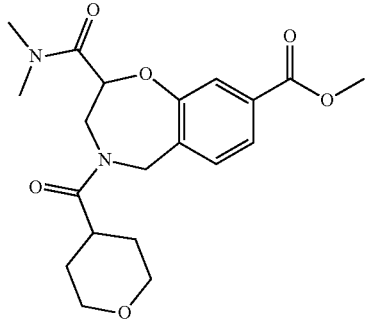

Into a 8-mL vial, were placed a solution of oxane-4-carboxylic acid (13 mg, 0.10 mmol, 1 equiv) in DMF (1.5 mL), and HATU (45 mg, 0.12 mmol, 1.2 equiv). This was followed by the addition of a solution of methyl 2-(dimethylcarbamoyl)-2,3,4,5-tetrahydrobenzo[f][1,4]oxazepine-8-carboxylate (30 mg, 0.11 mmol, 1.00 equiv) in DMF (0.5 mL) and DIEA (38 mg, 0.29 mmol, 3 equiv). The resulting solution was stirred at room temperature for 17 h. Water was added and the resulting solution was extracted with EtOAc (2×10 mL). The organic layer was washed with $H_2O$ (2×10 mL) and brine (2×10 mL), dried over anhydrous $Na_2SO_4$, and filtered. The solvent was removed in vacuo and the residue was purified by silica gel chromatography (EtOAc/pet. ether, 1:3) to afford the title compound as a yellow oil (15 mg, 36% yield). MS: (ES, m/z): 391 [M+H]$^+$.

Step-6: $N^8$-Hydroxy-$N^2$,$N^2$-dimethyl-4-(tetrahydro-2H-pyran-4-carbonyl)-2,3,4,5-tetrahydrobenzo[f][1,4]oxazepine-2,8-dicarboxamide

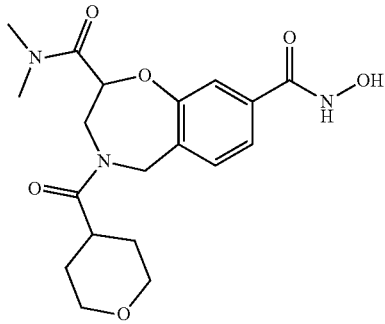 [SMILES: CN(C)C(=O)C1CN(C(=O)C2CCOCC2)Cc2ccc(C(=O)NO)cc2O1]

Into a 8-mL vial, were placed a solution of methyl 2-(dimethylcarbamoyl)-4-(tetrahydro-2H-pyran-4-carbonyl)-2,3,4,5-tetrahydrobenzo[f][1,4]oxazepine-8-carboxylate (15 mg, 0.04 mmol, 1 equiv) in THF/MeOH (4:1, 1.5 mL), then $NH_2OH$ (50% in water, 0.1 mL, 30 equiv) and aq. 1N NaOH (0.1 mL, 2 equiv) were added simultaneously. The resulting solution was stirred for 2 h at room temperature and the crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 5% B to 30% B in 8 min; Detector, UV 254, 220 nm) to afford the title compound as a brown oil (3.7 mg, 25% yield). $^1$H-NMR (400 MHz, DMSO-d$_6$) δ(ppm): 11.41-11.11 (br, 1H), 7.61-7.42 (m, 1H), 7.40-7.32 (m, 2H), 5.01-4.91 (m, 1H), 4.89-4.72 (m, 1H), 4.69-4.42 (m, 1H), 4.19-4.16 (m, 1H), 4.02-3.99 (m, 1H), 3.82-3.75 (m, 3H), 3.41-3.30 (m, 2H), 3.12-3.05 (m, 3H), 2.92-2.86 (m, 3H), 1.61-1.24 (m, 4H). MS: (ES, m/z): 392 [M+H]$^+$.

Example 28

Preparation of N-hydroxy-3,3-dimethyl-4-(1-methylcyclobutane-1-carbonyl)-2,3,4,5-tetrahydrobenzo[f][1,4]oxazepine-8-carboxamide

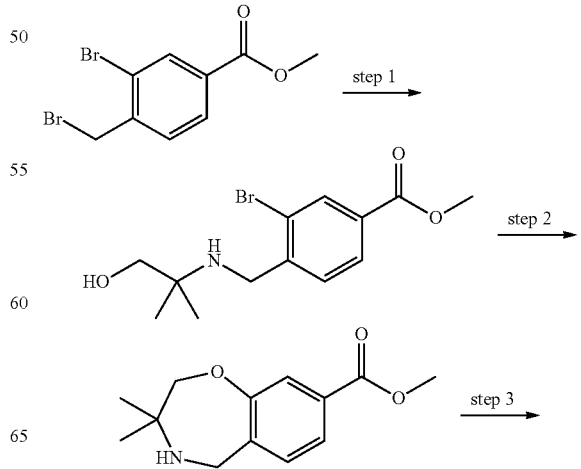

-continued

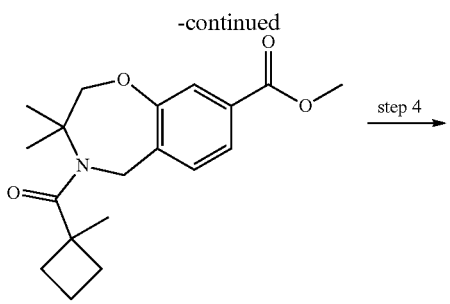

step 4

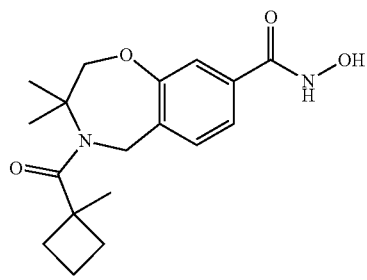

Step-1: Methyl 3-bromo-4-[[(1-hydroxy-2-methyl-propan-2-yl)amino]methyl]benzoate

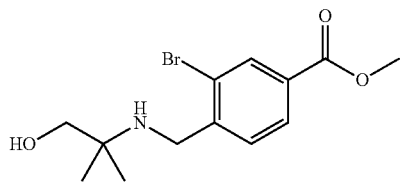 [SMILES: COC(=O)c1ccc(CNC(C)(C)CO)c(Br)c1]

Into a 500-mL round-bottom flask, were placed a solution of 2-amino-2-methylpropan-1-ol (11.52 g, 129.24 mmol, 2 equiv) in MeCN (150 mL), K₂CO₃ (13.40 g, 97.10 mmol, 1.5 equiv). This was followed by the addition of a solution of methyl 3-bromo-4-(bromomethyl)benzoate (20 g, 64.94 mmol, 1 equiv) in MeCN (50 mL) dropwise with stirring at room temperature. The resulting solution was stirred for 16 h at room temperature, then concentrated under vacuum. The residue was diluted with H₂O (200 mL). The resulting solution was extracted with EtOAc (3×200 mL) and the organic layers combined, washed with H₂O (3×200 mL), and concentrated. The residue was purified by silica gel chromatography (EtOAc/pet. ether, 1:4) to afford the title compound as an off-white solid (8.7 g, 42% yield). MS: (ES, m/z): 316 [M+H]⁺.

Step 2: Methyl 3,3-dimethyl-2,3,4,5-tetrahydrobenzo[f][1,4]oxazepine-8-carboxylate

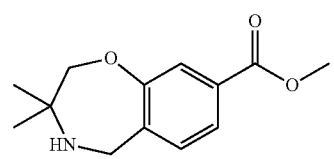

Into a 250-mL pressure tank reactor purged and maintained with an inert atmosphere of nitrogen, were placed a solution of methyl 3-bromo-4-[[(1-hydroxy-2-methylpropan-2-yl)amino]methyl]benzoate (8.7 g, 27.52 mmol, 1 equiv) in isopropanol (150 mL), K₂CO₃ (5.7 g, 41.30 mmol, 1.5 equiv) and CuI (1.57 g, 8.26 mmol, 0.3 equiv). The resulting solution was stirred overnight at 110° C. in an oil bath, then concentrated under vacuum. The residue was diluted with H₂O (200 mL). The resulting solution was extracted with EtOAc (3×200 mL) and the combined organic layers was washed with H₂O (3×200 mL) and concentrated. The residue was purified by silica gel chromatography (EtOAc/pet. ether, 1:2) to afford the title compound as a green oil (3.9 g, 60% yield). 1H-NMR (400 MHz, DMSO-d6) δ(ppm): 7.63-7.60 (d, J=12.8 Hz, 1H), 7.54-7.52 (s, 1H), 7.25-7.23 (d, J=7.6 Hz, 1H), 4.01 (s, 2H), 3.94-3.89 (m, 5H), 1.23 (s, 6H). MS: (ES, m/z): 236 [M+H]⁺.

Step-3: Methyl 3,3-dimethyl-4-(1-methylcyclobutane-1-carbonyl)-2,3,4,5-tetrahydrobenzo[f][1,4]oxazepine-8-carboxylate

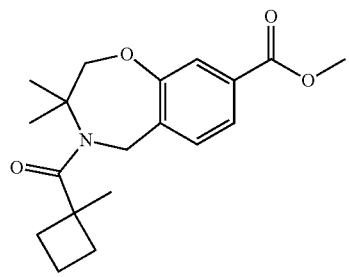 [SMILES: COC(=O)c1ccc2c(c1)OCC(C)(C)N(C(=O)C1(C)CCC1)C2]

Into a 8-mL vial, were placed a solution of methyl 3,3-dimethyl-2,3,4,5-tetrahydrobenzo[f][1,4]oxazepine-8-carboxylate (200 mg, 0.85 mmol, 1 equiv) in THF (3 mL), and pyridine (336 mg, 4.25 mmol, 5 equiv). This was followed by the addition of a solution of 1-methylcyclobutane-1-carbonyl chloride (120 mg, 0.91 mmol, 1 equiv) in THF (1 mL) dropwise with stirring. The resulting solution was stirred for 17 h at room temperature, then concentrated under vacuum. The residue was diluted with H₂O (10 mL). The resulting solution was extracted with EtOAc (3×10 mL) and the combined organic layers was washed with H₂O (3×10 mL) and concentrated. The residue was purified by silica gel chromatography (EtOAc/pet. ether, 1:3) to afford the title compound as a yellow oil (54 mg, 19% yield). MS: (ES, m/z): 332 [M+H]⁺.

Step-4: N-hydroxy-3,3-dimethyl-4-(1-methylcyclobutane-1-carbonyl)-2,3,4,5-tetrahydrobenzo[f][1,4]oxazepine-8-carboxamide

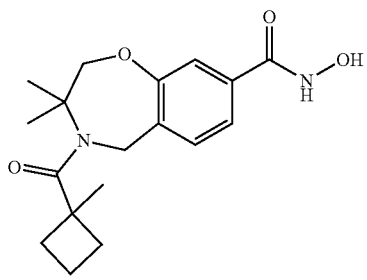 [SMILES: CC1(C(=O)N2Cc3ccc(C(=O)NO)cc3OCC2(C)C)CCC1]

Into a 8-mL sealed tube, was placed a solution of methyl 3,3-dimethyl-4-(1-methylcyclobutane-1-carbonyl)-2,3,4,5-tetrahydrobenzo[f][1,4]oxazepine-8-carboxylate (54 mg, 0.16 mmol, 1 equiv) in THF/MeOH (4:1, 2 mL). This was followed by the addition of NH$_2$OH (50% in water, 0.33 mL, 30 equiv). To this was added aq. 1N NaOH (0.33 mL, 2 equiv). The resulting solution was stirred for 2 h at room temperature. The crude product was purified by Prep-HPLC (Column: XBridge C18 OBD, 5 μm, 19×150 mm; Mobile Phase A: Water/0.05% TFA; Mobile Phase B: MeCN; Flow rate: 20 mL/min; Gradient: 15% B to 41% B in 10 min; Detector, UV 254, 220 nm) to afford the title compound as a light pink solid (13 mg, 24% yield). $^1$H-NMR (400 MHz, DMSO-d$_6$) δ(ppm): 11.13 (s, 1H), 7.26-7.19 (m, 3H), 4.51-4.22 (m, 4H), 2.13-2.10 (s, 2H), 1.88-1.83 (s, 3H), 1.51-1.45 (m, 7H), 1.34 (s, 1H). MS: (ES, m/z): 333 [M+H]$^+$.

Example 29

Preparation of 4-acetyl-N-hydroxy-3,3-dimethyl-2,3,4,5-tetrahydrobenzo[f][1,4]oxazepine-8-carboxamide

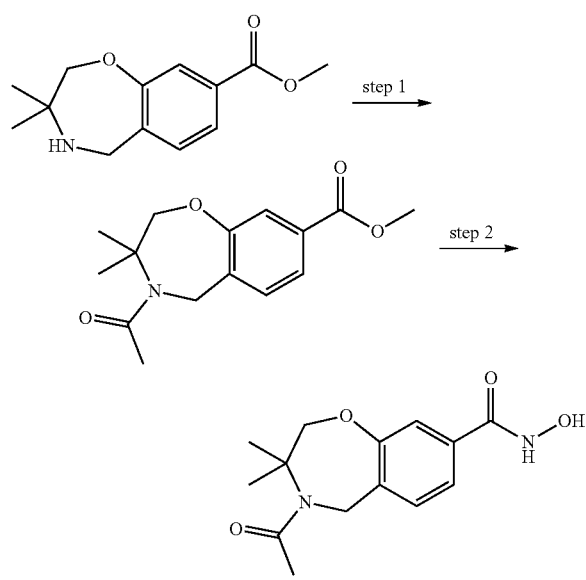

Step-1: Methyl 4-acetyl-3,3-dimethyl-2,3,4,5-tetrahydrobenzo[f][1,4]oxazepine-8-carboxylate

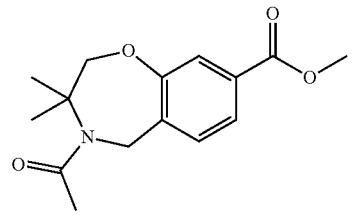 [SMILES: COC(=O)c1ccc2c(c1)OCC(C)(C)N(C(C)=O)C2]

Into a 8-mL vial, were placed a solution of methyl 3,3-dimethyl-2,3,4,5-tetrahydrobenzo[f][1,4]oxazepine-8-carboxylate (100 mg, 0.43 mmol, 1 equiv) in CH$_2$Cl$_2$ (2 mL) and Et$_3$N (172 mg, 1.70 mmol, 4 equiv). This was followed by the addition of a solution of acetyl chloride (37 mg, 0.47 mmol, 1.1 equiv) in CH$_2$Cl$_2$ (0.5 mL) dropwise with stirring at 0° C. The resulting solution was stirred for 18 h at room temperature and concentrated under vacuum. The residue was dissolved in in CH$_2$Cl$_2$ (30 mL) and washed with H$_2$O (3×20 mL). The organic layer was dried over anhydrous MgSO$_4$, filtered, and concentrated to afford the title compound as a green oil (80 mg) which was used without further purification. MS: (ES, m/z): 278 [M+H]$^+$.

Step-2: 4-Acetyl-N-hydroxy-3,3-dimethyl-2,3,4,5-tetrahydrobenzo[f][1,4]oxazepine-8-carboxamide

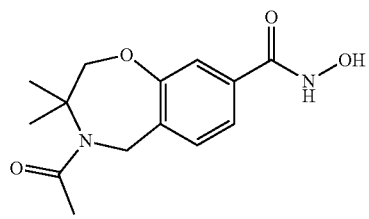 [SMILES: CC(=O)N1Cc2ccc(C(=O)NO)cc2OCC1(C)C]

Into a 8-mL vial, were placed a solution of methyl 4-acetyl-3,3-dimethyl-2,3,4,5-tetrahydrobenzo[f][1,4]oxazepine-8-carboxylate (171 mg, 0.62 mmol, 1 equiv) in THF/MeOH (4:1, 2.5 mL), followed by aq. 1N NaOH (1.23 mL, 2 equiv) and NH$_2$OH (50% in H$_2$O, 1.22 mL, 30 equiv). The resulting solution was stirred for 3 h at room temperature. The crude product was purified by Prep-HPLC (Column: XBridge RP C18 OBD, 5 μm, 19×150 mm; Mobile Phase A: Water/0.05% TFA; Mobile Phase B: MeCN; Flow rate: 25 mL/min; Gradient: 4% B to 23% B in 6 min; Detector, UV 254, 220 nm) to afford the title compound as a brown solid (41 mg, 24% yield). $^1$H-NMR (400 MHz, DMSO-d$_6$) δ(ppm): 11.13 (br, 1H), 9.01 (br, 1H), 7.26 (s, 2H), 7.17 (s, 1H), 4.75 (s, 2H), 4.28 (s, 2H), 1.98 (s, 3H), 1.44 (s, 6H). MS: (ES, m/z): 279 [M+H]$^+$.

Example 30

Preparation of N-hydroxy-4-(tetrahydro-2H-pyran-4-carbonyl)-4,5-dihydro-2H-spiro[benzo[f][1,4]oxazepine-3,1'-cyclopropane]-8-carboxamide

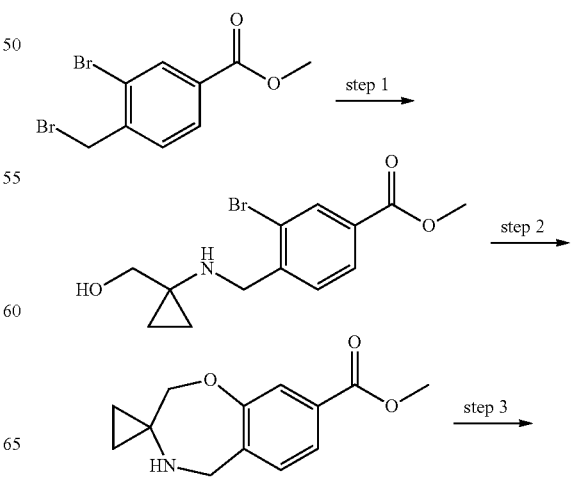

-continued

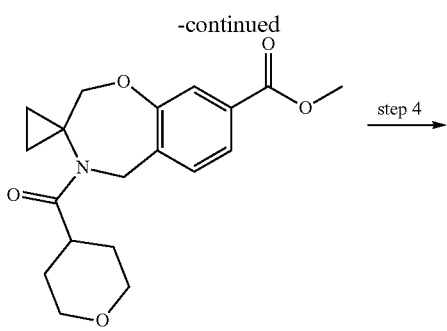

step 4 →

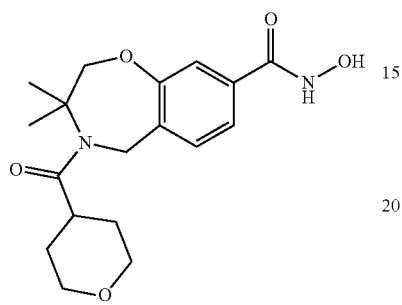

Step-1: Methyl 3-bromo-4-(((1-(hydroxymethyl)cyclopropyl)amino)methyl)benzoate

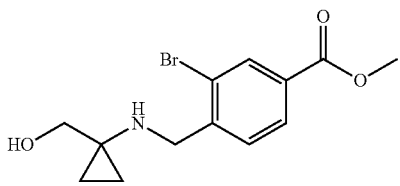 [SMILES: COC(=O)c1ccc(CNC2(CO)CC2)c(Br)c1]

Into a 500-mL round-bottom flask, was placed (1-aminocyclopropyl)methanol hydrochloride (6 g, 48.55 mmol, 2 equiv), $K_2CO_3$ (11 g, 79.59 mmol, 3.5 equiv) in MeCN (120 mL), The mixture was stirred at room temperature for 10 min. This was followed by the addition of a solution of methyl 3-bromo-4-(bromomethyl)benzoate (15 g, 48.71 mmol, 1 equiv) in MeCN (150 mL) dropwise with stirring at 0° C. over 2 h. The resulting solution was stirred overnight at room temperature. The resulting mixture was concentrated under vacuum. The residue was purified by silica gel chromatography (EtOAc/pet. ether, 1:3) to afford the title compound as a yellow oil (7 g, 46% yield). MS: (ES, m/z): 314,316 [M+H]$^+$.

Step-2: Methyl 4,5-dihydro-2H-spiro[benzo[f][1,4]oxazepine-3,1'-cyclopropane]-8-carboxylate

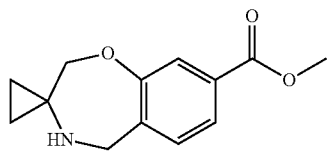 [SMILES: COC(=O)c1ccc2c(c1)OCC1(CC1)NC2]

Into a 40-mL sealed tube purged and maintained with an inert atmosphere of nitrogen, was placed a solution of methyl 3-bromo-4-(((1-(hydroxymethyl)cyclopropyl)amino)methyl)benzoate (1.5 g, 4.77 mmol, 1 equiv), CuI (273 mg, 1.43 mmol, 0.3 equiv), $K_2CO_3$ (992 mg, 7.18 mmol, 1.5 equiv) in isopropanol (28 mL). The resulting solution was stirred overnight at 110° C. in an oil bath. The resulting mixture was concentrated under vacuum and the residue was diluted with $CH_2Cl_2$ (150 mL). The solids were filtered out and the filtrate was concentrated under vacuum. The residue was purified by C18 chromatography (MeCN/$H_2O$+0.05% TFA, 1:4) to afford the title compound as a yellow solid (0.8 g, 72% yield). MS: (ES, m/z): 234 [M+H]$^+$.

Step-3: Methyl 4-(tetrahydro-2H-pyran-4-carbonyl)-4,5-dihydro-2H-spiro[benzo[f][1,4]oxazepine-3,1'-cyclopropane]-8-carboxylate

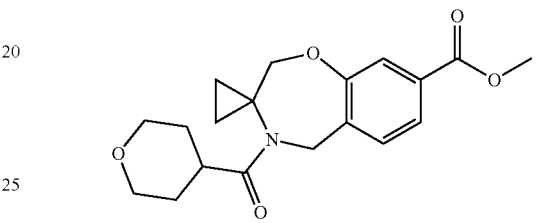

Into a 100-mL round-bottom flask, was placed a solution of methyl 4,5-dihydro-2H-spiro[benzo[f][1,4]oxazepine-3,1'-cyclopropane]-8-carboxylate (130 mg, 0.56 mmol, 1 equiv) in $CH_2Cl_2$ (10 mL), and pyridine (1 mL). The mixture was stirred for 1 h followed by addition of oxane-4-carbonyl chloride (400 mg, 2.69 mmol, 4.83 equiv). The resulting mixture was stirred overnight at room temperature and then concentrated under vacuum. The residue was purified by silica gel chromatography (EtOAc/pet. ether, 1:1) to afford the title compound as a yellow solid (60 mg, 31% yield). MS: (ES, m/z): 346 [M+H]$^+$.

Step-4: N-Hydroxy-4-(tetrahydro-2H-pyran-4-carbonyl)-4,5-dihydro-2H-spiro[benzo[f][1,4]oxazepine-3,1'-cyclopropane]-8-carboxamide

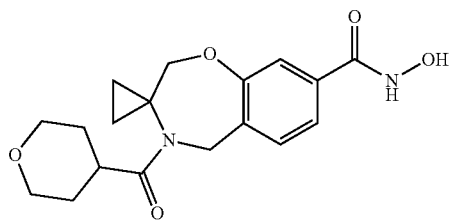 [SMILES: O=C(NO)c1ccc2c(c1)OCC1(CC1)N(C(=O)C1CCOCC1)C2]

Into a 50-mL round-bottom flask, was placed methyl 4-(tetrahydro-2H-pyran-4-carbonyl)-4,5-dihydro-2H-spiro[benzo[f][1,4]oxazepine-3,1'-cyclopropane]-8-carboxylate (60 mg, 0.17 mmol, 1 equiv), $NH_2OH$ (50% in water, 0.50 mL, 44.56 equiv), aq. 1N NaOH (1.5 mL, 8.82 equiv), and THF/MeOH (4:1, 3 mL). The resulting solution was stirred overnight at room temperature. The crude product was purified by Prep-HPLC (Column: XBridge RP C18 OBD, 5 μm, 19×150 mm; Mobile Phase A: Water/0.05% formic acid; Mobile Phase B: MeCN; Flow rate: 20 mL/min; Gradient: 12% B to 34% B in 9 min; Detector, UV 254 nm) to afford the title compound as a white solid (21.5 mg, 32% yield).

1H-NMR (300 MHz, DMSO-d6) δ(ppm): 11.18 (br, 1H), 7.57-7.29 (m, 3H), 4.61 (s, 2H), 3.82-3.76 (m, 4H), 3.57-3.24 (m, 2H), 3.23-2.75 (m, 1H), 1.48-0.85 (m, 8H). MS: (ES, m/z): 347 [M+H]+.

Example 31

Preparation of (R)-4-acetyl-N-hydroxy-3-isopropyl-2,3,4,5-tetrahydrobenzo[f][1,4]oxazepine-8-carboxamide

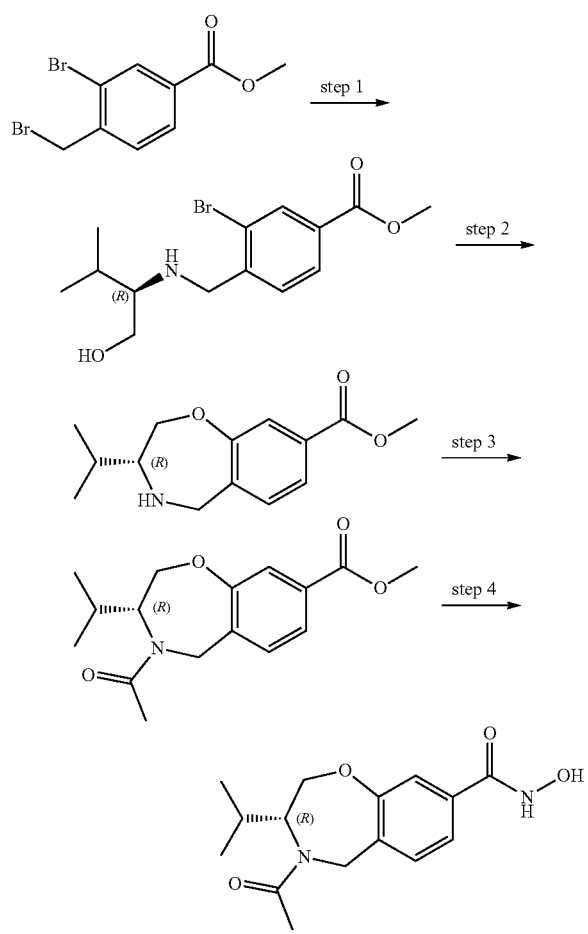

Step-1: Methyl (R)-3-bromo-4-(((1-hydroxy-3-methylbutan-2-yl)amino)methyl)benzoate

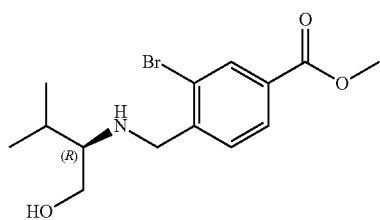

Into a 1-L round-bottom flask, was placed a solution of (R)-2-amino-3-methylbutan-1-ol (23.33 g, 226.15 mmol, 2 equiv) in MeCN (300 mL). This was followed by the addition of a solution of methyl 3-bromo-4-(bromomethyl)benzoate (35 g, 113.65 mmol, 1 equiv) in MeCN (200 mL) dropwise with stirring. The resulting solution was stirred for 15 h at room temperature, then concentrated under vacuum. The residue was diluted with H2O (300 mL), extracted with EtOAc (3×200 mL) and the combined organic layers were concentrated. The residue was purified by silica gel chromatography (EtOAc/pet. ether, 1:4) to afford the title compound as an off-white solid (22 g, 59% yield). MS: (ES, m/z): 330 [M+H]+.

Step-2: Methyl (R)-3-isopropyl-2,3,4,5-tetrahydrobenzo[f][1,4]oxazepine-8-carboxylate

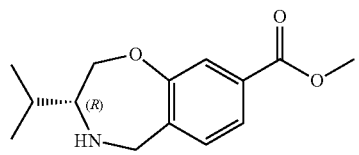

Into a 500-mL pressure tank reactor purged and maintained with an inert atmosphere of nitrogen, were placed a solution of methyl (R)-3-bromo-4-(((1-hydroxy-3-methylbutan-2-yl)amino)methyl)benzoate (13 g, 39.37 mmol, 1 equiv) in isopropanol (260 mL), K2CO3 (8.16 g, 59.13 mmol, 1.5 equiv) and CuI (2.25 g, 11.84 mmol, 0.3 equiv). The resulting mixture was stirred for 24 h at 110° C. in an oil bath and then concentrated under vacuum. The residue was diluted with H2O (300 mL), extracted with CH2Cl2 (3×300 mL). The combined organic layers were washed with H2O (3×300 mL) and concentrated. The residue was purified by silica gel chromatography (EtOAc/pet. ether, 1:1) to afford the title compound as a yellow oil (4.9 g, 50% yield). 1H-NMR (400 MHz, DMSO-d6) δ(ppm): 7.66-7.64 (d, J=8.0 Hz, 1H), 7.57 (s, 1H), 7.30-7.28 (d, J=8.0 Hz, 1H), 4.52-4.22 (m, 1H), 4.07-3.94 (m, 2H), 3.94-3.84 (m, 3H), 3.81-3.62 (m, 1H), 1.92-1.72 (m, 1H) 1.09-0.91 (m, 6H). MS: (ES, m/z): 250 [M+H]+.

Step-3: Methyl (R)-4-acetyl-3-isopropyl-2,3,4,5-tetrahydrobenzo[f][1,4]oxazepine-8-carboxylate

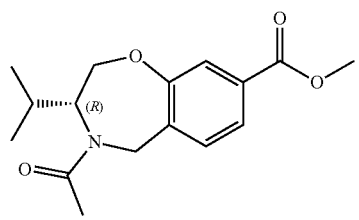

Into a 8-mL vial, were placed a solution of methyl (R)-3-isopropyl-2,3,4,5-tetrahydrobenzo[f][1,4]oxazepine-8-carboxylate (150 mg, 0.60 mmol, 1 equiv) in CH2Cl2 (3 mL) and Et3N (243 mg, 2.40 mmol, 4 equiv). This was followed by the addition of a solution of acetyl chloride (52 mg, 0.66 mmol, 1.1 equiv) in CH2Cl2 (0.5 mL) dropwise with stirring at 0° C. The resulting solution was stirred for 18 h at room temperature and then concentrated under vacuum. The residue was dissolved in CH2Cl2 (30 mL), washed with H₂O (3×20 mL), dried over anhydrous magnesium sulfate, filtered, and concentrated to afford the title compound as a yellow oil (120 mg, 68% yield). MS: (ES, m/z): 292 [M+H]⁺.

Step-4: (R)-4-Acetyl-N-hydroxy-3-isopropyl-2,3,4,5-tetrahydrobenzo[f][1,4]oxazepine-8-carboxamide

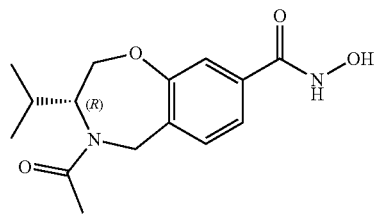

Into a 8-mL vial, was placed a solution of methyl (R)-4-acetyl-3-isopropyl-2,3,4,5-tetrahydrobenzo[f][1,4]oxazepine-8-carboxylate (120 mg, 0.41 mmol, 1 equiv) in THF/MeOH (4:1, 2 mL), followed by the addition of aq. 1N NaOH (0.82 mL, 2 equiv) and NH₂OH (50% in H₂O, 0.82 mL, 30 equiv). The resulting solution was stirred for 3 h at room temperature. The crude product was purified by Prep-HPLC (Column Sunfire Prep C18 OBD, 5 μm, 19×150 mm; Mobile Phase A: Water/0.05% TFA; Mobile Phase B: MeCN; Flow rate: 25 mL/min; Gradient: 5% B to 40% B in 7 min; Detector, UV 254, 220 nm) to afford the title compound as an off-white solid (81 mg, 67% yield). ¹H-NMR (400 MHz, DMSO-d₆) δ(ppm): 11.14 (br, 1H), 7.37-7.19 (m, 3H), 4.95-4.90 (d, J=15.0 Hz, 0.3H), 4.80-4.75 (d, J=15.0 Hz, 0.6H), 4.58-4.47 (m, 1.4H), 4.36-4.22 (m, 2H), 3.88-3.81 (m, 0.7H), 2.08-2.01 (m, 1H), 1.95-1.83 (m, 3H), 1-0.98 (m, 6H). MS: (ES, m/z): 293 [M+H]⁺.

Example 32

Preparation of (R)—N-hydroxy-3-isopropyl-4-(1-methylcyclobutane-1-carbonyl)-2,3,4,5-tetrahydrobenzo[f][1,4]oxazepine-8-carboxamide

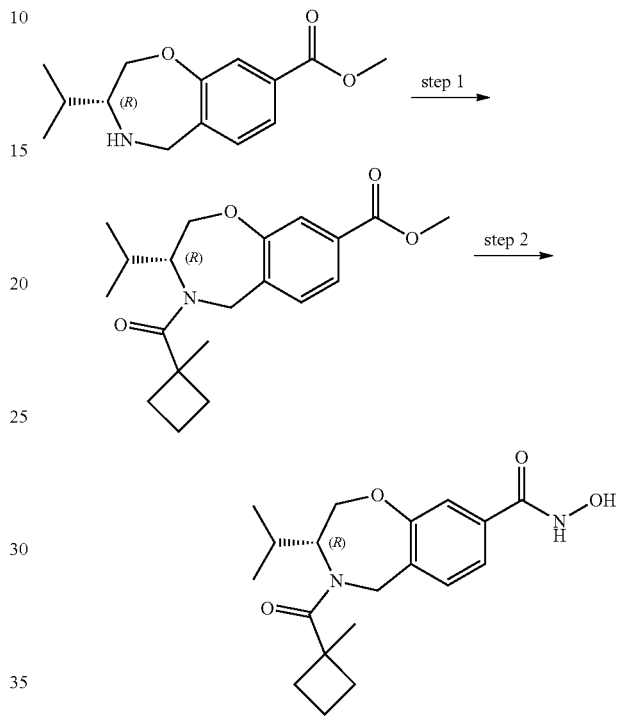

TABLE 17

The following compounds were prepared according to the method of Example 31, using (S)-2-amino-3-methylbutan-1-ol.

| Structure | Found M + H | ¹H-NMR (400 MHz, DMSO-d₆) δ (ppm) |
|---|---|---|
| | (ES, m/z): 293 [M + H]⁺ | 11.13 (s, 1H), 7.41-7.11 (m, 3H), 4.98-4.72 (m, 1H), 4.62-4.41 (m, 2H), 4.39-4.17 (m, 2H), 2.11-1.88 (m, 4H), 1.08-0.81 (m, 6H) |
| | (ES, m/z): 363 [M + H]⁺ | 11.17 (br, 1H), 9.01 (br, 1H), 7.43-7.17 (m, 3H), 4.92-4.77 (m, 2H), 4.57-4.55 (m, 0.6H), 4.38-4.28 (m, 2.4H), 4.08-4.01 (m, 0.4H), 3.85-3.83 (m, 1H), 3.81-3.65 (m, 1H), 3.43-3.33 (m, 1H), 3.14-3.11 (m, 0.6H), 2.95-2.92 (m, 0.4H), 2.76 (m, 0.6H), 2.01-1.72 (m, 1H), 1.70-1.23 (m, 3H), 1.02-0.81 (m, 6H), 0.71-0.68 (m, 1H) |

Step-1: Methyl (R)-3-isopropyl-4-(1-methylcyclobutane-1-carbonyl)-2,3,4,5-tetrahydrobenzo[f][1,4]oxazepine-8-carboxylate Step-2: (R)—N-hydroxy-3-isopropyl-4-(1-methylcyclobutane-1-carbonyl)-2,3,4,5-tetrahydrobenzo[f][1,4]oxazepine-8-carboxamide

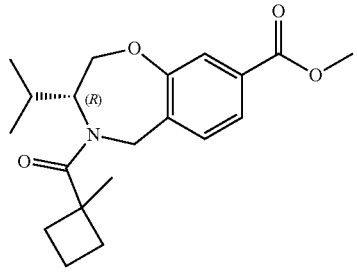

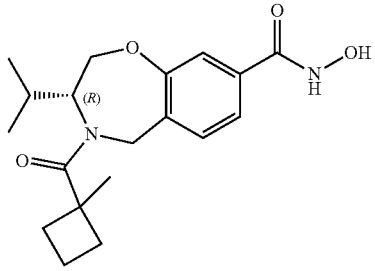

Into a 8-mL vial, were placed a solution of methyl (R)-3-isopropyl-2,3,4,5-tetrahydrobenzo[f][1,4]oxazepine-8-carboxylate (100 mg, 0.40 mmol, 1 equiv) in DMF (2 mL), HATU (184 mg, 0.48 mmol, 1.20 equiv), 1-methylcyclobutane-1-carboxylic acid (46 mg, 0.40 mmol, 1 equiv) and DIEA (156 mg, 1.21 mmol, 3 equiv). The resulting solution was stirred for 19 h at room temperature. The reaction was diluted with H$_2$O (10 mL) and extracted with EtOAc (3×10 mL). The combined organic layers were washed with H$_2$O (3×10 mL) and concentrated. The residue was purified by silica gel chromatography (EtOAc/pet. ether, 1:4) to afford the title compound as a brown oil (75 mg, 54% yield). MS: (ES, m/z): 346 [M+H]$^+$.

Into a 8-mL vial, was placed a solution of methyl (R)-3-isopropyl-4-(1-methylcyclobutane-1-carbonyl)-2,3,4,5-tetrahydrobenzo[f][1,4]oxazepine-8-carboxylate (75 mg, 0.22 mmol, 1 equiv) in THF/MeOH (4:1, 2 mL), followed by the addition of NH$_2$OH (50% in water, 0.43 mL, 30 equiv) and aq. 1N NaOH (0.44 mL, 2 equiv). The resulting solution was stirred for 2 h at room temperature. The crude product was purified by Prep-HPLC (Column Sunfire Prep C18 OBD, 5 μm, 19×150 mm; Mobile Phase A: Water/0.05% TFA; Mobile Phase B: MeCN; Flow rate: 25 mL/min; Gradient: 5% B to 70% B in 7 min; Detector, UV 254, 220 nm) to afford the title compound as a pink solid (45 mg, 60% yield). $^1$H-NMR (400 MHz, DMSO-d$_6$) δ(ppm): 11.39-10.80 (br, 1H), 7.40-7.09 (m, 3H), 4.80-4.63 (m, 1H), 4.41-4.29 (m, 2H), 4.25-4.15 (m, 1H), 2.35-2.22 (m, 1H), 1.98-1.60 (m, 5H), 1.57-1.43 (m, 1H), 1.39-1.21 (m, 3H), 1.08-0.72 (m, 6H). MS: (ES, m/z): 347 [M+H]$^+$.

TABLE 18

The following compounds were prepared according to the method of Example 32, using methyl (S)-3-isopropyl-2,3,4,5-tetrahydrobenzo[f][1,4]oxazepine-8-carboxylate.

| Structure | Found M + H | $^1$H-NMR (400 MHz, DMSO-d$_6$) δ (ppm) |
|---|---|---|
| (S)-isomer structure | (ES, m/z): 347 [M + H]$^+$ | 11.15 (br, 1H), 7.39-7.19 (m, 3H), 4.75-4.71 (d, J = 17.6 Hz, 1H), 4.66-4.53 (m, 1H), 4.41-4.29 (m, 2H), 4.23-4.17 (m, 1H), 2.37-2.27 (m, 1H), 2.01-1.59 (m, 5H), 1.59-1.42 (m, 1H), 1.39-1.22 (m, 3H), 0.99-0.89 (m, 3H), 0.87-0.72 (m, 3H) |
| (S)-isomer with tetrahydropyran structure | (ES, m/z): 378 [M + H]$^+$ | 11.13 (br, 1H), 7.71 (br, 1H), 7.35-7.29 (m, 2H), 7.22-7.17 (m, 1H), 4.98-4.89 (m, 0.3H), 4.81-4.55 (m, 2H), 4.34-4.28 (m, 2H), 3.98-3.87 (m, 0.3H), 3.76-3.72 (m, 1.3H), 3.66-3.63 (m, 0.7H), 3.20-3.12 (m, 2H), 2.49-2.30 (m, 1H), 2.27-2.09 (m, 0.3H), 1.89-1.79 (m, 2.7H), 1.54-1.38 (m, 1H), 1.32-1.28 (m, 1H), 1.14-1.09 (m, 1H), 0.99-0.90 (m, 4H), 0.86-0.80 (m, 3H) |

Example 33

Preparation of (R)-4-formyl-N-hydroxy-3-methyl-2,3,4,5-tetrahydrobenzo[f][1,4]oxazepine-8-carboxamide

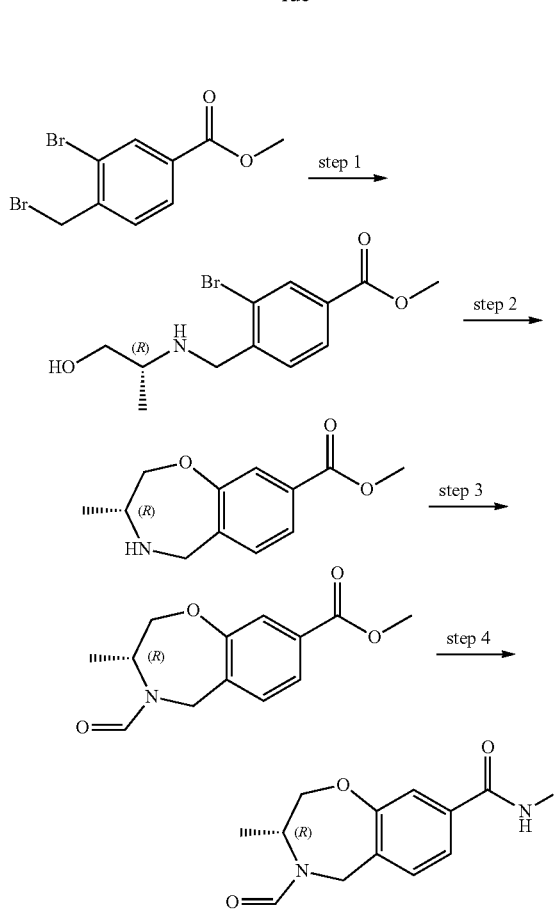

Step-1: Methyl (R)-3-bromo-4-(((1-hydroxypropan-2-yl)amino)methyl)benzoate

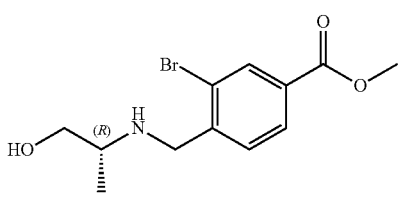

Into a 250-mL round-bottom flask, was placed (R)-2-aminopropan-1-ol (3.64 g, 48.46 mmol, 1 equiv), MeCN (120 mL), K₂CO₃ (10.05 g, 72.72 mmol, 1.5 equiv) and methyl 3-bromo-4-(bromomethyl)benzoate (15 g, 48.71 mmol, 1 equiv). The resulting solution was stirred for 3 h at room temperature. The resulting mixture was concentrated under vacuum and diluted with water (200 mL). The resulting solution was extracted with EtOAc (2×300 mL), dried and concentrated under vacuum. The residue was purified by silica gel chromatography (EtOAc/pet. ether, 1:5) to afford the title compound as an off-white solid (6.5 g, 44% yield). MS: (ES, m/z): 302 [M+H]⁺.

Step-2: Methyl (R)-3-methyl-2,3,4,5-tetrahydrobenzo[f][1,4]oxazepine-8-carboxylate

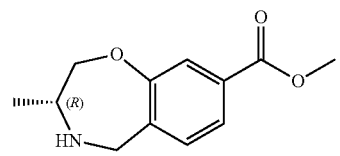

Into a 100-mL pressure tank reactor purged and maintained with an inert atmosphere of nitrogen, was placed methyl (R)-3-bromo-4-(((1-hydroxypropan-2-yl)amino)methyl)benzoate (4 g, 13.24 mmol, 1 equiv), isopropanol (80 mL), K₂CO₃ (2.67 g, 19.32 mmol, 1.5 equiv) and CuI (760 mg, 3.99 mmol, 0.3 equiv). The resulting solution was stirred for 16 h at 110° C. in an oil bath. The resulting mixture was concentrated under vacuum and diluted with water (200 mL). The resulting solution was extracted with CH₂Cl₂ (2×200 mL), dried and concentrated under vacuum. The residue was purified by silica gel chromatography (EtOAc/pet. ether, 1:2) to afford the title compound as a yellow oil (2.1 g, 72% yield). ¹H-NMR (400 MHz, DMSO-d₆) δ(ppm): 9.30-9.15 (br, 1H), 7.74-7.72 (d, J=8.0 Hz, 1H), 7.62-7.57 (m, 2H), 4.47-4.36 (m, 3H), 3.85-3.79 (s, 3H), 3.77-3.75 (m, 2H), 1.23-1.22 (d, J=6.0 Hz, 2H). MS: (ES, m/z): 222 [M+H]⁺.

Step-3: Methyl (R)-4-formyl-3-methyl-2,3,4,5-tetrahydrobenzo[f][1,4]oxazepine-8-carboxylate

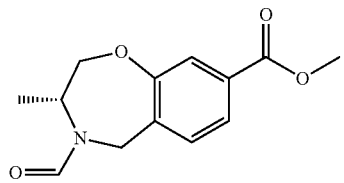 [SMILES: COC(=O)c1ccc2c(c1)OC[C@@H](C)N(C=O)C2]

Into a 8-mL vial, was placed methyl (R)-3-methyl-2,3,4,5-tetrahydrobenzo[f][1,4]oxazepine-8-carboxylate (94 mg, 0.42 mmol, 1 equiv) and ethyl formate (2 mL, 1 equiv). The resulting solution was stirred for 20 h at 57° C. in an oil bath. The mixture was concentrated under vacuum to afford the title compound as yellow oil (100 mg) which was used without further purification. MS: (ES, m/z): 250 [M+H]⁺.

Step-4: (R)-4-Formyl-N-hydroxy-3-methyl-2,3,4,5-tetrahydrobenzo[f][1,4]oxazepine-8-carboxamide

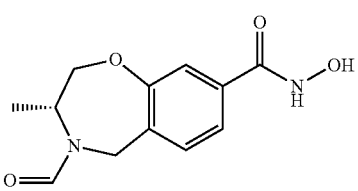 [SMILES: C[C@@H]1COc2cc(C(=O)NO)ccc2CN1C=O]

Into a 8-mL vial, was placed methyl (R)-4-formyl-3-methyl-2,3,4,5-tetrahydrobenzo[f][1,4]oxazepine-8-carboxylate (100 mg, 0.40 mmol, 1 equiv) and THF/MeOH (4:1, 2.5 mL). To this was added aq. 1N NaOH (0.8 mL, 2 equiv) and NH₂OH (50% in H₂O, 0.8 mL, 30 equiv). The resulting solution was stirred for 3 h at room temperature. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 0.7 mL/min; Gradient: 5% B to 24% B in 6 min; Detector: UV 254, 220 nm) to afford the title compound as an off-white solid (66 mg, 45% yield). ¹H-NMR (400 MHz, DMSO-d₆) δ(ppm): 11.14 (br, 1H), 8.15-8.13 (d, J=9.6 Hz, 1H), 7.34-7.21 (m, 3H), 4.91-4.79 (q, 1H), 4.68-4.43 (m, 2H), 4.39-4.11 (m, 3H), 1.23-1.09 (m, 3H). MS: (ES, m/z): 251 [M+H]⁺.

Example 34

Preparation of (R)—N-hydroxy-3-methyl-4-(1-methylcyclobutane-1-carbonyl)-2,3,4,5-tetrahydrobenzo[f][1,4]oxazepine-8-carboxamide

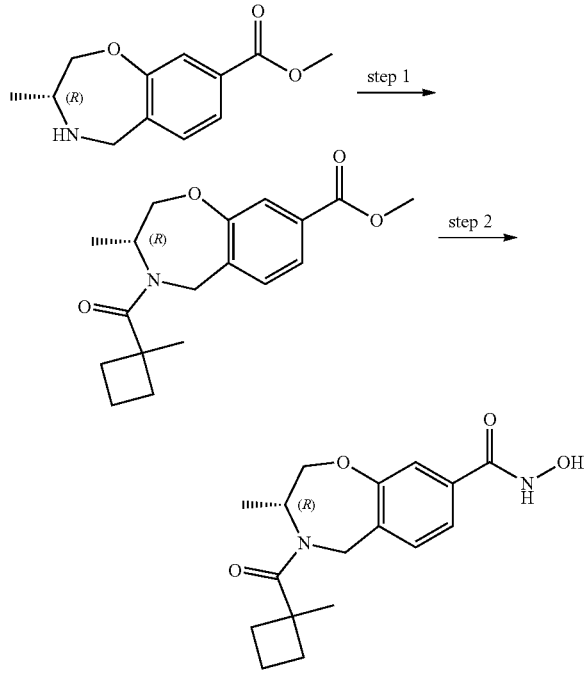

Step-1: Methyl (R)-3-methyl-4-(1-methylcyclobutane-1-carbonyl)-2,3,4,5-tetrahydrobenzo[f][1,4]oxazepine-8-carboxylate Into a 20-mL vial, was placed a solution of methyl (R)-3-methyl-2,3,4,5-tetrahydrobenzo[f][1,4]oxazepine-8-carboxylate (100 mg, 0.45 mmol, 1 equiv) in DMF (13 mL), 1-methylcyclobutane-1-carboxylic acid (80 mg, 0.70 mmol, 1.2 equiv), HATU (150 mg, 0.39 mmol, 1.2 equiv) and DIEA (150 mg, 1.16 mmol, 3 equiv). The resulting solution was stirred for 10 h at room temperature. The resulting mixture was concentrated under vacuum. The residue was purified by silica gel chromatography (EtOAc/pet. ether, 1:5) to afford the title compound as a light yellow oil (80 mg, 56% yield). MS: (ES, m/z): 318 [M+H]⁺.

Step-2: (R)—N-hydroxy-3-methyl-4-(1-methylcyclobutane-1-carbonyl)-2,3,4,5-tetrahydrobenzo[f][1,4]oxazepine-8-carboxamide

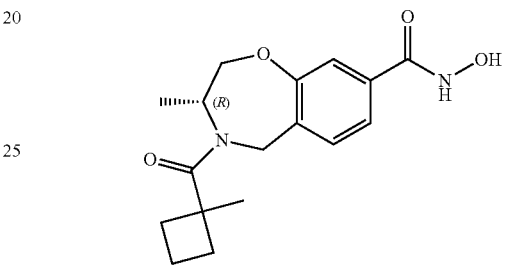

Into a 10-mL round-bottom flask, was placed a solution of methyl (R)-3-methyl-4-(1-methylcyclobutane-1-carbonyl)-2,3,4,5-tetrahydrobenzo[f][1,4]oxazepine-8-carboxylate (80 mg, 0.25 mmol, 1 equiv) in THF/MeOH (4:1, 2.5 mL). This was followed by the addition of aq. 1N NaOH (0.50 mL, 2 equiv) and NH₂OH (50% in water, 0.50 mL, 30 equiv). The resulting solution was stirred for 3 h at room temperature. The crude product was purified by Prep-HPLC (Column: XBridge XP C18 OBD, 5 μm, 19×150 mm; Mobile Phase A: Water/0.05% TFA; Mobile Phase B: MeCN; Flow rate: 0.7 mL/min; Gradient: 12% B to 47% B in 12 min; Detector: UV 254, 220 nm) to afford the title compound as a light yellow solid (41 mg, 51% yield). ¹H-NMR (400 MHz, DMSO-d₆) δ(ppm): 11.13 (br, 1H), 9.01 (br, 1H), 7.32-7.18 (m, 3H), 4.85-4.68 (m, 1.5H), 4.41-4.37 (m, 0.5H), 4.28-4.06 (m, 3H), 2.50-2.43 (m, 0.6H), 2.32-2.25 (m, 1H), 1.96-1.73 (m, 3H), 1.59-1.47 (m, 1H), 1.34 (s, 1.4H), 1.27 (s, 1.5H), 1.21-1.20 (m, 1.4H), 1-0.99 (m, 1.5H). MS: (ES, m/z): 319 [M+H]⁺.

Example 35

Preparation of (R)-4-acetyl-N-hydroxy-3-methyl-2,3,4,5-tetrahydrobenzo[f][1,4]oxazepine-8-carboxamide

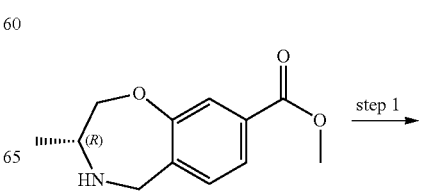

-continued

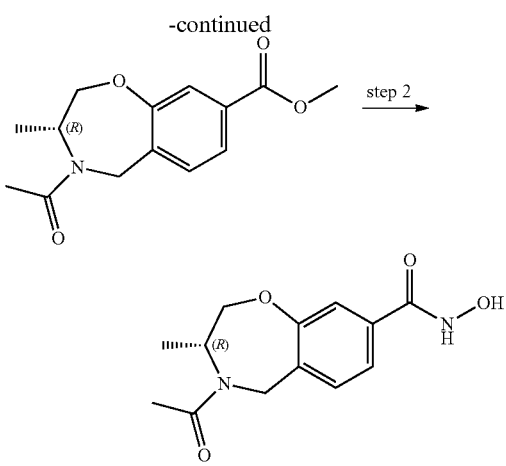

Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 4% B to 18% B in 6 min; Detector: UV 254, 220 nm) to afford the title compound as a brown oil (12 mg, 20% yield). $^1$H-NMR (400 MHz, DMSO-$d_6$) δ(ppm): 11.17 (br, 1H), 9 (s, 1H), 7.32-7.16 (m, 4H), 4.96-4.79 (m, 2H), 4.53-4.42 (m, 1H), 4.36-4.12 (m, 3H), 2.03 (s, 1H), 1.20 (s, 2H), 1.21-1.19 (m, 1H), 1.18-1.08 (m, 2H). MS: (ES, m/z): 265 [M+H]$^+$.

Example 36

Preparation of (S)—N-hydroxy-3-methyl-4-(4-methyltetrahydro-2H-pyran-4-carbonyl)-2,3,4,5-tetrahydrobenzo[f][1,4]oxazepine-8-carboxamide Step-1: Methyl (R)-4-acetyl-3-methyl-2,3,4,5-tetrahydrobenzo[f][1,4]oxazepine-8-carboxylate

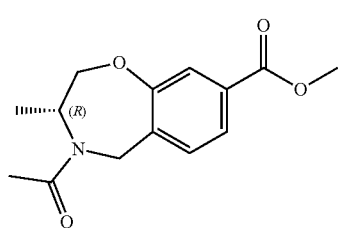

Into a 8-mL vial, were placed a solution of methyl (R)-3-methyl-2,3,4,5-tetrahydrobenzo[f][1,4]oxazepine-8-carboxylate (80 mg, 0.24 mmol, 1 equiv) in CH$_2$Cl$_2$ (2 mL) and Et$_3$N (96 mg, 0.95 mmol, 4 equiv), followed by the addition of a solution of acetyl chloride (20 mg, 0.25 mmol, 1.1 equiv) in CH$_2$Cl$_2$ (1 mL) dropwise at 0° C. The resulting solution was stirred for 18 h at room temperature. The resulting mixture was concentrated under vacuum to afford the title compound as a brown oil (60 mg) which was used without further purification. MS: (ES, m/z): 264 [M+H]$^+$.

Step-2: (R)-4-Acetyl-N-hydroxy-3-methyl-2,3,4,5-tetrahydrobenzo[f][1,4]oxazepine-8-carboxamide

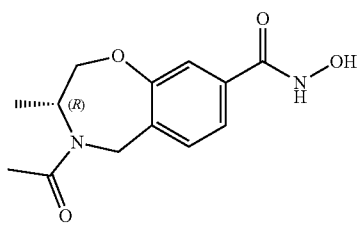

Into a 8-mL vial, were placed a solution of methyl (R)-4-acetyl-3-methyl-2,3,4,5-tetrahydrobenzo[f][1,4] oxazepine-8-carboxylate (60 mg, 0.23 mmol, 1 equiv) in THF/MeOH (4:1, 1.5 mL), followed by the addition of aq. 1N NaOH (0.45 mL, 2 equiv) and NH$_2$OH (50% in water, 0.44 mL, 30 equiv). The resulting solution was stirred for 14 h at room temperature. The crude product was purified by

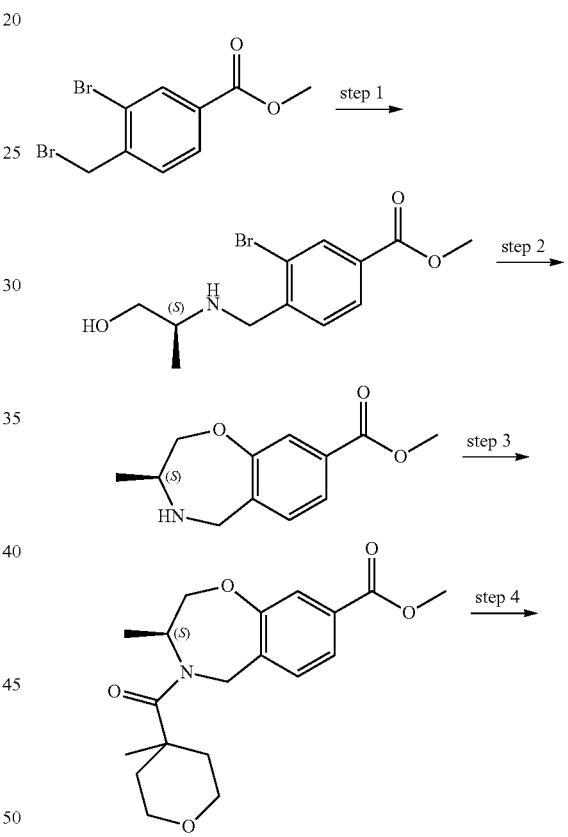

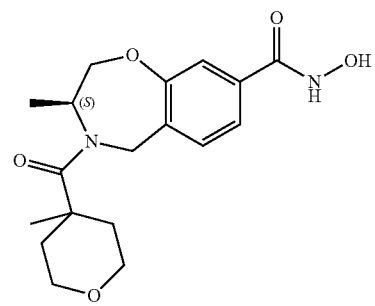

Step-1: Methyl (S)-3-bromo-4-(((1-hydroxypropan-2-yl)amino)methyl)benzoate

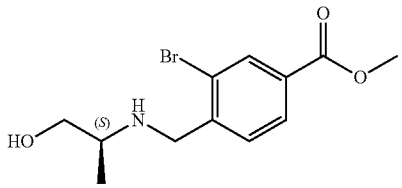

Into a 500-mL round-bottom flask, was placed a solution of methyl 3-bromo-4-(bromomethyl)benzoate (10 g, 32.47 mmol, 1 equiv) in THF (150 mL), (S)-2-aminopropan-1-ol (2.4 g, 31.95 mmol, 1 equiv) and $K_2CO_3$ (6.7 g, 1.5 equiv). The resulting solution was stirred for 3 h at room temperature, then concentrated under vacuum. The residue was washed with EtOAc/pet. ether (1:10, 20 mL) to afford the title compound as an off-white solid (5 g, 51% yield). MS: (ES, m/z): 302 [M+H]$^+$.

Step-2: Methyl (S)-3-methyl-2,3,4,5-tetrahydrobenzo[f][1,4]oxazepine-8-carboxylate

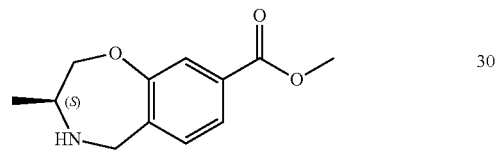

Into a 100-mL round-bottom flask purged and maintained with an inert atmosphere of nitrogen, was placed a solution of methyl (S)-3-bromo-4-(((1-hydroxypropan-2-yl)amino)methyl)benzoate (3.2 g, 10.59 mmol, 1 equiv) in isopropanol (35 mL), $K_2CO_3$ (2.20 g, 15.92 mmol, 1.5 equiv) and CuI (610 mg, 3.20 mmol, 0.3 equiv). The resulting solution was stirred for 19 h at 110° C. in an oil bath. The resulting mixture was concentrated under vacuum, diluted with EtOAc (300 mL), and washed with $H_2O$ (3×100 mL). The organic phase was concentrated and the residue was purified by silica gel chromatography (EtOAc/pet. ether, 1:4) to afford the title compound as a light yellow oil (1 g, 43% yield). $^1$H-NMR (400 MHz, DMSO-$d_6$) δ(ppm): 7.57-7.50 (m, 1H), 7.45 (s, 1H), 7.35-7.29 (m, 1H), 4.27-4.19 (m, 1H), 3.99-3.81 (m, 5H), 3.37-3.21 (m, 2H), 3.17-3.10 (s, 1H), 1.05-0.94 (d, J=6.4 Hz, 3H). MS: (ES, m/z): 222 [M+H]$^+$.

Step-3: Methyl (S)-3-methyl-4-(4-methyltetrahydro-2H-pyran-4-carbonyl)-2,3,4,5-tetrahydrobenzo[f][1,4]oxazepine-8-carboxylate

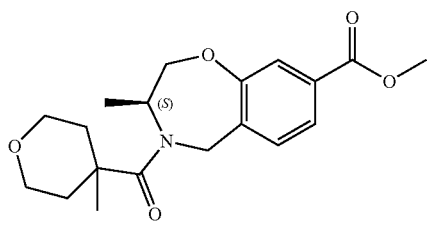

Into a 8-mL vial, was placed methyl (S)-3-methyl-2,3,4,5-tetrahydrobenzo[f][1,4]oxazepine-8-carboxylate (100 mg, 0.45 mmol, 1 equiv) in DMF (2.0 mL), HATU (205 mg, 0.54 mmol, 1.2 equiv), 4-methyltetrahydro-2H-pyran-4-carboxylic acid (77.8 mg, 0.54 mmol, 1.2 equiv), and DIEA (174 mg, 1.35 mmol, 3 equiv). The resulting mixture was stirred overnight at room temperature. The mixture was diluted with $H_2O$ (20 mL) and extracted with EtOAc (3×20 mL). The organic layer was washed with $H_2O$ (3×20 mL), dried over anhydrous $Na_2SO_4$, filtered, and concentrated. The residue was purified by silica gel chromatography (EtOAc/pet. ether, 2:3) to afford the title compound as an orange oil (52 mg, 33% yield). MS: (ES, m/z): 348 [M+H]$^+$.

Step-4: (S)—N-Hydroxy-3-methyl-4-(4-methyltetrahydro-2H-pyran-4-carbonyl)-2,3,4,5-tetrahydrobenzo[f][1,4]oxazepine-8-carboxamide

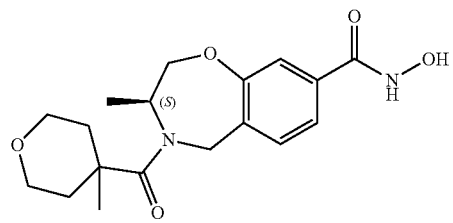

Into a 8-mL vial, was placed methyl (S)-3-methyl-4-(4-methyltetrahydro-2H-pyran-4-carbonyl)-2,3,4,5-tetrahydrobenzo[f][1,4]oxazepine-8-carboxylate (52 mg, 0.15 mmol, 1 equiv) in THF/MeOH (4:1, 2.0 mL). Then aq. 1N NaOH (0.3 mL, 2 equiv) and $NH_2OH$ (50% in $H_2O$, 0.3 mL, 30 equiv) were added simultaneously. The resulting solution was stirred for 2 h at room temperature. The crude product was purified by Prep-HPLC (Column: Sunfire C18, 5 μm, 19×150 mm; Mobile Phase A: Water/0.05% TFA; Mobile Phase B: MeCN; Flow rate: 25 mL/min; Gradient: 5% B to 35% B in 8 min; Detector, UV 254, 220 nm) to afford the title compound as an orange solid (20.7 mg, 30% yield). $^1$H-NMR (400 MHz, DMSO-$d_6$) δ(ppm): 11.13 (s, 1H), 9.02-8.93 (br, 1H), 7.31-7.25 (s, 2H), 7.21-7.17 (s, 1H), 4.80-4.87 (m, 3H), 4.25-4.10 (m, 2H), 3.59-3.55 (m, 2H), 3.41-3.36 (m, 2H), 1.96-1.93 (d, 2H), 1.47-1.35 (m, 2H), 1.210 (s, 3H), 1.11 (s, 3H). MS: (ES, m/z): 349 [M+H]$^+$.

TABLE 19

The following compounds were prepared according to the method of Example 36, with these modifications: (1) In Step 3, the solvent can be DMF, DMA, or $CH_2Cl_2$; (2) In Step 3, the base can be DIEA or $Et_3N$; (3) In Step 4, the Prep-HPLC column can be Sunfire C18, 5 μm, 19 × 150 mm using TFA, formic acid, or $NH_4HCO_3$ as the additive to the water Mobile Phase A; or the column XBridge RP C18 OBD, 5 μm, 19 × 150 mm using TFA, formic acid, or $NH_4HCO_3$ as the additive to the water Mobile Phase A.

| Structure | Found M + H | $^1$H-NMR (300 or 400 MHz, DMSO-$d_6$) δ (ppm) |
|---|---|---|
| (structure 1) | (ES, m/z): 319 [M + H]$^+$ | 11.14 (s, 1H), 7.32-7.19 (m, 3H), 4.85-4.77 (m, 2H), 4.42-4.37 (m, 1H), 4.29-4.07 (m, 3H), 2.29-2.26 (d, J = 9 Hz 1H), 1.96-1.90 (m, 4H), 1.87-1.81 (m, 1H), 1.49-1.46 (m, 3H), 1.34-1.27 (m, 2H), 1.01-0.98 (m, 2H) |
| (structure 2) | (ES, m/z): 383 [M + H]$^+$ | 11.15 (br, 1H), 9.50-8.47 (br, 1H), 7.44-7.16 (m, 3H), 4.94-4.87 (m, 1H), 4.67-4.63 (m, 1H), 4.52-4.48 (m, 1H), 4.30-4.16 (m, 2H), 3.28-2.92 (m, 5H), 2.11-1.97 (m, 2.5H), 1.87-1.76 (m, 1H), 1.30-1.27 (m, 0.5H), 1.21-1.05 (m, 3H) |
| (structure 3) | (ES, m/z): 349 [M + H]$^+$ | 11.14 (br, 1H), 9.01 (br, 1H), 7.37-7.29 (m, 1H), 7.38-7.19 (m, 1H), 7.18 (s, 1H), 5.14-4.93 (m, 1H), 4.85-4.49 (m, 2H), 4.27-4.10 (m, 2H), 3.02 (s, 1.4H), 2.61 (s, 1.6H), 2.11-1.78 (m, 3H), 1.69-1.39 (m, 5H), 1.21 (m, 1.4H), 1.05 (m, 1.6H) |
| (structure 4) | (ES, m/z): 369 [M + H]$^+$ | 11.23-11.03 (m, 1H), 9.21-8.76 (br, 1H), 7.49-7.12 (m, 3H), 5.01-4.79 (m, 2H), 4.77-4.43 (m, 1H), 4.38-4.09 (m, 2H), 3.79-3.61 (m, 1H), 3.41-3.29 (m, 1H), 3.27-3.05 (m, 2H), 2.97-2.81 (m, 1H), 2.39-2.01 (m, 1H), 1.89-1.52 (m, 1H), 1.29-1.01 (m, 3H) |

TABLE 19-continued

The following compounds were prepared according to the method of Example 36, with these modifications: (1) In Step 3, the solvent can be DMF, DMA, or CH$_2$Cl$_2$; (2) In Step 3, the base can be DIEA or Et$_3$N; (3) In Step 4, the Prep-HPLC column can be Sunfire C18, 5 μm, 19 × 150 mm using TFA, formic acid, or NH$_4$HCO$_3$ as the additive to the water Mobile Phase A; or the column XBridge RP C18 OBD, 5 μm, 19 × 150 mm using TFA, formic acid, or NH$_4$HCO$_3$ as the additive to the water Mobile Phase A.

| Structure | Found M + H | $^1$H-NMR (300 or 400 MHz, DMSO-d$_6$) δ (ppm) |
|---|---|---|
| 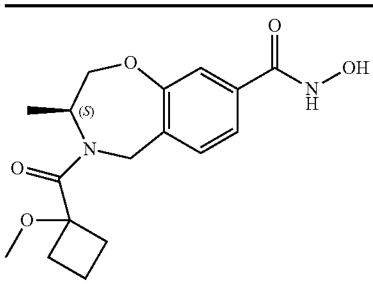 | (ES, m/z): 335 [M + H]$^+$ | 11.15 (br, 1H), 7.34-7.16 (m, 3H), 4.85-4.67 (m, 2H), 4.53-4.49 (m, 1H), 4.25-4.12 (m, 2H), 2.97 (s, 1H), 2.68-2.54 (m, 2H), 2.50-2.33 (m, 1H), 2.22-2.15 (m, 2H), 2.02-1.89 (m, 1H), 1.75-1.70 (m, 1H), 1.49-1.44 (m, 1H), 1.19-1.06 (m, 3H) |
| | (ES, m/z): 321 [M + H]$^+$ | 11.16-11.14 (br, 1H), 9.29-8.71 (br, 1H), 7.34-7.27 (m, 2H), 7.21-7.20 (m, 1H), 4.94-4.71 (m, 3H), 4.48-4.44 (d, J = 16.0 Hz, 1H), 4.35-4.06 (m, 4H), 3.79-3.75 (d, J = 16.0 Hz, 1H), 1.54-1.50 (d, J = 16.0 Hz, 3H), 1.20-1.05 (m, 3H) |
| 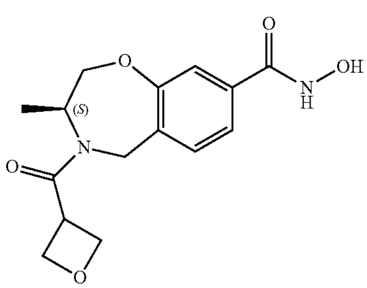 | (ES, m/z): 307 [M + H]$^+$ | 11.21-10.95 (s, 1H), 9.31-8.65 (br, 1H), 7.39-7.25 (m, 2H), 7.24-7.12 (s, 1H), 4.98-4.81 (m, 2H), 4.78-4.61 (m, 2H), 4.58-4.34 (m, 1H), 4.31-4.13 (m, 3H), 4.11-3.85 (m, 2H), 1.19-1.01 (m, 3H) |
| 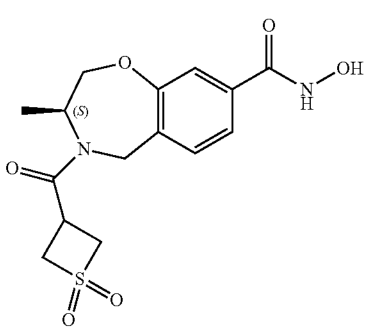 | (ES, m/z): 355 [M + H]$^+$ | 11.23-10.98 (s, 1H), 9.39-8.63 (br, 1H), 7.52-7.26 (m, 2H), 7.23-7.13 (m, 1H), 4.98-4.73 (m, 1H), 4.62-4.29 (m, 4H), 4.25-4.17 (m, 1H), 4.09-3.87 (m, 2H), 3.77-3.63 (m, 1H), 3.59-3.45 (m, 1H), 1.31-1.02 (m, 3H) |
| | (ES, m/z): 321 [M + H]$^+$ | 11.13 (br, 1H), 8.97 (br, 1H), 7.39-7.10 (m, 3H), 5.03-4.51 (m, 3H), 4.32-4.10 (m, 2H), 3.18 (s, 1.8H), 2.69 (s, 1.2H), 1.34-0.96 (m, 5H), 0.85-0.60 (m, 2H) |

TABLE 19-continued

The following compounds were prepared according to the method of Example 36, with these modifications: (1) In Step 3, the solvent can be DMF, DMA, or CH$_2$Cl$_2$; (2) In Step 3, the base can be DIEA or Et$_3$N; (3) In Step 4, the Prep-HPLC column can be Sunfire C18, 5 μm, 19 × 150 mm using TFA, formic acid, or NH$_4$HCO$_3$ as the additive to the water Mobile Phase A; or the column XBridge RP C18 OBD, 5 μm, 19 × 150 mm using TFA, formic acid, or NH$_4$HCO$_3$ as the additive to the water Mobile Phase A.

| Structure | Found M + H | $^1$H-NMR (300 or 400 MHz, DMSO-d$_6$) δ (ppm) |
|---|---|---|
| 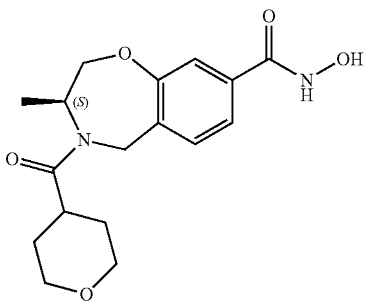 | (ES, m/z): 335 [M + H]$^+$ | 11.02 (br, 1H), 9.37-8.41 (br, 1H), 7.42-7.15 (m, 3H), 4.92-4.70 (m, 2H), 4.48-4.44 (m, 1H), 4.28-4.18 (m, 2H), 3.86-3.83 (m, 2H), 3.67-3.64 (m, 1H), 3.41-3.35 (m, 1.5H), 3.15-3.09 (m, 0.5H), 2.87-2.77 (m, 1H), 1.72-1.58 (m, 1H), 1.56-1.49 (m, 1H), 1.42-1.35 (m, 1H), 1.21-1.19 (m, 1H), 1.04-1.03 (m, 2H) |
| 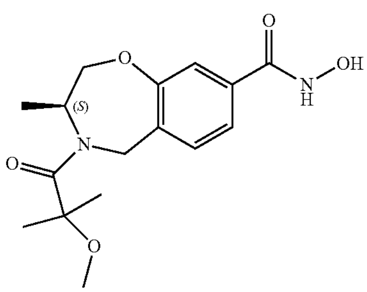 | (ES, m/z): 323 [M + H]$^+$ | 11.31-10.88 (s, 1H), 7.38-7.29 (m, 1H), 7.27-7.12 (m, 2H), 5.35-5.09 (m, 1H), 4.92-4.45 (m, 2H), 4.28-4.09 (m, 2H), 3.21-2.98 (m, 1H), 2.87-2.67 (m, 2H), 1.39-1.27 (m, 4H), 1.25-1.19 (m, 1H), 1.17-1.11 (m, 2H), 1.09-0.99 (m, 2H) |
| 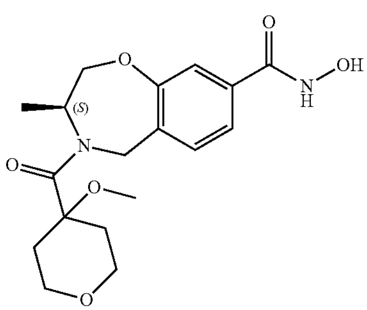 | (ES, m/z): 365 [M + H]$^+$ | 11.15-11.21 (d, 2H), 9.05 (br, 1H), 7.34-7.17 (m, 3H), 5.36-5.22 (m, 1H), 4.87-4.49 (m, 2H), 4.22-4.09 (m, 2H), 3.61-3.46 (m, 4H), 2.68-2.50 (m, 3H), 1.93-1.56 (m, 4H), 1.23-1.06 (m, 3H) |
| 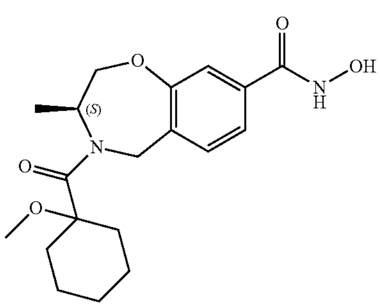 | (ES, m/z): 363 [M + H]$^+$ | 11.15 (m, 1H), 8.96 (br, 1H), 7.37-7.14 (m, 3H), 5.42-5.21 (m, 1H), 4.84-4.45 (m, 2H), 4.23-4.10 (m, 2H), 3.06 (s, 1.4H), 2.67 (s, 1.6H), 1.99-1.58 (m, 3H), 1.57-1.29 (m, 6H), 1.23 (d, J = 6.4 Hz, 1.4H), 1.22-1.11 (m, 1H), 1.03 (d, J = 6.4 Hz, 1.6H) |

TABLE 19-continued

The following compounds were prepared according to the method of Example 36, with these modifications: (1) In Step 3, the solvent can be DMF, DMA, or $CH_2Cl_2$; (2) In Step 3, the base can be DIEA or $Et_3N$; (3) In Step 4, the Prep-HPLC column can be Sunfire C18, 5 μm, 19 × 150 mm using TFA, formic acid, or $NH_4HCO_3$ as the additive to the water Mobile Phase A; or the column XBridge RP C18 OBD, 5 μm, 19 × 150 mm using TFA, formic acid, or $NH_4HCO_3$ as the additive to the water Mobile Phase A.

| Structure | Found M + H | $^1$H-NMR (300 or 400 MHz, DMSO-d$_6$) δ (ppm) |
|---|---|---|
| 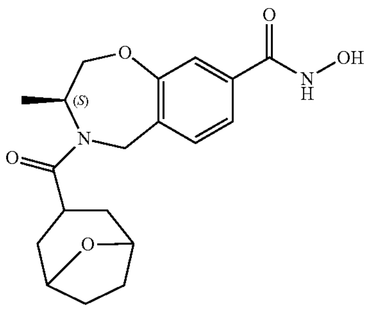 | (ES, m/z): 361 [M + H]$^+$ | 11.16 (br, 1H), 7.43-7.15 (m, 3H), 4.91-4.71 (m, 2H), 4.47-4.43 (m, 1H), 4.31-4.14 (m, 4H), 4.07-4.06 (d, J = 4.0 Hz, 1H), 2.96 (m, 1H), 1.92-1.72 (m, 4H), 1.49-1.34 (m, 3H), 1.21-1.19 (d, J = 8.0 Hz, 1H), 1.03-1.02 (d, J = 4.0 Hz, 1H), 0.56-0.55 (m, 1H) |
| 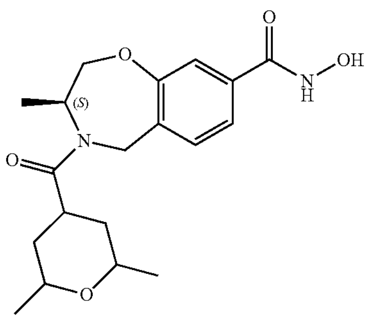 | (ES, m/z): 363 [M + H]$^+$ | 11.15 (br, 1H), 7.39-7.16 (m, 3H), 4.92-4.86 (m, 1.5H), 4.72-4.67 (m, 0.6H), 4.48-4.44 (m, 1H), 4.29-4.14 (m, 2H), 3.65-3.64 (m, 1H), 3.51-3.48 (m, 1H), 2.98-2.79 (m, 1H), 1.67-1.39 (m, 2H), 1.20-1.18 (m, 2H), 1.17-1.01 (m, 6H), 0.98-0.95 (m, 1H), 0.88-0.83 (m, 2H) |
| 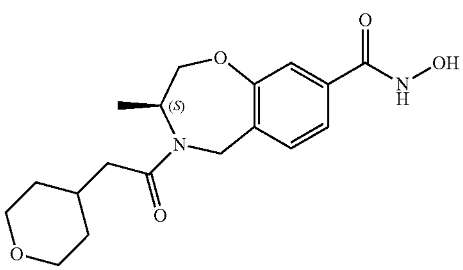 | (ES, m/z): 349 [M + H]$^+$ | 11.12 (br, 1H), 7.35-7.15 (m, 3H), 4.95-4.83 (m, 2H), 4.61-4.56 (d, J = 8.70 Hz, 1H), 4.47-4.42 (m, 1H), 4.25-4.14 (m, 2H), 3.78-3.61 (m, 2H), 3.22-3.07 (m, 2H), 2.34-2.19 (m, 1H), 1.99-1.70 (m, 2H), 1.50-1.46 m, 1H), 1.39-1.26 (m, 1H), 1.17-1.09 (m, 2H), 1.04-1.1.02 (d, J = 3.30 Hz, 2H), 0.85-0.80 (m, 1H) |
| 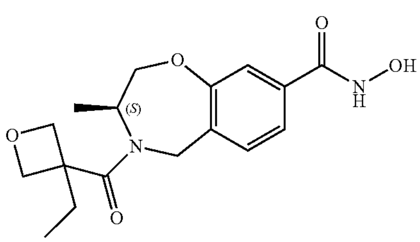 | (ES, m/z): 335 [M + H]$^+$ | 11.20-10.00 (br, 1H), 9.50-8.45 (br, 1H), 7.34-7.19 (m, 3H), 4.93-4.77 (m, 2H), 4.69-4.67 (m, 1H), 4.48-4.08 (m, 5H), 3.81-3.31 (m, 1H), 2.01-1.88 (m, 2H), 1.20-1.02 (m, 3H), 0.77-0.66 (m, 3H) |
| 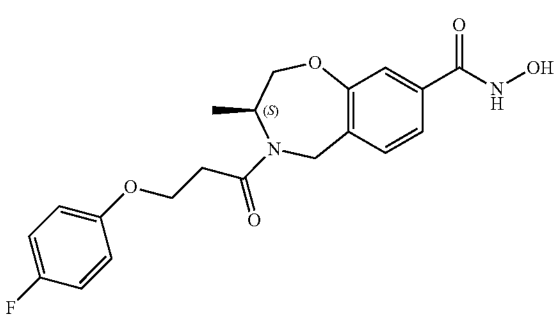 | (ES, m/z): 389 [M +H]$^+$ | 11.25 (s, 1H), 9.08 (s, 1H), 7.35-7.20 (m, 3H), 7.18-7.02 (m, 2H), 6.92-6.79 (m, 2H), 4.99-4.85 (m, 2H), 4.67-4.61 (d, J = 17.7 Hz, 1H), 4.54-4.48 (d, J = 15.9 Hz, 1H), 4.31-4.05 (m, 4H), 3.08-2.99 (m, 1H), 2.85-2.71 (m, 1H), 2.38-2.22 (m, 1H), 1.22-11.05 (m, 3H) |

TABLE 19-continued

The following compounds were prepared according to the method of Example 36, with these modifications: (1) In Step 3, the solvent can be DMF, DMA, or CH$_2$Cl$_2$; (2) In Step 3, the base can be DIEA or Et$_3$N; (3) In Step 4, the Prep-HPLC column can be Sunfire C18, 5 μm, 19 × 150 mm using TFA, formic acid, or NH$_4$HCO$_3$ as the additive to the water Mobile Phase A; or the column XBridge RP C18 OBD, 5 μm, 19 × 150 mm using TFA, formic acid, or NH$_4$HCO$_3$ as the additive to the water Mobile Phase A.

| Structure | Found M + H | $^1$H-NMR (300 or 400 MHz, DMSO-d$_6$) δ (ppm) |
|---|---|---|
| cis isomer | (ES, m/z): 335 [M + H]$^+$ | 11.10 (s, 1H), 9.02 (s, 1H), 7.34-7.27 (m, 1.5H), 7.24-7.22 (d, J = 8 Hz, 0.5H), 7.16-7.14 (m, 1H), 4.89-4.78 (m, 1.5H), 4.46-4.42 (d, J = 16.4 Hz, 1H), 4.26-4.13 (m, 2.4H), 3.75-3.65 (m, 1H), 3.07-3.03 (d, J = 15.2 Hz, 3H), 2.91-2.82 (m, 0.5H), 2.73-2.65 (m, 0.6H), 2.40-2.29 (m, 1H) 2.00-1.88 (m, 1.5H), 1.80-1.72 (m, 0.5H), 1.68-1.61 (m, 0.6H), 1.15-1.01 (m, 3H) |
| trans isomer | (ES, m/z): 335 [M + H]$^+$ | 11.13 (s, 1H), 9.02 (s, 1H), 7.32-7.23 (m, 2H), 7.16 (s, 1H), 4.93-4.81 (m, 2H), 4.49-4.13 (m, 3H), 3.80-3.74 (m, 1H), 3.27 (s, 0.5H), 3.13-3.04 (m, 3.5H), 2.49-1.76 (m, 4H), 1.15-1.02 (m, 3H) |
|  | (ES, m/z): 335 [M + H]$^+$ | 11.12 (s, 1H), 9.04 (s, 1H), 7.33-7.17 (m, 3H), 4.91-4.35 (m, 3H), 4.33-3.95 (m, 3H), 3.75-3.42 (m, 2H), 2.74-2.56 (m, 1H), 2.49-2.18 (m, 1H), 2.07-1.64 (m, 3H), 1.47-1.45 (m, 1H), 1.18-1.17 (d, J = 8.7 Hz, 1H), 1.05-1.03 (d, J = 6.6 Hz, 2H) |
| 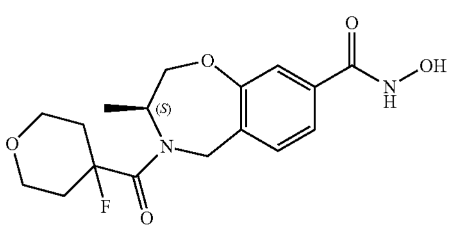 | (ES, m/z): 353 [M + H]$^+$ | 11.12 (br, 1H), 9.00 (br, 1H), 7.30-7.21 (m, 2H), 7.15 (s, 1H), 4.90-4.83 (m, 1H), 4.74-4.59 (m, 2H), 4.31-4.18 (m, 2H), 3.75-3.42 (m, 4H), 2.18-1.82 (m, 3H), 1.73-1.42 (m, 1H), 1.21-1.05 (m, 3H) |
| 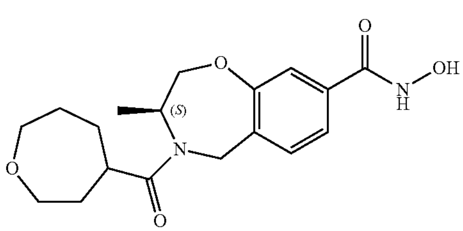 | (ES, m/z): 349 [M + H]$^+$ | 11.15 (s, 1H), 9.07 (s, 1H), 7.40-7.22 (m, 2H), 7.19-7.15 (t, J = 9.3 Hz, 1H), 4.92-4.50 (m, 2H), 4.44-4.16 (m, 3H), 3.71-3.43 (m, 4H), 2.80-2.75 (d, J = 13.2 Hz, 1H), 1.80-1.61 (m, 4H), 1.46-1.22 (m, 2H), 1.20-1.02 (m, 3H) |

TABLE 19-continued

The following compounds were prepared according to the method of Example 36, with these modifications: (1) In Step 3, the solvent can be DMF, DMA, or CH$_2$Cl$_2$; (2) In Step 3, the base can be DIEA or Et$_3$N; (3) In Step 4, the Prep-HPLC column can be Sunfire C18, 5 μm, 19 × 150 mm using TFA, formic acid, or NH$_4$HCO$_3$ as the additive to the water Mobile Phase A; or the column XBridge RP C18 OBD, 5 μm, 19 × 150 mm using TFA, formic acid, or NH$_4$HCO$_3$ as the additive to the water Mobile Phase A.

| Structure | Found M + H | $^1$H-NMR (300 or 400 MHz, DMSO-d$_6$) δ (ppm) |
|---|---|---|
| [Structure] | (ES, m/z): 363 [M + H]$^+$ | 11.16 (s, 1H), 9.04 (s, 1H), 7.45-7.15 (m, 3H), 4.98-4.81 (m, 2H), 4.64-4.52 (m, 1H), 4.30-4.19 (m, 2H), 3.87-3.50 (m, 3H), 3.14-3.03 (m, 0.5H), 2.92-2.86 (m, 0.1H), 2.67-2.61 (m, 0.4H), 2.42-2.32 (m, 0.4H), 2.23-2.12 (m, 0.3H), 1.90-1.83 (m, 0.2H), 1.79-1.52 (m, 1.2H), 1.47-1.38 (m, 0.3H), 1.25-1.18 (m, 1.8H), 1.05-1.02 (t, J = 7.4 Hz, 2H), 0.91-0.88 (t, J = 5.6 Hz, 1.6H), 0.82-0.78 (m, 2H), 0.65-0.63 (d, J = 6.8 Hz, 0.6H), 0.51-0.49 (d, J = 6.8 Hz, 1H), 0.25-0.23 (d, J = 8 Hz, 1H) |
| [Structure] | (ES, m/z): 349 [M + H]$^+$ | 7.33-7.24 (m, 3H), 5.00-4.92 (m, 2H), 4.86-4.68 (m, 2H), 4.62-4.48 (m, 1H), 4.29-4.22 (m, 2H), 2.29-1.71 (m, 4H), 1.37-1.26 (m, 4.7H), 1.23 (s, 0.5H), 1.19-1.12 (m, 3H), 0.89 (s, 1H) |
| [Structure] | (ES, m/z): 335 [M + H]$^+$ | 11.14 (s, 1H), 9.00 (s, 1H), 7.31-7.23 (m, 3H), 5.59-5.54 (d, J = 20.0 Hz, 0.3H), 5.09-4.85 (m, 0.7H), 4.84-4.74 (m, 0.8H), 4.72-4.68 (m, 0.7H), 4.53-4.43 (m, 0.5H), 4.30-4.10 (m, 2H), 3.93-3.76 (m, 1H), 3.74-3.56 (m, 0.8H), 3.45-3.35 (m, 0.2H), 2.60-2.50 (m, 1H), 1.89-1.75 (m, 1H), 1.72-1.60 (m, 0.5H), 1.57-1.46 (m, 0.5H), 1.44-1.30 (m, 2.5H), 1.29-1.18 (m, 1.5H), 1.15-0.97 (m, 3H) |
| [Structure] | (ES, m/z): 349 [M + H]$^+$ | 11.15 (s, 1H), 9.05 (s, 1H), 7.35-7.22 (m, 3H), 4.84-4.09 (m, 5H), 3.63-3.34 (m, 2H), 3.21-3.14 (m, 3H), 2.42-1.78 (m, 5H), 1.53-1.50 (m, 1H), 1.25-0.99 (m, 3H) |

TABLE 19-continued

The following compounds were prepared according to the method of Example 36, with these modifications: (1) In Step 3, the solvent can be DMF, DMA, or CH₂Cl₂; (2) In Step 3, the base can be DIEA or Et₃N; (3) In Step 4, the Prep-HPLC column can be Sunfire C18, 5 μm, 19 × 150 mm using TFA, formic acid, or NH₄HCO₃ as the additive to the water Mobile Phase A; or the column XBridge RP C18 OBD, 5 μm, 19 × 150 mm using TFA, formic acid, or NH₄HCO₃ as the additive to the water Mobile Phase A.

| Structure | Found M + H | $^1$H-NMR (300 or 400 MHz, DMSO-d$_6$) δ (ppm) |
|---|---|---|
| | (ES, m/z): 379 [M + H]⁺ | 11.10 (s, 1H), 9.00 (s, 1H), 7.28-7.25 (m, 2H), 7.18-7.15 (m, 1H), 4.89-4.44 (m, 3H), 4.28-4.17 (m, 2H), 3.74-3.60 (m, 4H), 3.58-3.52 (m, 1H), 3.28-3.24 (m, 2H), 2.80-2.10 (m, 2H), 1.72-1.68 (m, 2H), 1.31-1.26 (m, 2H), 1.23-1.02 (m, 3H) |
| | (ES, m/z): 335 [M + H]⁺ | 11.13 (s, 1H), 9.01 (s, 1H), 7.33-7.19 (d, J = 52.8 Hz, 3H), 5.02-4.39 (m, 3H), 4.19 (s, 2H), 3.60-3.49 (d, J = 44 Hz, 1H), 3.18-3.01 (d, J = 68 Hz, 4H), 1.27-1.02 (m, 3H), 0.93-0.61 (m, 4H) |
| | (ES, m/z): 349 [M + H]⁺ | 11.16 (s, 1H), 7.37-7.16 (m, 3H), 5.83 (br, 1H), 4.95-4.78 (m, 2H), 4.71-4.39 (m, 1H), 4.28-4.17 (m, 2H), 3.97-3.75 (m, 1H), 3.62-3.56 (m, 1H), 3.34-3.31 (m, 1H), 2.75-2.51 (m, 1H), 1.74-1.55 (m, 3H), 1.21-1.01 (m, 5H), 0.79-0.77 (d, J = 6.6 Hz, 1H), 0.56-0.54 (d, J = 6.6 Hz, 1H) |
| | (ES, m/z): 377 [M + H]⁺ | 10.70 (s, 1H), 9.03 (s, 1H), 7.31-7.16 (m 3H), 4.96-4.32 (m, 3H), 4.28-4.14 (m 2H), 4.06-3.90 (m, 2H), 3.82-3.68 (m, 2H), 2.90-2.12 (m, 2H), 1.19-1.03 (m, 3H) |

TABLE 19-continued

The following compounds were prepared according to the method of Example 36, with these modifications: (1) In Step 3, the solvent can be DMF, DMA, or CH$_2$Cl$_2$; (2) In Step 3, the base can be DIEA or Et$_3$N; (3) In Step 4, the Prep-HPLC column can be Sunfire C18, 5 μm, 19 × 150 mm using TFA, formic acid, or NH$_4$HCO$_3$ as the additive to the water Mobile Phase A; or the column XBridge RP C18 OBD, 5 μm, 19 × 150 mm using TFA, formic acid, or NH$_4$HCO$_3$ as the additive to the water Mobile Phase A.

| Structure | Found M + H | $^1$H-NMR (300 or 400 MHz, DMSO-d$_6$) δ (ppm) |
|---|---|---|
| 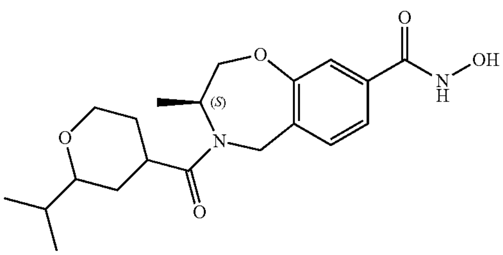 | (ES, m/z): 377 [M + H]$^+$ | 10.97 (s, 0.3H), 9.02 (s, 0.4H), 7.34-7.16 (m, 3H), 4.91-4.69 (m, 2H), 4.68-4.35 (m, 1H), 4.27-4.20 (m, 2H), 4.00-3.40 (m, 2H), 3.28-2.96 (m, 1H), 2.94-2.69 (m, 1H), 1.82-1.42 (m, 3H), 1.40-1.18 (m, 2H), 1.17-1.02 (m, 2H), 0.87-0.78 (m, 4H), 0.77-0.64 (m, 2H), 0.55-0.35 (m, 1H) |
| 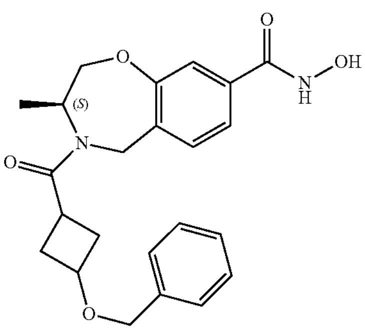 | (ES, m/z): 411 [M + H]$^+$ | 10.88 (s, 1H), 9.01 (s, 1H), 7.37-7.23 (m, 7H), 7.17 (m, 1H), 4.91-4.78 (m, 1H), 4.48-4.39 (m, 1H), 4.34-4.30 (m, 2H), 4.25-4.17 (m, 2H), 3.99-3.86 (m, 1H), 3.15-2.79 (m, 1H), 2.38-2.31 (m, 1H), 2.27-2.09 (m, 2H), 1.98-1.70 (m, 2H), 1.16-1.14 (d, J = 6.0 Hz, 1H), 1.04-1.02 (d, J = 6.3 Hz, 2H) |
| cis/trans | (ES, m/z): 417 [M + H]$^+$ | 7.39-7.26 (m, 3H), 5.06-4.92 (m, 2H), 4.76-4.59 (m, 1H), 4.56-4.50 (m, 2H), 2.78-2.22 (m, 2H), 2.18-1.43 (m, 5H), 1.37-1.32 (m, 2H), 1.19-0.99 (m, 2H) |
| cis/trans | (ES, m/z): 417 [M + H]$^+$ | 7.38-7.26 (m, 3H), 5.03-4.92 (m, 2H), 4.75-4.69 (m, 1H), 4.56-4.50 (m, 1H), 4.29-4.19 (m, 3H), 2.78-2.54 (m, 1H), 2.18-2.05 (m, 1H), 1.94-1.82 (m, 2H), 1.70-1.59 (m, 2H), 1.38-1.31 (m, 2H), 1.18-1.16 (m, 2H) |
| cis/trans | (ES, m/z): 349 [M + H]$^+$ | 11.09 (br s, 1H), 9.02 (br s, 1H), 7.32-7.16 (m, 3H), 5.18-5.12 (d, J = 16.8 Hz, 1H), 4.78-4.50 (m, 2H), 4.25-4.09 (m, 2H), 3.45-3.43 (m, 1H), 2.73-2.15 (m, 2H), 1.55-1.44 (m, 2H), 1.37-1.33 (m, 4H), 1.27-1.22 (m, 2H), 1.20-1.12 (m, 2H), 1.12-1.09 (m, 2H) |

TABLE 19-continued

The following compounds were prepared according to the method of Example 36, with these modifications: (1) In Step 3, the solvent can be DMF, DMA, or CH₂Cl₂; (2) In Step 3, the base can be DIEA or Et₃N; (3) In Step 4, the Prep-HPLC column can be Sunfire C18, 5 μm, 19 × 150 mm using TFA, formic acid, or NH₄HCO₃ as the additive to the water Mobile Phase A; or the column XBridge RP C18 OBD, 5 μm, 19 × 150 mm using TFA, formic acid, or NH₄HCO₃ as the additive to the water Mobile Phase A.

| Structure | Found M + H | $^1$H-NMR (300 or 400 MHz, DMSO-$d_6$) δ (ppm) |
|---|---|---|
| cis/trans | (ES, m/z): 349 [M + H]⁺ | 11.14-11.10 (br s, 1H), 9.03-9.01 (br s, 1H), 7.32-7.14 (m, 3H), 5.75-5.69 (d, J = 17.4 Hz, 1H), 4.98-4.88 (m, 2H), 4.32-4.15 (m, 2H), 3.87-3.65 (m, 1H), 3.24-3.17 (m, 1H), 2.27-2.07 (m, 1H), 1.58-1.48 (m, 3H), 1.35 (s, 2H), 1.25-1.23 (d, J = 6.6 Hz, 1H), 1.19-1.17 (d, J = 6.6 Hz, 1H), 1.17-1.09 (m, 2H), 0.95 (s, 2H) |
| cis/trans | (ES, m/z): 397 [M + H]⁺ | 11.16 (s, 1H), 9.02 (s, 1H), 7.40-7.16 (m, 5H), 6.93-6.77 (m, 3H), 4.92-4.86 (d, 1H), 4.86-4.19 (m, 5H), 3.11-1.9 (m, 5H), 1.19-1.03 (m, 3H) |
| cis/trans | (ES, m/z): 397 [M + H]⁺ | 11.12 (s, 1H), 9.00 (s, 1H), 7.36-7.21 (m, 4H), 7.17 (s, 1H), 6.91-6.87 (t, J = 7.2 Hz, 1H), 6.76-6.72 (t, J = 8.6 Hz, 2H), 4.94-4.85 (m, 1.5H), 4.64-4.61 (m, 1H), 4.50-4.36 (m, 1H), 4.26-4.17 (m, 2H), 3.28-2.00 (m, 5H), 1.15-1.04 (m, 3H) |
| | (ES, m/z): 367 [M + H]⁺ | 13.13 (br s, 3H), 8.37 (br s, 2H), 7.24-7.45 (m, 7H), 7.16-7.24 (m, 2H), 6.51 (br d, J = 16.7 Hz, 2H), 5.69 (br dd, J = 10.0, 5.3 Hz, 2H), 4.92-5.29 (m, 4H), 4.66-4.92 (m, 2H), 4.18-4.53 (m, 4H), 4.08 (q, J = 7.0 Hz, 2H), 1.41 (d, J = 6.4 Hz, 3H), 1.10-1.35 (m, 4H) |

Example 37

Preparation of (S)—N-hydroxy-3-methyl-4-((R)-tetrahydro-2H-pyran-3-carbonyl)-2,3,4,5-tetrahydrobenzo[f][1,4]oxazepine-8-carboxamide and (S)—N-hydroxy-3-methyl-4-((S)-tetrahydro-2H-pyran-3-carbonyl)-2,3,4,5-tetrahydrobenzo[f][1,4]oxazepine-8-carboxamide

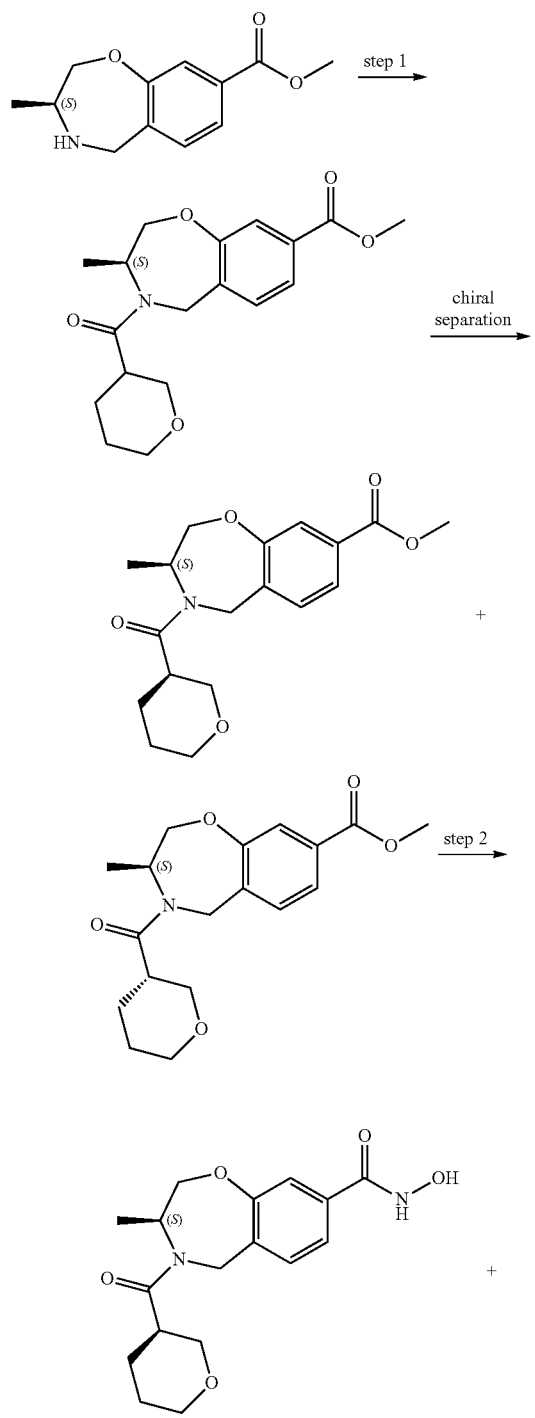

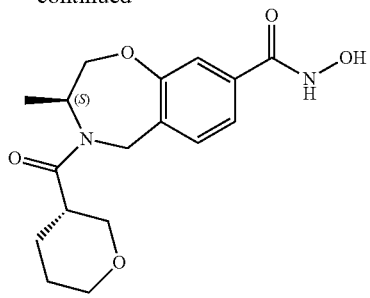

Step-1: Methyl (S)-3-methyl-4-((R)-tetrahydro-2H-pyran-3-carbonyl)-2,3,4,5-tetrahydrobenzo[f][1,4]oxazepine-8-carboxylate and Methyl (S)-3-methyl-4-((S)-tetrahydro-2H-pyran-3-carbonyl)-2,3,4,5-tetrahydrobenzo[f][1,4]oxazepine-8-carboxylate

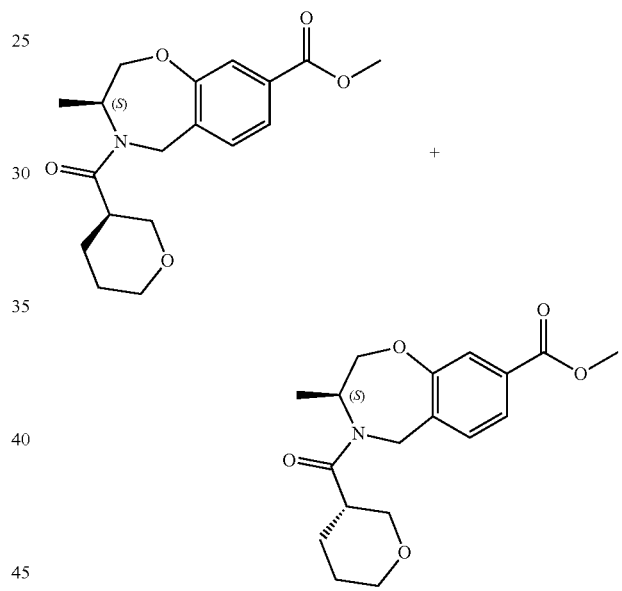

Into a 8-mL vial, were placed a solution of tetrahydro-2H-pyran-3-carboxylic acid (106 mg, 0.81 mmol, 1 equiv) in DMF (3 mL), HATU (371 mg, 0.98 mmol, 1.2 equiv), methyl (S)-3-methyl-2,3,4,5-tetrahydrobenzo[f][1,4]oxazepine-8-carboxylate (180 mg, 0.81 mmol, 1 equiv), and DIEA (315 mg, 2.44 mmol, 3 equiv). The resulting solution was stirred overnight at room temperature. The reaction was then quenched by the addition of H$_2$O (5 mL) and extracted with EtOAc (3×10 mL). The combined organic layers was washed with H$_2$O (2×10 mL), dried over anhydrous Na$_2$SO$_4$, filtered, and concentrated under vacuum. The residue was purified by silica gel chromatography (EtOAc/pet. ether, 1:1). The product mixture was separated by Chiral-Prep-HPLC (Column Chiralpak IB, 5 µm, 2×25 cm; Mobile Phase A: hexanes; Mobile Phase B: EtOH; Gradient: 40% B for 22 min; Detector, UV 254, 220 nm) to afford the title compounds as off-white solids (first eluting isomer: 60 mg, 22% yield; second eluting isomer: 86 mg, 32% yield). MS: (ES, m/z): 334 [M+H]$^+$.

Step-2: (S)—N-Hydroxy-3-methyl-4-((R)-tetra-hydro-2H-pyran-3-carbonyl)-2,3,4,5-tetrahydrobenzo[f][1,4]oxazepine-8-carboxamide and (S)—N-Hydroxy-3-methyl-4-((S)-tetrahydro-2H-pyran-3-carbonyl)-2,3,4,5-tetrahydrobenzo[f][1,4]oxazepine-8-carboxamide

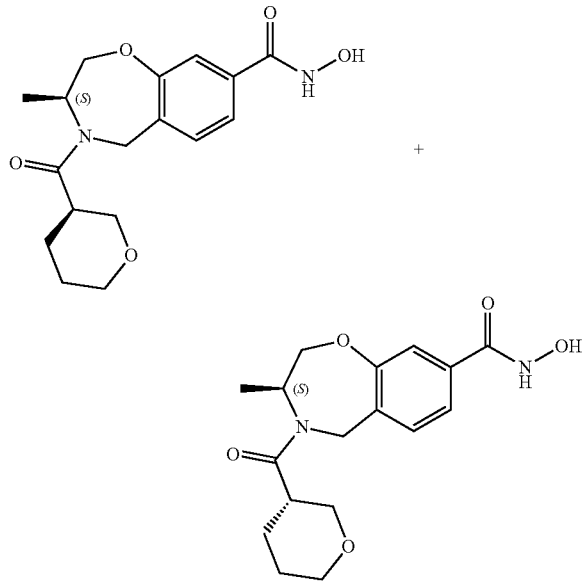

Into 8-mL vials, was placed each of the separated isomers from Step 1 (60 mg, 0.18 mmol; and 86 mg, 0.26 mmol; 1 equiv) in THF/MeOH (4:1, 2 mL). Then aq. 1N NaOH (2 equiv) and NH$_2$OH (50% in H$_2$O, 30 equiv) were added simultaneously. The resulting solution was stirred for 2 h at room temperature. The crude products were purified by Prep-HPLC (Column: Xbridge RP C18 OBD, 5 μm, 19×150 mm; Mobile Phase A: Water/0.05% formic acid; Mobile Phase B: MeCN; Flow rate: 25 mL/min; Gradient: 5% B to 40% B in 7 min; Detector, UV 254, 220 nm) to afford the title compounds as off-white solids. The product from the reaction with the first eluting isomer from Step 1: (30.3 mg, 50% yield). $^1$H-NMR (400 MHz, DMSO-d$_6$) δ(ppm): 11.16 (br s, 1H), 7.50-7.10 (m, 3H), 4.96-4.72 (m, 2H), 4.56-4.41 (m, 1H), 4.32-4.15 (m, 2H), 3.92-3.75 (m, 2H), 3.37-3.31 (m, 1H), 3.27-3.16 (m, 1H), 2.95-2.75 (m, 1H), 1.90-1.52 (m, 2H), 1.42-1.32 (m, 2H), 1.25-1.18 (m, 1H), 1.13-0.95 (m, 2H). MS: (ES, m/z): 335 [M+H]$^+$. The product from the reaction with the second eluting isomer from Step 1: (31.3 mg, 36% yield). $^1$H-NMR (400 MHz, DMSO-d$_6$) δ(ppm): 11.17 (br s, 1H), 7.46-7.13 (m, 3H), 4.96-4.84 (m, 1H), 4.85-4.76 (m, 0.5H), 4.71-4.65 (m, 0.5H), 4.51-4.44 (m, 1H), 4.33-4.15 (m, 2H), 3.85-3.71 (m, 1.5H), 3.42-3.35 (m, 0.5H), 3.30-3.07 (m, 2H), 2.87-2.65 (m, 1H), 1.97-1.76 (m, 1H), 1.70-1.34 (m, 3H), 1.20 (d, J=6.4 Hz, 1.4H), 1.03 (d, J=6.4 Hz, 1.6H). MS: (ES, m/z): 335 [M+H]$^+$.

TABLE 20

The following compounds were prepared according to the method of Example 37, with these modifications: (1) In Step 1, the reaction solvent can be DMF or CH$_2$Cl$_2$; (2) In Step 1, the chiral separation can be performed by Prep-HPLC using the Chiralpak IB, 5 μm, 2 × 25 cm column or the Chiralpak IC, 5 μm, 2 × 25 cm column; by Prep-SFC using the Chiralpak AS-H, 5 μm, 5 × 25 cm column; Mobile Phase: 50% CO$_2$, 50% MeOH; Detector, UV 220 nm; or by silica gel prep-TLC (EtOAc/pet. ether, 1:1); (3) In Step 2, the Prep-HPLC column can be XBridge RP C18 OBD, 5 μm, 19 × 150 mm using formic acid as the additive to the water Mobile Phase A; or the column Sunfire C18, 5 μm, 19 × 150 mm using NH$_4$HCO$_3$ as the additive to the water Mobile Phase A.

| Structure | Found M + H | $^1$H-NMR (400 MHz, DMSO-d$_6$) δ (ppm) |
| --- | --- | --- |
| cis/trans | (ES, m/z): 363 [M + H]$^+$ | 11.14 (br s, 1H), 9.02 (br s, 1H), 7.47-7.11 (m, 3H), 4.94-4.62 (m, 2H), 4.50-4.37 (m, 1H), 4.33-4.10 (m, 2H), 3.22-3.19 (d, 3H), 3.09-2.94 (m, 1H), 2.42-2.39 (m, 1H), 2.06-1.92 (m, 1H), 1.84-1.60 (m, 2H), 1.55-1.30 (m, 1H), 1.30-1.07 (m, 4H), 1.06-0.81 (m, 3H) |

TABLE 20-continued

The following compounds were prepared according to the method of Example 37, with these modifications: (1) In Step 1, the reaction solvent can be DMF or CH₂Cl₂; (2) In Step 1, the chiral separation can be performed by Prep-HPLC using the Chiralpak IB, 5 μm, 2 × 25 cm column or the Chiralpak IC, 5 μm, 2 × 25 cm column; by Prep-SFC using the Chiralpak AS-H, 5 μm, 5 × 25 cm column; Mobile Phase: 50% CO₂, 50% MeOH; Detector, UV 220 nm; or by silica gel prep-TLC (EtOAc/pet. ether, 1:1); (3) In Step 2, the Prep-HPLC column can be XBridge RP C18 OBD, 5 μm, 19 × 150 mm using formic acid as the additive to the water Mobile Phase A; or the column Sunfire C18, 5 μm, 19 × 150 mm using NH₄HCO₃ as the additive to the water Mobile Phase A.

| Structure | Found M + H | $^{1}$H-NMR (400 MHz, DMSO-d$_6$) δ (ppm) |
|---|---|---|
| [Structure: (S)-methyl benzoxazepine with cyclohexyl-OMe amide, cis/trans] | (ES, m/z): 363 [M + H]⁺ | 11.13 (br, 1H), 9.02 (br s, 1H), 7.45-7.12 (m, 3H), 4.95-4.61 (m, 2H), 4.51-4.38 (m, 1H), 4.35-4.11 (m, 2H), 3.45-3.35 (m, 1H), 3.16-3.15 (d, 3H), 2.65-2.55 (m, 1H), 1.92-1.55 (m, 3H), 1.53-1.25 (m, 4H), 1.19 (m, 1.5 H), 1.18-1.10 (m, 0.5H), 1.03 (m, 1.5H), 0.75-0.62 (m, 0.5H) |
| [Structure: (S)-methyl benzoxazepine with tetrahydrofuran-3-yl amide] | (ES, m/z): 321 [M + H]⁺ | 11.18 (br s, 1H), 7.49-7.14 (m, 3H), 4.95-4.82 (m, 1.5H), 4.74-4.41 (m, 1.5H), 4.35-4.13 (m, 2H), 4.06-3.89 (m, 1H), 3.78-3.18 (m, 4H), 2.12-1.90 (m, 1H), 1.67-1.45 (m, 1H), 1.20-1.04 (m, 3H) |
| [Structure: (S)-methyl benzoxazepine with tetrahydrofuran-3-yl amide, other isomer] | (ES, m/z): 321 [M + H]⁺ | 11.12 (br s, 1H), 9.01 (br s, 1H), 7.38-7.22 (m, 2H), 7.16-7.15 (m, 1H), 4.92-4.71 (m, 1.5H), 4.66-4.50 (m, 0.5H), 4.50-4.46 (m, 1H), 4.26-4.18 (m, 2H), 3.84-3.82 (m, 0.5H), 3.74-3.73 (m, 0.5H), 3.65-3.60 (m, 2H), 3.34-3.31 (m, 1H), 3.20-3.19 (m, 1H), 2.17-2.06 (m, 1H), 2.00-1.95 (m, 0.5H), 1.75-1.70 (m, 0.5H), 1.17-1.02 (m, 3H) |
| [Structure: (S)-methyl benzoxazepine with oxabicyclic amide, (R)/(S) isomer] | (ES, m/z): 347 [M + H]⁺ | 10.90 (br s, 1H), 9.10 (br s, 1H), 7.36-7.16 (m, 3H), 4.91-4.17 (m, 7H), 2.85-2.82 (m, 1H), 1.70-1.39 (m, 6H), 1.22-1.04 (m, 3H) |

TABLE 20-continued

The following compounds were prepared according to the method of Example 37, with these modifications: (1) In Step 1, the reaction solvent can be DMF or CH$_2$Cl$_2$; (2) In Step 1, the chiral separation can be performed by Prep-HPLC using the Chiralpak IB, 5 μm, 2 × 25 cm column or the Chiralpak IC, 5 μm, 2 × 25 cm column; by Prep-SFC using the Chiralpak AS-H, 5 μm, 5 × 25 cm column; Mobile Phase: 50% CO$_2$, 50% MeOH; Detector, UV 220 nm; or by silica gel prep-TLC (EtOAc/pet. ether, 1:1); (3) In Step 2, the Prep-HPLC column can be XBridge RP C18 OBD, 5 μm, 19 × 150 mm using formic acid as the additive to the water Mobile Phase A; or the column Sunfire C18, 5 μm, 19 × 150 mm using NH$_4$HCO$_3$ as the additive to the water Mobile Phase A.

| Structure | Found M + H | $^1$H-NMR (400 MHz, DMSO-d$_6$) δ (ppm) |
|---|---|---|
| (R)/(S) isomer | (ES, m/z): 347 [M + H]$^+$ | 11.15 (br s, 1H), 9.00 (br s, 1H), 7.48-7.17 (m, 3H), 4.96-4.90 (m, 2H), 4.72-4.66 (m, 2H), 4.51-4.16 (m, 2H), 3.84-2.70 (m, 2H), 2.00-1.79 (m, 1H), 1.52-1.03 (m, 8H) |
| (R)/(S) isomer | (ES, m/z): 363 [M + H]$^+$ | 11.11 (br s, 1H), 9.05 (br s, 1H), 7.40-7.25 (m, 2H), 7.18-7.15 (m, 1H), 4.92-4.49 (m, 3H), 4.32-4.15 (m, 2H), 3.64-3.56 (m, 2H), 3.02-2.99 (m, 1H), 1.49-1.42 (m, 2H), 1.32-1.78 (m, 3.5H), 1.12-1.03 (m, 4H), 0.96 (s, 2H), 0.88 (s, 0.5H) |
| (R)/(S) isomer | (ES, m/z): 363 [M + H]$^+$ | 11.09 (br s, 1H), 9.06 (br s, 1H), 7.34 (s, 1H), 7.31-7.19 (m, 1H), 7.16-1.15 (d, J = 1.5 Hz, 1H), 4.94-4.58 (m, 2H), 4.50-4.16 (m, 3H), 3.63-3.62 (m, 1H), 3.42-3.41 (m, 1H), 3.13-2.73 (m, 1H), 1.59-1.45 (m, 1H), 1.29-1.23 (m, 1.5H), 1.21-1.17 (m, 5H), 1.13 (s, 2H), 1.04-0.82 (m, 3H), 0.86-0.82 (m, 0.5H) |
| (R)/(S) isomer | (ES, m/z): 335 [M + H]$^+$ | 11.15 (br s, 1H), 9.02 (br s, 1H), 7.18-7.33 (m, 3H), 4.93-3.78 (m, 7H), 3.52-3.45 (m, 1H), 1.74-1.38 (m, 5.5H), 1.38-1.02 (m, 3.5H) |

TABLE 20-continued

The following compounds were prepared according to the method of Example 37, with these modifications: (1) In Step 1, the reaction solvent can be DMF or CH₂Cl₂; (2) In Step 1, the chiral separation can be performed by Prep-HPLC using the Chiralpak IB, 5 μm, 2 × 25 cm column or the Chiralpak IC, 5 μm, 2 × 25 cm column; by Prep-SFC using the Chiralpak AS-H, 5 μm, 5 × 25 cm column; Mobile Phase: 50% CO₂, 50% MeOH; Detector, UV 220 nm; or by silica gel prep-TLC (EtOAc/pet. ether, 1:1); (3) In Step 2, the Prep-HPLC column can be XBridge RP C18 OBD, 5 μm, 19 × 150 mm using formic acid as the additive to the water Mobile Phase A; or the column Sunfire C18, 5 μm, 19 × 150 mm using NH₄HCO₃ as the additive to the water Mobile Phase A.

| Structure | Found M + H | ¹H-NMR (400 MHz, DMSO-d₆) δ (ppm) |
|---|---|---|
| (R)/(S) isomer | (ES, m/z): 335 [M + H]⁺ | 11.15 (br s, 1H), 9.02 (br s, 1H), 7.18-7.33 (m, 3H), 4.93-4.12 (m, 6H), 3.82-3.78 (m, 0.5H), 3.52-3.24 (m, 1.5H), 1.74-1.20 (m, 6H), 1.20-1.02 (m, 3H) |
| (R)/(S) isomer | (ES, m/z): 335 [M + H]⁺ | 11.07-11.12 (br s, 1H), 9.02 (br s, 1H), 7.42-7.18 (m, 3H), 4.94-4.43 (m, 3H), 4.24-4.15 (m, 2H), 4.12-3.67 (m, 4H), 2.28-2.21 (m, 1H), 1.95-1.80 (m, 1H), 1.28-1.17 (m, 6H) |
| (R)/(S) isomer | (ES, m/z): 335 [M + H]⁺ | 11.09 (br s, 1H), 9.00 (br s, 1H), 7.16-7.40 (m, 3H), 4.90-4.43 (m, 3H), 4.21-4.12 (m, 2H), 3.79-3.72 (m, 2H), 3.57-3.48 (m, 2H), 2.48-2.26 (m, 0.5H), 1.86-1.84 (m, 1H), 1.83-1.60 (m, 0.5H), 0.89-1.32 (m, 6H) |

Example 38

Preparation of (S)-4-(1-acetylpiperidine-4-carbonyl)-N-hydroxy-3-methyl-2,3,4,5-tetrahydrobenzo[f][1,4]oxazepine-8-carboxamide

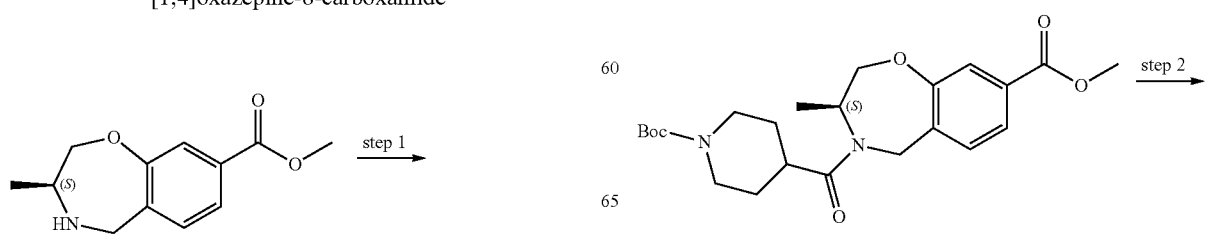

-continued

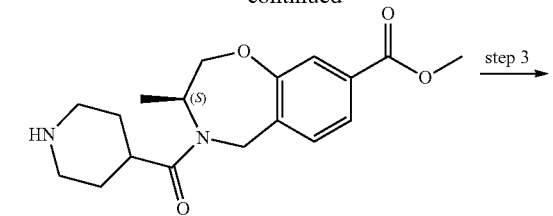

Step-2: Methyl (S)-3-methyl-4-(piperidine-4-carbonyl)-2,3,4,5-tetrahydrobenzo[f][1,4]oxazepine-8-carboxylate

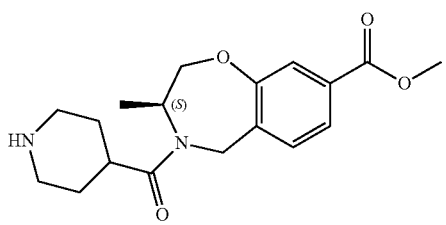

Into a 8-mL vial, was placed methyl (S)-4-(1-(tert-butoxycarbonyl)piperidine-4-carbonyl)-3-methyl-2,3,4,5-tetrahydrobenzo[f][1,4]oxazepine-8-carboxylate (400 mg, 0.92 mmol, 1 equiv) in $CH_2Cl_2$ (1.5 mL). This was followed by the addition of TFA (1.5 mL) dropwise with stirring at 0° C. The resulting solution was stirred for 5 h at room temperature, then concentrated under vacuum. The residue was dissolved in $H_2O$ (30 mL) and the pH was adjusted to 9 with aq. 1N NaOH. The resulting solution was extracted with EtOAc (3×30 mL). The combined organic layers were washed sequentially with $H_2O$ (2×20 mL) and brine (2×20 mL), dried over anhydrous $Na_2SO_4$, filtered, and concentrated under vacuum to afford the title compound as a brown oil (290 mg, 94% yield). MS: (ES, m/z): 333 [M+H]$^+$.

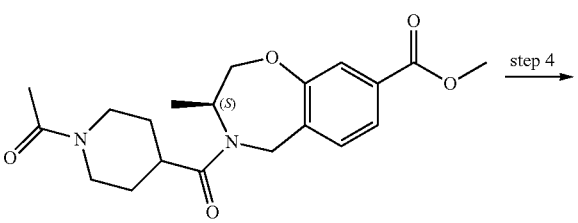

Step-3: Methyl (S)-4-(1-acetylpiperidine-4-carbonyl)-3-methyl-2,3,4,5-tetrahydrobenzo[f][1,4]oxazepine-8-carboxylate

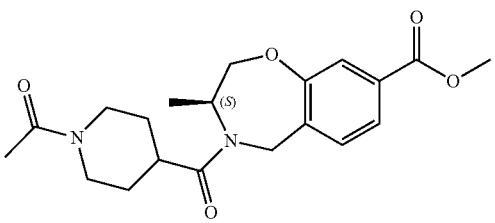

Step-1: Methyl (S)-4-(1-(tert-butoxycarbonyl)piperidine-4-carbonyl)-3-methyl-2,3,4,5-tetrahydrobenzo[f][1,4]oxazepine-8-carboxylate

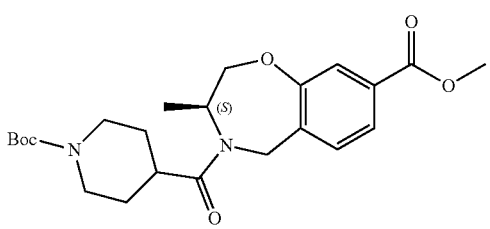

Into a 8-mL vial, was placed 1-(tert-butoxycarbonyl)piperidine-4-carboxylic acid (311 mg, 1.36 mmol, 1.2 equiv). Then HATU (516 mg, 1.36 mmol, 1.2 equiv), methyl (S)-3-methyl-2,3,4,5-tetrahydrobenzo[f][1,4]oxazepine-8-carboxylate (250 mg, 1.13 mmol, 1 equiv) in DMF (0.5 mL) and DIEA (438 mg, 3.39 mmol, 3 equiv) were added with stirring at 0° C. The resulting solution was stirred for 18 h at room temperature. The reaction was diluted with $H_2O$ (30 mL) and extracted with EtOAc (3×30 mL). The combined organic layers were washed sequentially with $H_2O$ (3×20 mL) and brine (2×20 mL), dried over anhydrous $Na_2SO_4$, filtered, and concentrated under vacuum to afford the title compound as a brown solid (400 mg, 82% yield). MS: (ES, m/z): 433 [M+H]$^+$.

Into a 8-mL vial, was placed a solution of methyl (S)-3-methyl-4-(piperidine-4-carbonyl)-2,3,4,5-tetrahydrobenzo[f][1,4]oxazepine-8-carboxylate (100 mg, 0.30 mmol, 1 equiv) in $CH_2Cl_2$ (2 mL). To this was added $Et_3N$ (121 mg, 1.20 mmol, 4 equiv) and a solution of acetyl chloride (26 mg, 0.33 mmol, 1.1 equiv) in $CH_2Cl_2$ (0.5 mL) dropwise with stirring at 0° C. The resulting solution was stirred for 18 h at room temperature, then concentrated under vacuum. The residue was dissolved in $CH_2Cl_2$ (30 mL) and washed with $H_2O$ (3×30 mL). The organic phase was dried over anhydrous $MgSO_4$, filtered, and concentrated under vacuum to afford the title compound as a brown solid (100 mg, 89% yield). MS: (ES, m/z): 375 [M+H]$^+$.

Step-4: (S)-4-(1-Acetylpiperidine-4-carbonyl)-N-hydroxy-3-methyl-2,3,4,5-tetrahydrobenzo[f][1,4]oxazepine-8-carboxamide

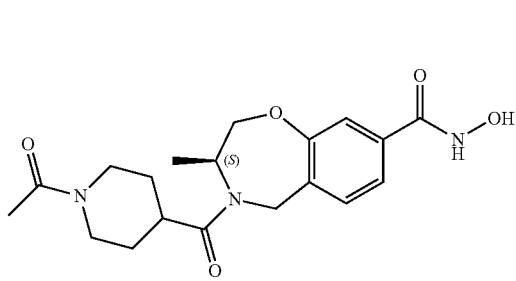

Into a 8-mL vial, was placed a solution of methyl (S)-4-(1-acetylpiperidine-4-carbonyl)-3-methyl-2,3,4,5-tetrahydrobenzo[f][1,4]oxazepine-8-carboxylate (100 mg, 0.27 mmol, 1 equiv) in THF/MeOH (4:1, 2 mL), then aq. 1N NaOH (0.53 mL, 2 equiv) and aq. NH$_2$OH (50% in H$_2$O, 0.53 mL, 30 equiv) were added simultaneously. The resulting solution was stirred for 3 h at room temperature. The crude product was purified by Prep-HPLC (Column: Sunfire C18, 5 μm, 19×150 mm; Mobile Phase A: Water/0.05% TFA; Mobile Phase B: MeCN; Flow rate: 25 mL/min; Gradient: 5% B to 40% B in 8 min; Detector, UV 254, 220 nm) to afford the title compound as an off-white solid (36.7 mg, 28% yield). $^1$H-NMR (400 MHz, DMSO-d$_6$) δ(ppm): 11.15 (br s, 1H), 9.18-8.62 (m, 1H), 7.44-7.16 (m, 3H), 4.92-4.76 (m, 2H), 4.49-4.45 (m, 1H), 4.34-4.14 (m, 3H), 3.82-3.61 (m, 1H), 3.11-3.09 (m, 1H), 2.88-2.79 (m, 1H), 2.60-2.57 (m, 1H), 1.97-1.91 (m, 3H), 1.64-1.56 (m, 2H), 1.40-1.29 (m, 1H), 1.24-1.03 (m, 3H), 0.92 (m, 1H). MS: (ES, m/z): 376 [M+H]$^+$.

Example 39

Preparation of (S)-4-(1-formylpiperidine-4-carbonyl)-N-hydroxy-3-methyl-2,3,4,5-tetrahydrobenzo[f][1,4]oxazepine-8-carboxamide

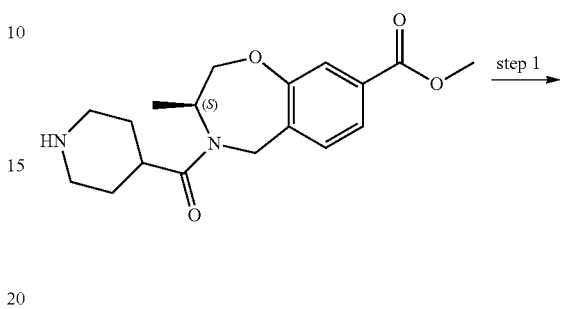

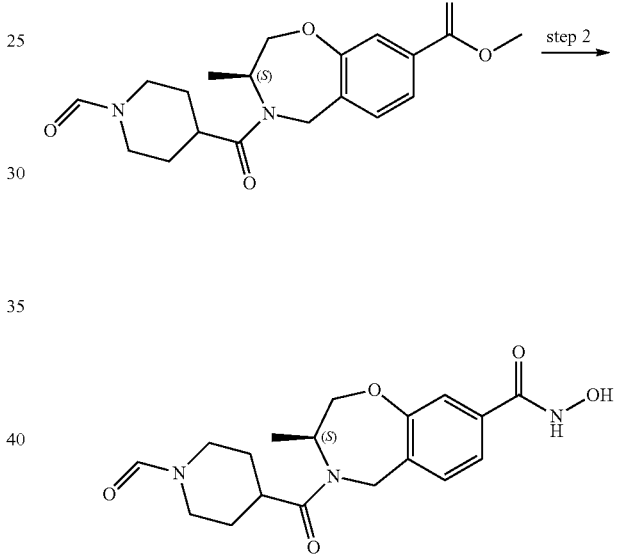

TABLE 21

The following compounds were prepared according to the method of Example 38.

| Structure | Found M + H | $^1$H-NMR (400 MHz, DMSO-d$_6$) δ (ppm) |
|---|---|---|
| 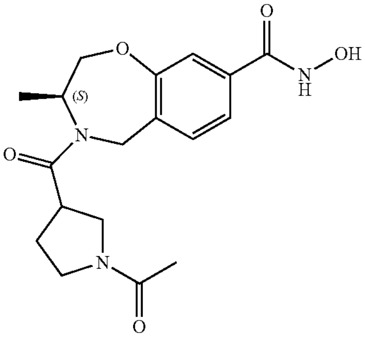 | (ES, m/z): 362 [M + H]$^+$ | 11.16 (br s, 1H), 9.32-8.55 (br s, 1H), 7.41-7.17 (m, 3H), 4.92-4.73 (m, 2H), 4.53-4.49 (m, 1H), 4.24-4.20 (m, 2H), 3.65-3.53 (m, 1H), 3.52-3.36 (m, 3H), 3.29-3.25 (m, 1H), 2.17-1.98 (m, 1H), 1.94-1.92 (m, 1H), 1.89-1.86 (m, 2H), 1.69-1.47 (m, 1H), 1.23-1.04 (m, 3H) |

Step-1: Methyl (S)-4-(1-formylpiperidine-4-carbonyl)-3-methyl-2,3,4,5-tetrahydrobenzo[f][1,4]oxazepine-8-carboxylate

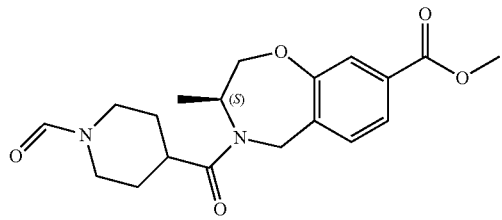

Into a 25-mL round-bottom flask, was placed methyl (S)-3-methyl-4-(piperidine-4-carbonyl)-2,3,4,5-tetrahydrobenzo[f][1,4]oxazepine-8-carboxylate (170 mg, 0.51 mmol, 1 equiv) in ethyl formate (10 mL). The resulting solution was stirred for 20 h at 60° C. in an oil bath, then concentrated under vacuum. The residue was dissolved in EtOAc (20 mL) and washed with $H_2O$ (2×20 mL), dried over anhydrous $Na_2SO_4$, filtered, and concentrated under vacuum. The residue was purified by silica gel chromatography (MeOH/$CH_2Cl_2$, 1:20) to afford the title compound as a colorless oil (79 mg, 43% yield). MS: (ES, m/z): 361 [M+H]$^+$.

Step-2: (S)-4-(1-Formylpiperidine-4-carbonyl)-N-hydroxy-3-methyl-2,3,4,5-tetrahydrobenzo[f][1,4]oxazepine-8-carboxamide

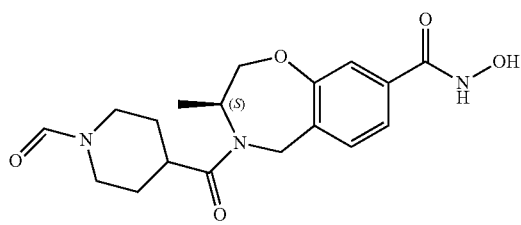

Into a 8-mL vial, was placed a solution of methyl (S)-4-(1-formylpiperidine-4-carbonyl)-3-methyl-2,3,4,5-tetrahydrobenzo[f][1,4]oxazepine-8-carboxylate (79 mg, 0.22 mmol, 1 equiv) in THF/MeOH (4:1, 2 mL), then aq. $NH_2OH$ (50% in $H_2O$, 0.43 mL, 30 equiv) and aq. 1N NaOH (0.44 mL, 2 equiv) were added simultaneously. The resulting solution was stirred for 2 h at room temperature. The crude product was purified by Prep-HPLC (Column: Sunfire C18, 5 μm, 19×150 mm; Mobile Phase A: Water/0.05% formic acid; Mobile Phase B: MeCN; Flow rate: 25 mL/min; Gradient: 5% B to 23% B in 7 min; Detector, UV 254, 220 nm) to afford the title compound as a light pink solid (11.2 mg, 14% yield). $^1$H-NMR (400 MHz, DMSO-$d_6$) δ(ppm): 11.15 (br s, 1H), 9.09 (br s, 1H), 7.94-7.88 (m, 1H), 7.44-7.16 (m, 3H), 4.93-4.71 (m, 2H), 4.50-4.46 (m, 1H), 4.30-4.14 (m, 3H), 3.75-3.54 (m, 1H), 3.13-3.10 (m, 1H), 2.92-2.70 (m, 2H), 1.79-1.61 (m, 2H), 1.45-1.30 (m, 1H), 1.27-1.20 (m, 4H). MS: (ES, m/z): 362 [M+H]$^+$.

Example 40

Preparation of (S)—N-hydroxy-4-(3-(methoxymethyl)oxetane-3-carbonyl)-3-methyl-2,3,4,5-tetrahydrobenzo[f][1,4]oxazepine-8-carboxamide

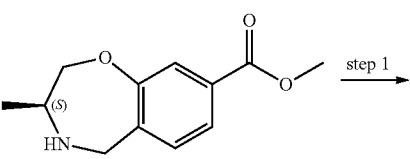

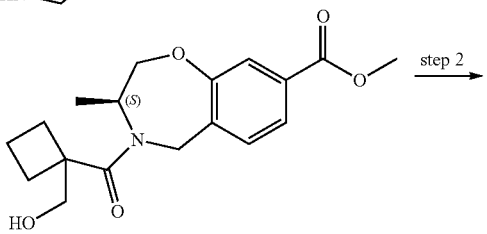

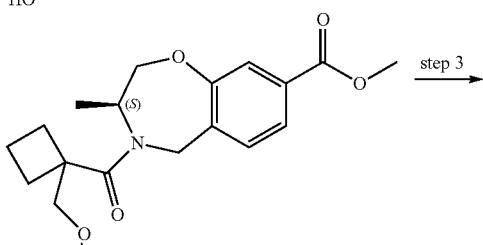

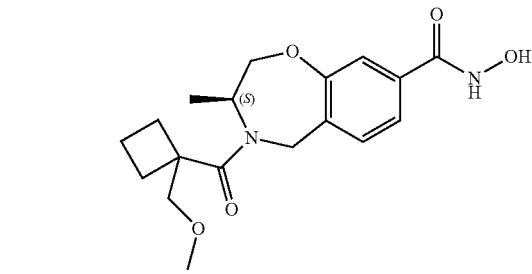

Step-1: Methyl (S)-4-(1-(hydroxymethyl)cyclobutane-1-carbonyl)-3-methyl-2,3,4,5-tetrahydrobenzo[f][1,4]oxazepine-8-carboxylate

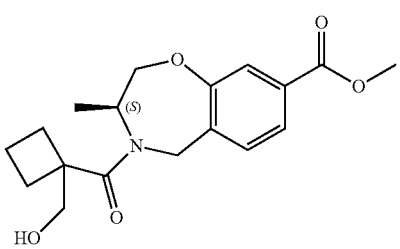

Into a 10-mL vial, were placed a solution of 3-(hydroxymethyl)oxetane-3-carboxylic acid (36 mg, 0.27 mmol, 1 equiv) in DMF (2 mL), HATU (155 mg, 0.41 mmol, 1.50 equiv), methyl (S)-3-methyl-2,3,4,5-tetrahydrobenzo[f][1,4]oxazepine-8-carboxylate (60 mg, 0.27 mmol, 1 equiv), and DIEA (175 mg, 1.35 mmol, 5 equiv) at 0° C. The resulting solution was stirred overnight at room temperature. The reaction was then quenched by the addition of H₂O (5 mL). The resulting solution was extracted with EtOAc (3×10 mL). The combined organic layers were washed sequentially with H₂O (10 mL) and brine (10 mL), dried over anhydrous Na₂SO₄, filtered, and concentrated under vacuum. The residue was purified by silica gel chromatography (EtOAc/pet. ether, 2:1) to afford the title compound as a yellow oil (50 mg, 55% yield). MS: (ES, m/z): 336 [M+H]⁺.

Step-2: Methyl (S)-4-(1-(methoxymethyl)cyclobutane-1-carbonyl)-3-methyl-2,3,4,5-tetrahydrobenzo[f][1,4]oxazepine-8-carboxylate

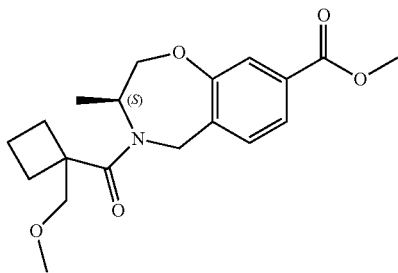

Into a 10-mL vial, were placed a solution of methyl (S)-4-(1-(hydroxymethyl)cyclobutane-1-carbonyl)-3-methyl-2,3,4,5-tetrahydrobenzo[f][1,4]oxazepine-8-carboxylate (40 mg, 0.12 mmol, 1 equiv) in THF (1 mL). This was followed by the addition of sodium hydride (60% dispersion in oil, 7 mg, 0.17 mmol, 1.5 equiv) in portions at 0° C. To this was added iodomethane (27 mg, 0.19 mmol, 1.6 equiv) dropwise with stirring at 0° C. The resulting solution was stirred for 30 min at room temperature. The reaction was then quenched by the addition of NH₄Cl aq. (2 mL). The resulting solution was extracted with EtOAc (3×10 mL). The combined organic layers were washed sequentially with H₂O (10 mL) and brine (10 mL), dried over anhydrous Na₂SO₄, filtered, and concentrated under vacuum. The residue was purified by silica gel chromatography (EtOAc/pet. ether, 1:1) to afford the title compound as a yellow oil (25 mg, 60% yield). MS: (ES, m/z): 350 [M+H]⁺.

Step-3: (S)—N-Hydroxy-4-(3-(methoxymethyl)oxetane-3-carbonyl)-3-methyl-2,3,4,5-tetrahydrobenzo[f][1,4]oxazepine-8-carboxamide

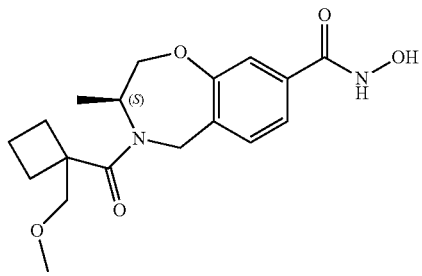

Into a 10-mL vial, were placed a solution of methyl (S)-4-(1-(methoxymethyl)cyclobutane-1-carbonyl)-3-methyl-2,3,4,5-tetrahydrobenzo[f][1,4]oxazepine-8-carboxylate (25 mg, 0.07 mmol, 1 equiv) in THF/MeOH (4:1, 2 mL), aq. 1N NaOH (0.14 mL, 2 equiv) and NH₂OH (50% in H₂O, 0.14 mL, 30 equiv) were added simultaneously. The resulting solution was stirred for 1 h at room temperature. The crude product was purified by Prep-HPLC (Column: Sunfire C18, 5 μm, 19×150 mm; Mobile Phase A: Water/0.05% formic acid; Mobile Phase B: MeCN; Flow rate: 25 mL/min; Gradient: 8% B to 60% B in 8 min; Detector, UV 254, 220 nm) to afford the title compound as an off-white solid (7.8 mg, 31% yield). ¹H-NMR (400 MHz, DMSO-d₆) δ(ppm): 11.15 (br s, 1H), 9.03 (br s, 1H), 7.36-7.24 (m, 2H), 7.23 (s, 1H), 4.86 (d, J=18.0 Hz, 1H), 4.80-4.70 (m, 1H), 4.70-4.59 (m, 1H), 4.49-4.32 (m, 3H), 4.29-4.19 (m, 1H), 4.10 (d, J=6.4 Hz, 1H), 3.95-3.71 (m, 2H), 3.66-3.48 (m, 1H), 3.26 (s, 1.5H), 3.16 (s, 1H), 1.24 (d, J=6.0 Hz, 1.5H), 1.04 (d, J=6.4 Hz, 1.5H). MS: (ES, m/z): 351 [M+H]⁺.

Example 41

Preparation of (S)-4-formyl-N-hydroxy-3-methyl-2,3,4,5-tetrahydrobenzo[f][1,4]oxazepine-8-carboxamide

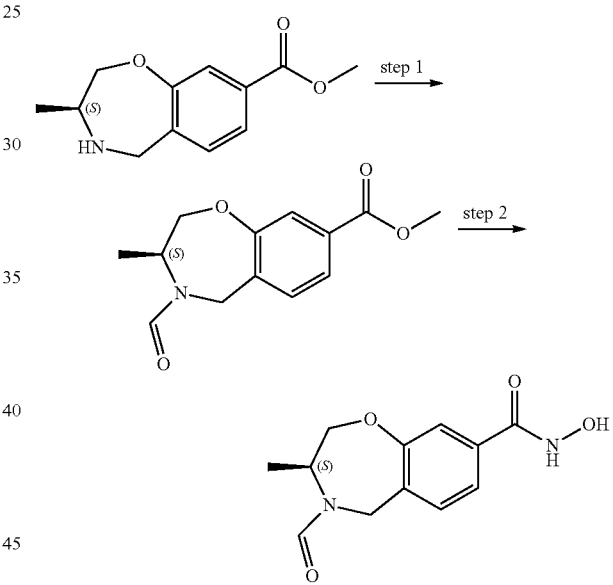

Step-1: Methyl (S)-4-formyl-3-methyl-2,3,4,5-tetrahydrobenzo[f][1,4]oxazepine-8-carboxylate

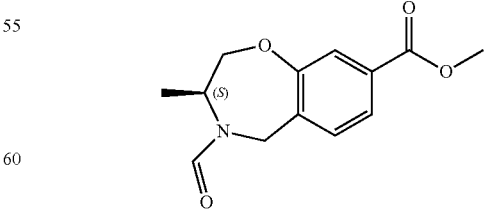

Into a 8-mL vial, was placed methyl (S)-3-methyl-2,3,4,5-tetrahydrobenzo[f][1,4]oxazepine-8-carboxylate (100 mg, 0.45 mmol, 1 equiv) and ethyl formate (2.5 mL, 1 equiv). The resulting solution was stirred for 16 h at 57° C. in an oil Step-2: (S)-4-Formyl-N-hydroxy-3-methyl-2,3,4,5-tetrahydrobenzo[f][1,4]oxazepine-8-carboxamide

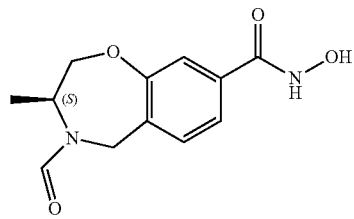

Into a 8-mL vial, was placed methyl (S)-4-formyl-3-methyl-2,3,4,5-tetrahydrobenzo[f][1,4]oxazepine-8-carboxylate (100 mg, 0.40 mmol, 1 equiv) in THF/MeOH (4:1, 2.5 mL). To this was added aq. 1N NaOH (0.8 mL, 2 equiv) and NH₂OH (50% in H₂O, 0.8 mL, 30 equiv). The resulting solution was stirred for 3 h at room temperature. The crude product was purified by Prep-HPLC (Column: Xbridge XP C18, 5 μm, 19×150 mm; Mobile Phase A: Water/0.05% TFA; Mobile Phase B: MeCN; Flow rate: 0.7 mL/min; Gradient: 5% B to 46% B in 7 min; Detector, UV 254, 220 nm) to afford the title compound as an off-white solid (50.6 mg, 35% yield). $^1$H-NMR (400 MHz, DMSO-$d_6$) δ(ppm): 11.15 (br s, 1H), 9.00 (br s, 1H), 8.15-8.13 (d, J=7.5 Hz, 1H), 7.35-7.22 (m, 3H), 4.91-4.79 (q, 1H), 4.69-4.10 (m, 4H), 1.23-1.09 (m, 3H). MS: (ES, m/z): 251 [M+H]⁺.

Example 42

Preparation of (S)-4-acetyl-N-hydroxy-3-methyl-2,3,4,5-tetrahydrobenzo[f][1,4]oxazepine-8-carboxamide

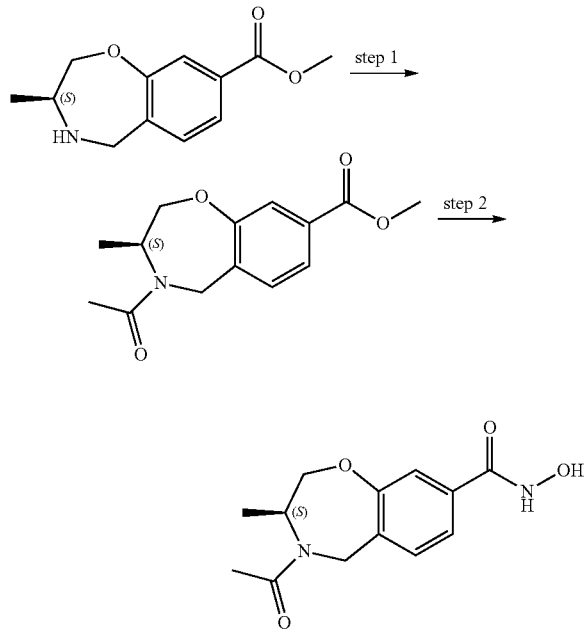

Step-1: Methyl (S)-4-acetyl-3-methyl-2,3,4,5-tetrahydrobenzo[f][1,4]oxazepine-8-carboxylate

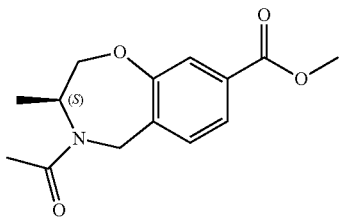

Into a 8-mL vial, was placed a solution of methyl (S)-3-methyl-2,3,4,5-tetrahydrobenzo[f][1,4]oxazepine-8-carboxylate (80 mg, 0.36 mmol, 1 equiv) in CH₂Cl₂ (2 mL) and Et₃N (110 mg, 1.09 mmol, 3 equiv). This was followed by the addition of acetyl chloride (31 mg, 0.39 mmol, 1.1 equiv) at 0° C. The resulting solution was stirred for 18 h at room temperature and concentrated under vacuum to afford the title compound as brown oil (90 mg), which was used without further purification. MS: (ES, m/z): 264 [M+H]⁺.

Step-2: (S)-4-Acetyl-N-hydroxy-3-methyl-2,3,4,5-tetrahydrobenzo[f][1,4]oxazepine-8-carboxamide

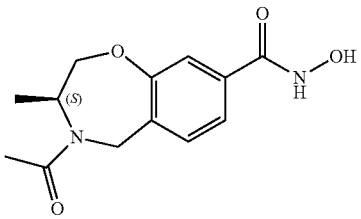

Into a 8-mL vial, was placed a solution of methyl (S)-4-acetyl-3-methyl-2,3,4,5-tetrahydrobenzo[f][1,4]oxazepine-8-carboxylate (90 mg, 0.34 mmol, 1 equiv) in THF/MeOH (4:1, 2 mL). Then aq. 1N NaOH (0.68 mL, 2 equiv) and NH₂OH (50% in water, 0.67 mL, 30 equiv) were added simultaneously. The resulting solution was stirred for 14 h at room temperature. The crude product was purified by Prep-HPLC (Column: Sunfire C18, 5 μm, 19×150 mm; Mobile Phase A: Water/0.05% TFA; Mobile Phase B: MeCN; Flow rate: 25 mL/min; Gradient: 4% B to 18% B in 6 min; Detector, UV 254, 220 nm) to afford the title compound as an off-white solid (12.3 mg, 10% yield). $^1$H-NMR (400 MHz, DMSO-$d_6$) δ(ppm): 11.15 (br s, 1H), 9.00 (br s, 1H), 8.15-8.13 (d, J=7.5 Hz, 1H), 7.35-7.22 (m, 3H), 4.91-4.79 (q, 1H), 4.69-4.10 (m, 4H), 1.23-1.09 (m, 3H). MS: (ES, m/z): 265 [M+H]⁺.

TABLE 22

The following compounds were prepared according to the method of Example 42.

| Structure | Found M + H | $^1$H-NMR (400 MHz, DMSO-d$_6$) δ (ppm) |
|---|---|---|
| 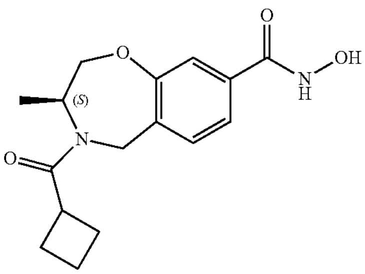 | (ES, m/z): 305 [M + H]$^+$ | 11.11 (br s, 1H), 9.00 (br s, 1H), 7.34-7.25 (m, 2H), 7.16 (s, 1H), 4.86-4.79 (m, 2H), 4.46-4.17 (m, 3H), 3.36-3.32 (m, 2H), 2.18-1.70 (m, 6H), 1.15-1.01 (m, 3H) |
| 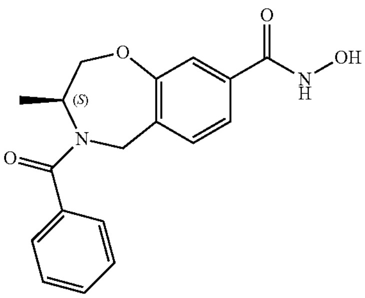 | (ES, m/z): 327 [M + H]$^+$ | 11.17-11.16 (br s, 1H), 9.03 (br s, 1H), 7.45-7.22 (m, 7H), 7.05-7.04 (d, J = 3.9 Hz, 1H), 5.02-4.63 (m, 2H), 4.31-4.29 (t, J = 5.4 Hz, 1H), 4.24-4.04 (m, 2H), 1.20-1.18 (d, J = 6.3 Hz, 3H) |

Example 43

Preparation of (S)—N-hydroxy-4-(4-(methoxymethyl)tetrahydro-2H-pyran-4-carbonyl)-3-methyl-2,3,4,5-tetrahydrobenzo[f][1,4]oxazepine-8-carboxamide

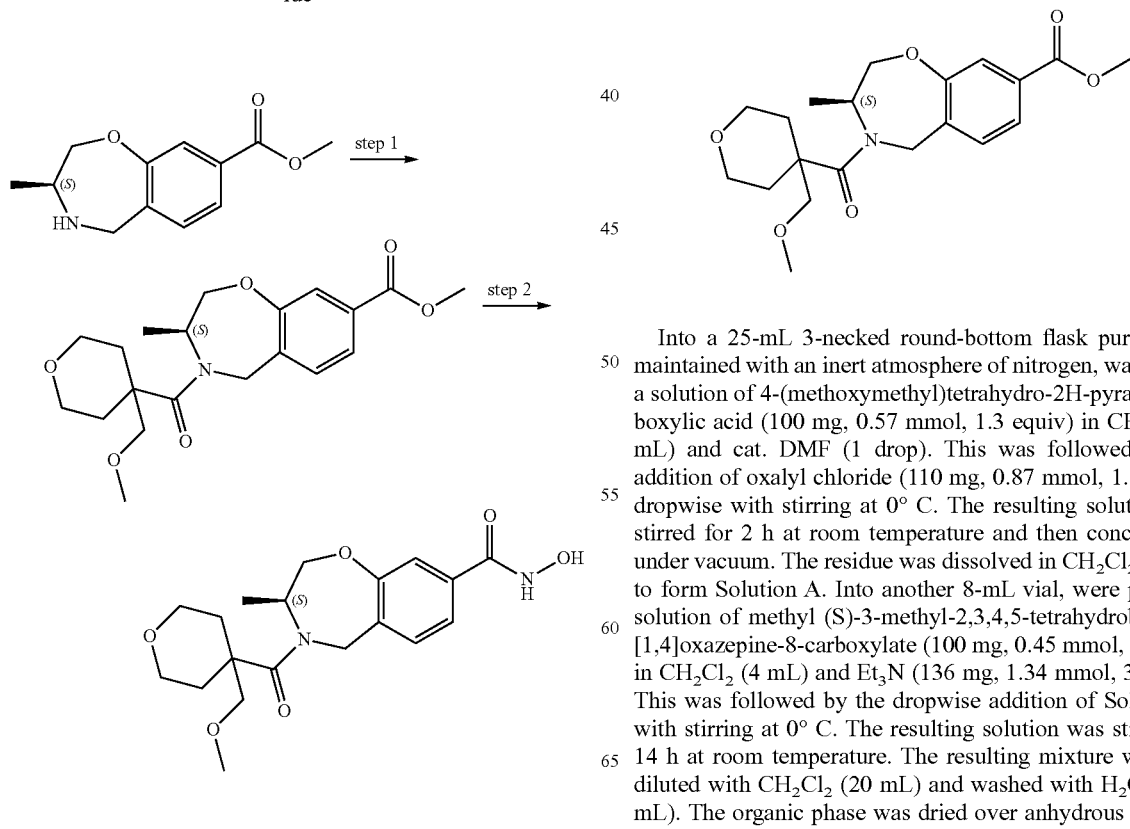

Step-1: Methyl (S)-4-(1-(methoxymethyl)cyclohexane-1-carbonyl)-3-methyl-2,3,4,5-tetrahydrobenzo[f][1,4]oxazepine-8-carboxylate Into a 25-mL 3-necked round-bottom flask purged and maintained with an inert atmosphere of nitrogen, was placed a solution of 4-(methoxymethyl)tetrahydro-2H-pyran-4-carboxylic acid (100 mg, 0.57 mmol, 1.3 equiv) in CH$_2$Cl$_2$ (5 mL) and cat. DMF (1 drop). This was followed by the addition of oxalyl chloride (110 mg, 0.87 mmol, 1.9 equiv) dropwise with stirring at 0° C. The resulting solution was stirred for 2 h at room temperature and then concentrated under vacuum. The residue was dissolved in CH$_2$Cl$_2$ (2 mL) to form Solution A. Into another 8-mL vial, were placed a solution of methyl (S)-3-methyl-2,3,4,5-tetrahydrobenzo[f][1,4]oxazepine-8-carboxylate (100 mg, 0.45 mmol, 1 equiv) in CH$_2$Cl$_2$ (4 mL) and Et$_3$N (136 mg, 1.34 mmol, 3 equiv). This was followed by the dropwise addition of Solution A with stirring at 0° C. The resulting solution was stirred for 14 h at room temperature. The resulting mixture was then diluted with CH$_2$Cl$_2$ (20 mL) and washed with H$_2$O (2×15 mL). The organic phase was dried over anhydrous Na$_2$SO$_4$ and concentrated under vacuum to afford the title compound as light brown oil (160 mg, 94% yield). MS: (ES, m/z): 378 [M+H]⁺.

Step-2: (S)—N-Hydroxy-4-(4-(methoxymethyl)tetrahydro-2H-pyran-4-carbonyl)-3-methyl-2,3,4,5-tetrahydrobenzo[f][1,4]oxazepine-8-carboxamide

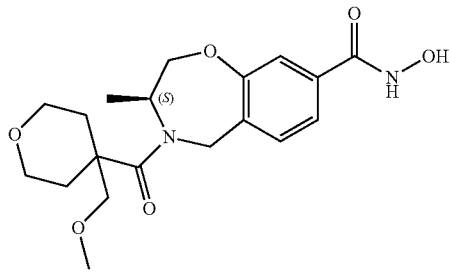

Into a 8-mL vial, was placed a solution of methyl (S)-4-(1-(methoxymethyl)cyclohexane-1-carbonyl)-3-methyl-2,3,4,5-tetrahydrobenzo[f][1,4]oxazepine-8-carboxylate (100 mg, 0.26 mmol, 1 equiv) in THF/MeOH (4:1, 2.5 mL). Then NH₂OH (50% in H₂O, 0.5 mL, 30 equiv) and aq. 1N NaOH (0.53 mL, 2 equiv) were added simultaneously. The resulting solution was stirred for 3 h at room temperature. The crude product was purified by Prep-HPLC (Column: Gemini-NX C18 110 Å, AXIA Packed, 5 μm, 21.2×150 mm; Mobile Phase A: Water/0.05% formic acid; Mobile Phase B: MeCN; Flow rate: 20 mL/min; Gradient: 5% B to 52% B in 8 min; Detector, UV 254, 220 nm) to afford the title compound as an off-white solid (8.8 mg, 9% yield). ¹H-NMR (400 MHz, DMSO-d₆) δ(ppm): 11.13 (br s, 1H), 8.98 (br s, 1H), 7.30 (s, 2H), 7.16 (s, 1H), 4.89-4.76 (m, 2H), 4.63-4.57 (m, 1H), 4.21-4.09 (m, 2H), 3.59-3.44 (m, 4H), 3.42-3.23 (m, 2H), 3.19-3.02 (m, 3H), 2.00-1.96 (m, 2H), 1.51-1.45 (m, 2H), 1.08-1.07 (d, J=2.6 Hz, 3H). MS: (ES, m/z): 379 [M+H]⁺.

TABLE 23

The following compounds were prepared according to the method of Example 43, with these modifications: In Step 2, the Prep-HPLC column can be XBridge RP C18 OBD, 5 μm, 19 × 150 mm or the column Sunfire C18, 5 μm, 19 × 150 mm, using formic as the additive to the water Mobile Phase A.

| Structure | Found M + H | ¹H-NMR (400 MHz, DMSO-d₆) δ(ppm) |
|---|---|---|
| (structure) | 387 [M + H]⁺ | (ES, m/z): 11.10 (br, 1H), 8.99 (br, 1H), 7.31-6.98 (m, 6.5H), 6.41-6.39 (d, J = 7.6 Hz, 0.5H), 4.84-4.81 (d, J = 13.7 Hz, 1H), 4.46-4.32 (m, 1H), 4.21-3.82 (m, 3H), 1.41-1.37 (d, J = 17.5 Hz, 4H), 1.22 (s, 2H), 1.01-0.99 (d, J = 6.4 Hz, 2H), 0.57 (s, 1H) |
| (structure) | 401 [M + H]⁺ | (ES, m/z): 11.09 (br s, 1H), 9.01 (br s, 1H), 7.32-7.31 (m, 2H), 7.20 (s, 1H), 7.11-7.07 (m, 2H), 6.98-6.95 (d, J = 9.7 Hz, 2H), 4.86-4.81 (m, 3H), 4.28-4.16 (m, 2H), 2.99-2.96 (d, J = 13.6 Hz, 1H), 2.76-2.73 (d, J = 13.6 Hz, 1H), 1.20-1.07 (m, 9H) |

TABLE 23-continued

The following compounds were prepared according to the method of Example 43, with these modifications: In Step 2, the Prep-HPLC column can be XBridge RP C18 OBD, 5 μm, 19 × 150 mm or the column Sunfire C18, 5 μm, 19 × 150 mm, using formic as the additive to the water Mobile Phase A.

| Structure | Found M + H | $^1$H-NMR (400 MHz, DMSO-$d_6$) δ(ppm) |
|---|---|---|
| 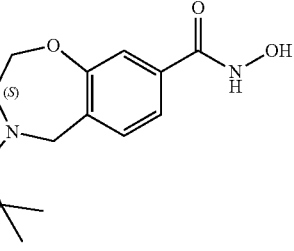 | (ES, m/z): 377 [M + H]$^+$ | 11.12 (br s, 1H), 8.98 (br s, 1H), 7.33-7.15 (m, 3H), 4.80-4.76 (m, 3H), 4.23-4.09 (m, 2H), 3.74-3.72 (m, 2H), 3.08-3.02 (m, 1H), 2.21-1.71 (m, 1H), 1.50-0.62 (m, 14H) |
| 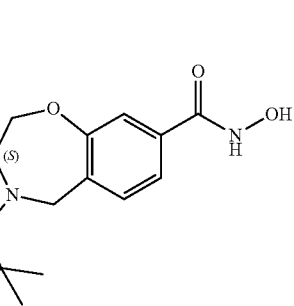 | (ES, m/z): 370 [M + H]$^+$ | 11.03 (br s, 1H), 8.98 (br s, 1H), 8.46-8.29 (m, 2H), 7.42-7.04 (m, 4.5H), 6.31-6.30 (d, J = 5.2 Hz, 0.5H), 4.85-4.81 (m, 1H), 4.51-4.33 (m, 1H), 4.21-4.18 (m, 0.5H), 4.05-3.82 (m, 2.5H), 1.49-1.22 (m, 6H), 1.08-1.01 (m, 2H), 0.52 (s, 1H) |

Example 44

Preparation of (R)—N-hydroxy-4-(tetrahydro-2H-pyran-4-carbonyl)-3-(trifluoromethyl)-2,3,4,5-tetra-hydrobenzo[f][1,4]oxazepine-8-carboxamide

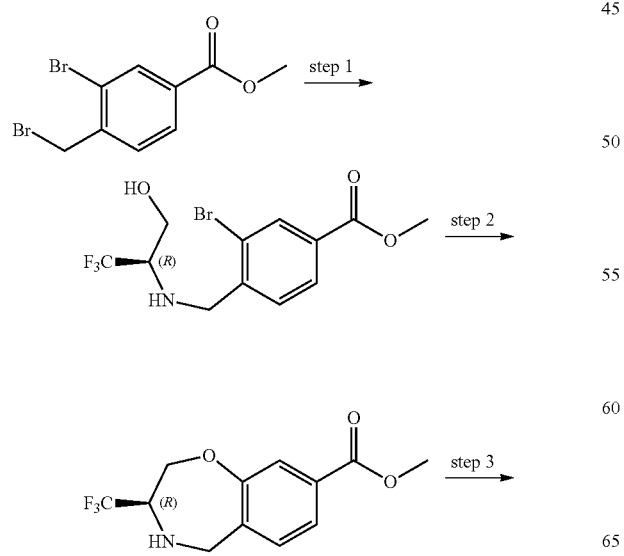

-continued

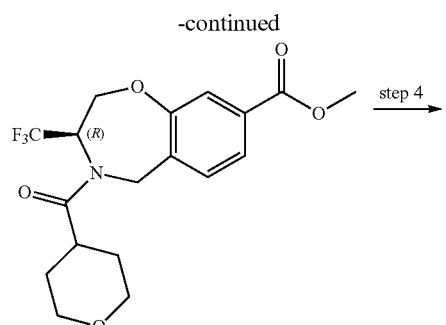

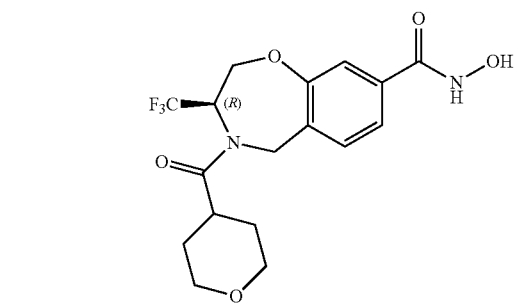

Step-1: Methyl (R)-3-bromo-4-(((1,1,1-trifluoro-3-hydroxypropan-2-yl)amino)methyl)benzoate

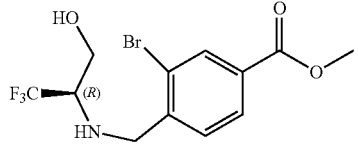

Into a 50-mL round-bottom flask, were placed a solution of methyl 3-bromo-4-(bromomethyl)benzoate (1.13 g, 3.67 mmol, 1 equiv) in MeCN/H$_2$O (1:1, 10 mL) and (2R)-2-amino-3,3,3-trifluoropropan-1-ol hydrochloride (600 mg, 3.62 mmol, 1 equiv). This was followed by the addition of a solution of K$_2$CO$_3$ (1.5 g, 10.87 mmol, 3 equiv) in H$_2$O (4 mL) dropwise with stirring at room temperature. The resulting solution was stirred for 72 h at room temperature and then concentrated under vacuum. The residue was purified by prep-TLC (EtOAc/pet. ether, 1:3) to afford the title compound as an off-white solid (200 mg). MS: (ES, m/z): 356 [M+H]$^+$.

Step-2: Methyl (R)-3-(trifluoromethyl)-2,3,4,5-tetrahydrobenzo[f][1,4]oxazepine-8-carboxylate

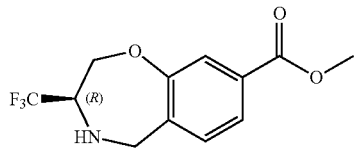

Into a 25-mL sealed tube purged and maintained with an inert atmosphere of nitrogen, were placed a solution of methyl (R)-3-bromo-4-(((1,1,1-trifluoro-3-hydroxypropan-2-yl)amino)methyl)benzoate (200 mg, 0.56 mmol, 1 equiv) in isopropanol (10 mL), K$_2$CO$_3$ (117 mg, 0.85 mmol, 1.5 equiv) and CuI (43 mg, 0.23 mmol, 0.4 equiv). The resulting solution was stirred for 19 h at 110° C. in an oil bath. The resulting mixture was concentrated under vacuum. The residue was diluted with H$_2$O (20 mL) and was extracted with CH$_2$Cl$_2$ (3×20 mL). The organic phase was washed with H$_2$O (2×20 mL) and concentrated under vacuum. The crude product was purified by silica gel chromatography (EtOAc/pet. ether, 3:10) to afford the title compound as a green oil (170 mg). MS: (ES, m/z): 276 [M+H]$^+$.

Step-3: Methyl (R)-4-(tetrahydro-2H-pyran-4-carbonyl)-3-(trifluoromethyl)-2,3,4,5-tetrahydrobenzo[f][1,4]oxazepine-8-carboxylate

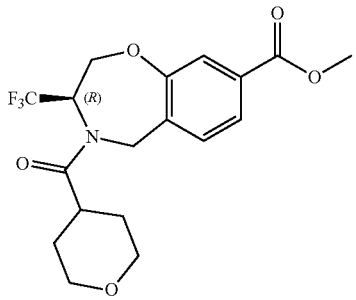

Into a 8-mL vial, were placed methyl (R)-3-(trifluoromethyl)-2,3,4,5-tetrahydrobenzo[f][1,4]oxazepine-8-carboxylate (25 mg, 0.09 mmol, 1 equiv), CH$_2$Cl$_2$ (1.5 mL), Et$_3$N (28 mg, 0.28 mmol, 3 equiv) and tetrahydro-2H-pyran-4-carbonyl chloride (16 mg, 0.11 mmol, 1.2 equiv). The resulting solution was stirred for 16 h at room temperature. The crude product was purified by Prep-TLC (EtOAc/pet. ether, 1:1) to afford the title compound as yellow oil (35 mg, 99% yield). MS: (ES, m/z): 388 [M+H]$^+$.

Step-4: (R)—N-Hydroxy-4-(tetrahydro-2H-pyran-4-carbonyl)-3-(trifluoromethyl)-2,3,4,5-tetrahydrobenzo[f][1,4]oxazepine-8-carboxamide

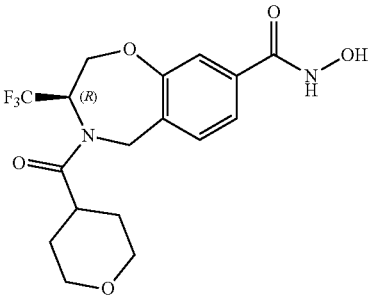

Into a 8-mL vial, were placed methyl (R)-4-(tetrahydro-2H-pyran-4-carbonyl)-3-(trifluoromethyl)-2,3,4,5-tetrahydrobenzo[f][1,4]oxazepine-8-carboxylate (35 mg, 0.09 mmol, 1 equiv) and THF/MeOH (4:1, 1.5 mL). Then NH$_2$OH (50% in water, 0.18 mL, 30 equiv) and aq. 1N NaOH (0.18 mL, 2 equiv) were added at the same time. The resulting solution was stirred for 2 h at room temperature. The crude product was purified by Prep-HPLC (Column: Xbridge C18, 5 μm, 19×150 mm; Mobile Phase A: Water/0.05% formic acid; Mobile Phase B: MeCN; Flow rate: 25 mL/min; Gradient: 5% B to 45% B in 7 min; Detector, UV 254, 220 nm) to afford the title compound as an off-white solid (15.4 mg, 44% yield). $^1$H-NMR (400 MHz, DMSO-d$_6$) δ(ppm): 11.15 (br s, 1H), 9.06 (br s, 1H), 7.49-7.23 (m, 3H), 5.70-5.50 (m, 1H), 5.11-5.04 (m, 1.7H), 4.88-4.76 (m, 1H), 4.60-4.53 (m, 1.3H), 3.90-3.61 (m, 2H), 3.48-3.39 (m, 1.3H), 3.16-3.05 (m, 0.7H), 2.99-2.90 (m, 1H), 1.75-1.48 (m, 2H), 1.37-1.20 (m, 2H). MS: (ES, m/z): 389 [M+H]$^+$.

Example 45

Preparation of (R)—N-hydroxy-4-(oxetane-3-carbonyl)-3-(trifluoromethyl)-2,3,4,5-tetrahydrobenzo[f][1,4]oxazepine-8-carboxamide

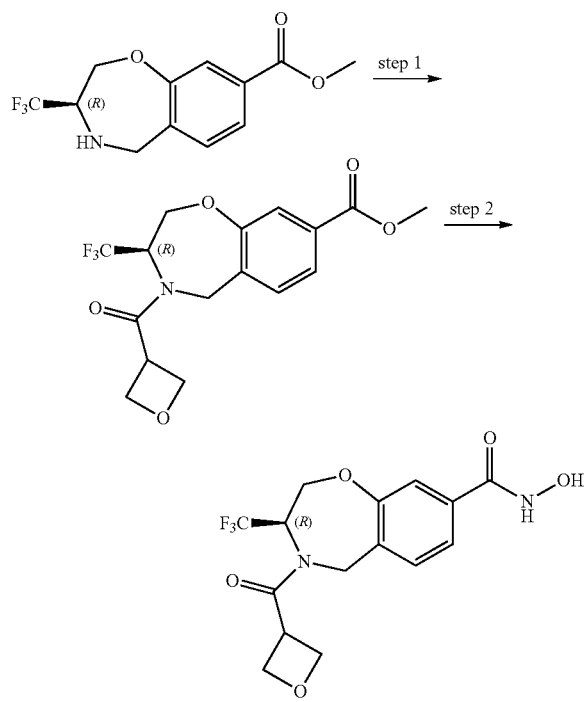

Step-1: Methyl (R)-4-(oxetane-3-carbonyl)-3-(trifluoromethyl)-2,3,4,5-tetrahydrobenzo[f][1,4]oxazepine-8-carboxylate Into a 10-mL vial (vial A) purged and maintained with an inert atmosphere of nitrogen, were placed a solution of cyclobutanecarboxylic acid (25 mg, 0.25 mmol, 1 equiv) in CH₂Cl₂ (5 mL), then oxalyl chloride (13.1 mg, 0.5 equiv) was added at 0° C. and stirred at room temperature for 2 h. In vial B was added methyl (R)-3-(trifluoromethyl)-2,3,4,5-tetrahydrobenzo[f][1,4]oxazepine-8-carboxylate (30 mg, 0.11 mmol, 1 equiv) and Et₃N (50 mg, 0.49 mmol, 6 equiv), then the solution of vial A was transferred to vial B dropwise. The resulting solution was stirred for 2 h at room temperature, then concentrated under vacuum. The residue was purified by silica gel chromatography (EtOAc/pet. ether, 1:1) to afford the title compound as a yellow oil (25 mg, 28% yield). MS: (ES, m/z): 360 [M+H]⁺.

Step-2: (R)—N-Hydroxy-4-(oxetane-3-carbonyl)-3-(trifluoromethyl)-2,3,4,5-tetrahydrobenzo[f][1,4]oxazepine-8-carboxamide

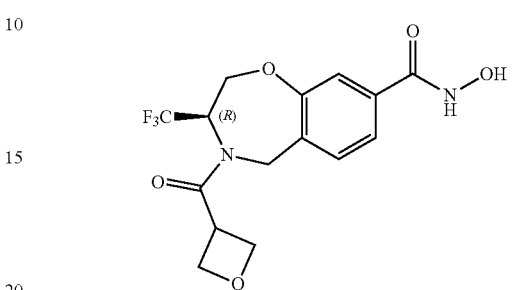

Into a 10-mL vial, were placed methyl (R)-4-(oxetane-3-carbonyl)-3-(trifluoromethyl)-2,3,4,5-tetrahydrobenzo[f][1,4]oxazepine-8-carboxylate (35 mg, 0.09 mmol, 1 equiv) and THF/MeOH (4:1, 3 mL). Then NH₂OH (50% in water, 0.14 mL, 30 equiv) and aq. 1N NaOH (0.14 mL, 2 equiv) were added at the same time. The resulting solution was stirred for 2 h at room temperature. The crude product was purified by Prep-HPLC (Column: Sunfire Prep C18 OBD, 5 µm, 19×150 mm; Mobile Phase A: Water/0.05% formic acid; Mobile Phase B: MeCN; Flow rate: 20 mL/min; Gradient: 5% B to 68% B in 10 min; Detector, UV 254, 220 nm) to afford the title compound as a brown oil (12.3 mg, 49% yield). ¹H-NMR (400 MHz, DMSO-d₆) δ(ppm): 11.21 (br s, 1H), 9.06 (br s, 1H), 7.37-7.36 (m, 1H), 7.35-7.34 (m, 1H), 7.18-7.16 (m, 1H), 6.08 (s, 1H), 5.68 (s, 1H), 4.71-4.68 (m, 1H), 4.60-4.56 (m, 1H), 4.46-4.44 (m, 1H), 4.02-3.96 (m, 1H), 3.78-3.74 (m, 1H), 3.46 (s, 3H). MS: (ES, m/z): 361 [M+H]⁺.

Example 46

Preparation of (S)-3-ethyl-N-hydroxy-4-(tetrahydro-2H-pyran-4-carbonyl)-2,3,4,5-tetrahydrobenzo[f][1,4]oxazepine-8-carboxamide

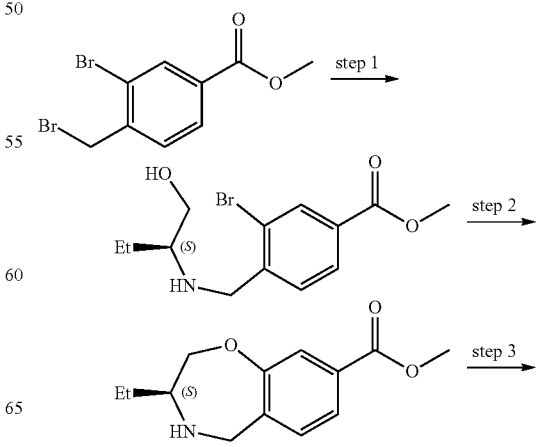

-continued

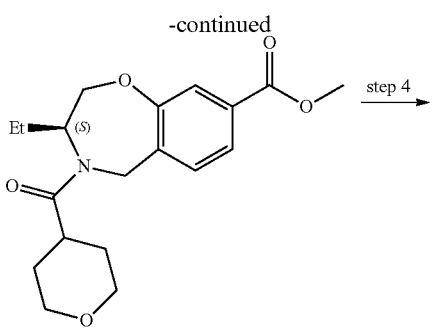

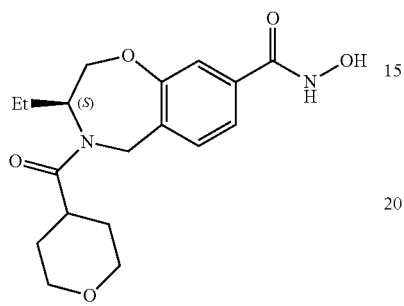

Step-1: Methyl (S)-3-bromo-4-(((1-hydroxybutan-2-yl)amino)methyl)benzoate

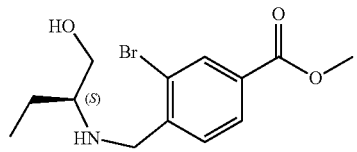

Into a 500-mL round-bottom flask, was placed a solution of (2S)-2-aminobutan-1-ol (7 g, 78.53 mmol, 1.8 equiv) in MeCN (150 mL), K$_2$CO$_3$ (9 g, 65.22 mmol, 1.5 equiv) and a solution of methyl 3-bromo-4-(bromomethyl)benzoate (13.5 g, 43.84 mmol, 1 equiv) in MeCN (100 mL). The resulting mixture was stirred for 14 h at room temperature and then concentrated under vacuum. The residue was diluted with H$_2$O (200 mL) and extracted with EtOAc (2×200 mL). The combined organic layers were washed with H$_2$O (2×200 mL) and concentrated under vacuum. The residue was purified by silica gel chromatography (EtOAc/pet. ether, 1:9) to afford the title compound as an off-white solid (6.9 g, 50% yield). MS: (ES, m/z): 316 [M+H]$^+$.

Step-2: Methyl (S)-3-ethyl-2,3,4,5-tetrahydrobenzo[f][1,4]oxazepine-8-carboxylate

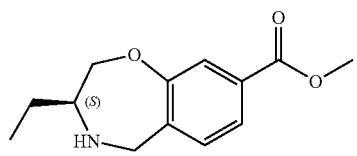

Into a 150-mL pressure tank reactor purged and maintained with an inert atmosphere of nitrogen, was placed a solution of methyl (S)-3-bromo-4-(((1-hydroxybutan-2-yl) amino)methyl)benzoate (6.9 g, 21.82 mmol, 1 equiv) in isopropanol (130 mL), K$_2$CO$_3$ (5.14 g, 37.25 mmol, 1.7 equiv) and CuI (2.08 g, 10.95 mmol, 0.5 equiv). The resulting mixture was stirred for 20 h at 110° C. in an oil bath, then was concentrated under vacuum. The residue was diluted with H$_2$O (1 mL) and extracted with CH$_2$Cl$_2$ (3×100 mL). The combined organic layers were washed with H$_2$O (3×100 mL) and concentrated under vacuum. The residue was purified by silica gel chromatography (EtOAc/pet. ether, 1:3) to afford the title compound as a green oil (2.1 g), which was used without further purification. MS: (ES, m/z): 236 [M+H]$^+$.

Step-3: Methyl (S)-3-ethyl-4-(tetrahydro-2H-pyran-4-carbonyl)-2,3,4,5-tetrahydrobenzo[f][1,4]oxazepine-8-carboxylate

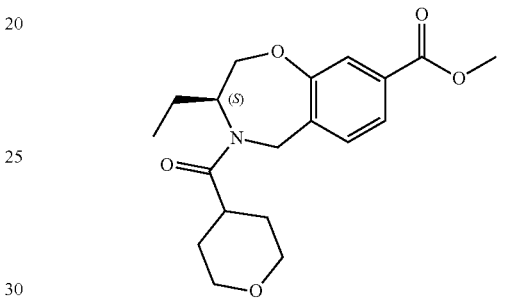

Into a 8-mL vial, was placed a solution of oxane-4-carboxylic acid (56 mg, 0.43 mmol, 1 equiv) in DMF (2.5 mL), HATU (120 mg, 0.32 mmol, 1.2 equiv), methyl (S)-3-ethyl-2,3,4,5-tetrahydrobenzo[f][1,4]oxazepine-8-carboxylate (100 mg, 0.43 mmol, 1 equiv), and DIEA (164 mg, 1.27 mmol, 3 equiv). The resulting solution was stirred for 20 h at room temperature. The resulting solution was diluted with H$_2$O (10 mL) and extracted with EtOAc (3×10 mL). The combined organic layers were washed with H$_2$O (2×10 mL) and concentrated under vacuum. The residue was purified by silica gel chromatography (EtOAc/pet. ether, 1:2) to afford the title compound as a yellow oil (100 mg, 68% yield). MS: (ES, m/z): 348 [M+H]$^+$.

Step-4: (S)-3-Ethyl-N-hydroxy-4-(tetrahydro-2H-pyran-4-carbonyl)-2,3,4,5-tetrahydrobenzo[f][1,4]oxazepine-8-carboxamide

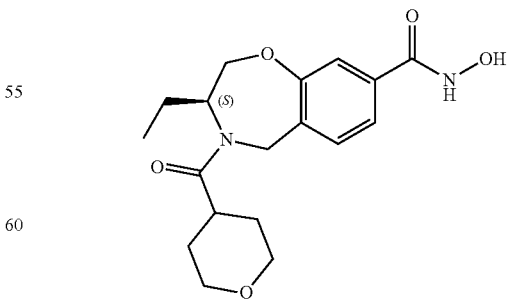

Into a 8-mL vial, were placed methyl (S)-3-ethyl-4-(tetrahydro-2H-pyran-4-carbonyl)-2,3,4,5-tetrahydrobenzo[f][1,4]oxazepine-8-carboxylate (100 mg, 0.29 mmol, 1 equiv) and THF/MeOH (4:1, 2 mL). Then NH$_2$OH (50% in water, 0.57 mL, 30 equiv) and aq. 1N NaOH (0.58 mL, 2 equiv) were added at the same time. The resulting solution was stirred for 2 h at room temperature. The crude product was purified by Prep-HPLC (Column: Xbridge Prep C18 OBD, 5 μm, 19×150 mm; Mobile Phase A: Water/0.05% formic acid; Mobile Phase B: MeCN; Flow rate: 30 mL/min; Gradient: 15% B to 60% B in 12 min; Detector, UV 254, 220 nm) to afford the title compound as an off-white solid (25.5 mg, 25% yield). $^1$H-NMR (400 MHz, DMSO-d$_6$) δ(ppm): 11.19 (s, 1H), 7.43-7.17 (m, 3H), 4.91-4.87 (m, 0.3H), 4.78-4.75 (m, 1.7H), 4.39-4.18 (m, 3H), 3.85 (m, 1H), 3.82 (m, 1H), 3.41-3.36 (m, 1H), 3.14-3.13 (m, 1H), 2.93-2.89 (m, 0.3H), 2.87-2.75 (m, 0.7H), 1.67-1.82 (m, 0.2H), 1.63-1.62 (m, 1.8H), 1.60-1.25 (m, 3H), 0.96 (m, 1H), 0.85-0.83 (m, 2H), 0.77-0.71 (m, 1H). MS: (ES, m/z): 349 [M+H]$^+$.

Example 47

Preparation of (S)-3-ethyl-N-hydroxy-4-(tetrahydro-2H-pyran-4-carbonyl)-2,3,4,5-tetrahydrobenzo[f][1,4]oxazepine-8-carboxamide

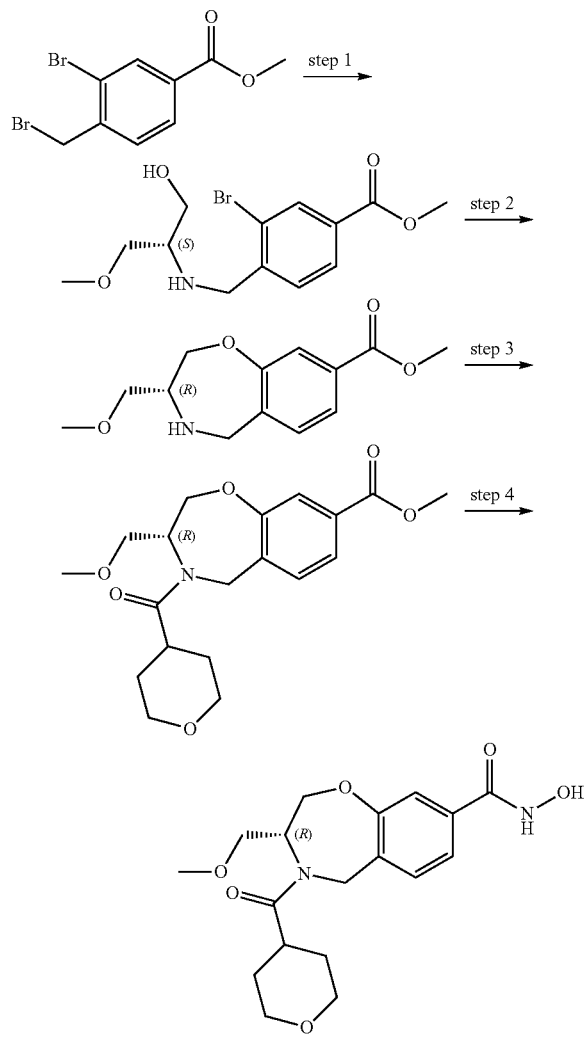

Step-1: Methyl (S)-3-bromo-4-(((1-hydroxy-3-methoxypropan-2-yl)amino)methyl)benzoate

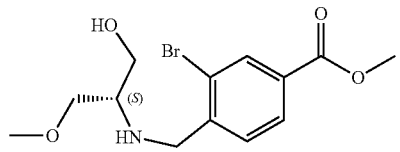

Into a 500-mL round-bottom flask, was placed (2S)-2-amino-3-methoxypropan-1-ol hydrochloride (8.5 g, 27.60 mmol, 1 equiv), a solution of K$_2$CO$_3$ (20.0 g, 144.71 mmol, 5 equiv) in MeCN (150 mL). This was followed by the addition of a solution of methyl 3-bromo-4-(bromomethyl)benzoate (15.0 g, 105.93 mmol, 2 equiv) in MeCN (100 mL) dropwise with stirring at 0° C. The resulting solution was stirred overnight at room temperature, then concentrated under vacuum. The residue was purified by silica gel chromatography (EtOAc/pet. ether, 1:1) to afford the title compound as a yellow solid (6.5 g, 71% yield). MS: (ES, m/z): 332, 334 [M+H]$^+$.

Step-2: Methyl (R)-3-(methoxymethyl)-2,3,4,5-tetrahydrobenzo[f][1,4]oxazepine-8-carboxylate

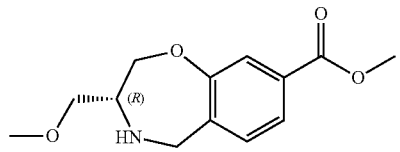

Into a 120-mL sealed tube, was placed a solution of methyl (S)-3-bromo-4-(((1-hydroxy-3-methoxypropan-2-yl)amino)methyl)benzoate (5.0 g, 15.05 mmol, 1 equiv) in isopropanol (120 mL), K$_2$CO$_3$ (3.13 g, 22.48 mmol, 1.5 equiv), and CuI (0.86 g, 4.52 mmol, 0.3 equiv). The resulting mixture was stirred overnight at 110° C. in an oil bath, then concentrated under vacuum. The residue was purified by silica gel chromatography (EtOAc/pet. ether, 1:1) to afford the title compound as a yellow-green oil (1 g, 26% yield). MS: (ES, m/z): 252 [M+H]$^+$.

Step-3: Methyl (R)-3-(methoxymethyl)-4-(tetrahydro-2H-pyran-4-carbonyl)-2,3,4,5-tetrahydrobenzo[f][1,4]oxazepine-8-carboxylate

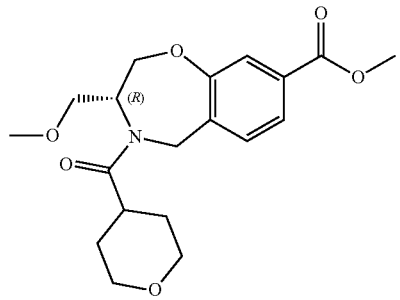

Into a 10-mL round-bottom flask, was placed a solution of oxane-4-carboxylic acid (120 mg, 0.92 mmol, 1.5 equiv) in DMF (3 mL), DMTMM (332 mg, 1.20 mmol, 2 equiv) and Methyl (R)-3-(methoxymethyl)-2,3,4,5-tetrahydrobenzo[f][1,4]oxazepine-8-carboxylate (150 mg, 0.60 mmol, 1 equiv).

The resulting solution was stirred overnight at room temperature. The crude product was purified by Flash-Prep-HPLC (Mobile Phase A: Water/0.05% TFA, Mobile Phase B: MeCN; Flow rate: 45 mL/min; Gradient: 5% B to 50% B in 25 min; Detector: 220, 254 nm) to afford the title compound as colorless oil (60 mg, 28% yield). MS: (ES, m/z): 364 [M+H]⁺.

Step-4: (R)—N-Hydroxy-3-(methoxymethyl)-4-(tetrahydro-2H-pyran-4-carbonyl)-2,3,4,5-tetrahydrobenzo[f][1,4]oxazepine-8-carboxamide

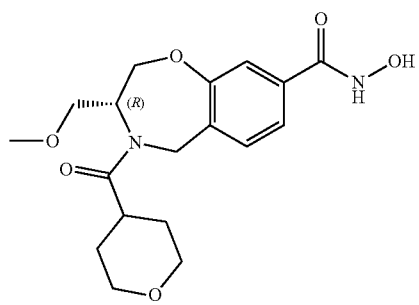

Into a 8-mL vial, were placed methyl (R)-3-(methoxymethyl)-4-(tetrahydro-2H-pyran-4-carbonyl)-2,3,4,5-tetrahydrobenzo[f][1,4]oxazepine-8-carboxylate (60 mg, 0.17 mmol, 1 equiv) and THF/MeOH (3:1, 4 mL). Then NH₂OH (50% in water, 1.0 mL, 100 equiv) and aq. 1N NaOH (1.0 mL, 6 equiv) were added at the same time. The resulting solution was stirred for 1 h at room temperature. The crude product was purified by Prep-HPLC (Column: Xbridge Prep C18 OBD, 5 μm, 19×150 mm; Mobile Phase A: Water/0.05% formic acid; Mobile Phase B: MeCN; Flow rate: 20 mL/min; Gradient: 12% B to 34% B in 9 min; Detector, UV 254, 220 nm) to afford the title compound as a yellow solid (22.7 mg, 34% yield). ¹H-NMR (400 MHz, DMSO-d₆) δ(ppm): 11.15 (br s, 1H), 7.40-7.20 (m, 3H), 4.98-4.83 (m, 2H), 4.51-4.27 (m, 3H), 3.85-3.29 (m, 7H), 3.28-3.12 (m, 2H), 3.01-2.80 (m, 1H), 1.72-0.80 (m, 4H). MS: (ES, m/z): 365 [M+H]⁺.

TABLE 24

The following compound was prepared according to the method of Example 47, using (2R)-2-amino-3-methoxypropan-1-ol hydrochloride in Step 1.

| Structure | Found M + H | ¹H-NMR (400 MHz, DMSO-d₆) δ(ppm) |
|---|---|---|
| (structure shown) | (ES, m/z): 365 [M + H]⁺ | 11.15 (br s, 1H), 7.94 (br, 1H), 7.42-7.18 (m, 3H), 4.99-4.79 (m, 2H), 4.61-4.20 (m, 3H), 3.86-3.68 (m, 2H), 3.67-3.16 (m, 7H), 2.93-2.78 (m, 1H), 1.77-0.78 (m, 4H) |

Example 48

Preparation of (S)-3-benzyl-N-hydroxy-4-(tetrahydro-2H-pyran-4-carbonyl)-2,3,4,5-tetrahydrobenzo[f][1,4]oxazepine-8-carboxamide

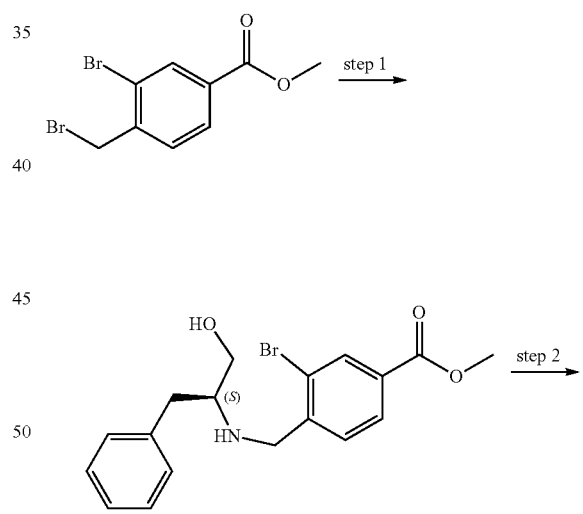

-continued

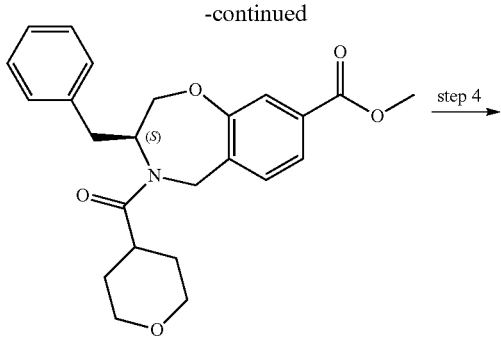 step 4

Step-2: Methyl (S)-3-benzyl-2,3,4,5-tetrahydrobenzo[f][1,4]oxazepine-8-carboxylate

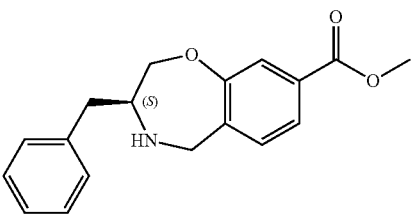

Into a 40-mL scintillation vial was placed methyl (S)-3-bromo-4-(((1-hydroxy-3-phenylpropan-2-yl)amino)methyl)benzoate hydrochloride (522 mg, 1.39 mmol, 1 equiv) in isopropanol (5 mL). $K_2CO_3$ (381 mg, 2.76 mmol, 2 equiv) was added followed by CuI (52.6 mg, 0.276 mmol, 0.2 equiv). The resulting solution was heated to reflux for 18 h. The resulting mixture was filtered through a celite pad and washed with isopropanol (10 mL). The filtrate was reduced in volume to ~5 mL and 10N HCl (1.1 equiv) was added dropwise, with stirring, to the filtrate. The resulting slurry was cooled in an ice bath for 30 min before being filtered to afford the title compound as the HCl salt as a yellow solid (252 mg, 49.3% yield). $^1$H-NMR (400 MHz, DMSO-$d_6$) δ(ppm): 7.68-7.77 (m, 1H), 7.58-7.66 (m, 1H), 7.54 (d, J=1.8 Hz, 1H), 7.23-7.45 (m, 4H), 4.36-4.58 (m, 2H), 4.26 (br d, J=11.4 Hz, 1H), 3.74-4.05 (m, 4H), 3.42 (s, 1H), 3.07-3.27 (m, 2H), 2.90 (br dd, J=13.6, 9.2 Hz, 1H), 1.03 (d, J=6.2 Hz, 1H). MS: (ES, m/z): 298 [M+H]$^+$.

Step-3: Methyl (S)-3-benzyl-4-(tetrahydro-2H-pyran-4-carbonyl)-2,3,4,5-tetrahydrobenzo[f][1,4]oxazepine-8-carboxylate

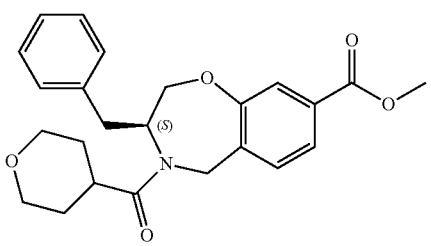

Into a 4-mL vial was placed methyl (S)-3-benzyl-2,3,4,5-tetrahydrobenzo[f][1,4]oxazepine-8-carboxylate hydrochloride (50 mg, 0.150 mmol, 1 equiv), Et$_3$N (0.063 ml, 0.449 mmol, 3 equiv), tetrahydro-2H-pyran-4-carboxylic acid (23.4 mg, 0.180 mmol, 1.2 equiv) and dichloroethane (3 mL). Next, DMC (30.4 mg, 0.180 mmol, 1.2 equiv) was added and the resulting solution was stirred at room temperature for 4 hours. The reaction was washed with aq. 1N NaOH (1 mL). The organic layer was separated, dried over Na$_2$SO$_4$, filtered and concentrated to dryness to afford the title compound (61.4 mg, 99% yield). MS: (ES, m/z): 410 [M+H]$^+$.

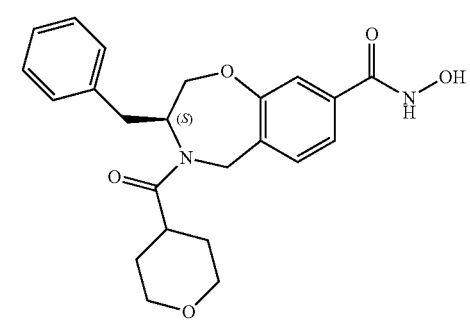

Step-1: Methyl (S)-3-bromo-4-(((1-hydroxy-3-phenylpropan-2-yl)amino)methyl)benzoate

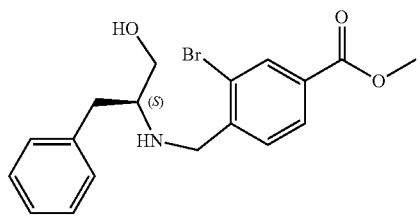

Into a 40-mL scintillation vial was placed (S)-2-amino-3-phenylpropan-1-ol (271 mg, 1.79 mmol, 1.30 equiv), K$_2$CO$_3$ (572 mg, 4.14 mmol, 3.00 equiv) and MeCN (15 ml). The resulting slurry was cooled to 0° C. in an ice-water bath. Next, a solution of methyl 3-bromo-4-(bromomethyl)benzoate (425 mg, 1.380 mmol, 1.00 equiv) in MeCN (3 mL) was added dropwise over 10 min while maintaining the internal temperature at 0° C. The ice bath was removed and the resulting slurry was allowed to slowly warm to room temperature. Stirring continued at room temperature for 16 h. The reaction was concentrated under reduced pressure to remove most of the MeCN. The concentrated mixture was partitioned between EtOAc (10 mL) and H$_2$O (5 ml). The organic phase was washed with brine (5 mL), dried over Na$_2$SO$_4$, filtered and concentrated to afford the title compound as a yellow oil (628 mg), which was used without further purification. MS: (ES, m/z): 379 [M+H]$^+$.

Step-4: (S)-3-Benzyl-N-hydroxy-4-(tetrahydro-2H-pyran-4-carbonyl)-2,3,4,5-tetrahydrobenzo[f][1,4]oxazepine-8-carboxamide

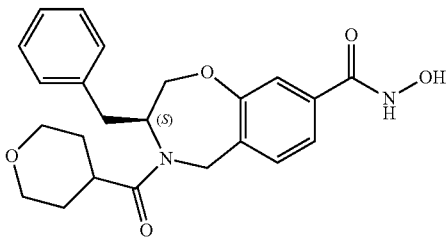

Into a 4-ml vial was placed methyl (S)-3-benzyl-4-(tetrahydro-2H-pyran-4-carbonyl)-2,3,4,5-tetrahydrobenzo[f][1,4]oxazepine-8-carboxylate (61.4 mg, 0.150 mmol, 1 equiv), NH$_2$OH (50% in water, 0.198 ml, 3 mmol, 20 equiv), and aq. 1N NaOH (0.3 ml, 0.3 mmol, 2 equiv) in a solution of THF/MeOH (4:1, 1.5 mL). The resulting solution was stirred at room temperature for 1 h. The reaction was concentrated and the residue was purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 0% B to 35% B in 8 min; Detector, UV 254, 220 nm) to afford the title compound (16 mg, 26% yield). MS: (ES, m/z): 411 [M+H]$^+$.

Example 49

Preparation of N-hydroxy-4-(tetrahydro-2H-pyran-4-carbonyl)-3-(tetrahydro-2H-pyran-4-yl)-2,3,4,5-tetrahydrobenzo[f][1,4]oxazepine-8-carboxamide

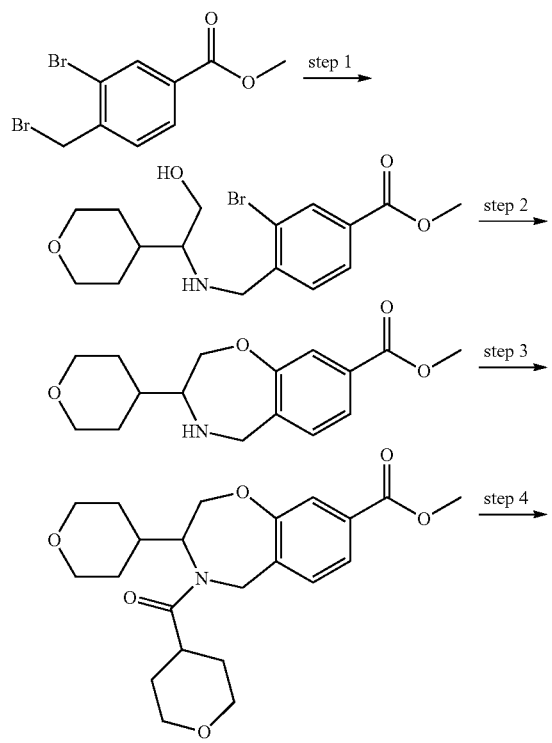

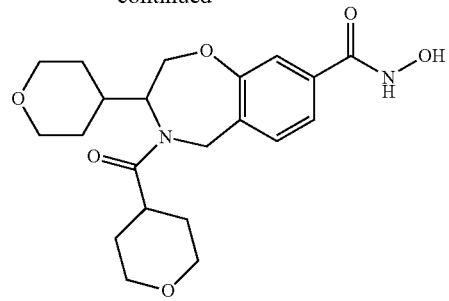

Step-1: Methyl 3-bromo-4-(((2-hydroxy-1-(tetrahydro-2H-pyran-4-yl)ethyl)amino)methyl)benzoate

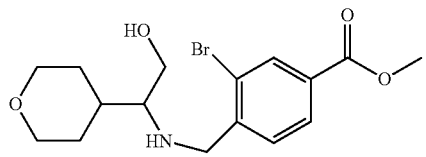 [SMILES: COC(=O)c1ccc(CNC(CO)C2CCOCC2)c(Br)c1]

Into a 40-mL scintillation vial was placed 2-amino-2-(tetrahydro-2H-pyran-4-yl)ethanol (102 mg, 0.705 mmol, 1.3 equiv), K$_2$CO$_3$ (225 mg, 1.63 mmol, 3 equiv) and MeCN (10 mL). The resulting slurry was cooled to 0° C. in an ice-water bath. Next, a solution of methyl 3-bromo-4-(bromomethyl)benzoate (167 mg, 0.542 mmol, 1 equiv) in MeCN (3 mL) was added dropwise over 10 minutes while maintaining the internal temperature at 0° C. The ice bath was removed and the resulting slurry was allowed to slowly warm to room temperature. Stirring continued at room temperature for 16 hours. The reaction was concentrated under reduced pressure to remove most of the MeCN. The concentrated mixture was partitioned between EtOAc (10 mL) and H$_2$O (5 mL). The organic phase was washed with brine (5 mL), dried over Na$_2$SO$_4$, filtered, and concentrated to afford the title compound as a pale yellow oil (265 mg), which was used without further purification. MS: (ES, m/z): 373 [M+H]$^+$.

Step-2: Methyl 3-(tetrahydro-2H-pyran-4-yl)-2,3,4,5-tetrahydrobenzo[f][1,4]oxazepine-8-carboxylate

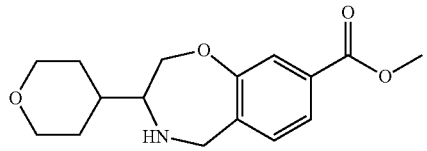 [SMILES: COC(=O)c1ccc2c(c1)OCC(C1CCOCC1)NC2]

Into a 40-mL scintillation vial was placed methyl 3-bromo-4-(((2-hydroxy-1-(tetrahydro-2H-pyran-4-yl)ethyl)amino)methyl)benzoate (202 mg, 0.542 mmol, 1 equiv) in isopropanol (5 mL). K$_2$CO$_3$ (150 mg, 1.08 mmol, 2 equiv) was added followed by CuI (20.6 mg, 0.108 mmol, 0.2 equiv). The resulting solution was heated to reflux for 18 h. The resulting mixture was filtered through a celite pad and washed with isopropanol (10 mL). The filtrate was reduced in volume to ~5 mL and 10N HCl (1.1 equiv) was added dropwise, with stirring, to the filtrate. The resulting slurry was cooled in an ice bath for 30 minutes before being filtered to afford the title compound as the HCl salt as a yellow solid (63.3 mg, 36% yield). MS: (ES, m/z): 292 [M+H]$^+$.

Step-3: Methyl 4-(tetrahydro-2H-pyran-4-carbonyl)-3-(tetrahydro-2H-pyran-4-yl)-2,3,4,5-tetrahydrobenzo[f][1,4]oxazepine-8-carboxylate

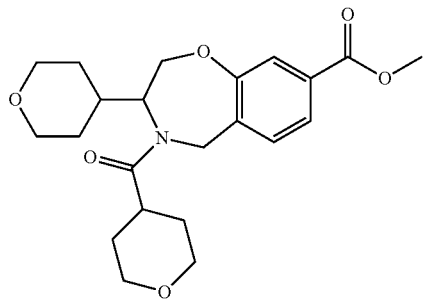 [SMILES: COC(=O)c1ccc2c(c1)OCC(C1CCOCC1)N(C(=O)C1CCOCC1)C2]

Into a 4-mL vial was placed methyl 3-(tetrahydro-2H-pyran-4-yl)-2,3,4,5-tetrahydrobenzo[f][1,4]oxazepine-8-carboxylate hydrochloride (20 mg, 0.061 mmol, 1 equiv), Et$_3$N (0.024 ml, 0.183 mmol, 3 equiv), tetrahydro-2H-pyran-4-carboxylic acid (9.5 mg, 0.073 mmol, 1.2 equiv) and dichloroethane (3 mL). Next, DMC (12.3 mg, 0.073 mmol, 1.2 equiv) was added and the resulting solution was stirred at room temperature for 4 hours. The reaction was washed with aq. 1N NaOH (1 mL). The organic layer was separated, dried over Na$_2$SO$_4$, filtered and concentrated to dryness to afford the title compound (24.6 mg, 99% yield). MS: (ES, m/z): 404 [M+H]$^+$.

Step-4: N-Hydroxy-4-(tetrahydro-2H-pyran-4-carbonyl)-3-(tetrahydro-2H-pyran-4-yl)-2,3,4,5-tetrahydrobenzo[f][1,4]oxazepine-8-carboxamide

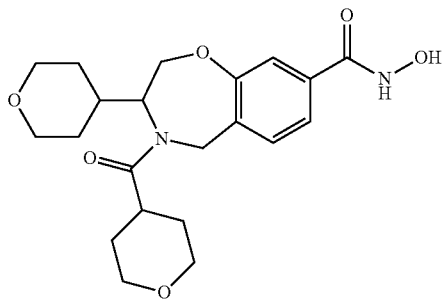 [SMILES: O=C(NO)c1ccc2c(c1)OCC(C1CCOCC1)N(C(=O)C1CCOCC1)C2]

Into a 4-ml vial was placed methyl 4-(tetrahydro-2H-pyran-4-carbonyl)-3-(tetrahydro-2H-pyran-4-yl)-2,3,4,5-tetrahydrobenzo[f][1,4]oxazepine-8-carboxylate (24.6 mg, 0.061 mmol, 1 equiv), NH$_2$OH (50% in water, 0.198 ml, 3 mmol, 49 equiv), and aq. 1N NaOH (0.3 ml, 0.3 mmol, 4.92 equiv) in a solution of THF/MeOH (4:1, 1.5 mL). The resulting solution was stirred at room temperature for 1 h. The reaction was concentrated and the residue was purified by Prep-HPLC (Column: Xbridge Prep C18 OBD, 5 μm, 19×50 mm; Mobile Phase A: Water/0.1% formic acid; Mobile Phase B: MeCN/0.1% formic acid; Flow rate: 23 mL/min; Gradient: 0% B to 35% B in 8 min; Detector, UV 254, 220 nm) to afford the title compound (16 mg, 26% yield). MS: (ES, m/z): 405 [M+H]$^+$.

Example 50

Preparation of (R)—N-hydroxy-5-isopropyl-4-(tetrahydro-2H-pyran-4-carbonyl)-2,3,4,5-tetrahydrobenzo[f][1,4]oxazepine-8-carboxamide

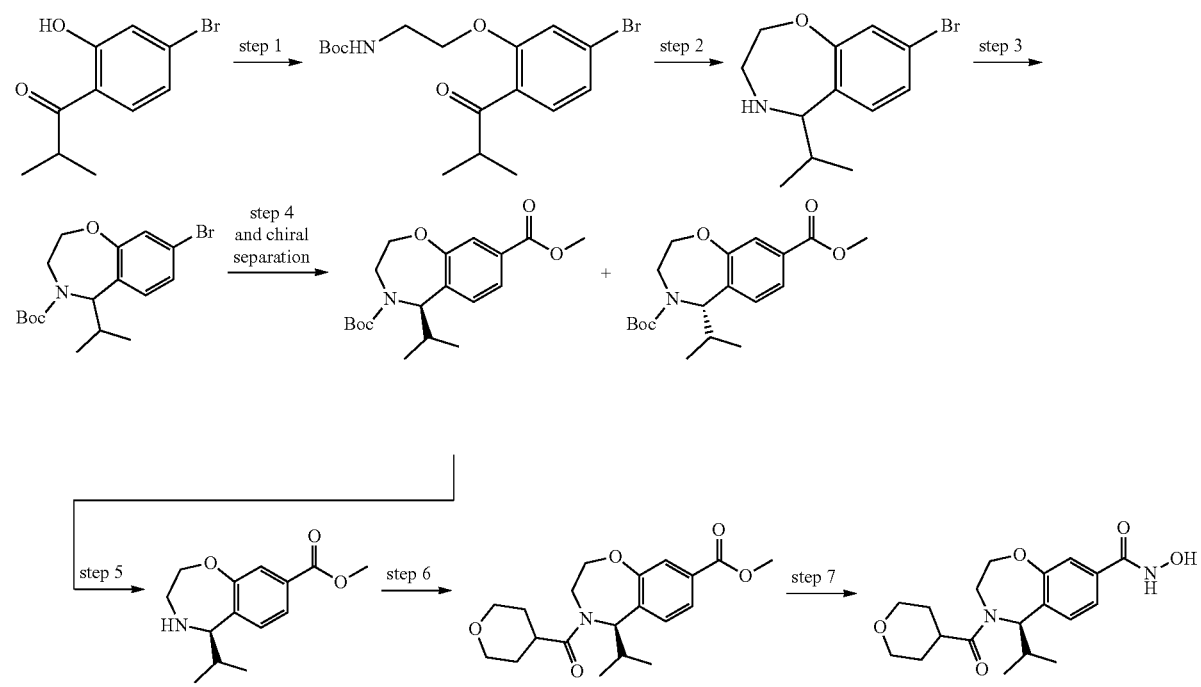

Step-1: tert-Butyl (2-(5-bromo-2-isobutyrylphenoxy)ethyl)carbamate

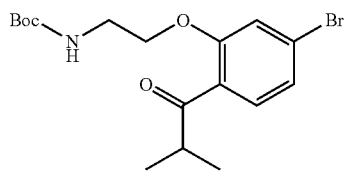 [SMILES: CC(C)C(=O)c1ccc(Br)cc1OCCNC(=O)OC(C)(C)C]

Into a 100-mL 3-necked round-bottom flask purged and maintained with an inert atmosphere of nitrogen, was placed 1-(4-bromo-2-hydroxyphenyl)-2-methylpropan-1-one (5 g, 20.57 mmol, 1 equiv) in DMF (30 mL), K$_2$CO$_3$ (9.2 g, 66.57 mmol, 3 equiv), potassium iodide (3.7 g, 1 equiv), and tert-butyl N-(2-bromoethyl)carbamate (6 g, 26.77 mmol, 1.2 equiv). The resulting solution was stirred overnight at 50° C. in an oil bath. The reaction was then quenched by the addition of H$_2$O (100 mL) and extracted with EtOAc (3×50 mL). The combined organic layers were washed with brine (50 mL), dried over anhydrous Na$_2$SO$_4$, filtered, and concentrated under vacuum. The residue was purified by silica gel chromatography (EtOAc/pet. ether, 1:5) to afford the title compound as a yellow solid (3.5 g, 44% yield). MS: (ES, m/z): 286 [M-Boc+H]$^+$.

Step-2: 8-Bromo-5-isopropyl-2,3,4,5-tetrahydrobenzo[f][1,4]oxazepine

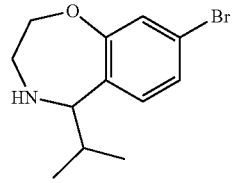

Into a 100-mL round-bottom flask, was placed tert-butyl (2-(5-bromo-2-isobutyrylphenoxy)ethyl)carbamate (3 g, 7.77 mmol, 1 equiv) in CH$_2$Cl$_2$ (10 mL) and TFA (2 mL). The resulting solution was stirred overnight at room temperature, then concentrated under vacuum. The residue was dissolved in MeOH (20 mL). The pH value of the solution was adjusted to 7 with saturated sodium acetate solution, then concentrated under vacuum. To the residue was added MeOH (50 mL) and Na(CN)BH$_3$ (2.6 g, 41.37 mmol, 3 equiv). The resulting mixture was stirred overnight at room temperature, then concentrated under vacuum. H$_2$O (50 mL) was added, and the solution was extracted with EtOAc (3×50 mL). The combined organic layers were dried over anhydrous Na$_2$SO$_4$, filtered, and concentrated under vacuum to afford the title compound as yellow oil (3.5 g, 87% yield). MS: (ES, m/z): 270 [M+H]$^+$.

Step-3: tert-Butyl 8-bromo-5-isopropyl-2,3-dihydrobenzo[f][1,4]oxazepine-4(5H)-carboxylate

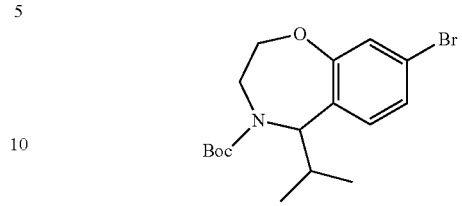

Into a 100-mL round-bottom flask, was placed 8-bromo-5-isopropyl-2,3,4,5-tetrahydrobenzo[f][1,4]oxazepine (3.5 g, 12.95 mmol, 1 equiv) in CH$_2$Cl$_2$ (30 mL), Et$_3$N (4 g, 39.53 mmol, 3 equiv) and di-tert-butyl dicarbonate (5.5 g, 25.20 mmol, 2 equiv). The resulting solution was stirred overnight at room temperature. The reaction was then quenched by the addition of H$_2$O (50 mL) and extracted with EtOAc (3×50 mL). The combined organic layers were washed with brine (50 mL), dried over anhydrous Na$_2$SO$_4$, filtered, and concentrated under vacuum. The residue was purified by silica gel chromatography (EtOAc/pet. ether, 1:5) to afford the title compound as a white-solid (2 g, 42% yield). MS: (ES, m/z): 370 [M+H]$^+$.

Step-4: 4-(tert-Butyl) 8-Methyl (R)-5-isopropyl-2,3-dihydrobenzo[f][1,4]oxazepine-4,8(5H)-dicarboxylate and 4-(tert-butyl) 8-Methyl (S)-5-isopropyl-2,3-dihydrobenzo[f][1,4]oxazepine-4,8(5H)-dicarboxylate

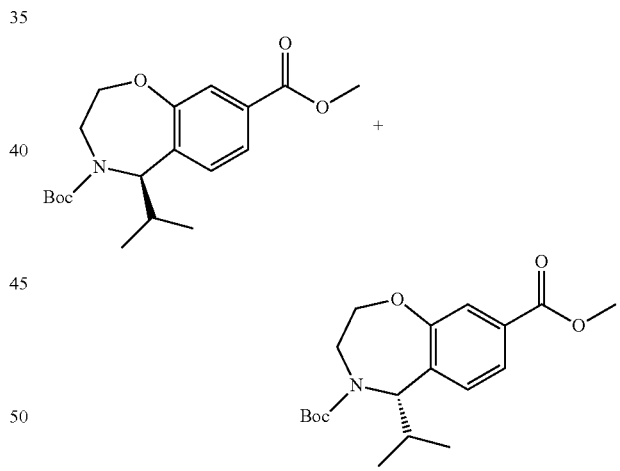

Into a 100-mL pressure tank reactor, was placed tert-butyl 8-bromo-5-(propan-2-yl)-2,3,4,5-tetrahydro-1,4-benzoxazepine-4-carboxylate (1 g, 2.70 mmol, 1 equiv) in MeOH (60 mL), Et$_3$N (820 mg, 8.10 mmol, 3 equiv) and Pd(dppf)Cl$_2$ (330 mg, 0.15 equiv). To the above reaction mixture CO (g) (60 atm) was introduced. The resulting mixture was stirred overnight at 130° C., then concentrated under vacuum. The reaction was then quenched by the addition of H$_2$O (30 mL) and extracted with EtOAc (3×30 mL). The combined organic layers were washed with brine (50 mL), dried over anhydrous Na$_2$SO$_4$, filtered, and concentrated under vacuum. The residue was purified by silica gel chromatography (EtOAc/pet. ether, 1:5) to afford the title compounds as a racemic mixture. The racemate was then purified by Prep-SFC (Column: Phenomenex Lux Cellulose-4, 5 μm, 50×250 mm; Mobile Phase A: 85% CO$_2$, 15% MeOH; Flow rate: 150 mL/min; Detector, UV 220 nm) to afford the single isomers as white solids (first eluting isomer: 200 mg, 21% yield; second eluting isomer: 300 mg, 32% yield). MS: (ES, m/z): 350 [M+H]$^+$.

Step-5: Methyl (R)-5-isopropyl-2,3,4,5-tetrahydrobenzo[f][1,4]oxazepine-8-carboxylate

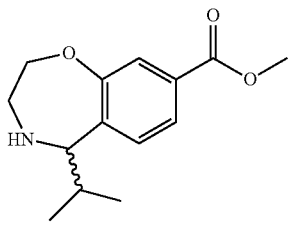 [SMILES: COC(=O)c1ccc2c(c1)OCCNC2C(C)C]

Into a 50-mL round-bottom flask, was placed the first eluting isomer from Step 4 (4-(tert-butyl) 8-Methyl (R)-5-isopropyl-2,3-dihydrobenzo[f][1,4]oxazepine-4,8(5H)-dicarboxylate) (200 mg, 0.57 mmol, 1 equiv), CH$_2$Cl$_2$ (8 mL), and TFA (2 mL). The resulting solution was stirred for 3 h at room temperature, then concentrated under vacuum to afford the title compound as the TFA salt as yellow oil (200 mg), which was used without further purification. MS: (ES, m/z): 250 [M+H]$^+$.

Step-6: Methyl (R)-5-isopropyl-4-(tetrahydro-2H-pyran-4-carbonyl)-2,3,4,5-tetrahydrobenzo[f][1,4]oxazepine-8-carboxylate

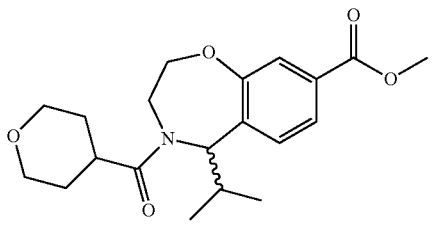 [SMILES: COC(=O)c1ccc2c(c1)OCCN(C(=O)C1CCOCC1)C2C(C)C]

Into a 10-mL round-bottom flask, was placed methyl (R)-5-isopropyl-2,3,4,5-tetrahydrobenzo[f][1,4]oxazepine-8-carboxylate.TFA (100 mg, 0.40 mmol, 1 equiv), CH$_2$Cl$_2$ (2 mL), Et$_3$N (100 mg, 0.99 mmol, 4 equiv) and oxane-4-carbonyl chloride (83 mg, 0.56 mmol, 2 equiv). The resulting solution was stirred for 2 h at room temperature. The reaction was then quenched with H$_2$O (30 mL) and extracted with CH$_2$Cl$_2$ (3×15 mL). The combined organic layers were washed with brine (20 mL), dried over anhydrous Na$_2$SO$_4$, filtered, and concentrated under vacuum to afford the title compound as a yellow oil (100 mg, 69% yield). MS: (ES, m/z): 362 [M+H]$^+$.

Step-7: (R)—N-Hydroxy-5-isopropyl-4-(tetrahydro-2H-pyran-4-carbonyl)-2,3,4,5-tetrahydrobenzo[f][1,4]oxazepine-8-carboxamide

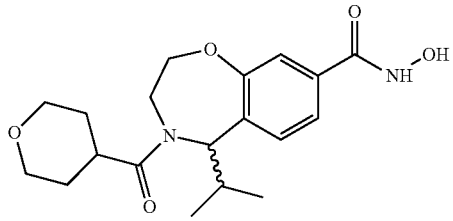 [SMILES: CC(C)C1c2ccc(C(=O)NO)cc2OCCN1C(=O)C1CCOCC1]

Into a 10-mL round-bottom flask, was placed methyl (R)-5-isopropyl-4-(tetrahydro-2H-pyran-4-carbonyl)-2,3,4,5-tetrahydrobenzo[f][1,4]oxazepine-8-carboxylate (100 mg, 0.28 mmol, 1 equiv), MeOH/THF (1:4, 2 mL), NH$_2$OH (50% in water, 1.4 g, 60 equiv), aq. 1N NaOH (0.6 mL, 2 equiv). The resulting solution was stirred for 2 h at room temperature. The solids were filtered out. The crude product was purified by Prep-HPLC (Column: Sunfire C18 OBD, 5 μm, 19×150 mm; Mobile Phase A: Water/0.05% formic acid; Mobile Phase B: MeCN; Flow rate: 25 mL/min; Gradient: 15% B to 39% B in 6 min; Detector, UV 254, 220 nm) to afford the title compound as a white solid (21.2 mg, 19% yield). $^1$H-NMR (DMSO, 300 MHz) δ (ppm): 11.20 (s, 1H), 7.51-7.22 (m, 3H), 5.14-5.11 (d, J=11.4 Hz, 1H), 4.62-4.58 (d, J=11.1 Hz, 1H), 4.43-4.39 (d, J=13.2 Hz, 1H), 4.12-3.66 (m, 3H), 3.63-3.27 (m, 3H), 3.21-2.91 (m, 1H), 2.50-2.49 (m, 1H), 1.65-1.18 (m, 4H), 0.93-0.82 (m, 3H), 0.67-0.60 (m, 3H). MS: (ES, m/z): 363 [M+H]$^+$.

TABLE 25

The following compound was prepared according to the method of Example 50, using the second eluting isomer of the Step 4 product in Step 5.

| Structure | Found M + H | $^1$H-NMR (300 MHz, DMSO-d$_6$) δ(ppm) |
|---|---|---|
| (R)/(S) isomer | (ES, m/z): 363 [M + H]$^+$ | 11.13 (s, 1H), 7.51-7.23 (m, 3H), 5.14-5.11 (d, J = 11.1 Hz, 1H), 4.62-4.58 (d, J = 10.8 Hz, 1H), 4.43-4.39 (d, J = 15.6 Hz, 1H), 4.13-3.71 (m, 3H), 3.66-3.32 (m, 3H), 3.29-2.91 (m, 1H), 2.52-2.50 (m, 1H), 1.65-1.17 (m, 4H), 0.93-0.91 (d, J = 6.3 Hz, 1H), 0.84-0.82 (d, J = 6.3 Hz, 2H), 0.67-0.60 (m, 3H) |

Example 51

Preparation of (R)—N-hydroxy-5-isopropyl-4-(oxetane-3-carbonyl)-2,3,4,5-tetrahydrobenzo[f][1,4]oxazepine-8-carboxamide

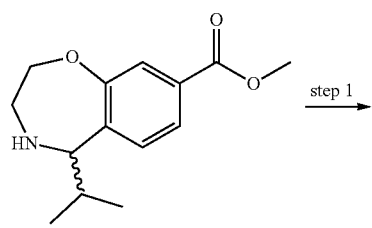

Step-1: Methyl (R)-5-isopropyl-4-(oxetane-3-carbonyl)-2,3,4,5-tetrahydrobenzo[f][1,4]oxazepine-8-carboxylate

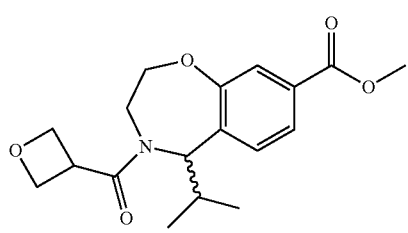 [SMILES: COC(=O)c1ccc2c(c1)OCCN(C(=O)C1COC1)C2C(C)C]

Into a 10-mL round-bottom flask, was placed the product from Example 45 Step 5 (methyl (R)-5-isopropyl-2,3,4,5-tetrahydrobenzo[f][1,4]oxazepine-8-carboxylate.TFA) (50 mg, 0.20 mmol, 1 equiv) in DMF (3 mL), DIEA (103 mg, 0.80 mmol, 4 equiv), HATU (115 mg, 0.30 mmol, 1.5 equiv) and oxetane-3-carboxylic acid (24 mg, 0.24 mmol, 1.2 equiv). The resulting solution was stirred overnight at room temperature. The reaction was then quenched with $H_2O$ (20 mL) and extracted with EtOAc (3×15 mL). The combined organic layers were washed with brine (20 mL), dried over anhydrous $Na_2SO_4$, filtered, and concentrated under vacuum to afford the title compound as yellow oil (60 mg, 90% yield). MS: (ES, m/z): 334 $[M+H]^+$.

Step-2: (R)—N-Hydroxy-5-isopropyl-4-(oxetane-3-carbonyl)-2,3,4,5-tetrahydrobenzo[f][1,4]oxazepine-8-carboxamide

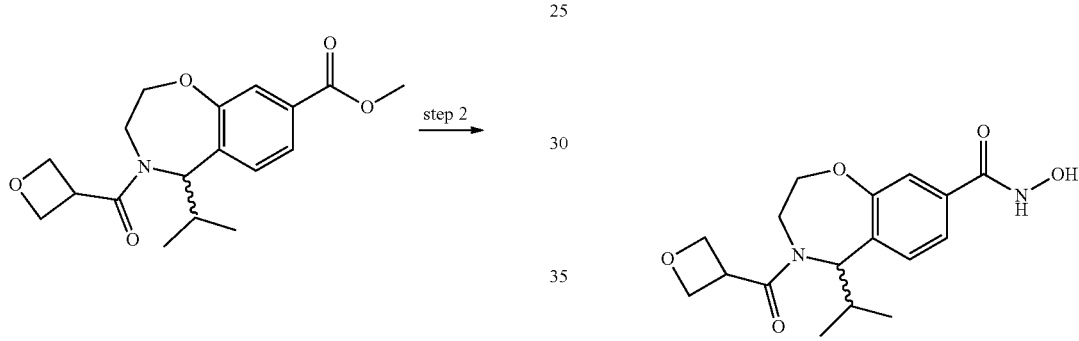

Into a 10-mL round-bottom flask, was placed methyl (R)-5-isopropyl-4-(oxetane-3-carbonyl)-2,3,4,5-tetrahydrobenzo[f][1,4]oxazepine-8-carboxylate (60 mg, 0.18 mmol, 1 equiv), MeOH/THF (1:4, 1 mL), $NH_2OH$ (50% in water, 711 mg, 60 equiv), aq. 1N NaOH (0.4 mL, 2 equiv). The resulting solution was stirred for 2 h at room temperature. The solids were filtered out. The crude product was purified by Prep-HPLC (Column: Sunfire C18 OBD, 5 μm, 19×150 mm; Mobile Phase A: Water/0.05% formic acid; Mobile Phase B: MeCN; Flow rate: 25 mL/min; Gradient: 5% B to 60% B in 8 min; Detector, UV 254, 220 nm) to afford the title compound as a white solid (6.6 mg, 11% yield). $^1$H-NMR (DMSO, 400 MHz) δ (ppm): 11.20 (br s, 1H), 9.06-9.05 (br s, 1H), 7.40-7.28 (m, 3H), 5.15-5.12 (d, J=11.2 Hz, 0.5H), 4.90-4.87 (m, 0.5H), 4.76-4.55 (m, 4H), 4.49-4.15 (m, 3H), 3.92-3.89 (d, J=10.8 Hz, 0.5H), 3.62-3.37 (m, 2.5H), 0.88-0.86 (m, 3H), 0.64-0.60 (t, J=7 Hz, 3H). MS: (ES, m/z): 335 $[M+H]^+$.

TABLE 26

The following compound was prepared according to the method of Example 51, using the second eluting isomer of the Example 45 Step 4 product.

| Structure | Found M + H | $^1$H-NMR (400 MHz, DMSO-d$_6$) δ(ppm) |
|---|---|---|
| 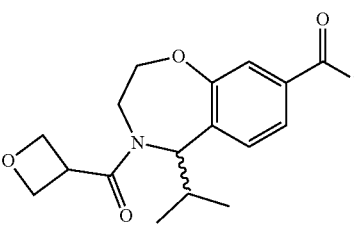 (R)/(S) isomer | (ES, m/z): 335 [M + H]$^+$ | 11.19 (br s, 1H), 9.06-9.05 (br s, 1H), 7.43-7.28 (m, 3H), 5.15-5.12 (d, J = 11.6 Hz, 0.5H), 4.90-4.87 (m, 0.5H), 4.77-4.55 (m, 4H), 4.49-4.15 (m, 3H), 3.92-3.89 (d, J = 10.8 Hz, 0.5H), 3.64-3.38 (m, 2.5H), 0.88-0.86 (m, 3H), 0.64-0.60 (t, J = 7 Hz, 3H) |

Example 52

Preparation of (R)—N-hydroxy-5-methyl-4-(1-methylcyclobutane-1-carbonyl)-2,3,4,5-tetrahydrobenzo[f][1,4]oxazepine-8-carboxamide

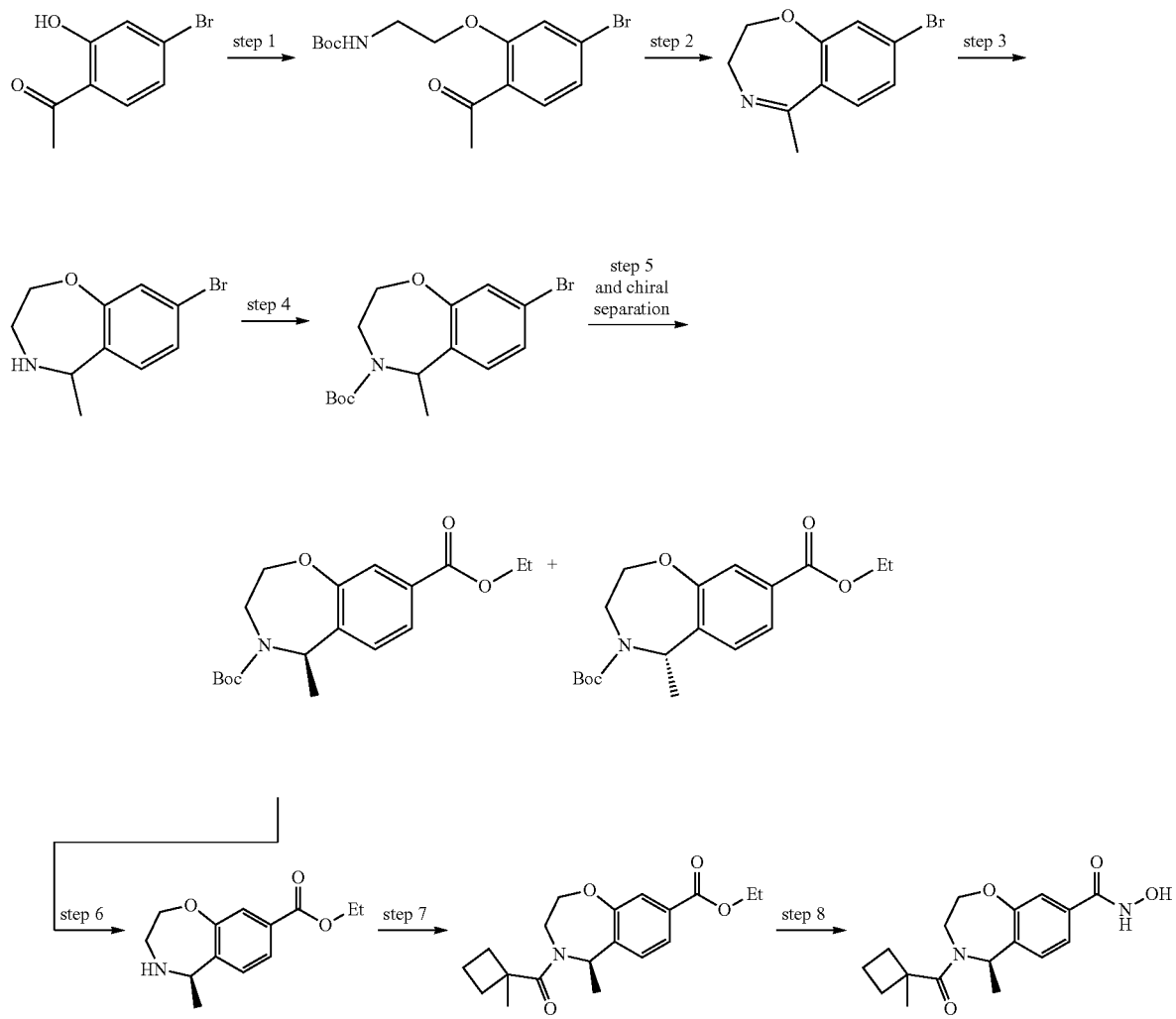

Step-1: tert-Butyl (2-(2-acetyl-5-bromophenoxy)ethyl)carbamate

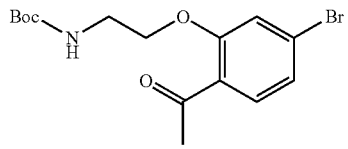 [SMILES: CC(=O)c1ccc(Br)cc1OCCNC(=O)OC(C)(C)C]

Into a 500-mL 3-necked round-bottom flask, was placed 1-(4-bromo-2-hydroxyphenyl)ethan-1-one (30 g, 139 mmol, 1 equiv) in DMF (150 mL), K$_2$CO$_3$ (29 g, 209 mmol, 1.5 equiv), potassium iodide (23.2 g, 1 equiv) and tert-butyl N-(2-bromoethyl)carbamate (47 g, 209 mmol, 1.5 equiv). The resulting mixture was stirred overnight at 50° C. The solids were filtered out. The filtrate was quenched with of H$_2$O (50 mL) and extracted with EtOAc (5×100 mL). The combined organic layers were washed with brine (3×50 mL), dried over anhydrous Na$_2$SO$_4$, filtered, and concentrated under vacuum. The residue was triturated with a solution of EtOAc/pet. ether (1:10, 100 mL) to afford the title compound as an off-white solid (42 g, 84% yield). MS: (ES, m/z): 358 [M+H]$^+$.

Step-2: 8-Bromo-5-methyl-2,3-dihydrobenzo[f][1,4]oxazepine

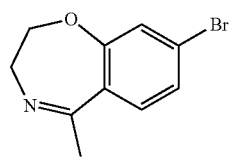

Into a 500-mL round-bottom flask, was placed tert-butyl 2-(2-acetyl-5-bromophenoxy)ethylcarbamate (23 g, 64.20 mmol, 1 equiv) in CH$_2$Cl$_2$ (100 mL) and TFA (25 mL). The resulting solution was stirred overnight at room temperature, then concentrated under vacuum to afford the title compound as a yellow solid (15.4 g), which was used without further purification. MS: (ES, m/z): 240 [M+H]$^+$.

Step-3: 8-Bromo-5-methyl-2,3,4,5-tetrahydrobenzo[f][1,4]oxazepine

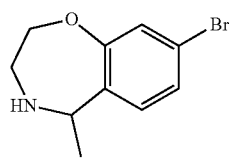

Into a 500-mL round-bottom flask, was placed a solution of 8-bromo-5-methyl-2,3-dihydrobenzo[f][1,4]oxazepine (15.4 g, 64.14 mmol, 1 equiv) in MeOH (200 mL). The pH value of the solution was adjusted to 7 with anhydrous NaOAc at 0° C. Then Na(CN)BH$_3$ (18.1 g, 288 mmol, 4.5 equiv) was added at 0° C. The resulting mixture was stirred for 4 h at room temperature and concentrated under vacuum. H$_2$O (50 mL) was added to the residue and the solids were collected by filtration to afford the title compound as a white solid (15 g). MS: (ES, m/z): 242 [M+H]$^+$.

Step-4: tert-Butyl 8-bromo-5-methyl-2,3-dihydrobenzo[f][1,4]oxazepine-4(5H)-carboxylate

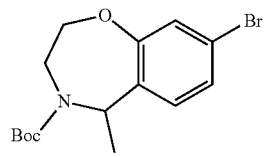 [SMILES: CC1c2ccc(Br)cc2OCCN1C(=O)OC(C)(C)C]

Into a 500-mL round-bottom flask, was placed tert-butyl 8-bromo-5-methyl-2,3-dihydrobenzo[f][1,4]oxazepine-4(5H)-carboxylate (9 g, 37.17 mmol, 1 equiv) in CH$_2$Cl$_2$ (80 mL), Et$_3$N (11.25 g, 111 mmol, 3 equiv) and di-tert-butyl dicarbonate (12.1 g, 55.44 mmol, 1.5 equiv). The resulting solution was stirred overnight at room temperature, then concentrated under vacuum. The crude product was purified by Flash-Prep-HPLC (Column: silica gel; Mobile Phase A: pet. ether, Mobile Phase B: EtOAc; Gradient: 0% B to 10% B in 50 min; Detector: 254 nm) to afford the title compound as white solid (11 g, 86% yield). MS: (ES, m/z): 342 [M+H]$^+$.

Step-5: 4-(tert-Butyl) 8-ethyl (R)-5-methyl-2,3-dihydrobenzo[f][1,4]oxazepine-4,8(5H)-dicarboxylate and 4-(tert-butyl) 8-ethyl (S)-5-methyl-2,3-dihydrobenzo[f][1,4]oxazepine-4,8(5H)-dicarboxylate

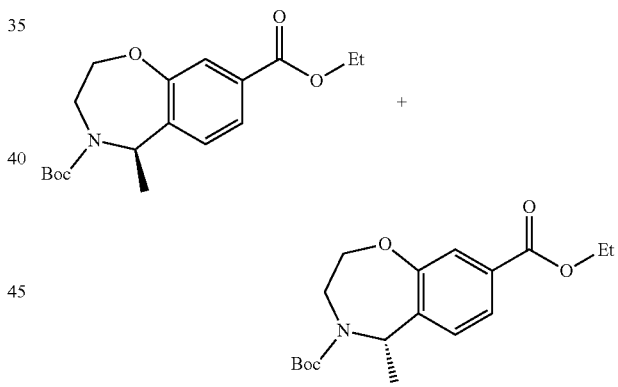

Into a 50-mL sealed tube, was placed tert-butyl 8-bromo-5-methyl-2,3-dihydrobenzo[f][1,4]oxazepine-4(5H)-carboxylate ((2.5 g, 7.33 mmol, 1 equiv) in EtOH (25 mL), Et$_3$N (2.22 g, 22 mmol, 3 equiv) and Pd(dppf)Cl$_2$ (0.534 g, 0.73 mmol, 0.1 equiv). To the above reaction mixture CO (g) (60 atm) was introduced. The resulting mixture was stirred overnight at 120° C., then concentrated under vacuum. The crude product was purified by Flash-Prep-HPLC (Column: silica gel; Mobile Phase A: pet. ether, Mobile Phase B: EtOAc; Gradient: 0% B to 10% B in 30 min; Detector: 254 nm) to afford the title compounds as a racemic mixture. The racemate was then purified by Prep-SFC (Column: (R,R) WHELK-01 Kromasil, 10 μm, 21.1×250 mm; Mobile Phase A: 75% CO$_2$, 25% isopropanol (0.2% N,N-diethylaniline); Flow rate: 45 mL/min; Detector, UV 254 nm) to afford the single isomers as a light yellow oil (first eluting isomer: 540 mg, 21.9% yield; second eluting isomer: 680 mg, 27.7% yield). MS: (ES, m/z): 336 [M+H]$^+$.

Step-6: Ethyl (R)-5-methyl-2,3,4,5-tetrahydrobenzo[f][1,4]oxazepine-8-carboxylate

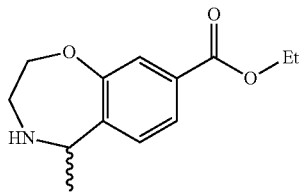 [SMILES: CCOC(=O)c1ccc2c(c1)OCCNC2C]

Into a 25-mL round-bottom flask, was placed the first eluting isomer from Step 5 (4-(tert-butyl) 8-ethyl (R)-5-methyl-2,3-dihydrobenzo[f][1,4]oxazepine-4,8(5H)-dicarboxylate) (540 mg, 1.61 mmol, 1 equiv), $CH_2Cl_2$ (5 mL), and TFA (2 mL). The resulting solution was stirred overnight at room temperature, then concentrated under vacuum. The crude product was purified by Flash-Prep-HPLC (Column: C18 silica gel; Mobile Phase A: $H_2O$/0.05% TFA, Mobile Phase B: MeCN; Gradient: 5% B to 50% B in 30 min; Detector: 254 nm) to afford the title compound as a white solid (450 mg), which was used without further purification. MS: (ES, m/z): 236 [M+H]$^+$.

Step-7: Ethyl (R)-5-methyl-4-(1-methylcyclobutane-1-carbonyl)-2,3,4,5-tetrahydrobenzo[f][1,4]oxazepine-8-carboxylate

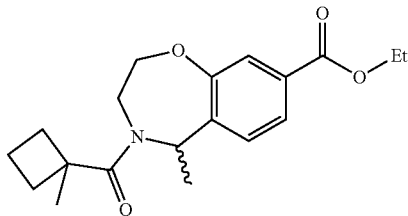 [SMILES: CCOC(=O)c1ccc2c(c1)OCCN(C(=O)C1(C)CCC1)C2C]

Into a 50-mL round-bottom flask, was placed ethyl (R)-5-methyl-2,3,4,5-tetrahydrobenzo[f][1,4]oxazepine-8-carboxylate (100 mg, 0.43 mmol, 1 equiv), DMF (2 mL), HATU (194 mg, 0.51 mmol, 1.2 equiv), DIEA (165 mg, 1.28 mmol, 3 equiv) and 1-methylcyclobutane-1-carboxylic acid (48.6 mg, 0.43 mmol, 1 equiv). The resulting solution was stirred overnight at room temperature. The reaction was then quenched with $H_2O$ (2 mL) and extracted with EtOAc (3×10 mL). The combined organic layers were washed with brine (3×5 mL), dried over anhydrous $Na_2SO_4$, filtered, and concentrated under vacuum. The crude product was purified by Flash-Prep-HPLC (Column: C18 silica gel; Mobile Phase A: pet. ether, Mobile Phase B: EtOAc; Gradient: 0% B to 30% B in 25 min; Detector: 254 nm) to afford the title compound as a yellow oil (90 mg, 64% yield). MS: (ES, m/z): 332 [M+H]$^+$.

Step-8: (R)—N-Hydroxy-5-methyl-4-(1-methylcyclobutane-1-carbonyl)-2,3,4,5-tetrahydrobenzo[f][1,4]oxazepine-8-carboxamide

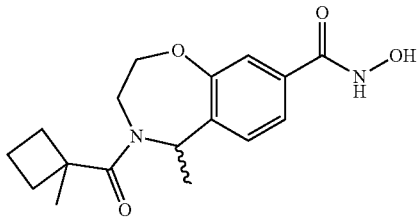 [SMILES: CC1c2ccc(C(=O)NO)cc2OCCN1C(=O)C1(C)CCC1]

Into a 25-mL round-bottom flask, was placed ethyl (R)-5-methyl-4-(1-methylcyclobutane-1-carbonyl)-2,3,4,5-tetrahydrobenzo[f][1,4]oxazepine-8-carboxylate (90 mg, 0.27 mmol, 1 equiv), MeOH/THF (1:4, 1.5 mL), $NH_2OH$ (50% in water, 1.077 g, 16.2 mmol, 60 equiv), aq. 1N NaOH (0.54 mL, 2 equiv). The resulting solution was stirred for 5 h at room temperature. The pH value of the solution was adjusted to 6 with 6N HCl at 0° C. The crude product was purified by Prep-HPLC (Column: Sunfire C18 OBD, 5 μm, 19×150 mm; Mobile Phase A: Water/0.05% formic acid; Mobile Phase B: MeCN; Flow rate: 25 mL/min; Gradient: 10% B to 40% B in 12 min; Detector, UV 254 nm) to afford the title compound as a white solid (44.8 mg, 52% yield). $^1$H-NMR (DMSO, 400 MHz) δ (ppm): 11.15 (br s, 1H), 9.04 (br s, 1H), 7.42-7.32 (m, 3H), 5.72-4.84 (m, 1H), 4.60-4.38 (m, 1H), 3.83-3.56 (m, 2H), 2.40-2.23 (m, 2H), 1.92-1.76 (m, 3H), 1.61-1.20 (m, 7H). MS: (ES, m/z): 319 [M+H]$^+$.

TABLE 27

The following compound was prepared according to the method of Example 52.

| Structure | Found M + H | $^1$H-NMR (300 MHz, DMSO-$d_6$) δ(ppm) |
|---|---|---|
| (R)/(S) isomer | 335 [M + H]$^+$ | (ES, m/z): 11.14 (br, 1H), 9.05 (br s, 1H), 7.56-7.30 (m, 3H), 5.74-5.38 (m, 1H), 4.56-4.06 (m, 2H), 3.88-3.33 (m, 4H), 3.11-2.87 (m, 1H), 1.62-1.19 (m, 7H) |

TABLE 28

The following compound was prepared according to the method of Example 52, using the second eluting isomer of the Step 5 product.

| Structure | Found M + H | ¹H-NMR (400 MHz, DMSO-d$_6$) δ(ppm) |
|---|---|---|
| (R)/(S) isomer | (ES, m/z): 319 [M + H]⁺ | 11.15 (br s, 1H), 9.05 (br s, 1H), 7.42-7.32 (m, 3H), 5.72-4.37 (m, 1H), 4.39-4.37 (m, 2H), 3.80-3.56 (m, 2H), 2.50-2.22 (m, 2H), 1.92-1.76 (m, 3H), 1.61-1.30 (m, 7H) |
| (R)/(S) isomer | (ES, m/z): 335 [M + H]⁺ | 11.14 (s, 1H), 9.07 (s, 1H), 7.56-7.30 (m, 3H), 5.74-5.38 (m, 1H), 4.56-4.06 (m, 2H), 3.88-3.50 (m, 4H), 3.11-2.86 (m, 1H), 1.63-1.20 (m, 7H) |
| (R)/(S) isomer | (ES, m/z): 349 [M + H]⁺ | 11.16 (s, 1H), 9.01 (s, 1H), 7.39-7.29 (m, 3H), 5.60-5.56 (m, 1H), 4.39-4.30 (m, 2H), 3.81-3.36 (m, 6H), 1.99-1.94 (m, 2H), 1.50-1.41 (m, 5H), 1.14 (s, 3H) |
| (R)/(S) isomer | (ES, m/z): 321 [M + H]⁺ | 11.17 (s, 1H), 9.04 (s, 1H), 7.41-7.32 (m, 3H), 5.74-5.72 (m, 0.5H), 4.81-4.72 (m, 1.5H), 4.62-4.58 (m, 1H), 4.45-4.33 (m, 2H), 4.26-4.21 (m, 1.5H), 3.87-3.70 (m, 1.5H), 3.36-3.01 (m, 1H), 1.56-1.48 (m, 6H) |
| (R)/(S) isomer | (ES, m/z): 307 [M + H]⁺ | 11.30-10.60 (br s, 1H), 9.40-8.60 (br s, 1H), 7.46-7.31 (m, 3H), 5.77-5.71 (m, 0.5H), 4.87-4.84 (m, 0.5H), 4.73-4.10 (m, 6.5H), 3.76-3.60 (m, 1.5H), 3.45-3.38 (m, 1H), 1.51-1.47 (m, 3H) |

Example 53

Preparation of (S)—N-hydroxy-4-(3-(methoxymethyl)oxetane-3-carbonyl)-5-methyl-2,3,4,5-tetrahydrobenzo[f][1,4]oxazepine-8-carboxamide

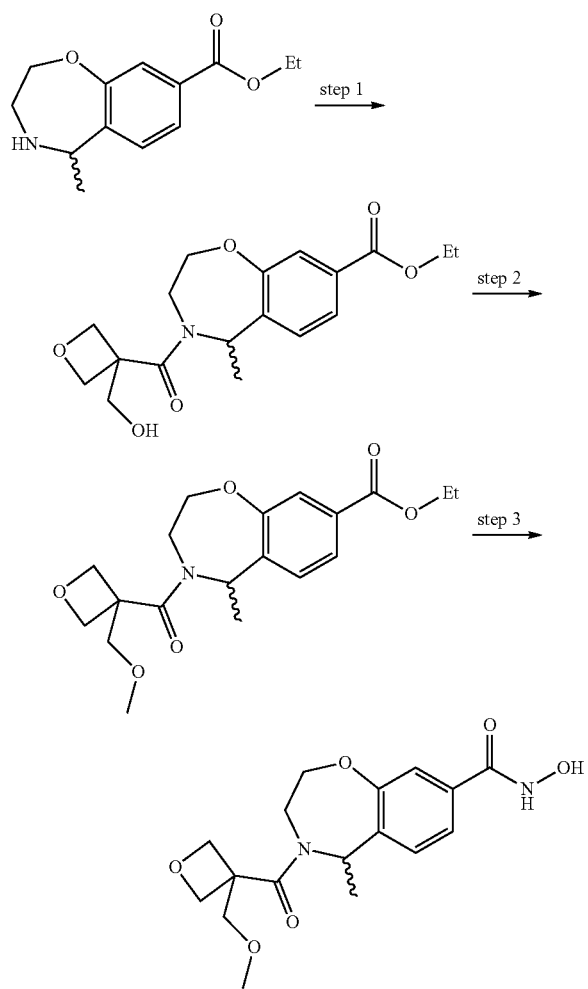

Step-1: Ethyl (S)-4-(3-(hydroxymethyl)oxetane-3-carbonyl)-5-methyl-2,3,4,5-tetrahydrobenzo[f][1,4]oxazepine-8-carboxylate

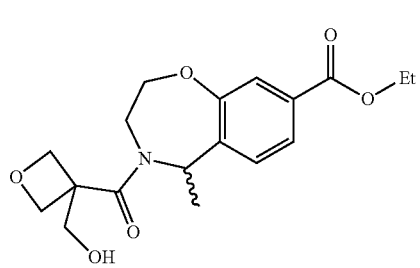 [SMILES: CCOC(=O)c1ccc2c(c1)OCCN(C(=O)C1(CO)COC1)C2C]

Into a 25-mL round-bottom flask, was placed ethyl (S)-5-methyl-2,3,4,5-tetrahydrobenzo[f][1,4]oxazepine-8-carboxylate (from the second eluting isomer of Example 47 Step 5) (150 mg, 0.64 mmol, 1 equiv) in DMF (5 mL), HATU (269 mg, 0.71 mmol, 1.5 equiv), DIEA (413 mg, 3.20 mmol, 5 equiv) and 3-(hydroxymethyl)oxetane-3-carboxylic acid (84 mg, 0.64 mmol, 1 equiv). The resulting solution was stirred overnight at room temperature. The reaction was then quenched with water and extracted with EtOAc (3×10 mL). The combined organic layers were washed with brine (2×5 mL), dried over anhydrous Na$_2$SO$_4$, filtered, and concentrated under vacuum. The residue was purified by silica gel chromatography (EtOAc/pet. ether, 1:4) to afford the title compound as a yellow oil (160 mg, 72% yield). MS: (ES, m/z): 350 [M+H]$^+$.

Step-2: Ethyl (S)-4-(3-(methoxymethyl)oxetane-3-carbonyl)-5-methyl-2,3,4,5-tetrahydrobenzo[f][1,4]oxazepine-8-carboxylate

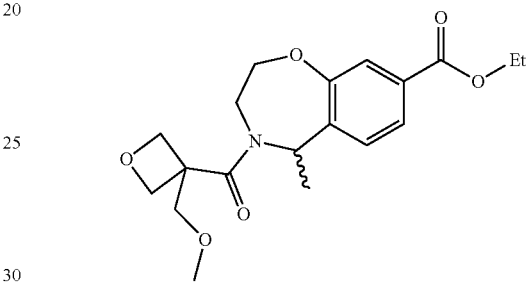

Into a 8-mL round-bottom flask, was placed ethyl (S)-4-(3-(hydroxymethyl)oxetane-3-carbonyl)-5-methyl-2,3,4,5-tetrahydrobenzo[f][1,4]oxazepine-8-carboxylate (100 mg, 0.29 mmol, 1 equiv), THF (2 mL), and sodium hydride (17.2 mg, 0.72 mmol, 2.5 equiv). After stirred for 30 min at room temperature, iodomethane (65 mg, 0.46 mmol, 1.6 equiv) was added. The resulting solution was stirred for 2 h at room temperature. The reaction was then quenched with aq. NH$_4$Cl at 0° C. The crude product was purified by Flash-Prep-HPLC (Column: C18 silica gel; Mobile Phase A: H$_2$O/0.05% TFA, Mobile Phase B: MeCN; Gradient: 0% B to 50% B in 30 min; Detector: 254 nm) to afford the title compound as a white solid (80 mg, 83% yield). MS: (ES, m/z): 364 [M+H]$^+$.

Step-3: (S)—N-hydroxy-4-(3-(methoxymethyl)oxetane-3-carbonyl)-5-methyl-2,3,4,5-tetrahydrobenzo[f][1,4]oxazepine-8-carboxamide

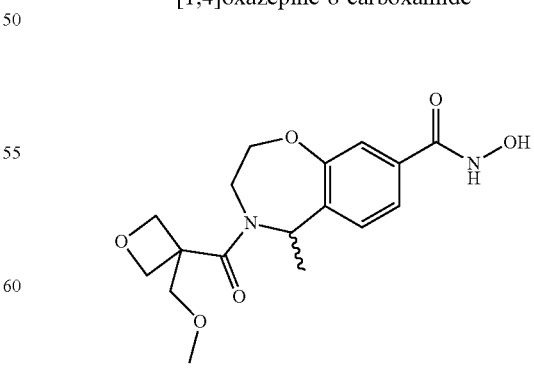

Into a 25-mL round-bottom flask, was placed ethyl (S)-4-(3-(methoxymethyl)oxetane-3-carbonyl)-5-methyl-2,3,4,5-tetrahydrobenzo[f][1,4]oxazepine-8-carboxylate (80 mg, 0.24 mmol, 1 equiv) in DMA (1 mL), isopropyl chloroformate (36.5 mg, 1 equiv), 4-methylmorpholine (30.2 mg, 0.30 mmol, 1 equiv), $NH_2OH \cdot HCl$ (20.6 mg, 1 equiv). The resulting mixture was stirred overnight at room temperature. The crude product was purified by Prep-HPLC (Column: Xbridge Prep C18 OBD, 5 μm, 19×50 mm; Mobile Phase A: Water/0.05% formic acid; Mobile Phase B: MeCN; Flow rate: 23 mL/min; Gradient: 5% B to 48% B in 7 min; Detector, UV 254, 220 nm) to afford the title compound as an off-white solid (5.9 mg, 7% yield). $^1$H-NMR (DMSO, 400 MHz) δ (ppm): 11.18 (s, 1H), 9.05 (s, 1H), 7.43-7.32 (m, 3H), 5.72-5.70 (m, 0.6H), 4.74-4.31 (m, 6H), 3.88-3.69 (m, 3.4H), 3.40-3.05 (m, 4H), 1.50-1.48 (d, 3H). MS: (ES, m/z): 351 [M+H]$^+$.

Example 54T

Preparation of (S)—N-hydroxy-5-methyl-4-((S)-3-methyltetrahydrofuran-3-carbonyl)-2,3,4,5-tetrahydrobenzo[f][1,4]oxazepine-8-carboxamide and (S)—N-hydroxy-5-methyl-4-((R)-3-methyltetrahydrofuran-3-carbonyl)-2,3,4,5-tetrahydrobenzo[f][1,4]oxazepine-8-carboxamide

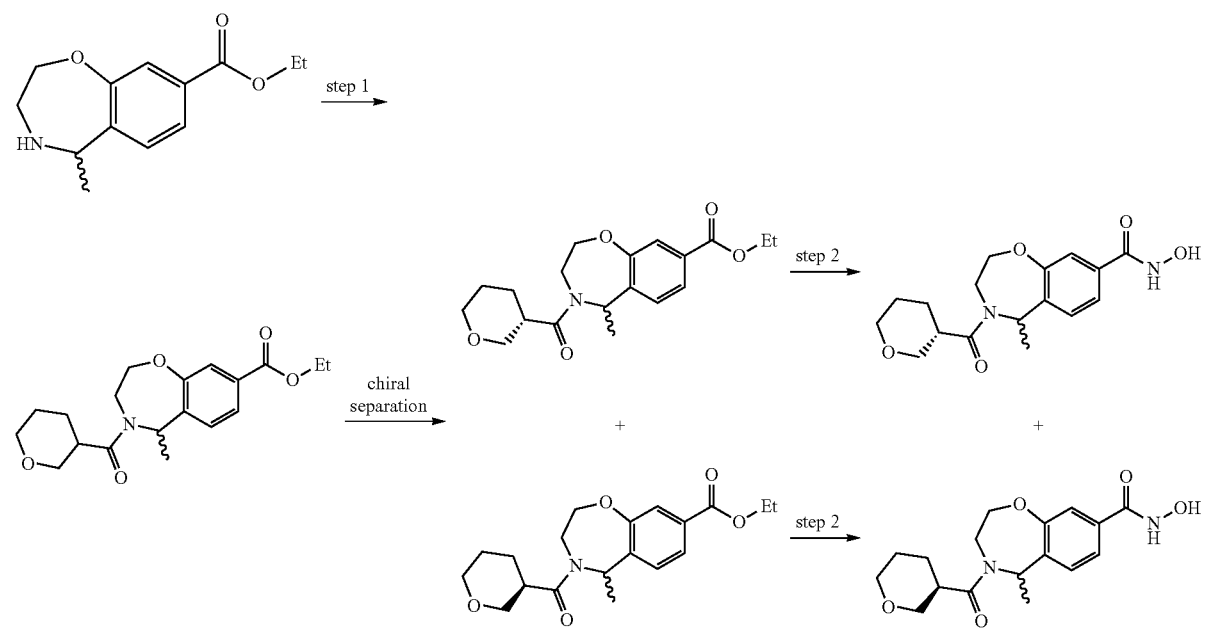

Step-1: Ethyl (S)-5-methyl-4-((S)-tetrahydro-2H-pyran-3-carbonyl)-2,3,4,5-tetrahydrobenzo[f][1,4]oxazepine-8-carboxylate and ethyl (S)-5-methyl-4-((R)-tetrahydro-2H-pyran-3-carbonyl)-2,3,4,5-tetrahydrobenzo[f][1,4]oxazepine-8-carboxylate

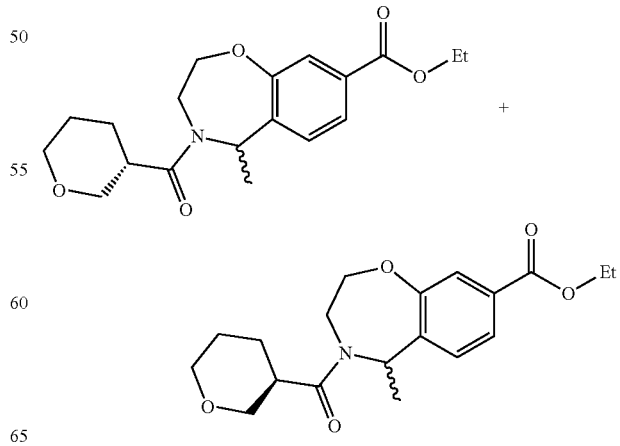

Into a 8-mL round-bottom flask, was placed ethyl (S)-5-methyl-2,3,4,5-tetrahydrobenzo[f][1,4]oxazepine-8-carboxylate (from the second eluting isomer of Example 47 Step 5) (200 mg, 0.85 mmol, 1 equiv) in DMF (4 mL), HATU (388 mg, 1.02 mmol, 1.2 equiv), DIEA (330 mg, 2.55 mmol, 3 equiv) and oxane-3-carboxylic acid (166 mg, 1.28 mmol, 1.5 equiv). The resulting solution was stirred overnight at room temperature. The reaction was then quenched with water. The resulting solution was extracted with EtOAc (3×5 mL). The combined organic layers were washed with brine (2×5 mL), dried over anhydrous Na$_2$SO$_4$, filtered, and concentrated under vacuum. The residue was purified by silica gel chromatography (EtOAc/pet. ether, 1:3) to afford the racemic mixture of the title compounds as a yellow oil (150 mg). The racemate was separated by Chiral-Prep-HPLC (Column Chiralpak IC, 5 μm, 2×25 cm; Mobile Phase A: hexanes; Mobile Phase B: EtOH; Gradient: 30% B for 21 min; Flow rate: 20 mL/min; Detector, UV 254, 220 nm) to afford the single isomers of title compounds as yellow oils (first eluting isomer: 20 mg, 7% yield; second eluting isomer: 20 mg, 7% yield). MS: (ES, m/z): 348 [M+H]$^+$.

Step-2: (S)—N-Hydroxy-5-methyl-4-((S)-3-methyl-tetrahydrofuran-3-carbonyl)-2,3,4,5-tetrahydrobenzo[f][1,4]oxazepine-8-carboxamide and (S)—N-hydroxy-5-methyl-4-((R)-3-methyltetrahydrofuran-3-carbonyl)-2,3,4,5-tetrahydrobenzo[f][1,4]oxazepine-8-carboxamide

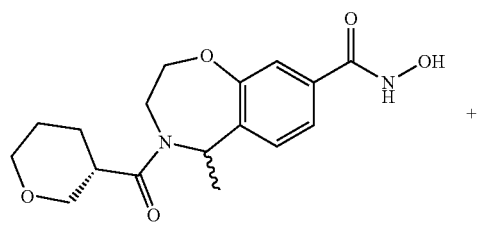

+

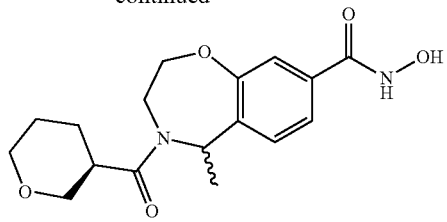

Into 8-mL vials, was placed each of the separated isomers from Step 1 (20 mg, 0.06 mmol; and 20 mg, 0.06 mmol; 1 equiv) in THF/MeOH (4:1, 1 mL). Then aq. 1N NaOH (0.12 mL, 2 equiv) and NH$_2$OH (50% in H$_2$O, 475 mg, 3.6 mmol, 60 equiv) were added. The resulting solution was stirred for 1 h at room temperature. The pH value of the solutions was adjusted to 6 with 6N HCl at 0° C. The solids were filtered out. The crude products were purified by Flash-Prep-HPLC (Column: C18 silica gel, 5 μm, 19×150 mm; Mobile Phase A: Water/0.1% formic acid; Mobile Phase B: MeCN; Flow rate: 0.7 mL/min; Gradient: 5% B to 60% B in 7 min; Detector, UV 254, 220 nm) to afford the title compounds as off-white solids. The product from the reaction with the first eluting isomer of Step 1: (7.8 mg, 41% yield). $^1$H-NMR (400 MHz, DMSO-d$_6$) δ(ppm): 11.15 (br s, 1H), 9.05-9.04 (br s, 1H), 7.56-7.29 (m, 3H), 5.71-5.31 (m, 1H), 4.52-4.02 (m, 2H), 4.07-3.24 (m, 6H), 2.97-2.83 (m, 1H), 1.97-1.44 (m, 7H). MS: (ES, m/z): 335 [M+H]$^+$. The product from the reaction with the second eluting isomer of Step 1: (12 mg, 66% yield). $^1$H-NMR (400 MHz, DMSO-d$_6$) δ(ppm): 11.15 (br s, 1H), 9.05 (br s, 1H), 7.53-7.29 (m, 3H), 5.72-5.40 (m, 1H), 4.53-4.02 (m, 2H), 3.89-3.23 (m, 6H), 3.11-2.80 (m, 1H), 1.89-1.43 (m, 7H). MS: (ES, m/z): 335 [M+H]$^+$.

TABLE 29

The following compounds were prepared according to the method of Example 54.

| Structure | Found M + H | $^1$H-NMR (400 MHz, DMSO-d$_6$) δ(ppm) |
|---|---|---|
| (R)/(S) isomer | 321 [M + H]$^+$ | (ES, m/z): 11.12 (br s, 1H), 9.05 (br s, 1H), 7.56-7.31 (m, 3H), 5.74-5.36 (m, 1H), 4.57-4.02 (m, 2H), 3.93-3.33 (m, 7H), 2.23-1.90 (m, 2H), 1.57-1.46 (m, 3H) |

TABLE 29-continued

The following compounds were prepared according to the method of Example 54.

| Structure | Found M + H | $^1$H-NMR (400 MHz, DMSO-$d_6$) δ(ppm) |
|---|---|---|
| (R)/(S) isomer | (ES, m/z): 321 [M + H]$^+$ | 11.13 (br s, 1H), 9.06 (br s, 1H), 7.56-7.31 (m, 3H), 5.75-5.32 (m, 1H), 4.53-3.53 (m, 8H), 3.35-3.33 (m, 1H), 2.08-1.79 (m, 2H), 1.56-1.47 (m, 3H) |
| (R)/(S) isomer; cis/trans | (ES, m/z): 363 [M + H]$^+$ | 11.14 (br s, 1H), 7.54-2.29 (m, 3H), 5.73-5.33 (m, 1H), 4.54-4.01 (m, 2H), 3.80-3.76 (m, 1H), 3.53-3.21 (m, 1H), 3.22-3.21 (m, 3H), 3.08-3.02 (m, 1H), 2.78-2.50 (m, 1H), 2.01-1.91 (m, 2H), 1.75-1.70 (m, 1H), 1.58-1.10 (m, 8H) |
| (R)/(S) isomer; cis/trans | (ES, m/z): 363 [M + H]$^+$ | 11.16 (br s, 1H), 8.99 (br s, 1H), 7.53-7.30 (m, 3H), 5.73-5.32 (m, 1H), 4.54-4.01 (m, 2H), 3.80-3.36 (m, 3H), 3.17 (s, 1H), 2.83-2.62 (m, 1H), 1.83-1.76 (m, 2H), 1.63-1.38 (m, 8H), 1.26-1.03 (m, 1H) |
| (R)/(S) isomer | (ES, m/z): 335 [M + H]$^+$ | 11.16 (br s, 1H), 9.05 (br, 1H), 7.42-7.32 (m, 3H), 5.80-5.00 (m, 1H), 4.42-4.39 (m, 1H), 3.88-3.56 (m, 7H), 2.23 (br, 1H), 1.89 (br, 1H), 1.52-1.50 (d, 3H), 1.28 (s, 3H) |

TABLE 29-continued

The following compounds were prepared according to the method of Example 54.

| Structure | Found M + H | ¹H-NMR (400 MHz, DMSO-d₆) δ(ppm) |
|---|---|---|
| 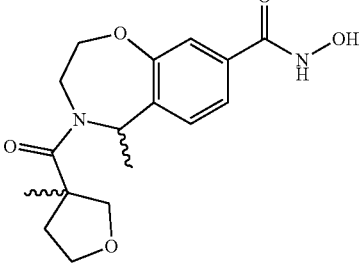 (R)/(S) isomer | (ES, m/z): 335 [M + H]⁺ | 11.12 (br s, 1H), 9.05 (br s, 1H), 7.51-7.28 (m, 3H), 5.61-5.22 (m, 1H), 4.41-4.39 (m, 1H), 3.90-3.55 (m, 7H), 2.33-1.95 (m, 1H), 1.52-1.26 (m, 6H) |
| 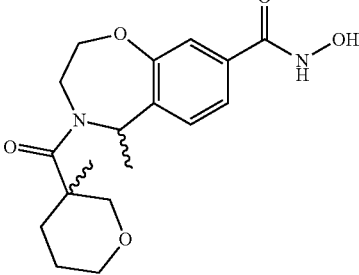 (R)/(S) isomer | (ES, m/z): 349 [M + H]⁺ | 11.20 (br s, 1H), 7.42-7.31 (m, 3H), 5.60-5.55 (m, 1H), 4.41-4.26 (m, 2H), 3.78-3.60 (m,. 4H), 3.38-3.29 (m, 2H), 1.79-1.73 (m, 2H), 1.65-1.57 (m, 1H), 1.47-1.39 (m, 4H), 1.22 (s, 3H) |
| 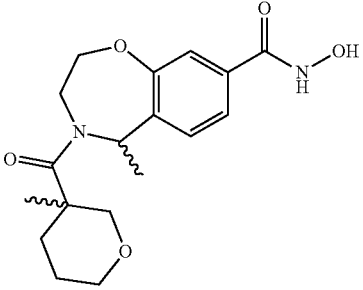 (R)/(S) isomer | (ES, m/z): 349 [M + H]⁺ | 11.18 (br s, 1H), 8.80-7.50 (br s, 1H), 7.42-7.31 (m, 3H), 5.59-5.53 (m, 1H), 4.41-4.25 (m, 2H), 3.80-3.75 (m, 1H), 3.68-3.58 (m, 3H), 3.37-3.31 (m, 2H), 1.86-1.80 (m, 2H), 1.63-1.36 (m, 5H), 1.22 (s, 3H) |

Example 55

Preparation of (S)—N-hydroxy-4-(4-(methoxymethyl)tetrahydro-2H-pyran-4-carbonyl)-5-methyl-2,3,4,5-tetrahydrobenzo[f][1,4]oxazepine-8-carboxamide

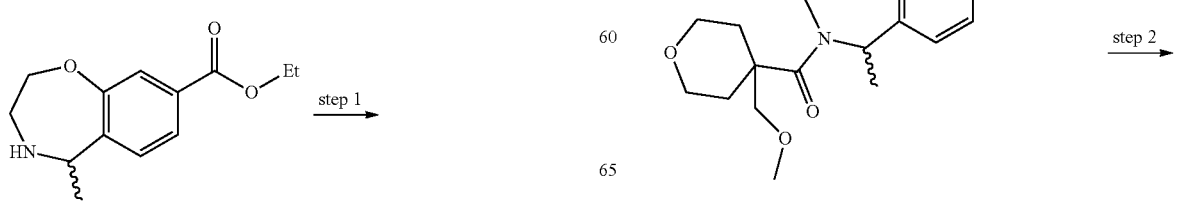

Step-1: Ethyl (S)-4-(4-(methoxymethyl)tetrahydro-2H-pyran-4-carbonyl)-5-methyl-2,3,4,5-tetrahydrobenzo[f][1,4]oxazepine-8-carboxylate

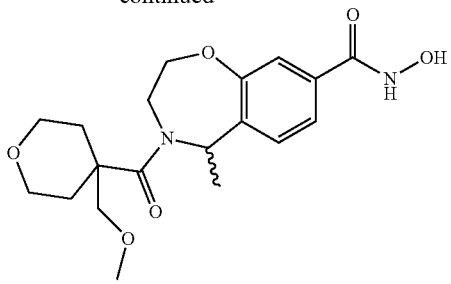

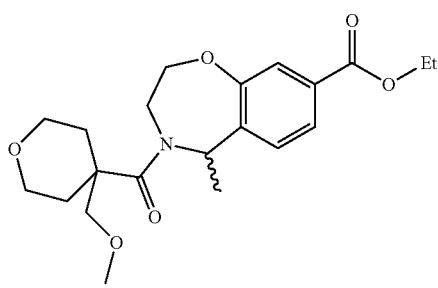 [SMILES: CCOC(=O)c1ccc2c(c1)OCCN(C(=O)C1(COC)CCOCC1)C2C]

Into a 50-mL 3-necked round-bottom flask purged and maintained with an inert atmosphere of nitrogen, was placed 1-(methoxymethyl)cyclohexane-1-carboxylic acid (147 mg, 0.85 mmol, 2 equiv), CH$_2$Cl$_2$ (2 mL), DMF (1 drop), then oxalyl chloride (2 mL) was added at 0° C., and stirred for 2 h at room temperature. The solvent was evaporated to afford 1-(methoxymethyl)cyclohexanecarbonyl chloride. Into another 50-mL 3-necked round-bottom flask purged and maintained with an inert atmosphere of nitrogen, was placed 4-dimethylaminopyridine (51.7 mg, 0.85 mmol, 1 equiv), Et$_3$N (172 mg, 1.70 mmol, 4 equiv), ethyl (S)-5-methyl-2,3,4,5-tetrahydrobenzo[f][1,4]oxazepine-8-carboxylate (from the second eluting isomer of Example 47 Step 5) (100 mg, 0.43 mmol, 1 equiv) and CH$_2$Cl$_2$ (2 mL). Then a solution of 1-(methoxymethyl)cyclohexanecarbonyl chloride in CH$_2$Cl$_2$ (2 mL) was added dropwise at 0° C. The resulting solution stirred for an additional 4 h at room temperature, then concentrated under vacuum. The crude product was purified by Flash-Prep-HPLC (Column: C18 silica gel; Mobile Phase A: pet. ether, Mobile Phase B: EtOAc; Gradient: 0% B to 20% B in 30 min; Detector: 254 nm) to afford the title compound as a yellow oil (90 mg, 54% yield). MS: (ES, m/z): 392 [M+H]$^+$.

Step-2: (S)—N-Hydroxy-4-(4-(methoxymethyl)tetrahydro-2H-pyran-4-carbonyl)-5-methyl-2,3,4,5-tetrahydrobenzo[f][1,4]oxazepine-8-carboxamide Into a 25-mL round-bottom flask, was placed ethyl (S)-4-(4-(methoxymethyl)tetrahydro-2H-pyran-4-carbonyl)-5-methyl-2,3,4,5-tetrahydrobenzo[f][1,4]oxazepine-8-carboxylate (90 mg, 0.23 mmol, 1 equiv), THF/MeOH (4:1, 0.5 mL), NH$_2$OH (50% in water, 910 mg, 13.8 mmol, 60 equiv), aq. 1N NaOH (0.46 mL, 0.46 mmol, 2 equiv). The resulting solution was stirred for 1.5 h at room temperature. The pH value of the solution was adjusted to 6 with 6N HCl at 0° C. The crude product was purified by Prep-HPLC (Column: Gemini-NX C18 110 Å, AXIA Packed, 5 μm, 21.2×150 mm; Mobile Phase A: Water/0.05% formic acid; Mobile Phase B: MeCN; Flow rate: 20 mL/min; Gradient: 5% B to 57% B in 8 min; Detector, UV 254, 220 nm) to afford the title compound as a white solid (19.7 mg, 23% yield). $^1$H-NMR (400 MHz, DMSO-d$_6$) δ(ppm): 11.17 (s, 1H), 9.02 (br s,1H), 7.42-7.30 (m, 3H), 5.58-5.56 (m, 1H), 4.40-4.31 (m, 2H), 3.75-3.53 (m, 5H), 3.46-3.29 (m, 3H), 3.12 (s, 3H), 2.70-1.96 (m, 2H), 1.62-1.55 (m, 5H). MS: (ES, m/z): 379 [M+H]$^+$.

Example 56

Preparation of (R)—N-hydroxy-5-methyl-4-(1-methylcyclobutane-1-carbonyl)-2,3,4,5-tetrahydrobenzo[f][1,4]oxazepine-7-carboxamide

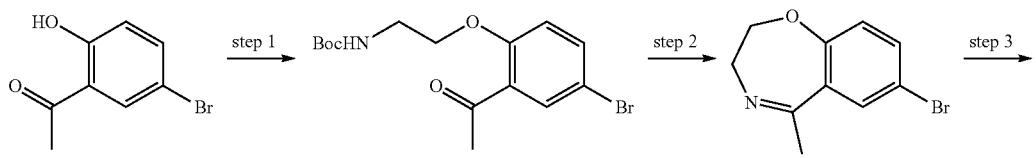

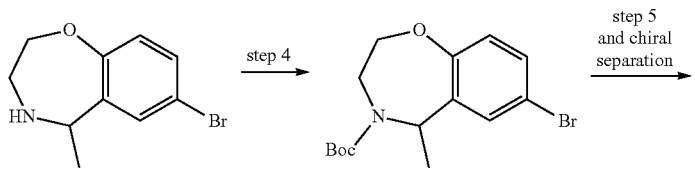

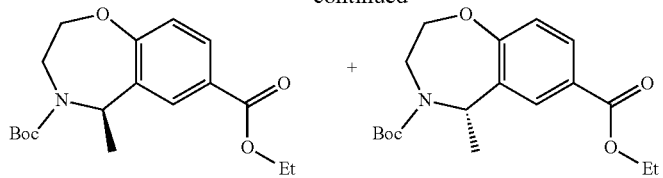

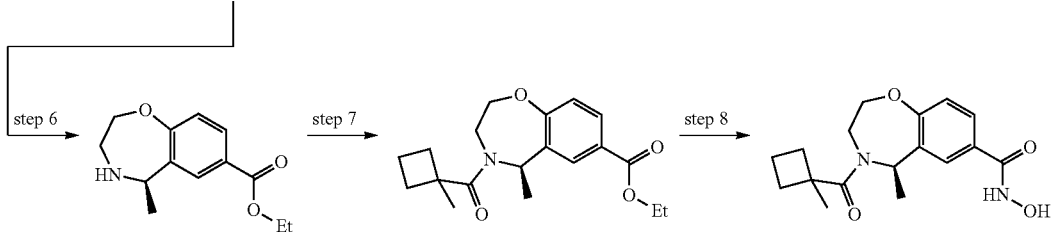

Step-1: tert-Butyl (2-(2-acetyl-4-bromophenoxy)ethyl)carbamate

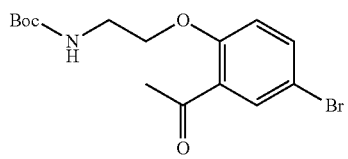 [SMILES: CC(=O)c1cc(Br)ccc1OCCNC(=O)OC(C)(C)C]

Into a 500-mL 3-necked round-bottom flask, was placed a solution of 1-(5-bromo-2-hydroxyphenyl)ethan-1-one (30 g, 139.51 mmol, 1 equiv), K$_2$CO$_3$ (29 g, 209.83 mmol, 3 equiv), potassium iodide (23.2 g, 1 equiv) and tert-butyl N-(2-bromoethyl)carbamate (37.5 g, 167.34 mmol, 1.2 equiv) in DMF (150 mL). The resulting solution was stirred overnight at 50° C. in an oil bath. The reaction mixture was cooled to 0° C. and quenched with H$_2$O (50 mL). The resulting solution was extracted with CH$_2$Cl$_2$ (2×100 mL), washed with brine (5×100 mL) and dried over anhydrous Na$_2$SO$_4$. The solids were filtered out and the filtrate was concentrated under vacuum. The crude product was purified by silica gel chromatography (Gradient 0-50% EtOAc/pet. ether over 50 min) to afford the title compound as a light yellow solid (39 g, 78% yield). MS: (ES, m/z): 358 [M+H]$^+$.

Step-2: 7-Bromo-5-methyl-2,3-dihydrobenzo[f][1,4]oxazepine

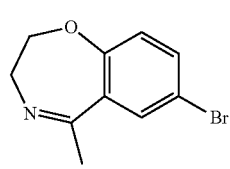

Into a 500-mL round-bottom flask, was placed tert-butyl N-[2-(2-acetyl-4-bromophenoxy)ethyl]carbamate (20 g, 55.83 mmol, 1 equiv), CH$_2$Cl$_2$ (100 mL) and TFA (20 mL). The resulting solution was stirred overnight at room temperature. The resulting mixture was concentrated under vacuum to afford the title compound as a red solid (20 g) which was used without further purification. MS: (ES, m/z): 240 [M+H]$^+$.

Step-3: 7-Bromo-5-methyl-2,3,4,5-tetrahydro-1,4-benzoxazepine

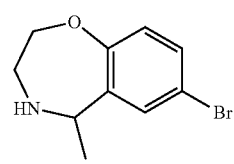

Into a 500-mL round-bottom flask, was placed a solution of 7-bromo-5-methyl-2,3-dihydrobenzo[f][1,4]oxazepine (10 g, 38.74 mmol, 1 equiv) in MeOH (100 mL), the pH value of the solution was adjusted to 7 with anhydrous sodium acetate at 0° C. Then Na(CN)BH$_3$ (7.9 g, 113.52 mmol, 3 equiv) was added at 0° C. The resulting solution was stirred for 2 h at room temperature. The resulting mixture was concentrated under vacuum and 20 mL of water was added. The solids were collected by filtration to afford the title compound as a white solid (7 g, 75% yield) which was used without further purification. MS: (ES, m/z): 242 [M+H]$^+$.

Step-4: tert-Butyl 7-bromo-5-methyl-2,3,4,5-tetrahydro-1,4-benzoxazepine-4-carboxylate

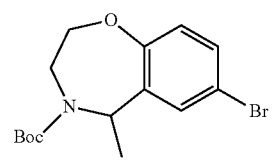 [SMILES: CC1c2cc(Br)ccc2OCCN1C(=O)OC(C)(C)C]

Into a 50-mL round-bottom flask, was placed 7-bromo-5-methyl-2,3,4,5-tetrahydro-1,4-benzoxazepine (2 g, 8.26 mmol, 1 equiv), CH$_2$Cl$_2$ (20 mL), Et$_3$N (2.51 g, 24.80 mmol, 3 equiv), di-tert-butyl dicarbonate (2.71 g, 12.42 mmol, 1.5 equiv). The resulting solution was stirred overnight at room temperature. The resulting mixture was concentrated under vacuum. The crude product was purified by silica gel chromatography (Gradient 0-30% EtOAc/pet. ether over 20 min) to afford the title compound as a light yellow oil (2.4 g, 85% yield). MS: (ES, m/z): 342 [M+H]$^+$.

Step-5: 4-(tert-Butyl) 7-ethyl (R)-5-methyl-2,3-dihydrobenzo[f][1,4]oxazepine-4,7(5H)-dicarboxylate

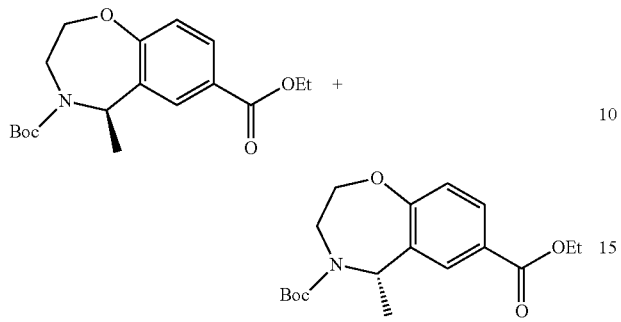

Into a 50-mL pressure tank reactor, was placed tert-butyl 7-bromo-5-methyl-2,3,4,5-tetrahydro-1,4-benzoxazepine-4-carboxylate (2.4 g, 7.01 mmol, 1 equiv), ethanol (40 mL), Et₃N (2.1 g, 20.75 mmol, 3 equiv), and Pd(dppf)Cl₂ (515.1 mg, 0.70 mmol, 0.1 equiv). CO (g) (60 atm) was introduced and the resulting solution was stirred overnight at 120° C. The solids were filtered out and the filtrate was concentrated under vacuum and purified by silica gel chromatography (Gradient 0-10% EtOAc/pet. ether over 30 min) to afford the racemic mixture of the title compounds, which were separated by Prep-SFC (Column Chiralpak IC OBD, 5 μm, 5×250 mm; Mobile Phase: 75% $CO_2$, 25% Isopropanol; Flow rate: 170 mL/min; Detector, UV 254, 220 nm) to afford the single isomers of the title compounds as light yellow oils (first eluting isomer: 440 mg, 19% yield; second eluting isomer: 500 mg, 21% yield). MS: (ES, m/z): 336 [M+H]⁺.

Step-6: Ethyl (R)-5-methyl-2,3,4,5-tetrahydrobenzo[f][1,4]oxazepine-7-carboxylate

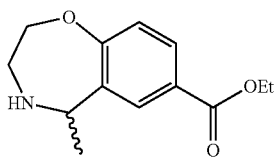 [SMILES: CCOC(=O)c1ccc2c(c1)C(C)NCCO2]

Into a 50-mL round-bottom flask, was placed the first eluting isomer from Step 5 (4-(tert-butyl) 7-ethyl (R)-5-methyl-2,3-dihydrobenzo[f][1,4]oxazepine-4,7(5H)-dicarboxylate) (440 mg, 1.31 mmol, 1 equiv), $CH_2Cl_2$ (5 mL), and TFA (2 mL). The resulting solution was stirred overnight at room temperature and concentrated under vacuum. The crude product was purified by silica gel chromatography (Gradient 10-50% EtOAc/pet. ether over 30 min) to afford the title compound as a light yellow oil (300 mg, 97% yield). MS: (ES, m/z): 236 [M+H]⁺.

Step-7: Ethyl (R)-5-methyl-4-(1-methylcyclobutane-1-carbonyl)-2,3,4,5-tetrahydrobenzo[f][1,4]oxazepine-7-carboxylate

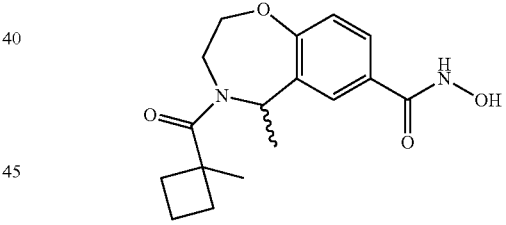

Into a 50-mL round-bottom flask, was placed 1-methylcyclobutane-1-carboxylic acid (48.6 mg, 0.43 mmol, 1 equiv), DMF (2 mL), ethyl (R)-5-methyl-2,3,4,5-tetrahydrobenzo[f][1,4]oxazepine-7-carboxylate (100 mg, 0.43 mmol, 1 equiv), HATU (194.4 mg, 0.51 mmol, 1.2 equiv), and DIEA (165.2 mg, 1.28 mmol, 3 equiv). The resulting solution was stirred overnight at room temperature. The reaction was then quenched with $H_2O$ (2 mL) and extracted with EtOAc (3×10 mL). The combined organic layers were washed with brine (3×5 mL) and dried over anhydrous $Na_2SO_4$, filtered, and concentrated under vacuum. The residue was purified by silica gel chromatography (Gradient 0-30% EtOAc/pet. ether over 25 min) to afford the title compounds as a yellow oil (80 mg, 57% yield). MS: (ES, m/z): 332 [M+H]⁺.

Step-8: (R)—N-hydroxy-5-methyl-4-(1-methylcyclobutane-1-carbonyl)-2,3,4,5-tetrahydrobenzo[f][1,4]oxazepine-7-carboxamide Into a 8-mL round-bottom flask, was placed ethyl (R)-5-methyl-4-(1-methylcyclobutane-1-carbonyl)-2,3,4,5-tetrahydrobenzo[f][1,4]oxazepine-7-carboxylate (40 mg, 0.12 mmol, 1 equiv), and THF/MeOH (4:1, 1.5 mL). This was followed by the addition of aq. 1N NaOH (0.24 mL, 2 equiv) and $NH_2OH$ (50% in water, 478 mg, 60 equiv). The resulting solution was stirred for 2.5 h at room temperature. The pH value of the solution was adjusted to 6 with 6N HCl. The crude product was purified by Prep-HPLC (Column: Sunfire Prep C18 OBD, 5 μm, 19×150 mm; Mobile Phase A: Water/0.05% TFA; Mobile Phase B: MeCN; Flow rate: 25 mL/min; Gradient: 5% B to 35% B in 7 min; Detector: UV 254, 220 nm) to afford the title compound as an off-white solid (11 mg, 22% yield). ¹H-NMR (400 MHz, DMSO-d₆) δ(ppm): 11.22-11.10 (s, 1H), 7.68 (s, 1H), 7.58-7.56 (d, 1H), 7-6.92 (d, 2H), 5.73-5.70 (d, 2H), 4.94-4.83 (d, 1H), 4.67-4.60 (d, 1H), 4.40-4.37 (d, 2H), 3.86-3.57 (m, 2H), 2.40-2.24 (m, 2H), 1.92-1.78 (m, 3H), 1.63-1.1.45 (m, 4H), 1.36-1.33 (m, 3H). MS: (ES, m/z): 319 [M+H]⁺.

TABLE 30

The following compounds were prepared according to the method of Example 56.

| Structure | Found M + H | $^1$H-NMR (400 MHz, DMSO-d$_6$) δ(ppm) |
|---|---|---|
| (R)/(S) isomer [structure with tetrahydropyran carbonyl, benzoxazepine, N-hydroxy carboxamide] | (ES, m/z): 335 [M + H]$^+$ | 11.25-11.12 (s, 1H), 8.99-8.94 (s, 1H), 7.87-7.67 (m, 1H), 7.67-7.55 (d, 1H), 7-6.98 (d, 1H), 5.78-5.37 (m, 1H), 4.55-4.09 (m, 2H), 3.88-3.70 (m, 4H), 3.50-3.37 (m, 2H), 3.17-2.87 (m, 1H), 1.63-1.19 (m, 7H) |

TABLE 31

The following compounds were prepared according to the method of Example 56, using the second eluting isomer of the Step 5 product.

| Structure | Found M + H | $^1$H-NMR (400 MHz, DMSO-d$_6$) δ(ppm) |
|---|---|---|
| (R)/(S) isomer [structure with 1-methylcyclobutyl carbonyl, benzoxazepine, N-hydroxy carboxamide] | (ES, m/z): 319 [M + H]$^+$ | 11.22-11.10 (s, 1H), 7.68 (s, 1H), 7.58-7.56 (d, 1H), 7-6.92 (d, 1H), 5.73-5.70 (m, 1H), 4.94-4.83 (d, 0.5H), 4.67-4.60 (m, 0.5H), 4.40-4.37 (m, 1H), 3.86-3.27 (m, 2H), 2.51-2.22 (m, 2H), 1.92-1.77 (m, 3H), 1.63-1.45 (m, 4H), 1.36-1.24 (m, 3H) |
| (R)/(S) isomer [structure with tetrahydropyran carbonyl, benzoxazepine, N-hydroxy carboxamide] | (ES, m/z): 335 [M + H]$^+$ | 11.25-11.12 (s, 1H), 9.50-8.50 (br, 1H), 7.87-7.67 (d, 1H), 7.67-7.55 (d, 1H), 7.01-6.98 (d, 1H), 5.76-5.37 (m, 1H), 4.55-4.05 (m, 2H), 3.84-3.30 (m, 6H), 3.11-2.86 (m, 1H), 1.63-1.20 s(m, 7H) |

Example 57

Preparation of (2R,5R)—N-Hydroxy-4-(tetrahydro-2H-pyran-4-carbonyl)-2,3,4,5-tetrahydro-2,5-methanobenzo[f][1,4]oxazepine-8-carboxamide

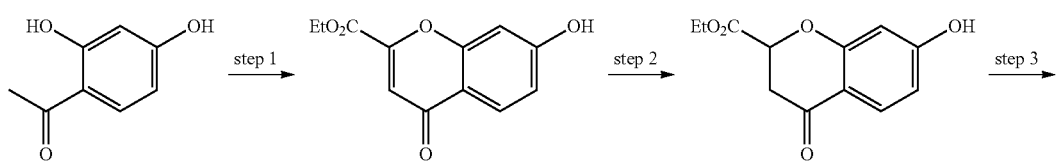

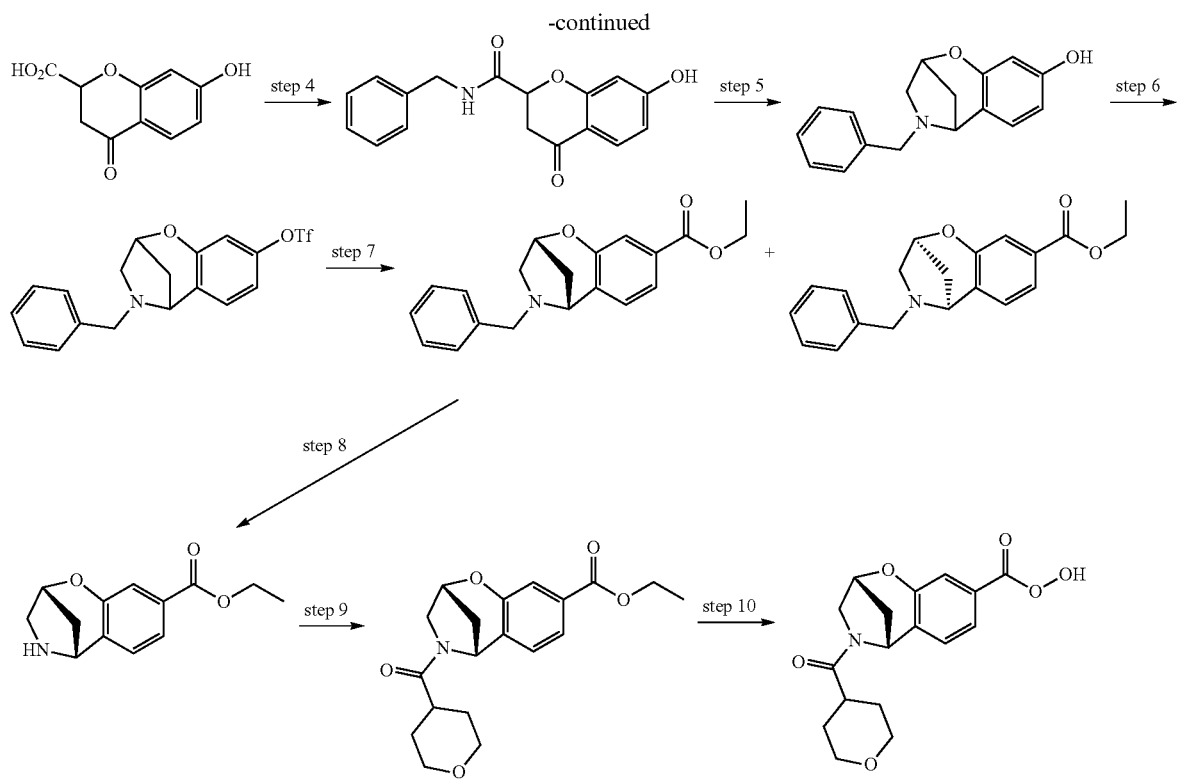

Step-1: Ethyl 7-hydroxy-4-oxo-4H-chromene-2-carboxylate

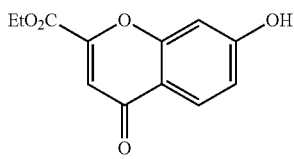 [SMILES: CCOC(=O)c1cc(=O)c2ccc(O)cc2o1]

Into a 1000-mL round-bottom flask, was placed ethanol (300 mL). This was followed by the addition of sodium (18 g, 783 mmol, 6 equiv), in portions and stirred at room temperature until the sodium was completely dissolved. To this was added 1-(2,4-dihydroxyphenyl)ethan-1-one (20 g, 131 mmol, 1 equiv), in portions. To the mixture was added diethyl oxalate (56 g, 383 mmol, 3 equiv) dropwise with stirring. The resulting solution was stirred for 2 h at 85° C. in an oil bath. Then 6N HCl (aq.) was added at room temperature and the resulting mixture was stirred for 10 min. The resulting mixture was extracted with CH$_2$Cl$_2$ (3×150 mL), dried over anhydrous MgSO$_4$, filtered, and concentrated under vacuum. The residue was dissolved in ethanol (200 mL). To the solution was added conc. HCl (6 mL). The resulting solution was stirred for 2 h at 85° C. in an oil bath. The product was precipitated by the addition of EtOAc (50 mL). The solids were collected by filtration to afford the title compound as a light yellow solid (21 g, 68% yield). MS: (ES, m/z): 235 [M+H]$^+$.

Step-2: Ethyl 7-hydroxy-4-oxochroman-2-carboxylate

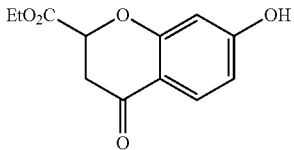 [SMILES: O=C1CC(C(=O)O)Oc2cc(O)ccc21]

Into a 1000-mL pressure tank reactor (10 atm), was placed a solution of ethyl 7-hydroxy-4-oxo-4H-chromene-2-carboxylate (10 g, 42.7 mmol, 1 equiv) in ethanol (600 mL) and Raney nickel (2 g). Hydrogen gas was introduced and the resulting solution was stirred overnight at 80° C. in an oil bath. The solids were filtered out. The resulting mixture was concentrated under vacuum and purified by silica gel chromatography (EtOAc/pet. ether, 1:3) to afford the title compound as a white solid (6 g, 59% yield). MS: (ES, m/z): 237 [M+H]$^+$.

Step-3: 7-Hydroxy-4-oxochroman-2-carboxylic acid

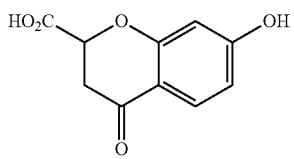

Into a 250-mL round-bottom flask, was placed a solution of ethyl 7-hydroxy-4-oxochroman-2-carboxylate (12 g, 50.8 mmol, 1 equiv) in THF (50 mL). This was followed by the addition of a solution of NaOH (6.1 g, 152 mmol, 3 equiv) in water (50 mL) dropwise with stirring. The resulting solution was stirred for 4 h at room temperature. The pH value of the solution was adjusted to 1 with 3N HCl. The resulting solution was extracted with EtOAc (3×100 mL), dried over anhydrous $Na_2SO_4$ and concentrated under vacuum to afford the title compound as a light yellow solid (10.5 g, 99% yield). MS: (ES, m/z): 209 [M+H]$^+$.

Step-4:
N-Benzyl-7-hydroxy-4-oxochroman-2-carboxamide

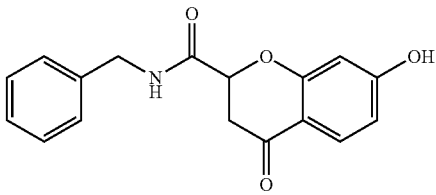 [SMILES: O=C1CC(C(=O)NCc2ccccc2)Oc2cc(O)ccc21]

Into a 250-mL round-bottom flask, was placed a solution of 7-hydroxy-4-oxochroman-2-carboxylic acid (10.5 g, 50 mmol, 1 equiv) in DMF (90 mL). This was followed by the addition of HATU (23 g, 60 mmol, 1.2 equiv), in portions. To this was added phenylmethanamine (5.9 g, 55 mmol, 1.1 equiv) and DIEA (19.5 g, 150 mmol, 3 equiv) dropwise with stirring. The resulting solution was stirred overnight at room temperature. The reaction was then quenched by the addition of water (300 mL). The resulting solution was extracted with EtOAc (3×400 mL). The combined organic layers were dried over anhydrous $Na_2SO_4$, concentrated under vacuum and purified by silica gel chromatography (EtOAc/pet. ether, 2:1) to afford the title compound as a white solid (11 g, 73% yield). MS: (ES, m/z): 298 [M+H]$^+$.

Step-5: 4-Benzyl-2,3,4,5-tetrahydro-2,5-methano-benzo[f][1,4]oxazepin-8-ol

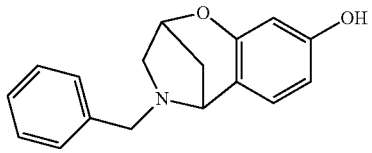 [SMILES: Oc1ccc2c(c1)OC1CC2N(Cc2ccccc2)C1]

Into a 500-mL round-bottom flask purged and maintained with an inert atmosphere of nitrogen, was placed a solution of sodium bis(2-methoxyethoxy)aluminum hydride solution (Red-Al®) (14.6 g, 51 mmol, 3 equiv, 70% in toluene). This was followed by the addition of a solution of N-benzyl-7-hydroxy-4-oxochroman-2-carboxamide (5 g, 17 mmol, 1 equiv) in THF (100 mL) dropwise with stirring at 0° C. The resulting solution was stirred for 4 h at 70° C. in an oil bath. The reaction was then quenched by the addition of saturated aqueous solution of potassium sodium tartrate tetrahydrate (100 mL) and extracted with EtOAc (3×150 mL). The combined organic layers were dried over anhydrous $Na_2SO_4$, concentrated under vacuum and purified by silica gel chromatography (EtOAc/pet. ether, 1:2) to afford the title compound as a light yellow solid (1 g, 22% yield). MS: (ES, m/z): 268 [M+H]$^+$.

Step-6: 4-Benzyl-2,3,4,5-tetrahydro-2,5-methano-benzo[f][1,4]oxazepin-8-yl trifluoromethane-sulfonate

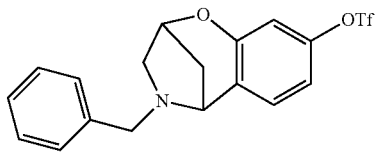 [SMILES: O=S(=O)(Oc1ccc2c(c1)OC1CC2N(Cc2ccccc2)C1)C(F)(F)F]

Into a 100-mL round-bottom flask, were placed a solution of 4-benzyl-2,3,4,5-tetrahydro-2,5-methanobenzo[f][1,4]oxazepin-8-ol (1.5 g, 5.61 mmol, 1 equiv) in $CH_2Cl_2$ (50 mL) and triethylamine (1.1 g, 10.89 mmol, 2 equiv). This was followed by the addition of (trifluoromethane)sulfonyl trifluoromethanesulfonate (2.4 g, 8.51 mmol, 1.5 equiv) dropwise with stirring at 0° C. The resulting solution was stirred for 2 h at 0° C. The reaction was then quenched by the addition of water (20 mL). The resulting mixture was washed with water (2×30 mL), dried over anhydrous $MgSO_4$, concentrated under vacuum and purified by silica gel chromatography (EtOAc/pet. ether, 1:5) to afford the title compound as a light yellow oil (1.2 g, 54% yield). MS: (ES, m/z): 400 [M+H]$^+$.

Step-7: Ethyl (2R,5R)-4-benzyl-2,3,4,5-tetrahydro-2,5-methanobenzo[f][1,4]oxazepine-8-carboxylate and Ethyl (2S,5S)-4-benzyl-2,3,4,5-tetrahydro-2,5-methanobenzo[f][1,4]oxazepine-8-carboxylate

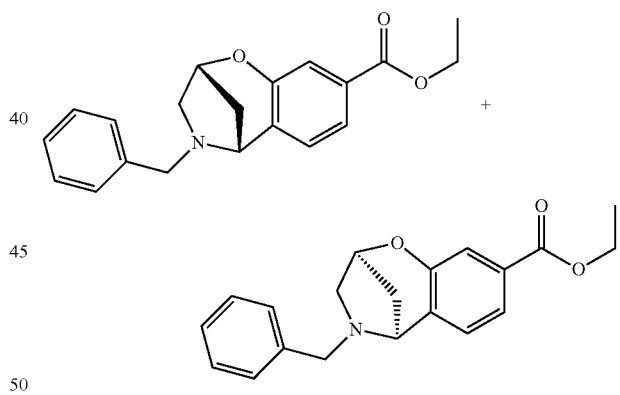

Into a 250-mL pressure tank reactor (50 atm) purged and maintained with an atmosphere of carbon monoxide, were placed a mixture of 4-benzyl-2,3,4,5-tetrahydro-2,5-methanobenzo[f][1,4]oxazepin-8-yl trifluoromethanesulfonate (2.2 g, 5.51 mmol, 1 equiv) in ethanol (180 mL), triethylamine (1.7 g, 16.80 mmol, 3 equiv) and Pd(dppf)Cl$_2$.CH$_2$Cl$_2$ (0.45 g, 0.1 equiv). The resulting mixture was stirred overnight at 120° C. in an oil bath. The solids were filtered out. The resulting mixture was concentrated under vacuum. The residue was dissolved in EtOAc (100 mL), washed with water (2×100 mL), dried over anhydrous sodium sulfate and concentrated under vacuum. The residue was purified by silica gel chromatography (EtOAc/pet. ether, 1:5) to afford a racemic mixture of the title compounds as a light yellow oil (1.2 g, 67% yield). $^1$H-NMR (400 MHz, DMSO-d$_6$) δ(ppm): 7.55-7.42 (m, 2H), 7.36-7.24 (m, 5H), 6.94-6.81 (m, 1H), 4.93-4.82 (m, 1H), 4.36 (q, J=7.2 Hz, 2H), 3.99-3.83 (m, 1H), 3.66-3.55 (m, 1H), 3.50-3.30 (m, 2H), 2.70-2.55 (m, 1H), 2.35-2.11 (m, 2H), 1.38 (t, J=7.2 Hz, 3H). MS: (ES, m/z): 324 [M+H]$^+$.

800 mg of the racemic mixture was separated by prep-SFC (Column: Chiralpak AD-H, 5 μm, 5×25 cm; Mobile Phase A: CO$_2$, Mobile Phase B: MeOH (0.2% N,N-diethylaniline); Flow rate: 150 mL/min; Detector, UV 254 nm) to afford the single isomers of the title compounds as light yellow oils (first eluting isomer: 360 mg; second eluting isomer: 430 mg). MS: (ES, m/z): 324 [M+H]$^+$.

Step-8: Ethyl (2R,5R)-2,3,4,5-tetrahydro-2,5-methanobenzo[f][1,4]oxazepine-8-carboxylate

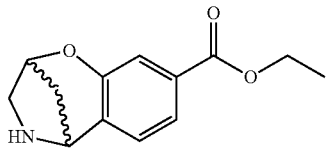

Into a 25-mL round-bottom flask purged and maintained with an atmosphere of hydrogen, was placed a solution of the first eluting isomer from Step 7 (ethyl (2R,5R)-4-benzyl-2,3,4,5-tetrahydro-2,5-methanobenzo[f][1,4]oxazepine-8-carboxylate) (80 mg, 0.25 mmol, 1 equiv) in MeOH (5 mL) and palladium on carbon. Hydrogen gas was introduced and the resulting solution was stirred for 3 h at room temperature. The solids were filtered out. The resulting mixture was concentrated under vacuum to afford the title compound as a light yellow oil (50 mg, 87% yield). MS: (ES, m/z): 234 [M+H]$^+$.

Step-9: Ethyl (2R,5R)-4-(tetrahydro-2H-pyran-4-carbonyl)-2,3,4,5-tetrahydro-2,5-methanobenzo[f][1,4]oxazepine-8-carboxylate

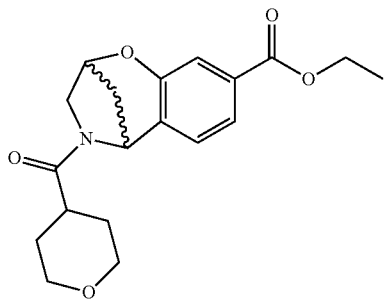

Into a 8-mL vial, were placed a solution of oxane-4-carboxylic acid (28 mg, 0.22 mmol, 1 equiv) in DMF (2 mL), HATU (98 mg, 0.26 mmol, 1.2 equiv), ethyl (2R,5R)-2,3,4,5-tetrahydro-2,5-methanobenzo[f][1,4]oxazepine-8-carboxylate (50 mg, 0.21 mmol, 1 equiv), and DIEA (89 mg, 0.69 mmol, 3 equiv). The resulting solution was stirred overnight at room temperature. The reaction was then quenched with water (5 mL) and extracted with EtOAc (3×15 mL). The combined organic layers were dried over anhydrous Na$_2$SO$_4$, filtered, and concentrated under vacuum. The residue was purified by silica gel chromatography (EtOAc/pet. ether, 2:1) to afford the title compound as a light yellow oil (45 mg, 61% yield). MS: (ES, m/z): 346 [M+H]$^+$.

Step-10: (2R,5R)—N-Hydroxy-4-(tetrahydro-2H-pyran-4-carbonyl)-2,3,4,5-tetrahydro-2,5-methanobenzo[f][1,4]oxazepine-8-carboxamide

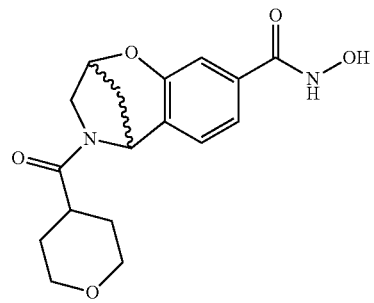

Into a 8-mL vial, was placed a solution of ethyl (2R,5R)-4-(tetrahydro-2H-pyran-4-carbonyl)-2,3,4,5-tetrahydro-2,5-methanobenzo[f][1,4]oxazepine-8-carboxylate (45 mg, 0.13 mmol, 1 equiv) in THF/MeOH (4:1, 1 mL). A. 1N NaOH (0.26 mL, 2 equiv) and NH$_2$OH (50% in water, 0.24 mL, 30 equiv) were added simultaneously. The resulting solution was stirred for 2 h at room temperature. The crude product was purified by Prep-HPLC (Column: XBridge Prep C18 OBD, 5 μm, 19×150 mm; Mobile Phase A: Water/0.1% formic acid, Mobile Phase B: MeCN; Gradient: 5% B to 26% B in 8 min; Detector: UV, 254 nm, 220 nm) to afford the title compound as an off-white solid (7.8 mg, 18% yield). $^1$H-NMR (400 MHz, DMSO-d$_6$) δ(ppm): 11.05 (br s, 1H), 9.01 (br s, 1H), 7.45-7.28 (m, 1H), 7.26-7.00 (m, 2H), 5.38-4.97 (m, 2H), 3.93-3.74 (m, 3H), 3.62-3.36 (m, 2H), 3.29-2.91 (m, 2H), 2.32-1.99 (m, 2H), 1.71-1.13 (m, 4H). MS: (ES, m/z): 333 [M+H]$^+$.

TABLE 32
The following compound was prepared according to the method of Example 57, using the second eluting isomer of the Step 7 product.
| Structure | Found M + H | $^1$H-NMR (400 MHz, DMSO-$d_6$) δ(ppm) |
|---|---|---|
| (R)/(S) isomer | (ES, m/z): 333 [M + H]$^+$ | 11.10 (br s, 1H), 9.00 (s, 1H), 7.39-7.20 (m, 2H), 7.18-7.01 (m, 2H), 5.30-5.07 (m, 2H), 3.88-3.76 (m, 3H), 3.64-3.43 (m, 2H), 3.43-3.01 (m, 1H), 2.31-2.02 (m, 2H), 1.64-1.16 (m, 4H) |
Example 58
Preparation of 4-(cyclohexanecarbonyl)-N-hydroxy-2,3,4,5-tetrahydropyrido[2,3-f][1,4]oxazepine-8-carboxamide
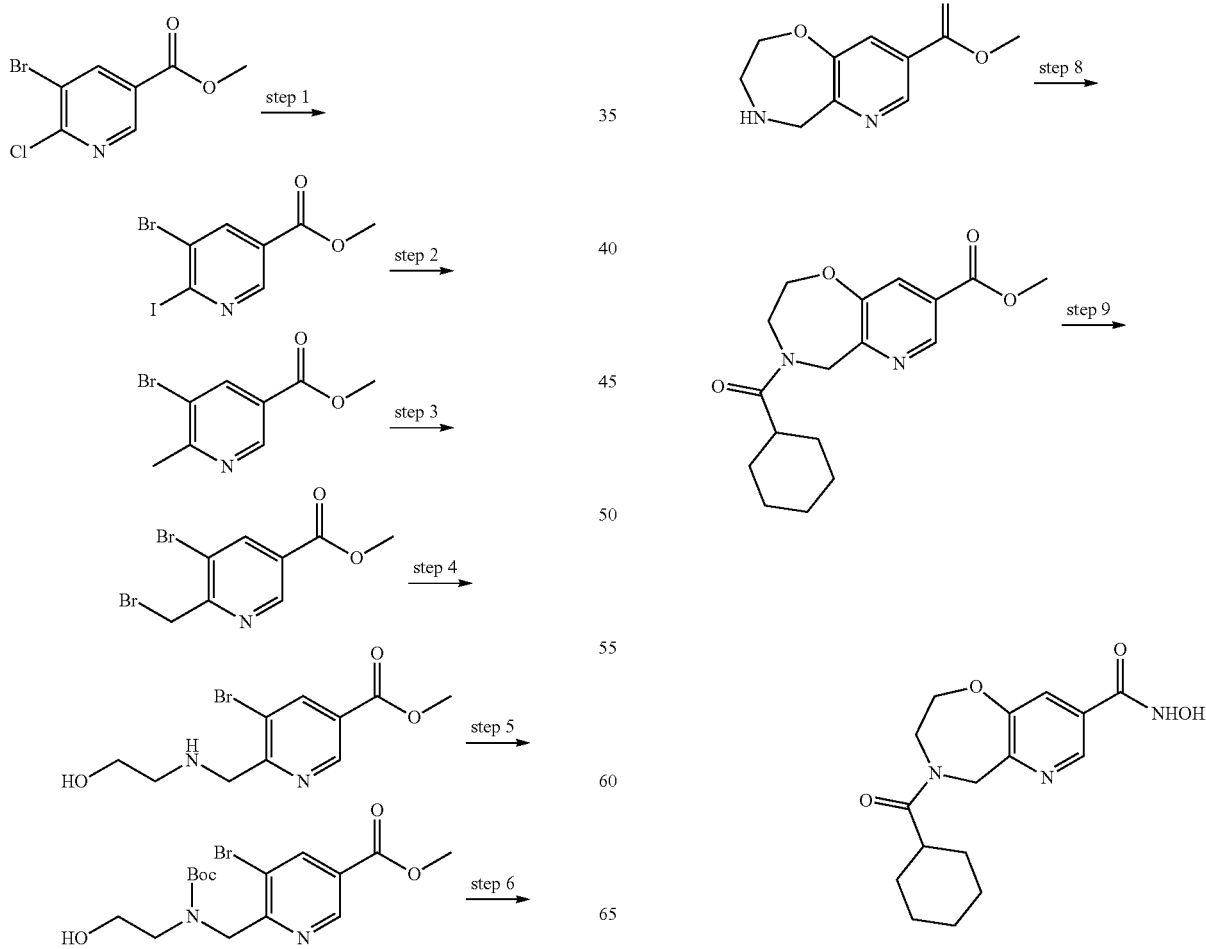

Step-1: Methyl 5-bromo-6-iodopyridine-3-carboxylate

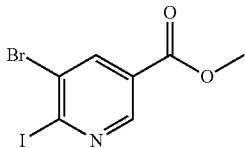

Into a 1000-mL round-bottom flask, was placed methyl 5-bromo-6-chloropyridine-3-carboxylate (11 g, 43.92 mmol, 1 equiv), MeCN (330 mL), trimethylsilyl iodide (8.767 g, 1 equiv) and sodium iodide (19.7 g, 3 equiv). The resulting mixture was stirred for 4 h at 25° C. and then concentrated. The residue was diluted with $H_2O$ (300 mL). The pH value of the solution was adjusted to 7 with 2N NaOH. The solids were collected by filtration to afford the title compound as a yellow solid (16 g) which was used without further purification. MS: (ES, m/z): 250 $[M+H]^+$.

Step-2: Methyl 5-bromo-6-methylpyridine-3-carboxylate

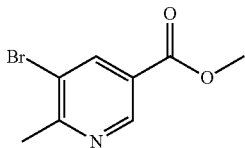

Into a 250-mL 3-necked round-bottom flask purged and maintained with an inert atmosphere of nitrogen, was placed methyl 5-bromo-6-iodopyridine-3-carboxylate (6 g, 17.55 mmol, 1 equiv), 1,4-dioxane (60 mL), trimethyl-1,3,5,2,4,6-trioxatriborinane (15 mL, 50% in THF, 3 equiv), Pd(dppf) $Cl_2 \cdot CH_2Cl_2$ (1.44 g, 0.1 equiv) and potassium carbonate (7.34 g, 53.10 mmol, 3 equiv). The resulting solution was stirred for 72 h at 75° C. in an oil bath. The reaction mixture was cooled to room temperature. The solids were filtered out. The filtrate was diluted with EtOAc (100 mL), washed with brine (3×30 mL), dried over anhydrous $Na_2SO_4$, filtered, and concentrated. The residue was purified by silica gel chromatography (EtOAc/pet. ether, 1:10) to afford the title compound as an off-white solid (3 g, 74% yield). MS: (ES, m/z): 230 $[M+H]^+$.

Step-3: Methyl 5-bromo-6-(bromomethyl)pyridine-3-carboxylate

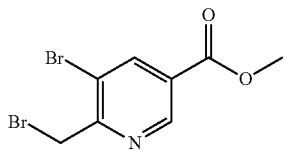

Into a 250-mL 3-necked round-bottom flask purged and maintained with an inert atmosphere of nitrogen, was placed methyl 5-bromo-6-methylpyridine-3-carboxylate (3 g, 13.04 mmol, 1 equiv), $CCl_4$ (60 mL), NBS (2.435 g, 13.68 mmol, 1.05 equiv) and benzoyl peroxide (158 mg, 0.62 mmol, 0.05 equiv). The resulting mixture was stirred for 16 h at 80° C. in an oil bath. The reaction mixture was cooled to room temperature. The solids were filtered out. The filtrate was concentrated and diluted with EtOAc (150 mL), washed with brine (3×50 mL). The organic phase was dried over anhydrous $Na_2SO_4$, filtered, and concentrated to afford the title compound as a brown oil (2.5 g) which was used without further purification. MS: (ES, m/z): 310 $[M+H]^+$.

Step-4: Methyl 5-bromo-6-[[(2-hydroxyethyl)amino]methyl]pyridine-3-carboxylate

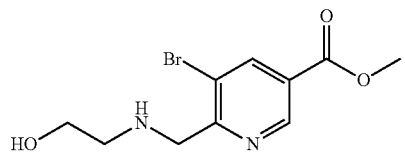 [SMILES: COC(=O)c1cnc(CNCCO)c(Br)c1]

Into a 250-mL round-bottom flask, was placed MeCN (50 mL), 2-aminoethan-1-ol (990 mg, 16.21 mmol, 2 equiv) and potassium carbonate (2.26 g, 16.32 mmol, 2 equiv). This was followed by the addition of a solution of methyl 5-bromo-6-(bromomethyl)pyridine-3-carboxylate (2.5 g, 4.86 mmol, 1 equiv 60%) in MeCN (20 mL) dropwise with stirring at 0° C. The resulting solution was stirred for additional 2 h at 0° C. The solids were filtered out. The filtrate was concentrated. The residue was purified by silica gel chromatography ($CH_2Cl_2$/MeOH, 20:1) to afford the title compound as a yellow solid (0.7 g, 50% yield). MS: (ES, m/z): 289 $[M+H]^+$.

Step-5: Methyl 5-bromo-6-(((tert-butoxycarbonyl)(2-hydroxyethyl)amino)methyl)nicotinate

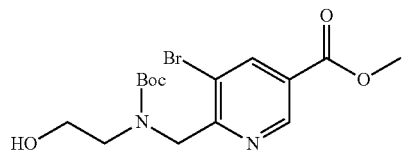 [SMILES: COC(=O)c1cnc(CN(CCO)C(=O)OC(C)(C)C)c(Br)c1]

Into a 25-mL round-bottom flask, was placed methyl 5-bromo-6-[[(2-hydroxyethyl)amino]methyl]pyridine-3-carboxylate (500 mg, 1.73 mmol, 1 equiv), THF (10 mL), di-tert-butyl dicarbonate (416 mg, 1.91 mmol, 1.10 equiv), and $Et_3N$ (350 mg, 3.47 mmol, 2 equiv). The resulting mixture was stirred for 1 h at 25° C. and then concentrated. The residue was purified by silica gel chromatography (EtOAc/pet. ether, 1:3) to afford the title compound as a yellow-green oil (0.55 g, 82% yield). MS: (ES, m/z): 389 $[M+H]^+$.

Step-6: 4-(tert-Butyl) 8-methyl 2,3-dihydropyrido[2,3-f][1,4]oxazepine-4,8(5H)-dicarboxylate

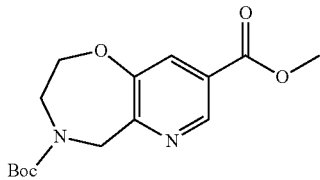 [SMILES: COC(=O)c1cnc2c(c1)OCCN(C(=O)OC(C)(C)C)C2]

Into a 100-mL 3-necked round-bottom flask purged and maintained with an inert atmosphere of nitrogen, was placed Pd(OAc)$_2$ (87 mg, 0.39 mmol, 0.05 equiv), Johnphos (0.184 g, 0.08 equiv), Cs$_2$CO$_3$ (3.784 g, 11.61 mmol, 1.5 equiv) and 1,4-dioxane (30 mL). This was followed by the addition of a solution of methyl 5-bromo-6-(((tert-butoxycarbonyl)(2-hydroxyethyl)amino)methyl)nicotinate (3 g, 7.71 mmol, 1 equiv) in 1,4-dioxane (20 mL). The resulting mixture was stirred for 16 h at 95° C. in an oil bath. The reaction mixture was cooled to room temperature and diluted with EtOAc (50 mL) and H$_2$O (50 mL). The resulting solution was washed with brine (3×50 mL). The organic phase was dried over anhydrous Na$_2$SO$_4$, filtered, and concentrated. The residue was purified by silica gel chromatography (CH$_2$Cl$_2$/MeOH, 20:1) to afford the title compound as an orange solid (1.2 g, 50% yield). MS: (ES, m/z): 309 [M+H]$^+$.

Step-7: Methyl 2,3,4,5-tetrahydropyrido[2,3-f][1,4]oxazepine-8-carboxylate

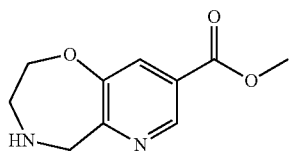

Into a 100-mL round-bottom flask, was placed 4-(tert-butyl) 8-methyl 2,3-dihydropyrido[2,3-f][1,4]oxazepine-4,8(5H)-dicarboxylate (1.2 g, 3.89 mmol, 1 equiv), CH$_2$Cl$_2$ (40 mL) and TFA (5 mL). The resulting solution was stirred for 2 h at 25° C. The pH value of the solution was adjusted to 7-8 with sodium bicarbonate. The solution was dried over anhydrous Na$_2$SO$_4$, filtered, and concentrated. The residue was purified by silica gel chromatography (CH$_2$Cl$_2$/MeOH, 10:1) to afford the title compound as an orange solid (0.6 g, 74% yield). $^1$H-NMR (400 MHz, DMSO-d$_6$) δ(ppm): 8.88 (s, 1H), 7.90 (s, 1H), 4.23 (s, 2H), 4.12-4.08 (t, 2H), 3.94 (s, 3H), 3.30-3.17 (t, 2H). MS: (ES, m/z): 209 [M+H]$^+$.

Step-8: Methyl 4-(cyclohexanecarbonyl)-2,3,4,5-tetrahydropyrido[2,3-f][1,4]oxazepine-8-carboxylate

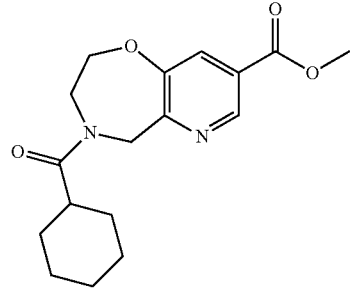 [SMILES: COC(=O)c1cnc2c(c1)OCCN(C(=O)C1CCCCC1)C2]

Into a 25-mL round-bottom flask, was placed methyl 2,3,4,5-tetrahydropyrido[2,3-f][1,4]oxazepine-8-carboxylate (50 mg, 0.24 mmol, 1 equiv), CH$_2$Cl$_2$ (2 mL), cyclohexanecarbonyl chloride (38 mg, 0.26 mmol, 1.1 equiv) and Et$_3$N (72 mg, 0.71 mmol, 3 equiv). The resulting mixture was stirred for 1 h at 25° C. and concentrated. The residue was diluted with water (10 mL) and extracted with CH$_2$Cl$_2$ (3×10 ml). The organic layer was dried over Na$_2$SO$_4$, filtered, and concentrated under vacuum. The residue was purified by silica gel chromatography (EtOAc/pet. ether, 1:3) to afford the title compound as a light yellow oil (60 mg, 78% yield). MS: (ES, m/z): 319 [M+H]$^+$.

Step-9: 4-(Cyclohexanecarbonyl)-N-hydroxy-2,3,4,5-tetrahydropyrido[2,3-f][1,4]oxazepine-8-carboxamide

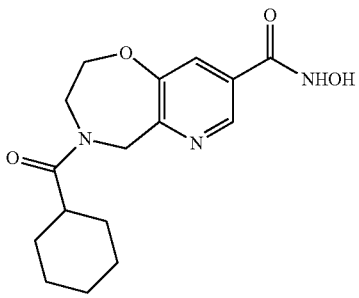

Into a 10-mL round-bottom flask, was placed methyl 4-(cyclohexanecarbonyl)-2,3,4,5-tetrahydropyrido[2,3-f][1,4]oxazepine-8-carboxylate (68 mg, 0.21 mmol, 1 equiv), THF/MeOH (4:1, 2.5 mL), aq. 1N NaOH (0.428 mL, 2 equiv) and NH$_2$OH (50% in water, 0.212 mL, 30 equiv). The resulting solution was stirred for 1 h at 25° C. The pH value of the solution was adjusted to 6 with 1N HCl. The crude product was purified by Prep-HPLC (Column: HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254, 220 nm) to afford the title compound as an off-white solid (47 mg, 70% yield). $^1$H-NMR (300 MHz, DMSO-d$_6$) δ(ppm): 11.34 (s, 1H), 8.53 (d, 1H), 8.48 (d, 1H), 4.84 (d, 2H), 4.64 (s, 1H), 4.54 (t, 1H), 3.88 (m, 2H), 2.62 (s, 1H), 1.52 (s, 4H), 1.37 (s, 1H), 1.06-1.26 (m, 5H). MS: (ES, m/z): 320 [M+H]$^+$.

Example 59

Preparation of 4-(cyclohexanecarbonyl)-N-hydroxy-2,3,4,5-tetrahydropyrido[3,2-f][1,4]oxazepine-8-carboxamide

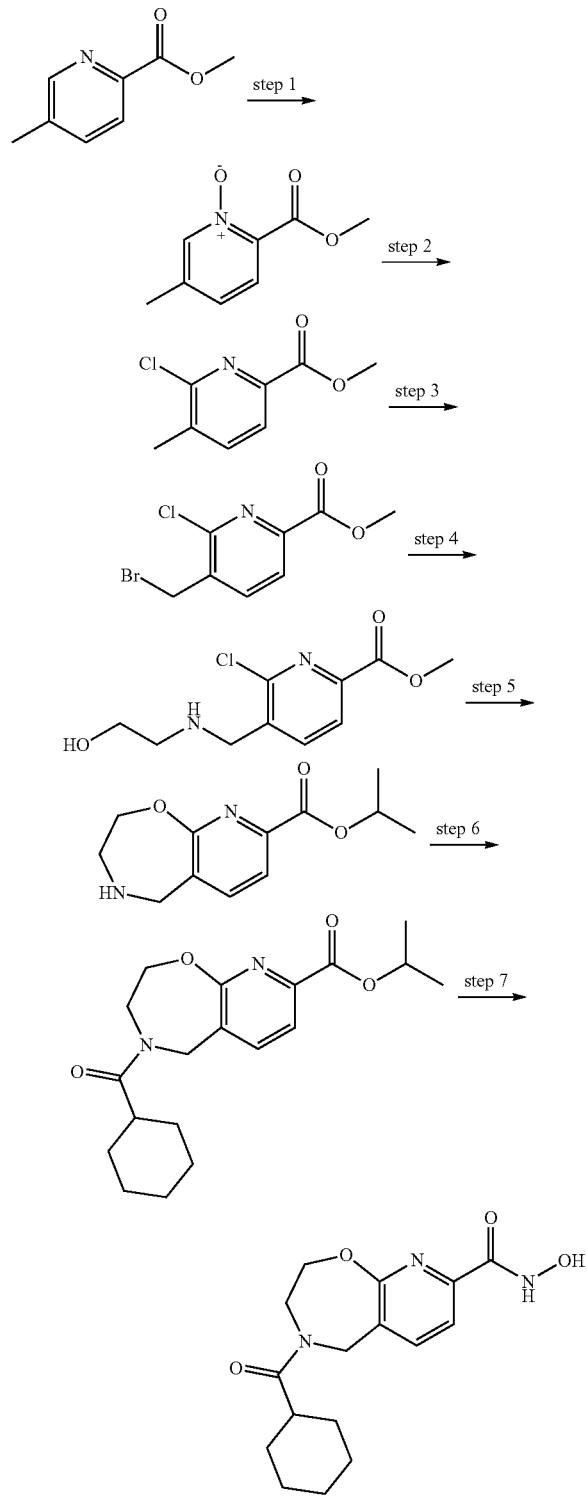

Step-1: 2-(Methoxycarbonyl)-5-methylpyridine 1-oxide

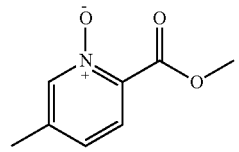

Into a 3 L 3-necked round-bottom flask, was placed methyl 5-methylpicolinate (43.7 g, 289 mmol, 1 equiv) and $CH_2Cl_2$ (1 L). This was followed by the addition of 3-chlorobenzene-1-carboperoxoic acid (106 g, 614 mmol, 2 equiv) in several batches at 0° C. The resulting mixture was stirred for overnight at room temperature. The reaction was then quenched with sat. aq. $Na_2SO_3$ (500 mL) and extracted with $CH_2Cl_2$ (3×100 mL) The combined organic layers were washed with sat. aq. $NaHCO_3$ solution (400 mL), dried over anhydrous $Na_2SO_4$, filtered, and concentrated under vacuum. The crude product was re-crystallized from pet. ether:$CH_2Cl_2$ (20:1) to afford the title compound as a yellow solid (40 g, 83% yield). MS: (ES, m/z): 168 $[M+H]^+$.

Step-2: Methyl 6-chloro-5-methylpyridine-2-carboxylate

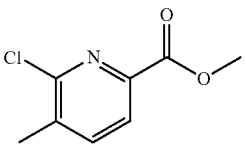

Into a 100-mL round-bottom flask, was placed 2-(methoxycarbonyl)-5-methylpyridine 1-oxide (10 g, 59.82 mmol, 1 equiv) and chloroform (50 mL), followed by the addition of phosphoroyl trichloride (42.2 mL, 9 equiv) dropwise with stirring. The resulting solution was stirred overnight at 80° C. in an oil bath. The resulting mixture was concentrated under vacuum and then quenched with water (20 mL). The pH value of the solution was adjusted to 7 with $K_2CO_3$ (10% in water) and extracted with EtOAc (3×20 mL). The combined organic layers were washed with $H_2O$ (3×20 mL), dried over anhydrous $Na_2SO_4$, filtered, and concentrated under vacuum. The residue was purified by silica gel chromatography (Gradient 0-10% MeOH/$CH_2Cl_2$) to afford the title compound as a yellow solid (7 g, 57% yield). $^1$H-NMR (400 MHz, DMSO-$d_6$) δ(ppm): 7.96-8.02 (m, 2H), 3.88 (s, 1H), 2.41-2.51 (m, 3H). MS: (ES, m/z): 186 $[M+H]^+$.

Step-3: Methyl 5-(bromomethyl)-6-chloropyridine-2-carboxylate

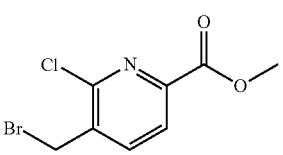

Into a 100-mL round-bottom flask purged and maintained with an inert atmosphere of nitrogen, was placed methyl 6-chloro-5-methylpyridine-2-carboxylate (4.2 g, 22.63 mmol, 1 equiv), benzoyl peroxide (549.9 mg, 2.27 mmol, 0.1 equiv), NBS (4.04 g, 22.70 mmol, 1 equiv) and $CCl_4$ (35 mL). The resulting mixture was stirred overnight at 80° C. in an oil bath. The reaction was concentrated under vacuum and quenched with water (20 mL), then extracted with EtOAc (3×30 mL). The combined organic layers were washed with $H_2O$ (3×20 mL), and dried over anhydrous $Na_2SO_4$, filtered, and concentrated under vacuum. The residue was purified by silica gel chromatography (Gradient 0-10% $MeOH/CH_2Cl_2$) to afford the title compound as a yellow solid (2.5 g, 38% yield). MS: (ES, m/z): 265 $[M+H]^+$.

Step-4: Methyl 6-chloro-5-(((2-hydroxyethyl)amino)methyl)picolinate

Into a 50-mL round-bottom flask, was placed a solution of 2-aminoethan-1-ol (1.4 g, 22.89 mmol, 2 equiv) in MeCN (20 mL) and $K_2CO_3$ (4.74 g, 34.03 mmol, 3 equiv). This was followed by the addition of a solution of methyl 5-(bromomethyl)-6-chloropyridine-2-carboxylate (3 g, 11.34 mmol, 1 equiv) in MeCN (10 mL) dropwise with stirring. The resulting mixture was stirred for 1 h at room temperature. The solids were filtered out. The filtrate was concentrated under vacuum. The residue was purified by silica gel chromatography (Gradient 0-10% $MeOH/CH_2Cl_2$) to afford the title compound as a yellow solid (1.5 g, 49% yield). MS: (ES, m/z): 245 $[M+H]^+$.

Step-5: Isopropyl 2,3,4,5-tetrahydropyrido[3,2-f][1,4]oxazepine-8-carboxylate

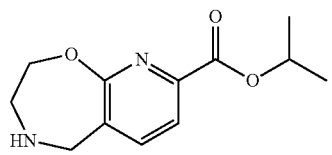 [SMILES: CC(C)OC(=O)c1ccc2c(n1)OCCNC2]

Into 20-mL sealed tube, was placed methyl 6-chloro-5-(((2-hydroxyethyl)amino) methyl)picolinate (1 g, 4.09 mmol, 1 equiv), $K_2CO_3$ (1.103 g, 7.98 mmol, 2 equiv), isopropanol (10 mL) and CuI (156 mg, 0.82 mmol, 0.2 equiv). The resulting solution was stirred overnight at 110° C. in an oil bath. The reaction was then quenched with water (10 mL) and extracted with EtOAc (3×10 mL). The combined organic layers were washed with $H_2O$ (3×10 mL), dried over anhydrous $Na_2SO_4$, filtered, and concentrated under vacuum. The residue purified by silica gel chromatography (Gradient 0-10% $MeOH/CH_2Cl_2$) to afford the title compound as a green solid (148 mg, 14% yield). MS: (ES, m/z): 237 $[M+H]^+$.

Step-6: Isopropyl 4-(cyclohexanecarbonyl)-2,3,4,5-tetrahydropyrido[3,2-f][1,4]oxazepine-8-carboxylate

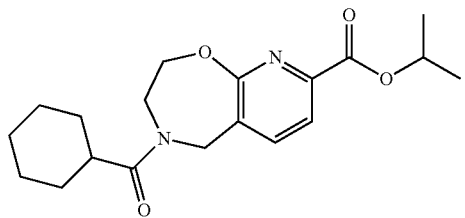 [SMILES: CC(C)OC(=O)c1ccc2c(n1)OCCN(C(=O)C1CCCCC1)C2]

Into a 10-mL round-bottom flask, was placed isopropyl 2,3,4,5-tetrahydropyrido[3,2-f][1,4]oxazepine-8-carboxylate (38 mg, 0.16 mmol, 1 equiv), cyclohexanecarbonyl chloride (24.88 mg, 0.17 mmol, 1.05 equiv), $CH_2Cl_2$ (10 mL) and $Et_3N$ (18 mg, 0.18 mmol, 1.1 equiv). The resulting mixture was stirred for 2 h at 0° C. The reaction was then quenched with water (10 mL) and extracted with EtOAc (3×20 mL). The combined organic layers were washed with $H_2O$ (3×20 mL), dried over anhydrous $Na_2SO_4$, filtered, and concentrated under vacuum. The residue purified by silica gel chromatography (Gradient 0-10% $MeOH/CH_2Cl_2$) to afford the title compound as a white solid (20 mg, 32% yield). MS: (ES, m/z): 347 $[M+H]^+$.

Step-7: 4-(Cyclohexanecarbonyl)-N-hydroxy-2,3,4,5-tetrahydropyrido[3,2-f][1,4]oxazepine-8-carboxamide

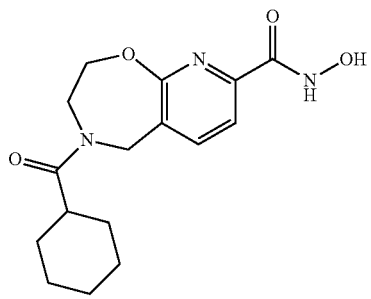 [SMILES: O=C(NO)c1ccc2c(n1)OCCN(C(=O)C1CCCCC1)C2]

Into a 8-mL vial, was placed a solution of isopropyl 4-(cyclohexanecarbonyl)-2,3,4,5-tetrahydropyrido[3,2-f][1,4]oxazepine-8-carboxylate (18 mg, 0.05 mmol, 1 equiv) in THF/MeOH (2 mL, 4:1), $NH_2OH$ (50% in water, 604 mg, 9.15 mmol, 176 equiv), aq. 1N NaOH (0.104 mL, 2 equiv). The resulting mixture was stirred for 1 h at room temperature, then cooled to 0° C. and the pH value of the solution was adjusted to 6 with 6N HCl. The crude product was purified by Prep-HPLC (Column HSS C18 OBD, 1.8 μm, 2.1×50 mm; Mobile Phase A: Water/0.05% TFA; Mobile Phase B: MeCN/0.05% TFA; Flow rate: 0.7 mL/min; Gradient: 5% B to 95% B in 2 min, hold 0.6 min; Detector: UV 254, 220 nm) to afford the title compound as a pink solid (8 mg, 37% yield). $^1$H-NMR (300 MHz, DMSO-$d_6$) δ(ppm): 11.21 (s, 1H), 8.96-9.02 (br s, 1H), 8.03-8.05 (d, J=8 Hz, 1H), 7.64-7.62 (d, J=8 Hz, 1H), 7.60-7.66 (dd, $J_1$=8 Hz, $J_2$=16 Hz, 1H), 4.80 (s, 1H), 4.65 (s, 1H), 4.36-4.39 (d, J=8 Hz, 2H), 3.84-3.94 (d, J=8 HZ, 2H), 2.61-2.67 (m, 1H), 1.60-1.65 (m, 4H), 1.04-1.38 (m, 6H). MS: (ES, m/z): 320 $[M+H]^+$.

Example 60

Preparation of N-hydroxy-8-(tetrahydro-2H-pyran-4-carbonyl)-6,7,8,9-tetrahydropyrazino[2,3-f][1,4]oxazepine-3-carboxamide

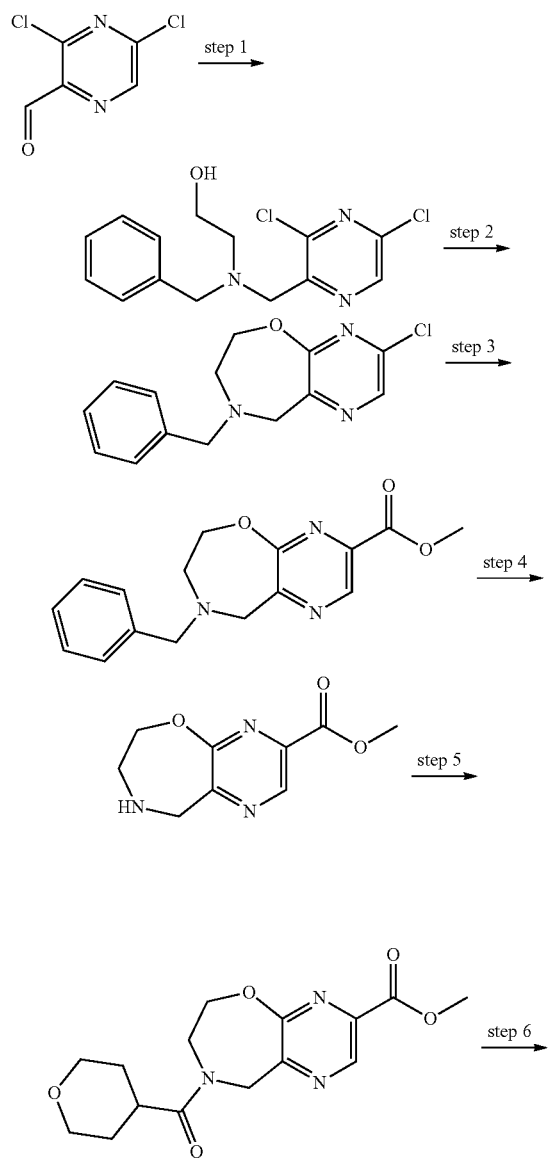

Step-1: 2-(Benzyl((3,5-dichloropyrazin-2-yl)methyl)amino)ethan-1-ol

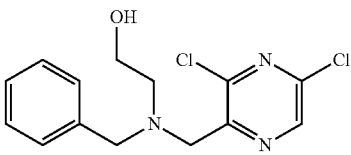 [SMILES: OCCN(Cc1ccccc1)Cc1ncc(Cl)nc1Cl]

Into a 500-mL round-bottom flask, was placed 3,5-dichloropyrazine-2-carbaldehyde (8 g, 45.20 mmol, 1 equiv), 2-(benzylamino)ethan-1-ol (6.85 g, 45.32 mmol, 1 equiv), acetic acid (13 mL), and THF (200 mL). The solution was stirred at room temperature for 30 min. To this was added sodium triacetoxyborohydride (19.25 g, 2 equiv) in portions at 0° C. The resulting solution was stirred overnight at room temperature. The reaction was then quenched with H₂O (50 mL), and extracted with EtOAc (3×50 mL). The combined organic layers were washed with brine (2×50 mL), dried over anhydrous Na₂SO₄, filtered and concentrated under vacuum. The residue was purified by silica gel chromatography (EtOAc/pet. ether, 4:1) to afford the title compound as a red oil (6.71 g, 48% yield). MS: (ES, m/z): 312 [M+H]⁺.

Step-2: 8-Benzyl-3-chloro-6,7,8,9-tetrahydropyrazino[2,3-f][1,4]oxazepine

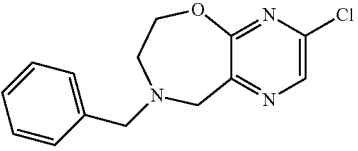 [SMILES: Clc1cnc2c(n1)OCCN(Cc1ccccc1)C2]

Into a 250-mL round-bottom flask, was placed 2-(benzyl((3,5-dichloropyrazin-2-yl)methyl)amino)ethan-1-ol (6.7 g, 21.46 mmol, 1 equiv) in THF (200 mL). This was followed by the addition of t-BuOK (2.88 g, 1.2 equiv) in portions at 0° C. The resulting solution was stirred for 3 h at 0° C. in an ice bath. The reaction was then quenched H₂O (30 mL), and extracted with EtOAc (3×50 mL). The combined organic layers were washed with brine (2×50 mL), dried over anhydrous Na₂SO₄, filtered and concentrated under vacuum. The residue was purified by silica gel chromatography (EtOAc/pet. ether, 1:3) to afford the title compound as a brown oil (3.2 g, 54% yield). MS: (ES, m/z): 276 [M+H]⁺.

Step-3: Methyl 8-benzyl-6,7,8,9-tetrahydropyrazino[2,3-f][1,4]oxazepine-3-carboxylate

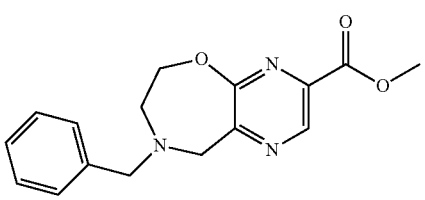 [SMILES: COC(=O)c1cnc2c(n1)OCCN(Cc1ccccc1)C2]

Into a 20-mL pressure tank reactor, was placed 8-benzyl-3-chloro-6,7,8,9-tetrahydropyrazino[2,3-f][1,4]oxazepine (2 g, 7.25 mmol, 1 equiv) in MeOH (10 mL), Et₃N (2.2 g, 21.74 mmol, 3 equiv) and Pd(dppf)Cl₂ (520 mg, 0.71 mmol, 0.1 equiv). To the above CO (g) (30 atm) was introduced in. The resulting solution was stirred overnight at 90° C. in an oil bath. The resulting mixture was concentrated under vacuum. The residue was purified by silica gel chromatography (EtOAc/pet. ether, 1:2) to afford the title compound as a yellow oil (1.7 g, 78% yield). MS: (ES, m/z): 300 [M+H]⁺.

Step-4: Methyl 6,7,8,9-tetrahydropyrazino[2,3-f][1,4]oxazepine-3-carboxylate

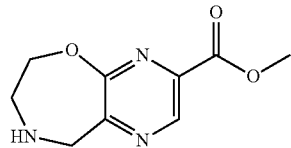

Into a 250-mL 3-necked round-bottom flask purged and maintained with an inert atmosphere of nitrogen, was placed methyl 8-benzyl-6,7,8,9-tetrahydropyrazino[2,3-f][1,4]oxazepine-3-carboxylate (800 mg, 2.67 mmol, 1 equiv) in 1,2-dichloroethane (30 mL). This was followed by the slow addition of chloro(1-chloroethoxy)methanone (800 mg, 5.60 mmol, 2.09 equiv) at 0° C. over 10 min. The resulting solution was stirred for 4 h at 80° C. in an oil bath. The mixture was concentrated under vacuum. Then to this was added MeOH (50 mL). The resulting solution was stirred for 1 h at 80° C. in an oil bath. The solids were collected by filtration. The crude product was purified by re-crystallization from MeOH to afford the title compound as a white solid (500 mg, 89% yield). MS: (ES, m/z): 210 [M+H]⁺.

Step-5: Methyl 8-(tetrahydro-2H-pyran-4-carbonyl)-6,7,8,9-tetrahydropyrazino[2,3-f][1,4]oxazepine-3-carboxylate

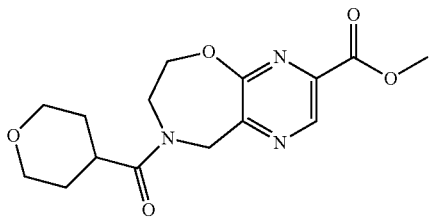 [SMILES: COC(=O)c1cnc2c(n1)OCCN(C(=O)C1CCOCC1)C2]

Into a 8-mL vial, was placed methyl 6,7,8,9-tetrahydropyrazino[2,3-f][1,4]oxazepine-3-carboxylate (100 mg, 0.48 mmol, 1 equiv), Et₃N (144.8 mg, 1.43 mmol, 2.98 equiv), CH₂Cl₂ (2 mL). To this was added oxane-4-carbonyl chloride (141.6 mg) dropwise with stirring at 0° C. The resulting solution was stirred for 2 h at room temperature. The resulting mixture was concentrated under vacuum. The residue was purified by silica gel chromatography (EtOAc/pet. ether, 1:3) to afford the title compound as a green solid (80 mg, 52% yield). MS: (ES, m/z): 322 [M+H]⁺.

Step-6: N-Hydroxy-8-(tetrahydro-2H-pyran-4-carbonyl)-6,7,8,9-tetrahydropyrazino[2,3-f][1,4]oxazepine-3-carboxamide

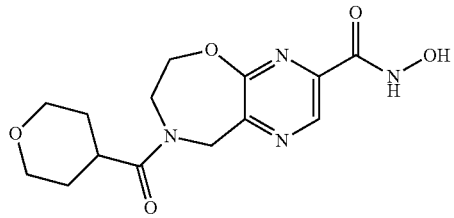 [SMILES: O=C(NO)c1cnc2c(n1)OCCN(C(=O)C1CCOCC1)C2]

Into a 8-mL vial, was placed methyl 8-(tetrahydro-2H-pyran-4-carbonyl)-6,7,8,9-tetrahydropyrazino[2,3-f][1,4]oxazepine-3-carboxylate (80 mg, 0.25 mmol, 1 equiv), THF/MeOH (4:1, 1.5 mL), NH₂OH (50% in water, 1.97 g, 29.85 mmol, 120 equiv), aq. 1N NaOH (0.50 mL, 0.50 mmol, 2 equiv). The resulting solution was stirred for 1 h at room temperature. The pH value of the solution was adjusted to 6 with 6N HCl at 0° C. The crude product was purified by Prep-HPLC (Column: Xbridge Prep C18 OBD, 5 μm, 19×50 mm; Mobile Phase A: Water/0.05% formic acid; Mobile Phase B: MeCN; Flow rate: 0.7 mL/min; Gradient: 5% B to 20% B in 7 min; Detector, UV 254, 220 nm) to afford the title compound as a white solid (34 mg, 38% yield). ¹H-NMR (400 MHz, DMSO-d₆) δ(ppm): 11.45 (br s, 1H), 9.19 (br s,1H),8.71-8.68 (m, 1H), 5.02 (s, 1H), 4.91 (s, 1H), 4.63-4.57 (m, 2H), 4.03-4.00 (m, 1H), 3.93-3.90 (m, 1H), 3.84-3.77 (m, 2H), 3.41-3.31 (m, 1H), 3.28-3.25 (m, 1H), 2.99-2.82 (m, 1H), 1.56-1.45 (m, 3H), 1.28-1.25 (m, 1H). MS: (ES, m/z): 323 [M+H]⁺.

TABLE 33

The following compound was prepared according to the method of Example 60.

| Structure | Found M + H | ¹H-NMR (400 MHz, DMSO-d₆) δ(ppm) |
|---|---|---|
| | (ES, m/z): 321 [M + H]⁺ | 11.52 (br s, 1H), 8.71-8.67 (d, 1H), 4.97 (s, 1H), 4.90 (s, 1H), 4.63-4.56 (m, 2H), 3.99-3.89 (m, 2H), 2.66-2.62 (m, 1H), 1.69-1.60 (m, 4H), 1.35-1.11 (m, 6H) |

Example 61

Preparation of N-hydroxy-4-(4-methoxybenzoyl)-2-oxo-2,3,4,5-tetrahydro-1H-benzo[e][1,4]diazepine-7-carboxamide

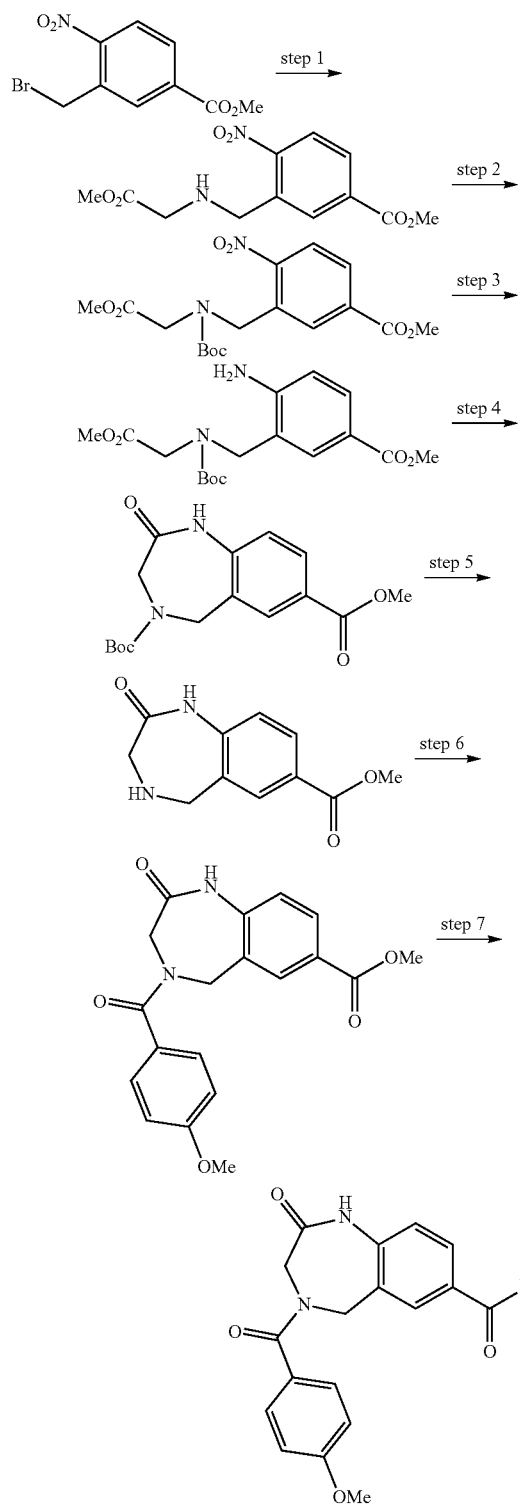

Step-1: Methyl 3-(((2-methoxy-2-oxoethyl)amino)methyl)-4-nitrobenzoate

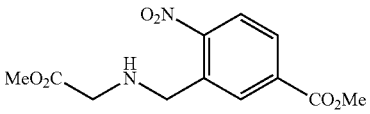 [SMILES: COC(=O)CNCc1cc(C(=O)OC)ccc1[N+](=O)[O-]]

Into a 250-mL round-bottom flask that has been purged and maintained with an inert atmosphere of nitrogen, were placed methyl 2-aminoacetate (12 g, 135 mmol, 1.5 equiv), methyl 3-(bromomethyl)-4-nitrobenzoate (12 g, 26 mmol, 1 equiv), DIEA (32 mL, 3 equiv) and DMF (120 mL). The resulting solution was stirred for 12 h at room temperature. The reaction was then quenched by the addition of water. The resulting solution was extracted with EtOAc (3×100 mL) and the combined organic layer was washed with brine (100 mL). The organic mixture was dried over anhydrous $Na_2SO_4$, filtered, and concentrated under vacuum. The residue was purified by silica gel chromatography (Gradient 1:10 to 1:1 EtOAc/hexanes) to afford the title compound as a yellow solid (4.9 g, 66% yield). MS: (ES, m/z): 283 $[M+H]^+$.

Step-2: Methyl 3-(((tert-butoxycarbonyl)(2-methoxy-2-oxoethyl)amino)methyl)-4-nitrobenzoate

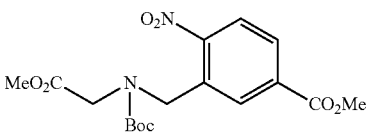

Into a 100-mL round-bottom flask, were placed methyl 3-(((2-methoxy-2-oxoethyl)amino)methyl)-4-nitrobenzoate (4.7 g, 16.8 mmol, 1 equiv), $CH_2Cl_2$ (100 mL), di-tert-butyl dicarbonate (4.4 g, 20.2 mmol, 1.2 equiv) and 4-dimethylaminopyridine (82 mg, 0.67 mmol, 0.04 equiv). The resulting solution was stirred for 4 h at room temperature. The resulting mixture was concentrated under vacuum. The residue was purified by silica gel chromatography (Gradient 1:10 to 1:1 EtOAc/petroleum ether) to afford the title compound as a yellow oil (2.8 g, 44% yield). MS: (ES, m/z): 283 $[M-Boc+H]^+$.

Step-3: Methyl 4-amino-3-(((tert-butoxycarbonyl)(2-methoxy-2-oxoethyl)amino)methyl)benzoate

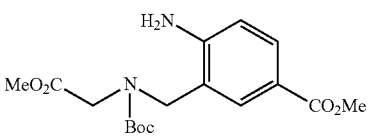 [SMILES: COC(=O)CN(Cc1cc(C(=O)OC)ccc1[N+](=O)[O-])C(=O)OC(C)(C)C]

Into a 100-mL round-bottom flask, were placed methyl 3-(((tert-butoxycarbonyl)(2-methoxy-2-oxoethyl)amino)methyl)-4-nitrobenzoate (2.8 g, 7.3 mmol, 1 equiv), MeOH (30 mL) and palladium on carbon (280 mg). The resulting solution was stirred for 18 h at room temperature under a $H_2$ balloon. The solids were filtered out and the filtrate was Step-4: 4-(tert-Butyl) 7-methyl 2-oxo-1,2,3,5-tetrahydro-4H-benzo[e][1,4]diazepine-4,7-dicarboxylate

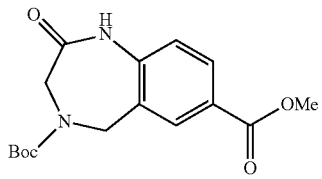 [SMILES: COC(=O)c1ccc2c(c1)CN(C(=O)OC(C)(C)C)CC(=O)N2]

Into a 250-mL round-bottom flask that has been purged and maintained with an inert atmosphere of nitrogen, were placed methyl 4-amino-3-(((tert-butoxycarbonyl)(2-methoxy-2-oxoethyl)amino)methyl)benzoate (1.9 g, 7.5 mmol, 1 equiv), THF (100 mL) and sodium hydride (239 mg, 10 mmol, 1.3 equiv). The resulting solution was stirred for 4 h at room temperature. The reaction mixture was poured into water/ice and extracted with EtOAc (3×150 mL). The combined organic layers was washed with brine (100 mL), dried over anhydrous $Na_2SO_4$, filtered, and concentrated under vacuum. The crude product was recrystallized from diethyl ether to afford the title compound as a white solid (0.5 g, 21% yield). $^1$H-NMR (400 MHz, $CDCl_3$) δ(ppm): 10.34-10.41 (m, 1H), 7.76-7.79 (m, 2H), 7.17-7.20 (m, 1H), 4.27-4.53 (m, 4H), 3.82 (s, 3H), 1.34 (s, 3H), 1.20 (s, 6H).

Step-5: Methyl 2-oxo-2,3,4,5-tetrahydro-1H-benzo[e][1,4]diazepine-7-carboxylate

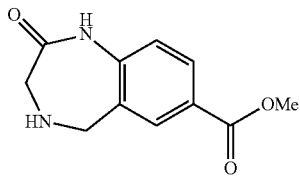 [SMILES: COC(=O)c1ccc2c(c1)CNCC(=O)N2]

Into a 500-mL round-bottom flask that has been purged and maintained with an inert atmosphere of nitrogen, were placed 4-(tert-butyl) 7-methyl 2-oxo-1,2,3,5-tetrahydro-4H-benzo[e][1,4]diazepine-4,7-dicarboxylate (12 g, 37 mmol, 1 equiv) and 4N HCl in dioxane (360 mL). The resulting solution was stirred for 6 h at room temperature. The resulting mixture was concentrated under vacuum and washed with diethyl ether (300 mL) to afford the title compound as the HCl salt as a white solid (9.5 g, 99% yield). MS: (ES, m/z): 221 [M+H]$^+$.

Step-6: Methyl 4-(4-methoxybenzoyl)-2-oxo-2,3,4,5-tetrahydro-1H-benzo[e][1,4]diazepine-7-carboxylate

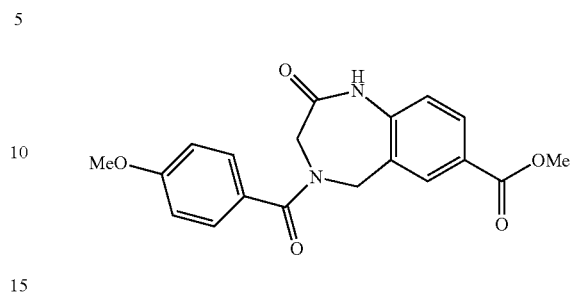

To a solution of 4-methoxybenzoic acid (20 mg, 0.136 mmol, 1 equiv) in 1,2-dichloroethane (1.4 mL) were added DMC (27.7 mg, 0.164 mmol, 1.2 equiv), DIEA (60 μL, 0.341 mmol, 2.5 equiv) and methyl 2-oxo-2,3,4,5-tetrahydro-1H-benzo[e][1,4]diazepine-7-carboxylate hydrochloride (35 mg, 0.136 mmol, 1 equiv). The reaction mixture was stirred at room temperature overnight. The reaction mixture was partitioned between $CH_2Cl_2$ and water. The layers were separated. The organic layer was washed with brine, and dried over anhydrous $Na_2SO_4$. The solution was filtered, and concentrated. This crude material was purified by silica gel chromatography (Gradient 20-80% EtOAc/hexanes) to afford the title compound as a white solid (29.7 mg, 62% yield). MS: (ES, m/z): 355 [M+H]$^+$.

Step-7: N-Hydroxy-4-(4-methoxybenzoyl)-2-oxo-2,3,4,5-tetrahydro-1H-benzo[e][1,4]diazepine-7-carboxamide

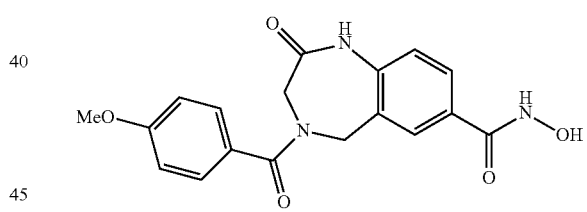

To a solution of methyl 4-(4-methoxybenzoyl)-2-oxo-2,3,4,5-tetrahydro-1H-benzo[e][1,4]diazepine-7-carboxylate (29 mg, 0.082 mmol, 1 equiv) in MeOH/THF (1:4, 1.6 mL) were added $NH_2OH$ (50% in $H_2O$, 200 μL, 3.27 mmol, 40 equiv) and aq. 2N NaOH (82 μL, 0.164 mmol, 2 equiv). The reaction was stirred at room temperature overnight. Additional $NH_2OH$ (50% in $H_2O$, 90 μL) and aq. 2N NaOH (90 μL) were added and the reaction was stirred at 30° C. for 2 days. The reaction was acidified with 2N HCl. The mixture was concentrated and the residue was purified by Prep-HPLC (Column XBridge RP C18 OBD, 5 μM, 19×50 mm; Mobile Phase A: Water/0.1% Formic Acid; Mobile Phase B: MeCN/0.1% Formic Acid; Flow rate: 20 mL/min; Gradient: 5% B to 70% B in 7 min; Detector: UV 254, 220 nm) to afford the title compound as a white solid (4.9 mg, 17% yield). $^1$H-NMR (300 MHz, DMSO-$d_6$) δ(ppm): 11.10 (br s, 1H), 10.40 (br s, 1H), 9.02 (br s, 1H), 7.76 (br s, 1H), 7.56-7.66 (m, 1H), 7.31 (br d, J=8.8 Hz, 2H), 7.11 (d, J=8.5 Hz, 1H), 6.95 (br d, J=8.8 Hz, 2H), 4.65 (s, 2H), 4.28 (br s, 2H), 3.76 (s, 3H). MS: (ES, m/z): 356 [M+H]$^+$.

concentrated under reduced pressure to afford the title compound as a brown oil (1.9 g, 74% yield). MS: (ES, m/z): 253 [M-Boc+H]$^+$.

TABLE 34

The following compound was prepared according to the method of Example 61.

| Structure | Found M + H | ¹H-NMR (400 MHz, DMSO-d$_6$) δ(ppm) |
|---|---|---|
| | (ES, m/z): 370 [M + H]⁺ | 11.15 (br s, 1H), 10.26 (br s, 1H), 9 (br s, 1H), 7.70-7.75 (m, 1H), 7.51-7.65 (m, 1H), 6.94-7.14 (m, 3H), 6.72-6.79 (m, 2H), 4.75 (s, 1H), 4.53 (s, 1H), 4.42 (s, 1H), 4.35 (s, 1H), 3.67 (s, 3H), 3.58-3.64 (m, 2H) |
| | (ES, m/z): 318 [M + H]⁺ | |

Example 62

Preparation of 4-Cyclohexanecarbonyl-N-hydroxy-2-oxo-2,3,4,5-tetrahydro-1H-1,4-benzodiazepine-7-carboxamide Step-1: Methyl 4-(cyclohexanecarbonyl)-2-oxo-2,3,4,5-tetrahydro-1H-benzo[e][1,4]diazepine-7-carboxylate

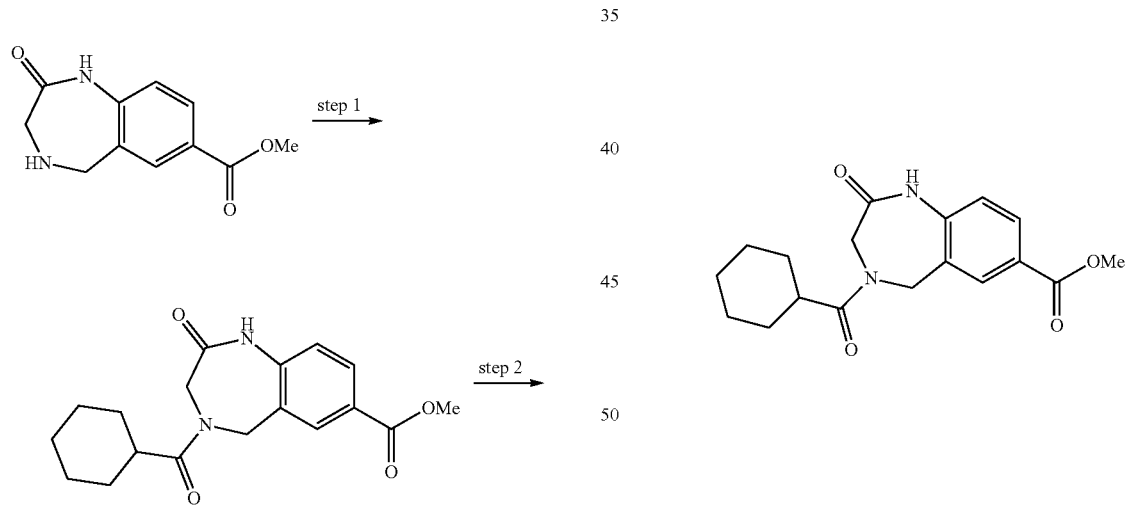

To a solution of methyl 2-oxo-2,3,4,5-tetrahydro-1H-benzo[e][1,4]diazepine-7-carboxylate (62.5 mg, 0.284 mmol, 1 equiv) in DMF (1.5 mL) was added cyclohexanecarboxylic acid (38.2 mg, 0.298 mmol, 1.05 equiv), DIEA (149 μL, 0.851 mmol, 3 equiv) and HBTU (124 mg, 0.326 mmol, 1.1 equiv). The reaction mixture was stirred at room temperature for 3 h. Water was added and the precipitate that formed was collected by filtration to afford the title compound (94 mg) which was used without further purification. MS: (ES, m/z): 331 [M+H]⁺.

Step-2: 4-Cyclohexanecarbonyl-N-hydroxy-2-oxo-2,3,4,5-tetrahydro-1H-1,4-benzodiazepine-7-carboxamide

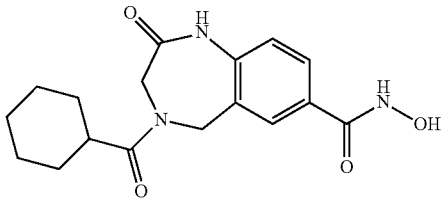 [SMILES: O=C1CN(C(=O)C2CCCCC2)Cc2cc(C(=O)NO)ccc2N1]

To a solution of methyl 4-(cyclohexanecarbonyl)-2-oxo-2,3,4,5-tetrahydro-1H-benzo[e][1,4]diazepine-7-carboxylate (94 mg, 0.285 mmol) in MeOH (750 µL) and THF (3 mL) was added NH₂OH (50% in H₂O, 1.48 mL, 24.2 mmol, 85 equiv) and aq. 2N NaOH (285 µL, 0.569 mmol, 2 equiv). The reaction was stirred at room temperature for 2 h and was directly purified by Prep-HPLC (Column XBridge RP C18 OBD, 5 µM, 19×50 mm; Mobile Phase A: Water/0.1% Formic Acid; Mobile Phase B: MeCN/0.1% Formic Acid; Flow rate: 20 mL/min; Gradient: 2% B to 50% B in 7 min; Detector: UV 254, 220 nm) to afford the title compound (1.7 mg, 2% yield over 2 steps). MS: (ES, m/z): 332 [M+H]⁺.

Example 63

Preparation of 4-(cyclohexanecarbonyl)-N-hydroxy-2,3,4,5-tetrahydrobenzo[f][1,4]oxazepine-8-carboxamide

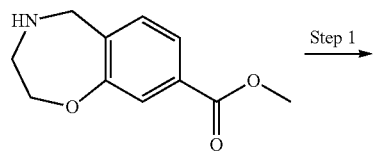

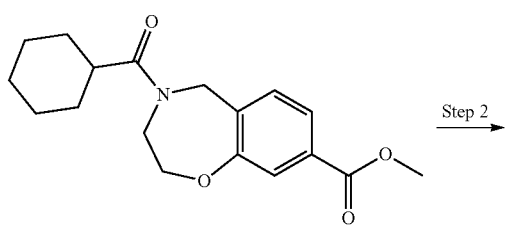

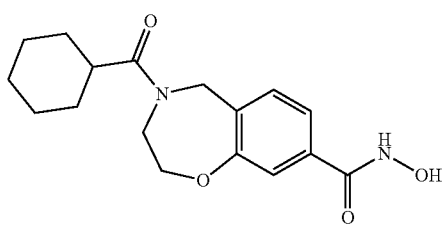

Step-1: Methyl 4-(cyclohexanecarbonyl)-2,3,4,5-tetrahydrobenzo[f][1,4]oxazepine-8-carboxylate

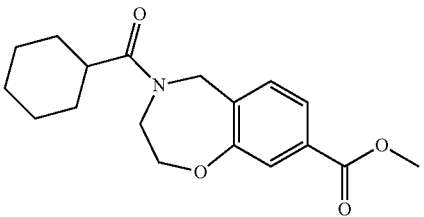 [SMILES: COC(=O)c1ccc2c(c1)OCCN(C(=O)C1CCCCC1)C2]

A 2 mL reaction vial was charged with methyl 2,3,4,5-tetrahydrobenzo[f][1,4]oxazepine-8-carboxylate (0.2M in 1,2-dichloroethane, 150 µL, 30 µmol) and cyclohexanecarboxylic acid (0.2M in N,N-dimethylacetamide/10% Et₃N, 165 µL, 33 µmol). A solution of DMC (0.2M in 1,2-dichloroethane, 165 µL, 33 µmol) was added and the vial was sealed and shaken at room temperature overnight. The reaction mixture was diluted with brine (500 µL) and extracted with EtOAc (2×600 µL). The combined organic layers were evaporated to dryness under reduced pressure.

Step-2: 4-(Cyclohexanecarbonyl)-N-hydroxy-2,3,4,5-tetrahydrobenzo[f][1,4]oxazepine-8-carboxamide

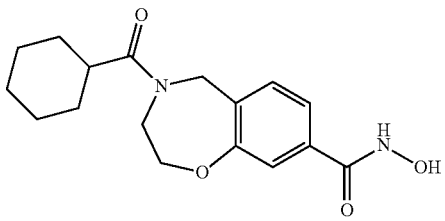 [SMILES: O=C(NO)c1ccc2c(c1)OCCN(C(=O)C1CCCCC1)C2]

Mixed solvent of THF/MeOH (3:1, 180 µL) was added to the vial of methyl 4-(cyclohexanecarbonyl)-2,3,4,5-tetrahydrobenzo[f][1,4]oxazepine-8-carboxylate and it was shaken at 50° C. for 15 min to dissolve the residue. NH₂OH (50% in water, 125 µL) was added followed by aq. 1N NaOH (85 µL) and the vial was sealed and shaken at room temperature overnight. The solvent was evaporated under reduce pressure and the residue was dissolved in DMSO (500 µL) then purified by HPLC to yield the title compound (1.9 mg, 30% yield). MS: (ES, m/z): 319 [M+H]⁺.

TABLE 35

The following compounds were prepared by the parallel synthesis method of Example 63.

| Structure | Found M + H (ES) |
|---|---|
| ![structure] | 343 |
| ![structure] | 343 |
| ![structure] | 357 |
| ![structure] | 357 |
| ![structure] | 381 |
| ![structure] | 357 |

TABLE 35-continued

The following compounds were prepared by the parallel synthesis method of Example 63.

| Structure | Found M + H (ES) |
|---|---|
| 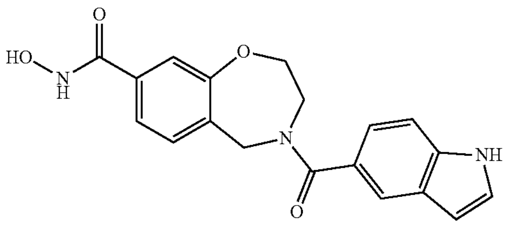 [SMILES: O=C(NO)c1ccc2c(c1)OCCN(C(=O)c1ccc3[nH]ccc3c1)C2] | 352 |
| 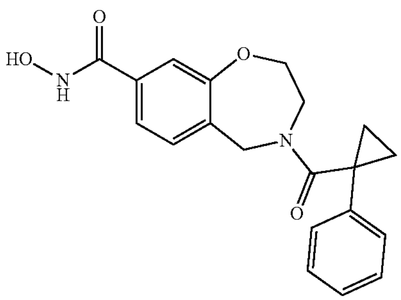 [SMILES: O=C(NO)c1ccc2c(c1)OCCN(C(=O)C1(c3ccccc3)CC1)C2] | 353 |
| 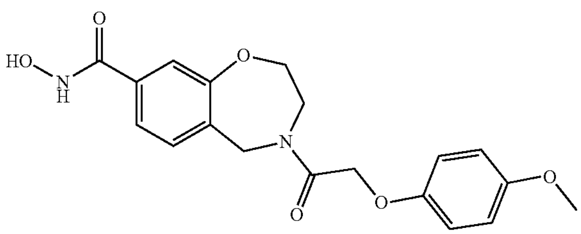 [SMILES: COc1ccc(OCC(=O)N2CCOc3cc(C(=O)NO)ccc3C2)cc1] | 373 |
| 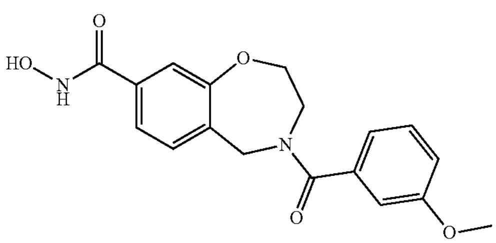 [SMILES: COc1cccc(C(=O)N2CCOc3cc(C(=O)NO)ccc3C2)c1] | 343 |
| 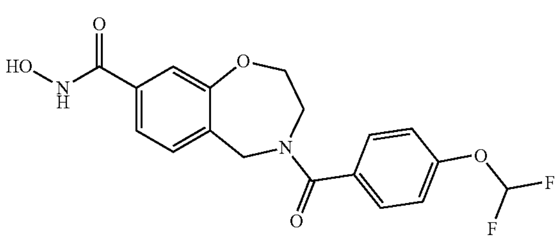 [SMILES: O=C(NO)c1ccc2c(c1)OCCN(C(=O)c1ccc(OC(F)F)cc1)C2] | 379 |
| 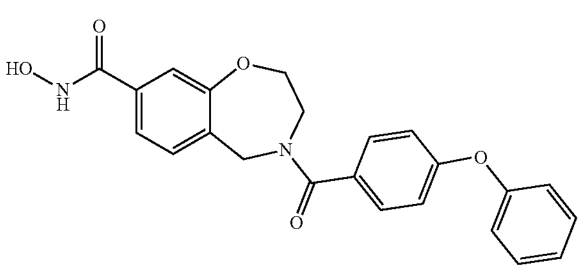 [SMILES: O=C(NO)c1ccc2c(c1)OCCN(C(=O)c1ccc(Oc3ccccc3)cc1)C2] | 405 |

TABLE 35-continued
The following compounds were prepared by the parallel synthesis method of Example 63.
| Structure | Found M + H (ES) |
|---|---|
| 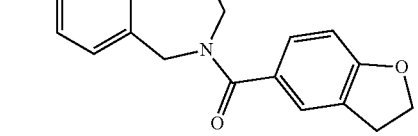 | 355 |
| 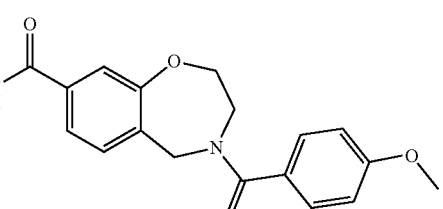 | 373 |
| 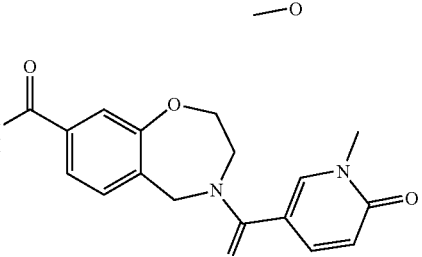 | 344 |
| 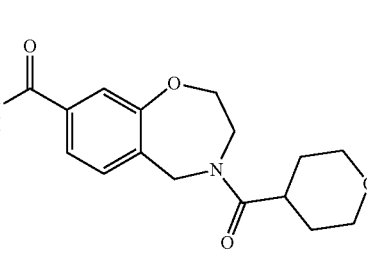 | 321 |
| 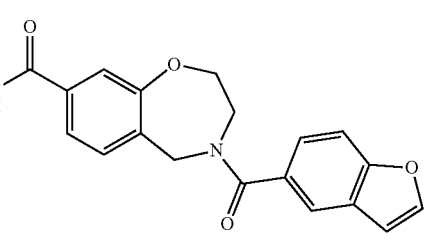 | 353 |
| 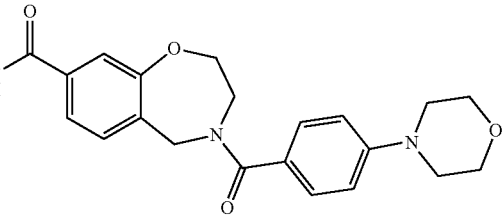 | 398 |

TABLE 35-continued

The following compounds were prepared by the parallel synthesis method of Example 63.

| Structure | Found M + H (ES) |
|---|---|
| 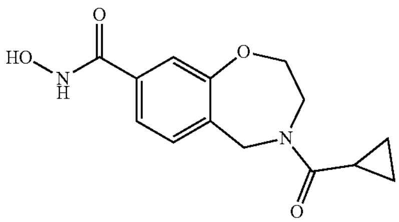 [SMILES: O=C(NO)c1ccc2c(c1)OCCN(C(=O)C1CC1)C2] | 277 |
| 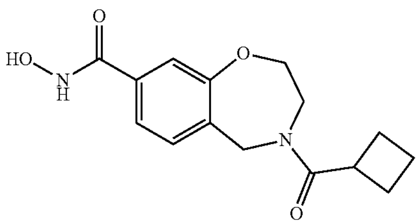 [SMILES: O=C(NO)c1ccc2c(c1)OCCN(C(=O)C1CCC1)C2] | 291 |
| 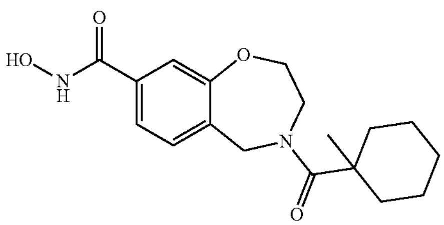 [SMILES: CC1(C(=O)N2CCOc3cc(C(=O)NO)ccc3C2)CCCCC1] | 333 |
| 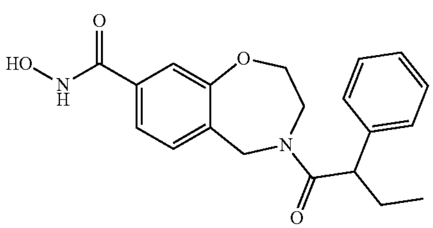 | 355 |
| 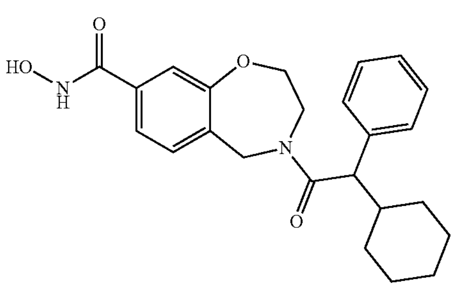 [SMILES: O=C(NO)c1ccc2c(c1)OCCN(C(=O)C(c1ccccc1)C1CCCCC1)C2] | 409 |
| 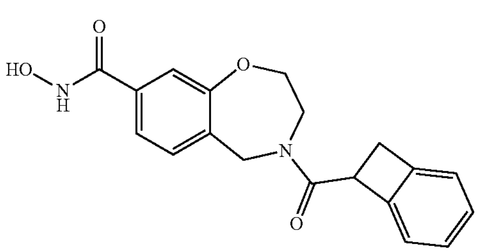 [SMILES: O=C(NO)c1ccc2c(c1)OCCN(C(=O)C1Cc3ccccc31)C2] | 339 |

TABLE 35-continued

The following compounds were prepared by the parallel synthesis method of Example 63.

| Structure | Found M + H (ES) |
|---|---|
| 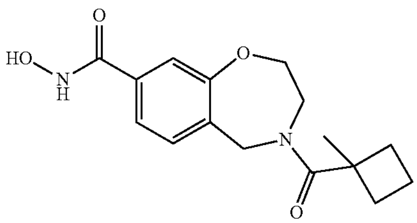 [SMILES: CC1(C(=O)N2CCOc3cc(C(=O)NO)ccc3C2)CCC1] | 305 |
| | 341 |
| | 341 |
| | 341 |
| 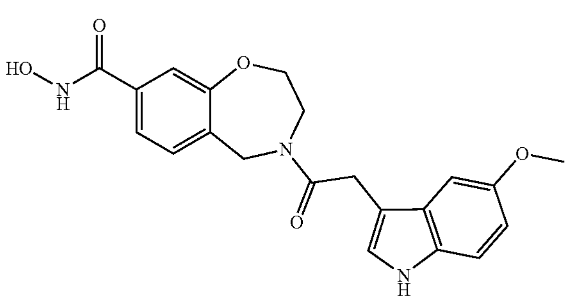 [SMILES: COc1ccc2[nH]cc(CC(=O)N3CCOc4cc(C(=O)NO)ccc4C3)c2c1] | 396 |

TABLE 35-continued

The following compounds were prepared by the parallel synthesis method of Example 63.

| Structure | Found M + H (ES) |
|---|---|
| 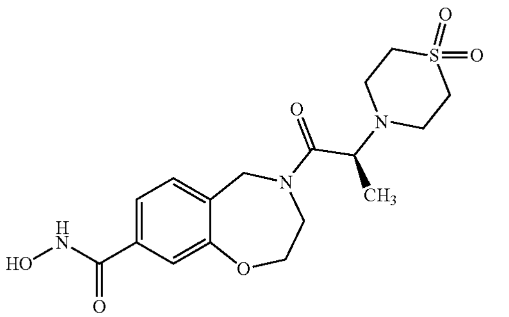 [SMILES: C[C@@H](C(=O)N1CCOc2cc(C(=O)NO)ccc2C1)N1CCS(=O)(=O)CC1] | 398 |
| 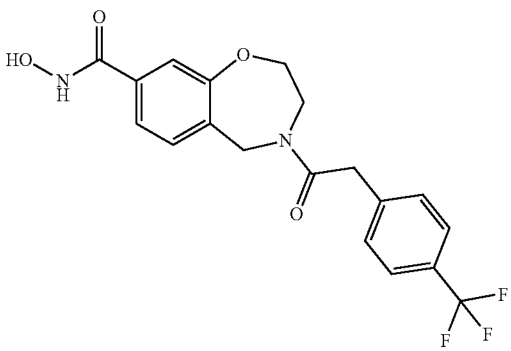 [SMILES: O=C(NO)c1ccc2c(c1)OCCN(C(=O)Cc1ccc(C(F)(F)F)cc1)C2] | 395 |
| 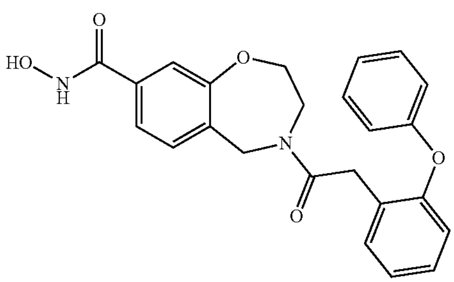 [SMILES: O=C(NO)c1ccc2c(c1)OCCN(C(=O)Cc1ccccc1Oc1ccccc1)C2] | 419 |
| 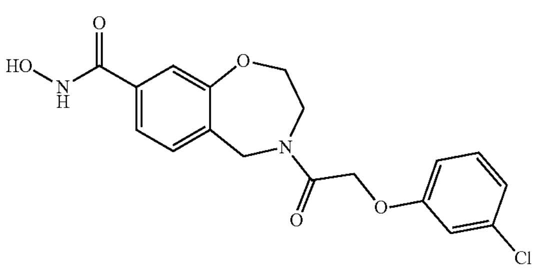 [SMILES: O=C(NO)c1ccc2c(c1)OCCN(C(=O)COc1cccc(Cl)c1)C2] | 377 |
| 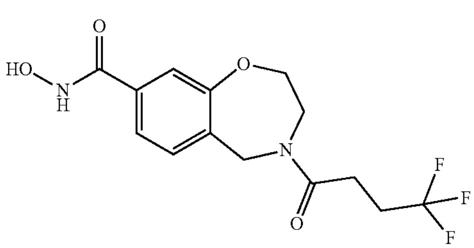 [SMILES: O=C(NO)c1ccc2c(c1)OCCN(C(=O)CCC(F)(F)F)C2] | 333 |

TABLE 35-continued

The following compounds were prepared by the parallel synthesis method of Example 63.

| Structure | Found M + H (ES) |
|---|---|
| 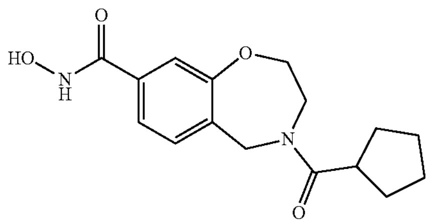 [SMILES: O=C(NO)c1ccc2c(c1)OCCN(C(=O)C1CCCC1)C2] | 305 |
| 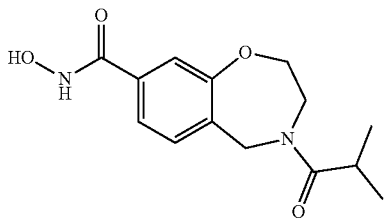 [SMILES: CC(C)C(=O)N1CCOc2cc(C(=O)NO)ccc2C1] | 279 |
| 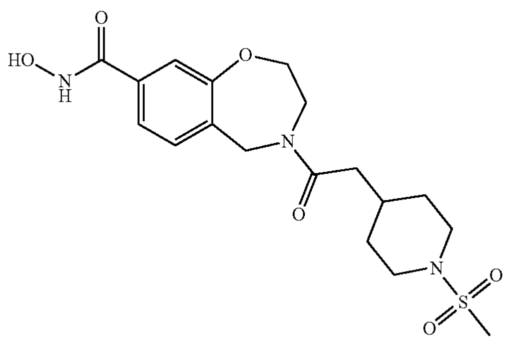 [SMILES: CS(=O)(=O)N1CCC(CC(=O)N2CCOc3cc(C(=O)NO)ccc3C2)CC1] | 412 |
| 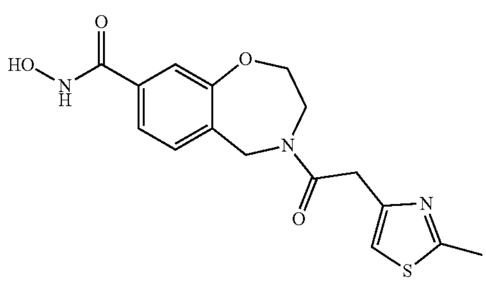 [SMILES: Cc1nc(CC(=O)N2CCOc3cc(C(=O)NO)ccc3C2)cs1] | 348 |
| 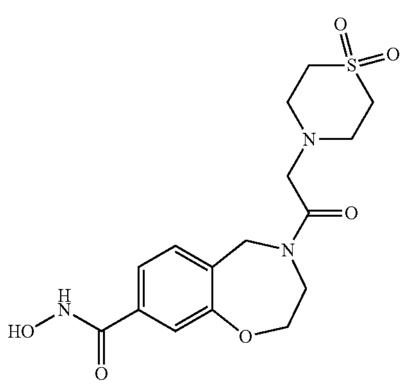 [SMILES: O=C(NO)c1ccc2c(c1)OCCN(C(=O)CN1CCS(=O)(=O)CC1)C2] | 384 |

TABLE 35-continued

The following compounds were prepared by the parallel synthesis method of Example 63.

| Structure | Found M + H (ES) |
| --- | --- |
| 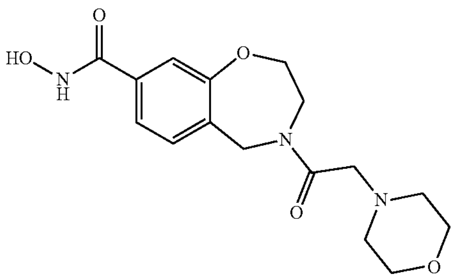 [SMILES: O=C(NO)c1ccc2c(c1)OCCN(C(=O)CN1CCOCC1)C2] | 336 |
| | 357 |
| 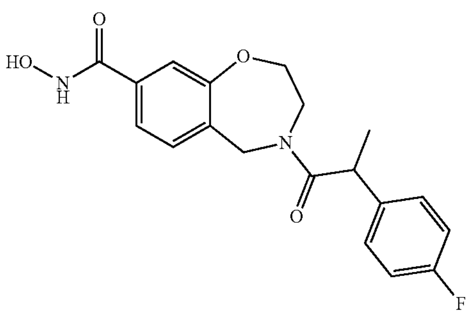 [SMILES: CC(C(=O)N1CCOc2cc(C(=O)NO)ccc2C1)c1ccc(F)cc1] | 359 |
| 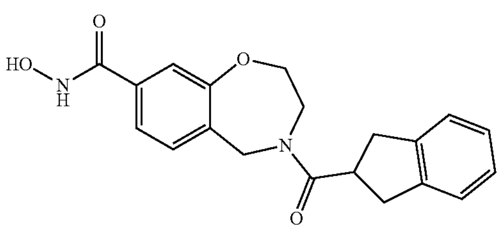 [SMILES: O=C(NO)c1ccc2c(c1)OCCN(C(=O)C1Cc3ccccc3C1)C2] | 353 |
| 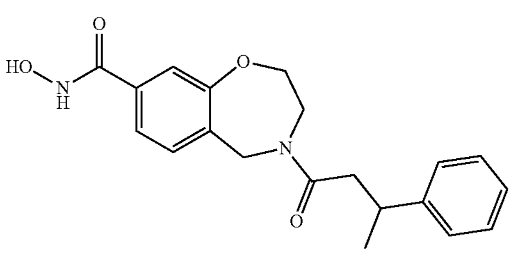 [SMILES: CC(CC(=O)N1CCOc2cc(C(=O)NO)ccc2C1)c1ccccc1] | 355 |
| | 357 |

TABLE 35-continued

The following compounds were prepared by the parallel synthesis method of Example 63.

| Structure | Found M + H (ES) |
|---|---|
| 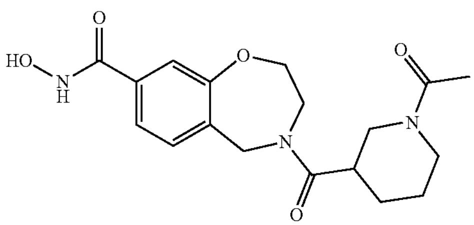 [SMILES: CC(=O)N1CCCC(C(=O)N2CCOc3cc(C(=O)NO)ccc3C2)C1] | 362 |
| 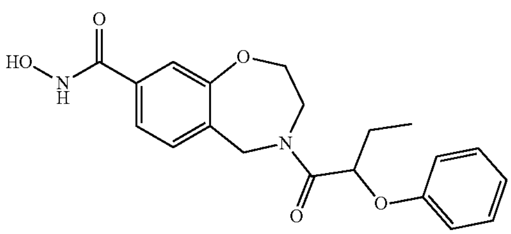 [SMILES: CCC(Oc1ccccc1)C(=O)N1CCOc2cc(C(=O)NO)ccc2C1] | 370 |
| 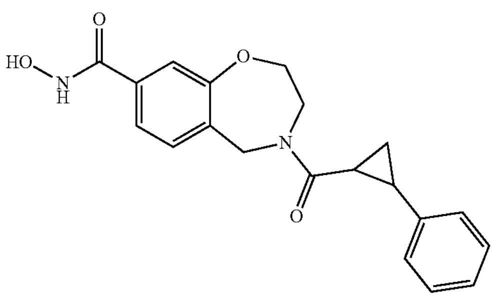 [SMILES: O=C(NO)c1ccc2c(c1)OCCN(C(=O)C1CC1c1ccccc1)C2] | 353 |
| 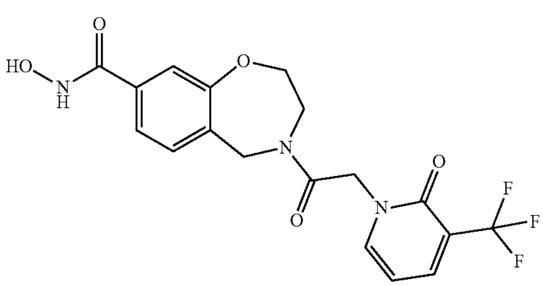 [SMILES: O=C(NO)c1ccc2c(c1)OCCN(C(=O)Cn1cccc(C(F)(F)F)c1=O)C2] | 412 |
| 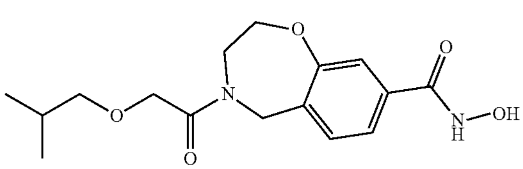 [SMILES: CC(C)COCC(=O)N1CCOc2cc(C(=O)NO)ccc2C1] | 323 |
| 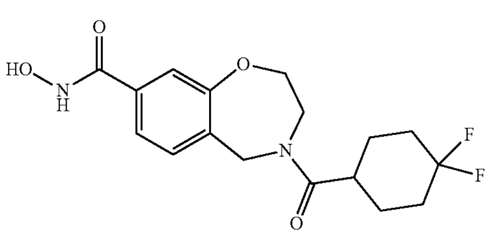 [SMILES: O=C(NO)c1ccc2c(c1)OCCN(C(=O)C1CCC(F)(F)CC1)C2] | 355 |

TABLE 35-continued

The following compounds were prepared by the parallel synthesis method of Example 63.

| Structure | Found M + H (ES) |
|---|---|
| (structure) | 358 |
| (structure) | 305 |
| (structure) | 327 |
| (structure) | 291 |
| (structure) | 281 |
| (structure) | 293 |

TABLE 35-continued

The following compounds were prepared by the parallel synthesis method of Example 63.

| Structure | Found M + H (ES) |
| --- | --- |
| 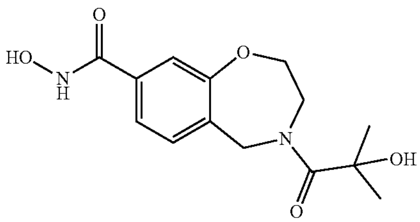 [SMILES: CC(C)(O)C(=O)N1CCOc2cc(C(=O)NO)ccc2C1] | 295 |
| 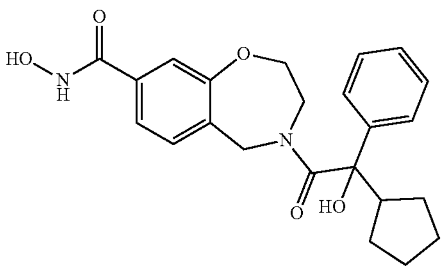 [SMILES: O=C(NO)c1ccc2c(c1)OCCN(C(=O)C(O)(c1ccccc1)C1CCCC1)C2] | 411 |
| 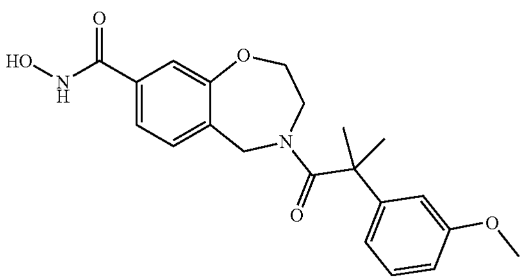 [SMILES: COc1cccc(C(C)(C)C(=O)N2CCOc3cc(C(=O)NO)ccc3C2)c1] | 385 |
| 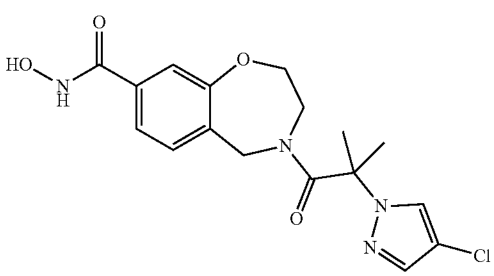 [SMILES: CC(C)(C(=O)N1CCOc2cc(C(=O)NO)ccc2C1)n1cc(Cl)cn1] | 379 |
| 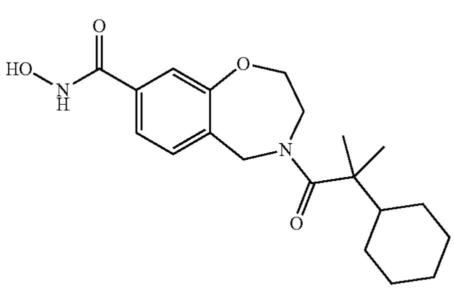 [SMILES: CC(C)(C(=O)N1CCOc2cc(C(=O)NO)ccc2C1)C1CCCCC1] | 361 |

TABLE 35-continued

The following compounds were prepared by the parallel synthesis method of Example 63.

| Structure | Found M + H (ES) |
|---|---|
| (structure) | 415 |
| (structure) | 431 |
| (structure) | 359 |
| (structure) | 405 |

TABLE 35-continued

The following compounds were prepared by the parallel synthesis method of Example 63.

| Structure | Found M + H (ES) |
|---|---|
| (structure) | 385 |
| (structure) | 356 |
| (structure) | 373 |
| (structure) | 413 |
| (structure) | 361 |

TABLE 35-continued
The following compounds were prepared by the parallel synthesis method of Example 63.
| Structure | Found M + H (ES) |
|---|---|
| 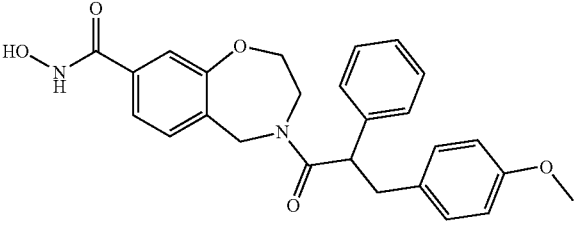 [SMILES: COc1ccc(CC(C(=O)N2CCOc3cc(C(=O)NO)ccc3C2)c2ccccc2)cc1] | 447 |
| 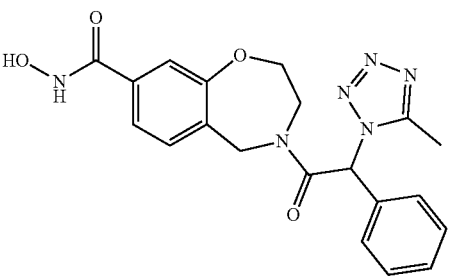 [SMILES: Cc1nnnn1C(C(=O)N1CCOc2cc(C(=O)NO)ccc2C1)c1ccccc1] | 409 |
| 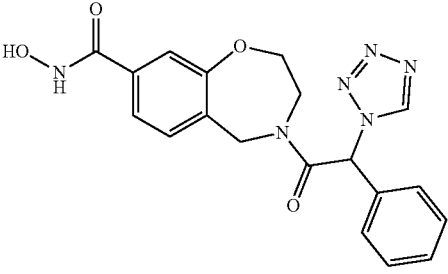 [SMILES: O=C(NO)c1ccc2c(c1)OCCN(C(=O)C(c1ccccc1)n1cnnn1)C2] | 395 |
| 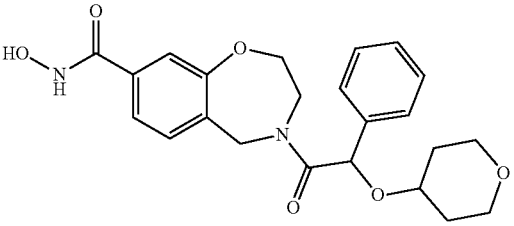 [SMILES: O=C(NO)c1ccc2c(c1)OCCN(C(=O)C(OC1CCOCC1)c1ccccc1)C2] | 427 |
| 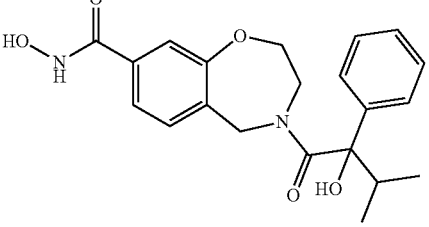 | 385 |

TABLE 35-continued

The following compounds were prepared by the parallel synthesis method of Example 63.

| Structure | Found M + H (ES) |
|---|---|
| 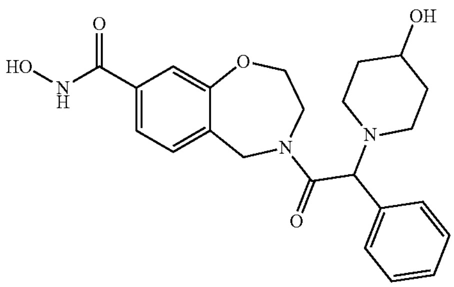 [SMILES: O=C(NO)c1ccc2c(c1)OCCN(C(=O)C(c1ccccc1)N1CCC(O)CC1)C2] | 426 |
| 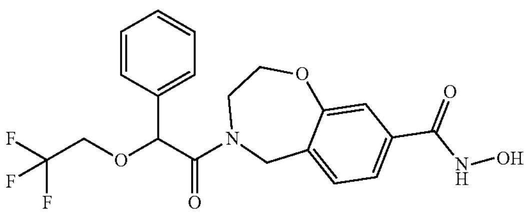 [SMILES: O=C(NO)c1ccc2c(c1)OCCN(C(=O)C(OCC(F)(F)F)c1ccccc1)C2] | 425 |
| 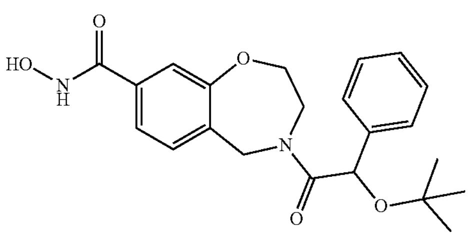 [SMILES: CC(C)(C)OC(C(=O)N1CCOc2cc(C(=O)NO)ccc2C1)c1ccccc1] | 399 |
| 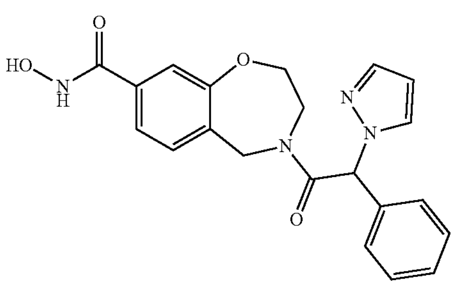 [SMILES: O=C(NO)c1ccc2c(c1)OCCN(C(=O)C(c1ccccc1)n1cccn1)C2] | 393 |
| 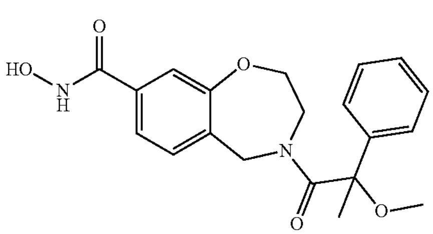 [SMILES: COC(C)(C(=O)N1CCOc2cc(C(=O)NO)ccc2C1)c1ccccc1] | 371 |
| 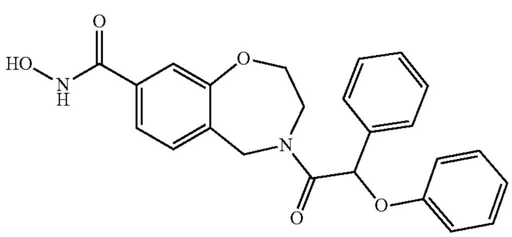 [SMILES: O=C(NO)c1ccc2c(c1)OCCN(C(=O)C(Oc1ccccc1)c1ccccc1)C2] | 419 |

TABLE 35-continued

The following compounds were prepared by the parallel synthesis method of Example 63.

| Structure | Found M + H (ES) |
|---|---|
| 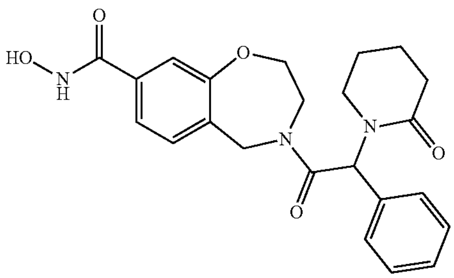 [SMILES: O=C(NO)c1ccc2c(c1)OCCN(C(=O)C(c1ccccc1)N1CCCCC1=O)C2] | 424 |
| 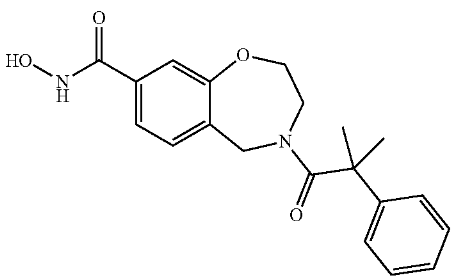 [SMILES: CC(C)(C(=O)N1CCOc2cc(C(=O)NO)ccc2C1)c1ccccc1] | 355 |
| 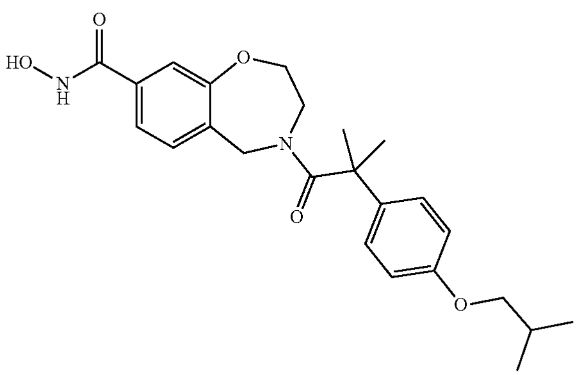 [SMILES: CC(C)COc1ccc(C(C)(C)C(=O)N2CCOc3cc(C(=O)NO)ccc3C2)cc1] | 427 |
| 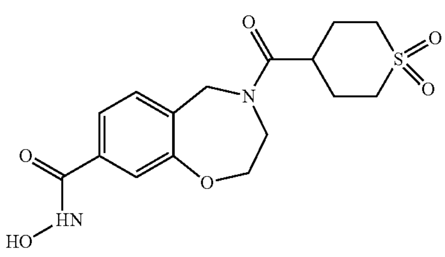 [SMILES: O=C(NO)c1ccc2c(c1)OCCN(C(=O)C1CCS(=O)(=O)CC1)C2] | 369 |
| 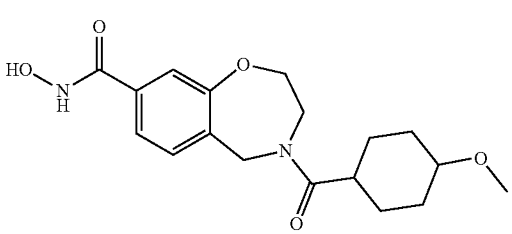 [SMILES: COC1CCC(C(=O)N2CCOc3cc(C(=O)NO)ccc3C2)CC1] | 349 |

TABLE 35-continued

The following compounds were prepared by the parallel synthesis method of Example 63.

| Structure | Found M + H (ES) |
|---|---|
| 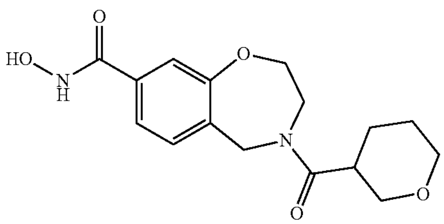 [SMILES: O=C(NO)c1ccc2c(c1)OCCN(C(=O)C1CCCOC1)C2] | 321 |
| 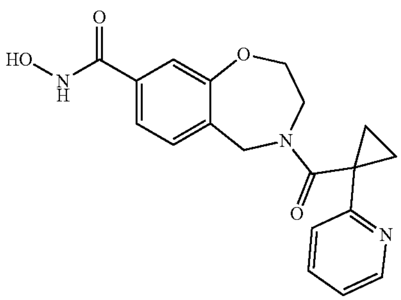 [SMILES: O=C(NO)c1ccc2c(c1)OCCN(C(=O)C1(c3ccccn3)CC1)C2] | 354 |
| 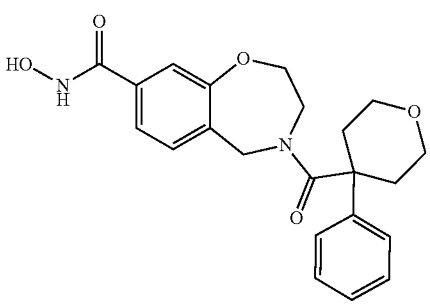 [SMILES: O=C(NO)c1ccc2c(c1)OCCN(C(=O)C1(c3ccccc3)CCOCC1)C2] | 397 |
| 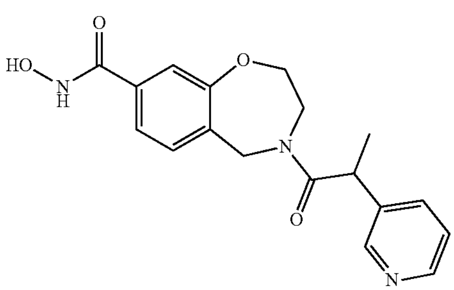 [SMILES: CC(C(=O)N1CCOc2cc(C(=O)NO)ccc2C1)c1cccnc1] | 342 |
| 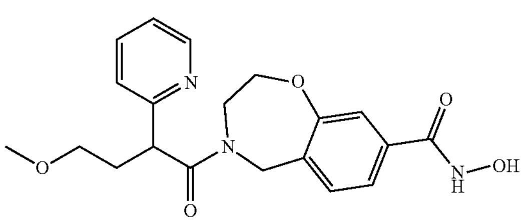 [SMILES: COCCC(C(=O)N1CCOc2cc(C(=O)NO)ccc2C1)c1ccccn1] | 386 |

TABLE 35-continued

The following compounds were prepared by the parallel synthesis method of Example 63.

| Structure | Found M + H (ES) |
|---|---|
| 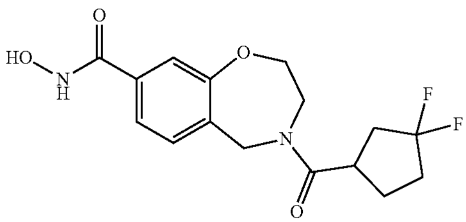 [SMILES: O=C(NO)c1ccc2c(c1)OCCN(C(=O)C1CCC(F)(F)C1)C2] | 341 |
| 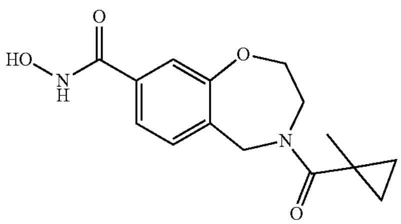 [SMILES: CC1(C(=O)N2CCOc3cc(C(=O)NO)ccc3C2)CC1] | 291 |
| 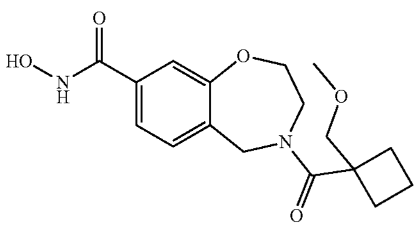 [SMILES: COCC1(C(=O)N2CCOc3cc(C(=O)NO)ccc3C2)CCC1] | 335 |
| 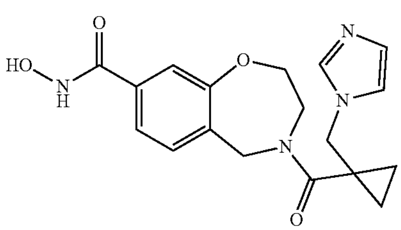 [SMILES: O=C(NO)c1ccc2c(c1)OCCN(C(=O)C1(Cn3ccnc3)CC1)C2] | 357 |
| 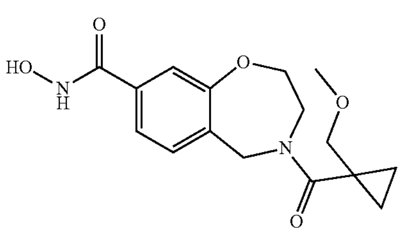 [SMILES: COCC1(C(=O)N2CCOc3cc(C(=O)NO)ccc3C2)CC1] | 321 |
| 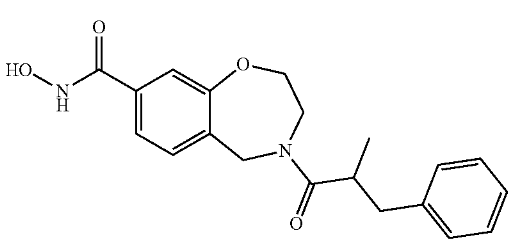 [SMILES: CC(Cc1ccccc1)C(=O)N1CCOc2cc(C(=O)NO)ccc2C1] | 355 |

TABLE 35-continued
The following compounds were prepared by the parallel synthesis method of Example 63.
| Structure | Found M + H (ES) |
|---|---|
| 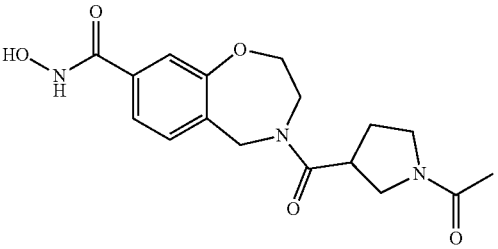 [SMILES: CC(=O)N1CCC(C(=O)N2CCOc3cc(C(=O)NO)ccc3C2)C1] | 348 |
| 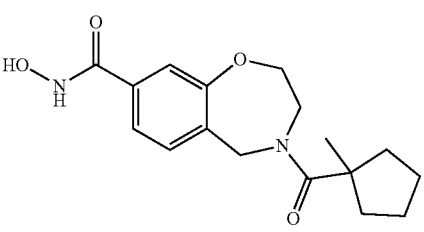 [SMILES: CC1(C(=O)N2CCOc3cc(C(=O)NO)ccc3C2)CCCC1] | 319 |
| 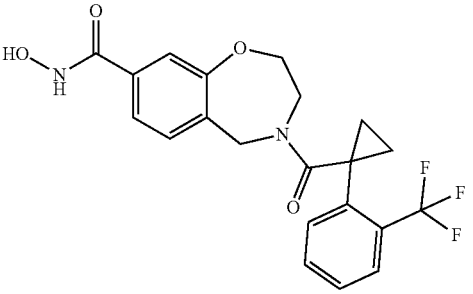 [SMILES: O=C(NO)c1ccc2c(c1)OCCN(C(=O)C1(c3ccccc3C(F)(F)F)CC1)C2] | 421 |
| 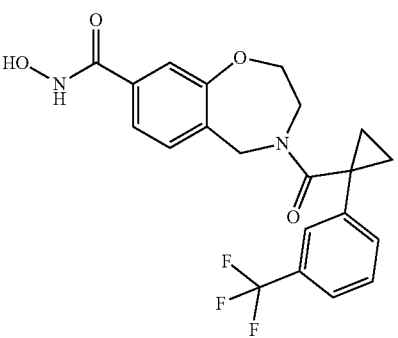 [SMILES: O=C(NO)c1ccc2c(c1)OCCN(C(=O)C1(c3cccc(C(F)(F)F)c3)CC1)C2] | 421 |
| 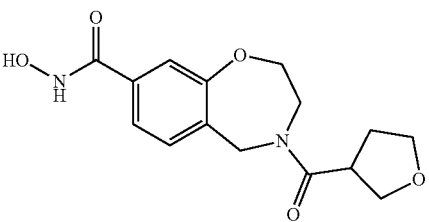 [SMILES: O=C(NO)c1ccc2c(c1)OCCN(C(=O)C1CCOC1)C2] | 307 |

TABLE 35-continued

The following compounds were prepared by the parallel synthesis method of Example 63.

| Structure | Found M + H (ES) |
|---|---|
| 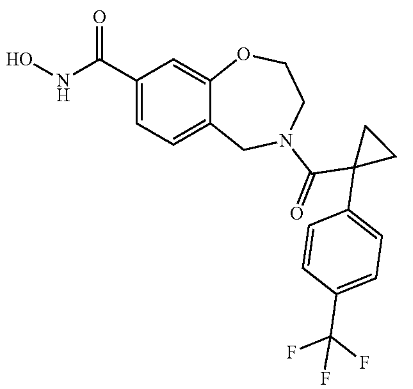 [SMILES: O=C(NO)c1ccc2c(c1)OCCN(C(=O)C1(c3ccc(C(F)(F)F)cc3)CC1)C2] | 421 |
| | 367 |
| | 367 |
| 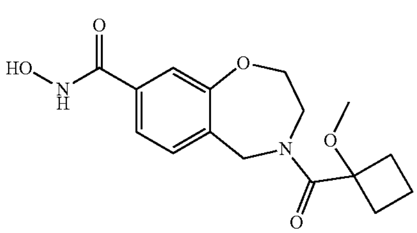 [SMILES: COC1(C(=O)N2CCOc3cc(C(=O)NO)ccc3C2)CCC1] | 321 |
| 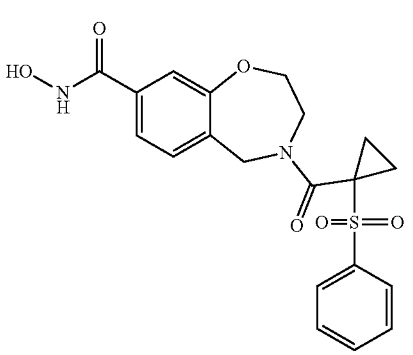 [SMILES: O=C(NO)c1ccc2c(c1)OCCN(C(=O)C1(S(=O)(=O)c3ccccc3)CC1)C2] | 417 |

TABLE 35-continued
The following compounds were prepared by the parallel synthesis method of Example 63.
| Structure | Found M + H (ES) |
|---|---|
| 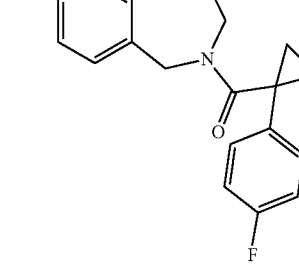 | 371 |
| 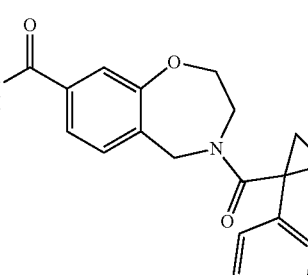 | 387 |
| 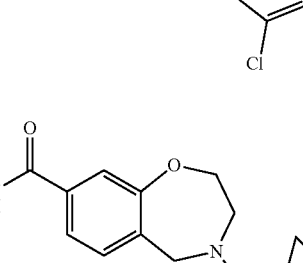 | 383 |
| 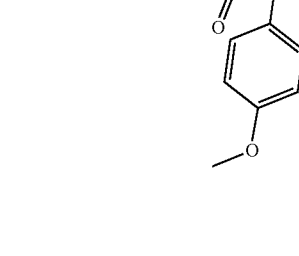 | 387 |

TABLE 35-continued

The following compounds were prepared by the parallel synthesis method of Example 63.

| Structure | Found M + H (ES) |
|---|---|
| 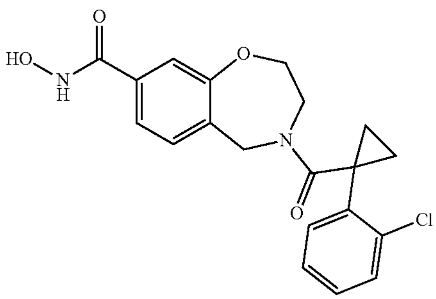 [SMILES: O=C(NO)c1ccc2c(c1)OCCN(C(=O)C1(c3ccccc3Cl)CC1)C2] | 387 |
| 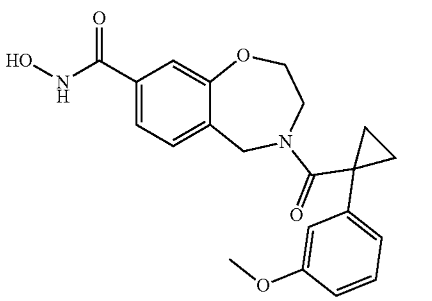 [SMILES: COc1cccc(C2(C(=O)N3CCOc4cc(C(=O)NO)ccc4C3)CC2)c1] | 383 |
| 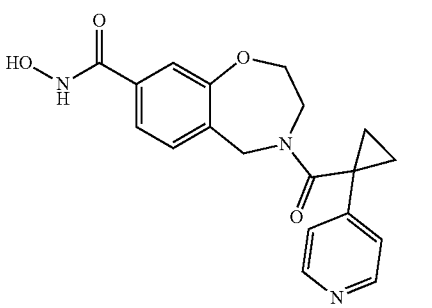 [SMILES: O=C(NO)c1ccc2c(c1)OCCN(C(=O)C1(c3ccncc3)CC1)C2] | 354 |
| 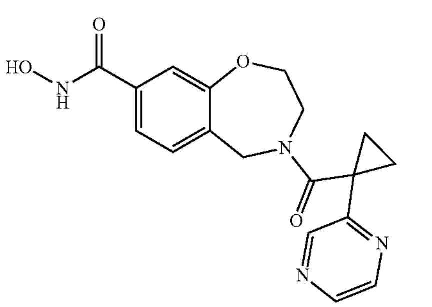 [SMILES: O=C(NO)c1ccc2c(c1)OCCN(C(=O)C1(c3cnccn3)CC1)C2] | 355 |
| 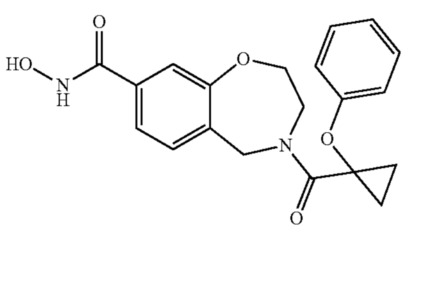 [SMILES: O=C(NO)c1ccc2c(c1)OCCN(C(=O)C1(Oc3ccccc3)CC1)C2] | 369 |

TABLE 35-continued

The following compounds were prepared by the parallel synthesis method of Example 63.

| Structure | Found M + H (ES) |
|---|---|
| (hydroxamic acid benzoxazepine with N-acyl cyclopropyl-CH2-pyrazole) | 357 |
| (hydroxamic acid benzoxazepine with N-acyl cyclopropyl-thiophene) | 359 |
| (hydroxamic acid benzoxazepine with N-acyl oxetane) | 293 |
| (hydroxamic acid benzoxazepine with N-acyl methyl-oxetane) | 307 |
| (S)-configured hydroxamic acid methyl benzoxazepine with N-acyl cyclohexyl | 333 |
| (S)-configured hydroxamic acid methyl benzoxazepine with N-acyl CH2CH2OMe | 309 |

TABLE 35-continued

The following compounds were prepared by the parallel synthesis method of Example 63.

| Structure | Found M + H (ES) |
|---|---|
| 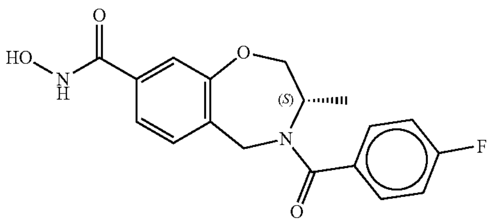 | 345 |
| 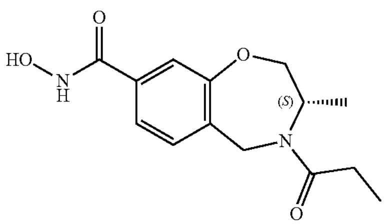 | 279 |
| 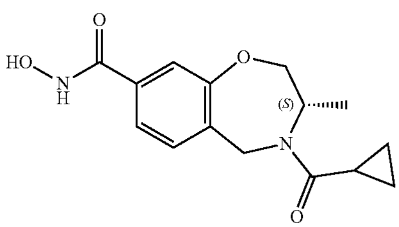 | 291 |
| 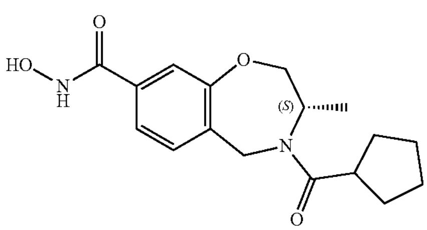 | 319 |
| 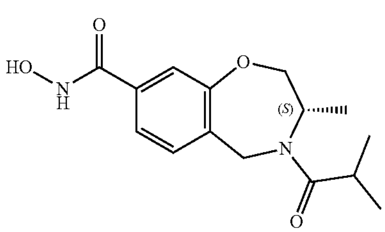 | 293 |
| 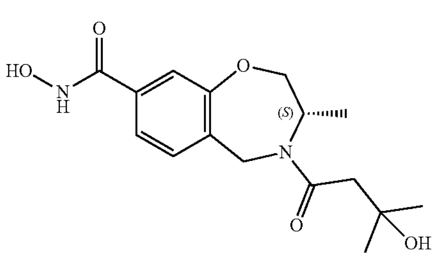 | 323 |

TABLE 35-continued

The following compounds were prepared by the parallel synthesis method of Example 63.

| Structure | Found M + H (ES) |
|---|---|
| (S)-configured benzo[f][1,4]oxazepine with hydroxamic acid at 7-position and N-acyl group —C(O)C(CH₃)₂CH₂OH | 323 |
| (S)-configured benzo[f][1,4]oxazepine with hydroxamic acid at 7-position and N-acyl group —C(O)CH₂C(CH₃)₂OCH₃ | 337 |

Example 64

Preparation of methyl 2,3,4,5-tetrahydrobenzo[f][1,4]oxazepine-7-carboxylate

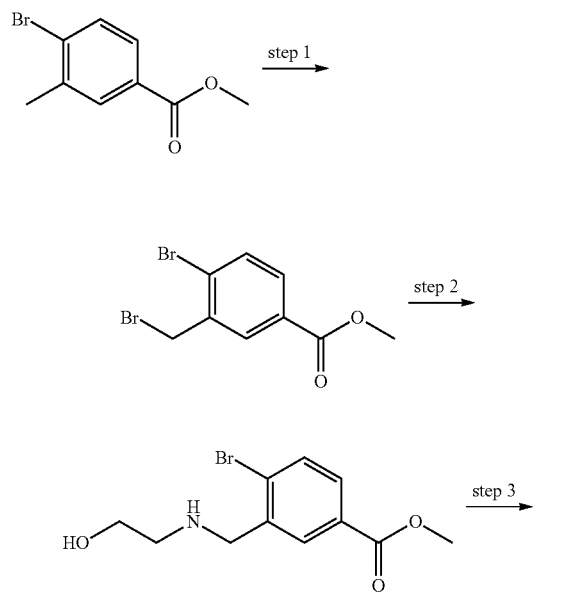

Step-1: Methyl 4-bromo-3-(bromomethyl)benzoate

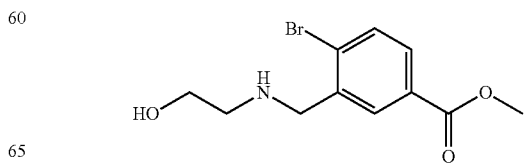

Methyl 4-bromo-3-methylbenzoate (11.4 g, 0.05 mol) was added to carbon tetrachloride (80 mL) in a 250 mL 3-three neck round-bottomed flask. To the resulting solution were added successively and in single portions, N-bromosuccinimide (9.3 g, 0.053 mol) and dibenzoylperoxide (0.6 g, 5 mol %). The resulting suspension was then heated to reflux for 4 h. Upon cooling to ambient temperature, the reaction mixture was filtered, and the filter cake washed with a few portions of carbon tetrachloride. The filtrate was then removed under reduced pressure, and the resulting semi-solid was partitioned between EtOAc and an aqueous ½ saturated sodium carbonate solution. The organic layer was washed with water and brine, and then dried over magnesium sulfate. The solution was filtered and solvent was removed under reduced pressure, providing 15.5 g of an off-white solid, which was purified by silica gel chromatography (0% to 6% EtOAc/hexanes) to afford the title compound (9.5 g, 61% yield).

Step-2: Methyl 4-bromo-3-(((2-hydroxyethyl)amino)methyl)benzoate

Ethanolamine (7.7 mL, 0.125 mol) was added to acetonitrile (80 mL) in a 500 mL 3-neck round-bottomed flask. To the resulting clear solution was added powdered potassium carbonate (3.5 g, 0.025 mol) in a single portion, washing in with more acetonitrile (10 mL). The resulting suspension was cooled in an ice-acetone bath. With the help of an ultrasonic bath, methyl 4-bromo-3-(bromomethyl)benzoate (7.7 g, 0.025 mol) was dissolved in acetonitrile (100 mL), and transferred to an addition funnel. This solution was added over 1 h to the stirring suspension, temperature remaining below 0° C. throughout. After the addition was complete, the reaction mixture was stirred for 3 h at ice temperature, before being allowed to warm to 10° C. The entire reaction mixture was evaporated, and the resulting residue partitioned between EtOAc and water. The organic layer was washed with water three times, and then once with brine. After drying over magnesium sulfate and filtering, solvent was removed under reduced pressure to obtain a clear oil, which solidified upon standing. This was placed under high vacuum to obtain the title compound (5.8 g, 80% yield), which was used without further purification.

Step-3: Methyl 2,3,4,5-tetrahydrobenzo[f][1,4]oxazepine-7-carboxylate

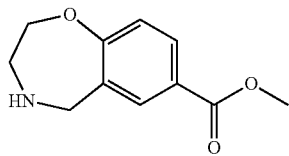

Methyl 4-bromo-3-(((2-hydroxyethyl)amino)methyl)benzoate (1.0 g, 0.0035 mol), potassium carbonate (1.0 g, 0.007 mol), and copper (I) iodide (0.13 g, 20 mol %) were placed into a 80 mL microwave tube along with a magnetic stir bar. Previously degassed 2-propanol (25 mL) was added, and the resulting suspension heated at 125° C. for 2.5 h. This process was repeated twice more. The three reactions were combined, the suspension was filtered, and the filter cake washed with more 2-propanol. The filtrate was pre-absorbed directly onto silica gel and was which was purified by silica gel chromatography (0% to 10% EtOH+5% NH$_4$OH/CH$_2$Cl$_2$) to afford a greenish oil (1.4 g). This material was further purified by silica gel chromatography (60% to 100% EtOAc+5% Et$_3$N/hexanes) to afford the title compound as an amber oil (1.0 g, 46% yield). $^1$H-NMR (300 MHz, CDCl$_3$) δ(ppm): 7.81-7.87 (m, 2H), 7.00-7.06 (m, 1H), 4.05-4.11 (m, 2H), 3.99 (s, 2H), 3.87 (s, 3H), 3.20-3.26 (m, 2H). MS: (APCI, m/z): 208 [M+H]$^+$.

Example 65

In Vitro Histone Deacetylase Assay

The enzymatic HDAC6 assay was performed using electrophoretic mobility shift assay. Full length human recombinant HDAC6 protein was expressed in baculoviral system and purified by affinity chromatography. The enzymatic reactions were assembled in 384 well plates in a total volume of 25 µL in a reaction buffer composing: 100 mM HEPES, pH 7.5, 25 mM KCl, 0.1% bovine serum albumin, 0.01% Triton X-100, 1% DMSO (from compounds) 2 µM of the fluorescently labeled peptide substrate and enzyme. The enzyme was added at a final concentration of 1 nM. The peptide substrate RHKK(Ac)-NH2 was used. The compounds were tested at 12 concentrations spaced by 3× dilution intervals. Negative control samples (0%-inhibition in the absence of inhibitor) and positive control samples (100%-inhibition) were assembled in replicates of four in each assay plate. The reactions were incubated at 25° C. and quenched by the addition of 45 µL of termination buffer (100 mM HEPES, pH 7.5, 0.01% Triton X-100, 0.05% SDS).

The terminated assay plates were analyzed on LabChip® 3000 microfluidic electrophoresis instrument (Perkin Elmer/Caliper Life Sciences). The fluorescence intensity of the electrophoretically separated de-acetylated product and substrate peptide was measured. Activity in each sample was determined as the product to sum ratio (PSR): P/(S+P), where P is the peak height of the product peptide and S is the peak height of the substrate peptide. Percent inhibition (P$_{inh}$) is determined using the following equation:

P$_{inh}$=(PSR$_{0\%}$−PSR$_{inh}$)/(PSR$_{0\%}$−PSR$_{100\%}$)*100, where PSR is the product sum ratio in the presence of inhibitor, PSR$_{0\%}$ is the average product sum ration in the absence of inhibitor and PSR$_{100\%}$ is the average product sum ratio in 100%-inhibition control samples. The IC$_{50}$ values of inhibitors were determined by fitting the %-inhibition curves with 4 parameter dose-response model using XLfit 4 software.

As set forth in Table 36, below, IC$_{50}$ values are defined as follows: IC50≤0.1 µM (+++); IC50>0.1 µM and ≤0.5 µM (++); IC50>0.5 µM (+).

TABLE 36

Inhibitory Concentration (IC$_{50}$) Values for Representative Compounds against HDAC6.

| ChemDraw IUPAC Name | Activity Range |
| --- | --- |
| 4-(2,2-dimethyltetrahydro-2H-pyran-4-carbonyl)-N-hydroxy-2,3,4,5-tetrahydrobenzo[f][1,4]oxazepine-8-carboxamide | ++ |
| N-hydroxy-4-(2-methyl-2-(pyridin-2-yl)propanoyl)-2,3,4,5-tetrahydrobenzo[f][1,4]oxazepine-8-carboxamide | ++ |
| 4-(2,6-dimethylbenzoyl)-N-hydroxy-2,3,4,5-tetrahydrobenzo[f][1,4]oxazepine-8-carboxamide | ++ |
| N-hydroxy-4-(3-methoxy-2,2-dimethylpropanoyl)-2,3,4,5-tetrahydrobenzo[f][1,4]oxazepine-8-carboxamide | +++ |
| 4-(8-oxabicyclo[3.2.1]octane-3-carbonyl)-N-hydroxy-2,3,4,5-tetrahydrobenzo[f][1,4]oxazepine-8-carboxamide | +++ |
| N-hydroxy-4-(3-(propylamino)benzo[b]thiophene-2-carbonyl)-2,3,4,5-tetrahydrobenzo[f][1,4]oxazepine-8-carboxamide | +++ |
| 4-(3-(dimethylamino)benzo[b]thiophene-2-carbonyl)-N-hydroxy-2,3,4,5-tetrahydrobenzo[f][1,4]oxazepine-8-carboxamide | +++ |

TABLE 36-continued

Inhibitory Concentration (IC$_{50}$) Values for Representative Compounds against HDAC6.

| ChemDraw IUPAC Name | Activity Range |
|---|---|
| tert-butyl 7-(8-(hydroxycarbamoyl)-2,3,4,5-tetrahydrobenzo[f][1,4]oxazepine-4-carbonyl)-5-oxa-2-azaspiro[3.4]octane-2-carboxylate | ++ |
| tert-butyl 7-(8-(hydroxycarbamoyl)-2,3,4,5-tetrahydrobenzo[f][1,4]oxazepine-4-carbonyl)-5-thia-2-azaspiro[3.4]octane-2-carboxylate 5,5-dioxide | ++ |
| (S)-N-hydroxy-4-(tetrahydro-2H-pyran-3-carbonyl)-2,3,4,5-tetrahydrobenzo[f][1,4]oxazepine-8-carboxamide | +++ |
| (R)-N-hydroxy-4-(tetrahydro-2H-pyran-3-carbonyl)-2,3,4,5-tetrahydrobenzo[f][1,4]oxazepine-8-carboxamide | +++ |
| (R)-N-hydroxy-4-(tetrahydrofuran-3-carbonyl)-2,3,4,5-tetrahydrobenzo[f][1,4]oxazepine-8-carboxamide | +++ |
| (S)-N-hydroxy-4-(tetrahydrofuran-3-carbonyl)-2,3,4,5-tetrahydrobenzo[f][1,4]oxazepine-8-carboxamide | +++ |
| 4-benzoyl-N-hydroxy-2,3,4,5-tetrahydrobenzo[f][1,4]oxazepine-8-carboxamide | +++ |
| N-hydroxy-4-pivaloyl-2,3,4,5-tetrahydrobenzo[f][1,4]oxazepine-8-carboxamide | +++ |
| 4-acetyl-N-hydroxy-2,3,4,5-tetrahydrobenzo[f][1,4]oxazepine-8-carboxamide | +++ |
| 4-formyl-N-hydroxy-2,3,4,5-tetrahydrobenzo[f][1,4]oxazepine-8-carboxamide | +++ |
| tert-butyl 3-(8-(hydroxycarbamoyl)-2,3,4,5-tetrahydrobenzo[f][1,4]oxazepine-4-carbonyl)-3H-spiro[isobenzofuran-1,4'-piperidine]-1'-carboxylate | ++ |
| N-hydroxy-4-(8-azaspiro[4.5]decane-2-carbonyl)-2,3,4,5-tetrahydrobenzo[f][1,4]oxazepine-8-carboxamide | +++ |
| tert-butyl 8-(8-(hydroxycarbamoyl)-2,3,4,5-tetrahydrobenzo[f][1,4]oxazepine-4-carbonyl)-2-azaspiro[4.5]decane-2-carboxylate | +++ |
| N-hydroxy-4-(2-azaspiro[4.5]decane-8-carbonyl)-2,3,4,5-tetrahydrobenzo[f][1,4]oxazepine-8-carboxamide | +++ |
| tert-butyl 6-(8-(hydroxycarbamoyl)-2,3,4,5-tetrahydrobenzo[f][1,4]oxazepine-4-carbonyl)-2-azaspiro[4.4]nonane-2-carboxylate | ++ |
| N-hydroxy-4-(2-azaspiro[4.4]nonane-6-carbonyl)-2,3,4,5-tetrahydrobenzo[f][1,4]oxazepine-8-carboxamide | ++ |
| N-hydroxy-4-(3H-spiro[isobenzofuran-1,4'-piperidine]-3-carbonyl)-2,3,4,5-tetrahydrobenzo[f][1,4]oxazepine-8-carboxamide | ++ |
| tert-butyl 2-(8-(hydroxycarbamoyl)-2,3,4,5-tetrahydrobenzo[f][1,4]oxazepine-4-carbonyl)-2H-spiro[benzofuran-3,4'-piperidine]-1'-carboxylate | ++ |
| N-hydroxy-4-(2H-spiro[benzofuran-3,4'-piperidine]-2-carbonyl)-2,3,4,5-tetrahydrobenzo[f][1,4]oxazepine-8-carboxamide | ++ |
| tert-butyl 3-(8-(hydroxycarbamoyl)-2,3,4,5-tetrahydrobenzo[f][1,4]oxazepine-4-carbonyl)-2,3-dihydrospiro[indene-1,4'-piperidine]-1'-carboxylate | ++ |
| 4-(2,3-dihydrospiro[indene-1,4'-piperidine]-3-carbonyl)-N-hydroxy-2,3,4,5-tetrahydrobenzo[f][1,4]oxazepine-8-carboxamide | ++ |
| tert-butyl 9-(8-(hydroxycarbamoyl)-2,3,4,5-tetrahydrobenzo[f][1,4]oxazepine-4-carbonyl)-3-azaspiro[5.5]undecane-3-carboxylate | ++ |
| tert-butyl 2-(8-(hydroxycarbamoyl)-2,3,4,5-tetrahydrobenzo[f][1,4]oxazepine-4-carbonyl)-8-azaspiro[4.5]decane-8-carboxylate | ++ |
| N-hydroxy-4-(3-azaspiro[5.5]undecane-9-carbonyl)-2,3,4,5-tetrahydrobenzo[f][1,4]oxazepine-8-carboxamide | +++ |
| N-hydroxy-4-(5-azaspiro[2.5]octane-1-carbonyl)-2,3,4,5-tetrahydrobenzo[f][1,4]oxazepine-8-carboxamide | + |
| N-hydroxy-4-(5-azaspiro[2.4]heptane-1-carbonyl)-2,3,4,5-tetrahydrobenzo[f][1,4]oxazepine-8-carboxamide | + |
| N-hydroxy-4-(6-azaspiro[2.5]octane-1-carbonyl)-2,3,4,5-tetrahydrobenzo[f][1,4]oxazepine-8-carboxamide | ++ |
| tert-butyl 1-(8-(hydroxycarbamoyl)-2,3,4,5-tetrahydrobenzo[f][1,4]oxazepine-4-carbonyl)-6-azaspiro[2.5]octane-6-carboxylate | ++ |
| (R)-N-hydroxy-2-methyl-4-(1-methylcyclobutane-1-carbonyl)-2,3,4,5-tetrahydrobenzo[f][1,4]oxazepine-8-carboxamide | +++ |
| (R)-4-formyl-N-hydroxy-2-methyl-2,3,4,5-tetrahydrobenzo[f][1,4]oxazepine-8-carboxamide | +++ |
| (R)-4-acetyl-N-hydroxy-2-methyl-2,3,4,5-tetrahydrobenzo[f][1,4]oxazepine-8-carboxamide | + |
| (S)-4-acetyl-N-hydroxy-2-methyl-2,3,4,5-tetrahydrobenzo[f][1,4]oxazepine-8-carboxamide | + |

TABLE 36-continued

Inhibitory Concentration ($IC_{50}$) Values for Representative Compounds against HDAC6.

| ChemDraw IUPAC Name | Activity Range |
| --- | --- |
| (S)-N-hydroxy-2-methyl-4-(1-methylcyclobutane-1-carbonyl)-2,3,4,5-tetrahydrobenzo[f][1,4]oxazepine-8-carboxamide | ++ |
| (S)-4-formyl-N-hydroxy-2-methyl-2,3,4,5-tetrahydrobenzo[f][1,4]oxazepine-8-carboxamide | +++ |
| N-hydroxy-3,3-dimethyl-4-(1-methylcyclobutane-1-carbonyl)-2,3,4,5-tetrahydrobenzo[f][1,4]oxazepine-8-carboxamide | + |
| 4-acetyl-N-hydroxy-3,3-dimethyl-2,3,4,5-tetrahydrobenzo[f][1,4]oxazepine-8-carboxamide | ++ |
| (R)-4-acetyl-N-hydroxy-3-isopropyl-2,3,4,5-tetrahydrobenzo[f][1,4]oxazepine-8-carboxamide | ++ |
| (R)-N-hydroxy-3-isopropyl-4-(1-methylcyclobutane-1-carbonyl)-2,3,4,5-tetrahydrobenzo[f][1,4]oxazepine-8-carboxamide | + |
| (S)-4-acetyl-N-hydroxy-3-isopropyl-2,3,4,5-tetrahydrobenzo[f][1,4]oxazepine-8-carboxamide | ++ |
| (S)-N-hydroxy-3-isopropyl-4-(1-methylcyclobutane-1-carbonyl)-2,3,4,5-tetrahydrobenzo[f][1,4]oxazepine-8-carboxamide | +++ |
| (R)-4-formyl-N-hydroxy-3-methyl-2,3,4,5-tetrahydrobenzo[f][1,4]oxazepine-8-carboxamide | +++ |
| (R)-N-hydroxy-3-methyl-4-(1-methylcyclobutane-1-carbonyl)-2,3,4,5-tetrahydrobenzo[f][1,4]oxazepine-8-carboxamide | ++ |
| (R)-4-acetyl-N-hydroxy-3-methyl-2,3,4,5-tetrahydrobenzo[f][1,4]oxazepine-8-carboxamide | + |
| (S)-N-hydroxy-3-methyl-4-(1-methylcyclobutane-1-carbonyl)-2,3,4,5-tetrahydrobenzo[f][1,4]oxazepine-8-carboxamide | +++ |
| (S)-4-(1,1-dioxidotetrahydro-2H-thiopyran-4-carbonyl)-N-hydroxy-3-methyl-2,3,4,5-tetrahydrobenzo[f][1,4]oxazepine-8-carboxamide | +++ |
| (S)-N-hydroxy-4-(1-methoxycyclopentane-1-carbonyl)-3-methyl-2,3,4,5-tetrahydrobenzo[f][1,4]oxazepine-8-carboxamide | +++ |
| (3S)-4-(1,1-dioxidotetrahydrothiophene-3-carbonyl)-N-hydroxy-3-methyl-2,3,4,5-tetrahydrobenzo[f][1,4]oxazepine-8-carboxamide | +++ |
| (S)-N-hydroxy-4-(1-methoxycyclobutane-1-carbonyl)-3-methyl-2,3,4,5-tetrahydrobenzo[f][1,4]oxazepine-8-carboxamide | +++ |
| (S)-N-hydroxy-3-methyl-4-(3-methyloxetane-3-carbonyl)-2,3,4,5-tetrahydrobenzo[f][1,4]oxazepine-8-carboxamide | +++ |
| (S)-N-hydroxy-3-methyl-4-(oxetane-3-carbonyl)-2,3,4,5-tetrahydrobenzo[f][1,4]oxazepine-8-carboxamide | +++ |
| (S)-4-(1,1-dioxidothietane-3-carbonyl)-N-hydroxy-3-methyl-2,3,4,5-tetrahydrobenzo[f][1,4]oxazepine-8-carboxamide | +++ |
| (S)-N-hydroxy-4-(1-methoxycyclopropane-1-carbonyl)-3-methyl-2,3,4,5-tetrahydrobenzo[f][1,4]oxazepine-8-carboxamide | +++ |
| (S)-N-hydroxy-3-methyl-4-(tetrahydro-2H-pyran-4-carbonyl)-2,3,4,5-tetrahydrobenzo[f][1,4]oxazepine-8-carboxamide | +++ |
| (S)-N-hydroxy-4-(2-methoxy-2-methylpropanoyl)-3-methyl-2,3,4,5-tetrahydrobenzo[f][1,4]oxazepine-8-carboxamide | +++ |
| (S)-N-hydroxy-3-methyl-4-(4-methyltetrahydro-2H-pyran-4-carbonyl)-2,3,4,5-tetrahydrobenzo[f][1,4]oxazepine-8-carboxamide | +++ |
| (S)-N-hydroxy-4-(4-methoxytetrahydro-2H-pyran-4-carbonyl)-3-methyl-2,3,4,5-tetrahydrobenzo[f][1,4]oxazepine-8-carboxamide | +++ |
| (S)-N-hydroxy-4-(1-methoxycyclohexane-1-carbonyl)-3-methyl-2,3,4,5-tetrahydrobenzo[f][1,4]oxazepine-8-carboxamide | +++ |
| (3S)-4-(8-oxabicyclo[3.2.1]octane-3-carbonyl)-N-hydroxy-3-methyl-2,3,4,5-tetrahydrobenzo[f][1,4]oxazepine-8-carboxamide | +++ |
| (3S)-4-(2,6-dimethyltetrahydro-2H-pyran-4-carbonyl)-N-hydroxy-3-methyl-2,3,4,5-tetrahydrobenzo[f][1,4]oxazepine-8-carboxamide | +++ |
| (S)-4-formyl-N-hydroxy-3-methyl-2,3,4,5-tetrahydrobenzo[f][1,4]oxazepine-8-carboxamide | +++ |
| (S)-4-acetyl-N-hydroxy-3-methyl-2,3,4,5-tetrahydrobenzo[f][1,4]oxazepine-8-carboxamide | ++ |
| (S)-4-(1-acetylpiperidine-4-carbonyl)-N-hydroxy-3-methyl-2,3,4,5-tetrahydrobenzo[f][1,4]oxazepine-8-carboxamide | +++ |
| (3S)-4-(1-acetylpyrrolidine-3-carbonyl)-N-hydroxy-3-methyl-2,3,4,5-tetrahydrobenzo[f][1,4]oxazepine-8-carboxamide | +++ |
| (R)-N-hydroxy-5-methyl-4-(1-methylcyclobutane-1-carbonyl)-2,3,4,5-tetrahydrobenzo[f][1,4]oxazepine-7-carboxamide | +++ |
| (S)-N-hydroxy-5-methyl-4-(1-methylcyclobutane-1-carbonyl)-2,3,4,5-tetrahydrobenzo[f][1,4]oxazepine-7-carboxamide | ++ |
| (R)-N-hydroxy-5-methyl-4-(tetrahydro-2H-pyran-4-carbonyl)-2,3,4,5-tetrahydrobenzo[f][1,4]oxazepine-7-carboxamide | +++ |
| (S)-N-hydroxy-5-methyl-4-(tetrahydro-2H-pyran-4-carbonyl)-2,3,4,5-tetrahydrobenzo[f][1,4]oxazepine-7-carboxamide | + |
| 4-(cyclohexanecarbonyl)-N-hydroxy-2,3,4,5-tetrahydropyrido[2,3-f][1,4]oxazepine-8-carboxamide | ++ |
| 4-(cyclohexanecarbonyl)-N-hydroxy-2,3,4,5-tetrahydropyrido[3,2-f][1,4]oxazepine-8-carboxamide | ++ |

TABLE 36-continued

Inhibitory Concentration (IC$_{50}$) Values for Representative Compounds against HDAC6.

| ChemDraw IUPAC Name | Activity Range |
| --- | --- |
| N-hydroxy-4-(2-(4-methoxyphenyl)acetyl)-2-oxo-2,3,4,5-tetrahydro-1H-benzo[e][1,4]diazepine-7-carboxamide | + |
| N-hydroxy-4-(4-methoxybenzoyl)-2-oxo-2,3,4,5-tetrahydro-1H-benzo[e][1,4]diazepine-7-carboxamide | + |
| 4-(cyclohexanecarbonyl)-N-hydroxy-2-oxo-2,3,4,5-tetrahydro-1H-benzo[e][1,4]diazepine-7-carboxamide | + |
| 4-(cyclohexanecarbonyl)-N-hydroxy-2,3,4,5-tetrahydrobenzo[f][1,4]oxazepine-8-carboxamide | +++ |
| N-hydroxy-4-(4-methoxybenzoyl)-2,3,4,5-tetrahydrobenzo[f][1,4]oxazepine-8-carboxamide | +++ |
| N-hydroxy-4-(4-methoxybenzoyl)-2,3,4,5-tetrahydrobenzo[f][1,4]oxazepine-7-carboxamide | + |
| N-hydroxy-4-(2-(4-methoxyphenyl)acetyl)-2,3,4,5-tetrahydrobenzo[f][1,4]oxazepine-8-carboxamide | + |
| N-hydroxy-4-(2-(4-methoxyphenyl)acetyl)-2,3,4,5-tetrahydrobenzo[f][1,4]oxazepine-7-carboxamide | + |
| N-hydroxy-4-(4-(trifluoromethyl)benzoyl)-2,3,4,5-tetrahydrobenzo[f][1,4]oxazepine-8-carboxamide | ++ |
| 4-(benzo[d][1,3]dioxole-5-carbonyl)-N-hydroxy-2,3,4,5-tetrahydrobenzo[f][1,4]oxazepine-8-carboxamide | +++ |
| N-hydroxy-4-(1H-indole-5-carbonyl)-2,3,4,5-tetrahydrobenzo[f][1,4]oxazepine-8-carboxamide | +++ |
| N-hydroxy-4-(1-phenylcyclopropane-1-carbonyl)-2,3,4,5-tetrahydrobenzo[f][1,4]oxazepine-8-carboxamide | +++ |
| N-hydroxy-4-(2-(4-methoxyphenoxy)acetyl)-2,3,4,5-tetrahydrobenzo[f][1,4]oxazepine-8-carboxamide | +++ |
| N-hydroxy-4-(3-methoxybenzoyl)-2,3,4,5-tetrahydrobenzo[f][1,4]oxazepine-8-carboxamide | ++ |
| 4-(4-(difluoromethoxy)benzoyl)-N-hydroxy-2,3,4,5-tetrahydrobenzo[f][1,4]oxazepine-8-carboxamide | ++ |
| N-hydroxy-4-(4-phenoxybenzoyl)-2,3,4,5-tetrahydrobenzo[f][1,4]oxazepine-8-carboxamide | +++ |
| 4-(2,3-dihydrobenzofuran-5-carbonyl)-N-hydroxy-2,3,4,5-tetrahydrobenzo[f][1,4]oxazepine-8-carboxamide | ++ |
| 4-(2,4-dimethoxybenzoyl)-N-hydroxy-2,3,4,5-tetrahydrobenzo[f][1,4]oxazepine-8-carboxamide | ++ |
| N-hydroxy-4-(1-methyl-6-oxo-1,6-dihydropyridine-3-carbonyl)-2,3,4,5-tetrahydrobenzo[f][1,4]oxazepine-8-carboxamide | + |
| N-hydroxy-4-(tetrahydro-2H-pyran-4-carbonyl)-2,3,4,5-tetrahydrobenzo[f][1,4]oxazepine-8-carboxamide | +++ |
| 4-(benzofuran-5-carbonyl)-N-hydroxy-2,3,4,5-tetrahydrobenzo[f][1,4]oxazepine-8-carboxamide | ++ |
| N-hydroxy-4-(4-morpholinobenzoyl)-2,3,4,5-tetrahydrobenzo[f][1,4]oxazepine-8-carboxamide | ++ |
| 4-(cyclopropanecarbonyl)-N-hydroxy-2,3,4,5-tetrahydrobenzo[f][1,4]oxazepine-8-carboxamide | ++ |
| 4-(cyclobutanecarbonyl)-N-hydroxy-2,3,4,5-tetrahydrobenzo[f][1,4]oxazepine-8-carboxamide | +++ |
| N-hydroxy-4-(1-methylcyclohexane-1-carbonyl)-2,3,4,5-tetrahydrobenzo[f][1,4]oxazepine-8-carboxamide | +++ |
| N-hydroxy-4-(2-phenylbutanoyl)-2,3,4,5-tetrahydrobenzo[f][1,4]oxazepine-8-carboxamide | ++ |
| 4-(2-cyclohexyl-2-phenylacetyl)-N-hydroxy-2,3,4,5-tetrahydrobenzo[f][1,4]oxazepine-8-carboxamide | + |
| 4-(bicyclo[4.2.0]octa-1(6),2,4-triene-7-carbonyl)-N-hydroxy-2,3,4,5-tetrahydrobenzo[f][1,4]oxazepine-8-carboxamide | +++ |
| N-hydroxy-4-(1-methylcyclobutane-1-carbonyl)-2,3,4,5-tetrahydrobenzo[f][1,4]oxazepine-8-carboxamide | +++ |
| (S)-N-hydroxy-4-(2-phenylpropanoyl)-2,3,4,5-tetrahydrobenzo[f][1,4]oxazepine-8-carboxamide | ++ |
| (R)-N-hydroxy-4-(2-phenylpropanoyl)-2,3,4,5-tetrahydrobenzo[f][1,4]oxazepine-8-carboxamide | + |
| N-hydroxy-4-(3-phenylpropanoyl)-2,3,4,5-tetrahydrobenzo[f][1,4]oxazepine-8-carboxamide | +++ |
| N-hydroxy-4-(2-(5-methoxy-1H-indol-3-yl)acetyl)-2,3,4,5-tetrahydrobenzo[f][1,4]oxazepine-8-carboxamide | + |
| 4-(2-(1,1-dioxidothiomorpholino)propanoyl)-N-hydroxy-2,3,4,5-tetrahydrobenzo[f][1,4]oxazepine-8-carboxamide | + |
| N-hydroxy-4-(2-(4-(trifluoromethyl)phenyl)acetyl)-2,3,4,5-tetrahydrobenzo[f][1,4]oxazepine-8-carboxamide | + |
| N-hydroxy-4-(2-(2-phenoxyphenyl)acetyl)-2,3,4,5-tetrahydrobenzo[f][1,4]oxazepine-8-carboxamide | + |
| 4-(2-(3-chlorophenoxy)acetyl)-N-hydroxy-2,3,4,5-tetrahydrobenzo[f][1,4]oxazepine-8-carboxamide | ++ |

TABLE 36-continued

Inhibitory Concentration (IC$_{50}$) Values for Representative Compounds against HDAC6.

| ChemDraw IUPAC Name | Activity Range |
| --- | --- |
| N-hydroxy-4-(4,4,4-trifluorobutanoyl)-2,3,4,5-tetrahydrobenzo[f][1,4]oxazepine-8-carboxamide | ++ |
| 4-(cyclopentanecarbonyl)-N-hydroxy-2,3,4,5-tetrahydrobenzo[f][1,4]oxazepine-8-carboxamide | +++ |
| N-hydroxy-4-isobutyryl-2,3,4,5-tetrahydrobenzo[f][1,4]oxazepine-8-carboxamide | +++ |
| N-hydroxy-4-(2-(1-(methylsulfonyl)piperidin-4-yl)acetyl)-2,3,4,5-tetrahydrobenzo[f][1,4]oxazepine-8-carboxamide | + |
| N-hydroxy-4-(2-(2-methylthiazol-4-yl)acetyl)-2,3,4,5-tetrahydrobenzo[f][1,4]oxazepine-8-carboxamide | ++ |
| 4-(2-(1,1-dioxidothiomorpholino)acetyl)-N-hydroxy-2,3,4,5-tetrahydrobenzo[f][1,4]oxazepine-8-carboxamide | + |
| N-hydroxy-4-(2-morpholinoacetyl)-2,3,4,5-tetrahydrobenzo[f][1,4]oxazepine-8-carboxamide | + |
| N-hydroxy-4-(2-methoxy-2-phenylacetyl)-2,3,4,5-tetrahydrobenzo[f][1,4]oxazepine-8-carboxamide | ++ |
| 4-(2-(4-fluorophenyl)propanoyl)-N-hydroxy-2,3,4,5-tetrahydrobenzo[f][1,4]oxazepine-8-carboxamide | ++ |
| 4-(2,3-dihydro-1H-indene-2-carbonyl)-N-hydroxy-2,3,4,5-tetrahydrobenzo[f][1,4]oxazepine-8-carboxamide | +++ |
| N-hydroxy-4-(3-phenylbutanoyl)-2,3,4,5-tetrahydrobenzo[f][1,4]oxazepine-8-carboxamide | ++ |
| N-hydroxy-4-(2-phenoxypropanoyl)-2,3,4,5-tetrahydrobenzo[f][1,4]oxazepine-8-carboxamide | ++ |
| 4-(1-acetylpiperidine-3-carbonyl)-N-hydroxy-2,3,4,5-tetrahydrobenzo[f][1,4]oxazepine-8-carboxamide | +++ |
| N-hydroxy-4-(2-phenoxybutanoyl)-2,3,4,5-tetrahydrobenzo[f][1,4]oxazepine-8-carboxamide | ++ |
| N-hydroxy-4-(2-phenylcyclopropane-1-carbonyl)-2,3,4,5-tetrahydrobenzo[f][1,4]oxazepine-8-carboxamide | +++ |
| N-hydroxy-4-(2-(2-oxo-3-(trifluoromethyl)pyridin-1(2H)-yl)acetyl)-2,3,4,5-tetrahydrobenzo[f][1,4]oxazepine-8-carboxamide | ++ |
| N-hydroxy-4-(2-isobutoxyacetyl)-2,3,4,5-tetrahydrobenzo[f][1,4]oxazepine-8-carboxamide | + |
| 4-(4,4-difluorocyclohexane-1-carbonyl)-N-hydroxy-2,3,4,5-tetrahydrobenzo[f][1,4]oxazepine-8-carboxamide | ++ |
| N-hydroxy-4-(N-methyl-N-(methylsulfonyl)glycyl)-2,3,4,5-tetrahydrobenzo[f][1,4]oxazepine-8-carboxamide | ++ |
| (S)-4-(2,2-dimethylcyclopropane-1-carbonyl)-N-hydroxy-2,3,4,5-tetrahydrobenzo[f][1,4]oxazepine-8-carboxamide | ++ |
| 4-(3,3-difluorocyclobutane-1-carbonyl)-N-hydroxy-2,3,4,5-tetrahydrobenzo[f][1,4]oxazepine-8-carboxamide | ++ |
| 4-(2-cyclopropylacetyl)-N-hydroxy-2,3,4,5-tetrahydrobenzo[f][1,4]oxazepine-8-carboxamide | +++ |
| N-hydroxy-4-(3-hydroxypropanoyl)-2,3,4,5-tetrahydrobenzo[f][1,4]oxazepine-8-carboxamide | + |
| N-hydroxy-4-(1-hydroxycyclopropane-1-carbonyl)-2,3,4,5-tetrahydrobenzo[f][1,4]oxazepine-8-carboxamide | + |
| N-hydroxy-4-(2-hydroxy-2-methylpropanoyl)-2,3,4,5-tetrahydrobenzo[f][1,4]oxazepine-8-carboxamide | ++ |
| 4-(2-cyclopentyl-2-hydroxy-2-phenylacetyl)-N-hydroxy-2,3,4,5-tetrahydrobenzo[f][1,4]oxazepine-8-carboxamide | + |
| N-hydroxy-4-(2-(3-methoxyphenyl)-2-methylpropanoyl)-2,3,4,5-tetrahydrobenzo[f][1,4]oxazepine-8-carboxamide | ++ |
| 4-(2-(4-chloro-1H-pyrazol-1-yl)-2-methylpropanoyl)-N-hydroxy-2,3,4,5-tetrahydrobenzo[f][1,4]oxazepine-8-carboxamide | +++ |
| 4-(2-cyclohexyl-2-methylpropanoyl)-N-hydroxy-2,3,4,5-tetrahydrobenzo[f][1,4]oxazepine-8-carboxamide | ++ |
| 4-(2-(3,4-dimethoxyphenyl)-2-methylpropanoyl)-N-hydroxy-2,3,4,5-tetrahydrobenzo[f][1,4]oxazepine-8-carboxamide | ++ |
| 4-(2-([1,1'-biphenyl]-4-yl)-2-methylpropanoyl)-N-hydroxy-2,3,4,5-tetrahydrobenzo[f][1,4]oxazepine-8-carboxamide | ++ |
| N-hydroxy-4-(2-methyl-2-(3-methyl-1H-pyrazol-1-yl)propanoyl)-2,3,4,5-tetrahydrobenzo[f][1,4]oxazepine-8-carboxamide | +++ |
| N-hydroxy-4-(2-methyl-2-(naphthalen-2-yl)propanoyl)-2,3,4,5-tetrahydrobenzo[f][1,4]oxazepine-8-carboxamide | ++ |
| N-hydroxy-4-(2-(2-methoxyphenyl)-2-methylpropanoyl)-2,3,4,5-tetrahydrobenzo[f][1,4]oxazepine-8-carboxamide | + |
| N-hydroxy-4-(2-methyl-2-(pyridin-3-yl)propanoyl)-2,3,4,5-tetrahydrobenzo[f][1,4]oxazepine-8-carboxamide | ++ |
| 4-(2-(4-fluorophenyl)-2-methylpropanoyl)-N-hydroxy-2,3,4,5-tetrahydrobenzo[f][1,4]oxazepine-8-carboxamide | ++ |
| 4-(2-(2,3-dihydrobenzo[b][1,4]dioxin-6-yl)-2-methylpropanoyl)-N-hydroxy-2,3,4,5-tetrahydrobenzo[f][1,4]oxazepine-8-carboxamide | ++ |

TABLE 36-continued

Inhibitory Concentration (IC$_{50}$) Values for Representative Compounds against HDAC6.

| ChemDraw IUPAC Name | Activity Range |
|---|---|
| N-hydroxy-4-(2-methyl-2-(thiophen-2-yl)propanoyl)-2,3,4,5-tetrahydrobenzo[f][1,4]oxazepine-8-carboxamide | +++ |
| N-hydroxy-4-(3-(4-methoxyphenyl)-2-phenylpropanoyl)-2,3,4,5-tetrahydrobenzo[f][1,4]oxazepine-8-carboxamide | ++ |
| N-hydroxy-4-(2-(5-methyl-1H-tetrazol-1-yl)-2-phenylacetyl)-2,3,4,5-tetrahydrobenzo[f][1,4]oxazepine-8-carboxamide | ++ |
| N-hydroxy-4-(2-phenyl-2-(1H-tetrazol-1-yl)acetyl)-2,3,4,5-tetrahydrobenzo[f][1,4]oxazepine-8-carboxamide | ++ |
| N-hydroxy-4-(2-phenyl-2-((tetrahydro-2H-pyran-4-yl)oxy)acetyl)-2,3,4,5-tetrahydrobenzo[f][1,4]oxazepine-8-carboxamide | + |
| N-hydroxy-4-(2-hydroxy-3-methyl-2-phenylbutanoyl)-2,3,4,5-tetrahydrobenzo[f][1,4]oxazepine-8-carboxamide | + |
| N-hydroxy-4-(2-(4-hydroxypiperidin-1-yl)-2-phenylacetyl)-2,3,4,5-tetrahydrobenzo[f][1,4]oxazepine-8-carboxamide | ++ |
| N-hydroxy-4-(2-phenyl-2-(2,2,2-trifluoroethoxy)acetyl)-2,3,4,5-tetrahydrobenzo[f][1,4]oxazepine-8-carboxamide | ++ |
| 4-(2-(tert-butoxy)-2-phenylacetyl)-N-hydroxy-2,3,4,5-tetrahydrobenzo[f][1,4]oxazepine-8-carboxamide | ++ |
| N-hydroxy-4-(2-phenyl-2-(1H-pyrazol-1-yl)acetyl)-2,3,4,5-tetrahydrobenzo[f][1,4]oxazepine-8-carboxamide | ++ |
| N-hydroxy-4-(2-methoxy-2-phenylpropanoyl)-2,3,4,5-tetrahydrobenzo[f][1,4]oxazepine-8-carboxamide | ++ |
| N-hydroxy-4-(2-phenoxy-2-phenylacetyl)-2,3,4,5-tetrahydrobenzo[f][1,4]oxazepine-8-carboxamide | ++ |
| N-hydroxy-4-(2-(2-oxopiperidin-1-yl)-2-phenylacetyl)-2,3,4,5-tetrahydrobenzo[f][1,4]oxazepine-8-carboxamide | ++ |
| N-hydroxy-4-(2-methyl-2-phenylpropanoyl)-2,3,4,5-tetrahydrobenzo[f][1,4]oxazepine-8-carboxamide | ++ |
| N-hydroxy-4-(2-(4-isobutoxyphenyl)-2-methylpropanoyl)-2,3,4,5-tetrahydrobenzo[f][1,4]oxazepine-8-carboxamide | ++ |
| 4-(1,1-dioxidotetrahydro-2H-thiopyran-4-carbonyl)-N-hydroxy-2,3,4,5-tetrahydrobenzo[f][1,4]oxazepine-8-carboxamide | +++ |
| N-hydroxy-4-(4-methoxycyclohexane-1-carbonyl)-2,3,4,5-tetrahydrobenzo[f][1,4]oxazepine-8-carboxamide | +++ |
| N-hydroxy-4-(1-(pyridin-2-yl)cyclopropane-1-carbonyl)-2,3,4,5-tetrahydrobenzo[f][1,4]oxazepine-8-carboxamide | +++ |
| N-hydroxy-4-(4-phenyltetrahydro-2H-pyran-4-carbonyl)-2,3,4,5-tetrahydrobenzo[f][1,4]oxazepine-8-carboxamide | ++ |
| N-hydroxy-4-(2-(pyridin-3-yl)propanoyl)-2,3,4,5-tetrahydrobenzo[f][1,4]oxazepine-8-carboxamide | +++ |
| N-hydroxy-4-(4-methoxy-2-(pyridin-2-yl)butanoyl)-2,3,4,5-tetrahydrobenzo[f][1,4]oxazepine-8-carboxamide | ++ |
| 4-(3,3-difluorocyclopentane-1-carbonyl)-N-hydroxy-2,3,4,5-tetrahydrobenzo[f][1,4]oxazepine-8-carboxamide | +++ |
| N-hydroxy-4-(1-methylcyclopropane-1-carbonyl)-2,3,4,5-tetrahydrobenzo[f][1,4]oxazepine-8-carboxamide | +++ |
| N-hydroxy-4-(1-(methoxymethyl)cyclobutane-1-carbonyl)-2,3,4,5-tetrahydrobenzo[f][1,4]oxazepine-8-carboxamide | +++ |
| 4-(1-((1H-imidazol-1-yl)methyl)cyclopropane-1-carbonyl)-N-hydroxy-2,3,4,5-tetrahydrobenzo[f][1,4]oxazepine-8-carboxamide | +++ |
| N-hydroxy-4-(1-(methoxymethyl)cyclopropane-1-carbonyl)-2,3,4,5-tetrahydrobenzo[f][1,4]oxazepine-8-carboxamide | +++ |
| N-hydroxy-4-(2-methyl-3-phenylpropanoyl)-2,3,4,5-tetrahydrobenzo[f][1,4]oxazepine-8-carboxamide | +++ |
| 4-(1-acetylpyrrolidine-3-carbonyl)-N-hydroxy-2,3,4,5-tetrahydrobenzo[f][1,4]oxazepine-8-carboxamide | ++ |
| N-hydroxy-4-(1-methylcyclopentane-1-carbonyl)-2,3,4,5-tetrahydrobenzo[f][1,4]oxazepine-8-carboxamide | +++ |
| N-hydroxy-4-(1-(2-(trifluoromethyl)phenyl)cyclopropane-1-carbonyl)-2,3,4,5-tetrahydrobenzo[f][1,4]oxazepine-8-carboxamide | +++ |
| N-hydroxy-4-(1-(3-(trifluoromethyl)phenyl)cyclopropane-1-carbonyl)-2,3,4,5-tetrahydrobenzo[f][1,4]oxazepine-8-carboxamide | +++ |
| N-hydroxy-4-(tetrahydrofuran-3-carbonyl)-2,3,4,5-tetrahydrobenzo[f][1,4]oxazepine-8-carboxamide | +++ |
| N-hydroxy-4-(1-(4-(trifluoromethyl)phenyl)cyclopropane-1-carbonyl)-2,3,4,5-tetrahydrobenzo[f][1,4]oxazepine-8-carboxamide | +++ |
| N-hydroxy-4-(1-phenylcyclobutane-1-carbonyl)-2,3,4,5-tetrahydrobenzo[f][1,4]oxazepine-8-carboxamide | +++ |
| 4-(1-benzylcyclopropane-1-carbonyl)-N-hydroxy-2,3,4,5-tetrahydrobenzo[f][1,4]oxazepine-8-carboxamide | +++ |
| N-hydroxy-4-(1-methoxycyclobutane-1-carbonyl)-2,3,4,5-tetrahydrobenzo[f][1,4]oxazepine-8-carboxamide | +++ |
| N-hydroxy-4-(1-(phenylsulfonyl)cyclopropane-1-carbonyl)-2,3,4,5-tetrahydrobenzo[f][1,4]oxazepine-8-carboxamide | +++ |

TABLE 36-continued

Inhibitory Concentration (IC$_{50}$) Values for Representative Compounds against HDAC6.

| ChemDraw IUPAC Name | Activity Range |
|---|---|
| 4-(1-(4-fluorophenyl)cyclopropane-1-carbonyl)-N-hydroxy-2,3,4,5-tetrahydrobenzo[f][1,4]oxazepine-8-carboxamide | +++ |
| 4-(1-(4-chlorophenyl)cyclopropane-1-carbonyl)-N-hydroxy-2,3,4,5-tetrahydrobenzo[f][1,4]oxazepine-8-carboxamide | +++ |
| N-hydroxy-4-(1-(4-methoxyphenyl)cyclopropane-1-carbonyl)-2,3,4,5-tetrahydrobenzo[f][1,4]oxazepine-8-carboxamide | +++ |
| 4-(1-(3-chlorophenyl)cyclopropane-1-carbonyl)-N-hydroxy-2,3,4,5-tetrahydrobenzo[f][1,4]oxazepine-8-carboxamide | +++ |
| 4-(1-(2-chlorophenyl)cyclopropane-1-carbonyl)-N-hydroxy-2,3,4,5-tetrahydrobenzo[f][1,4]oxazepine-8-carboxamide | +++ |
| N-hydroxy-4-(1-(3-methoxyphenyl)cyclopropane-1-carbonyl)-2,3,4,5-tetrahydrobenzo[f][1,4]oxazepine-8-carboxamide | +++ |
| N-hydroxy-4-(1-(pyridin-4-yl)cyclopropane-1-carbonyl)-2,3,4,5-tetrahydrobenzo[f][1,4]oxazepine-8-carboxamide | +++ |
| N-hydroxy-4-(1-(pyrazin-2-yl)cyclopropane-1-carbonyl)-2,3,4,5-tetrahydrobenzo[f][1,4]oxazepine-8-carboxamide | +++ |
| N-hydroxy-4-(1-phenoxycyclopropane-1-carbonyl)-2,3,4,5-tetrahydrobenzo[f][1,4]oxazepine-8-carboxamide | ++ |
| 4-(1-((1H-pyrazol-1-yl)methyl)cyclopropane-1-carbonyl)-N-hydroxy-2,3,4,5-tetrahydrobenzo[f][1,4]oxazepine-8-carboxamide | +++ |
| N-hydroxy-4-(1-(thiophen-2-yl)cyclopropane-1-carbonyl)-2,3,4,5-tetrahydrobenzo[f][1,4]oxazepine-8-carboxamide | +++ |
| N-hydroxy-4-(oxetane-3-carbonyl)-2,3,4,5-tetrahydrobenzo[f][1,4]oxazepine-8-carboxamide | +++ |
| N-hydroxy-4-(3-methyloxetane-3-carbonyl)-2,3,4,5-tetrahydrobenzo[f][1,4]oxazepine-8-carboxamide | +++ |
| N-hydroxy-8-(tetrahydro-2H-pyran-4-carbonyl)-6,7,8,9-tetrahydropyrazino[2,3-f][1,4]oxazepine-3-carboxamide | ++ |
| 8-(cyclohexanecarbonyl)-N-hydroxy-6,7,8,9-tetrahydropyrazino[2,3-f][1,4]oxazepine-3-carboxamide | +++ |
| (R)-N-hydroxy-2-isopropyl-4-(tetrahydro-2H-pyran-4-carbonyl)-2,3,4,5-tetrahydrobenzo[f][1,4]oxazepine-8-carboxamide | ++ |
| (R)-N-hydroxy-2-isopropyl-4-(1-methylcyclobutane-1-carbonyl)-2,3,4,5-tetrahydrobenzo[f][1,4]oxazepine-8-carboxamide | ++ |
| (R)-4-formyl-N-hydroxy-2-isopropyl-2,3,4,5-tetrahydrobenzo[f][1,4]oxazepine-8-carboxamide | ++ |
| (R)-N-hydroxy-2-(methoxymethyl)-4-(tetrahydro-2H-pyran-4-carbonyl)-2,3,4,5-tetrahydrobenzo[f][1,4]oxazepine-8-carboxamide | ++ |
| (R)-N-hydroxy-2-(methoxymethyl)-4-(1-methylcyclobutane-1-carbonyl)-2,3,4,5-tetrahydrobenzo[f][1,4]oxazepine-8-carboxamide | ++ |
| (R)-4-formyl-N-hydroxy-2-(methoxymethyl)-2,3,4,5-tetrahydrobenzo[f][1,4]oxazepine-8-carboxamide | +++ |
| (S)-N-hydroxy-2-(methoxymethyl)-4-(tetrahydro-2H-pyran-4-carbonyl)-2,3,4,5-tetrahydrobenzo[f][1,4]oxazepine-8-carboxamide | ++ |
| (S)-N-hydroxy-2-(methoxymethyl)-4-(1-methylcyclobutane-1-carbonyl)-2,3,4,5-tetrahydrobenzo[f][1,4]oxazepine-8-carboxamide | +++ |
| (S)-4-formyl-N-hydroxy-2-(methoxymethyl)-2,3,4,5-tetrahydrobenzo[f][1,4]oxazepine-8-carboxamide | ++ |
| (R)-N-hydroxy-2-phenyl-4-(tetrahydro-2H-pyran-4-carbonyl)-2,3,4,5-tetrahydrobenzo[f][1,4]oxazepine-8-carboxamide | ++ |
| (R)-N-hydroxy-4-(1-methylcyclobutane-1-carbonyl)-2-phenyl-2,3,4,5-tetrahydrobenzo[f][1,4]oxazepine-8-carboxamide | ++ |
| (R)-4-formyl-N-hydroxy-2-phenyl-2,3,4,5-tetrahydrobenzo[f][1,4]oxazepine-8-carboxamide | +++ |
| (S)-N-hydroxy-2-phenyl-4-(tetrahydro-2H-pyran-4-carbonyl)-2,3,4,5-tetrahydrobenzo[f][1,4]oxazepine-8-carboxamide | +++ |
| (S)-N-hydroxy-4-(1-methylcyclobutane-1-carbonyl)-2-phenyl-2,3,4,5-tetrahydrobenzo[f][1,4]oxazepine-8-carboxamide | +++ |
| (S)-4-formyl-N-hydroxy-2-phenyl-2,3,4,5-tetrahydrobenzo[f][1,4]oxazepine-8-carboxamide | +++ |
| (R)-N-hydroxy-4-(tetrahydro-2H-pyran-4-carbonyl)-3-(trifluoromethyl)-2,3,4,5-tetrahydrobenzo[f][1,4]oxazepine-8-carboxamide | +++ |
| (R)-N-hydroxy-4-(oxetane-3-carbonyl)-3-(trifluoromethyl)-2,3,4,5-tetrahydrobenzo[f][1,4]oxazepine-8-carboxamide | +++ |
| N-hydroxy-4-(tetrahydro-2H-pyran-4-carbonyl)-4,5-dihydro-2H-spiro[benzo[f][1,4]oxazepine-3,1'-cyclopropane]-8-carboxamide | +++ |
| (S)-3-ethyl-N-hydroxy-4-(tetrahydro-2H-pyran-4-carbonyl)-2,3,4,5-tetrahydrobenzo[f][1,4]oxazepine-8-carboxamide | +++ |
| (S)-N-hydroxy-3-isopropyl-4-(2-(tetrahydro-2H-pyran-4-yl)acetyl)-2,3,4,5-tetrahydrobenzo[f][1,4]oxazepine-8-carboxamide | ++ |
| (S)-N-hydroxy-3-isopropyl-4-(tetrahydro-2H-pyran-4-carbonyl)-2,3,4,5-tetrahydrobenzo[f][1,4]oxazepine-8-carboxamide | +++ |
| (S)-N-hydroxy-4-((1s,4R)-4-methoxycyclohexane-1-carbonyl)-3-methyl-2,3,4,5-tetrahydrobenzo[f][1,4]oxazepine-8-carboxamide | +++ |

TABLE 36-continued

Inhibitory Concentration (IC$_{50}$) Values for Representative Compounds against HDAC6.

| ChemDraw IUPAC Name | Activity Range |
| --- | --- |
| (S)-N-hydroxy-4-((1r,4S)-4-methoxycyclohexane-1-carbonyl)-3-methyl-2,3,4,5-tetrahydrobenzo[f][1,4]oxazepine-8-carboxamide | +++ |
| (S)-4-(1-formylpiperidine-4-carbonyl)-N-hydroxy-3-methyl-2,3,4,5-tetrahydrobenzo[f][1,4]oxazepine-8-carboxamide | +++ |
| (S)-N-hydroxy-4-(3-(methoxymethyl)oxetane-3-carbonyl)-3-methyl-2,3,4,5-tetrahydrobenzo[f][1,4]oxazepine-8-carboxamide | +++ |
| (S)-N-hydroxy-3-methyl-4-((R)-tetrahydro-2H-pyran-3-carbonyl)-2,3,4,5-tetrahydrobenzo[f][1,4]oxazepine-8-carboxamide | +++ |
| (S)-N-hydroxy-3-methyl-4-((S)-tetrahydro-2H-pyran-3-carbonyl)-2,3,4,5-tetrahydrobenzo[f][1,4]oxazepine-8-carboxamide | +++ |
| (S)-N-hydroxy-3-methyl-4-((R)-tetrahydrofuran-3-carbonyl)-2,3,4,5-tetrahydrobenzo[f][1,4]oxazepine-8-carboxamide | +++ |
| (S)-N-hydroxy-3-methyl-4-((S)-tetrahydrofuran-3-carbonyl)-2,3,4,5-tetrahydrobenzo[f][1,4]oxazepine-8-carboxamide | +++ |
| (S)-N-hydroxy-3-methyl-4-(2-(tetrahydro-2H-pyran-4-yl)acetyl)-2,3,4,5-tetrahydrobenzo[f][1,4]oxazepine-8-carboxamide | ++ |
| (S)-N-hydroxy-4-(4-(methoxymethyl)tetrahydro-2H-pyran-4-carbonyl)-3-methyl-2,3,4,5-tetrahydrobenzo[f][1,4]oxazepine-8-carboxamide | +++ |
| (S)-4-(3-ethyloxetane-3-carbonyl)-N-hydroxy-3-methyl-2,3,4,5-tetrahydrobenzo[f][1,4]oxazepine-8-carboxamide | +++ |
| (S)-4-(3-(4-fluorophenoxy)propanoyl)-N-hydroxy-3-methyl-2,3,4,5-tetrahydrobenzo[f][1,4]oxazepine-8-carboxamide | +++ |
| (S)-N-hydroxy-3-methyl-4-((1s,4R)-4-(trifluoromethoxy)cyclohexane-1-carbonyl)-2,3,4,5-tetrahydrobenzo[f][1,4]oxazepine-8-carboxamide | +++ |
| (S)-N-hydroxy-3-methyl-4-((1r,4S)-4-(trifluoromethoxy)cyclohexane-1-carbonyl)-2,3,4,5-tetrahydrobenzo[f][1,4]oxazepine-8-carboxamide | +++ |
| (S)-N-hydroxy-4-((1s,3R)-3-methoxycyclobutane-1-carbonyl)-3-methyl-2,3,4,5-tetrahydrobenzo[f][1,4]oxazepine-8-carboxamide | +++ |
| (S)-N-hydroxy-4-((1r,3S)-3-methoxycyclobutane-1-carbonyl)-3-methyl-2,3,4,5-tetrahydrobenzo[f][1,4]oxazepine-8-carboxamide | +++ |
| (S)-4-(3-(benzyloxy)cyclobutane-1-carbonyl)-N-hydroxy-3-methyl-2,3,4,5-tetrahydrobenzo[f][1,4]oxazepine-8-carboxamide | +++ |
| (3S)-N-hydroxy-3-methyl-4-(2-(tetrahydrofuran-2-yl)acetyl)-2,3,4,5-tetrahydrobenzo[f][1,4]oxazepine-8-carboxamide | +++ |
| (S)-4-(cyclohexanecarbonyl)-N-hydroxy-3-methyl-2,3,4,5-tetrahydrobenzo[f][1,4]oxazepine-8-carboxamide | +++ |
| (S)-N-hydroxy-4-(3-methoxypropanoyl)-3-methyl-2,3,4,5-tetrahydrobenzo[f][1,4]oxazepine-8-carboxamide | +++ |
| (S)-4-(4-fluorobenzoyl)-N-hydroxy-3-methyl-2,3,4,5-tetrahydrobenzo[f][1,4]oxazepine-8-carboxamide | +++ |
| (S)-N-hydroxy-3-methyl-4-propionyl-2,3,4,5-tetrahydrobenzo[f][1,4]oxazepine-8-carboxamide | +++ |
| (S)-4-(cyclopropanecarbonyl)-N-hydroxy-3-methyl-2,3,4,5-tetrahydrobenzo[f][1,4]oxazepine-8-carboxamide | +++ |
| (S)-4-(cyclobutanecarbonyl)-N-hydroxy-3-methyl-2,3,4,5-tetrahydrobenzo[f][1,4]oxazepine-8-carboxamide | +++ |
| (S)-4-(cyclopentanecarbonyl)-N-hydroxy-3-methyl-2,3,4,5-tetrahydrobenzo[f][1,4]oxazepine-8-carboxamide | +++ |
| (S)-N-hydroxy-4-isobutyryl-3-methyl-2,3,4,5-tetrahydrobenzo[f][1,4]oxazepine-8-carboxamide | +++ |
| (S)-N-hydroxy-4-(3-hydroxy-3-methylbutanoyl)-3-methyl-2,3,4,5-tetrahydrobenzo[f][1,4]oxazepine-8-carboxamide | +++ |
| (S)-N-hydroxy-4-(3-hydroxy-2,2-dimethylpropanoyl)-3-methyl-2,3,4,5-tetrahydrobenzo[f][1,4]oxazepine-8-carboxamide | +++ |
| (S)-N-hydroxy-4-(3-methoxy-3-methylbutanoyl)-3-methyl-2,3,4,5-tetrahydrobenzo[f][1,4]oxazepine-8-carboxamide | +++ |
| (S)-4-(4-fluorotetrahydro-2H-pyran-4-carbonyl)-N-hydroxy-3-methyl-2,3,4,5-tetrahydrobenzo[f][1,4]oxazepine-8-carboxamide | +++ |
| (3S)-N-hydroxy-3-methyl-4-(oxepane-4-carbonyl)-2,3,4,5-tetrahydrobenzo[f][1,4]oxazepine-8-carboxamide | +++ |
| (S)-N-hydroxy-3-methyl-4-((S)-2-methyltetrahydro-2H-pyran-2-carbonyl)-2,3,4,5-tetrahydrobenzo[f][1,4]oxazepine-8-carboxamide | +++ |
| (S)-N-hydroxy-3-methyl-4-((R)-2-methyltetrahydro-2H-pyran-2-carbonyl)-2,3,4,5-tetrahydrobenzo[f][1,4]oxazepine-8-carboxamide | ++ |
| (3S)-N-hydroxy-4-(2-isopropyltetrahydrofuran-3-carbonyl)-3-methyl-2,3,4,5-tetrahydrobenzo[f][1,4]oxazepine-8-carboxamide | +++ |
| (3S)-4-(5,5-dimethyltetrahydrofuran-2-carbonyl)-N-hydroxy-3-methyl-2,3,4,5-tetrahydrobenzo[f][1,4]oxazepine-8-carboxamide | +++ |
| (3S)-N-hydroxy-3-methyl-4-(2-methyltetrahydrofuran-2-carbonyl)-2,3,4,5-tetrahydrobenzo[f][1,4]oxazepine-8-carboxamide | +++ |
| (3S)-4-((2R)-7-oxabicyclo[2.2.1]heptane-2-carbonyl)-N-hydroxy-3-methyl-2,3,4,5-tetrahydrobenzo[f][1,4]oxazepine-8-carboxamide | +++ |

TABLE 36-continued

Inhibitory Concentration (IC$_{50}$) Values for Representative Compounds against HDAC6.

| ChemDraw IUPAC Name | Activity Range |
|---|---|
| (3S)-4-((2S)-7-oxabicyclo[2.2.1]heptane-2-carbonyl)-N-hydroxy-3-methyl-2,3,4,5-tetrahydrobenzo[f][1,4]oxazepine-8-carboxamide | +++ |
| (S)-N-hydroxy-4-(1-(methoxymethyl)cyclobutane-1-carbonyl)-3-methyl-2,3,4,5-tetrahydrobenzo[f][1,4]oxazepine-8-carboxamide | +++ |
| (S)-N-hydroxy-3-methyl-4-(3-((tetrahydro-2H-pyran-4-yl)oxy)propanoyl)-2,3,4,5-tetrahydrobenzo[f][1,4]oxazepine-8-carboxamide | ++ |
| (S)-N-hydroxy-4-(1-(methoxymethyl)cyclopropane-1-carbonyl)-3-methyl-2,3,4,5-tetrahydrobenzo[f][1,4]oxazepine-8-carboxamide | +++ |
| (S)-N-hydroxy-3-methyl-4-((1r,3S)-3-phenoxycyclobutane-1-carbonyl)-2,3,4,5-tetrahydrobenzo[f][1,4]oxazepine-8-carboxamide | +++ |
| (S)-N-hydroxy-3-methyl-4-((1s,3R)-3-phenoxycyclobutane-1-carbonyl)-2,3,4,5-tetrahydrobenzo[f][1,4]oxazepine-8-carboxamide | +++ |
| (S)-N-hydroxy-3-methyl-4-((2R,3S)-2-methyltetrahydro-2H-pyran-3-carbonyl)-2,3,4,5-tetrahydrobenzo[f][1,4]oxazepine-8-carboxamide | +++ |
| (S)-N-hydroxy-3-methyl-4-(3-(2,2,2-trifluoroethoxy)propanoyl)-2,3,4,5-tetrahydrobenzo[f][1,4]oxazepine-8-carboxamide | +++ |
| (S)-N-hydroxy-4-((2S,4S)-2-isopropyltetrahydro-2H-pyran-4-carbonyl)-3-methyl-2,3,4,5-tetrahydrobenzo[f][1,4]oxazepine-8-carboxamide | +++ |
| (S)-4-benzoyl-N-hydroxy-3-methyl-2,3,4,5-tetrahydrobenzo[f][1,4]oxazepine-8-carboxamide | +++ |
| (S)-4-(2-(4-fluorophenyl)-2-methylpropanoyl)-N-hydroxy-3-methyl-2,3,4,5-tetrahydrobenzo[f][1,4]oxazepine-8-carboxamide | +++ |
| (S)-4-(3-(4-fluorophenyl)-2,2-dimethylpropanoyl)-N-hydroxy-3-methyl-2,3,4,5-tetrahydrobenzo[f][1,4]oxazepine-8-carboxamide | +++ |
| (S)-4-((S)-2,2-dimethyltetrahydro-2H-pyran-4-carbonyl)-N-hydroxy-3-methyl-2,3,4,5-tetrahydrobenzo[f][1,4]oxazepine-8-carboxamide | +++ |
| (S)-4-((R)-2,2-dimethyltetrahydro-2H-pyran-4-carbonyl)-N-hydroxy-3-methyl-2,3,4,5-tetrahydrobenzo[f][1,4]oxazepine-8-carboxamide | +++ |
| (R)-N-hydroxy-3-(methoxymethyl)-4-(tetrahydro-2H-pyran-4-carbonyl)-2,3,4,5-tetrahydrobenzo[f][1,4]oxazepine-8-carboxamide | + |
| (S)-N-hydroxy-3-(methoxymethyl)-4-(tetrahydro-2H-pyran-4-carbonyl)-2,3,4,5-tetrahydrobenzo[f][1,4]oxazepine-8-carboxamide | +++ |
| N-hydroxy-4-(1-methoxycyclopropane-1-carbonyl)-2,3,4,5-tetrahydrobenzo[f][1,4]oxazepine-8-carboxamide | +++ |
| N-hydroxy-4-(4-methyltetrahydro-2H-pyran-4-carbonyl)-2,3,4,5-tetrahydrobenzo[f][1,4]oxazepine-8-carboxamide | +++ |
| 4-(3-ethyloxetane-3-carbonyl)-N-hydroxy-2,3,4,5-tetrahydrobenzo[f][1,4]oxazepine-8-carboxamide | +++ |
| N-hydroxy-4-(1-methyl-1H-pyrrole-2-carbonyl)-2,3,4,5-tetrahydrobenzo[f][1,4]oxazepine-8-carboxamide | +++ |
| N-hydroxy-4-(1-methyl-1H-indole-2-carbonyl)-2,3,4,5-tetrahydrobenzo[f][1,4]oxazepine-8-carboxamide | +++ |
| 4-(2-(3,5-bis(trifluoromethyl)phenyl)acetyl)-N-hydroxy-2,3,4,5-tetrahydrobenzo[f][1,4]oxazepine-8-carboxamide | ++ |
| 4-(3,5-bis(trifluoromethyl)benzoyl)-N-hydroxy-2,3,4,5-tetrahydrobenzo[f][1,4]oxazepine-8-carboxamide | ++ |
| N-hydroxy-4-(1-methyl-1H-pyrazole-3-carbonyl)-2,3,4,5-tetrahydrobenzo[f][1,4]oxazepine-8-carboxamide | +++ |
| N-hydroxy-4-(2-mesitylacetyl)-2,3,4,5-tetrahydrobenzo[f][1,4]oxazepine-8-carboxamide | +++ |
| N8-hydroxy-N2,N2-dimethyl-4-(tetrahydro-2H-pyran-4-carbonyl)-2,3,4,5-tetrahydrobenzo[f][1,4]oxazepine-2,8-dicarboxamide | ++ |
| (R)-N-hydroxy-5-isopropyl-4-(tetrahydro-2H-pyran-4-carbonyl)-2,3,4,5-tetrahydrobenzo[f][1,4]oxazepine-8-carboxamide | + |
| (R)-N-hydroxy-5-isopropyl-4-(oxetane-3-carbonyl)-2,3,4,5-tetrahydrobenzo[f][1,4]oxazepine-8-carboxamide | + |
| (S)-N-hydroxy-5-isopropyl-4-(tetrahydro-2H-pyran-4-carbonyl)-2,3,4,5-tetrahydrobenzo[f][1,4]oxazepine-8-carboxamide | + |
| (S)-N-hydroxy-5-isopropyl-4-(oxetane-3-carbonyl)-2,3,4,5-tetrahydrobenzo[f][1,4]oxazepine-8-carboxamide | + |
| (R)-N-hydroxy-5-methyl-4-(1-methylcyclobutane-1-carbonyl)-2,3,4,5-tetrahydrobenzo[f][1,4]oxazepine-8-carboxamide | + |

TABLE 36-continued

Inhibitory Concentration (IC$_{50}$) Values for Representative Compounds against HDAC6.

| ChemDraw IUPAC Name | Activity Range |
|---|---|
| (R)-N-hydroxy-5-methyl-4-(tetrahydro-2H-pyran-4-carbonyl)-2,3,4,5-tetrahydrobenzo[f][1,4]oxazepine-8-carboxamide | + |
| (S)-N-hydroxy-5-methyl-4-(1-methylcyclobutane-1-carbonyl)-2,3,4,5-tetrahydrobenzo[f][1,4]oxazepine-8-carboxamide | +++ |
| (S)-N-hydroxy-5-methyl-4-(tetrahydro-2H-pyran-4-carbonyl)-2,3,4,5-tetrahydrobenzo[f][1,4]oxazepine-8-carboxamide | +++ |
| (S)-N-hydroxy-5-methyl-4-(4-methyltetrahydro-2H-pyran-4-carbonyl)-2,3,4,5-tetrahydrobenzo[f][1,4]oxazepine-8-carboxamide | +++ |
| (S)-N-hydroxy-5-methyl-4-(3-methyloxetane-3-carbonyl)-2,3,4,5-tetrahydrobenzo[f][1,4]oxazepine-8-carboxamide | +++ |
| (S)-N-hydroxy-5-methyl-4-(oxetane-3-carbonyl)-2,3,4,5-tetrahydrobenzo[f][1,4]oxazepine-8-carboxamide | +++ |
| (S)-N-hydroxy-4-(3-(methoxymethyl)oxetane-3-carbonyl)-5-methyl-2,3,4,5-tetrahydrobenzo[f][1,4]oxazepine-8-carboxamide | +++ |
| (S)-N-hydroxy-5-methyl-4-((S)-tetrahydro-2H-pyran-3-carbonyl)-2,3,4,5-tetrahydrobenzo[f][1,4]oxazepine-8-carboxamide | +++ |
| (S)-N-hydroxy-5-methyl-4-((R)-tetrahydro-2H-pyran-3-carbonyl)-2,3,4,5-tetrahydrobenzo[f][1,4]oxazepine-8-carboxamide | +++ |
| (S)-N-hydroxy-5-methyl-4-((S)-tetrahydrofuran-3-carbonyl)-2,3,4,5-tetrahydrobenzo[f][1,4]oxazepine-8-carboxamide | +++ |
| (S)-N-hydroxy-5-methyl-4-((R)-tetrahydrofuran-3-carbonyl)-2,3,4,5-tetrahydrobenzo[f][1,4]oxazepine-8-carboxamide | +++ |
| (S)-N-hydroxy-4-((1s,4R)-4-methoxycyclohexane-1-carbonyl)-5-methyl-2,3,4,5-tetrahydrobenzo[f][1,4]oxazepine-8-carboxamide | +++ |
| (S)-N-hydroxy-4-((1r,4S)-4-methoxycyclohexane-1-carbonyl)-5-methyl-2,3,4,5-tetrahydrobenzo[f][1,4]oxazepine-8-carboxamide | +++ |
| (S)-N-hydroxy-5-methyl-4-((R)-3-methyltetrahydrofuran-3-carbonyl)-2,3,4,5-tetrahydrobenzo[f][1,4]oxazepine-8-carboxamide | +++ |
| (S)-N-hydroxy-5-methyl-4-((S)-3-methyltetrahydrofuran-3-carbonyl)-2,3,4,5-tetrahydrobenzo[f][1,4]oxazepine-8-carboxamide | +++ |
| (S)-N-hydroxy-5-methyl-4-((R)-3-methyltetrahydro-2H-pyran-3-carbonyl)-2,3,4,5-tetrahydrobenzo[f][1,4]oxazepine-8-carboxamide | +++ |
| (S)-N-hydroxy-5-methyl-4-((S)-3-methyltetrahydro-2H-pyran-3-carbonyl)-2,3,4,5-tetrahydrobenzo[f][1,4]oxazepine-8-carboxamide | +++ |
| (S)-N-hydroxy-4-(4-(methoxymethyl)tetrahydro-2H-pyran-4-carbonyl)-5-methyl-2,3,4,5-tetrahydrobenzo[f][1,4]oxazepine-8-carboxamide | +++ |
| (2R,5R)-N-hydroxy-4-(tetrahydro-2H-pyran-4-carbonyl)-2,3,4,5-tetrahydro-2,5-methanobenzo[f][1,4]oxazepine-8-carboxamide | ++ |
| (2S,5S)-N-hydroxy-4-(tetrahydro-2H-pyran-4-carbonyl)-2,3,4,5-tetrahydro-2,5-methanobenzo[f][1,4]oxazepine-8-carboxamide | + |
| (S)-N-hydroxy-3-methyl-4-(2-methyl-2-(tetrahydro-2H-pyran-4-yl)propanoyl)-2,3,4,5-tetrahydrobenzo[f][1,4]oxazepine-8-carboxamide | +++ |
| (S)-N-hydroxy-3-methyl-4-(2-methyl-2-(pyridin-3-yl)propanoyl)-2,3,4,5-tetrahydrobenzo[f][1,4]oxazepine-8-carboxamide | +++ |
| (S)-4-(1H-benzo[d]imidazole-2-carbonyl)-N-hydroxy-3-methyl-2,3,4,5-tetrahydrobenzo[f][1,4]oxazepine-8-carboxamide | +++ |
| (S)-N-hydroxy-3-methyl-4-((S)-tetrahydro-2H-pyran-2-carbonyl)-2,3,4,5-tetrahydrobenzo[f][1,4]oxazepine-8-carboxamide | +++ |
| (S)-N-hydroxy-3-methyl-4-((R)-tetrahydro-2H-pyran-2-carbonyl)-2,3,4,5-tetrahydrobenzo[f][1,4]oxazepine-8-carboxamide | +++ |
| (S)-N-hydroxy-3-methyl-4-((R)-3-methyltetrahydrofuran-3-carbonyl)-2,3,4,5-tetrahydrobenzo[f][1,4]oxazepine-8-carboxamide | +++ |
| (S)-N-hydroxy-3-methyl-4-((S)-3-methyltetrahydrofuran-3-carbonyl)-2,3,4,5-tetrahydrobenzo[f][1,4]oxazepine-8-carboxamide | +++ |
| N-hydroxy-4-(1-methylcyclobutane-1-carbonyl)-2-oxo-2,3,4,5-tetrahydro-1H-benzo[e][1,4]diazepine-7-carboxamide | ++ |
| (S)-3-benzyl-N-hydroxy-4-(tetrahydro-2H-pyran-4-carbonyl)-2,3,4,5-tetrahydrobenzo[f][1,4]oxazepine-8-carboxamide | +++ |
| N-hydroxy-4-(tetrahydro-2H-pyran-4-carbonyl)-3-(tetrahydro-2H-pyran-4-yl)-2,3,4,5-tetrahydrobenzo[f][1,4]oxazepine-8-carboxamide | + |

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

The invention claimed is:
1. A compound of Formula I:

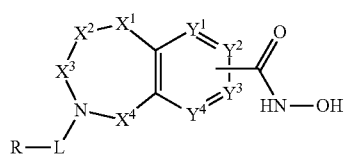

(I)

or a pharmaceutically acceptable salt thereof, wherein:
$X^1$ is O;
$X^2$ and $X^4$ are each $CR^1R^2$;
$X^3$ is $CR^{1'}R^{2'}$;
$Y^1$ and $Y^4$ are not bound to —C(O)NHOH and are each $CR^1$;
$Y^2$ and $Y^3$ are $CR^1$ when not bonded to —C(O)NHOH and $Y^2$ and $Y^3$ are C when bonded to —C(O)NHOH;
L is selected from the group consisting of —C(O)—, —C(O)(CR$^1$R$^2$)$_m$—, and —C(O)(CR$^1$R$^2$)$_m$O—, wherein L is bound to the ring nitrogen through the carbonyl group;
R is independently selected from the group consisting of —H, —C$_1$-C$_6$ alkyl, —C$_2$-C$_6$ alkenyl, —C$_4$-C$_8$ cycloalkenyl, —C$_2$-C$_6$ alkynyl, —C$_3$-C$_8$ cycloalkyl, —C$_5$-C$_{12}$ spirocyclyl, heterocyclyl, spiroheterocyclyl, aryl, and heteroaryl containing 1-5 heteroatoms selected from the group consisting of N, S, P, and O, wherein each alkyl, alkenyl, cycloalkenyl, alkynyl, cycloalkyl, spirocyclyl, heterocyclyl, spiroheterocyclyl, aryl, or heteroaryl is optionally substituted with one or more substituents selected from the group consisting of —OH, halogen, oxo, —NO$_2$, —CN, —R$^1$, —R$^2$, —OR$^3$, —NHR$^3$, —NR$^3$R$^4$, —S(O)$_2$NR$^3$R$^4$, —S(O)$_2$R$^1$, —C(O)R$^1$, —CO$_2$R$^1$, —NR$^3$S(O)$_2$R$^1$, —S(O)R$^1$, —S(O)NR$^3$R$^4$, —NR$^3$S(O)R$^1$, heterocyclyl, aryl, and heteroaryl containing 1-5 heteroatoms selected from the group consisting of N, S, P, and O, with the proviso that R is not bound to L via a nitrogen atom;
$R^1$ and $R^2$ are independently, at each occurrence, selected from the group consisting of —H, —R$^3$, —R$^4$, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, and —(CHR$^5$)$_n$NR$^3$R$^4$, wherein each alkyl, alkenyl, cycloalkenyl, alkynyl, cycloalkyl, heterocyclyl, aryl, or heteroaryl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$ N(R$^3$)$_2$, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl containing 1-5 heteroatoms selected from the group consisting of N, S, P, and O;
and one of $R^1$ and $R^2$ of $X^2$ combines with one of $R^1$ and $R^2$ of $X^4$ to form a bridging ring;
$R^{1'}$ and $R^{2'}$ are independently, at each occurrence, selected from the group consisting of —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, —OH, halogen, —NO$_2$, —CN, —NHC$_1$-C$_6$ alkyl, —N(C$_1$-C$_6$ alkyl)$_2$, —S(O)$_2$N(C$_1$-C$_6$ alkyl)$_2$, —N(C$_1$-C$_6$ alkyl)S(O)$_2$R$^5$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, and —(CHR$^5$)$_n$NR$^3$R$^4$, wherein each alkyl, alkenyl, cycloalkenyl, alkynyl, cycloalkyl, or heterocyclyl is optionally substituted with one or more substituents selected from the group consisting of —OH, halogen, —NO$_2$, oxo, —CN, —R$^5$, —OR$^3$, —NHR$^3$, —NR$^3$R$^4$, —S(O)$_2$N(R$^3$)$_2$, —S(O)$_2$R$^5$, —C(O)R$^5$, —CO$_2$R$^5$, —NR$^3$S(O)$_2$R$^5$, —S(O)R$^5$, —S(O)NR$^3$R$^4$, —NR$^3$S(O)R$^5$, heterocyclyl, aryl, and heteroaryl containing 1-5 heteroatoms selected from the group consisting of N, S, P, and O;
$R^3$ and $R^4$ are independently, at each occurrence, selected from the group consisting of —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —S(O)$_2$N(C$_1$-C$_6$ alkyl)$_2$, —S(O)$_2$(C$_1$-C$_6$ alkyl), —(C$_1$-C$_6$ alkyl)S(O)$_2$R$^5$, —C(O)C$_1$-C$_6$ alkyl, —CO$_2$C$_1$-C$_6$ alkyl, and —(CHR$^5$)$_n$ N(C$_1$-C$_6$ alkyl)$_2$, wherein each alkyl, alkenyl, cycloalkenyl, alkynyl, cycloalkyl, heterocyclyl, aryl, and heteroaryl is optionally substituted with one or more substituents selected from the group consisting of —OH, halogen, —NO$_2$, oxo, —CN, —R$^5$, —O(C$_1$-C$_6$ alkyl), —NH(C$_1$-C$_6$ alkyl), —N(C$_1$-C$_6$ alkyl)$_2$, —S(O)$_2$N(C$_1$-C$_6$ alkyl)$_2$, —S(O)$_2$NHC$_1$-C$_6$ alkyl, —C(O)C$_1$-C$_6$ alkyl, —CO$_2$C$_1$-C$_6$ alkyl, —N(C$_1$-C$_6$ alkyl)S(O)$_2$C$_1$-C$_6$ alkyl, —S(O)R$^5$, —S(O)N(C$_1$-C$_6$ alkyl)$_2$, —N(C$_1$-C$_6$ alkyl)S(O)R$^5$, heterocyclyl, aryl, and heteroaryl containing 1-5 heteroatoms selected from the group consisting of N, S, P, and O;
$R^5$ is independently, at each occurrence, selected from the group consisting of —H, —C$_1$-C$_6$ alkyl, —C$_2$-C$_6$ alkenyl, —C$_3$-C$_8$ cycloalkenyl, —C$_2$-C$_6$ alkynyl, —C$_3$-C$_8$ cycloalkyl, heterocyclyl, aryl, heteroaryl containing 1-5 heteroatoms selected from the group consisting of N, S, P, and O, —OH, halogen, —NO$_2$, —CN, —NH(C$_1$-C$_6$ alkyl), —N(C$_1$-C$_6$ alkyl)$_2$, —S(O)$_2$NH(C$_1$-C$_6$ alkyl), —S(O)$_2$N(C$_1$-C$_6$ alkyl)$_2$, —S(O)$_2$C$_1$-C$_6$ alkyl, —C(O)C$_1$-C$_6$ alkyl, —CO$_2$C$_1$-C$_6$ alkyl, —N(C$_1$-C$_6$ alkyl)SO$_2$C$_1$-C$_6$ alkyl, —S(O)(C$_1$-C$_6$ alkyl), —S(O)N(C$_1$-C$_6$ alkyl)$_2$, —N(C$_1$-C$_6$ alkyl)S(O)(C$_1$-C$_6$ alkyl), and —(CH$_2$)$_n$N(C$_1$-C$_6$ alkyl)$_2$;
each n is independently and at each occurrence an integer from 0 to 6; and
each m is independently and at each occurrence an integer from 1 to 6.

2. The compound of claim 1, wherein the compound is of the Formula IA:

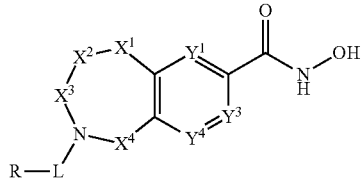

(IA)

or a pharmaceutically acceptable salt thereof.

3. The compound of claim 2, wherein the compound is of Formula IA-1:

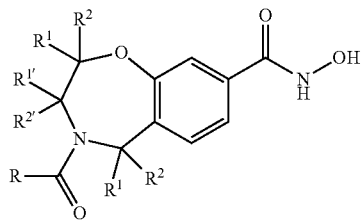

(IA-1)

or a pharmaceutically acceptable salt thereof.

4. The compound of claim 3, wherein the compound is of the Formula IA-1e:

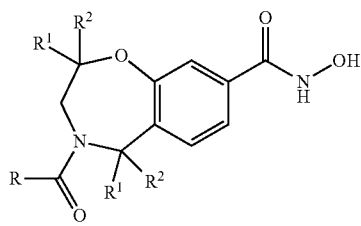

(IA-1e)

or a pharmaceutically acceptable salt thereof.

5. The compound of claim 1, wherein the compound is of the Formula IB:

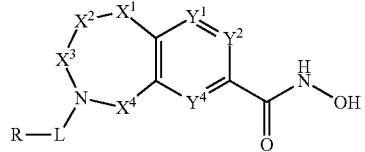

(IB)

or a pharmaceutically acceptable salt thereof.

6. The compound of claim 5, wherein the compound is of Formula IB-1:

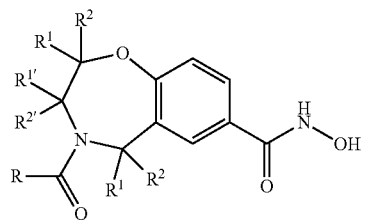

(IB-1)

or a pharmaceutically acceptable salt thereof.

7. The compound of claim 1, wherein the compound is:
(2R,5R)—N-hydroxy-4-(tetrahydro-2H-pyran-4-carbonyl)-2,3,4,5-tetrahydro-2,5-methanobenzo[f][1,4]oxazepine-8-carboxamide; or
(2S,5S)—N-hydroxy-4-(tetrahydro-2H-pyran-4-carbonyl)-2,3,4,5-tetrahydro-2,5-methanobenzo[f][1,4]oxazepine-8-carboxamide.

8. The compound of claim 1, wherein L is —C(O)—.

9. The compound of claim 8, wherein $R^{1'}$ and $R^{2'}$ are both —H.

10. The compound of claim 9, wherein R is an optionally substituted group selected from the group consisting of —$C_1$-$C_6$ alkyl, —$C_3$-$C_8$ cycloalkyl, —$C_5$-$C_{12}$ spirocyclyl, heterocyclyl, spiroheterocyclyl, aryl, and heteroaryl.

11. The compound of claim 10, wherein R is optionally substituted heterocyclyl.

12. The compound of claim 8, wherein R is an optionally substituted group selected from the group consisting of —$C_1$-$C_6$ alkyl, —$C_3$-$C_8$ cycloalkyl, —$C_5$-$C_{12}$ spirocyclyl, heterocyclyl, spiroheterocyclyl, aryl, or heteroaryl.

13. The compound of claim 12, wherein R is optionally substituted heterocyclyl.

14. A pharmaceutical composition comprising a compound of claim 1, and a pharmaceutically acceptable carrier.

* * * * *